(12) United States Patent
Levine et al.

(10) Patent No.: US 11,938,124 B2
(45) Date of Patent: Mar. 26, 2024

(54) COMBINATION THERAPY FOR TREATMENT OF CANCER

(71) Applicant: PMV Pharmaceuticals, Inc., Cranbury, NJ (US)

(72) Inventors: Arnold Levine, Doylestown, PA (US); Melissa Dumble, Watchung, NJ (US)

(73) Assignee: PMV Pharmaceuticals, Inc., Princeton, NJ (US)

( * ) Notice: Subject to any disclaimer, the term of this patent is extended or adjusted under 35 U.S.C. 154(b) by 60 days.

(21) Appl. No.: 17/348,490

(22) Filed: Jun. 15, 2021

(65) Prior Publication Data

US 2023/0033324 A1 Feb. 2, 2023

Related U.S. Application Data

(60) Provisional application No. 63/162,184, filed on Mar. 17, 2021, provisional application No. 63/043,342, filed on Jun. 24, 2020.

(51) Int. Cl.
| | | |
|---|---|---|
| *A61K 31/454* | (2006.01) | |
| *A61K 31/404* | (2006.01) | |
| *A61K 31/4045* | (2006.01) | |
| *A61K 31/438* | (2006.01) | |
| *A61K 31/4439* | (2006.01) | |

(Continued)

(52) U.S. Cl.
CPC .......... *A61K 31/454* (2013.01); *A61K 31/404* (2013.01); *A61K 31/4045* (2013.01); *A61K 31/438* (2013.01); *A61K 31/4439* (2013.01); *A61K 31/4545* (2013.01); *A61K 31/496* (2013.01); *A61K 31/506* (2013.01);

(Continued)

(58) Field of Classification Search
None
See application file for complete search history.

(56) References Cited

U.S. PATENT DOCUMENTS

| | | |
|---|---|---|
| 4,302,589 A | 11/1981 | Fanshawe et al. |
| 7,601,714 B2 | 10/2009 | Barbosa et al. |
| | (Continued) | |

FOREIGN PATENT DOCUMENTS

| | | |
|---|---|---|
| CA | 3084777 A1 | 7/2019 |
| CN | 104672241 | 6/2015 |
| | (Continued) | |

OTHER PUBLICATIONS

Hardwick et al., Clinical Cancer Research (2014), 20(17), 4459-4470 (Year: 2014).*

(Continued)

*Primary Examiner* — Karl J Puttlitz
(74) *Attorney, Agent, or Firm* — Wilson Sonsini Goodrich & Rosati

(57) ABSTRACT

Mutations in oncogenes and tumor suppressors contribute to the development and progression of cancer. The present disclosure describes methods of recovering wild-type function to p53 mutants by treating a cancer with a compound and a second agent. The compounds of the present invention can bind to mutant p53 and restore the ability of the p53 mutant to bind DNA and activate downstream effectors involved in tumor suppression. The disclosed compounds can be used in combination with a secondary agent to reduce the progression of cancers that contain a p53 mutation.

28 Claims, 17 Drawing Sheets

Specification includes a Sequence Listing.

(51) Int. Cl.
  A61K 31/4545 (2006.01)
  A61K 31/496 (2006.01)
  A61K 31/506 (2006.01)
  A61K 31/5377 (2006.01)
  A61K 31/538 (2006.01)
  A61K 39/395 (2006.01)
  A61P 35/00 (2006.01)

(52) U.S. Cl.
  CPC ........ *A61K 31/5377* (2013.01); *A61K 31/538* (2013.01); *A61K 39/3955* (2013.01); *A61P 35/00* (2018.01)

(56) References Cited

U.S. PATENT DOCUMENTS

| | | | |
|---|---|---|---|
| 8,124,766 | B2 | 2/2012 | Bolin et al. |
| 8,822,689 | B2 | 9/2014 | Soll et al. |
| 8,859,780 | B2 | 10/2014 | Ehring et al. |
| 8,865,715 | B2 | 10/2014 | Dorsch et al. |
| 8,933,113 | B2 | 1/2015 | Crespo et al. |
| 9,090,661 | B2 | 7/2015 | Coburn et al. |
| 10,138,219 | B2 | 11/2018 | Vu et al. |
| 10,640,485 | B2 | 5/2020 | Vu et al. |
| 2002/0048271 | A1 | 4/2002 | Rastinejad et al. |
| 2012/0258920 | A1 | 10/2012 | Sal et al. |
| 2017/0114098 | A1 | 4/2017 | Aivado et al. |
| 2017/0240525 | A1* | 8/2017 | Vu .................. C07D 401/14 |
| 2018/0222982 | A1 | 8/2018 | Dranoff et al. |
| 2019/0002460 | A1 | 1/2019 | Whitehead et al. |
| 2019/0038713 | A1* | 2/2019 | Sobol .................. A61K 45/06 |
| 2019/0119249 | A1 | 4/2019 | Vu et al. |
| 2020/0397738 | A1 | 12/2020 | Yuan et al. |
| 2021/0002252 | A1 | 1/2021 | Vu et al. |
| 2022/0184087 | A1* | 6/2022 | Dinavahi ................ A61P 35/00 |
| 2022/0213062 | A1 | 7/2022 | Vu et al. |
| 2022/0315564 | A1 | 10/2022 | Vu et al. |
| 2022/0339141 | A1 | 10/2022 | Abrahmsén et al. |
| 2022/0387434 | A1 | 12/2022 | Rothbaum |
| 2023/0002403 | A1 | 1/2023 | Vu et al. |
| 2023/0024905 | A1 | 1/2023 | Vu et al. |
| 2023/0044826 | A1 | 2/2023 | Dumble |
| 2023/0049952 | A1 | 2/2023 | Levine et al. |
| 2023/0312539 | A1 | 10/2023 | Vu et al. |

FOREIGN PATENT DOCUMENTS

| | | |
|---|---|---|
| WO | WO-0032175 A2 | 6/2000 |
| WO | WO-03032911 A3 | 7/2003 |
| WO | WO-2006136823 A1 | 12/2006 |
| WO | WO-2009136175 A1 | 11/2009 |
| WO | WO-2012175962 A1 | 12/2012 |
| WO | WO-2013036208 A1 | 3/2013 |
| WO | WO-2015178955 A1 | 11/2015 |
| WO | WO-2015179799 A1 | 11/2015 |
| WO | WO-2016004513 A1 | 1/2016 |
| WO | WO-2017143291 A1 | 8/2017 |
| WO | WO-2018075937 A1 | 4/2018 |
| WO | WO-2018191587 A1 | 10/2018 |
| WO | WO-2021087096 A1 | 5/2021 |
| WO | WO-2021113644 A1 | 6/2021 |
| WO | WO-2021170772 A1 | 9/2021 |
| WO | 2021207598 | * 10/2021 |
| WO | WO-2021207598 A1 | 10/2021 |

OTHER PUBLICATIONS

Chung et al., Clinical and Translational Oncology (2019), 21(3), 363-372 (Year: 2019).*
International Search Report and Written Opinion issued in PCT/US2021/037473 dated Dec. 6, 2021.
Patani, G.A. et al., "Bioisosterism: A rational approach in drug design," Chemical Reviews, 1996;96:3147-3176.
U.S. Appl. No. 18/330,978, inventors Vu; Binh et al., filed Jun. 7, 2023.
U.S. Appl. No. 17/351,970 Non-Final Office Action dated Sep. 25, 2023.
Ansel, Howard C, et al. Pharmaceutical Dosage Forms and Drug Delivery Systems. Philadelphia, PA: Lippincott-Williams & Wilkins, 1999. Print.
Bilbao, et al., Two-Dimensional Nanoporous Networks Formed by Liquid-to-Solid Transfer of Hydrogen-Bonded Macrocycles Built from DNA Bases, 2015.
Coburn et al., (CAPLUS abstract of WO2010111483 (Sep. 30, 2010)).
Dell'Acqua, et al., MediaChrom: Discovering a Class of Pyrimidinedione-Based Polarity-Sensitive Dyes, 2015, Journal of Organic Chemistry, vol. 80 (21, pp. 10939-10954.
English Translation of JP Application No. 2018-544186 Office Action dated Jan. 27, 2021.
English Translation of Second Office Action issued in Chinese Application No. 2017800134506 dated Apr. 13, 2021.
European Application No. 17753995.4 Office Action dated Jan. 13, 2021.
European Serial No. 17753995.4 Extended Search Report dated Jun. 17, 2019.
Fiandanese, et al., A straightforward synthesis of indole and benzofuran derivatives, 2007, Tetrahedron, Elsevier Science Publishers, vol. 64 (1), pp. 53-60.
Gangjee, et al., Synthesis and Biological Activity of N4-phenylsubstituted-6-(2,4-dichloro phenylmethyl)-7H-pyrrolo[2,3-d]pyrimidine-2,4-diamines as Vascular Endothelial Growth Factor Receptor-2 Inhibitors and Antiangiogenic and Antitumor Agents, 2010, Bioorg Med Chem, vol. 18(10), pp. 1-33.
Gennaro, A.R., Remington: The science and practice of pharmacy. 19th edition. 1995. 12 Pages.
Gergely, et al., C2-Selective Direct Alkynylation of Indoles, 2012, Organic Letters, vol. 15(1), pp. 112-115.
Guo, et al., PIM inhibitors target CD25-positive AML cells through concomitant suppression of STAT5 activation and degradation of MYC oncogene, 2014, BLOOD, vol. 124 (11), pp. 1777-1789.
Hoover, J. et al., Remington's Pharmaceutical science. 1970.
International Search Report and written opinion dated Jun. 21, 2017 for International Application No. PCT/US2017/018511.
Joerger, et al., Structure-function-rescue: the diverse nature of common p53 cancer mutants. Oncogene (2007) 26, 2226-2242.
Kubinyi. 3D QSAR in Drug Design: Ligand-Protein Interactions and Molecular Similarity. (vol. 2-3, Springer, 1998, 800 pages). pp. 243-244 provided.
Leblanc, et al., Homogeneous time-resolved fluorescence assay for identifying p53 interactions with its protein partners, directly in a cellular extract. Analytical Biochemistry 308 (2002) 247-254.
Liberman, H.A., Pharmaceutical Dosage Forms: Parenteral Medications. 1992. vol. 1. 4 pages.
Liu, et al., Small molecule induced reactivation of mutant p53 in cancer cells. Nucleic Acids Research, 2013, vol. 41, No. 12. 6034-6044.
Notice of Allowance issued in Israeli Patent Application No. 261175 dated Jun. 30, 2021.
Notice of Allowance issued in Japanese Patent Application No. 2018-544186 dated Sep. 3, 2021.
Notice of Allowance issued in Mexican Patent Application No. MX/a/2018/009947 dated Apr. 15, 2021.
Office Action issued in Brazilian Application No. BR112018016890-4 dated Aug. 11, 2021.
Patent Certificate 371916 issued in Indian Application No. 201817032237 on Jul. 14, 2021.
Ribeiro, et al., Chemical Variations on the p53 reactivation theme. Pharmaceuticals, May 2016; 9(25):1-33.
Selivanova, et al., Reactivation of mutant p53: molecular mechanisms and therapeutic potential, Oncogene, Apr. 2, 2007; vol. 26: p. 2243-2254.
Shinohara, et al., Design of environmentally sensitive fluorescent 2-deoxyguanosine containing aryl ethynyl moieties: Distinction of

(56) References Cited

OTHER PUBLICATIONS thymine base by base-discriminating fluorescent (BDF) probe, 2010, Bioorganic & Medicinal Chemistry Letters, vol. 20, pp. 2817-2820.
U.S. Appl. No. 15/436,333 Notice of Allowance dated Aug. 27, 2018.
U.S. Appl. No. 15/436,333 Notice of Allowance dated Jul. 23, 2018.
U.S. Appl. No. 16/163,829 Notice of Allowance dated Dec. 20, 2019.
U.S. Appl. No. 16/163,829 Non-Final Office Action dated May 2, 2019.
U.S. Appl. No. 16/819,934 Non-Final Office Action dated May 25, 2021.
U.S. Appl. No. 15/436,333 Office Action dated Dec. 7, 2017.
Wermuth. The Practice of Medicinal Chemistry, 2d ed. 768 pages, chapters 9-10 provided (2003).
Wilcken, et al., Halogen-Enriched Fragment Libraries as Leads for Drug Rescue of Mutant p53.Journal of the American chemical society. 2012; 134:6810-6818.

* cited by examiner

SEQUENCE LISTING

```
<160> NUMBER OF SEQ ID NOS: 1

<210> SEQ ID NO 1
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Ser Ser Val Pro Ser Gln Lys Thr Tyr Gln Gly Ser Tyr Gly Phe
1               5                   10                  15

Arg Leu Gly Phe Leu His Ser Gly Thr Ala Lys Ser Val Thr Cys Thr
            20                  25                  30
```

```
Tyr Ser Pro Ala Leu Asn Lys Met Phe Cys Gln Leu Ala Lys Thr Cys
    35              40                  45
Pro Val Gln Leu Trp Val Asp Ser Thr Pro Pro Gly Thr Arg Val
    50              55              60
Arg Ala Met Ala Ile Tyr Lys Gln Ser Gln His Met Thr Glu Val Val
65              70              75              80
Arg Arg Cys Pro His His Glu Arg Cys Ser Asp Ser Asp Gly Leu Ala
            85              90              95
Pro Pro Gln His Leu Ile Arg Val Glu Gly Asn Leu Arg Val Glu Tyr
            100             105             110
Leu Asp Asp Arg Asn Thr Phe Arg His Ser Val Val Val Pro Cys Glu
        115             120             125
Pro Pro Glu Val Gly Ser Asp Cys Thr Thr Ile His Tyr Asn Tyr Met
    130             135             140
Cys Asn Ser Ser Cys Met Gly Gly Met Asn Arg Arg Pro Ile Leu Thr
145             150             155             160
Ile Ile Thr Leu Glu Asp Ser Ser Gly Asn Leu Leu Gly Arg Asn Ser
            165             170             175
Phe Glu Val His Val Cys Ala Cys Pro Gly Arg Asp Arg Arg Thr Glu
            180             185             190
Glu Glu Asn Leu Arg Lys Lys Gly Glu Pro His His Glu Leu Pro Pro
            195             200             205
Gly Ser Thr Lys Arg Ala Leu Ser Asn Asn Thr
    210             215
```

COMBINATION THERAPY FOR TREATMENT OF CANCER

CROSS-REFERENCE

This application claims the benefit of U.S. Provisional Application No. 63/043,342, filed Jun. 24, 2020; and U.S. Provisional Application No. 63/162,184, filed Mar. 17, 2021, which are incorporated herein by reference.

The instant application contains a Sequence Listing, which has been submitted electronically in ASCII format and is hereby incorporated by reference in its entirety. The ASCII copy, created on Jul. 28, 2021, is named 44727-714.201_SL.txt and is 4,096 bytes in size.

BACKGROUND

Cancer, an uncontrolled proliferation of cells, is a multifactorial disease characterized by tumor formation, growth, and in some instances, metastasis. Cells carrying an activated oncogene, damaged genome, or other cancer-promoting alterations can be prevented from replicating through an elaborate tumor suppression network. A central component of this tumor suppression network is p53, one of the most potent tumor suppressors in the cell. Both the wild type and mutant conformations of p53 are implicated in the progression of cancer.

INCORPORATION BY REFERENCE

Each patent, publication, and non-patent literature cited in the application is hereby incorporated by reference in its entirety as if each was incorporated by reference individually.

SUMMARY OF THE INVENTION

Provided herein is a method of treating cancer in a subject in need thereof, the method comprising: (i) administering to the subject a therapeutically-effective amount of a compound, wherein the compound binds to a mutant p53 protein and reconforms the mutant p53 protein to a conformation of p53 that exhibits anti-cancer activity; and (ii) administering to the subject a therapeutically-effective amount of an anti-cancer agent that functions through a pathway other than p53-induced apoptosis.

Also provided herein is a method of treating cancer in a subject in need thereof, the method comprising: (i) administering to the subject a therapeutically-effective amount of a compound that increases anti-cancer activity of a mutant p53 protein in the subject; and (ii) administering to the subject a therapeutically-effective amount of an anti-cancer agent that functions through a pathway other than p53-induced apoptosis.

Further provided herein is a method of treating cancer, the method comprising: (i) administering to a subject in need thereof a therapeutically-effective amount of a compound that binds to a mutant p53 protein and reconforms the mutant p53 protein to a conformation of p53 that exhibits anti-cancer activity; and (ii) administering to the subject a therapeutically-effective amount of an additional anti-cancer agent that functions through a pathway other than p53-induced apoptosis, wherein if in a controlled study of treatment of the cancer in a first patient population and a second patient population: (a) a first median survival time of the first patient population is determined, wherein the first patient population is treated with the therapeutically-effective amount of the compound that binds to a mutant p53 protein and reconforms the mutant p53 protein to a conformation of p53 that exhibits anti-cancer activity; and (b) a second median survival time of the second patient population is determined, wherein the second patient population is treated with the therapeutically-effective amount of the compound that binds to a mutant p53 protein and reconforms the mutant p53 protein to a conformation of p53 that exhibits anti-cancer activity and the therapeutically-effective amount of the additional therapeutic agent; then the second median survival time is at least about 50% greater than is the first median survival time.

Figure 9:
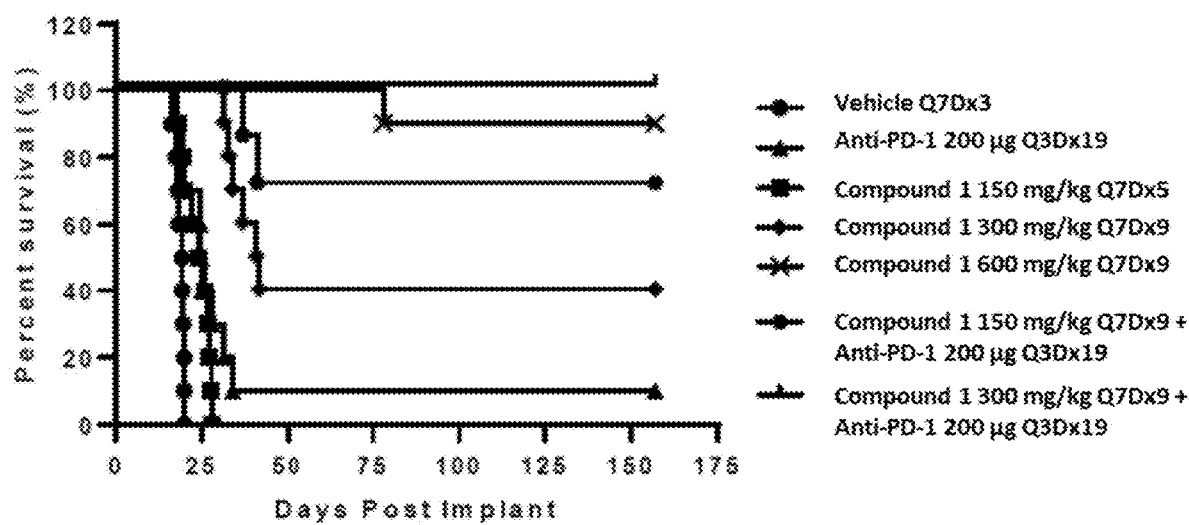

FIG. 9 provides a Kaplan-Meier survival curve of C57Bl/6 mice implanted with MT245 mouse syngeneic sarcoma tumors upon receiving treatment with vehicle (Q7Dx3); anti-PD-1 200 µg (Q3Dx19); Compound 1, 150 mg/kg (Q7Dx5); Compound 1, 300 mg/kg (Q7Dx9); Compound 1, 600 mg/kg (Q7Dx9); Compound 1, 150 mg/kg (Q7Dx9)+anti-PD-1 200 µg (Q3Dx19); or Compound 1, 300 mg/kg (Q7Dx9)+anti-PD-1 200 µg (Q3Dx19).

Figure 10:
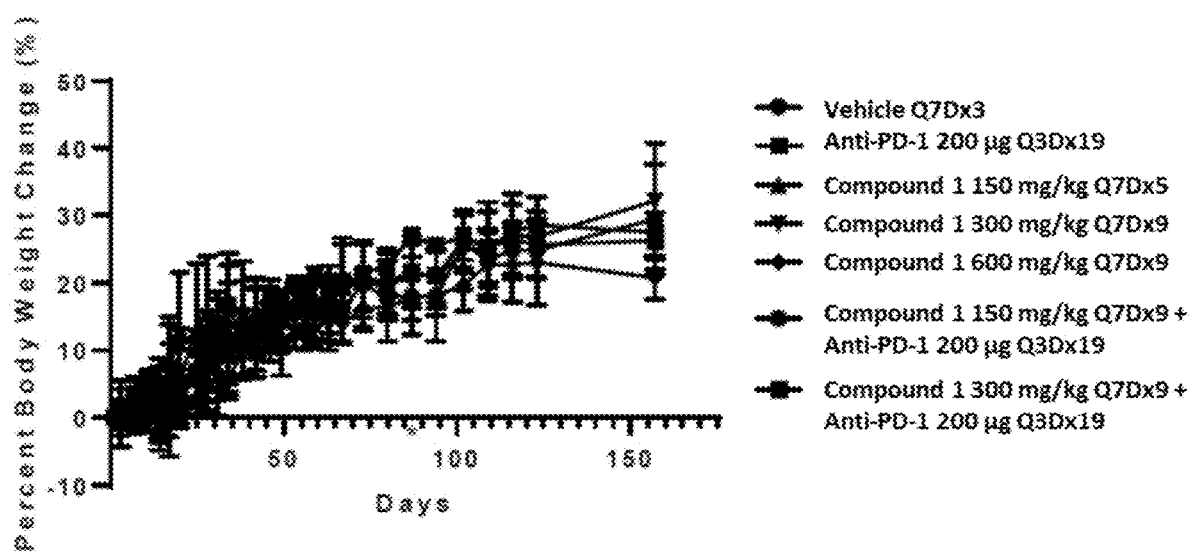

FIG. 10 shows changes in percent body weight C57Bl/6 mice implanted with MT245 mouse syngeneic sarcoma tumors upon receiving treatment with vehicle (Q7Dx3); anti-PD-1 200 µg (Q3Dx19); Compound 1, 150 mg/kg (Q7Dx5); Compound 1, 300 mg/kg (Q7Dx9); Compound 1, 600 mg/kg (Q7Dx9); Compound 1, 150 mg/kg (Q7Dx9)+anti-PD-1 200 µg (Q3Dx19); or Compound 1, 300 mg/kg (Q7Dx9)+anti-PD-1 200 µg (Q3Dx19).

Figure 11:
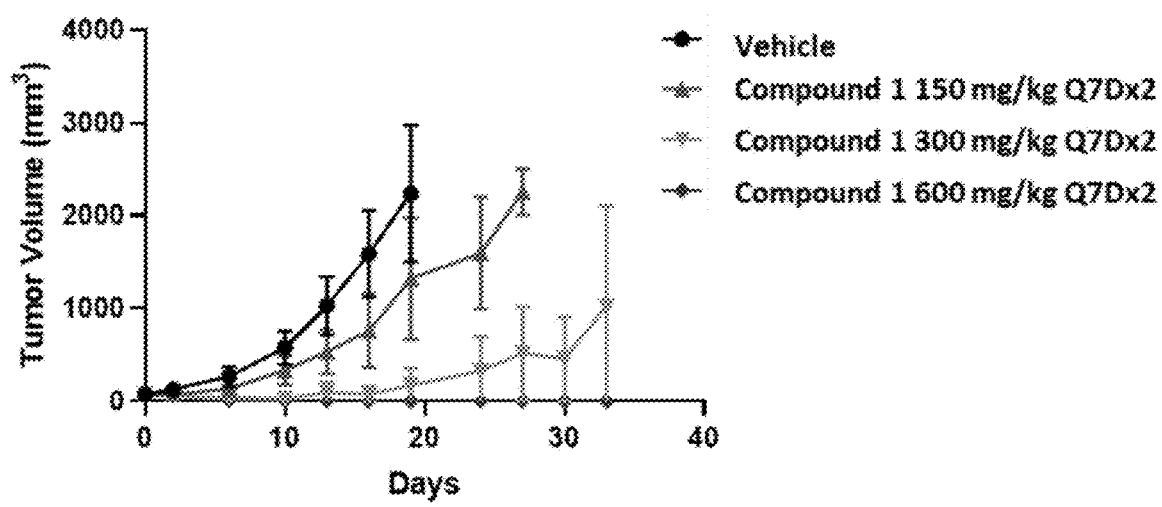

FIG. 11 shows changes in tumor volume (mm$^3$) of C57Bl/6 mice implanted with MT245 mouse syngeneic sarcoma tumors upon receiving treatment with Vehicle; Compound 1, 150 mg/kg (Q7Dx2); Compound 1, 300 mg/kg (Q7Dx2); or Compound 1, 600 mg/kg (Q7Dx2).

Figure 12:
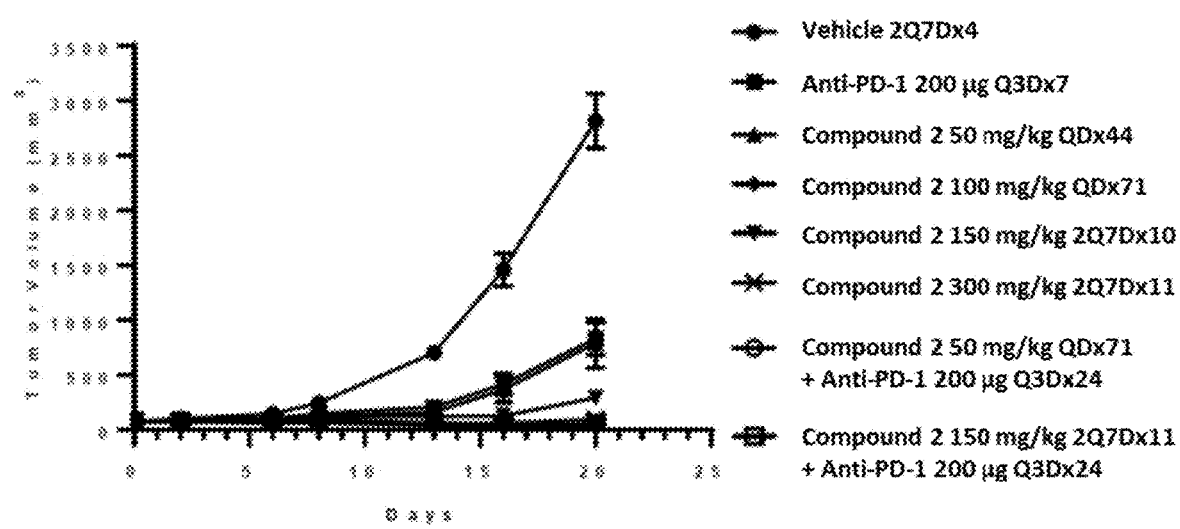

FIG. 12 shows changes in tumor volume (mm$^3$) for C57Bl/6 mice implanted with MT373 mouse sarcoma tumors over 20 days upon receiving treatment with vehicle (2Q7Dx4); anti-PD-1 200 µg (Q3Dx7); Compound 2, 50 mg/kg (QDx44); Compound 2, 100 mg/kg (QDx71); Compound 2, 150 mg/kg (2Q7Dx10); Compound 2, 300 mg/kg (2Q7Dx11); Compound 2 50 mg/kg (QDx71)+anti-PD-1 200 µg (Q3Dx24); or Compound 2, 150 mg/kg (2Q7Dx11)+anti-PD-1 200 µg (Q3Dx24).

Figure 13:
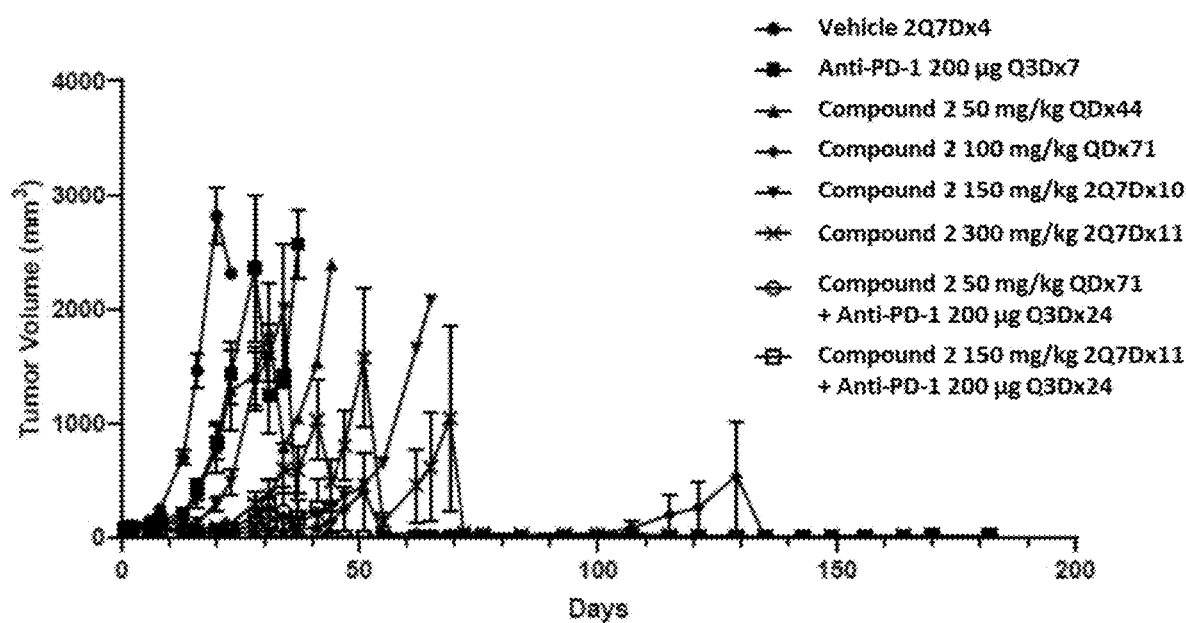

FIG. 13 shows changes in tumor volume (mm$^3$) for C57Bl/6 mice implanted with MT373 mouse sarcoma tumors over 182 days upon receiving treatment with vehicle (2Q7Dx4); anti-PD-1 200 µg (Q3Dx7); Compound 2, 50 mg/kg (QDx44); Compound 2, 100 mg/kg (QDx71); Compound 2, 150 mg/kg (2Q7Dx10); Compound 2, 300 mg/kg (2Q7Dx11); Compound 2 50 mg/kg (QDx71)+anti-PD-1 200 µg (Q3Dx24); or Compound 2, 150 mg/kg (2Q7Dx11)+anti-PD-1 200 µg (Q3Dx24).

Figure 14:
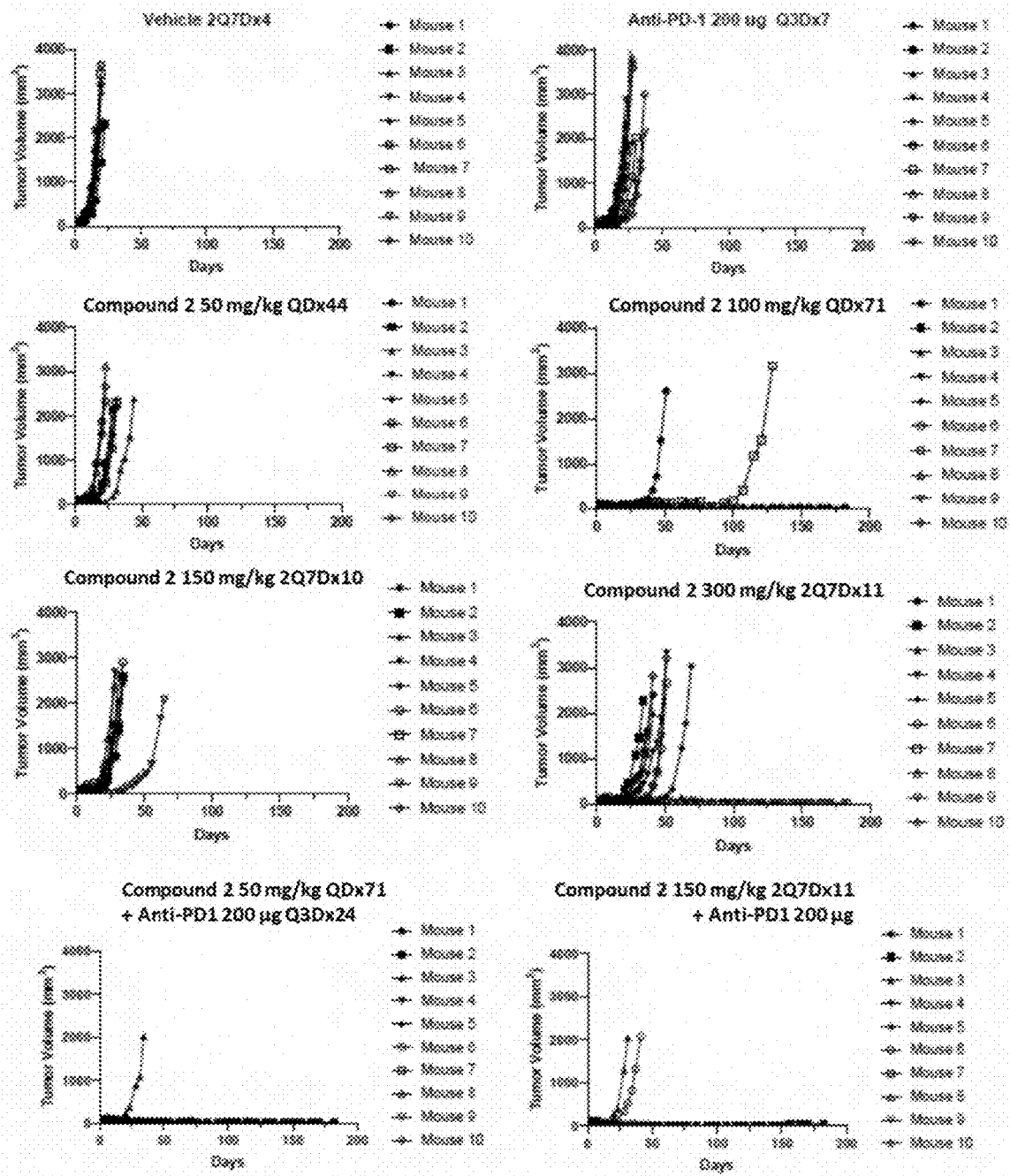

FIG. 14 shows changes in tumor volume (mm$^3$) of individual C57Bl/6 mice implanted with MT373 mouse sarcoma tumors upon receiving treatment with vehicle (2Q7Dx4); anti-PD-1 200 µg (Q3Dx7); Compound 2, 50 mg/kg (QDx44); Compound 2, 100 mg/kg (QDx71); Compound 2, 150 mg/kg (2Q7Dx10); Compound 2, 300 mg/kg (2Q7Dx11); Compound 2 50 mg/kg (QDx71)+anti-PD-1 200 µg (Q3Dx24); or Compound 2, 150 mg/kg (2Q7Dx11)+anti-PD-1 200 µg (Q3Dx24).

Figure 15:
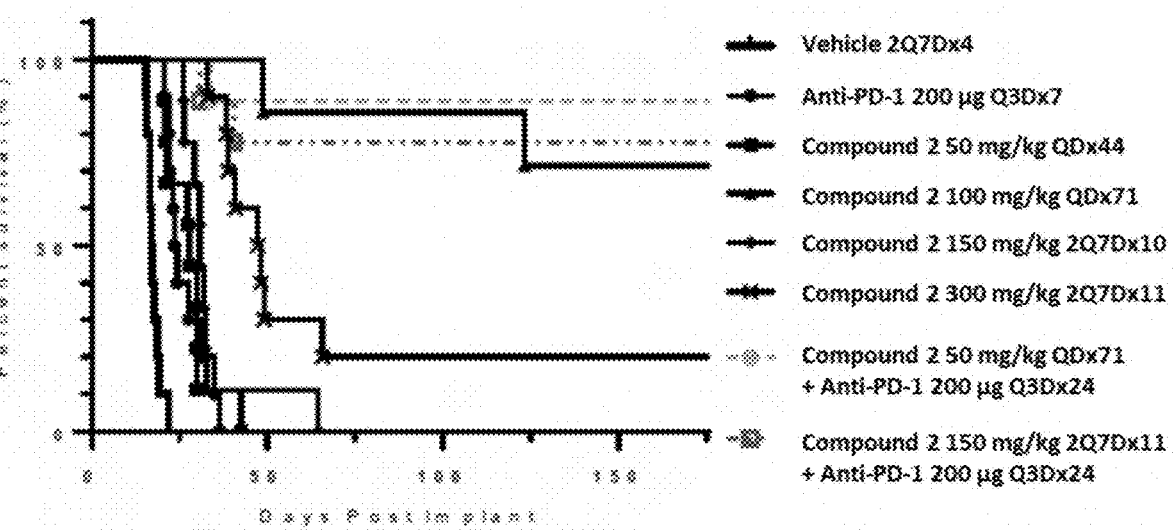

FIG. 15 shows changes in percent survival of C57Bl/6 mice implanted with MT373 mouse sarcoma tumors upon receiving treatment with vehicle (2Q7Dx4); anti-PD-1 200 µg (Q3Dx7); Compound 2, 50 mg/kg (QDx44); Compound 2, 100 mg/kg (QDx71); Compound 2, 150 mg/kg (2Q7Dx10); Compound 2, 300 mg/kg (2Q7Dx11); Compound 2 50 mg/kg (QDx71)+anti-PD-1 200 µg (Q3Dx24); or Compound 2, 150 mg/kg (2Q7Dx11)+anti-PD-1 200 µg (Q3Dx24).

Figure 16:
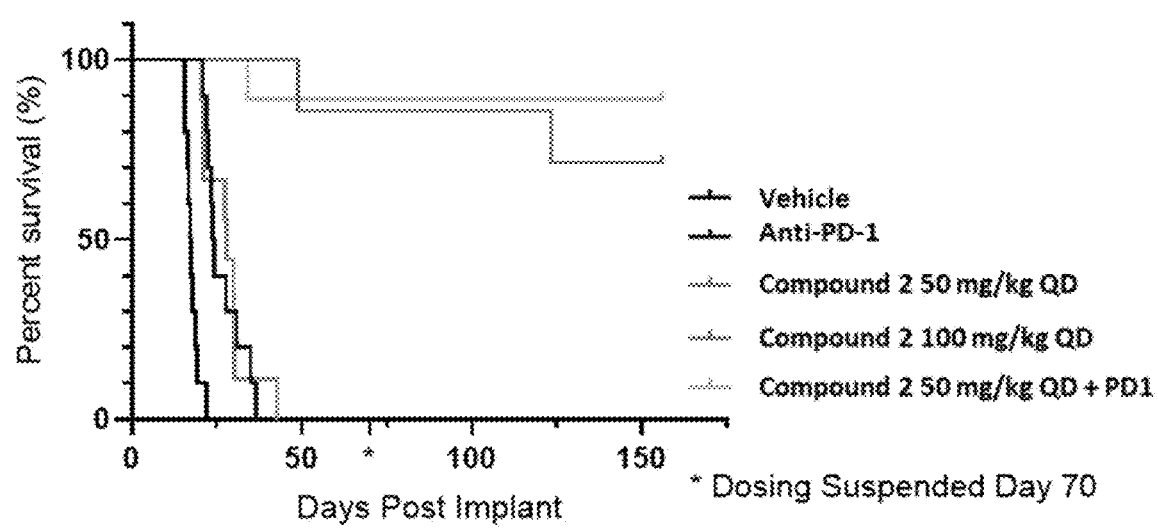

FIG. 16 shows changes in percent survival of C57Bl/6 mice implanted with MT373 mouse sarcoma tumors upon receiving treatment with vehicle; anti-PD-1; Compound 2, 50 mg/kg (QD); Compound 2, 100 mg/kg (QD); or Compound 2, 50 mg/kg (QD)+anti-PD-1.

Figure 17:
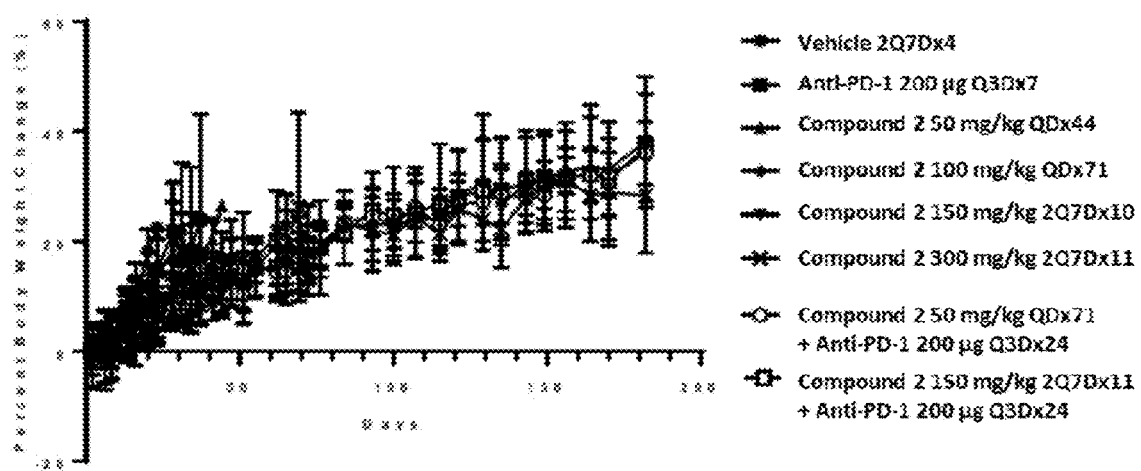

FIG. 17 shows changes in percentage body weight of C57Bl/6 mice implanted with MT373 mouse sarcoma tumors upon receiving treatment with vehicle (2Q7Dx4); anti-PD-1 200 µg (Q3Dx7); Compound 2, 50 mg/kg (QDx44); Compound 2, 100 mg/kg (QDx71); Compound 2, 150 mg/kg (2Q7Dx10); Compound 2, 300 mg/kg (2Q7Dx11); Compound 2 50 mg/kg (QDx71)+anti-PD-1 200 µg (Q3Dx24); or Compound 2, 150 mg/kg (2Q7Dx11)+anti-PD-1 200 µg (Q3Dx24).

DETAILED DESCRIPTION

The present invention provides compounds and methods for restoring wild-type function to mutant p53. The compounds of the present invention can bind to mutant p53 and restore the ability of the p53 mutant to bind DNA. The restoration of activity of the p53 mutant can allow for the activation of downstream effectors of p53 leading to inhibition of cancer progression. The invention further provides methods of treatment of a cancerous lesion or a tumor harboring a p53 mutation.

Cancer is a collection of related diseases characterized by uncontrolled proliferation of cells with the potential to metastasize throughout the body. Cancer can be classified into five broad categories including, for example: carcinomas, which can arise from cells that cover internal and external parts of the body such as the lung, breast, and colon; sarcomas, which can arise from cells that are located in bone, cartilage, fat, connective tissue, muscle, and other supportive tissues; lymphomas, which can arise in the lymph nodes and immune system tissues; leukemia, which can arise in the bone marrow and accumulate in the bloodstream; and adenomas, which can arise in the thyroid, the pituitary gland, the adrenal gland, and other glandular tissues.

Although different cancers can develop in virtually any of the body's tissues, and contain unique features, the basic processes that cause cancer can be similar in all forms of the disease. Cancer begins when a cell breaks free from the normal restraints on cell division and begins to grow and divide out of control. Genetic mutations in the cell can preclude the ability of the cell to repair damaged DNA or initiate apoptosis, and can result in uncontrolled growth and division of cells.

The ability of tumor cell populations to multiply is determined not only by the rate of cell proliferation but also by the rate of cell attrition. Programmed cell death, or apoptosis, represents a major mechanism of cellular attrition. Cancer cells can evade apoptosis through a variety of strategies, for example, through the suppression of p53 function, thereby suppressing expression of pro-apoptotic proteins.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf kinase, K-Ras, and myc. Tumor suppressor genes that can be mutated in cancer include, for example, BRCA1, BRCA2, cyclin-dependent kinase inhibitor 1C, Retinoblastoma protein (pRb), PTEN, p16, p27, p53, and p73.

Tumor Suppressor p53.

The tumor suppressor protein p53 is a 393 amino acid transcription factor that can regulate cell growth in response to cellular stresses including, for example, UV radiation, hypoxia, oncogene activation, and DNA damage. p53 has various mechanisms for inhibiting the progression of cancer including, for example, initiation of apoptosis, maintenance of genomic stability, cell cycle arrest, induction of senescence, and inhibition of angiogenesis. Due to the critical role of p53 in tumor suppression, p53 is inactivated in almost all cancers either by direct mutation or through perturbation of associated signaling pathways involved in tumor suppression. Homozygous loss of the p53 gene occurs in almost all types of cancer, including carcinomas of the breast, colon, and lung. The presence of certain p53 mutations in several types of human cancer can correlate with less favorable patient prognosis.

In the absence of stress signals, p53 levels are maintained at low levels via the interaction of p53 with Mdm2, an E3 ubiquitin ligase. In an unstressed cell, Mdm2 can target p53 for degradation by the proteasome. Under stress conditions, the interaction between Mdm2 and p53 is disrupted, and p53 accumulates. The critical event leading to the activation of p53 is phosphorylation of the N-terminal domain of p53 by protein kinases, thereby transducing upstream stress signals. The phosphorylation of p53 leads to a conformational change, which can promote DNA binding by p53 and allow transcription of downstream effectors. The activation of p53 can induce, for example, the intrinsic apoptotic pathway, the extrinsic apoptotic pathway, cell cycle arrest, senescence, and DNA repair. p53 can activate proteins involved in the above pathways including, for example, Fas/Apo1, KILLER/DR5, Bax, Puma, Noxa, Bid, caspase-3, caspase-6, caspase-7, caspase-8, caspase-9, and p21 (WAF1). Additionally, p53 can repress the transcription of a variety of genes including, for example, c-MYC, Cyclin B, VEGF, RAD51, and hTERT.

Each chain of the p53 tetramer is composed of several functional domains including the transactivation domain (amino acids 1-100), the DNA-binding domain (amino acids 101-306), and the tetramerization domain (amino acids 307-355), which are highly mobile and largely unstructured. Most p53 cancer mutations are located in the DNA-binding core domain of the protein, which contains a central β-sandwich of anti-parallel β-sheets that serves as a basic scaffold for the DNA-binding surface. The DNA-binding surface is composed of two β-turn loops, L2 and L3, which are stabilized by a zinc ion, for example, at Arg175 and Arg248, and a loop-sheet-helix motif. Altogether, these structural elements form an extended DNA-binding surface that is rich in positively-charged amino acids, and makes specific contact with various p53 response elements.

Due to the prevalence of p53 mutations in virtually every type of cancer, the reactivation of wild type p53 function in a cancerous cell can be an effective therapy. Mutations in p53 located in the DNA-binding domain of the protein or periphery of the DNA-binding surface result in aberrant protein folding required for DNA recognition and binding. Mutations in p53 can occur, for example, at amino acids Val143, His168, Arg175, Tyr220, Gly245, Arg248, Arg249, Phe270, Arg273, and Arg282. p53 mutations that can abrogate the activity of p53 include, for example, R175H, Y220C, G245S, R248Q, R248W, R273H, and R282H. These p53 mutations can either distort the structure of the DNA-binding site or thermodynamically destabilize the folded protein at body temperature. Wild-type function of p53 mutants can be recovered by binding of the p53 mutant to a compound that can shift the folding-unfolding equilibrium towards the folded state, thereby reducing the rate of unfolding and destabilization.

Non-limiting examples of amino acids include: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val).

Mechanism of Compounds of the Invention.

The compounds of the present invention can selectively bind to a p53 mutant and can recover wild-type activity of the p53 mutant including, for example, DNA binding function and activation of downstream targets involved in tumor suppression. In some embodiments, a compound of the invention selectively binds to the p53 Y220C mutant. The Y220C mutant is a temperature sensitive mutant, which binds to DNA at lower temperature and is denatured at body temperature. A compound of the invention can stabilize the Y220C mutant to reduce the likelihood of denaturation of the protein at body temperature.

In some embodiments, the compounds of the disclosure stabilize a mutant p53 and allows the mutant p53 to bind to DNA, thereby shifting the equilibrium of wild type and mutant p53 proteins to wild type p53. In some embodiments, the compounds of the disclosure reactivate the mutant p53 protein to provide wild type p53 activity. In some embodiments, the compounds of the disclosure reactivate the mutant p53 protein to provide pro-apoptotic p53 activity. In some embodiments, the compounds of the disclosure reactivate the mutant p53 protein to block angiogenesis. In some embodiments, the compounds of the disclosure reactivate the mutant p53 protein to induce cellular senescence. In some embodiments, the compounds of the disclosure reactivate the mutant p53 protein to induce cell cycle arrest.

In some embodiments, the compounds of the disclosure can reconform mutant p53 to a conformation of p53 that exhibits anti-cancer activity. In some embodiments, the mutant p53 is reconformed to a wild type conformation p53. In some embodiments, the mutant p53 is reconformed to a pro-apoptotic conformation of p53. In some embodiments, the mutant p53 is reconformed to a conformation of p53 that blocks angiogenesis. In some embodiments, the mutant p53 is reconformed to a conformation of p53 that induces cellular senescence. In some embodiments, the mutant p53 is reconformed to a conformation of p53 that induces cell-cycle arrest.

Located in the periphery of the p53 β-sandwich connecting β-strands S7 and S8, the aromatic ring of Y220 is an integral part of the hydrophobic core of the β-sandwich. The Y220C mutation can be highly destabilizing, due to the formation of an internal surface cavity. A compound of the invention can bind to and occupy this surface crevice to stabilize the β-sandwich, thereby restoring wild-type p53 DNA-binding activity.

To determine the ability of a compound of the invention to bind and stabilize mutant p53, assays can be employed to detect, for example, a conformational change in the p53 mutant or activation of wild-type p53 targets. Conformational changes in p53 can be measured by, for example, differential scanning fluorimetry (DSF), isothermal titration calorimetry (ITC), nuclear magnetic resonance spectrometry (NMR), or X-ray crystallography. Additionally, antibodies specific for the wild type of mutant conformation of p53 can be used to detect a conformational change via, for example, immunoprecipitation (IP), immunofluorescence (IF), or immunoblotting.

Methods used to detect the ability of the p53 mutant to bind DNA can include, for example, DNA affinity immunoblotting, modified enzyme-linked immunosorbent assay (ELISA), electrophoretic mobility shift assay (EMSA), fluorescence resonance energy transfer (FRET), homogeneous time-resolved fluorescence (HTRF), and a chromatin immunoprecipitation (ChIP) assay.

To determine whether a compound described herein is able to reactivate the transcriptional activity of p53, the activation of downstream targets in the p53 signaling cascade can be measured. Activation of p53 effector proteins can be detected by, for example, immunohistochemistry (IHC-P), reverse transcription polymerase chain reaction (RT-PCR), and western blotting. The activation of p53 can also be measured by the induction of apoptosis via the caspase cascade and using methods including, for example, Annexin V staining, TUNEL assays, pro-caspase and caspase levels, and cytochrome c levels. Another consequence of p53 activation is senescence, which can be measured using methods such as β-galactosidase staining.

A p53 mutant that can be used to determine the effectiveness of a compound of the invention to increase the DNA binding ability of a p53 mutant is a p53 truncation mutant, which contains only amino acids 94-312, encompassing the DNA-binding domain of p53. For example, the sequence of the p53 Y220C mutant used for testing compound efficacy can be:

```
                                         (SEQ ID NO. 1)
SSSVPSQ KTYQGSYGFR LGFLHSGTAK SVTCTYSPAL

NKMFCQLAKT CPVQLWVDST PPPGTRVRAM AIYKQSQHMT

EVVRRCPHHE RCSDSDGLAP PQHLIRVEGN LRVEYLDDRN

TFRHSVVVPC EPPEVGSDCT TIHYNYMCNS SCMGGMNRRP

ILTIITLEDS SGNLLGRNSF EVHVCACPGR DRRTEEENLR

KKGEPHHELP PGSTKRALSN NT
```

A compound of the invention can increase the ability of a p53 mutant to bind DNA by at least or up to about 0.1%, at least or up to about 0.2%, at least or up to about 0.3%, at least or up to about 0.4%, at least or up to about 0.5%, at least or up to about 0.6%, at least or up to about 0.7%, at least or up to about 0.8%, at least or up to about 0.9%, at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 11%, at least or up to about 12%, at least or up to about 13%, at least or up to about 14%, at least or up to about 15%, at least or up to about 16%, at least or up to about 17%, at least or up to about 18%, at least or up to about 19%, at least or up to about 20%, at least or up to about 21%, at least or up to about 22%, at least or up to about 23%, at least or up to about 24%, at least or up to about 25%, at least or up to about 26%, at least or up to about 27%, at least or up to about 28%, at least or up to about 29%, at least or up to about 30%, at least or up to about 31%, at least or up to about 32%, at least or up to about 33%, at least or up to about 34%, at least or up to about 35%, at least or up to about 36%, at least or up to about 37%, at least or up to about 38%, at least or up to about 39%, at least or up to about 40%, at least or up to about 41%, at least or up to about 42%, at least or up to about 43%, at least or up to about 44%, at least or up to about 45%, at least or up to about 46%, at least or up to about 47%, at least or up to about 48%, at least or up to about 49%, at least or up to about 50%, at least or up to about 51%, at least or up to about 52%, at least or up to about 53%, at least or up to about 54%, at least or up to about 55%, at least or up to about 56%, at least or up to about 57%, at least or up to about 58%, at least or up to about 59%, at least or up to about 60%, at least or up to about 61%, at least or up to about 62%, at least or up to about 63%, at least or up to about 64%, at least or up to about 65%, at least or up to about 66%, at least or up to about 67%, at least or up to about 68%, at least or up to about 69%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, at least or up to about 100%, at least or up to about 125%, at least or up to about 150%, at least or up to about 175%, at least or up to about 200%, at least or up to about 225%, or at least or up to about 250% as compared to the ability of the p53 mutant to bind DNA in the absence of a compound of the invention.

A compound described herein can increase the activity of the p53 mutant that is, for example, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 11-fold, at least or up to about 12-fold, at least or up to about 13-fold, at least or up to about 14-fold, at least or up to about 15-fold, at least or up to about 16-fold, at least or up to about 17-fold, at least or up to about 18-fold, at least or up to about 19-fold, at least or up to about 20-fold, at least or up to about 25-fold, at least or up to about 30-fold, at least or up to about 35-fold, at least or up to about 40-fold, at least or up to about 45-fold, at least or up to about 50-fold, at least or up to about 55-fold, at least or up to about 60-fold, at least or up to about 65-fold, at least or up to about 70-fold, at least or up to about 75-fold, at least or up to about 80-fold, at least or up to about 85-fold, at least or up to about 90-fold, at least or up to about 95-fold, at least or up to about 100-fold, at least or up to about 110-fold, at least or up to about 120-fold, at least or up to about 130-fold, at least or up to about 140-fold, at least or up to about 150-fold, at least or up to about 160-fold, at least or up to about 170-fold, at least or up to about 180-fold, at least or up to about 190-fold, at least or up to about 200-fold, at least or up to about 250-fold, at least or up to about 300-fold, at least or up to about 350-fold, at least or up to about 400-fold, at least or up to about 450-fold, at least or up to about 500-fold, at least or up to about 550-fold, at least or up to about 600-fold, at least or up to about 650-fold, at least or up to about 700-fold, at least or up to about 750-fold, at least or up to about 800-fold, at least or up to about 850-fold, at least or up to about 900-fold, at least or up to about 950-fold, at least or up to about 1,000-fold, at least or up to about 1,500-fold, at least or up to about 2,000-fold, at least or up to about 3,000-fold, at least or up to about 4,000-fold, at least or up to about 5,000-fold, at least or up to about 6,000-fold, at least or up to about 7,000-fold, at least or up to about 8,000-fold, at least or up to about 9,000-fold, or at least or up to about 10,000-fold greater than the activity of the p53 mutant in the absence of the compound.

A compound of the invention can be used, for example, to induce apoptosis, cell cycle arrest, or senescence in a cell. In some embodiments, the cell is a cancer cell. In some embodiments, the cell carries a mutation in p53.

Compounds of the Invention.

In some embodiments, a compound of the disclosure comprises a substituted heterocyclyl group, wherein the compound binds a mutant p53 protein and increases wild-type p53 activity of the mutant protein. In some embodiments, a compound of the disclosure comprises a heterocyclyl group comprising a halo substituent, wherein the compound binds a mutant p53 protein and increases wild-type p53 activity of the mutant protein. In some embodiments, the compound further comprises an indole group. In some embodiments, the indole group has a 1,1,1,-trifluoro-ethyl substituent at a 1-position of the indole group.

In some embodiments, the indole group has a propargyl substituent at a 2-position of the indole group. In some embodiments, the propargyl substituent is attached to the indole group via an sp carbon atom of the propargyl substituent. In some embodiments, the propargyl substituent is attached to a nitrogen atom of an aniline group via a methylene group of the propargyl substituent. In some embodiments, the indole group comprises an amino substituent at a 4-position of the indole group. In some embodiments, the amino substituent is attached to the heterocyclyl group. In some embodiments, the heterocyclyl group is a piperidine group. In some embodiments, the halo substituent is a fluoro group. In some embodiments, the halo substituent is a chloro group. In some embodiments, the compound has oral bioavailability that is at least about 50% greater than that of an analogous compound that lacks the halo substituent on the heterocyclyl group.

Non-limiting examples of compounds of the invention include compounds of any of the following formulae:

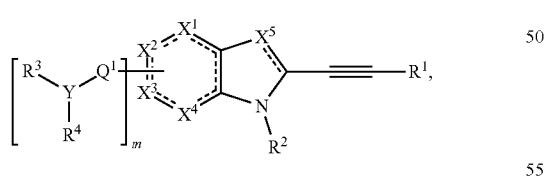

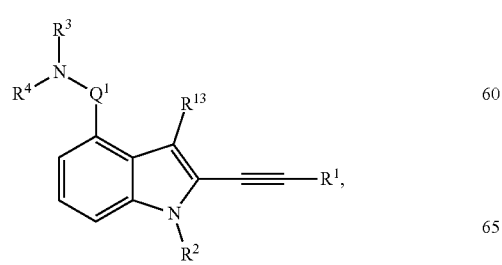

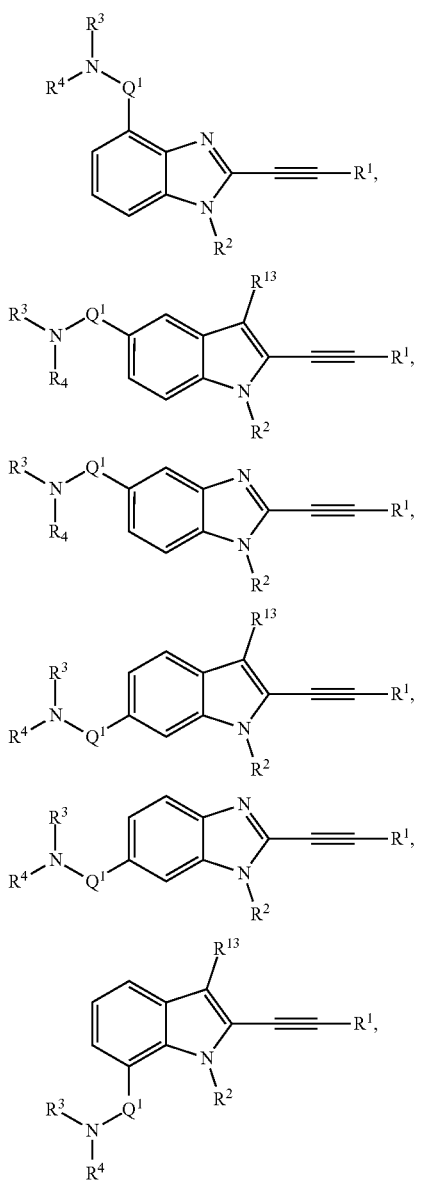

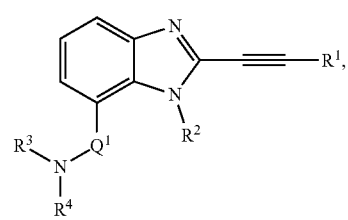

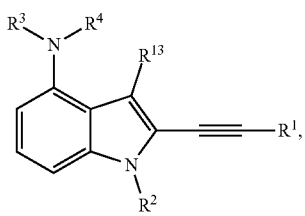

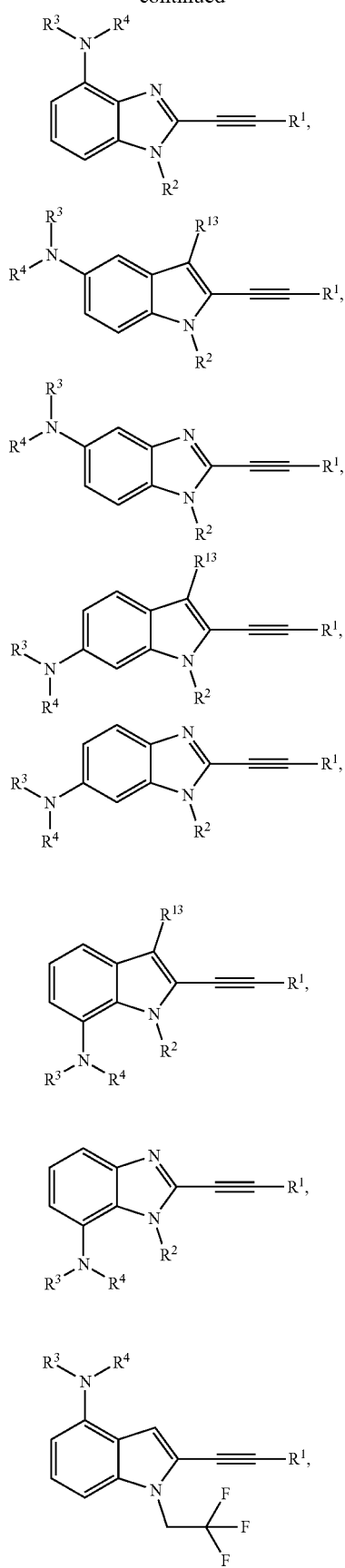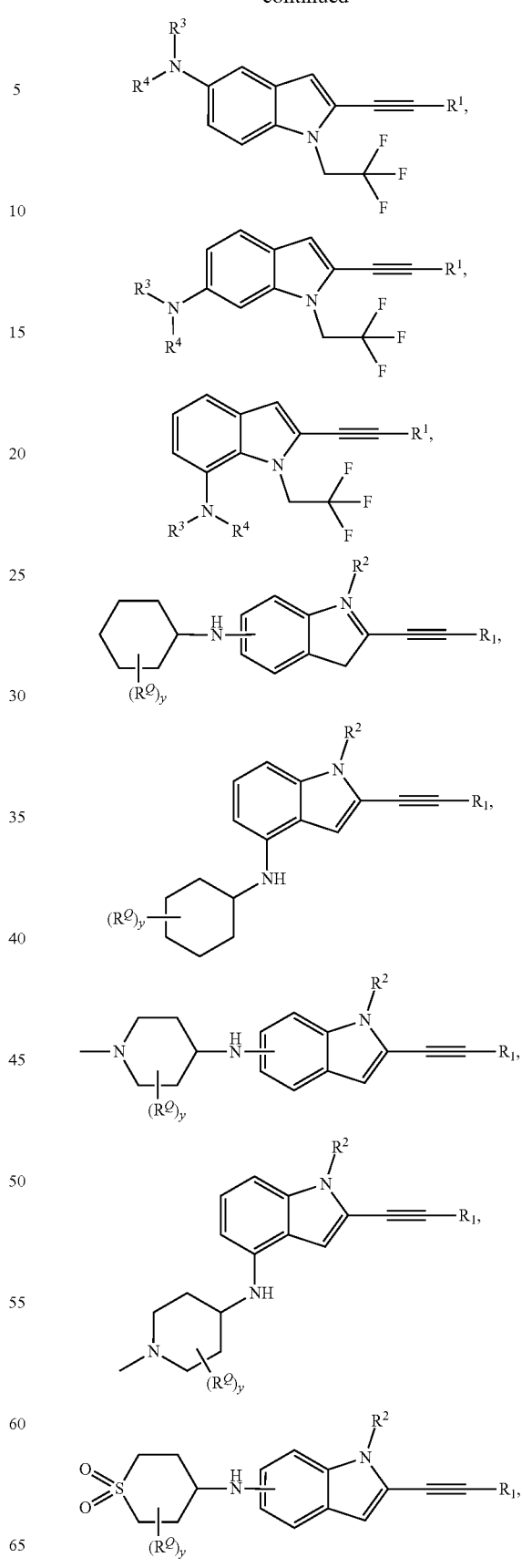

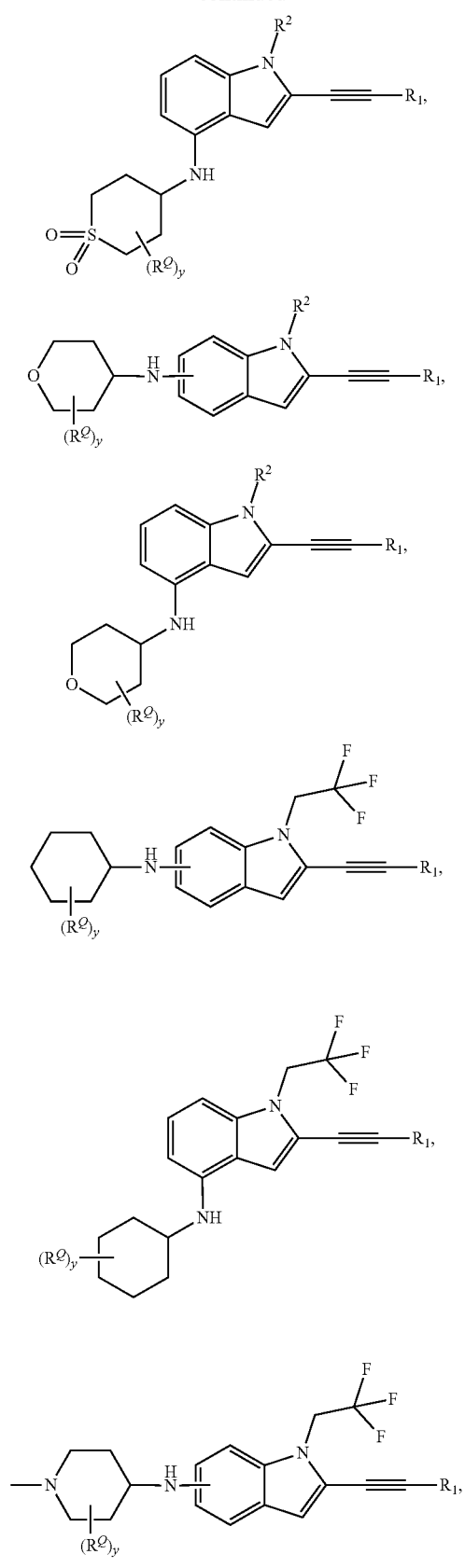
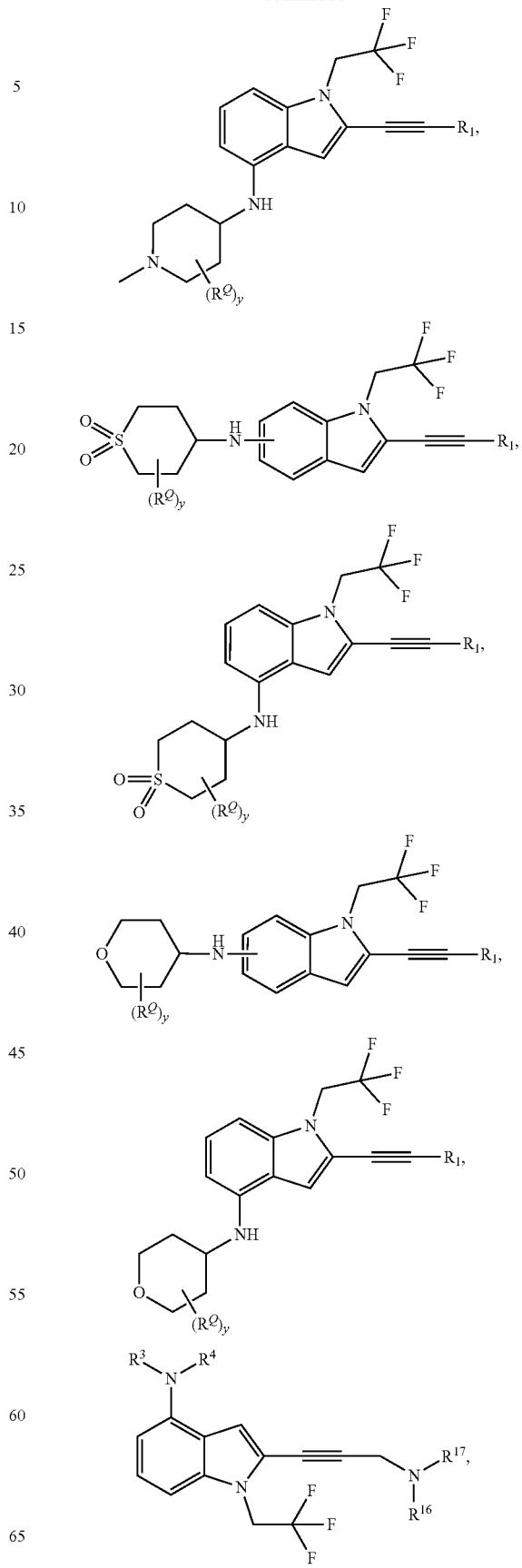

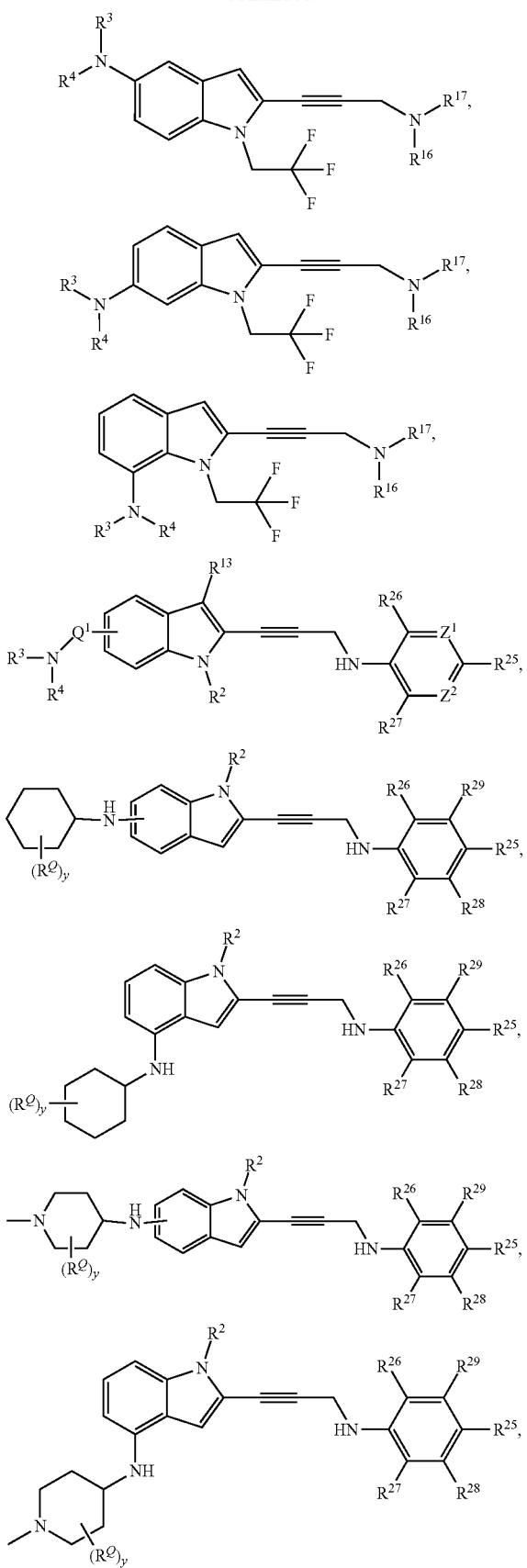
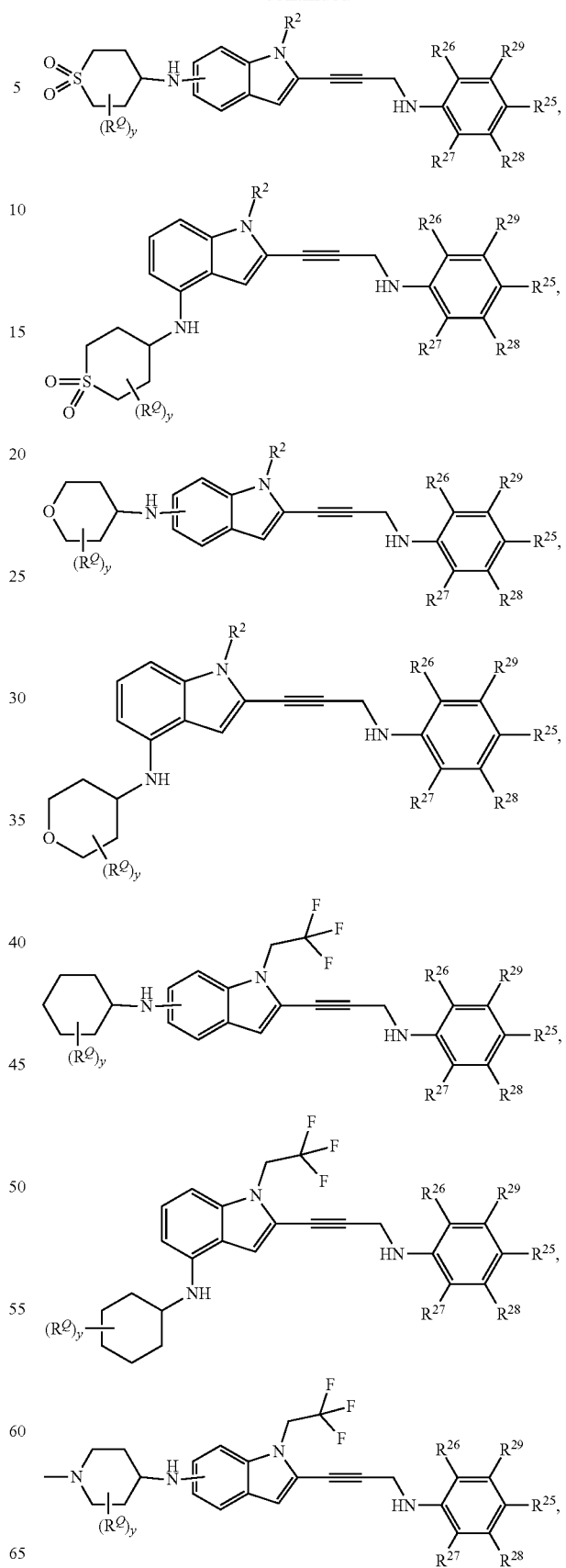

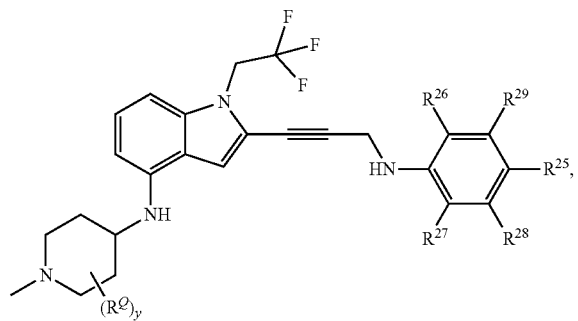
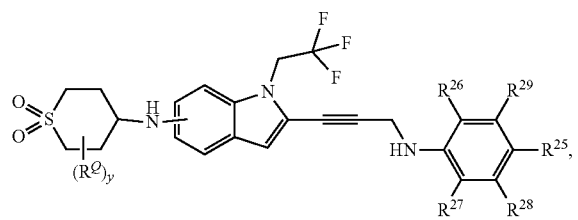
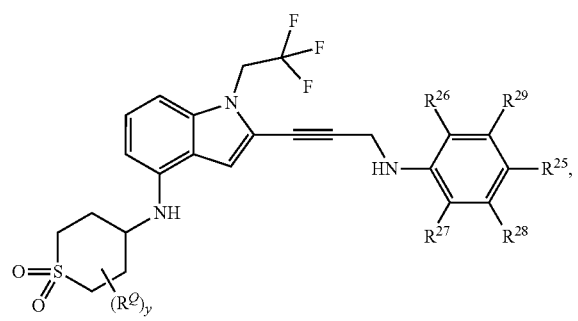
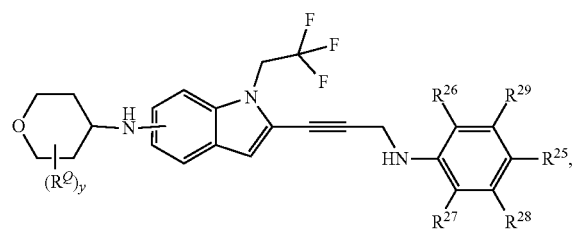
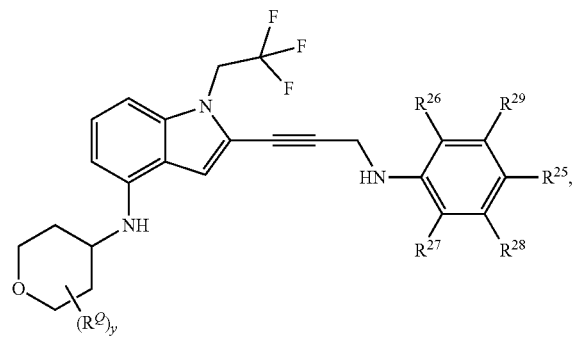
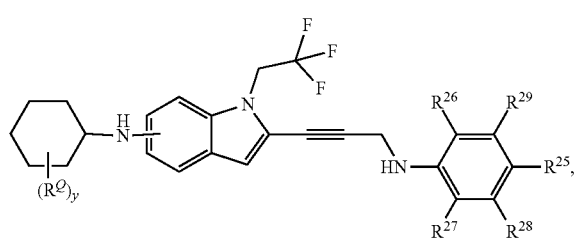
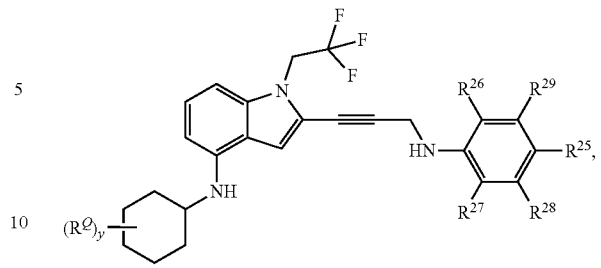
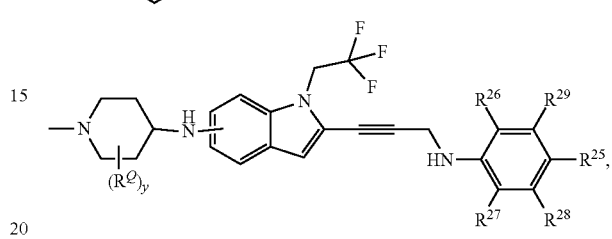
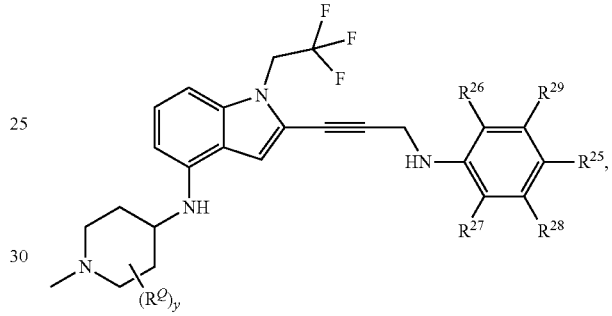
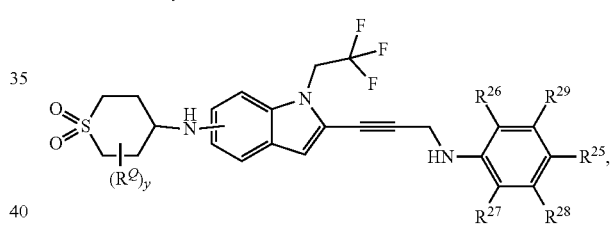
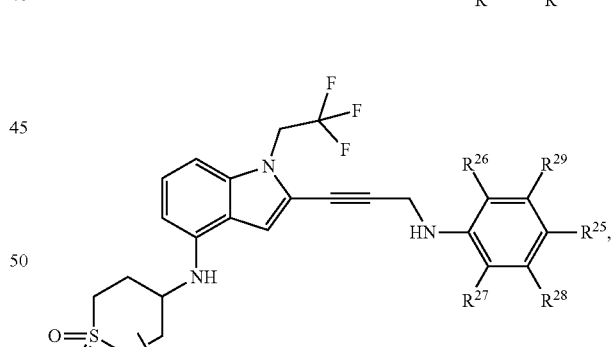
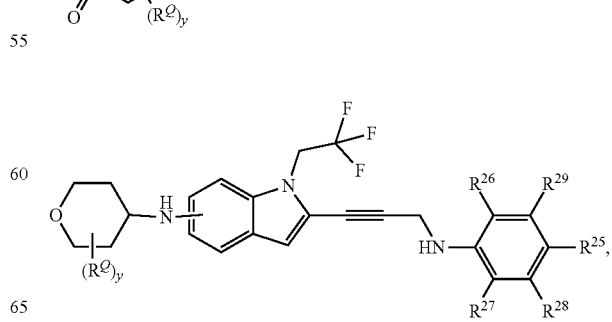

-continued

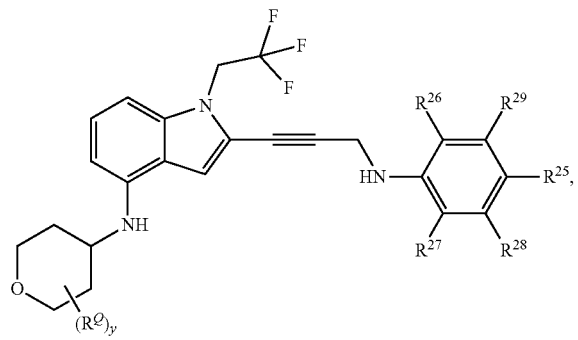

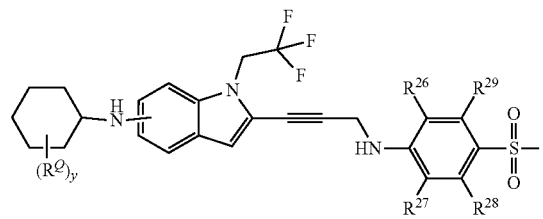

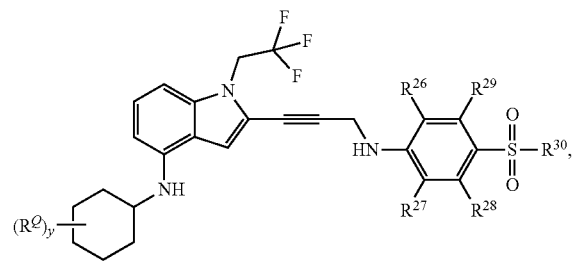

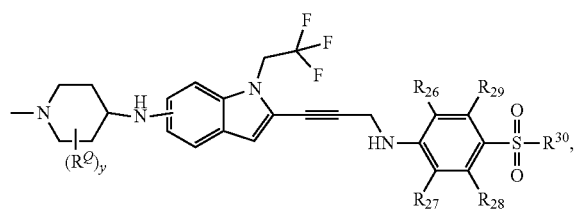

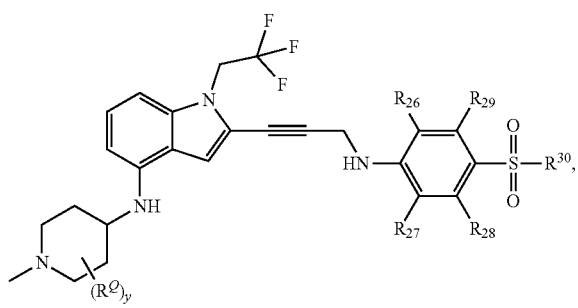

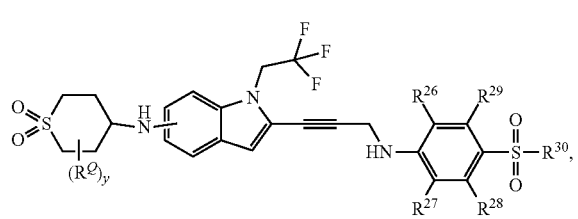

-continued

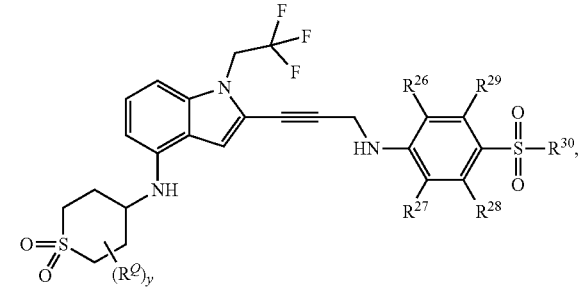

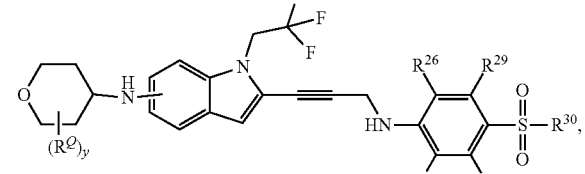

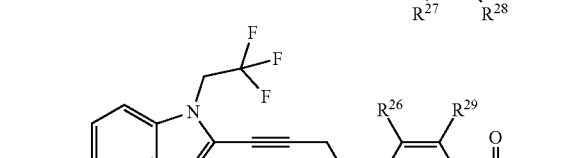

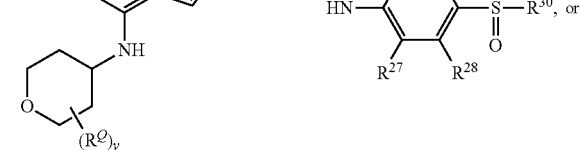

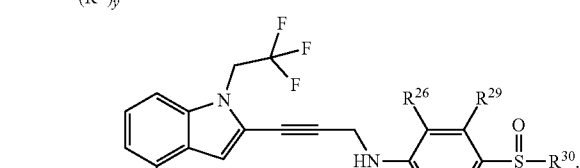

In some embodiments, the compound is of the formula:

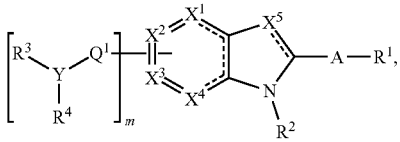

wherein:
- each ------- is independently a single bond or a double bond;
- $X^1$ is $CR^5$, $CR^5R^6$, N, $NR^5$, O, S, C=O, C=S, or a carbon atom connected to $Q^1$;
- $X^2$ is $CR^7$, $CR^7R^8$, N, $NR^7$, O, S, C=O, C=S, or a carbon atom connected to $Q^1$;
- $X^3$ is $CR^9$, $CR^9R^{10}$, N, $NR^9$, O, S, C=O, C=S, or a carbon atom connected to $Q^1$;
- $X^4$ is $CR^{11}$, $CR^{11}R^{12}$, N, $NR^{11}$, O, S, C=O, C=S, or a carbon atom connected to $Q^1$;
- $X^5$ is $CR^{13}$, N, or $NR^{13}$;

wherein at least one of $X^1$, $X^2$, $X^3$, and $X^4$ is a carbon atom connected to $Q^1$;

A is a linking group;

$Q^1$ is C=O, C=S, C=CR$^{14}$R$^{15}$, C=NR$^{14}$, alkylene, alkenylene, or alkynylene, each of which is independently substituted or unsubstituted, or a bond;

m is 1, 2, 3, or 4;

Y is N, O, or absent;

$R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, A is alkylene, alkenylene, or alkynylene, each of which is substituted or unsubstituted. In some embodiments, A is alkylene. In some embodiments, A is alkenylene. In some embodiments, A is alkynylene.

In some embodiments, A is aryl, heteroaryl, or heterocyclyl, each of which is substituted or unsubstituted. In some embodiments, A is substituted aryl. In some embodiments, A is substituted heteroaryl. In some embodiments, A is substituted heterocyclyl.

In some embodiments, $R^1$ is alkyl, alkenyl, —C(O)R$^{16}$, —C(O)OR$^{16}$, or —C(O)NR$^{16}$R$^{17}$, each of which is unsubstituted or substituted. In some embodiments, $R^1$ is substituted alkyl. In some embodiments, $R^1$ is alkyl substituted with NR$^{16}$R$^{17}$.

In some embodiments, the compound of the formula is:

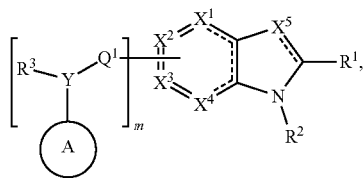

each ——— is independently a single bond or a double bond;

$X^1$ is CR$^5$, CR$^5$R$^6$, N, NR$^5$, O, S, C=O, C=S, or a carbon atom connected to $Q^1$;

$X^2$ is CR$^7$, CR$^7$R$^8$, N, NR$^7$, O, S, C=O, C=S, or a carbon atom connected to $Q^1$;

$X^3$ is CR$^9$, CR$^9$R$^{10}$, N, NR$^9$, O, S, C=O, C=S, or a carbon atom connected to $Q^1$;

$X^4$ is CR$^{11}$, CR$^{11}$R$^{12}$, N, NR$^{11}$, O, S, C=O, C=S, or a carbon atom connected to $Q^1$;

$X^5$ is CR$^{13}$, N, or NR$^{13}$;

wherein at least one of $X^1$, $X^2$, $X^3$, and $X^4$ is a carbon atom connected to $Q^1$;

$Q^1$ is C=O, C=S, C=CR$^{14}$R$^{15}$, C=NR$^{14}$, alkylene, alkenylene, or alkynylene, each of which is independently substituted or unsubstituted, or a bond;

m is 1, 2, 3, or 4;

Y is N, O, or absent;

ring A is a cyclic group;

$R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;

$R^3$ is —C(O)R$^{19}$, —C(O)OR$^{19}$, —C(O)NR$^{19}$R$^{20}$, —SOR$^{19}$, —SO$_2$R$^{19}$, alkyl, alkylene, alkenyl, alkenylene, alkynyl, aryl, heteroaryl, or heterocyclyl, each of which is independently substituted or unsubstituted, or hydrogen, or $R^3$ and A together with the nitrogen atom to which $R^3$ and A are bound form a ring, wherein the ring is substituted or unsubstituted, or $R^3$ is absent, each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, a compound of the invention is a compound of the formula

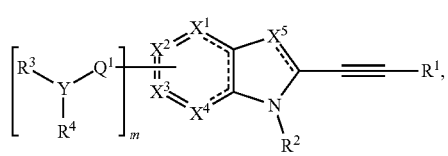

wherein:

each ——— is independently a single bond or a double bond;

$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;
each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

In some embodiments, the compound is of the formula:

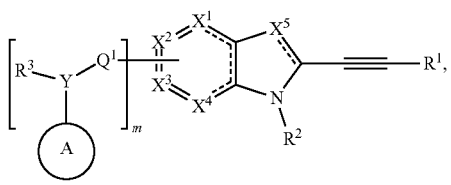

wherein:
each ------- is independently a single bond or a double bond;

$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
ring A is a cyclic group;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;
$R^3$ is —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and A together with the nitrogen atom to which $R^3$ and A are bound form a ring, wherein the ring is substituted or unsubstituted, or $R^3$ is absent,
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

In some embodiments, the pattern of dashed bonds is chosen to provide an aromatic system, for example, an indole, an indolene, a pyrrolopyridine, a pyrrolopyrimidine, or a pyrrolopyrazine.

In some embodiments, $X^1$ is $CR^5$, $CR^5R^6$, or a carbon atom connected to $Q^1$. In some embodiments, $X^2$ is $CR^7$, $CR^7R^8$, or a carbon atom connected to $Q^1$. In some embodiments, $X^3$ is $CR^9$, $CR^9R^{10}$, or a carbon atom connected to $Q^1$. In some embodiments, $X^4$ is $CR^{11}$, $CR^{11}R^{12}$, or a carbon atom connected to $Q^1$. In some embodiments, $X^5$ is $CR^{13}$, N, or $NR^{13}$. In some embodiments, $X^1$ is a carbon atom connected to $Q^1$. In some embodiments, $X^2$ is a carbon atom connected to $Q^1$. In some embodiments, $X^3$ is a carbon atom connected to $Q^1$. In some embodiments, $X^4$ is a carbon atom connected to $Q^1$. In some embodiments, $X^5$ is N.

In some embodiments, $Q^1$ is a bond. In some embodiments, $Q^1$ is $C_1$-alkylene. In some embodiments, m is 1. In some embodiments, m is 2. In some embodiments, m is 3. In some embodiments, m is 4.

In some embodiments, $R^1$ is alkyl, alkenyl, —C(O)$R^{16}$, —C(O)O$R^{16}$, or —C(O)N$R^{16}R^{17}$, each of which is unsubstituted or substituted. In some embodiments, $R^1$ is substituted alkyl. In some embodiments, $R^1$ is alkyl substituted with N$R^{16}R^{17}$.

In some embodiments, ring A is aryl, heteroaryl, or heterocyclyl, each of which is substituted or unsubstituted. In some embodiments, ring A is substituted aryl. In some embodiments, ring A is aryl substituted with fluoro-. In some embodiments, ring A is aryl substituted with chloro-. In some embodiments, ring A is substituted heteroaryl. In some embodiments, ring A is heteroaryl substituted with fluoro-. In some embodiments, ring A is heteroaryl substituted with chloro-. In some embodiments, ring A is substituted heterocyclyl. In some embodiments, ring A is heterocyclyl substituted with fluoro-. In some embodiments, A is heterocyclyl substituted with chloro-.

In some embodiments, ring A is piperidinyl, piperazinyl, tetahydropyranyl, morpholinyl, or pyrrolidinyl, each of which is independently substituted or unsubstituted. In some embodiments, ring A is piperidinyl, piperazinyl, tetahydropyranyl, morpholinyl, or pyrrolidinyl, each of which is independently substituted with at least halo-. In some embodiments, ring A is piperidinyl substituted with halo-. In some embodiments, ring A is methylpiperidinyl substituted with halo-. In some embodiments, ring A is 3-fluoro-1-methylpiperidinyl. In some embodiments, ring A is 3-fluoro-1-(2-hydroxy-3-methoxypropyl)piperidinyl. In some embodiments, ring A is tetrahydropyranyl substituted with at least halo-.

In some embodiments, each $R^{16}$ and $R^{17}$ is independently alkyl, alkenyl, aryl, heteroaryl, heterocyclyl, each of which is independently substituted or unsubstituted, or hydrogen. In some embodiments, $R^{16}$ is hydrogen or alkyl. In some embodiments, $R^{17}$ is aryl, heteroaryl, or heterocyclyl, each of which is independently substituted or unsubstituted. In some embodiments, $R^{17}$ is substituted aryl. In some embodiments, $R^{17}$ is substituted phenyl. In some embodiments, $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted. In some embodiments, $R^{17}$ is phenyl substituted with methoxy. In some embodiments, $R^{17}$ is phenyl substituted with a substituted sulfoxide group. In some embodiments, $R^{17}$ is phenyl substituted with a carboxyl group. In some embodiments, $R^{17}$ is phenyl substituted with a substituted amide group.

In some embodiments, the compound is of the formula:

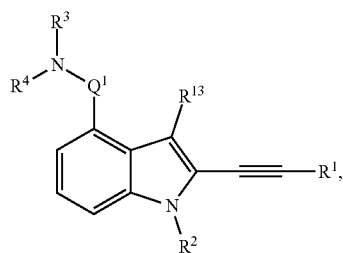

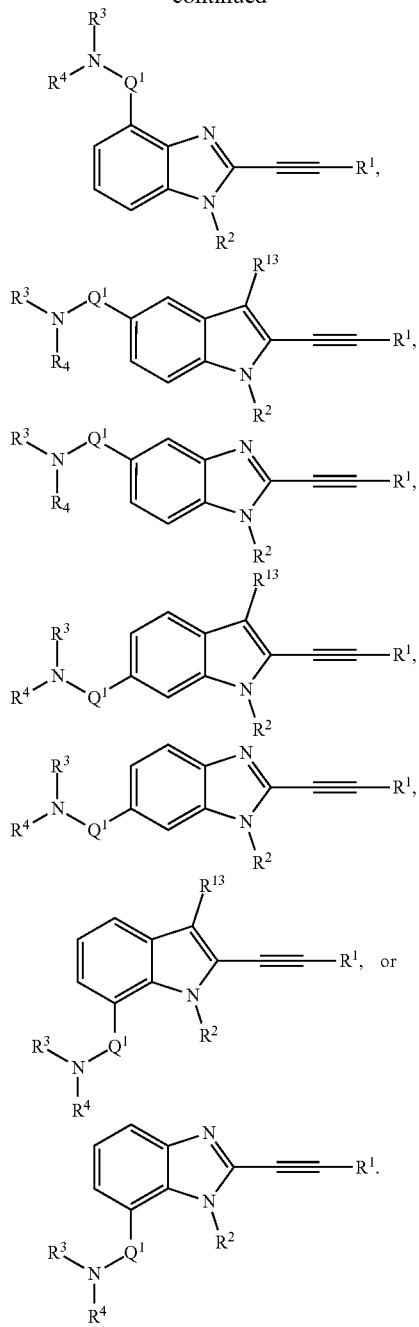

In some embodiments, $Q^1$ is C=O, C=S, C=C$R^{14}R^{15}$, C=N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene or a bond. In some embodiments, $Q^1$ is $C_1$-alkylene. In some embodiments, $Q^1$ is a bond.

In some embodiments, Y is N. In some embodiments, Y is O. In some embodiments, Y is absent.

In some embodiments, $R^2$ is hydrogen or alkyl. In some embodiments, $R^2$ is alkyl. In some embodiments, $R^2$ is substituted $C_1$-$C_5$-alkyl. In some embodiments, $R^2$ is trifluoroethyl. In some embodiments, $R^2$ is cycloalkyl. In some embodiments, $R^2$ is cyclopropyl.

In some embodiments, $R^{13}$ is alkyl, alkenyl, hydrogen, or halogen. In some embodiments, $R^{13}$ is hydrogen.

In some embodiments, $R^2$ is $C_1$-$C_5$-alkyl, and $R^{13}$ is $C_1$-$C_5$-alkyl. In some embodiments, $R^2$ is $C_1$-$C_5$-alkyl, and $R^{13}$ is hydrogen. In some embodiments, $R^2$ is substituted $C_1$-$C_5$-alkylene. In some embodiments, $R^2$ is methyl, ethyl, propyl, iso-propyl, butyl, or tert-butyl, each of which is substituted or unsubstituted. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, the compound is of the formula:

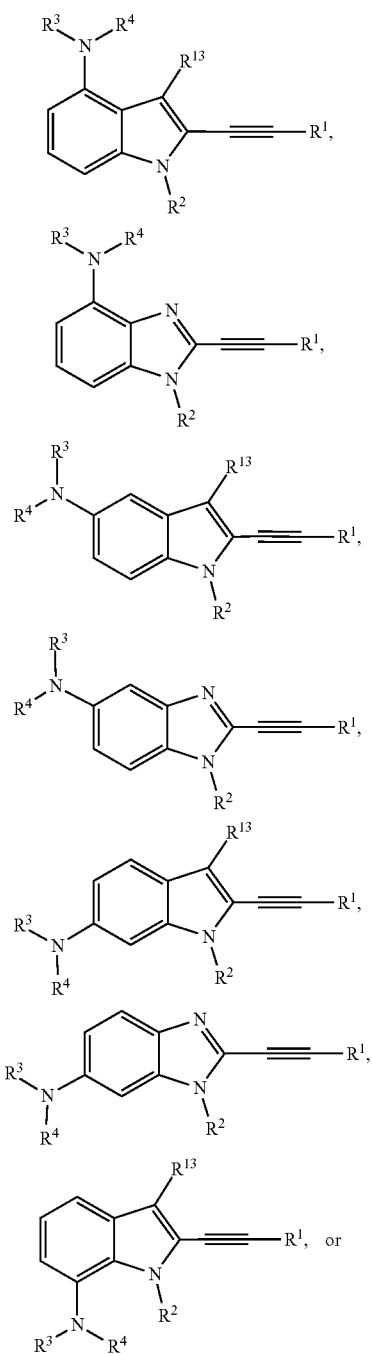

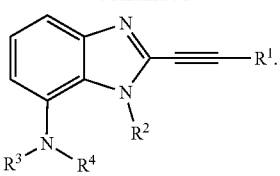

In some embodiments, the compound is of the formula:

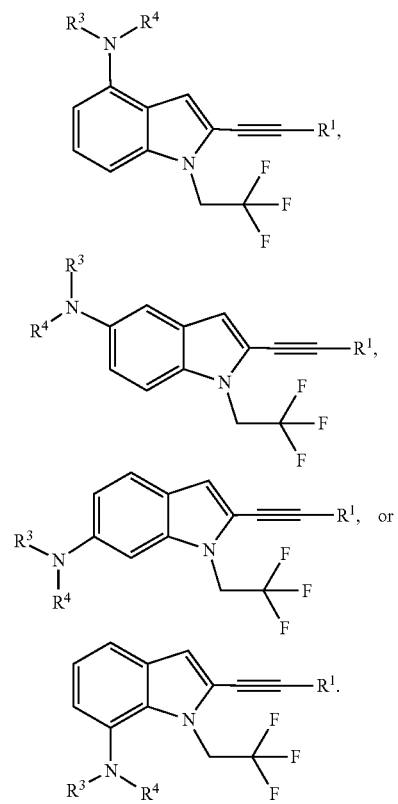

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted. In some embodiments, each $R^3$ and $R^4$ is independently substituted or unsubstituted $C_1$-$C_6$-alkylene. In some embodiments, $R^3$ is H, and $R^4$ is substituted or unsubstituted $C_1$-$C_4$ alkylene. In some embodiments, $R^3$ is H, and $R^4$ is substituted or unsubstituted heterocyclyl. In some embodiments, $R^3$ is H, and $R^4$ is substituted or unsubstituted piperidinyl. In some embodiments, $R^3$ is H, and $R^4$ is substituted or unsubstituted cycloalkyl. In some embodiments, $R^3$ is H, and $R^4$ is cycloalkyl substituted with an amino group. In some embodiments, $R^3$ is H, and $R^4$ is substituted or unsubstituted cyclobutyl. In some embodiments, $R^3$ is H, and $R^4$ is cyclobutyl substituted with an amino group. In some embodiments, $R^3$ is H, and $R^4$ is substituted or unsubstituted cyclohexyl. In some embodiments, $R^3$ is H, and $R^4$ is cyclohexyl substituted with an amino group.

In some embodiments, the compound is of the formula:

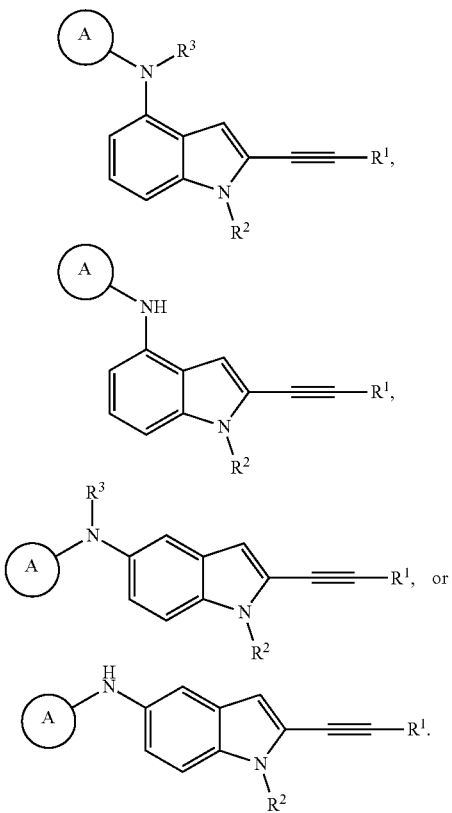

In some embodiments, the compound is of the formula:

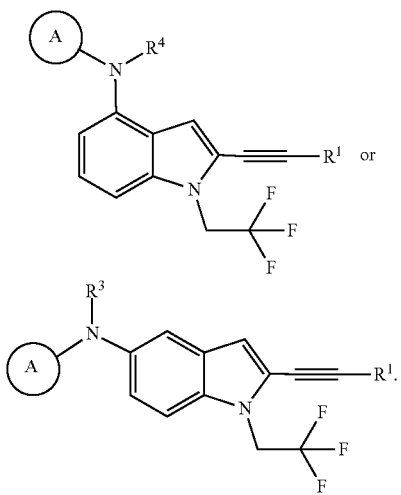

$R^1$ can be a group substituted with one or more substituents selected from a hydroxyl group, sulfhydryl group, halogens, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group. In some embodiments, $R^1$ is alkyl, alkenyl, $-C(O)R^{16}$, $-C(O)OR^{16}$, or $-C(O)NR^{16}R^{17}$.

In some embodiments, $R^1$ is substituted or unsubstituted $C_1$-$C_3$ alkyl. In some embodiments, $R^1$ is $C_1$-$C_3$-alkyl substituted with an amine group. In some embodiments, $R^1$ is $C_1$-alkyl substituted with $NR^{16}R^{17}$. In some embodiments, each $R^{16}$ and $R^{17}$ is independently aryl, heteroaryl, or heterocyclyl, each of which is independently substituted or unsubstituted, or hydrogen. In some embodiments, $R^{16}$ is H, and $R^{17}$ is substituted aryl. In some embodiments, $R^{16}$ is H, and $R^{17}$ is substituted phenyl. In some embodiments, $R^{16}$ is H, and $R^{17}$ is phenyl substituted with alkyl, alkoxy, halo, sulfonamide, a sulfone, or a carboxy group. In some embodiments, $R^{16}$ is H, and $R^{17}$ is substituted heteroaryl. In some embodiments, $R^{16}$ is H, and $R^{17}$ is substituted heterocyclyl.

In some embodiments, $Q^1$ is C=O, C=S, C=$CR^{14}R^{15}$, C=$NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is $C_1$-alkylene, $R^{16}$ is aryl, and $R^{17}$ is alkyl. In some embodiments, $Q^1$ is $C_1$-alkylene, $R^{16}$ is aryl, and $R^{17}$ is hydrogen. In some embodiments, $Q^1$ is $C_1$-alkylene, $R^{16}$ is heteroaryl, and $R^{17}$ is alkyl. In some embodiments, $Q^1$ is $C_1$-alkylene, $R^{16}$ is heteroaryl, and $R^{17}$ is hydrogen. In some embodiments, $Q^1$ is $C_1$-alkylene, $R^{16}$ is substituted heteroaryl, and $R^{17}$ is hydrogen. In some embodiments, $Q^1$ is $C_1$-alkylene, $R^{16}$ is substituted alkyl, and $R^{17}$ is hydrogen. In some embodiments, $R^{17}$ is aryl, heteroaryl, or heterocyclyl, each of which is independently substituted or unsubstituted with halogen, alkyl, or hydroxyl. In some embodiments, $R^{16}$ is hydrogen, and $R^{17}$ is aryl or heteroaryl, substituted or unsubstituted with halogen or alkyl. In some embodiments, $R^{16}$ is alkyl, and $R^{17}$ is heteroaryl substituted with halogen or alkyl. In some embodiments, $R^{17}$ is aryl, heteroaryl, or heterocyclyl, each of which is independently substituted or unsubstituted with alkyl. In some embodiments, $R^{17}$ is aryl or heteroaryl, each of which is independently substituted with alkyl, wherein the alkyl is optionally substituted with fluorine, chlorine, bromine, iodine, or cyano.

In some embodiments, $R^2$ is alkyl, and $R^{13}$ is alkyl, each of which is substituted or substituted. In some embodiments, $R^2$ is hydrogen, and $R^{13}$ is unsubstituted or substituted alkyl. In some embodiments, $R^2$ is methyl, ethyl, propyl, iso-propyl, butyl, or tert-butyl, each of which is substituted or unsubstituted. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is hydrogen, and $R^{13}$ is alkyl. In some embodiments, $R^2$ is trifluoroethyl, and $R^{13}$ is hydrogen.

In some embodiments, $R^3$ is $-C(O)R^{19}$, $-C(O)OR^{19}$, alkyl, alkenyl, alkynyl, aryl, heteroaryl, or heterocyclyl, each of which is independently substituted or unsubstituted, or hydrogen, and $R^4$ is $-C(O)R^{19}$, $-C(O)OR^{19}$, alkyl, alkenyl, alkynyl, aryl, heteroaryl, or heterocyclyl, each of which is independently substituted or unsubstituted, or hydrogen. In some embodiments, $R^3$ is alkyl, alkenyl, alkynyl, aryl, heteroaryl, or heterocyclyl, each of which is independently substituted or unsubstituted, or hydrogen. In some embodiments, $R^3$ is substituted alkyl. In some embodiments, $R^3$ is H.

In some embodiments, R³ is H, and R⁴ is unsubstituted or substituted alkyl. In some embodiments, R³ is H, and R⁴ is unsubstituted or substituted cycloalkyl. In some embodiments, R³ is H, and R⁴ is substituted cyclohexyl. In some embodiments, R³ is H, and R⁴ is substituted cyclobutyl.

In some embodiments, at least one of R³ and R⁴ is alkyl, alkylene, alkenyl, alkenylene, alkynyl, aryl, heteroaryl, or heterocyclyl, each of which is substituted at least with halo-. In some embodiments, R³ is hydrogen and R⁴ is a ring A. In some embodiments, R⁴ or ring A is cycloalkyl, aryl, heteroaryl, or heterocyclyl, each of which is independently substituted or unsubstituted. In some embodiments, R⁴ or ring A is substituted or unsubstituted aryl. In some embodiments, R⁴ or ring A is substituted or unsubstituted phenyl. In some embodiments, R⁴ or ring A is substituted or unsubstituted cycloalkyl. In some embodiments, R⁴ or ring A is substituted or unsubstituted cyclopropyl. In some embodiments, R⁴ or ring A is substituted cyclopropyl. In some embodiments, R⁴ or ring A is substituted cyclohexyl. In some embodiments, R⁴ or ring A is cyclohexyl substituted with an amino group.

In some embodiments, R³ is H, and R⁴ or ring A is unsubstituted or substituted heterocyclyl. In some embodiments, R⁴ or ring A is heterocyclyl. In some embodiments, R⁴ or ring A is piperidinyl, piperazinyl, tetahydropyranyl, morpholinyl, or pyrrobdinyl, each of which is independently substituted or unsubstituted. In some embodiments, R³ is H, and R⁴ or ring A is substituted piperidinyl. In some embodiments, R³ is H, and R⁴ or ring A is piperidine substituted with alkyl, carboxy, heterocyclyl, or an amide group. In some embodiments, R³ is H, and R⁴ or ring A is unsubstituted or substituted methyl piperidinyl. In some embodiments, R³ is H, and R⁴ or ring A is 3-fluoro-1-methylpiperidinyl. In some embodiments, R³ is H, and R⁴ or ring A is piperidinyl substituted with methoxypropanol. In some embodiments, R³ is H, and R⁴ or ring A is 3-fluoro-1-(2-hydroxy-3-methoxypropyl)piperidinyl. In some embodiments, R³ is H, and R⁴ or ring A is unsubstituted or substituted tetrahydropyranyl. In some embodiments, R³ is H, and R⁴ or ring A is unsubstituted tetrahydropyranyl. In some embodiments, R³ is H, and R⁴ or ring A is tetrahydropyranyl substituted with alkyl. In some embodiments, R³ is H, and R⁴ or ring A is tetrahydrothiopyran-1,1-diooxide.

In some embodiments, R⁴ or ring A is cycloalkyl, aryl, heteroaryl, or heterocyclyl, each of which is substituted at least with halo-. In some embodiments, R⁴ or ring A is C₄-C₆-cycloalkyl substituted with at least halo-. In some embodiments, R⁴ or ring A is cyclohexyl substituted with at least halo-. In some embodiments, R⁴ or ring A is aryl substituted with at least halo-. In some embodiments, R⁴ or ring A is phenyl substituted with at least halo-. In some embodiments, R⁴ or ring A is aryl substituted with fluoro-. In some embodiments, R⁴ or ring A is phenyl substituted with fluoro-. In some embodiments, R⁴ or ring A is aryl substituted with chloro-. In some embodiments, R⁴ or ring A is phenyl substituted with chloro-. In some embodiments, R⁴ or ring A is heteroaryl substituted with at least halo-. In some embodiments, R⁴ or ring A is heteroaryl substituted with fluoro-. In some embodiments, R⁴ or ring A is heteroaryl substituted with chloro-. In some embodiments, R⁴ or ring A is C₄-C₆-heterocyclyl substituted with at least halo-. In some embodiments, R⁴ or ring A is heterocyclyl substituted with fluoro-. In some embodiments, R⁴ or ring A is heterocyclyl substituted with chloro-.

In some embodiments, R⁴ or ring A is piperidinyl, piperazinyl, tetahydropyranyl, morpholinyl, or pyrrolidinyl, each of which is independently substituted with at least halo-. In some embodiments, R⁴ or ring A is piperidinyl substituted with halo-. In some embodiments, R⁴ or ring A is methylpiperidinyl substituted with halo-. In some embodiments, R⁴ or ring A is 3-fluoro-1-methylpiperidinyl. In some embodiments, R⁴ or ring A is 3-fluoro-1-(2-hydroxy-3-methoxypropyl)piperidinyl. In some embodiments, R⁴ or ring A is tetrahydropyranyl substituted with at least halo-.

In some embodiments, R⁴ or Ring A is a ring that is:

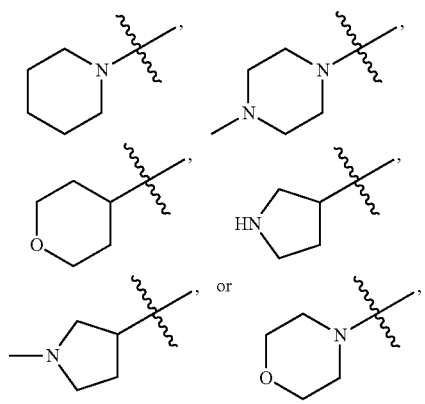

wherein the ring is substituted or unsubstituted. In some embodiments, the ring is substituted with halo-. In some embodiments, the ring is substituted with fluoro. In some embodiments, R³ is H, and R⁴ is a ring that is

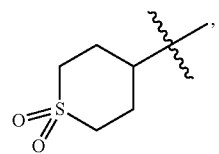 [SMILES: *C1CCS(=O)(=O)CC1]

wherein the ring is substituted or unsubstituted. In some embodiments, the ring is substituted with halo-. In some embodiments, the ring is substituted with fluoro. In some embodiments, R³ is H, and R⁴ is a ring that is

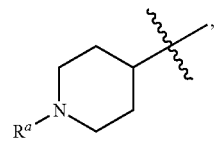

wherein the ring is substituted or unsubstituted. In some embodiments, R$^a$ is alkylene. In some embodiments, R$^a$ is methyl. In some embodiments, the ring is substituted with halo. In some embodiments, the ring is substituted with fluoro. In some embodiments, R³ is H, and R⁴ is a ring that is

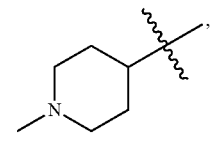 [SMILES: *C1CCN(C)CC1]

wherein the ring is substituted or unsubstituted. In some embodiments, the ring is substituted with halo. In some embodiments, the ring is substituted with fluoro. In some embodiments, R³ is H, and R⁴ is a ring that is

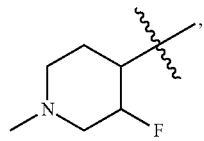 [SMILES: *C1CCN(C)CC1F]

wherein the ring is substituted or unsubstituted.

In some embodiments, the R⁴ or ring A is substituted with one or more substituents selected from a hydroxyl group, sulfhydryl group, halogens, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, R³ and R⁴ together with the nitrogen atom to which R³ and R⁴ are bound form a ring, wherein the ring is substituted or unsubstituted. In some embodiments, R³ and R⁴ together with the nitrogen atom to which R³ and R⁴ are bound form a substituted heterocycle. In some embodiments, R³ and R⁴ together with the nitrogen atom to which R³ and R⁴ are bound form a heterocycle substituted with a hydroxyl group, halogen, amino group, or alkyl group. In some embodiments, R³ and R⁴ together with the nitrogen atom to which R³ and R⁴ are bound form a heterocycle, wherein the heterocycle is substituted by a substituted or unsubstituted heterocycle.

In some embodiments, R³ and R⁴ together with the nitrogen atom to which R³ and R⁴ are bound form a ring of a following formula:

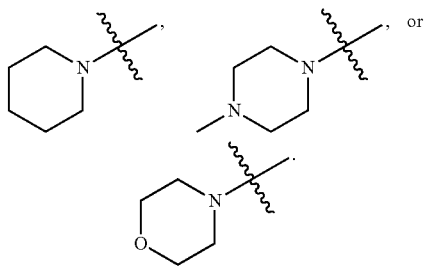

In some embodiments, the compound is of the formula:

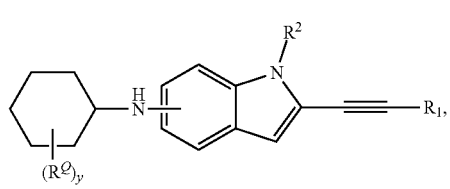

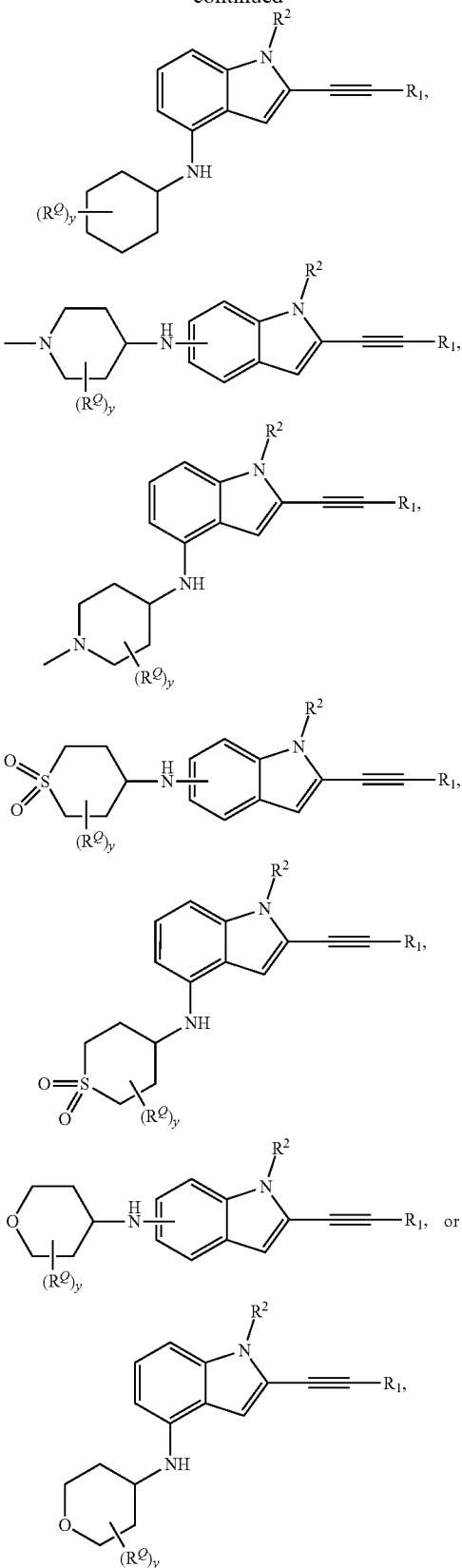

R¹ is —C(O)R¹⁶, —C(O)OR¹⁶, —C(O)NR¹⁶R¹⁷, —OR¹⁶, —SR¹⁶, —NR¹⁶R¹⁷, —NR¹⁶C(O)R¹⁶, —OC (O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;

each R$^Q$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

y is 0, 1, 2, 3, or 4;

each R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, R$^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, or heterocyclyl, each of which is independently substituted or unsubstituted, or hydrogen. In some embodiments, R$^1$ is alkyl, alkylene, alkoxy, —NR$^{21}$R$^{22}$, or aryl, each of which is independently substituted or unsubstituted; halo or hydrogen.

In some embodiments, R$^1$ is substituted C$_1$-C$_3$-alkyl. In some embodiments, R$^1$ is C$_1$-C$_3$-alkyl substituted with NR$^{16}$R$^{17}$. In some embodiments, R$^1$ is methyl substituted with NR$^{16}$R$^{17}$, wherein each R$^{16}$ and R$^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, R$^1$ is methyl substituted with NR$^{16}$R$^{17}$, wherein R$^{16}$ is hydrogen, and R$^{17}$ is a substituted carboxyl group. In some embodiments, R$^1$ is methyl substituted with NR$^{16}$R$^{17}$, wherein R$^{16}$ is hydrogen, and R$^{17}$ is substituted aryl. In some embodiments, R$^1$ is methyl substituted with NR$^{16}$R$^{17}$, wherein R$^{16}$ is hydrogen, and R$^{17}$ is substituted phenyl. In some embodiments, R$^1$ is methyl substituted with NR$^{16}$R$^{17}$, wherein R$^{16}$ is hydrogen, and R$^{17}$ is phenyl, substituted with a sulfoxide group, carboxyl group, amide group, amino group, alkyl, alkoxy, hydroxy, halo, cyano, or heterocyclyl, each of which is independently substituted or unsubstituted. In some embodiments, R$^{17}$ is phenyl substituted with methoxy. In some embodiments, R$^{17}$ is phenyl substituted with a substituted sulfoxide group. In some embodiments, R$^{17}$ is phenyl substituted with a carboxyl group. In some embodiments, R$^{17}$ is a substituted amide group. In some embodiments, R$^{17}$ is substituted with methoxy and sulfonamide.

In some embodiments, R$^2$ is hydrogen or alkyl. In some embodiments, R$^2$ is substituted C$_1$-C$_5$-alkylene. In some embodiments, R$^2$ is trifluoroethyl. In some embodiments, R$^{13}$ is alkyl, alkenyl, hydrogen, or halogen. In some embodiments, R$^2$ is alkyl, and R$^{13}$ is alkyl. In some embodiments, R$^2$ is hydrogen, and R$^{13}$ is alkyl. In some embodiments, R$^2$ is methyl, ethyl, propyl, iso-propyl, butyl, or tert-butyl. In some embodiments, R$^{13}$ is methyl, ethyl, propyl, iso-propyl, butyl or tert-butyl. In some embodiments, R$^2$ is hydrogen, and R$^{13}$ is hydrogen.

In some embodiments, the compound is of the formula:

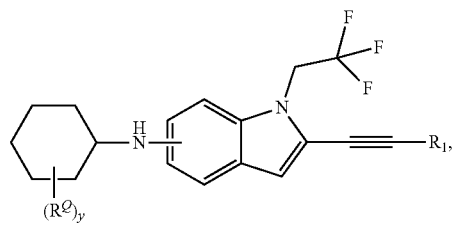

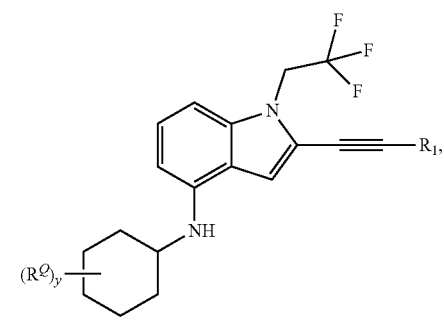

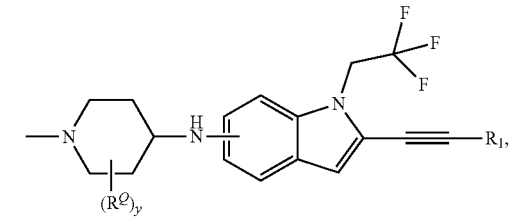

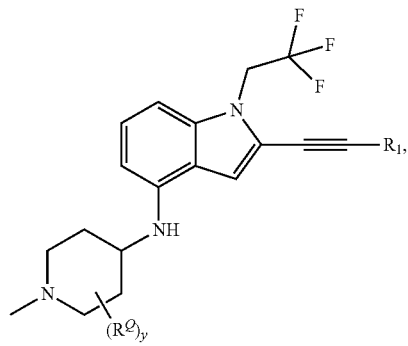

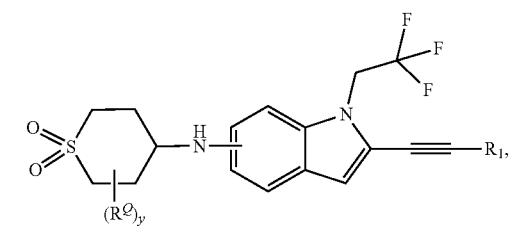

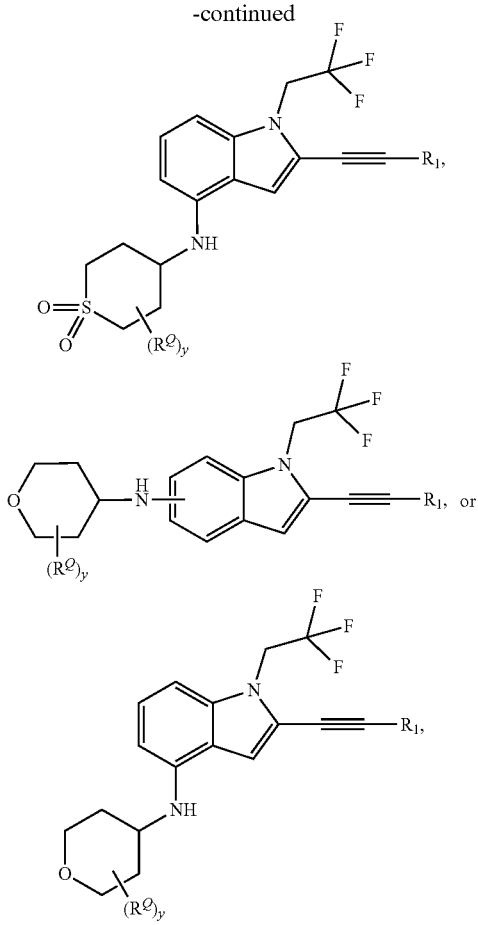

or a pharmaceutically-acceptable salt thereof, wherein the variables are as defined above.

In some embodiments, each $R^Q$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen. In some embodiments, each $R^Q$ is In some embodiments, y is 1. In some embodiments, y is 2. In some embodiments, y is 3. In some embodiments, y is 4.

In some embodiments, $R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —NR$^{21}$R$^{22}$, or aryl, each of which is independently substituted or unsubstituted; halo or hydrogen.

In some embodiments, $R^1$ is substituted alkyl. In some embodiments, $R^1$ is substituted $C_1$-$C_3$-alky 1. In some embodiments, $R^1$ is alkyl substituted with NR$^{16}$R$^{17}$. In some embodiments, $R^1$ is $C_1$-$C_3$-alkyl substituted with NR$^{16}$R$^{17}$. In some embodiments, $R^1$ is methyl substituted with NR$^{16}$R$^{17}$, wherein each R$^{16}$ and R$^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with NR$^{16}$R$^{17}$, wherein R$^{16}$ is hydrogen, and R$^{17}$ is a substituted carboxyl group.

In some embodiments, R$^{16}$ is alkyl, alkenyl, aryl, heteroaryl, heterocyclyl, or hydrogen, and R$^{17}$ is aryl, heteroaryl, or heterocyclyl. In some embodiments, R$^{16}$ is hydrogen, and R$^{17}$ is phenyl, indolyl, piperidinyl, imidazolyl, thiazolyl, morpholinyl, pyrrolyl, or pyridinyl, each of which is substituted or unsubstituted.

In some embodiments, the compound is of the formula:

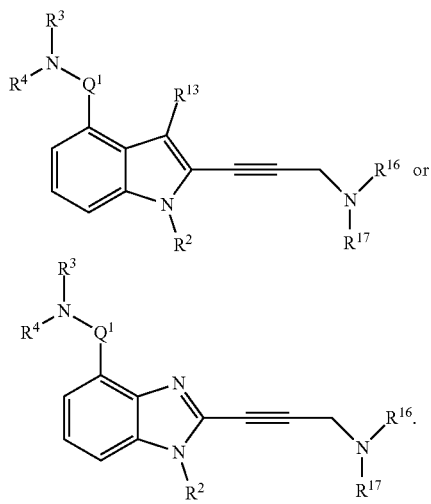

In some embodiments, the compound is of the formula:

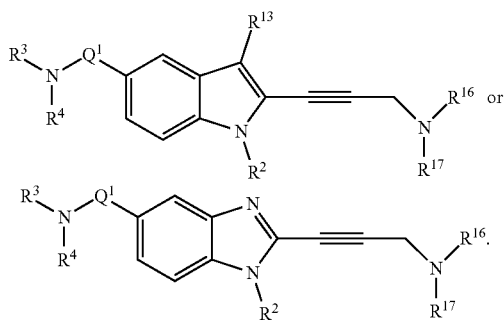

In some embodiments, the compound is of the formula:

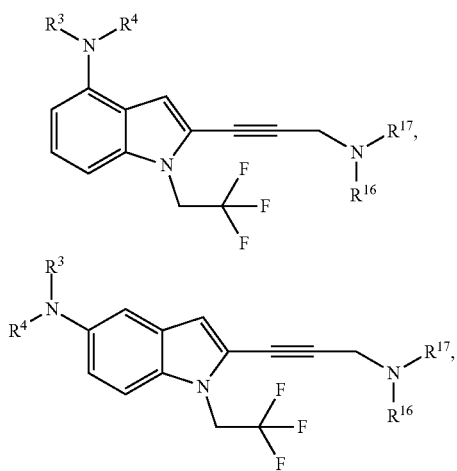

-continued

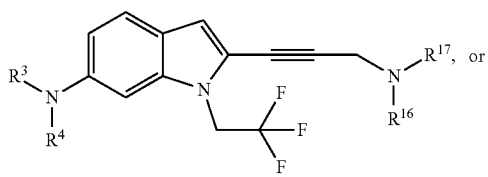

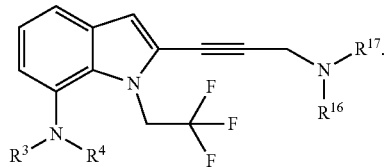

In some embodiments, each $R^{16}$ and $R^{17}$ is independently alkyl, alkenyl, aryl, heteroaryl, heterocyclyl, or hydrogen. In some embodiments, $R^{16}$ is aryl, and $R^{17}$ is alkyl. In some embodiments, $R^{16}$ is aryl, and $R^{17}$ is hydrogen. In some embodiments, $R^{16}$ is heteroaryl, and $R^{17}$ is alkyl. In some embodiments, $R^{16}$ is heteroaryl, and $R^{17}$ is hydrogen. In some embodiments, $R^{16}$ is substituted heteroaryl, and $R^{17}$ is hydrogen. In some embodiments, $R^{16}$ is substituted alkyl, and $R^{17}$ is hydrogen. In some embodiments, $R^{17}$ is aryl, heteroaryl, or heterocyclyl, each of which is independently substituted or unsubstituted with halogen, alkyl, or hydroxyl. In some embodiments, $R^{16}$ is hydrogen, and $R^{17}$ is aryl or heteroaryl, substituted or unsubstituted with halogen or alkyl. In some embodiments, $R^{16}$ is alkyl, and $R^{17}$ is heteroaryl substituted with halogen or alkyl. In some embodiments, $R^{16}$ is hydrogen. In some embodiments, $R^{17}$ is aryl, heteroaryl, or heterocyclyl, each of which is independently substituted or unsubstituted with alkyl. In some embodiments, $R^{17}$ is aryl or heteroaryl, each of which is independently substituted with alkyl, wherein the alkyl is optionally substituted with fluorine, chlorine, bromine, iodine, or cyano. In some embodiments, $R^{16}$ is alkyl, alkenyl, aryl, heteroaryl, heterocyclyl, or hydrogen, and $R^{17}$ is aryl, heteroaryl, or heterocyclyl. In some embodiments, $R^{16}$ is hydrogen, and $R^{17}$ is phenyl, indolyl, piperidinyl, imidazolyl, thiazolyl, morpholinyl, pyrrolyl, or pyridinyl, each of which is substituted or unsubstituted. In some embodiments, $R^{16}$ is hydrogen, and $R^{17}$ is substituted phenyl. In some embodiments, $R^{16}$ is hydrogen, and $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted. In some embodiments, $R^{17}$ is phenyl substituted with methoxy. In some embodiments, $R^{17}$ is phenyl substituted with a substituted sulfoxide group. In some embodiments, $R^{17}$ is phenyl substituted with a carboxyl group. In some embodiments, $R^{17}$ is a substituted amide group. In some embodiments, $R^{17}$ is substituted with methoxy and sulfonamide.

In some embodiments, each $R^3$ and $R^4$ is independently unsubstituted or substituted alkyl. In some embodiments, $R^3$ is hydrogen and $R^4$ is —C(O)$R^{19}$, —C(O)O$R^{19}$, alkyl, alkenyl, alkynyl, aryl, heteroaryl, or heterocyclyl, each of which is independently substituted or unsubstituted. In some embodiments, $R^3$ is hydrogen, and $R^4$ is alkyl, aryl, heteroaryl, or heterocyclyl, each of which is independently substituted or unsubstituted. In some embodiments, $R^3$ is H, and $R^4$ is substituted heterocyclyl. In some embodiments, $R^3$ is H, and $R^4$ is substituted or unsubstituted $C_4$-$C_6$-heterocyclyl. In some embodiments, $R^3$ is H, and $R^4$ is substituted alkyl. In some embodiments, $R^3$ is H, and $R^4$ is substituted $C_1$-$C_6$-alkyl. In some embodiments, $R^3$ is H, and $R^4$ is substituted or unsubstituted cycloalkyl. In some embodiments, $R^3$ is H, and $R^4$ is substituted or unsubstituted $C_4$-$C_6$-cycloalkyl. In some embodiments, $R^3$ is H, and $R^4$ is $C_4$-$C_6$-cycloalkyl substituted with an amino group.

In some embodiments, the compound is of the formula:

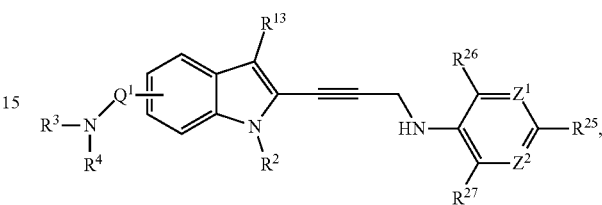

wherein:
- $Q^1$ is C=O, C=S, C=CR$^{14}$R$^{15}$, C=NR$^{14}$, alkylene, alkenylene, or alkynylene, each of which is independently substituted or unsubstituted, or a bond;
- $R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;
- each $R^3$ and $R^4$ is independently, —C(O)R$^{19}$, —C(O)OR$^{19}$, —C(O)NR$^{19}$R$^{20}$, —SOR$^{19}$, —SO$_2$R$^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
- each $Z^1$ and $Z^2$ is independently CR$^{28}$, CR$^{29}$, or N;
- each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;
- each $R^{21}$ and $R^{22}$ is independently alkyl, alkenyl, alkynyl, aryl, heteroaryl, or heterocyclyl, each of which is independently substituted or unsubstituted, or hydrogen;
- each $R^{23}$ and $R^{24}$ is independently alkyl, alkenyl, alkynyl, aryl, heteroaryl, or heterocyclyl, each of which is independently substituted or unsubstituted, or hydrogen; and
- each $R^{25}$, $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group, or a pharmaceutically-acceptable salt thereof.

In some embodiments, $Z^1$ is N. In some embodiments, $Z^1$ and $Z^2$ are N. In some embodiments, each $R^{25}$ and $R^{26}$ is independently a halogen. In some embodiments, $R^{25}$ is

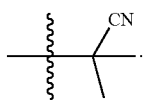

In some embodiments, $R^{25}$ is a substituted sulfone group. In some embodiments, $R^{25}$ is a sulfone group substituted with alkyl. In some embodiments, $R^{25}$ is a methanesulfonyl group. In some embodiments, $R^{25}$ is a sulfone group substituted with an amino group. In some embodiments, $R^{25}$ is a sulfonamide. In some embodiments, $R^{25}$ is a carboxy group. In some embodiments, $R^{25}$ is a methoxycarbonyl group.

In some embodiments, the compound is of the formula:

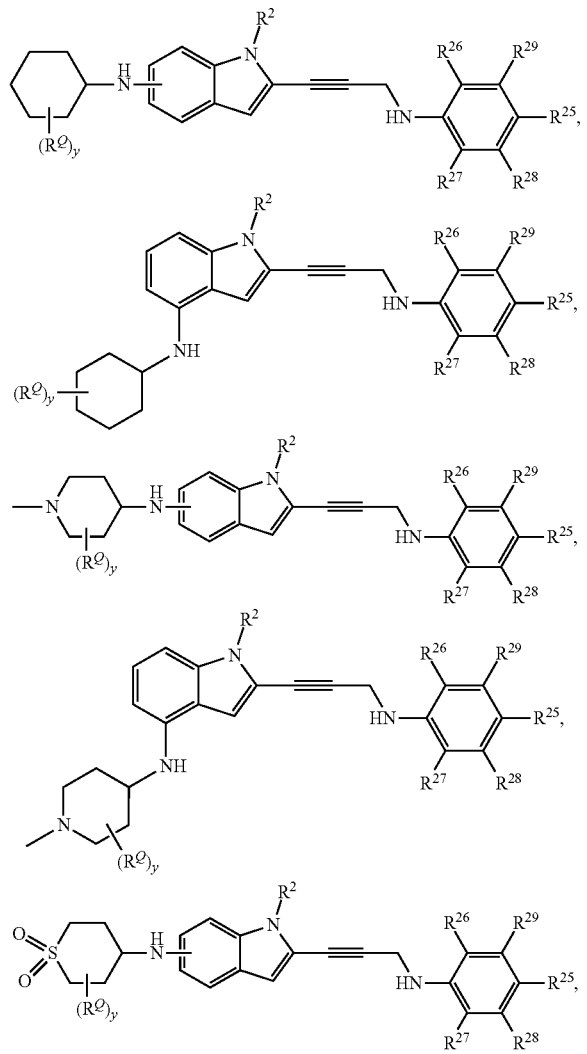

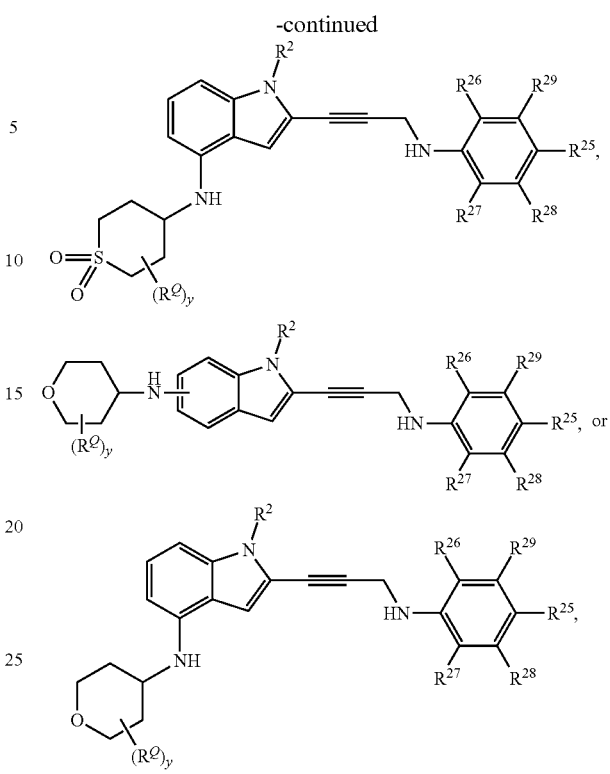

wherein:

$R^2$ is —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^Q$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted;

y is 0, 1, 2, 3, or 4;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{25}$, $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group, or a pharmaceutically-acceptable salt thereof.

In some embodiments, the compound is of the formula:

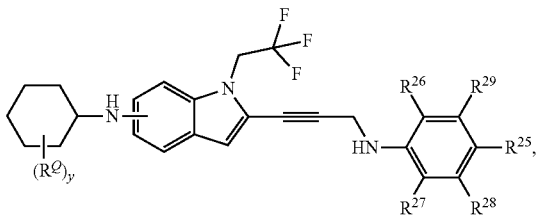

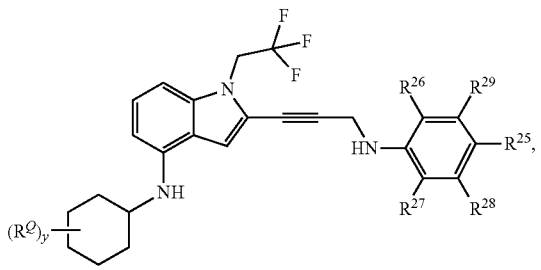

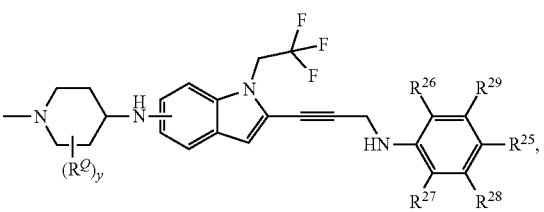

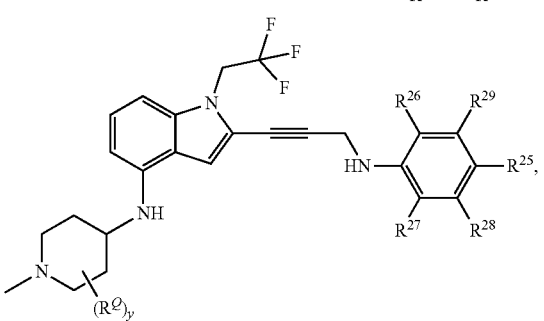

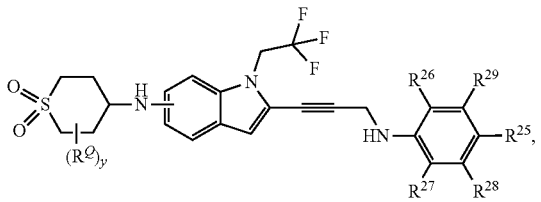

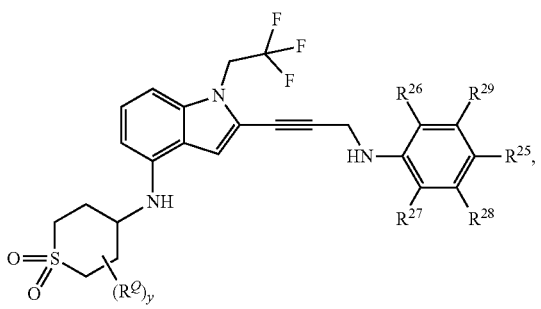

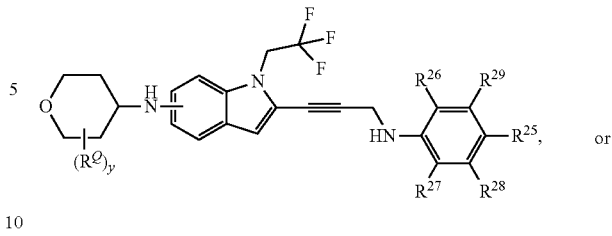

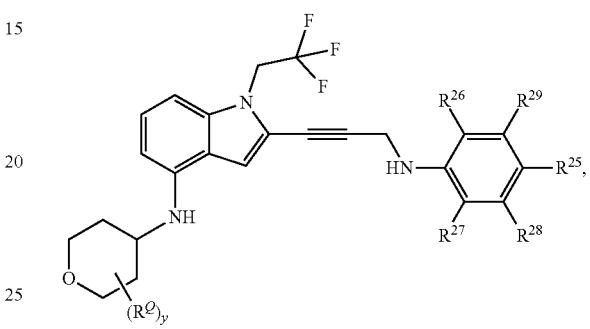

In some embodiments, $R^{25}$ is a substituted sulfone group. In some embodiments, $R^{25}$ is a sulfone group substituted with alkyl. In some embodiments, $R^{25}$ is a methanesulfonyl group. In some embodiments, $R^{25}$ is a sulfone group substituted with an amino group. In some embodiments, $R^{25}$ is a sulfonamide. In some embodiments, $R^{25}$ is a carboxy group. In some embodiments, $R^{25}$ is a methoxycarbonyl group.

In some embodiments, the compound is of the formula:

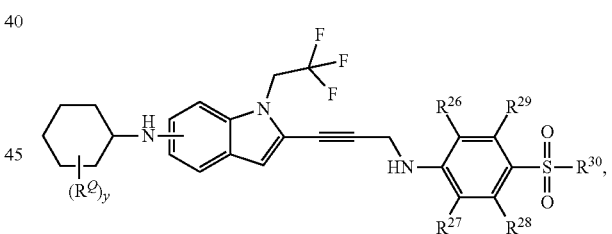

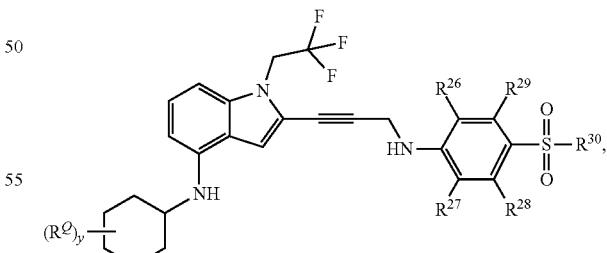

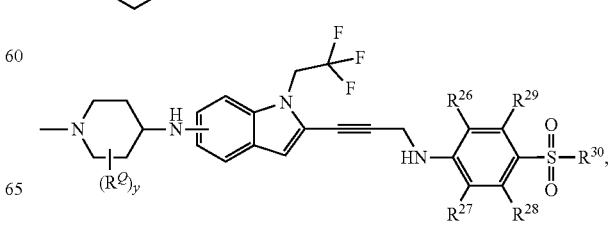

-continued

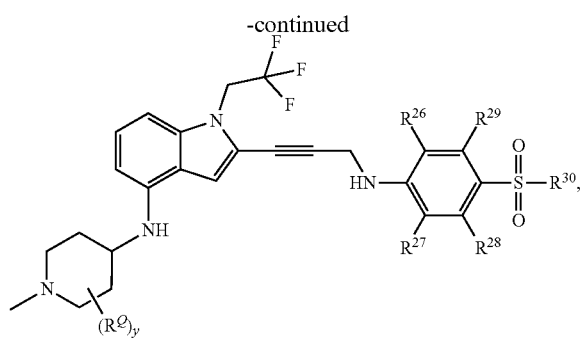

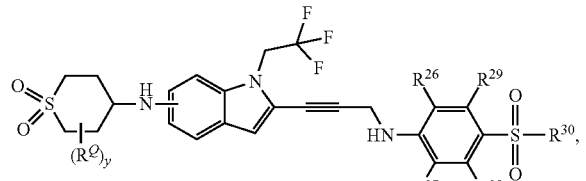

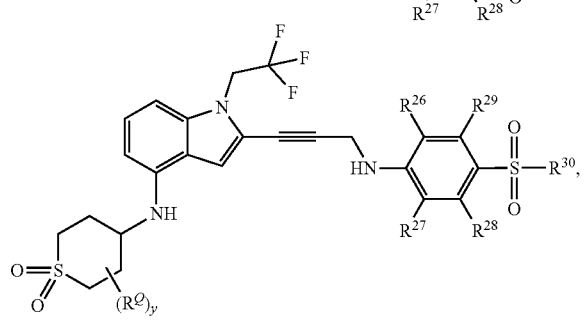

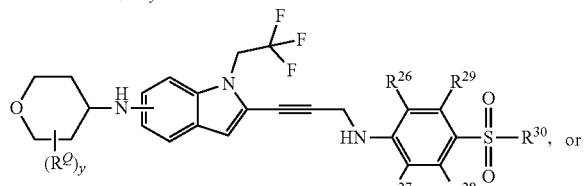

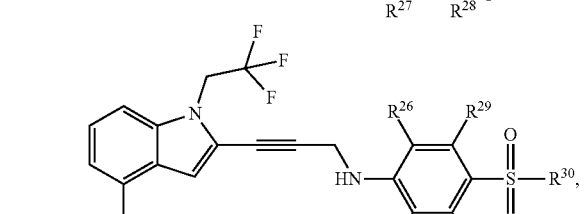

wherein:
each $R^Q$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted;

y is 0, 1, 2, 3, or 4;

each $R^{21}$ and $R^{22}$ is independently alkyl, alkenyl, alkynyl, aryl, heteroaryl, or heterocyclyl, each of which is independently substituted or unsubstituted, or hydrogen;

each $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, haloalkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group; and $R^{30}$ is alkyl or an amino group, each of which is substituted or unsubstituted, or a pharmaceutically-acceptable salt thereof.

In some embodiments, $R^{30}$ is methyl. In some embodiments, $R^{30}$ is NH$_2$. In some embodiments, $R^{30}$ is NHMe. In some embodiments, $R^{30}$ is NMe$_2$.

In some embodiments, the compound is of the formula:

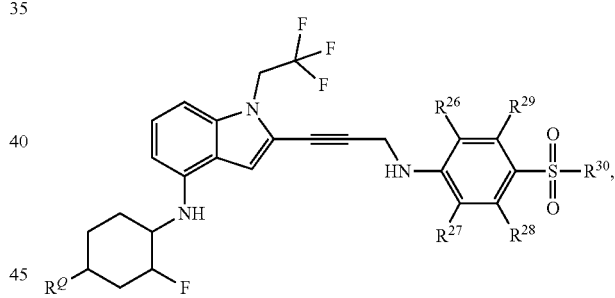

wherein $R^{30}$ is alkyl or an amino group, each of which is unsubstituted or substituted. In some embodiments, $R^{30}$ is methyl.

Non-limiting examples of compounds of the current disclosure include the following:

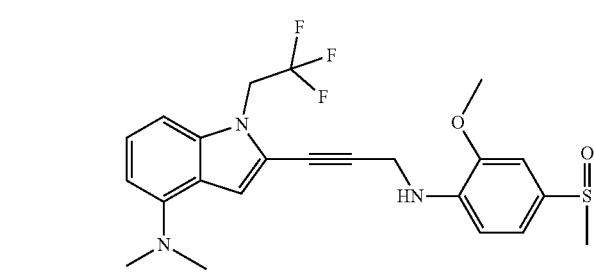

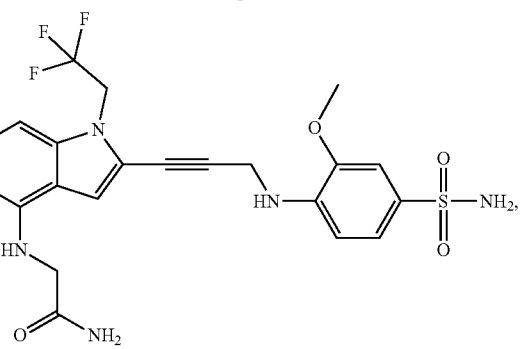

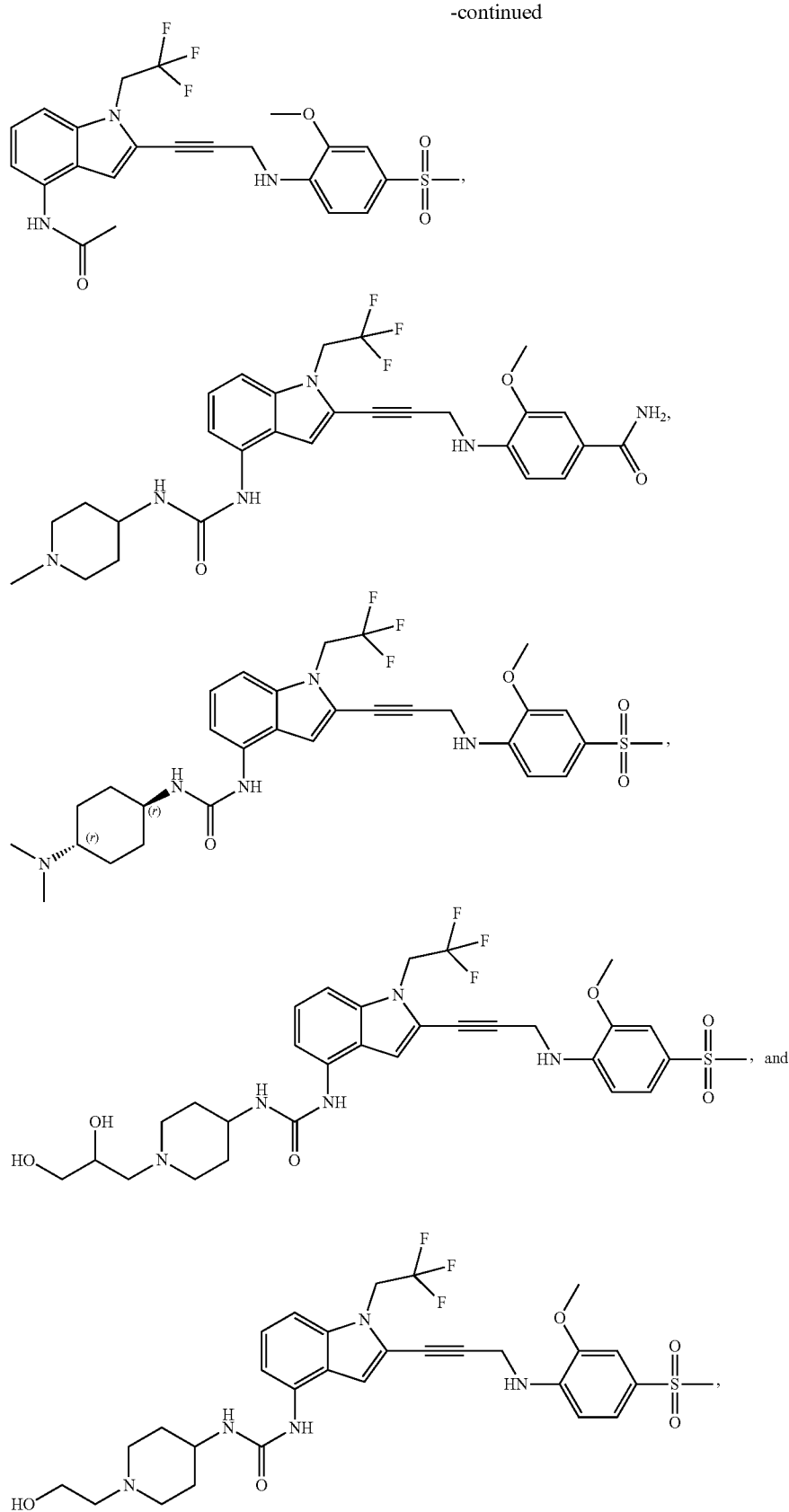
or a pharmaceutically-acceptable salt thereof.

Non-limiting examples of compounds of the current disclosure include the following:
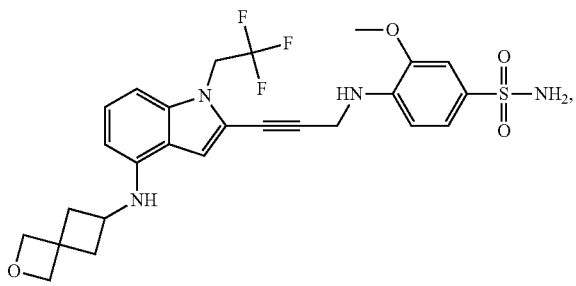
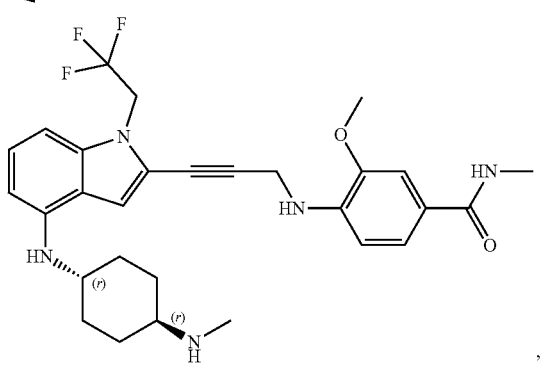
,
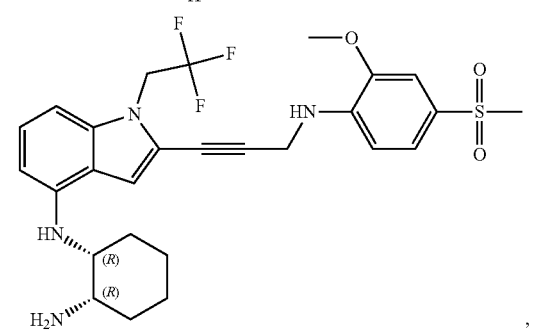
,
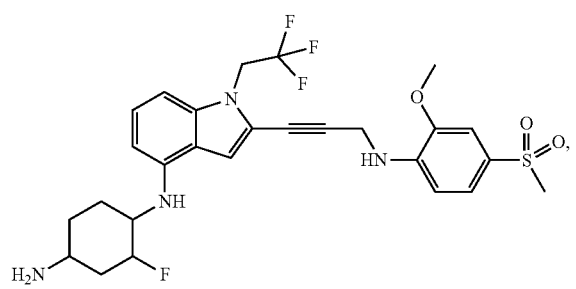
,
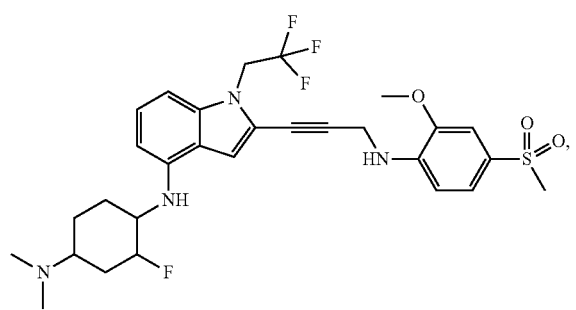

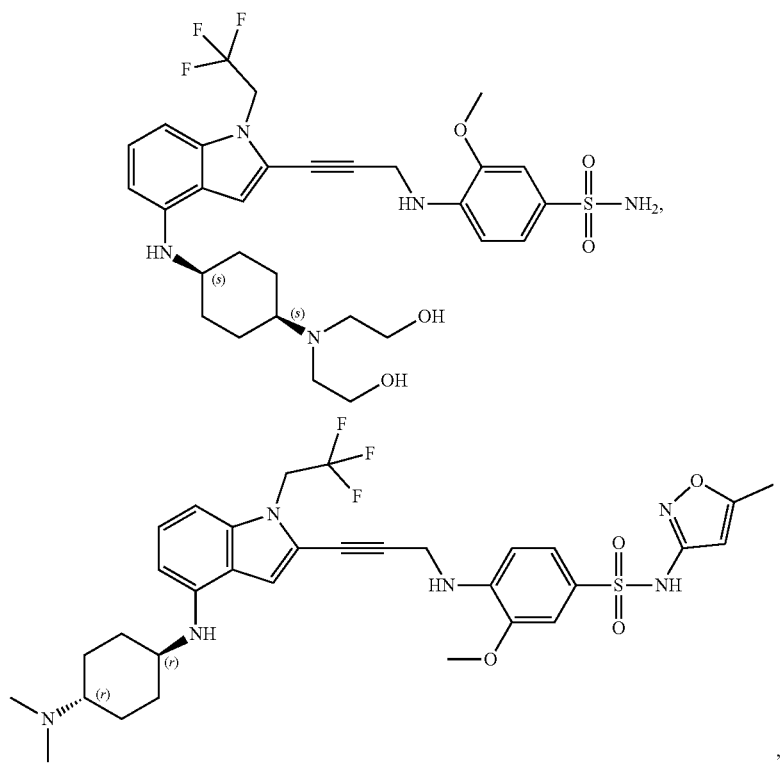
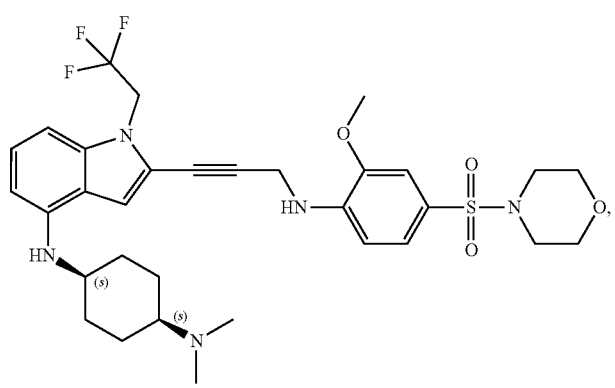
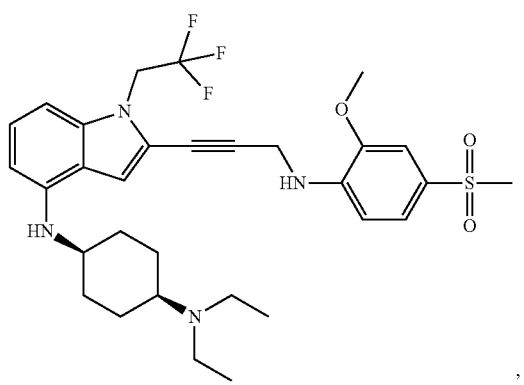

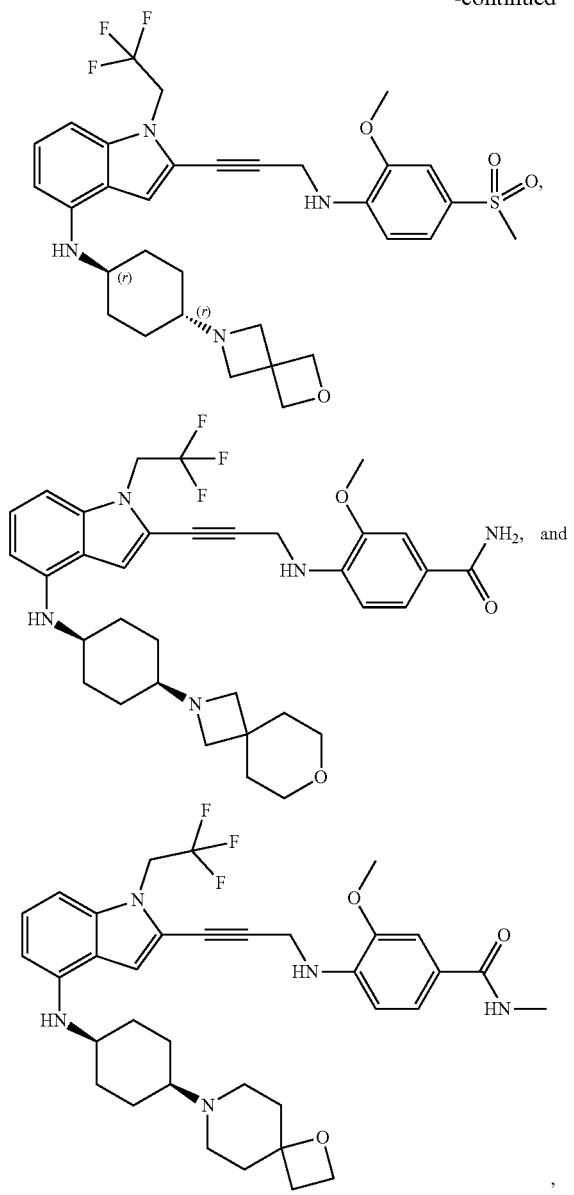
or a pharmaceutically-acceptable salt thereof.
Non-limiting examples of compounds of the current disclosure include the following:
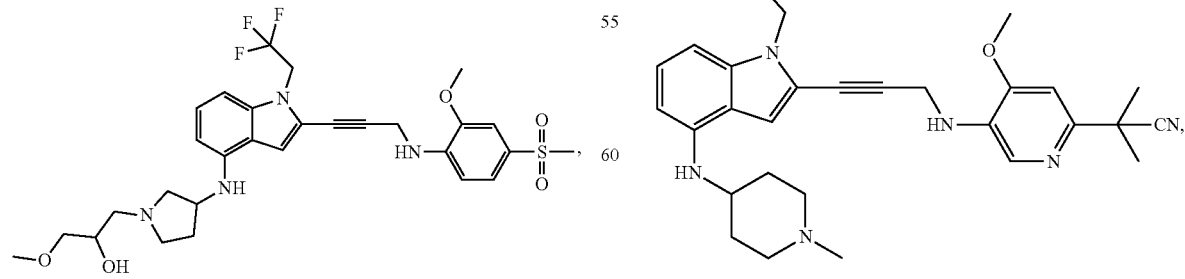

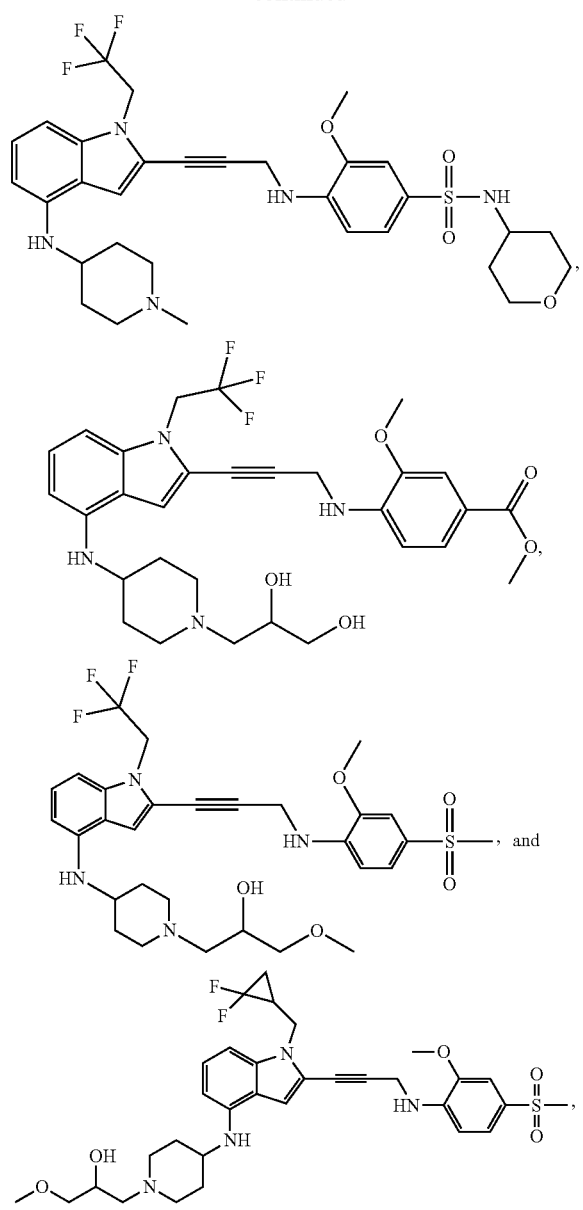
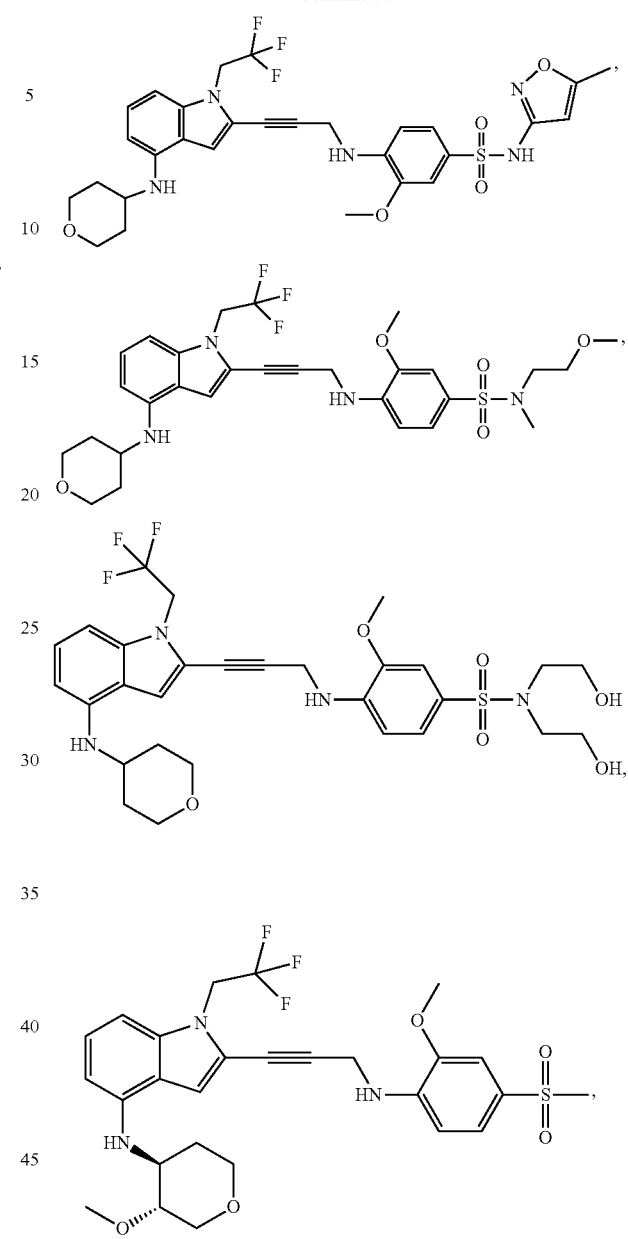
or a pharmaceutically-acceptable salt thereof.
Non-limiting examples of compounds of the current disclosure include the following:
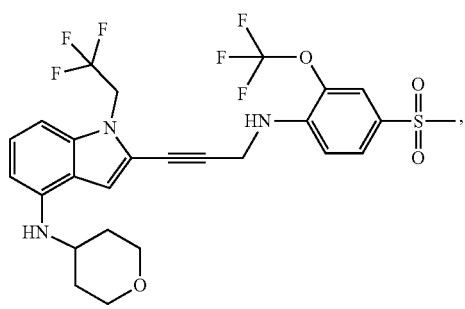
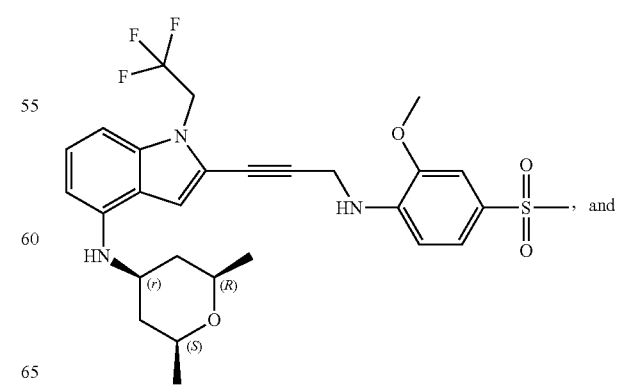

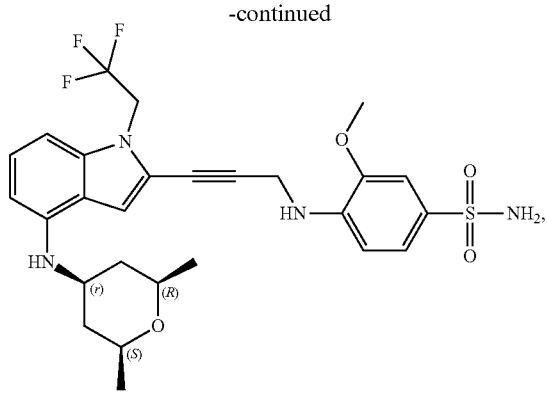
or a pharmaceutically-acceptable salt thereof.
Non-limiting examples of compounds of the current disclosure include the following:
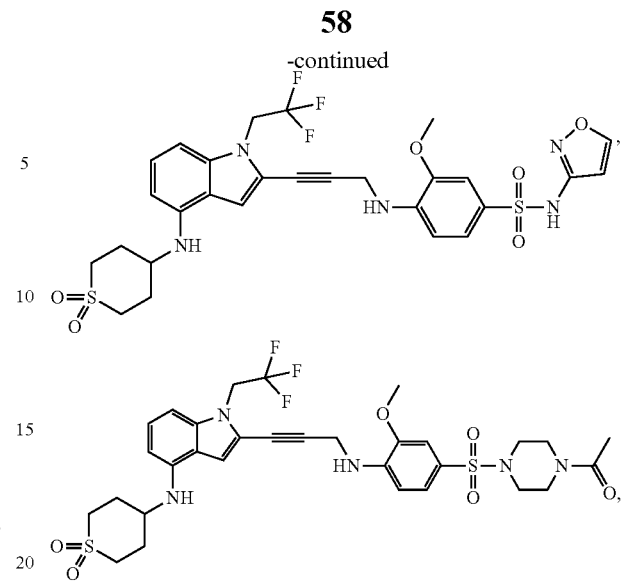
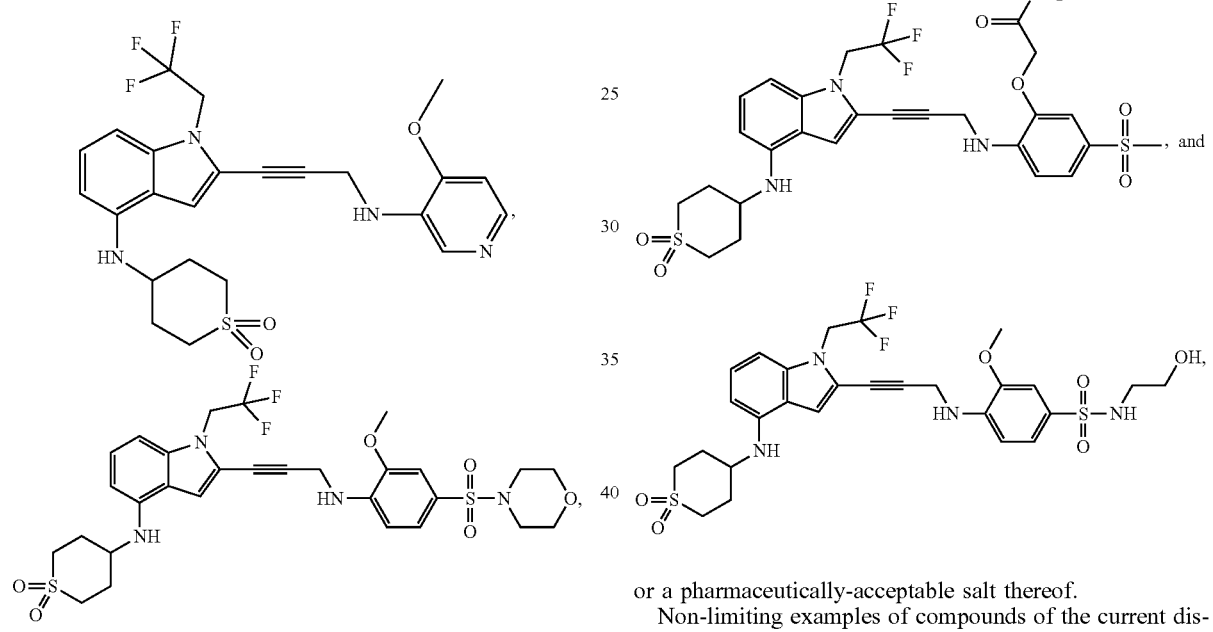
or a pharmaceutically-acceptable salt thereof.
Non-limiting examples of compounds of the current disclosure include the following:
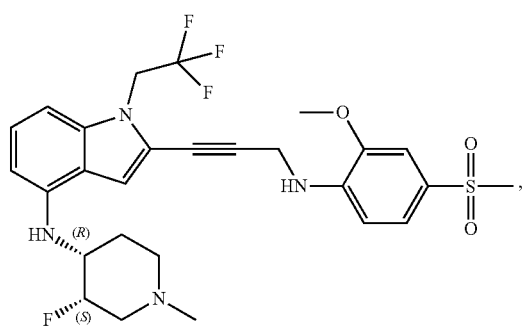
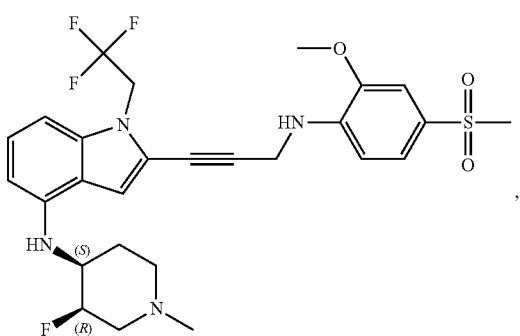

-continued
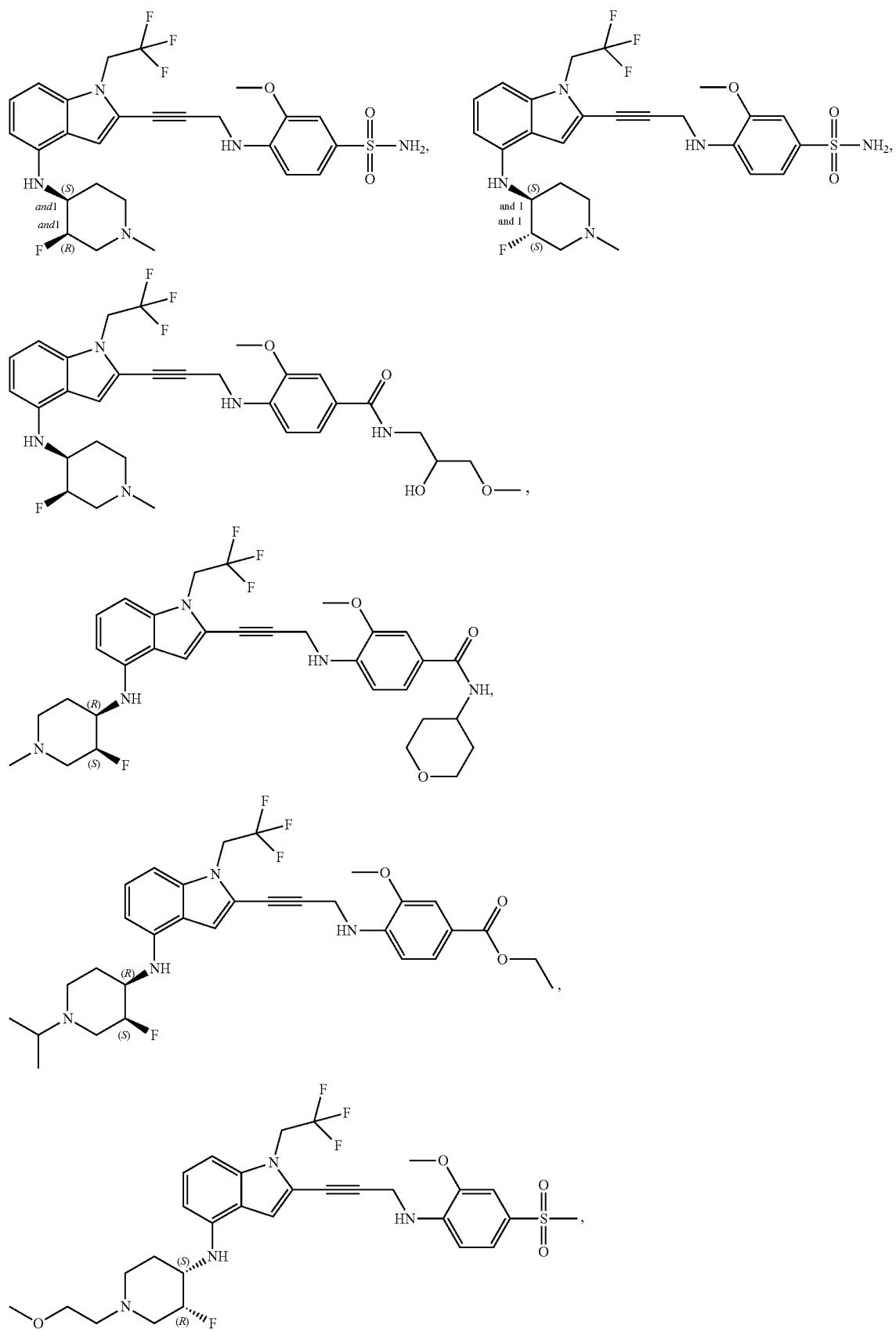

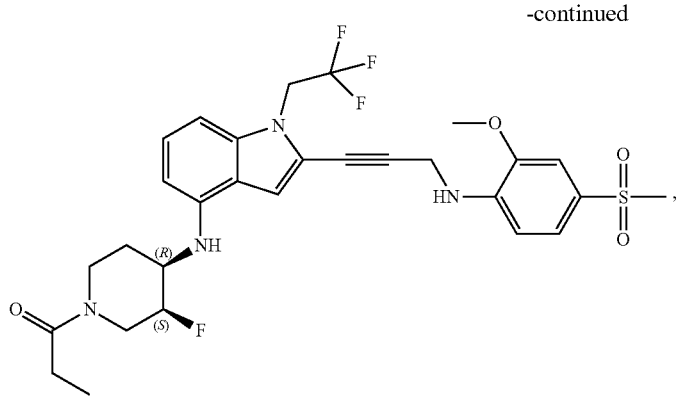
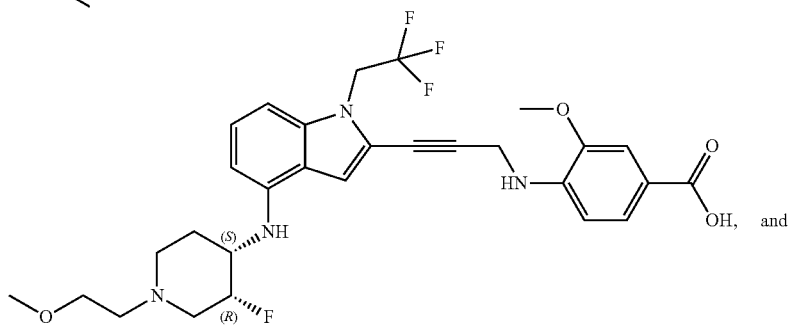
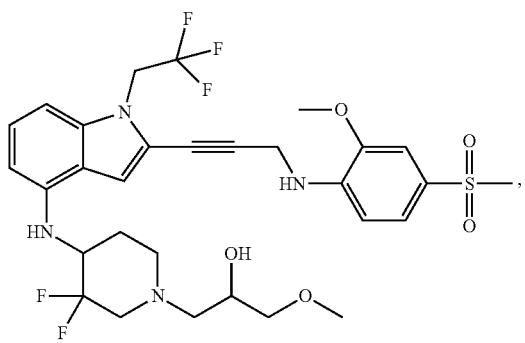
or a pharmaceutically-acceptable salt thereof.
Non-limiting examples of compounds of the current disclosure include the following:
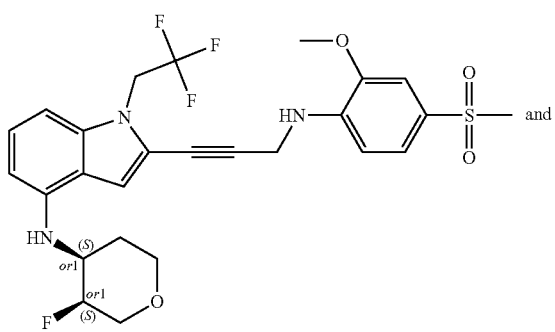
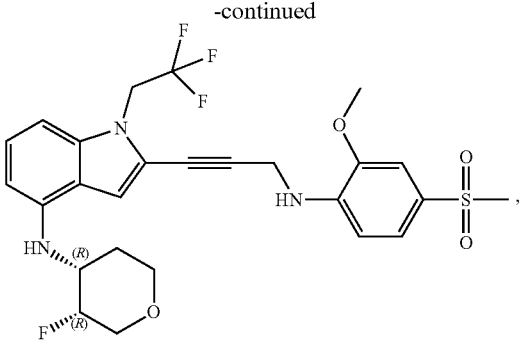
or a pharmaceutically-acceptable salt thereof.
Non-limiting examples of compounds of the current disclosure include the following:

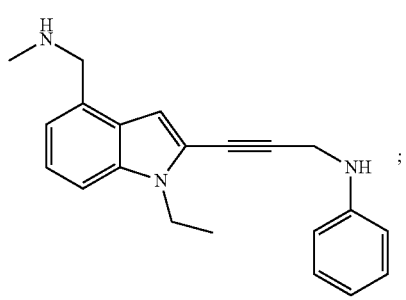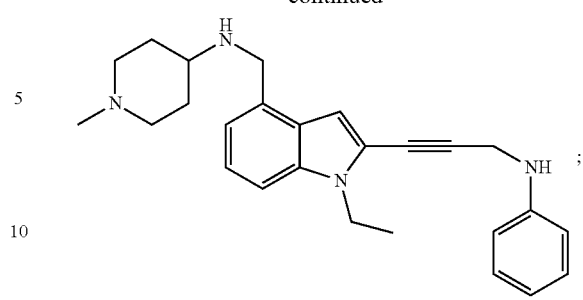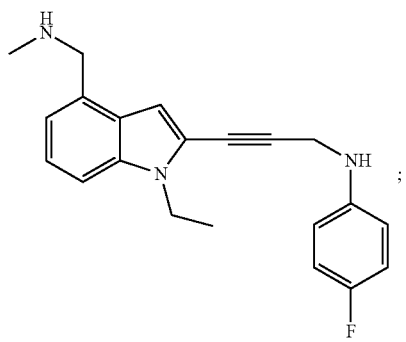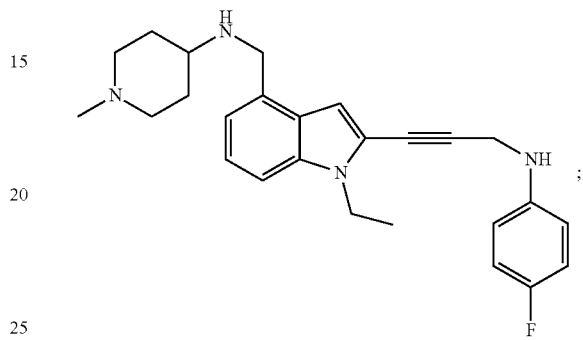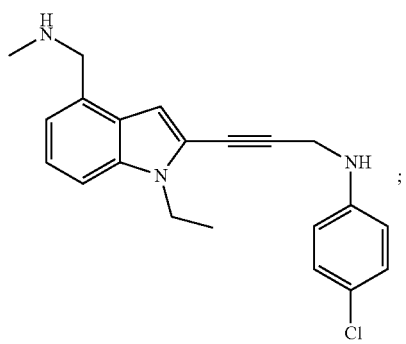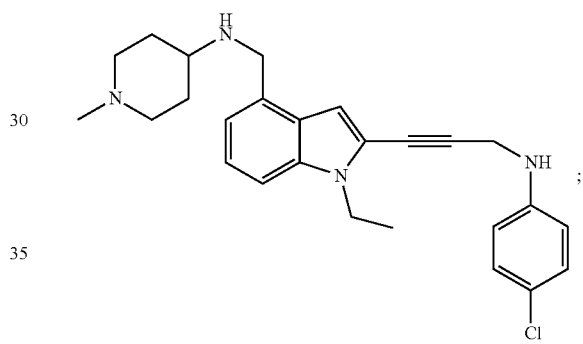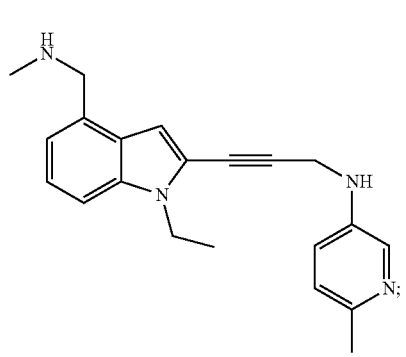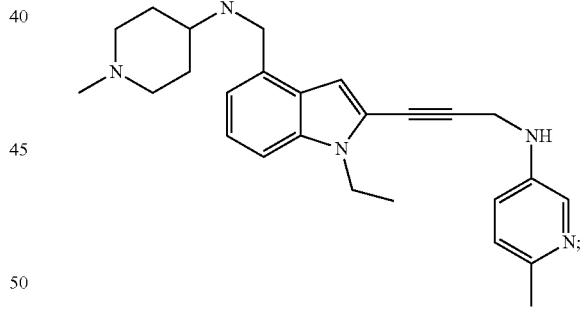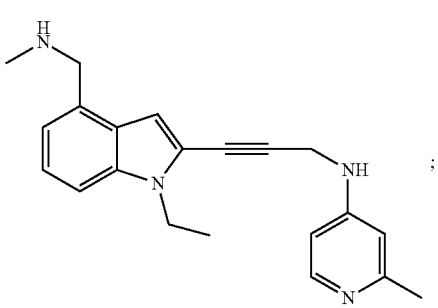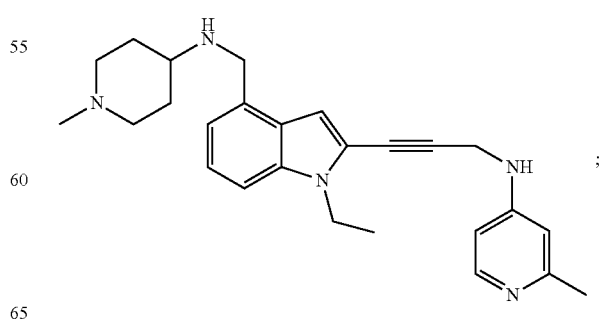

65
-continued
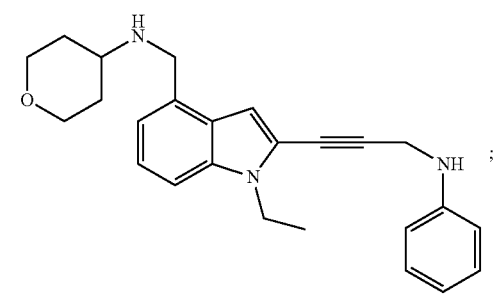
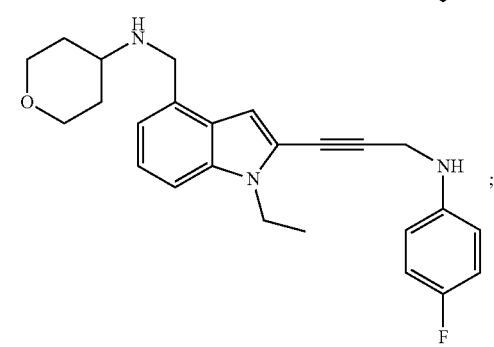
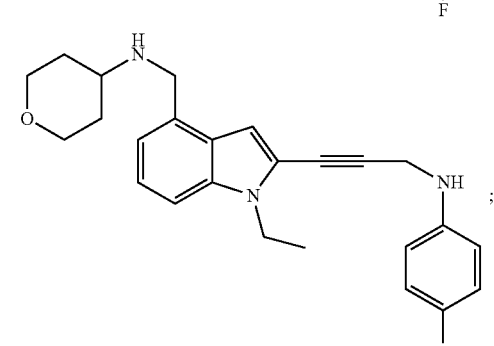
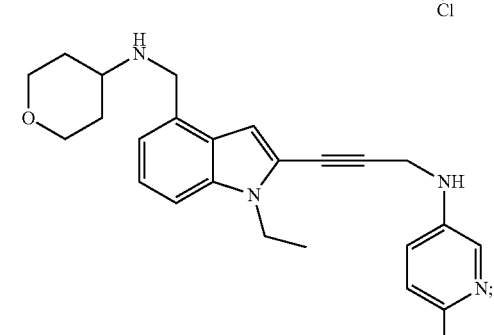
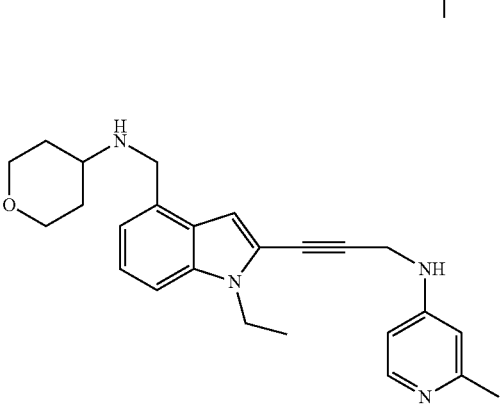
66
-continued
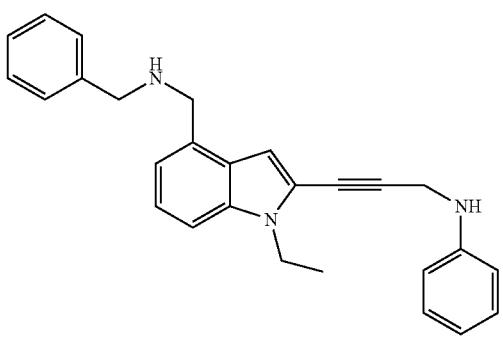
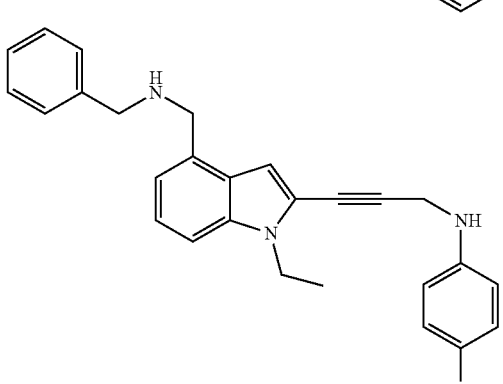
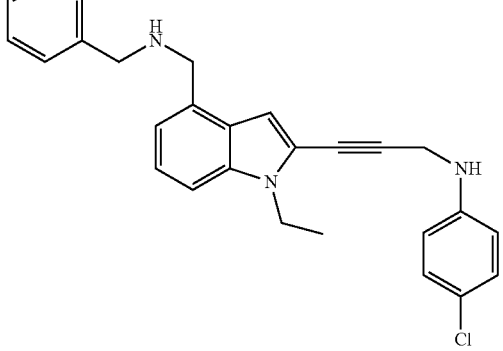
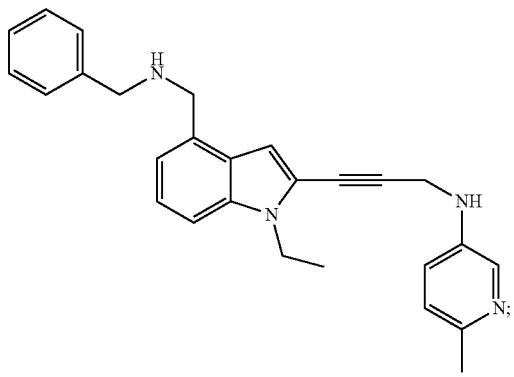

67
-continued
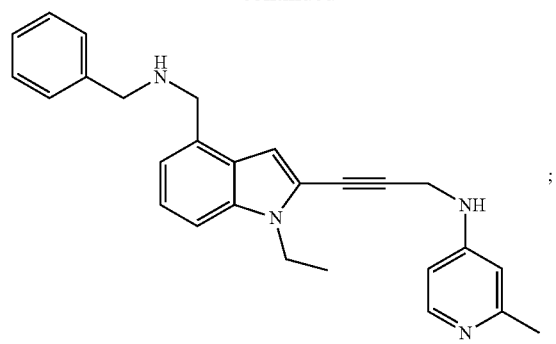
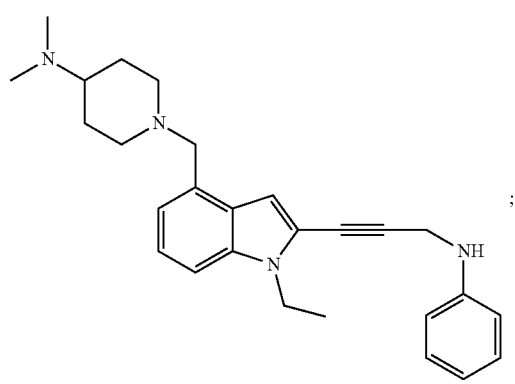
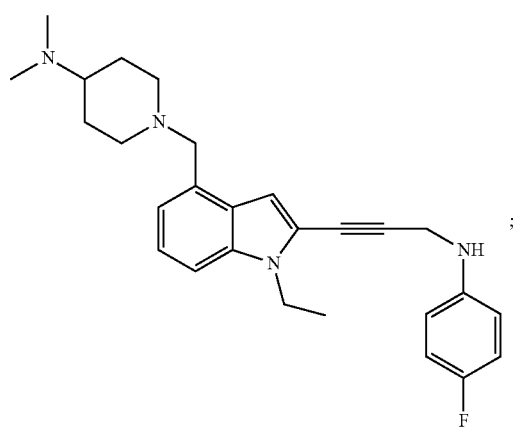
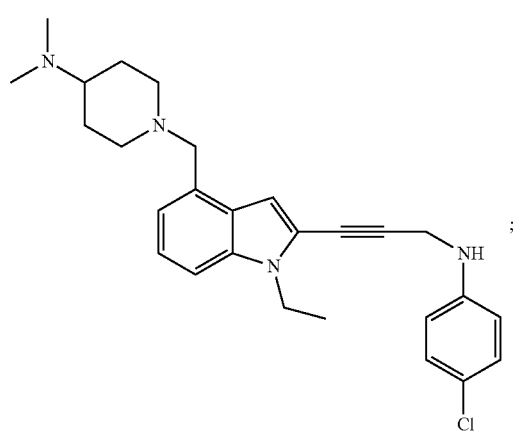
68
-continued
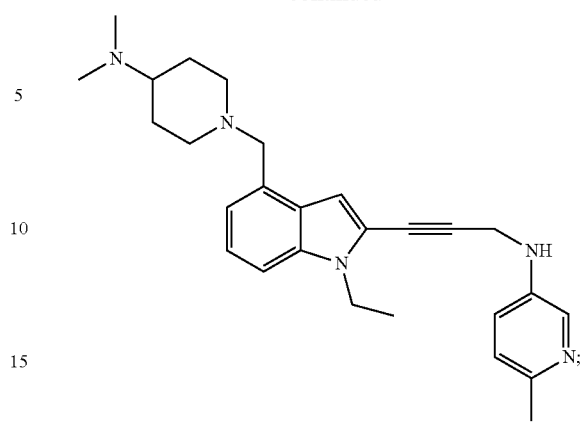
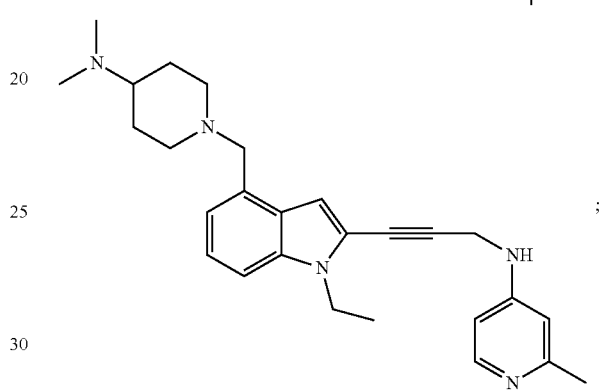
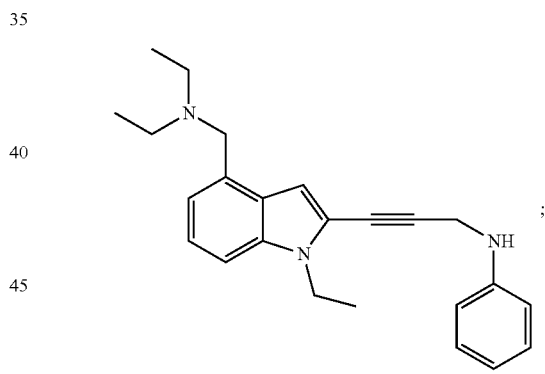
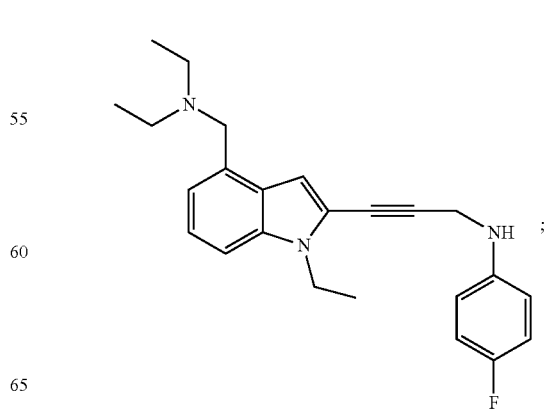

69
-continued
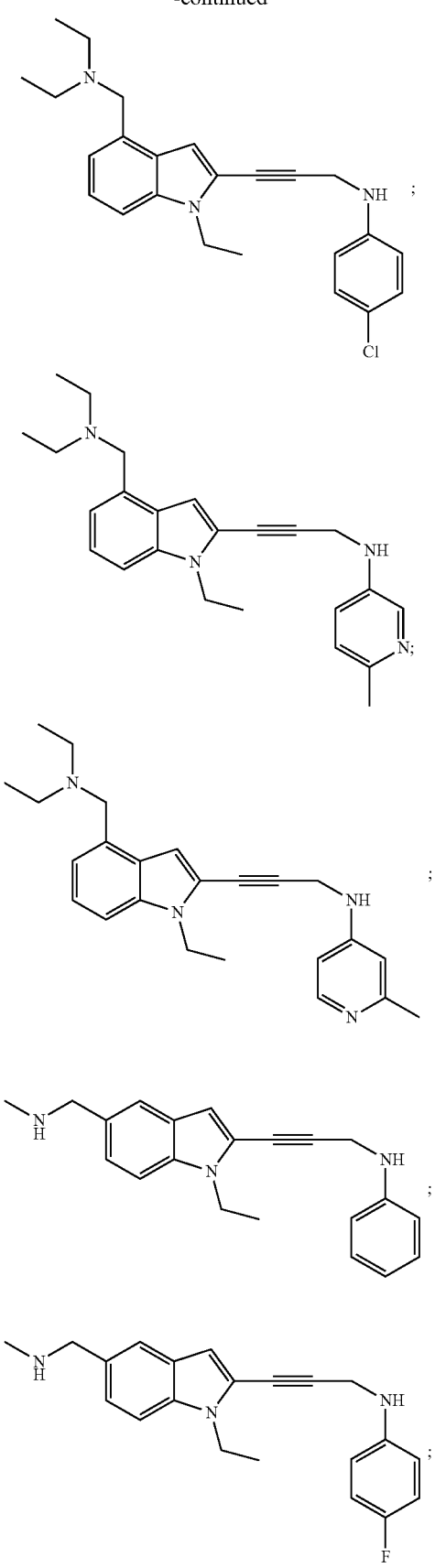
70
-continued
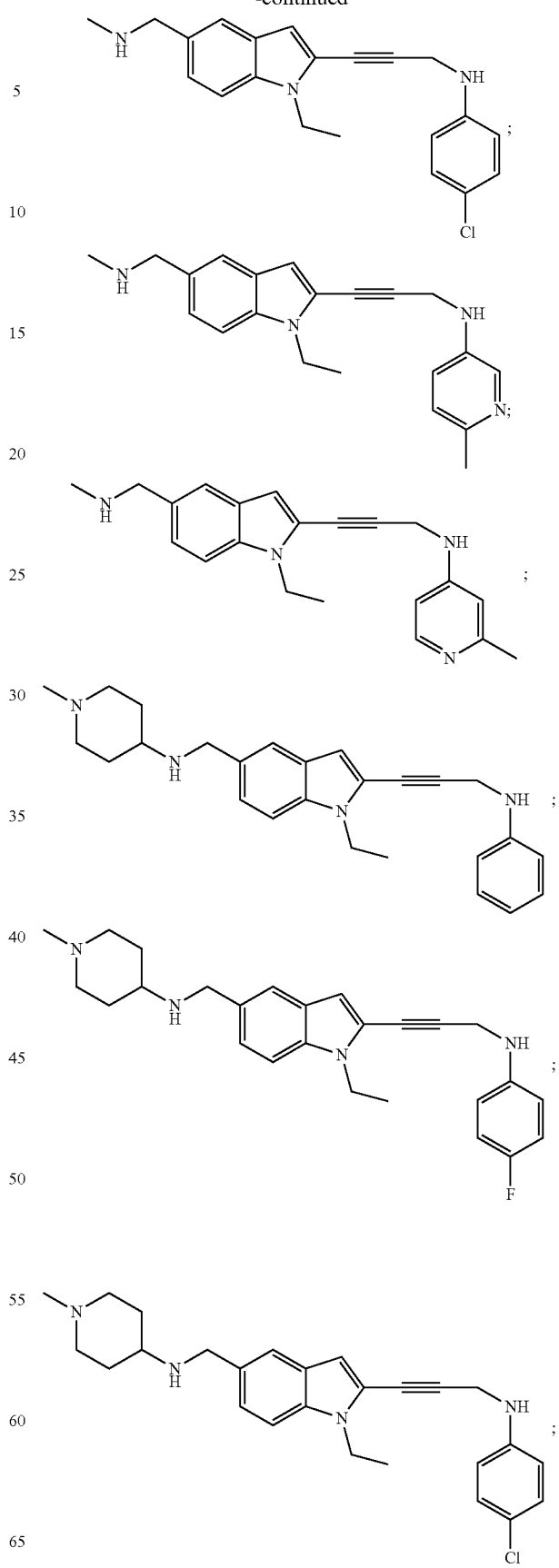

-continued
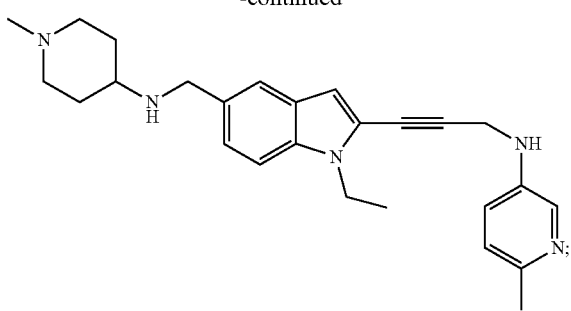
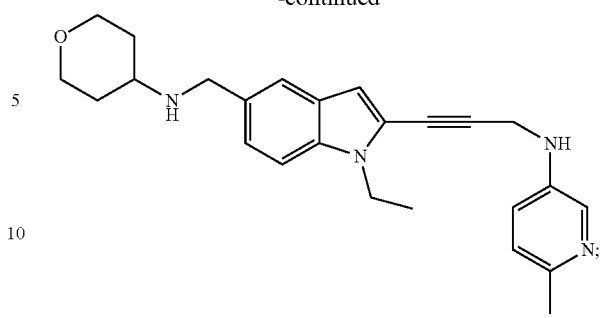
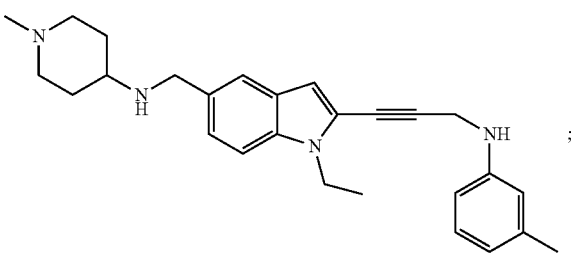
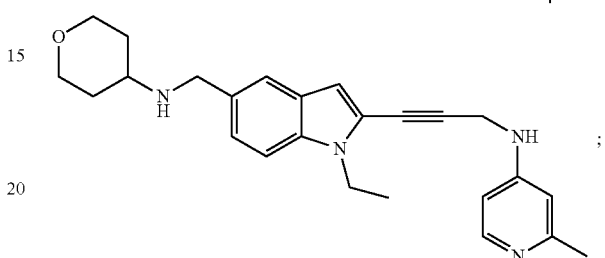
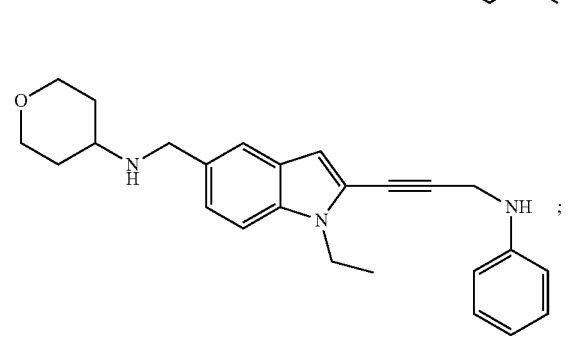
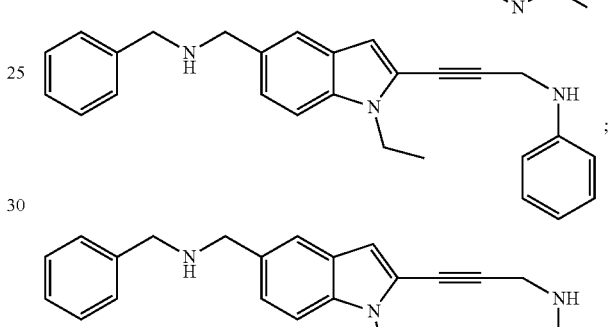
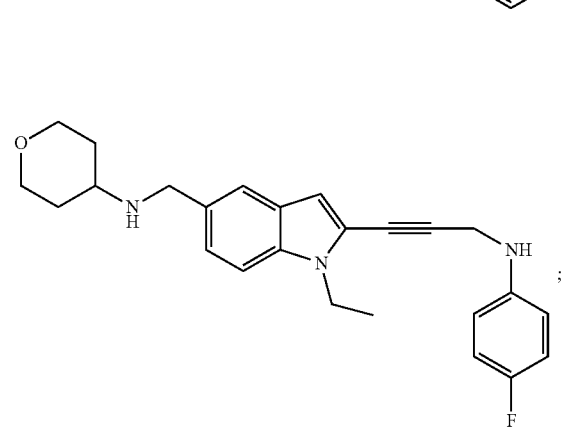
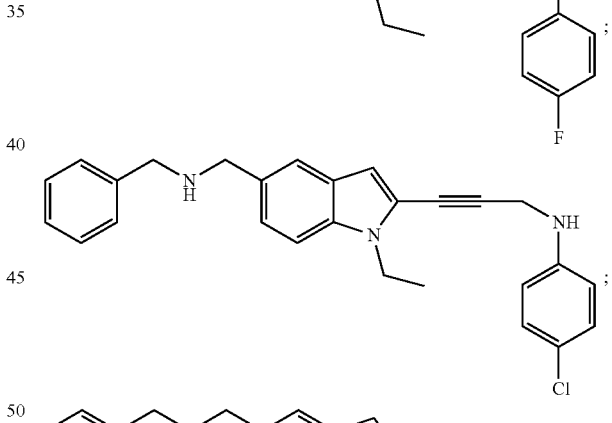
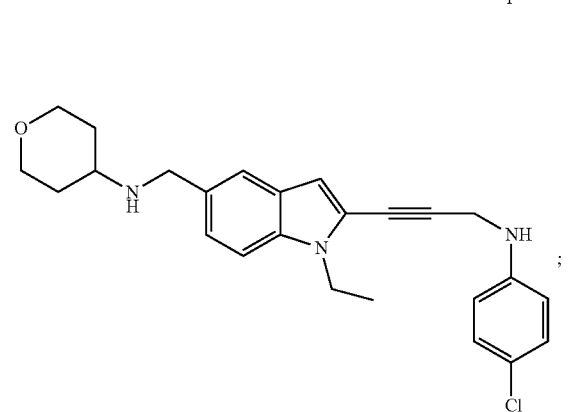
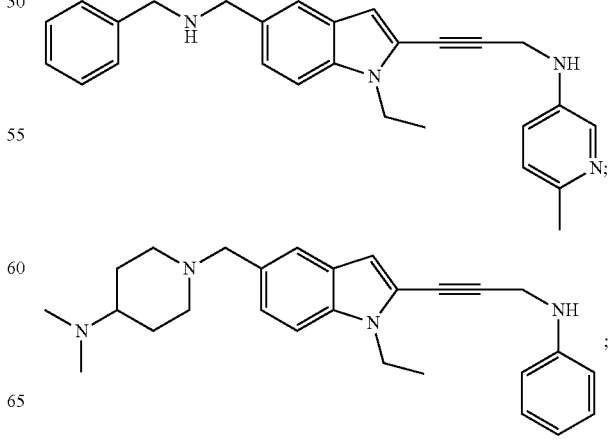

-continued
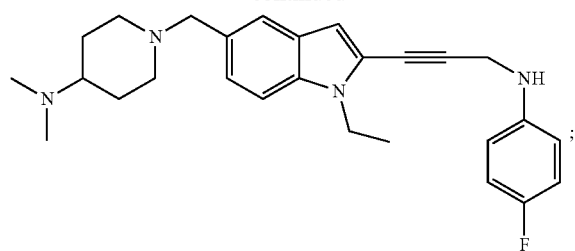
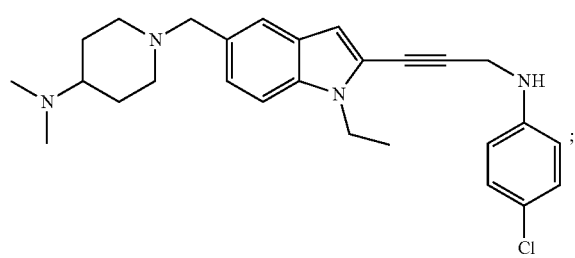
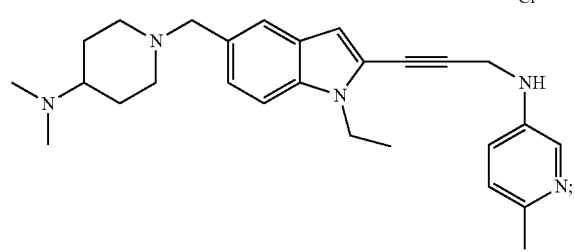
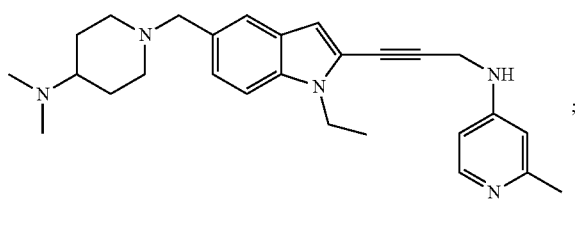
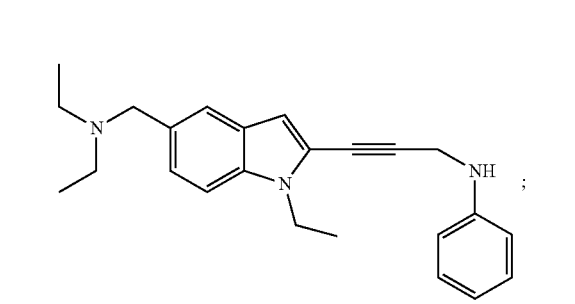
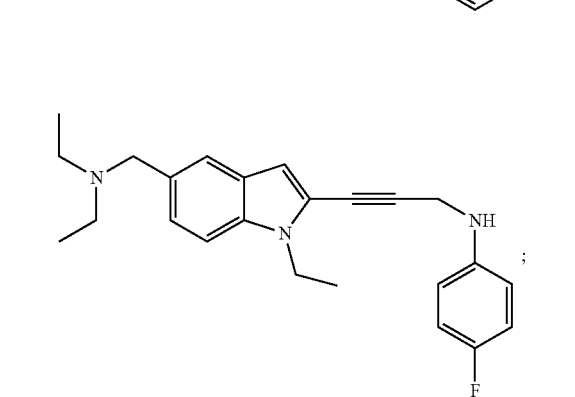
-continued
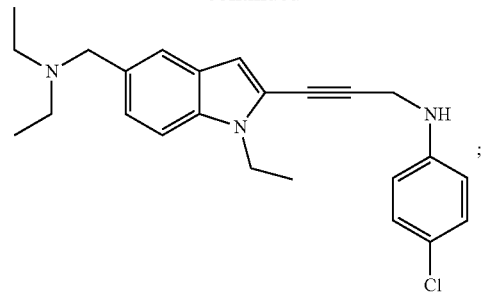
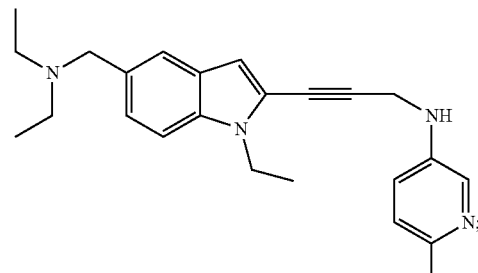
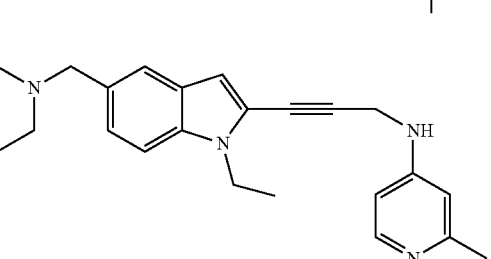
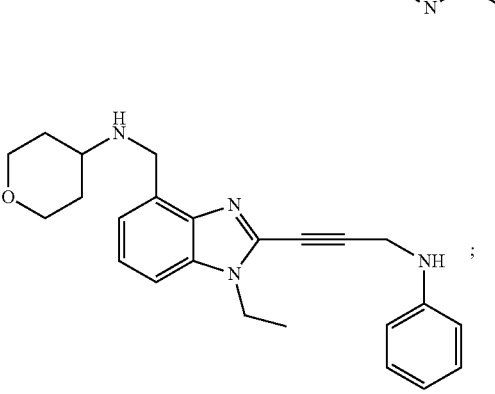; and
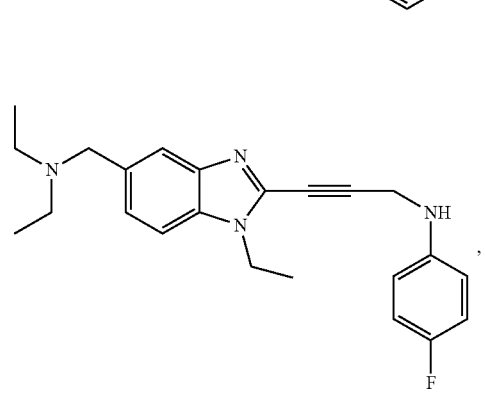
or a pharmaceutically-acceptable salt of any of the foregoing.
Non-limiting examples of compounds of the current disclosure include the following:

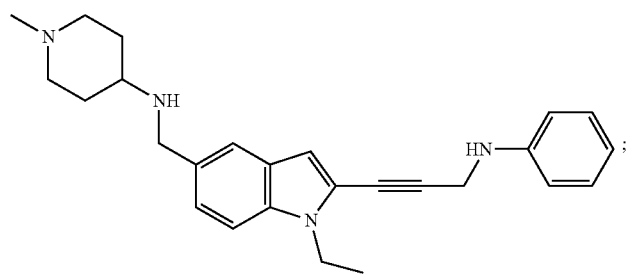
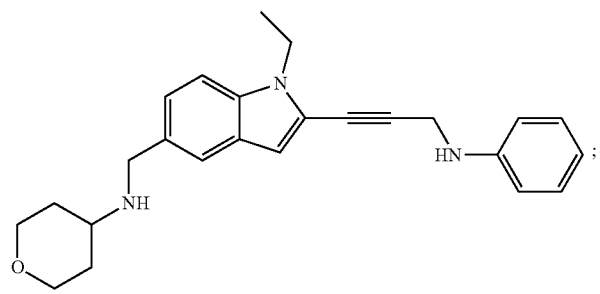
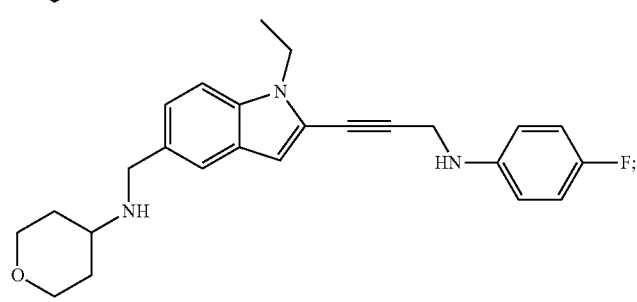
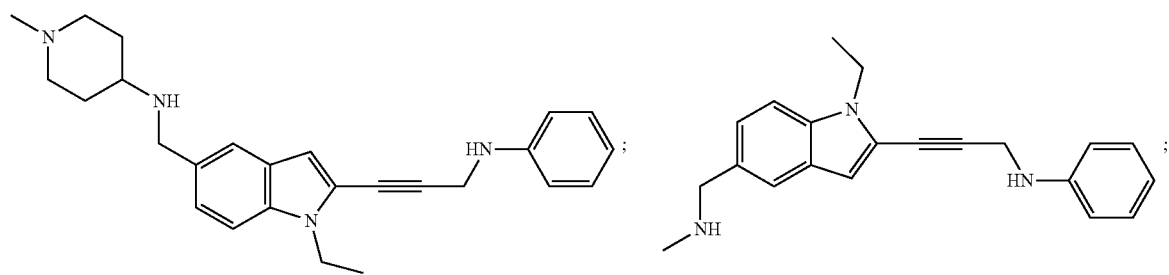
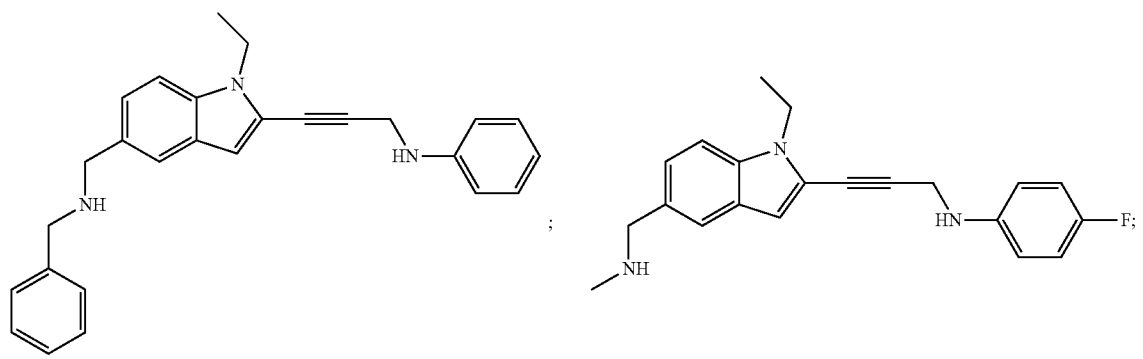

-continued
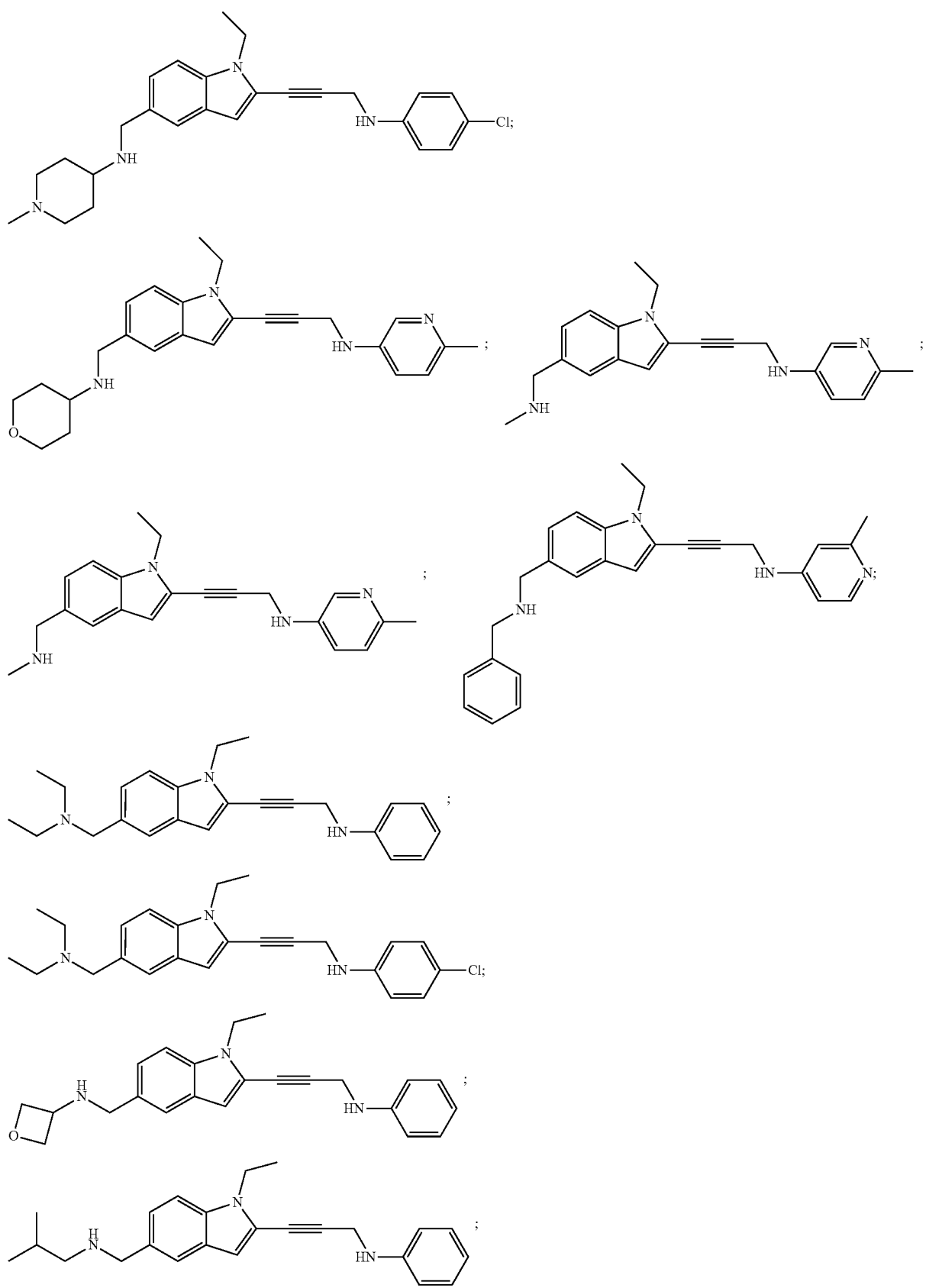

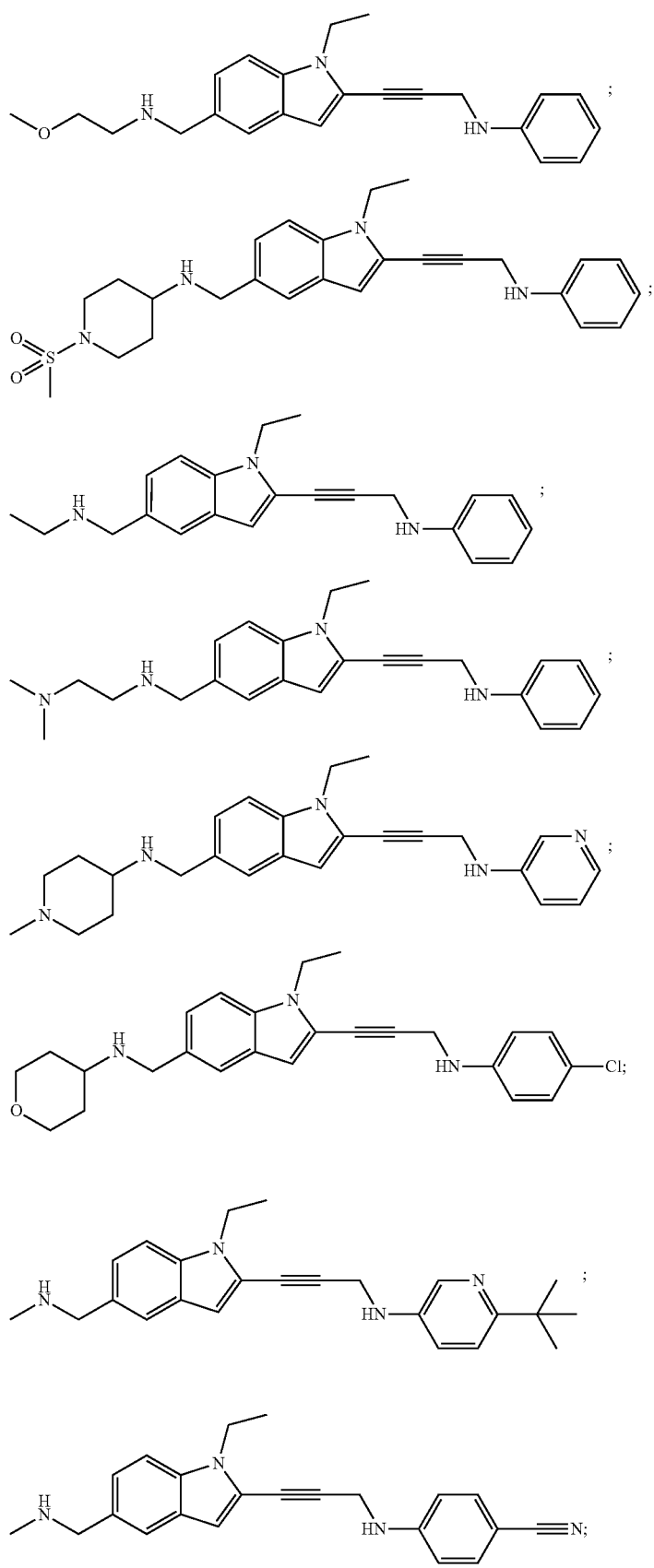

-continued
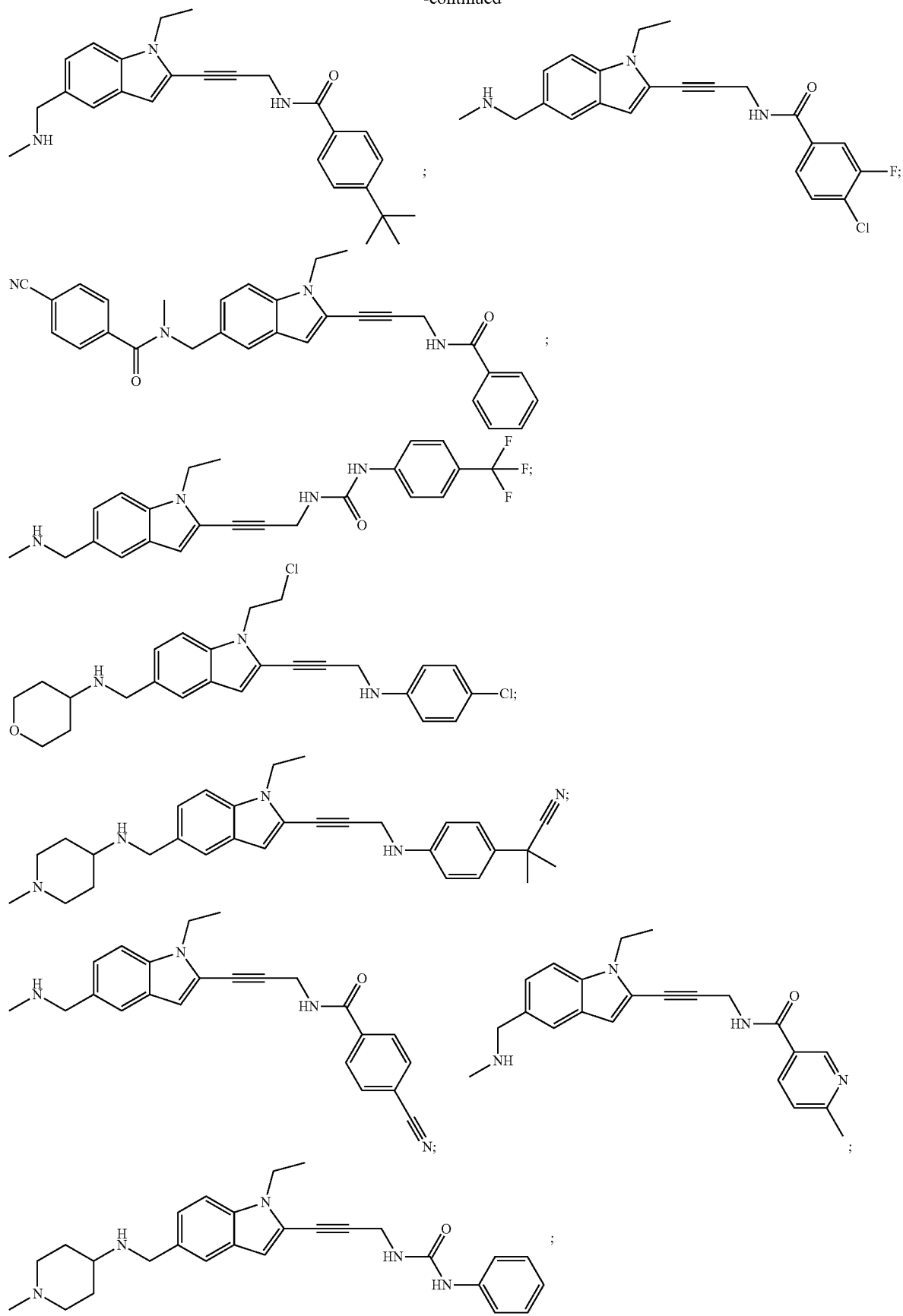

-continued
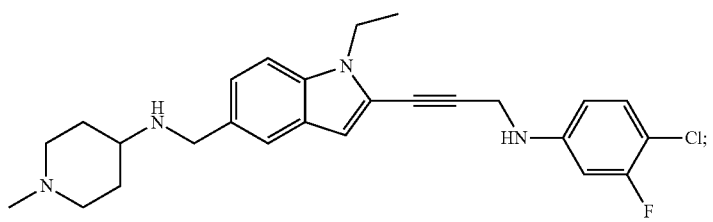
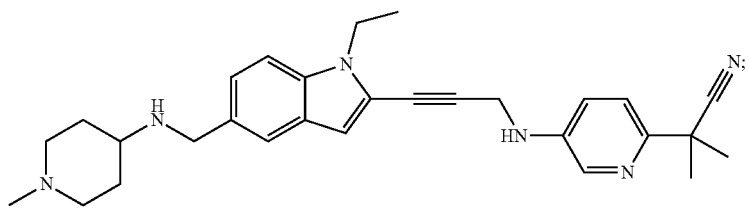
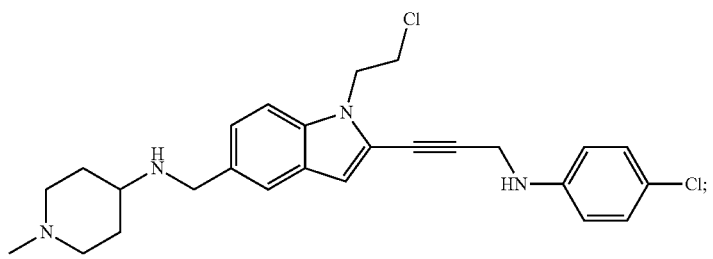
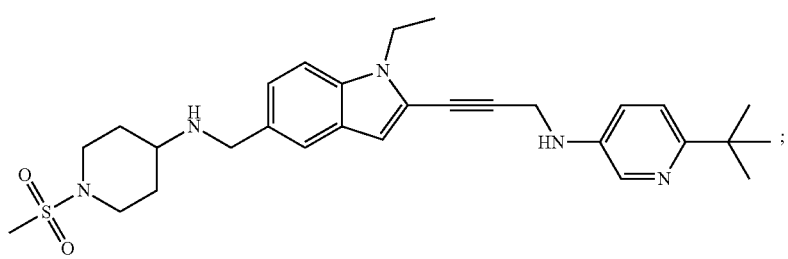
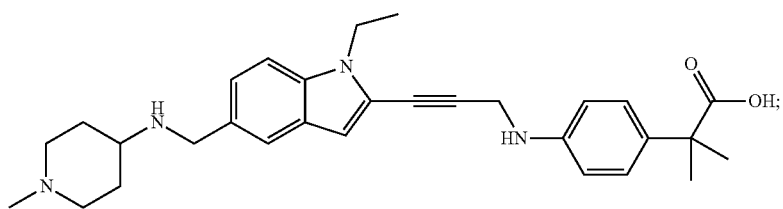
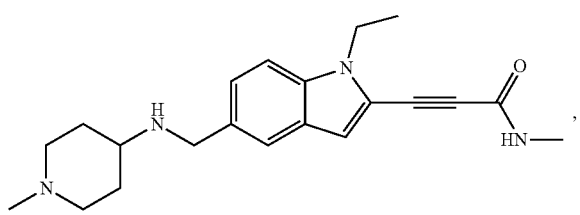
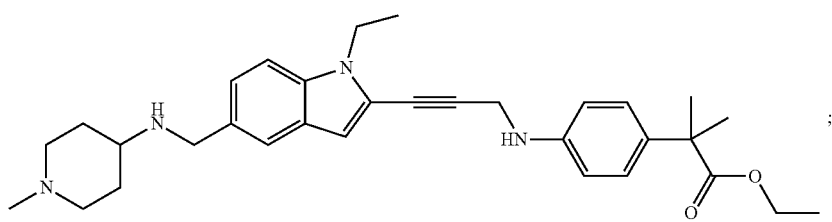

-continued
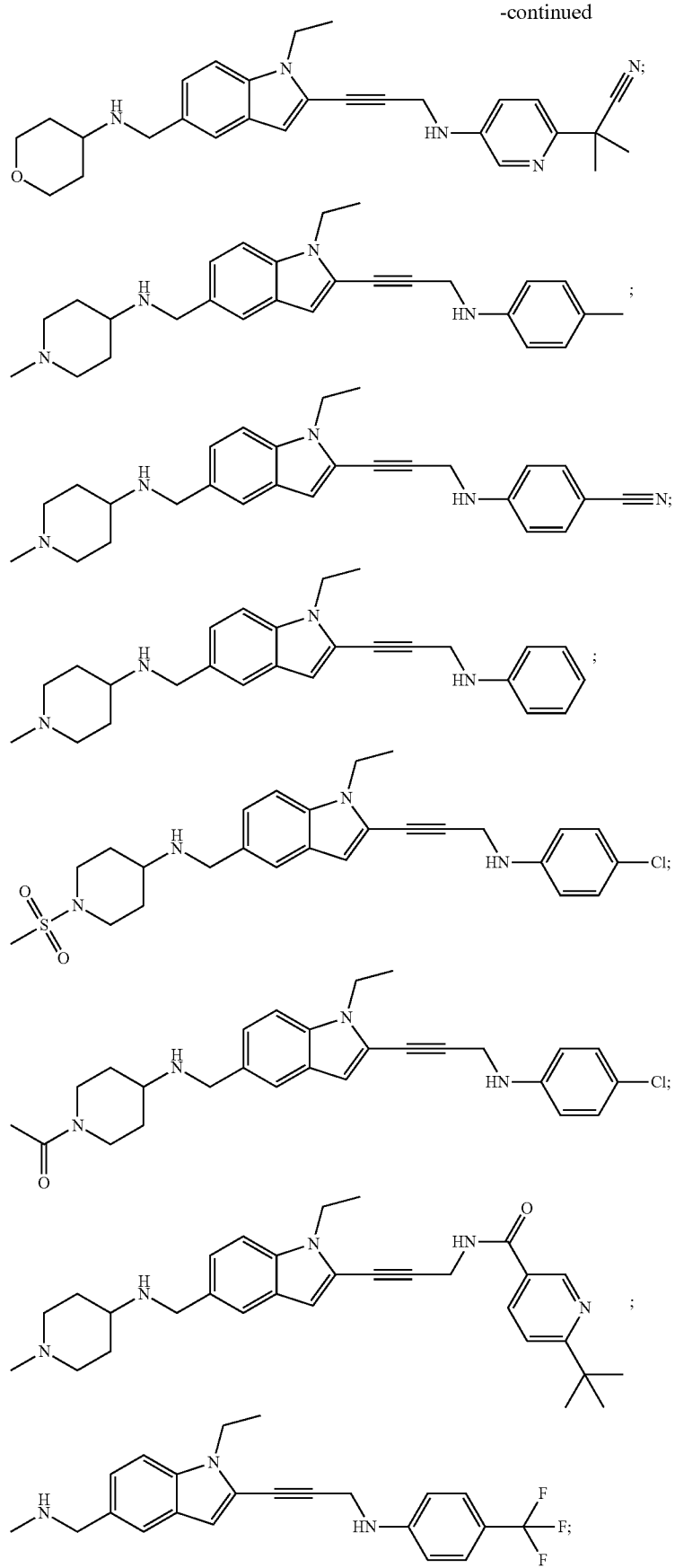

-continued
87
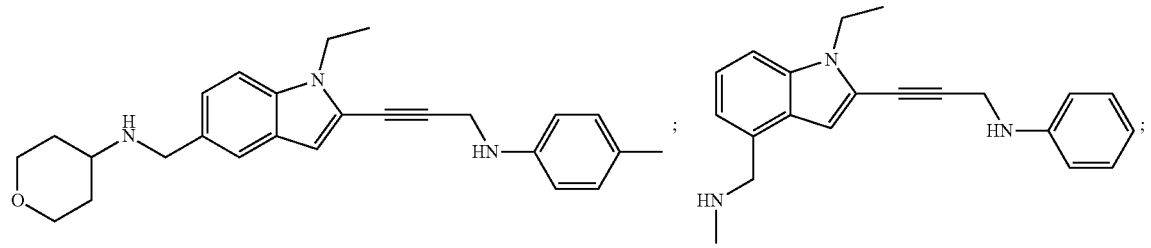
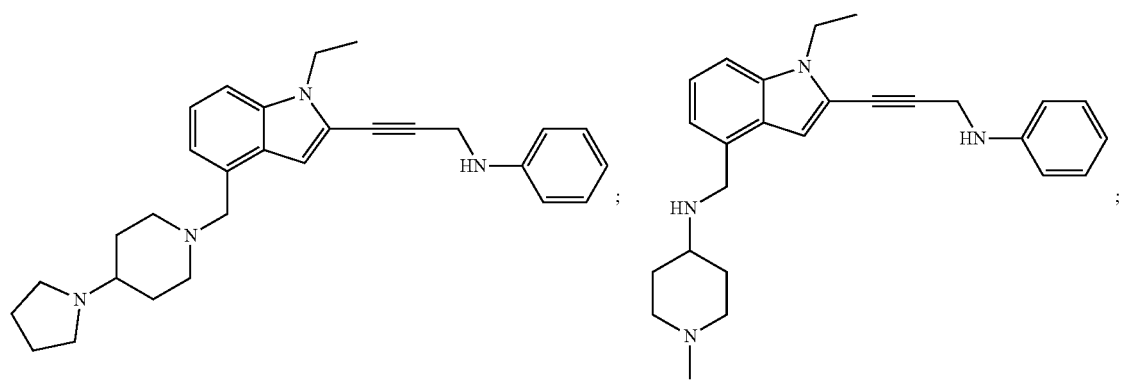
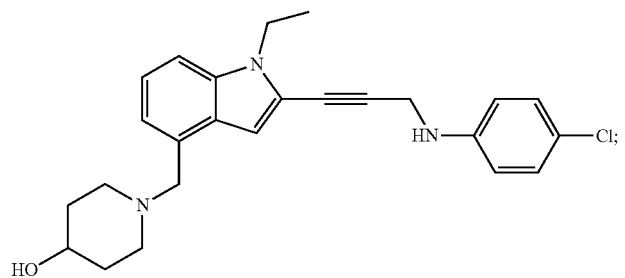
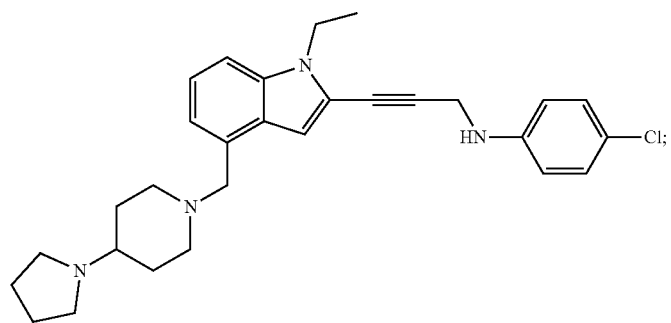
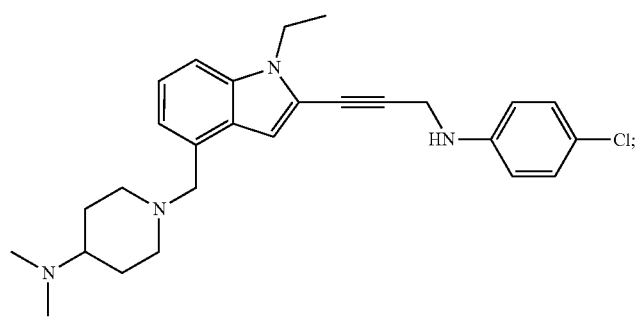
88

-continued
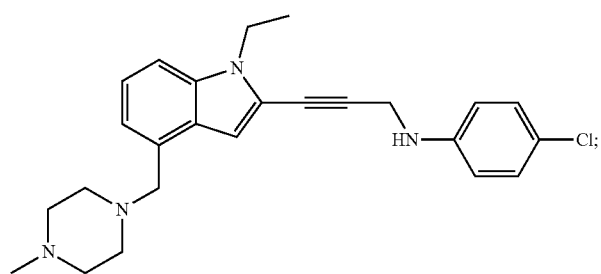
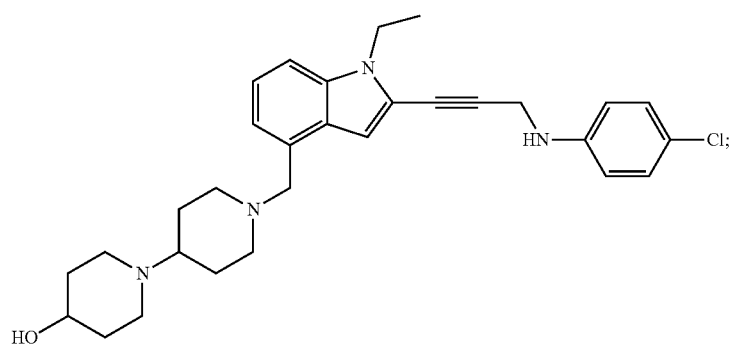
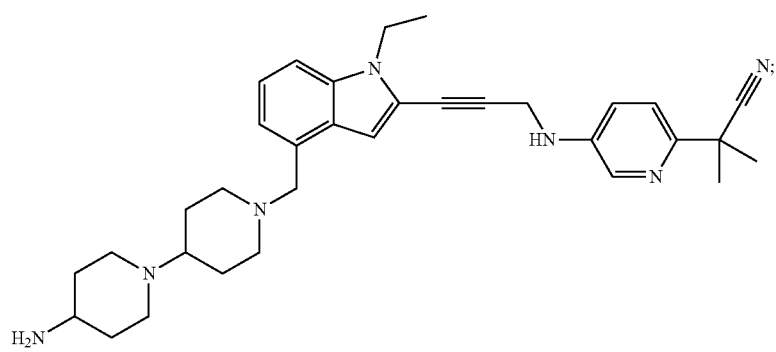
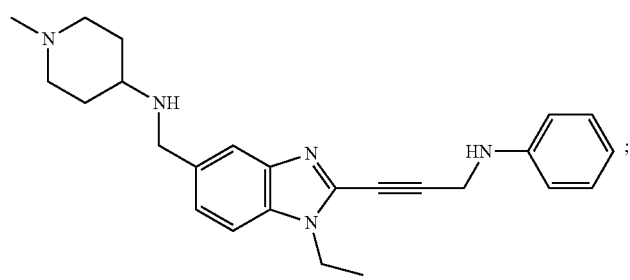
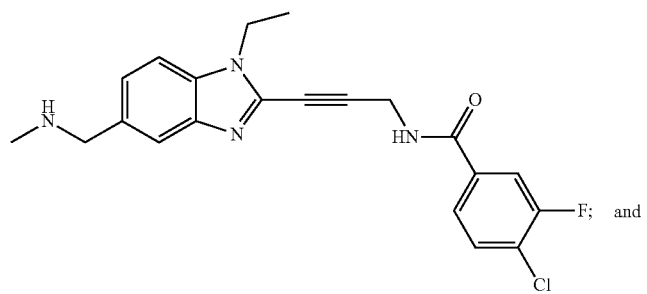

-continued
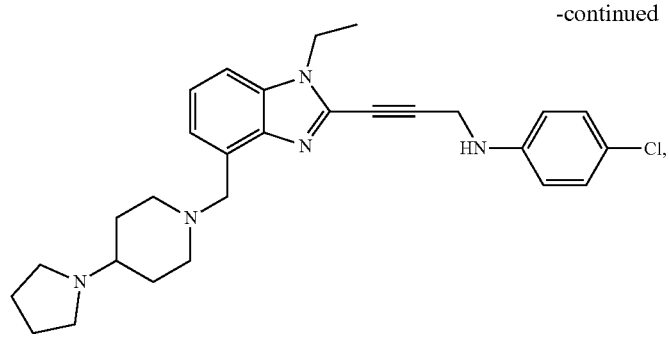
15
or a pharmaceutically-acceptable salt of any of the foregoing.
Non-limiting examples of compounds of the current disclosure include the following:
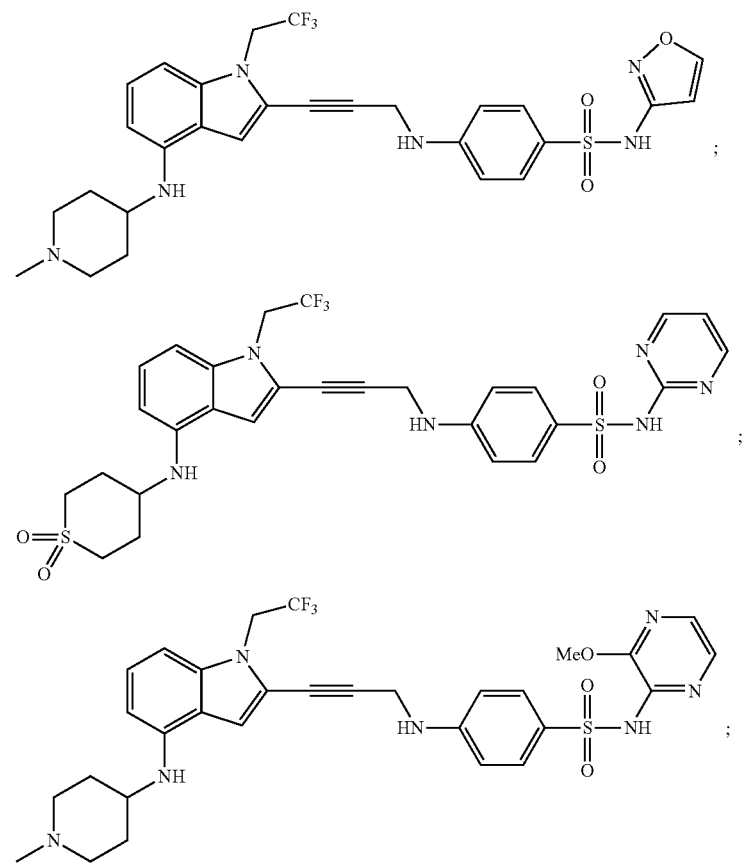
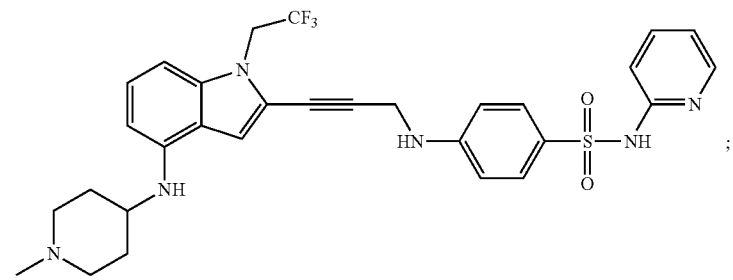

-continued
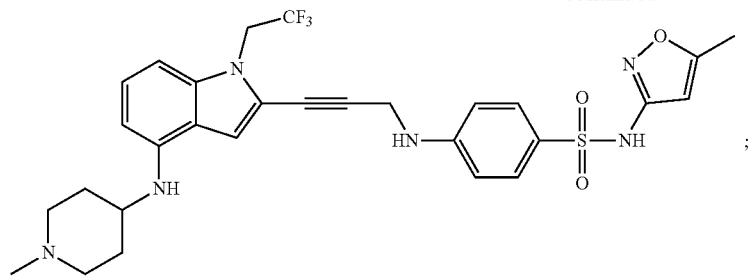
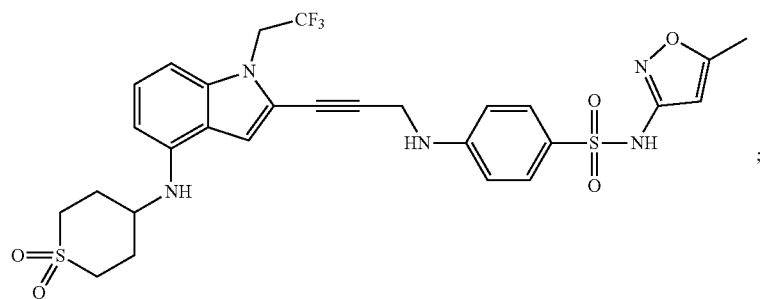
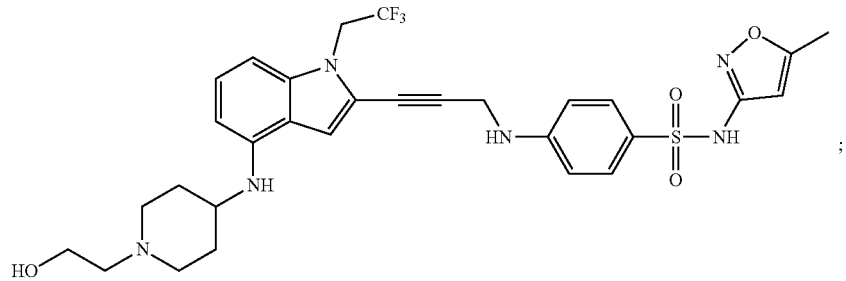
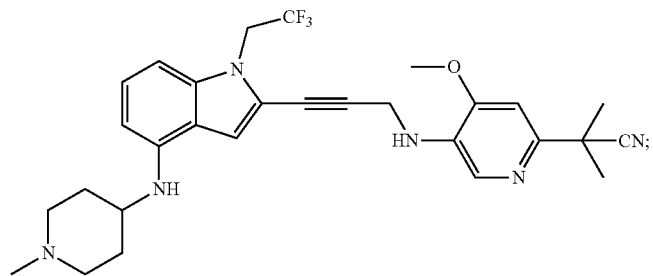
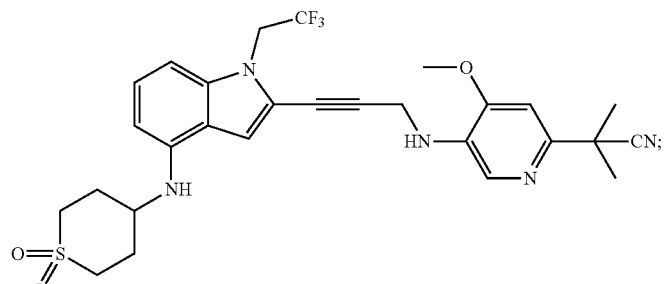
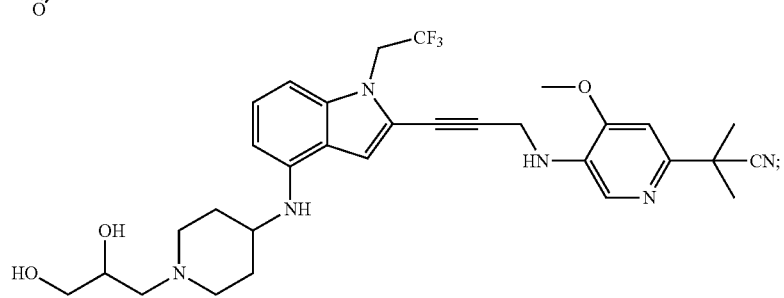

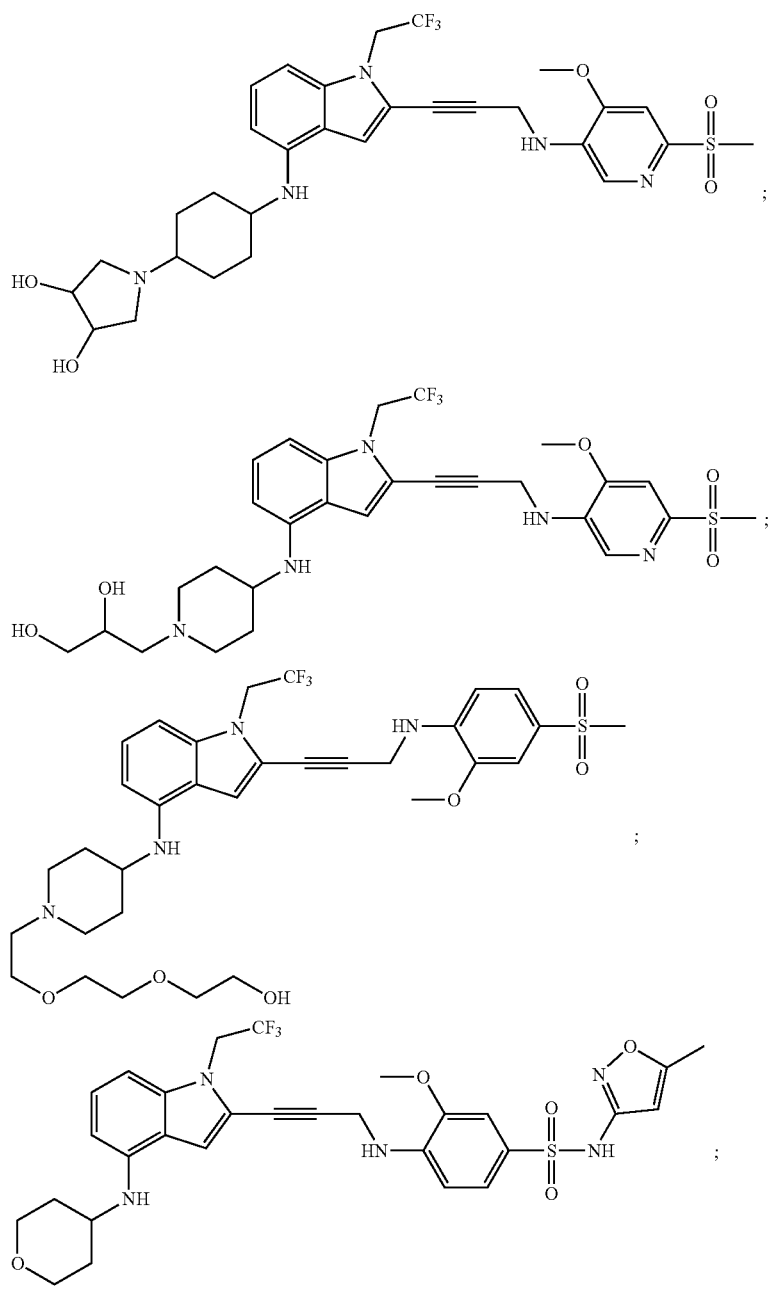
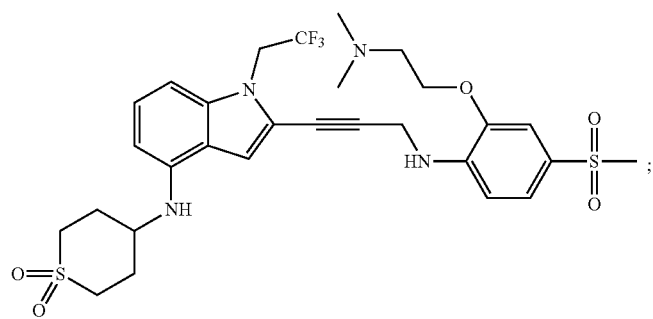

-continued
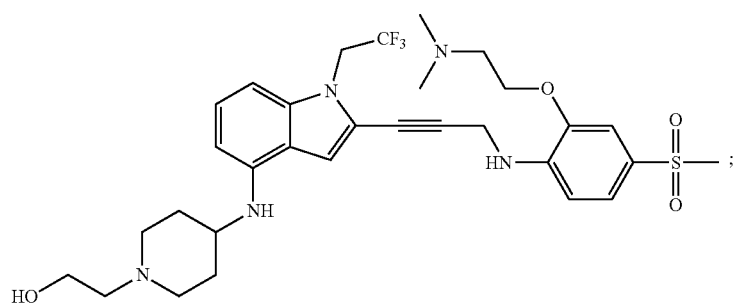
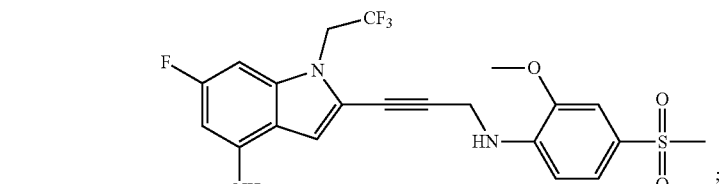
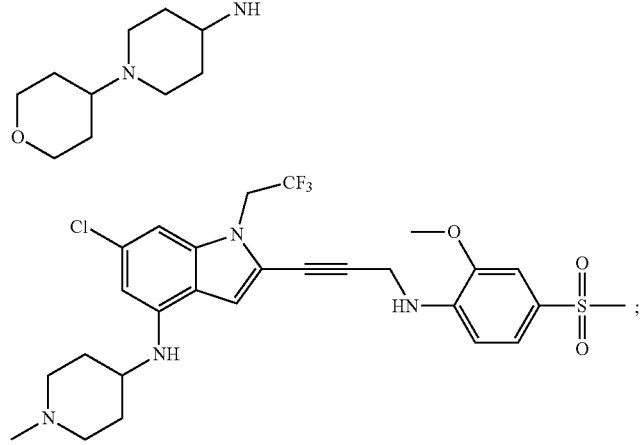
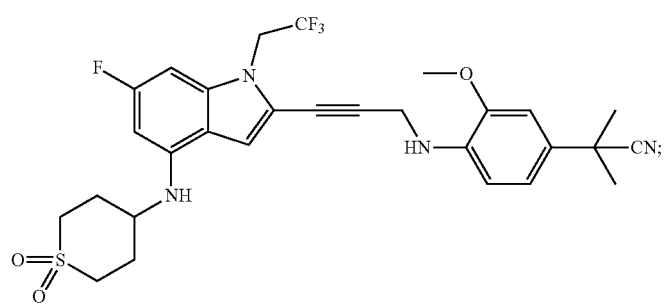
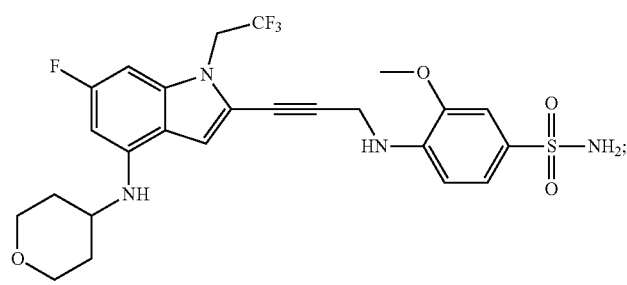

-continued
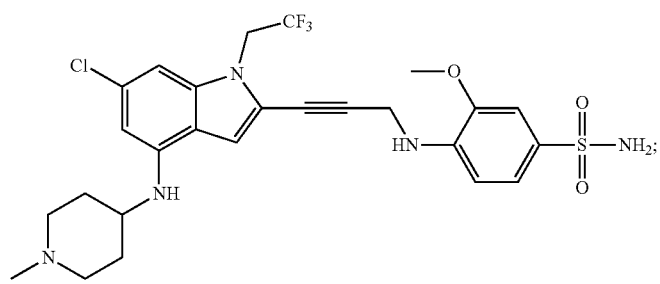
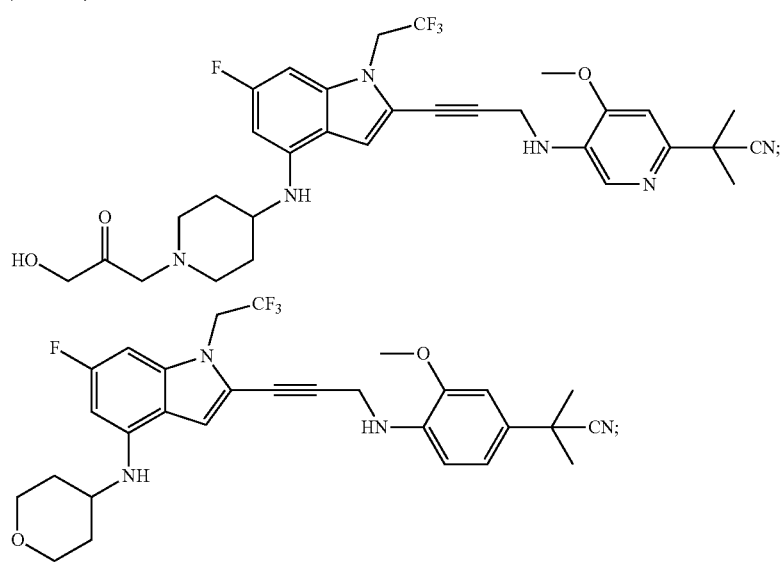
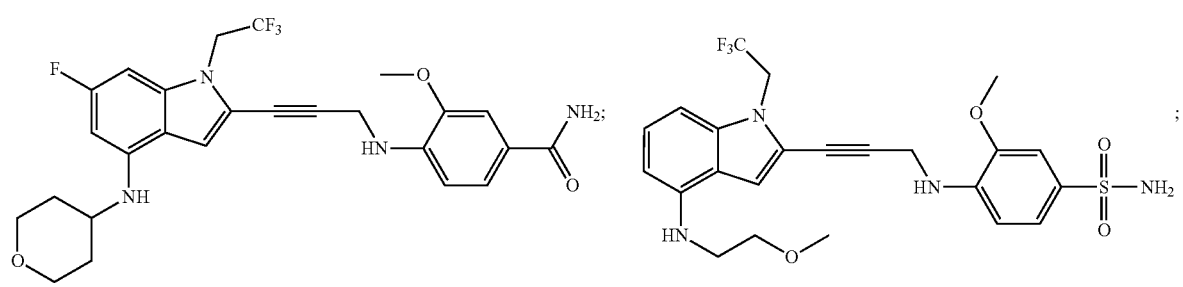
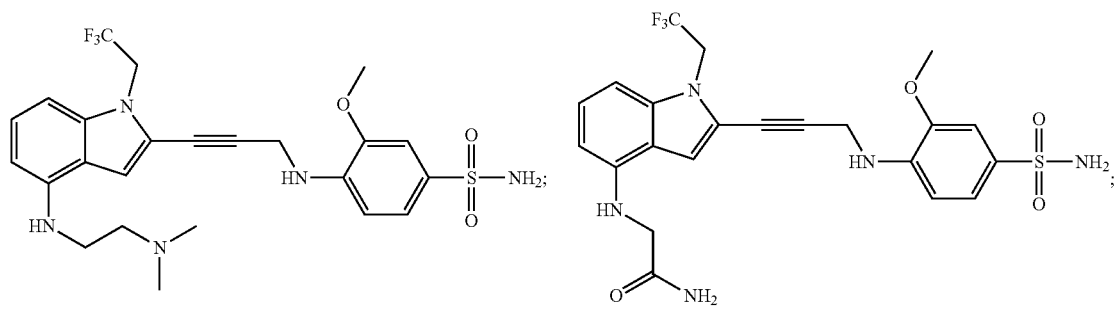

-continued
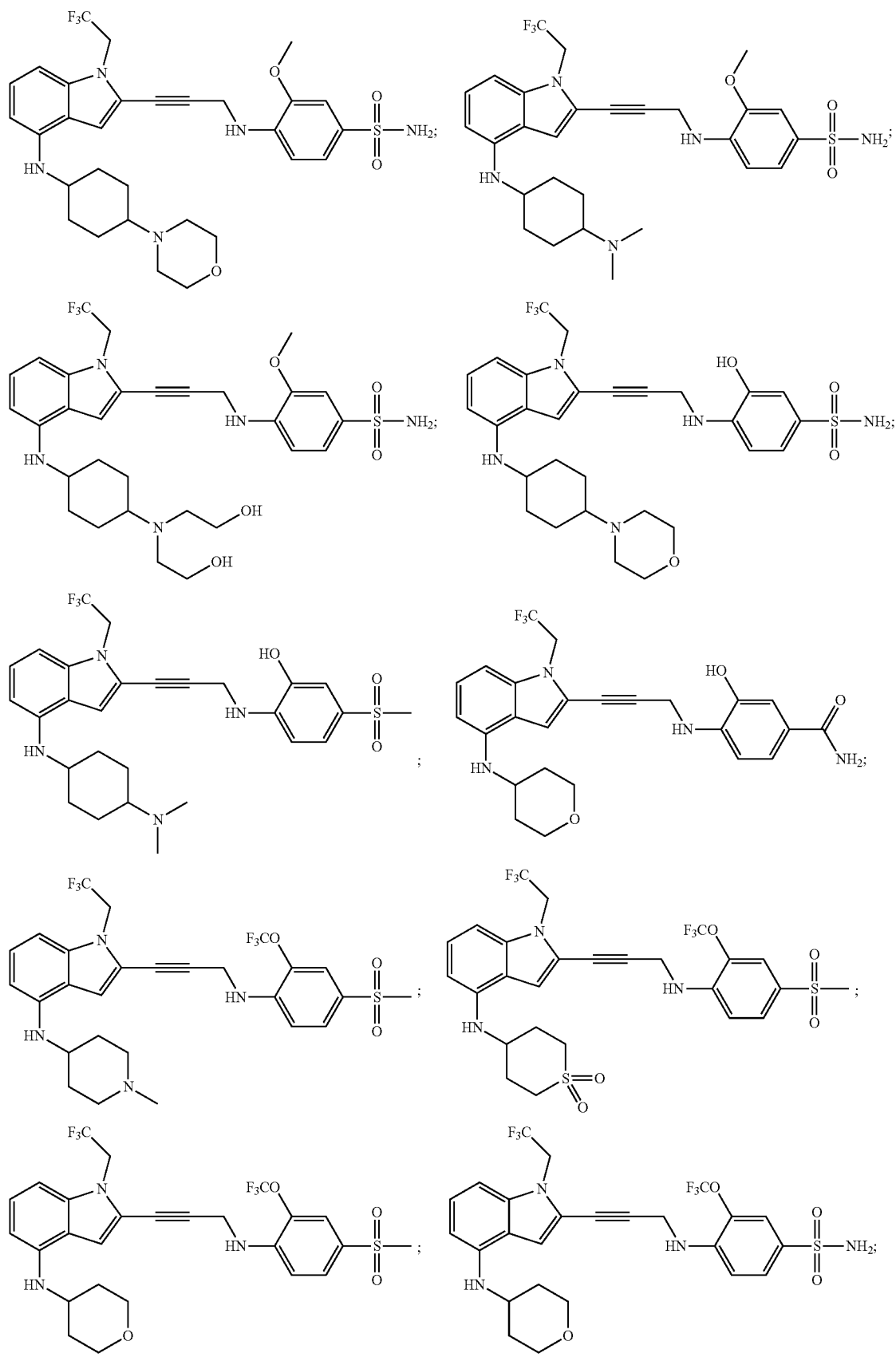

-continued
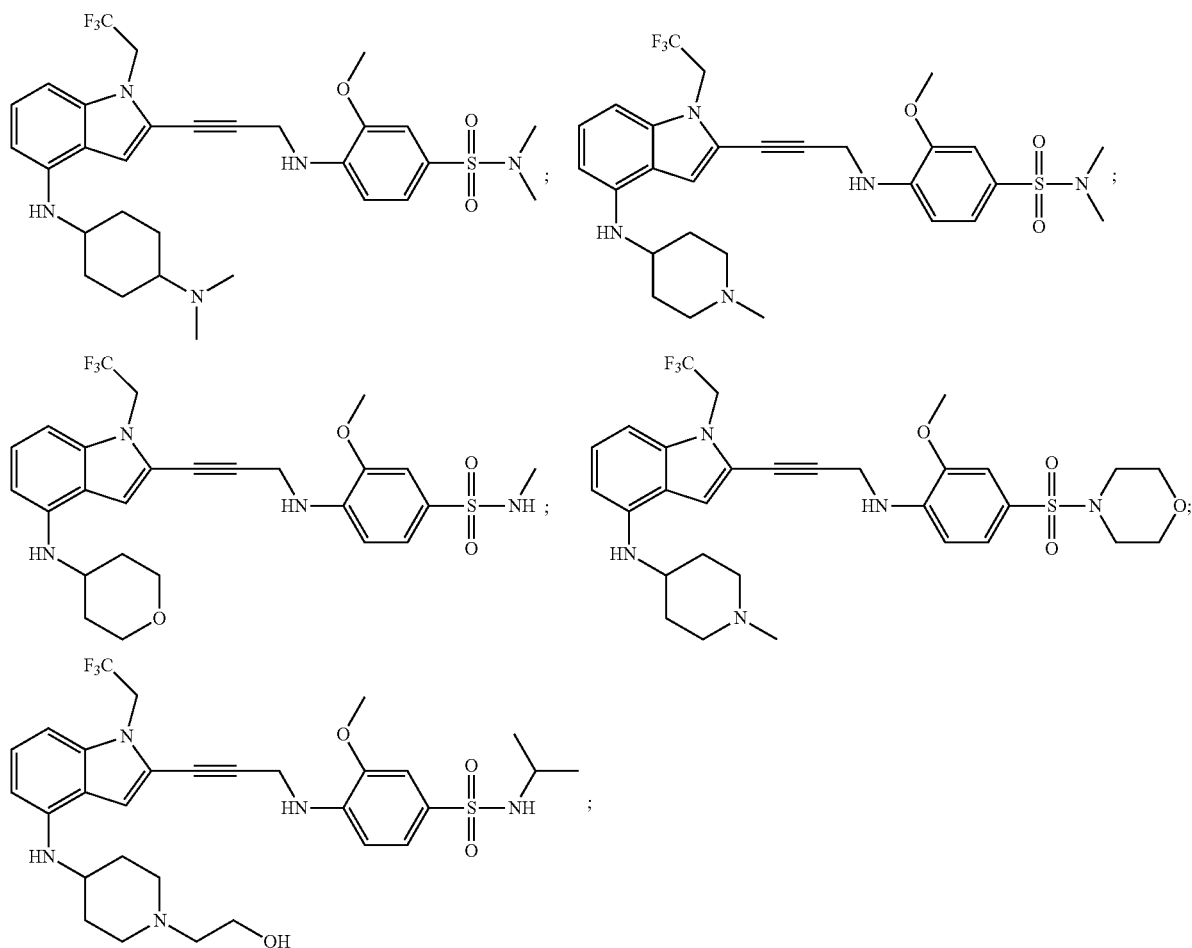
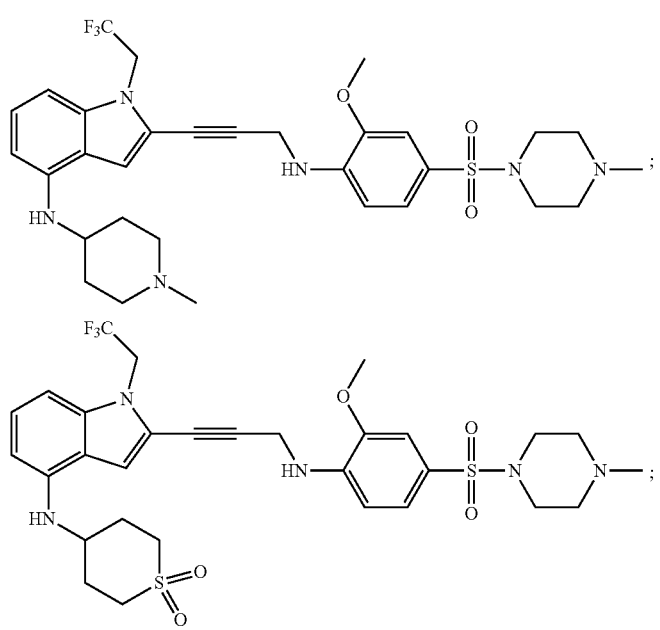

-continued
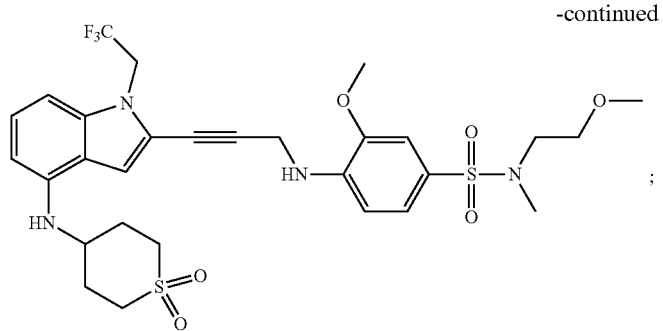
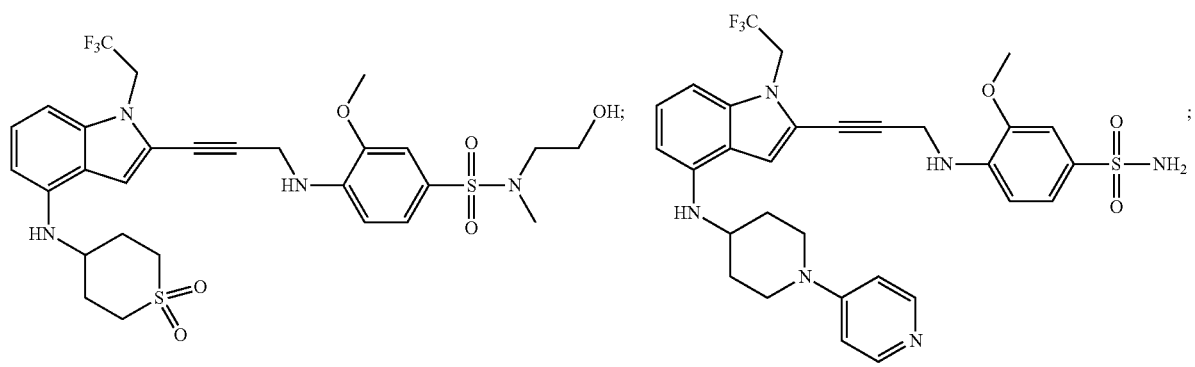
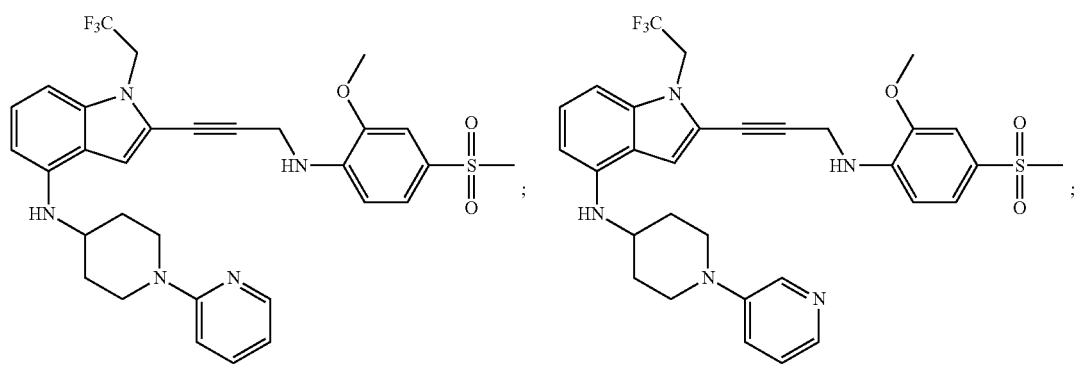
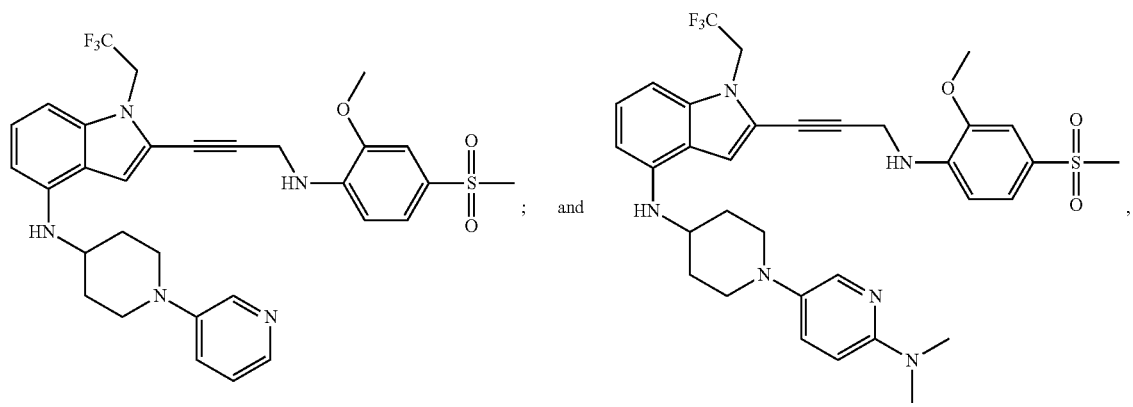 [SMILES: COc1cc(S(C)(=O)=O)ccc1NCC#Cc1cc2c(NC3CCN(c4cccnc4)CC3)cccc2n1CC(F)(F)F ; COc1cc(S(C)(=O)=O)ccc1NCC#Cc1cc2c(NC3CCN(c4ccc(N(C)C)nc4)CC3)cccc2n1CC(F)(F)F]
or a pharmaceutically-acceptable salt of any of the forgoing.
Non-limiting examples of compounds of the current disclosure include the following:

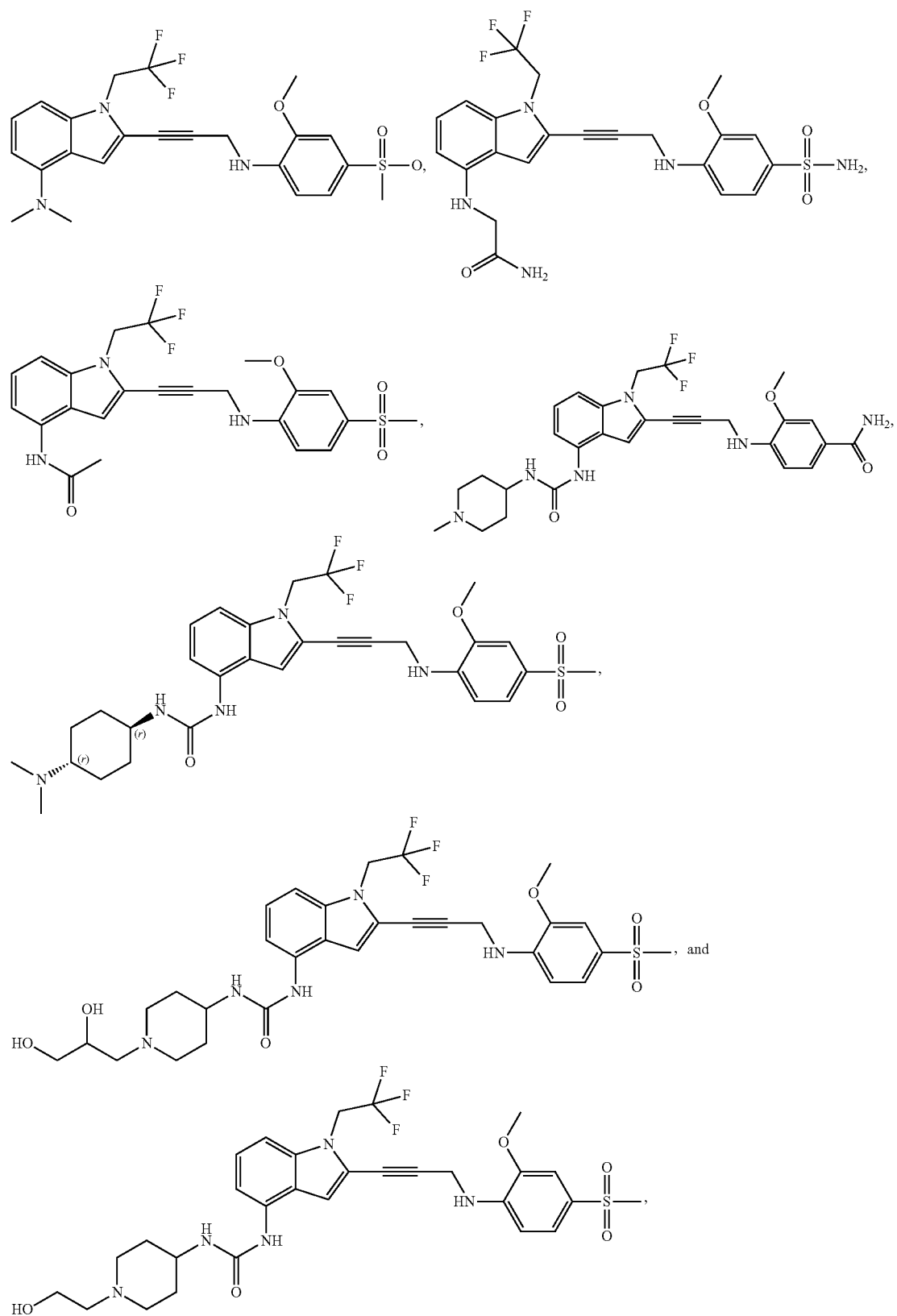
or a pharmaceutically-acceptable salt thereof.

Non-limiting examples of compounds of the current disclosure include the following:
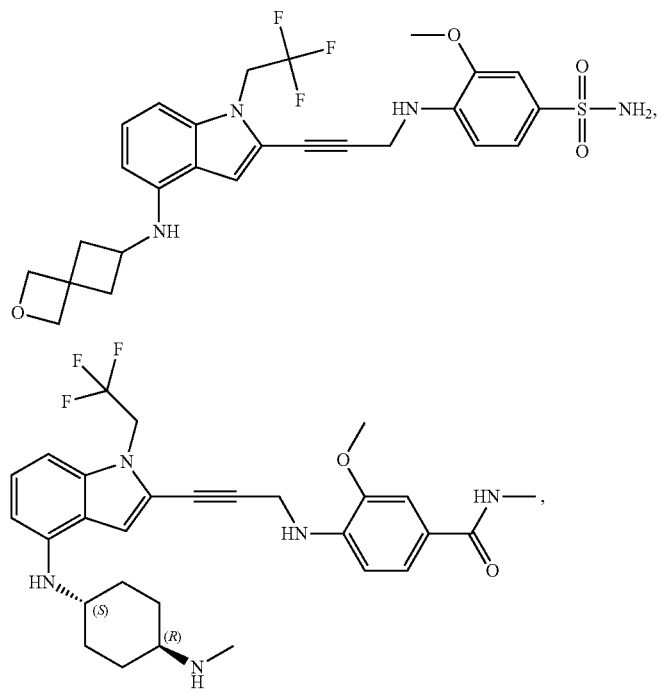
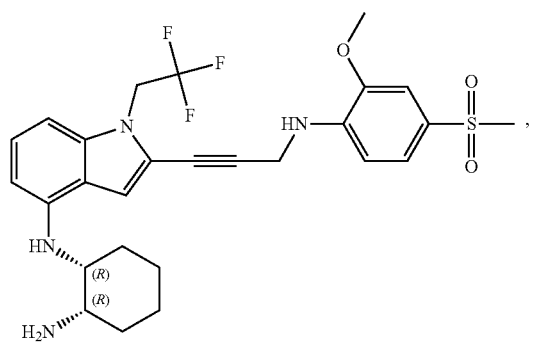
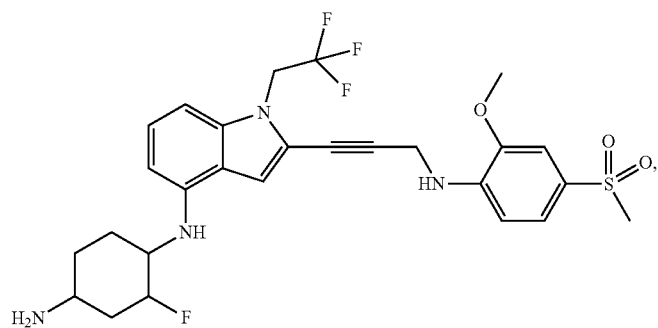

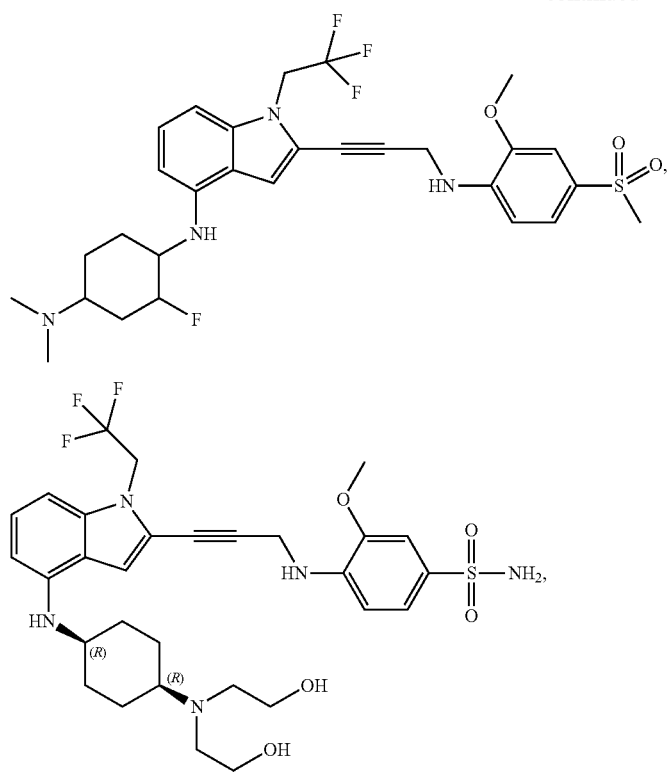
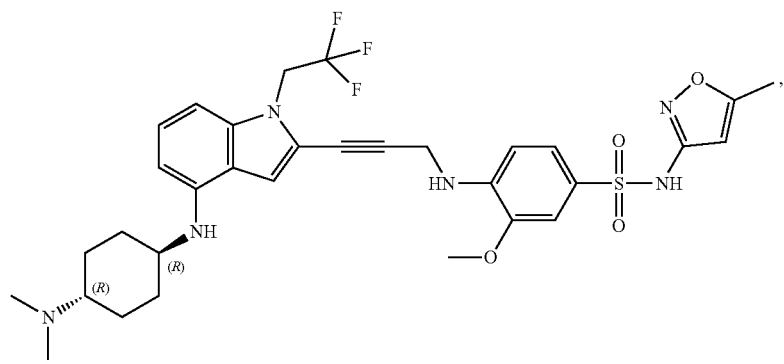
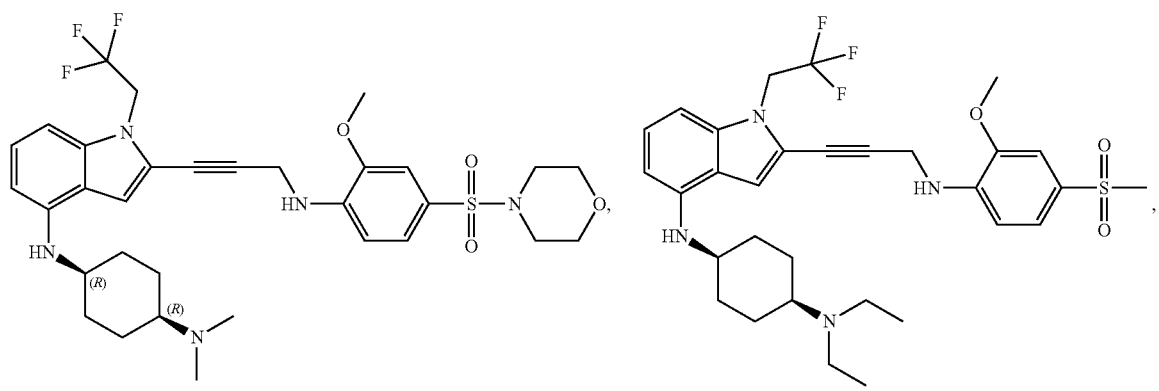

-continued
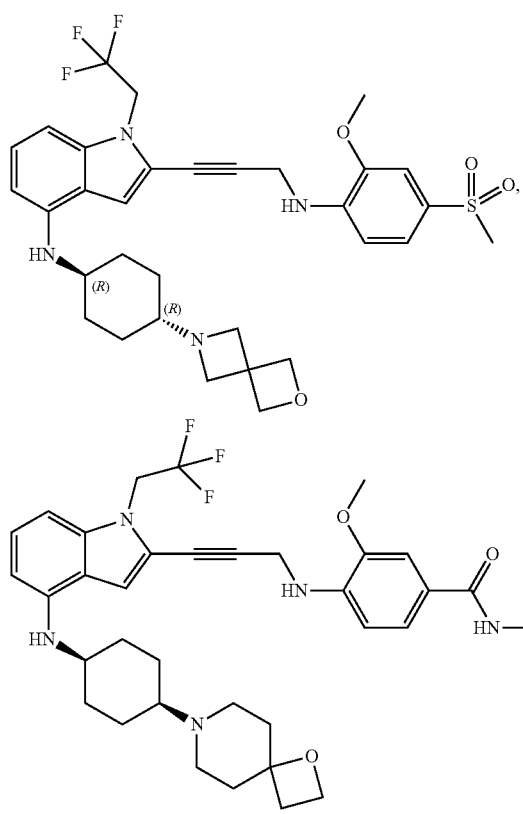
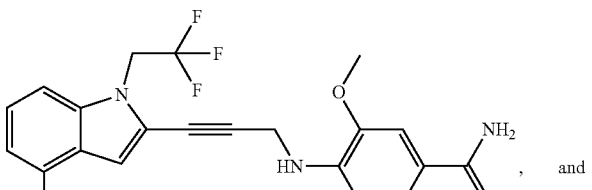
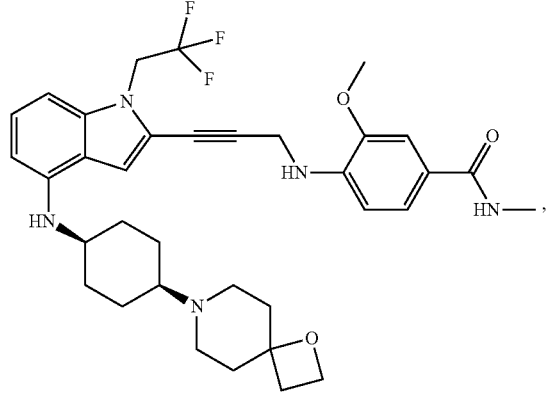 [SMILES: CNC(=O)c1ccc(NCC#Cc2cc3c(N[C@H]4CC[C@@H](N5CCC6(CCO6)CC5)CC4)cccc3n2CC(F)(F)F)c(OC)c1]
or a pharmaceutically-acceptable salt thereof.
Non-limiting examples of compounds of the current disclosure include the following:
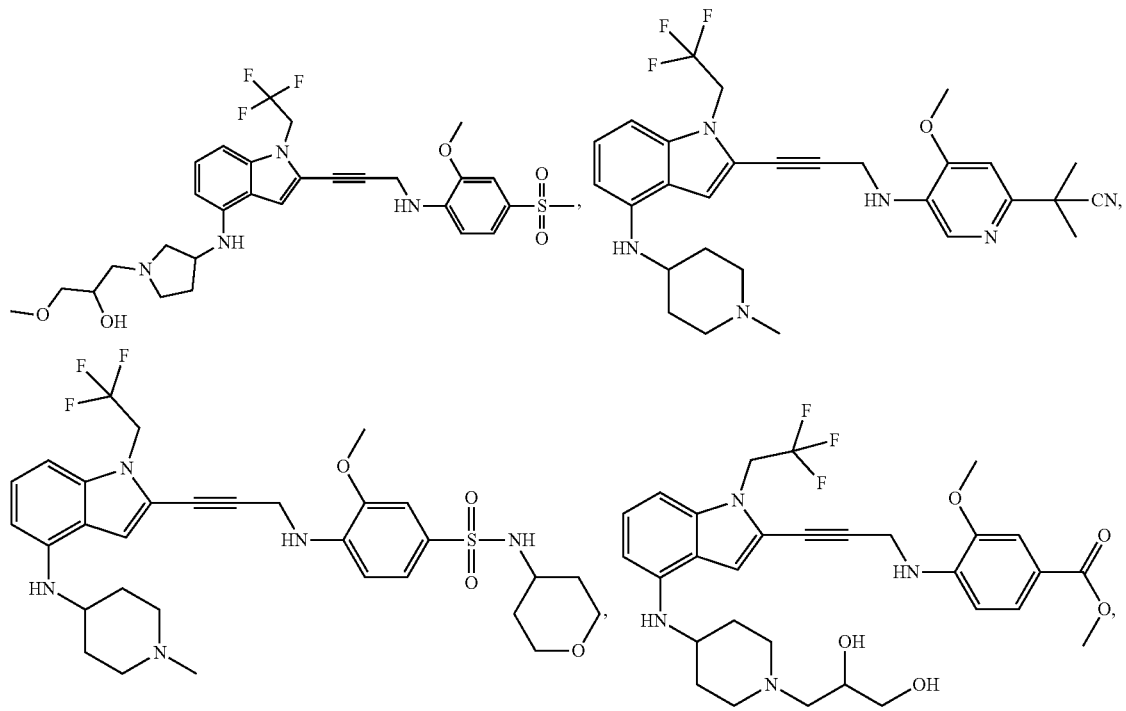

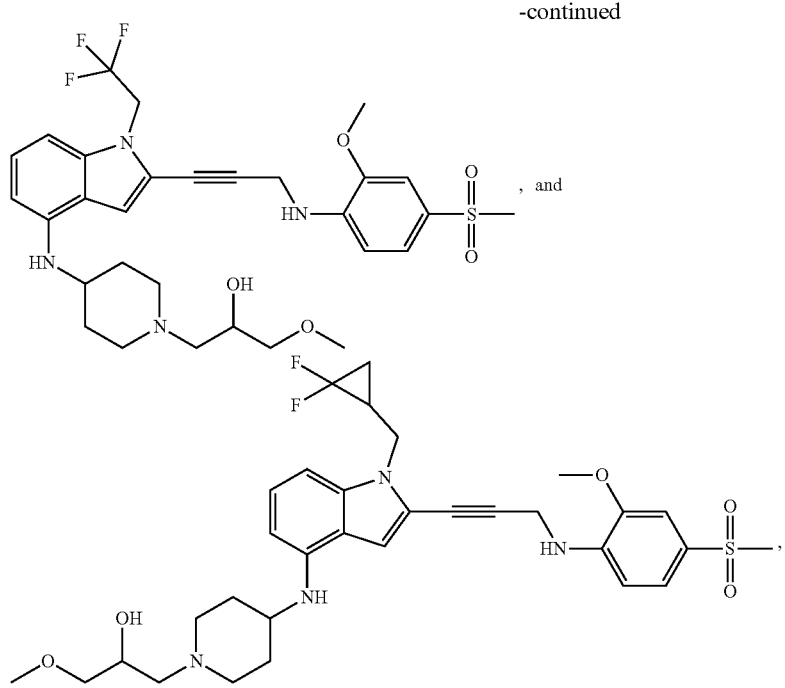
or a pharmaceutically-acceptable salt thereof.
Non-limiting examples of compounds of the current disclosure include the following:
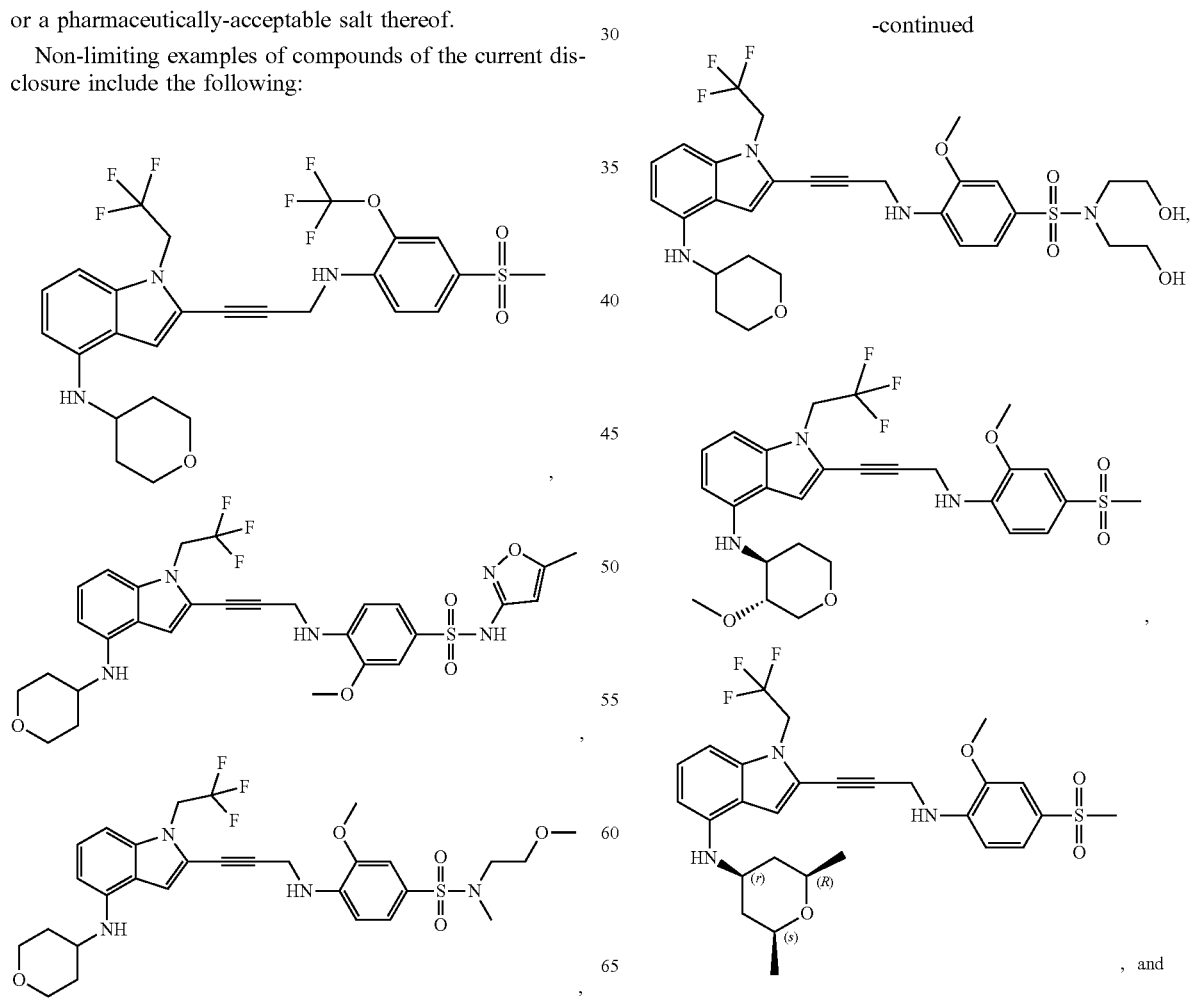

-continued
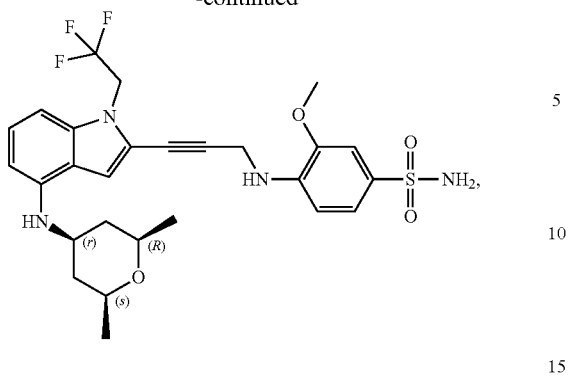
or a pharmaceutically-acceptable salt thereof.
Non-limiting examples of compounds of the current disclosure include the following:
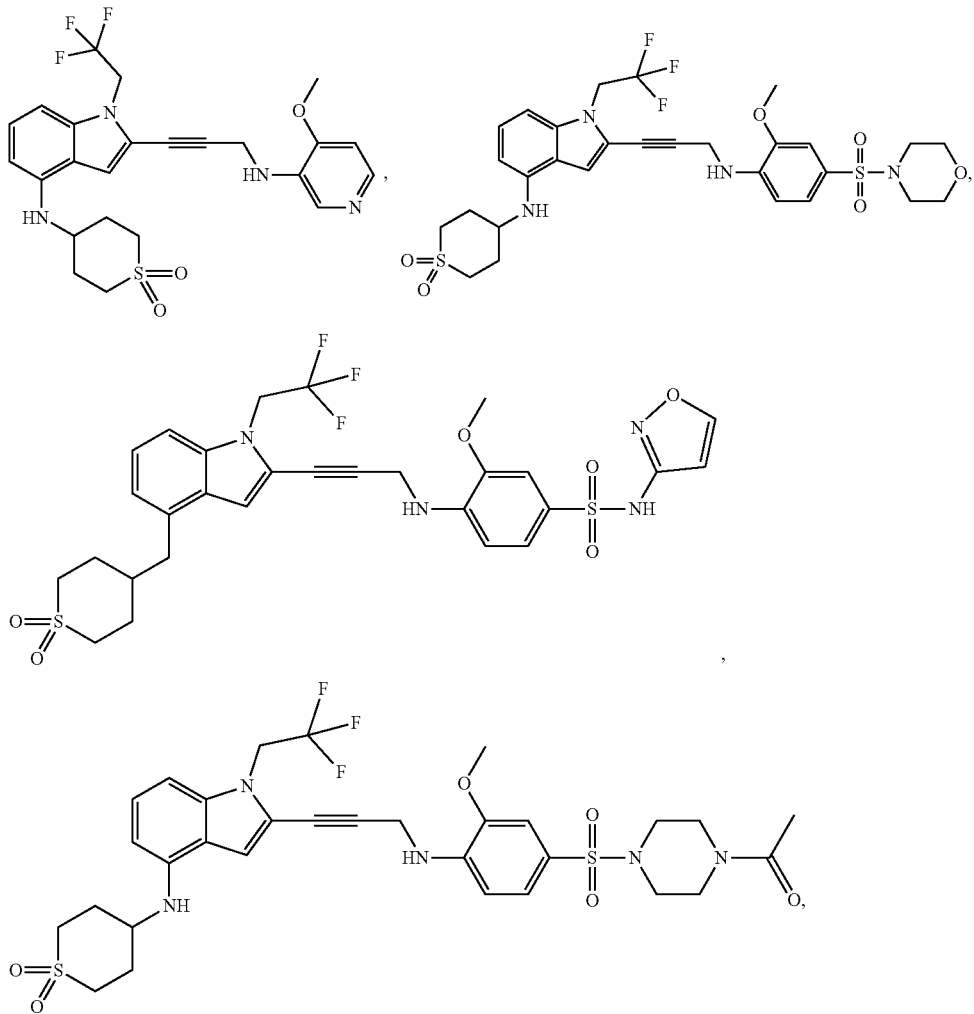

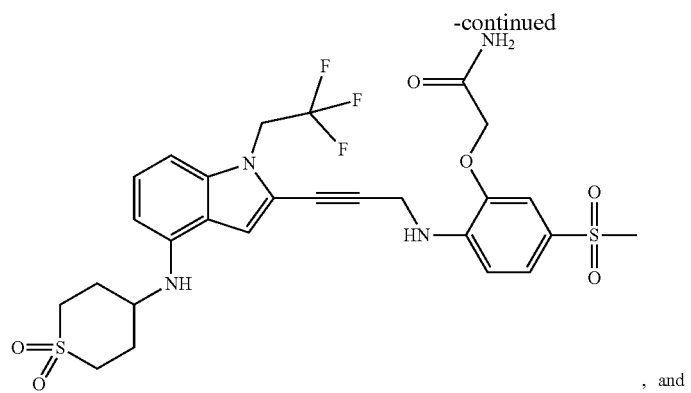
, and
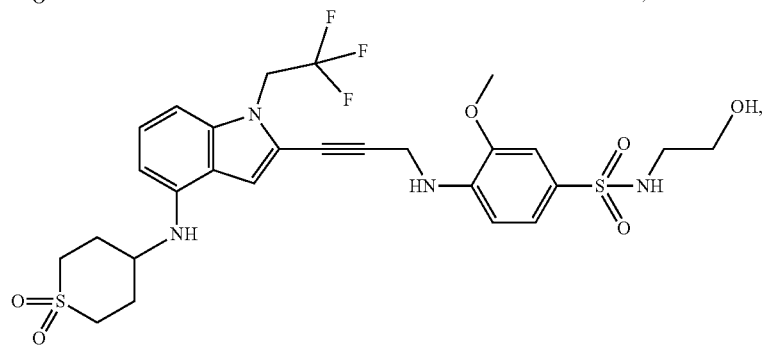
or a pharmaceutically-acceptable salt thereof.
Non-limiting examples of compounds of the current disclosure include the following:
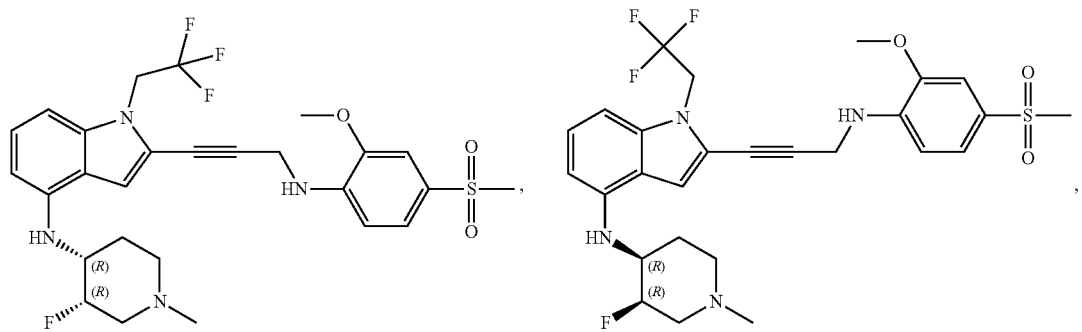
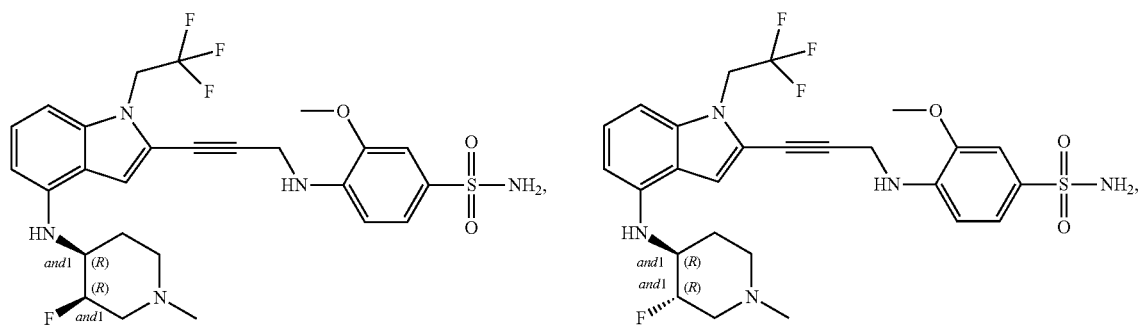

-continued
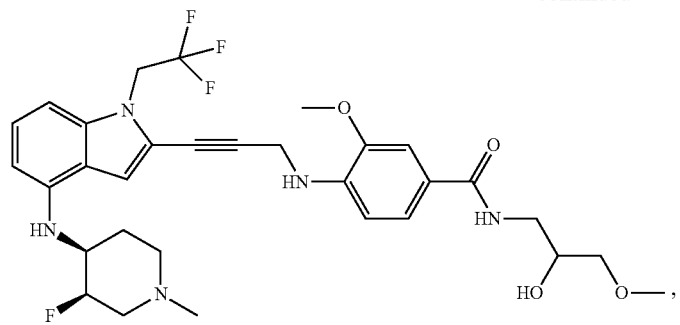
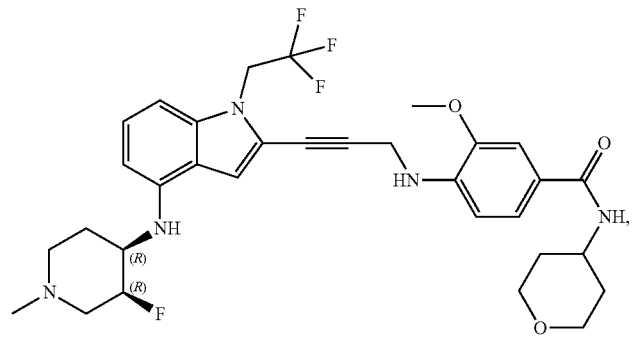
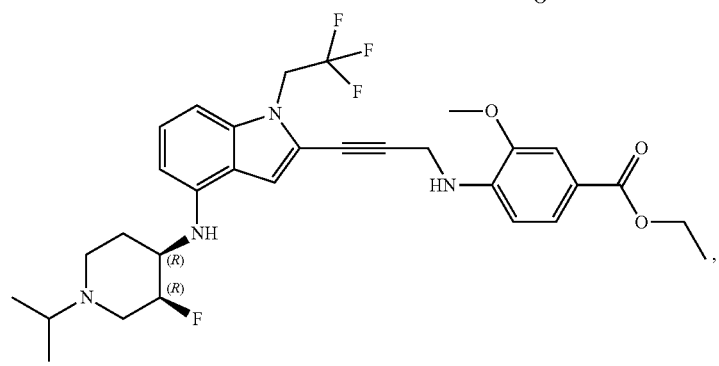
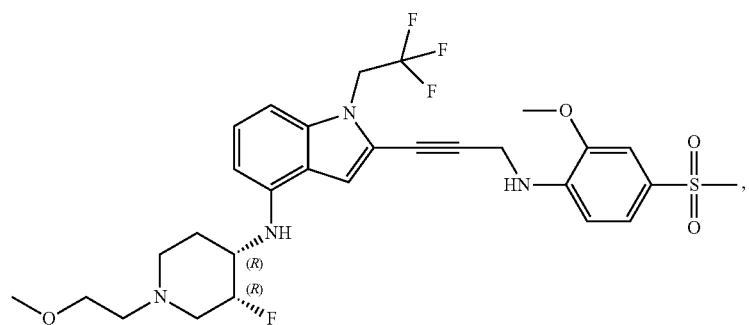
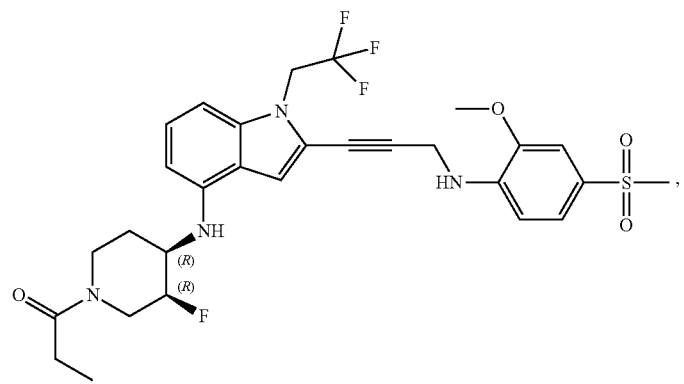

-continued

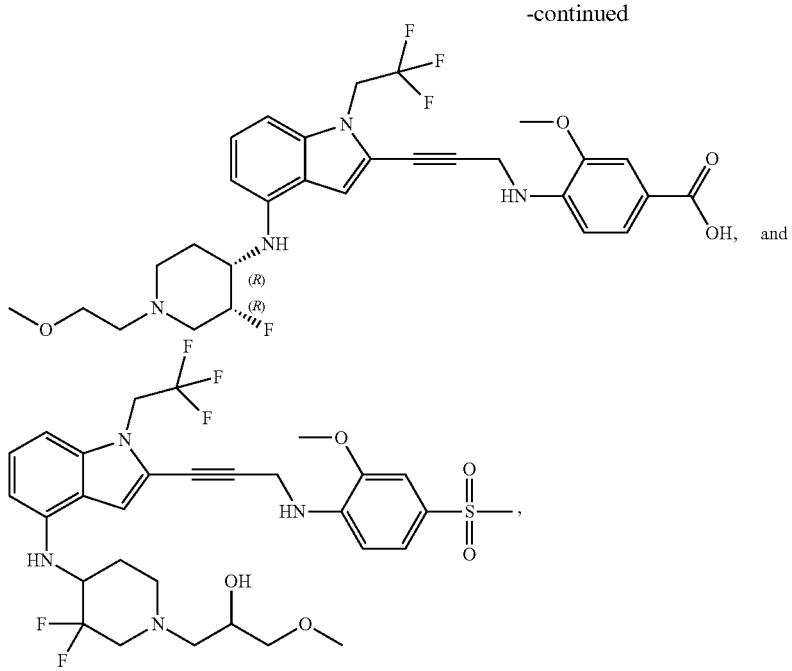

or a pharmaceutically-acceptable salt thereof.

Non-limiting examples of compounds of the current disclosure include the following:

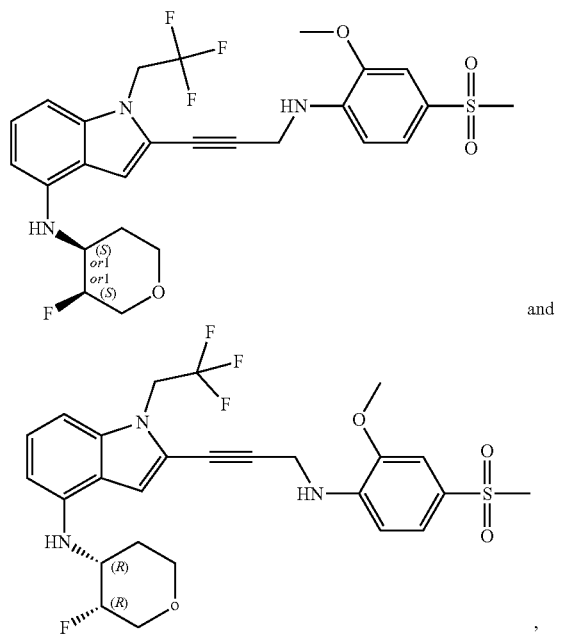

or a pharmaceutically-acceptable salt thereof.

In some embodiments, the disclosure provides a compound comprising: an indole group, wherein the indole group comprises: a) a haloalkyl group at a 1-position of the indole group; b) a first substituent at a 2-position of the indole group, wherein the first substituent is a cyclic group; and c) a second substituent, wherein the second substituent is substituted with at least halo-; or a pharmaceutically-acceptable salt thereof.

In some embodiments, the cyclic group is aryl, heteroaryl, or heterocyclyl, each of which is substituted or unsubstituted. In some embodiments, the cyclic group is unsubstituted aryl. In some embodiments, the cyclic group is substituted aryl. In some embodiments, the cyclic group is substituted phenyl. In some embodiments, the cyclic group is substituted or unsubstituted heteroaryl. In some embodiments, the heteroaryl is an aromatic 5-membered or 6-membered monocyclic ring. In some embodiments, the heteroaryl is thiazolyl, thiadiazolyl, pyrazolyl, thiophenyl, or oxadiazolyl. In some embodiments, the heteroaryl is pyridinyl or pyrimidinyl.

In some embodiments, the second substituent is at a 4-position of the indole group. In some embodiments, the second substituent is a second cyclic group that is substituted or unsubstituted. In some embodiments, the second cyclic group is heterocyclyl. In some embodiments, the heterocyclyl is piperidinyl. In some embodiments, the heterocyclyl is tetrahydropyranyl. In some embodiments, the heterocyclyl is substituted with fluoro-. In some embodiments, the heterocyclyl is substituted with chloro-. In some embodiments, the haloalkyl group is trifluoroethyl.

In some embodiments, the disclosure provides a compound, the compound comprising an indole group, wherein the indole group comprises: a) a substituted or unsubstituted non-cyclic group at a 3-position of the indole group; and b) a substituted or unsubstituted cyclic group at a 2-position of the indole group, wherein the compound increases a stability of a biologically-active conformation of a p53 mutant relative to a stability of a biologically-active conformation of the p53 mutant in an absence of the compound, or a pharmaceutically-acceptable salt thereof.

In some embodiments, the non-cyclic group is hydrogen. In some embodiments, the non-cyclic group is halo-. In some embodiments, the cyclic group is aryl, heteroaryl, heterocyclyl, or cycloalkylene, each of which is substituted or unsubstituted. In some embodiments, the cyclic group is aryl or heteroaryl, each of which is substituted or unsubstituted. In some embodiments, the cyclic group is substituted aryl. In some embodiments, the cyclic group is substituted phenyl. In some embodiments, the cyclic group is phenyl substituted with alkyl, cycloalkyl, alkoxy, an amine group, a carboxyl group, a carboxylic acid group, a carbamide group, or an amide group, each of which is substituted or unsubstituted; cyano, halo-, or hydrogen.

In some embodiments, the cyclic group is substituted heteroaryl. In some embodiments, the cyclic group is an aromatic 5-membered, 6-membered, 7-membered, or 8-membered monocyclic ring system comprising 1, 2, or 3 heteroatoms as ring members, wherein each heteroatom is independently selected from O, N, or S. In some embodiments, the cyclic group is pyridinyl, pyrimidinyl, thiadiazolyl, thiazolyl, pyrazolyl, thiophenyl, or oxadiazolyl, In some embodiments, the cyclic group is 1,3,5-thiadiazol-2-yl. In some embodiments, the cyclic group is 1,3,4-oxadiazol-2-yl or 1,2,4-oxadiazol-2-yl. In some embodiments, the cyclic group is pyridinyl.

In some embodiments, the indole group further comprises a substituent at a 4-position of the indole group. In some embodiments, the substituent is an amino group that is substituted or unsubstituted. In some embodiments, the amino group is substituted with a second cyclic group. In some embodiments, the second cyclic group is a heterocyclyl group substituted with at least halo-. In some embodiments, the heterocyclyl group is substituted with at least fluoro-. In some embodiments, the heterocyclyl group is substituted with at least chloro-. In some embodiments, the heterocyclyl group is piperidinyl. In some embodiments, the heterocyclyl group is tetrahydropyranyl.

Non-limiting examples of compounds of the disclosure include compounds of any of the following formulae:

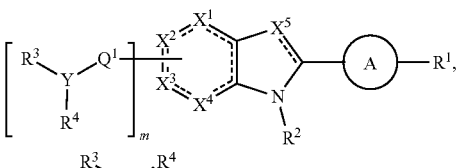

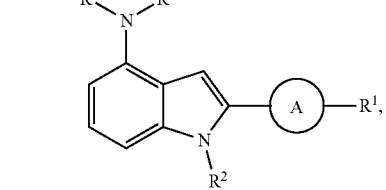

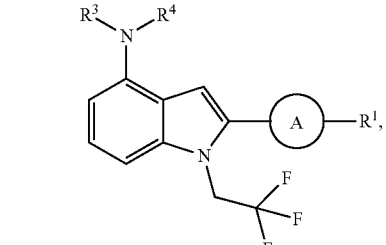

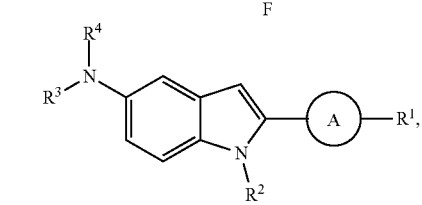

-continued

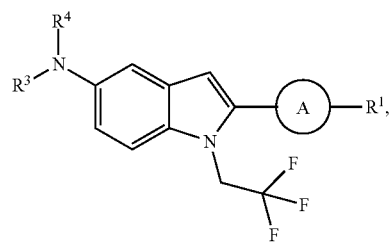

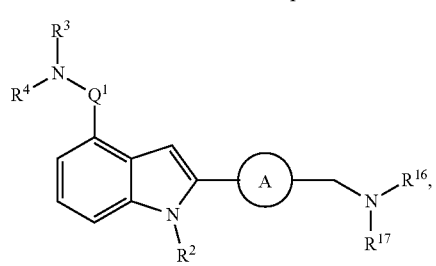

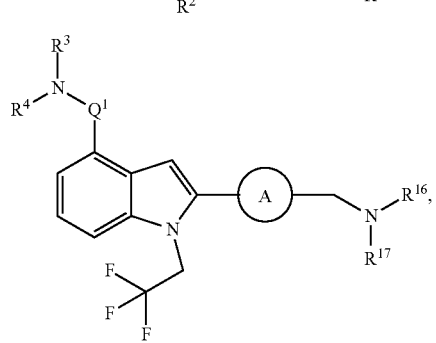

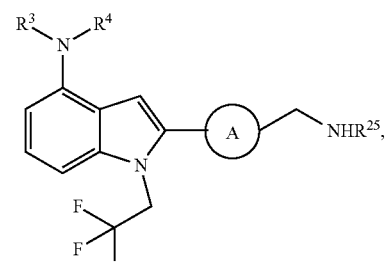

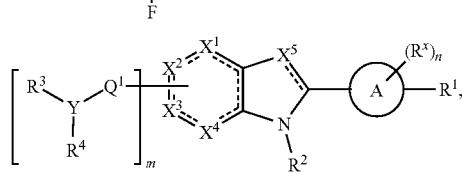

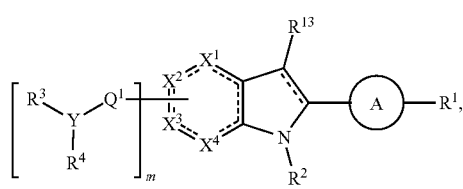

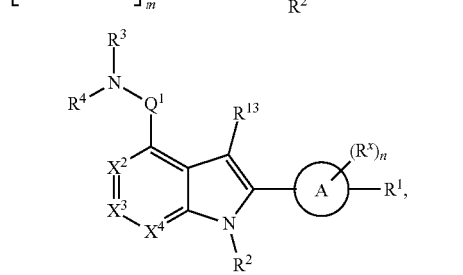

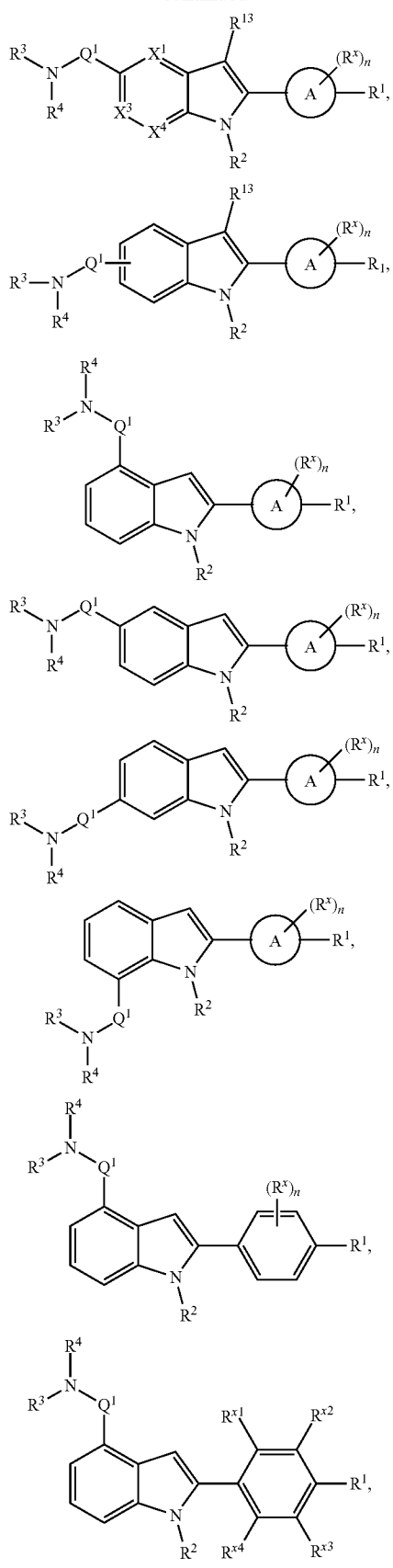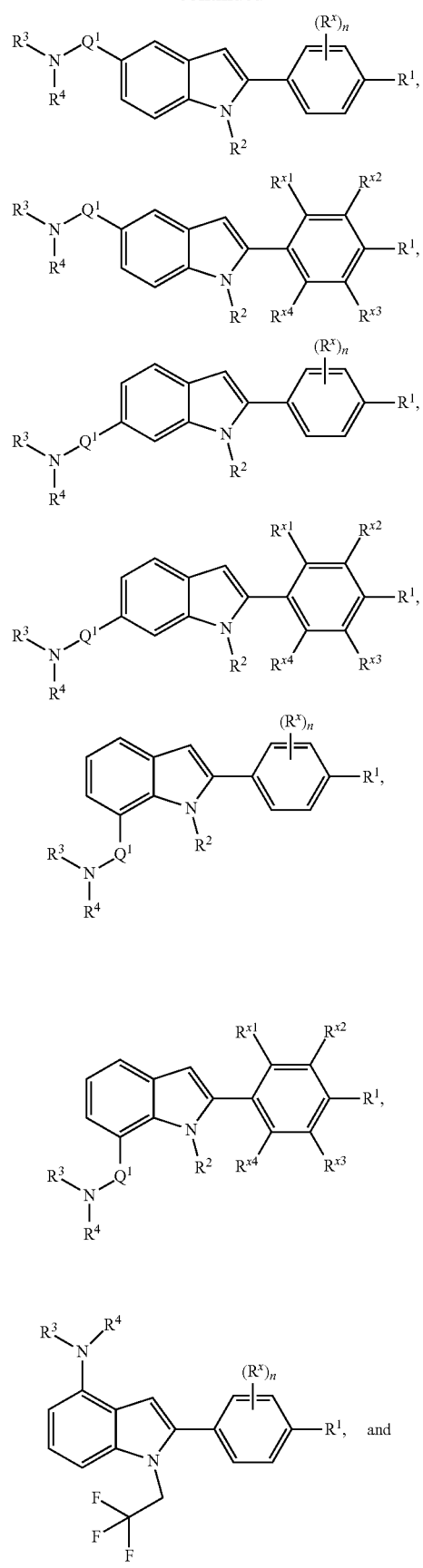

-continued

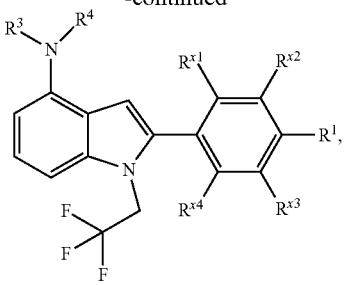

or a pharmaceutically-acceptable salt thereof.

In some embodiments, the disclosure provides a compound of the formula:

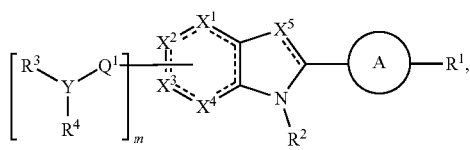

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
A is a substituted or unsubstituted ring;
$Q^1$ is C=O, C=S, C=$CR^{14}R^{15}$, C=$NR^{14}$, alkylene, alkenylene, or alkynylene, each of which is independently substituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, A is substituted or unsubstituted aryl, heteroaryl, heterocyclyl, cycloalkylene. In some embodiments, A is a 6-carbon monocyclic or 10-carbon bicyclic aromatic ring system wherein 0, 1, 2, 3, or 4 atoms of each ring are optionally substituted. In some embodiments, A is naphthyl. In some embodiments, A is indazolyl.

In some embodiments, A is substituted aryl. In some embodiments, A is substituted phenyl. In some embodiments, A is phenyl substituted with alkyl, cycloalkyl, alkoxy, an amine group, a carboxyl group, a carboxylic acid group, a carbamide group, or an amide group, each of which is substituted or unsubstituted; cyano, halogen, or hydrogen, hi some embodiments, A is phenyl substituted with alkyl, wherein alkyl is substituted. In some embodiments, A is phenyl substituted with alkyl, wherein alkyl is substituted with an amino group that is substituted or unsubstituted. In some embodiments, A is phenyl substituted with an amine group that is substituted or unsubstituted. In some embodiments, A is phenyl substituted with a carboxyl group that is substituted or unsubstituted. In some embodiments, A is phenyl substituted with cyano. In some embodiments, A is phenyl substituted with halo-.

In some embodiments, A is substituted or unsubstituted heterocyclyl. In some embodiments, A is substituted heterocyclyl.

In some embodiments, A is an aromatic 5-membered, 6-membered, 7-membered, or 8-membered monocyclic ring system comprising 1, 2, or 3 heteroatoms as ring members, wherein each heteroatom is independently selected from O, N, or S. In some embodiments, A is an aromatic 8-membered, 9-membered, 10-membered, 11-membered, or 12-membered bicyclic ring system comprising 1, 2, 3, 4, 5, or 6 heteroatoms, wherein each heteroatom is independently selected from O, N, or S. In some embodiments, A is an aromatic 5-membered, 6-membered, 7-membered, or 8-membered monocyclic ring system comprising 1, 2, or 3 heteroatoms, and the aromatic 5-membered, 6-membered, 7-membered, or 8-membered monocyclic ring system is substituted. In some embodiments, A is an 8-membered, 9-membered, 10-membered, 11-membered, or 12-membered bicyclic ring system having 1, 2, 3, 4, 5, or 6 heteroatoms, and the 8-membered, 9-membered, 10-membered, 11-membered, or 12-membered bicyclic ring system is substituted.

In some embodiments, A is pyridinyl, pyrimidinyl, thiadiazolyl, thiazolyl, pyrazolyl, thiophenyl, or oxadiazolyl, each of which is independently substituted or unsubstituted. In some embodiments, A is 1,3,5-thiadiazol-2-yl. In some embodiments, A is 1,3,4-oxadiazol-2-yl or 1,2,4-oxadiazol-2-yl. In some embodiments, A is 1,3,4-oxadiazol-2-yl.

In some embodiments, m is 1. In some embodiments, m is 2. In some embodiments, $Q^1$ is alkylene, alkenylene, or alkynylene, each of which is independently substituted or unsubstituted, or a bond. In some embodiments, $Q^1$ is a bond. In some embodiments, Y is N.

In some embodiments, $R^2$ is hydrogen. In some embodiments, $R^2$ is substituted or unsubstituted alkyl. In some embodiments, $R^2$ is trifluoroethyl. In some embodiments, $R^2$ is cycloalkyl.

In some embodiments, $R^1$ is $-C(O)R^{16}$, $-C(O)OR^{16}$, $-C(O)NR^{16}R^{17}$, $-OR^{16}$, $-NR^{16}R^{17}$, $-NR^{16}C(O)R^{16}$, $-OC(O)R^{16}$, alkyl, alkoxy, aryl, heteroaryl, or heterocyclyl, each of which is independently substituted or unsubstituted; cyano, halo, or halogen. In some embodiments, $R^1$ is $-NR^{16}R^{17}$. In some embodiments, $R^1$ is substituted alkyl.

In some embodiments, each $R^3$ and $R^4$ is independently aryl, heteroaryl, or heterocyclyl, each of which is independently substituted or unsubstituted; or hydrogen. In some embodiments, $R^3$ is hydrogen, and $R^4$ is heterocyclyl substituted at least with halo-. In some embodiments, $R^4$ is heterocyclyl substituted with fluoro. In some embodiments, $R^4$ is heterocyclyl substituted with chloro.

In some embodiments, $R^{13}$ is alkyl, alkenyl, hydrogen, or halogen. In some embodiments, $R^{13}$ is hydrogen.

In some embodiments, the compound has the formula:

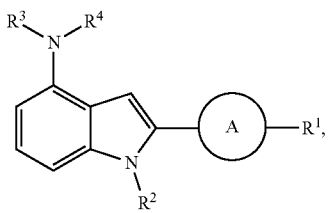

or a pharmaceutically-acceptable salt thereof, wherein the variable are as defined above.

In some embodiments, the compound has the formula:

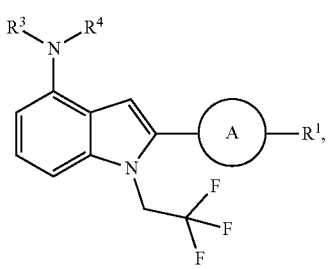

or a pharmaceutically-acceptable salt thereof, wherein the variables are as defined above.

In some embodiments, the compound has the formula:

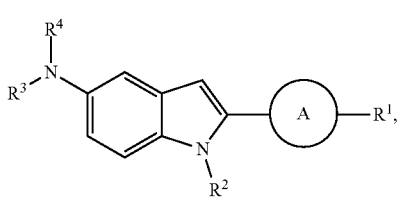

or a pharmaceutically-acceptable salt thereof, wherein the variables are as defined above.

In some embodiments, the compound has the formula:

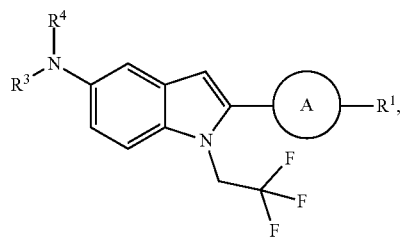

or a pharmaceutically-acceptable salt thereof, wherein the variables are as defined above.

In some embodiments, the disclosure provides a compound of the formula:

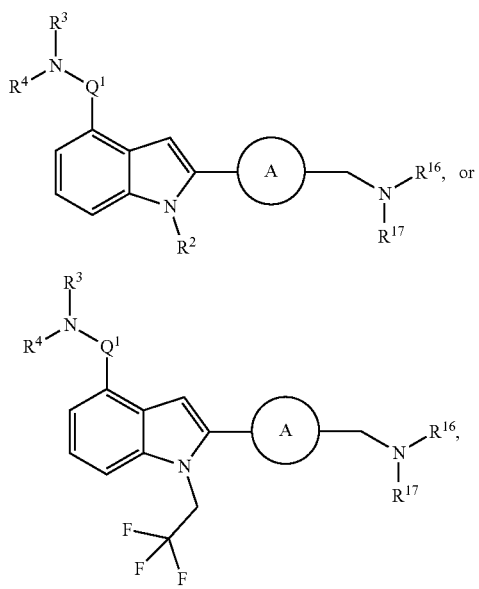

or a pharmaceutically-acceptable salt thereof, wherein the variables are as defined above.

In some embodiments, $Q^1$ is C=O, C=S, $C=CR^{14}R^{15}$, $C=NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is $-C(O)R^{19}$, $-C(O)OR^{19}$, $-C(O)NR^{19}R^{20}$, $-SOR^{19}$, $-SO_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

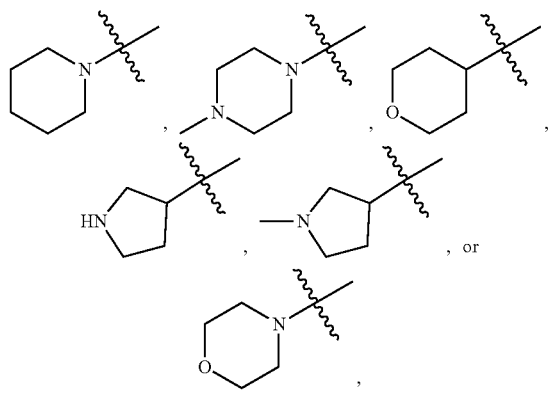

wherein the ring is substituted or unsubstituted. In some embodiments, $R^3$ is H, and $R^4$ is a ring that is

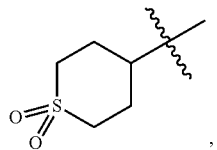

wherein the ring is substituted or unsubstituted. In some embodiments, $R^3$ is H, and $R^4$ is a ring that is

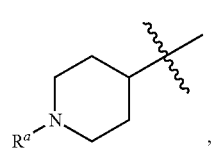

wherein the ring is substituted or unsubstituted. In some embodiments, $R^a$ is alkylene. In some embodiments, $R^a$ is methyl. In some embodiments, $R^3$ is H, and $R^4$ is a ring that is

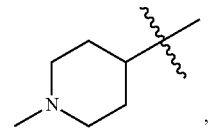 [SMILES: *C1CCN(C)CC1]

wherein the ring is substituted or unsubstituted. In some embodiments, $R^3$ is H, and $R^4$ is a ring that is

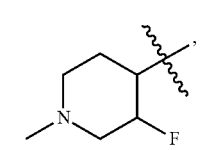

wherein the ring is substituted or unsubstituted.

In some embodiments, each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group.

In some embodiments, the compound is of the formula:

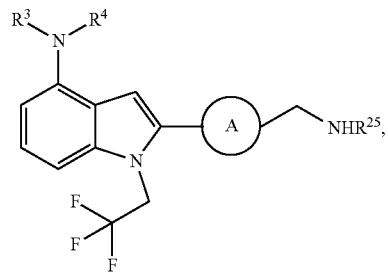

wherein $R^{25}$ is $-C(O)R^{16}$, $-C(O)NR^{16}R^{17}$, alkyl, alkenyl, alkynyl, aryl, heteroaryl, or heterocyclyl, each of which is independently substituted or unsubstituted, or hydrogen. In some embodiments, $R^{25}$ is aryl that is substituted or unsubstituted. In some embodiments, $R^{25}$ is substituted phenyl. In some embodiments, $R^{25}$ is $-C(O)R^{16}$, wherein $R^{16}$ is alkyl, aryl, heteroaryl, or heterocyclyl. In some embodiments, $R^{25}$ is $-C(O)R^{16}$, wherein $R^{16}$ is substituted phenyl.

In some embodiments, the disclosure provides a compound of the formula:

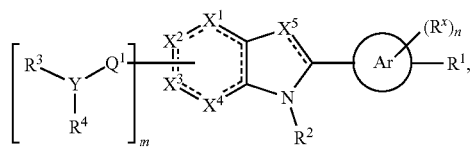

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
Ar is unsubstituted or substituted aryl;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
n is 0, 1, 2, 3, or 4;
Y is N, O, or absent;
each $R^x$ and $R^1$ is independently $C(O)R^{16}$, $-C(O)OR^{16}$, $-C(O)NR^{16}R^{17}$, $-OR^{16}$, $-SR^{16}$, $-NR^{16}R^{17}$, $-NR^{16}C(O)R^{16}$, $-OC(O)R^{16}$, $-SiR^{16}R^{17}R^{18}$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;

each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

The pattern of dashed bonds can be chosen to provide an aromatic system, for example, an indole, an indolene, a pyrrolopyridine, a pyrrolopyrimidine, or a pyrrolopyrazine. In some embodiments, $X^1$ is C$R^5$, C$R^5R^6$, or a carbon atom connected to $Q^1$. In some embodiments, $X^2$ is C$R^7$, C$R^7R^8$, or a carbon atom connected to $Q^1$. In some embodiments, $X^3$ is C$R^9$, C$R^9R^{10}$, or a carbon atom connected to $Q^1$. In some embodiments, $X^4$ is C$R^{11}$, C$R^{11}R^{12}$, or a carbon atom connected to $Q^1$. In some embodiments, $X^5$ is C$R^{13}$, N, or N$R^{13}$. In some embodiments, $X^1$ is a carbon atom connected to $Q^1$. In some embodiments, $X^2$ is a carbon atom connected to $Q^1$. In some embodiments, $X^3$ is a carbon atom connected to $Q^1$. In some embodiments, $X^4$ is a carbon atom connected to $Q^1$. In some embodiments, $X^5$ is N.

In some embodiments, Ar is a 6-carbon monocyclic or 10-carbon bicyclic aromatic ring system wherein 0, 1, 2, 3, or 4 atoms of each ring are optionally substituted. In some embodiments, Ar is phenyl. In some embodiments, Ar is naphthyl. In some embodiments, Ar is indazolyl.

$R^1$ can be —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —N$R^{21}R^{22}$, or aryl, each of which is independently substituted or unsubstituted; halo or hydrogen. In some embodiments, $R^1$ is methyl, cyclohexyl, methylene, methoxy, or benzyl. In some embodiments, $R^1$ is fluoro or chloro. In some embodiments, $R^1$ is phenyl. In some embodiments, $R^1$ is hydrogen.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with N$R^{16}R^{17}$. In some embodiments, $R^1$ is alkyl substituted with —C(O)N$R^{16}R^{17}$. In some embodiments, $R^1$ is methyl substituted with —C(O)N$R^{16}R^{17}$. In some embodiments, $R^1$ is alkyl substituted with —C(O)O$R^{16}$. In some embodiments, $R^1$ is methyl substituted with COOH.

In some embodiments, m is 1, 2, 3, or 4. In some embodiments, m is 1. In some embodiments, $X^3$ is carbon atom connected to $Q^1$, and m is 1. In some embodiments, n is 1, 2, or 3. In some embodiments, n is 1. In some embodiments, n is 2. In some embodiments, n is 0.

In some embodiments, $Q^1$ is C=O, C=S, C=C$R^{14}R^{15}$, C=N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is a bond. In some embodiments, $Q^1$ is $C_1$-alkylene.

In some embodiments, $R^2$ is hydrogen or alkyl. In some embodiments, $R^{13}$ is alkyl, alkenyl, hydrogen, or halogen. In some embodiments, $R^2$ is alkyl, and $R^{13}$ is alkyl. In some embodiments, $R^2$ is hydrogen, and $R^{13}$ is alkyl. In some embodiments, $R^2$ is methyl, ethyl, propyl, iso-propyl, butyl, or tert-butyl. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen, and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

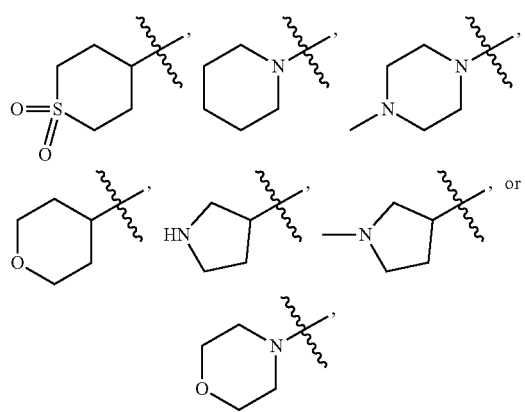

wherein the ring is substituted or unsubstituted. In some embodiments, R³ is H, and R⁴ is a ring that is

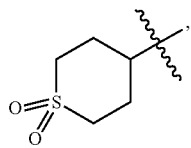

wherein the ring is substituted or unsubstituted. In some embodiments, R³ is H, and R⁴ is a ring that is

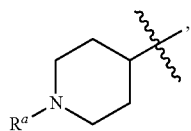

wherein the ring is substituted or unsubstituted. In some embodiments, R^a is alkylene. In some embodiments, R^a is methyl. In some embodiments, R³ is H, and R⁴ is a ring that is

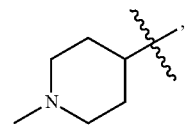

wherein the ring is substituted or unsubstituted. In some embodiments, R³ is H, and R⁴ is a ring that is

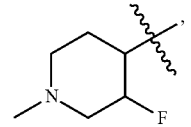

wherein the ring is substituted or unsubstituted. In some embodiments, R³ is H, and R⁴ is a ring that is

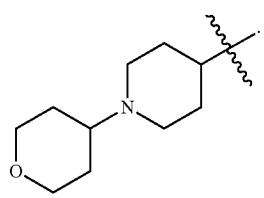

In some embodiments, the disclosure provides a compound of the formula:

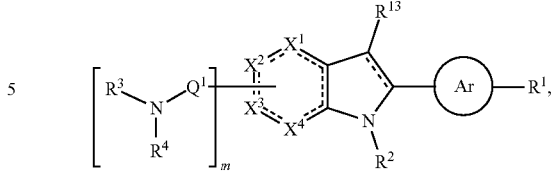

wherein the variables are as defined above.

In some embodiments, the disclosure provides a compound of the formula:

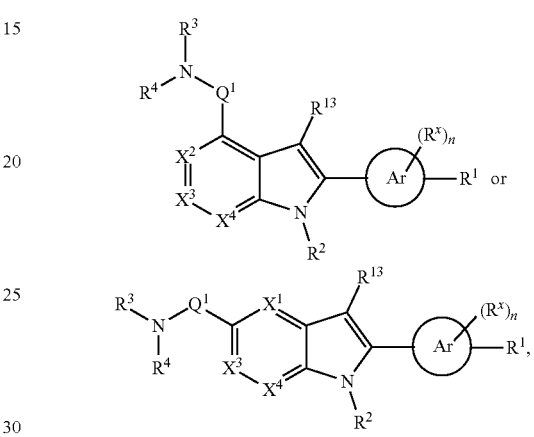

wherein:
X¹ is CR⁵, CR⁵R⁶, N, NR⁵, O, S, C=O, C=S, or a carbon atom connected to Q¹;
X² is CR⁷, CR⁷R⁸, N, NR⁷, O, S, C=O, C=S, or a carbon atom connected to Q¹;
X³ is CR⁹, CR⁹R¹⁰, N, NR⁹, O, S, C=O, C=S, or a carbon atom connected to Q¹;
X⁴ is CR¹¹, CR¹¹R¹², N, NR¹¹, O, S, C=O, C=S, or a carbon atom connected to Q¹;
Ar is unsubstituted or substituted aryl;
Q¹ is C=O, C=S, C=CR¹⁴R¹⁵, C=NR¹⁴, alkylene, alkenylene, or alkynylene, each of which is independently substituted or unsubstituted, or a bond;
n is 0, 1, 2, 3, or 4;
each R^x and R¹ is independently C(O)R¹⁶, —C(O)OR¹⁶, —C(O)NR¹⁶R¹⁷, —OR¹⁶, —SR¹⁶, —NR¹⁶R¹⁷, —NR¹⁶C(O)R¹⁶, —OC(O)R¹⁶, —SiR¹⁶R¹⁷R¹⁸, alkyl, alkenyl, alkynyl, alkoxy, aryl, heteroaryl, or heterocyclyl, each of which is independently substituted or unsubstituted; cyano, halo, or hydrogen; or R¹ and R^x together with Ar form a fused ring;
each R³ and R⁴ is independently —C(O)R¹⁹, —C(O)OR¹⁹, —C(O)NR¹⁹R²⁰, —SOR¹⁹, —SO₂R¹⁹, alkyl, alkenyl, alkynyl, aryl, heteroaryl, or heterocyclyl, each of which is independently substituted or unsubstituted, or hydrogen, or R³ and R⁴ together with the nitrogen atom to which R³ and R⁴ are bound form a ring, wherein the ring is substituted or unsubstituted, or R³ is absent;
each R², R⁵, R⁶, R⁷, R⁸, R⁹, R¹⁰, R¹¹, R¹², R¹³, R¹⁴, R¹⁵, R¹⁶, R¹⁷, and R¹⁸ is independently —C(O)R²¹, —C(O)OR²¹, —C(O)NR²¹R²², —OR²¹, —SR²¹, —NR²¹R²², —NR²¹C(O)R²², —OC(O)R²¹, alkyl, alkenyl, alkynyl, aryl, heteroaryl, or heterocyclyl, each of which is independently substituted or unsubstituted, or hydrogen or halogen;

each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

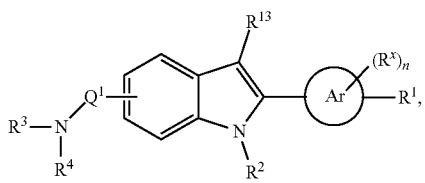

wherein the variables are as defined above.

In some embodiments, Ar is a 6-carbon monocyclic or 10-carbon bicyclic aromatic ring system wherein 0, 1, 2, 3, or 4 atoms of each ring are optionally substituted. In some embodiments, Ar is phenyl. In some embodiments, Ar is naphthyl. In some embodiments, Ar is indazolyl.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with N$R^{16}R^{17}$. In some embodiments, $R^1$ is alkyl substituted with —C(O)N$R^{16}R^{17}$. In some embodiments, $R^1$ is methyl substituted with —C(O)N$R^{16}R^{17}$. In some embodiments, $R^1$ is alkyl substituted with —C(O)O$R^{16}$. In some embodiments, $R^1$ is methyl substituted with COOH.

In some embodiments, $Q^1$ is C=O, C=S, C=C$R^{14}R^{15}$, C=N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is a bond. In some embodiments, $Q^1$ is $C_1$-alkylene.

In some embodiments, $R^2$ is hydrogen or alkyl. In some embodiments, $R^{13}$ is alkyl, alkenyl, hydrogen, or halogen. In some embodiments, $R^2$ is alkyl, and $R^{13}$ is alkyl. In some embodiments, $R^2$ is hydrogen, and $R^{13}$ is alkyl. In some embodiments, $R^2$ is methyl, ethyl, propyl, iso-propyl, butyl, or tert-butyl. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen, and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

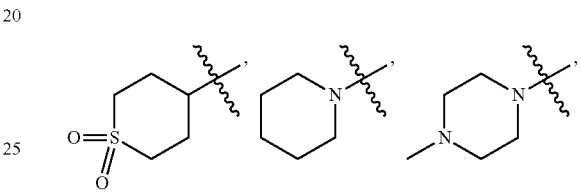

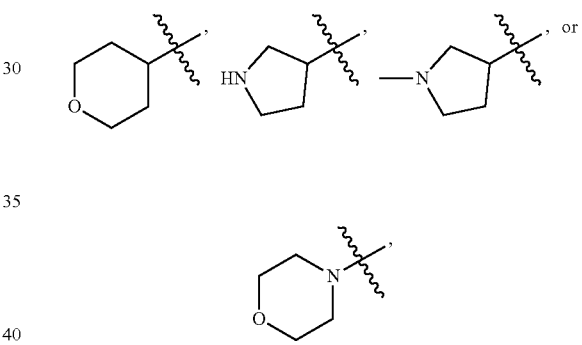

wherein the ring is substituted or unsubstituted. In some embodiments, $R^3$ is H, and $R^4$ is a ring that is

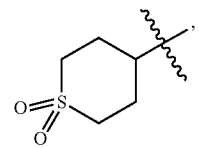

wherein the ring is substituted or unsubstituted. In some embodiments, $R^3$ is H, and $R^4$ is a ring that is

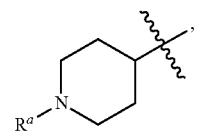

wherein the ring is substituted or unsubstituted. In some embodiments, $R^a$ is alkylene. In some embodiments, $R^a$ is methyl.

In some embodiments, $R^3$ is H, and $R^4$ is a ring that is

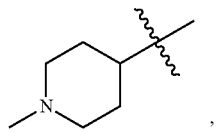 [SMILES: *C1CCN(C)CC1], wherein the ring is substituted or unsubstituted. In some embodiments, $R^3$ is H, and $R^4$ is a ring that is

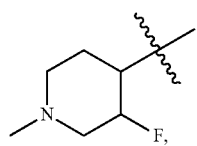, wherein the ring is substituted or unsubstituted. In some embodiments, $R^3$ is H, and $R^4$ is a ring that is

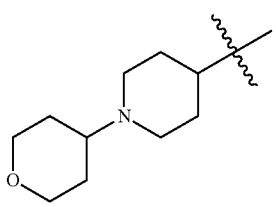.

In some embodiments, the disclosure provides a compound of the formula:

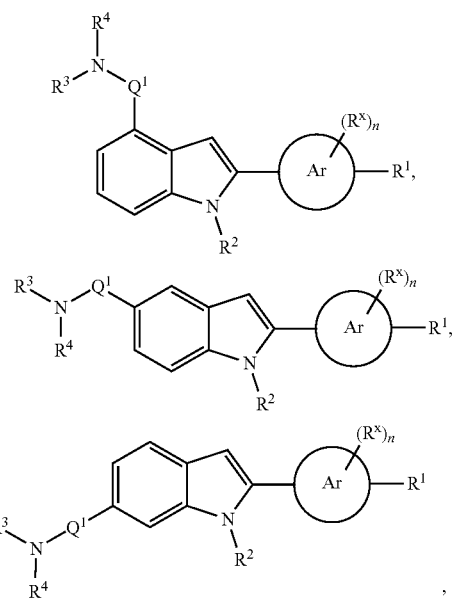

, or

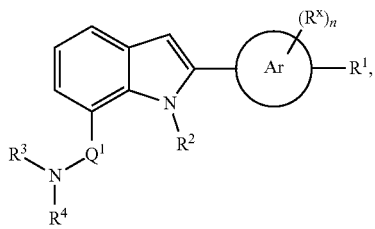

or a pharmaceutically-acceptable salt thereof, wherein the variables are as defined above.

In some embodiments, the disclosure provides a compound of the formula:

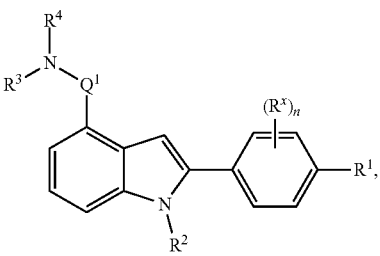

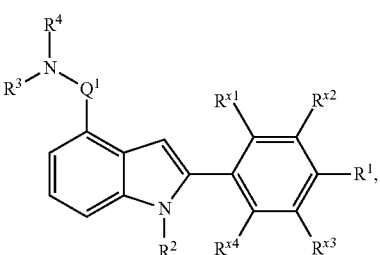

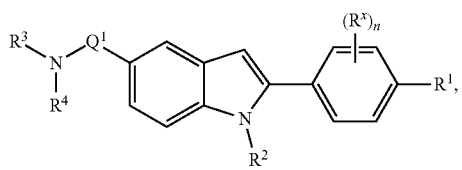

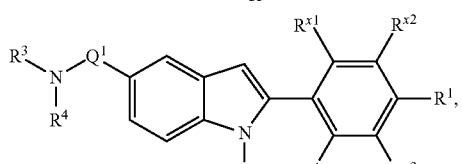

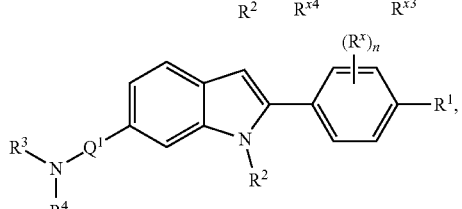

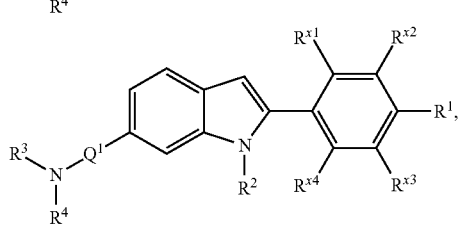

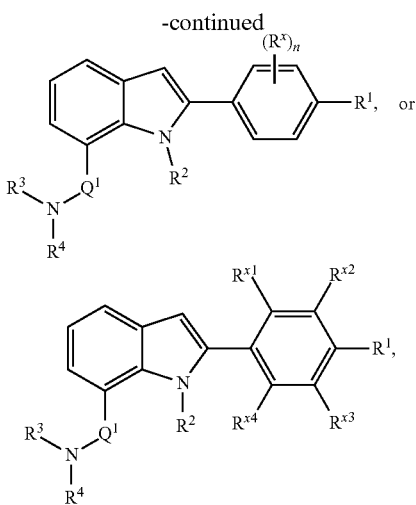

wherein:
Q$^1$ is C=O, C=S, C=CR$^{14}$R$^{15}$, C=NR$^{14}$, alkylene, alkenylene, or alkynylene, each of which is independently substituted or unsubstituted, or a bond;
each R$^1$, R$^x$, R$^{x1}$, R$^{x2}$, R$^{x3}$, and R$^{x4}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, or heterocyclyl, each of which is independently substituted or unsubstituted; cyano, halo, or hydrogen; or R$^1$ and R$^x$ together with Ar form a fused ring;
each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;
n is 0, 1, 2, 3, or 4;
each R$^2$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;
each R$^{19}$ and R$^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;
each R$^{21}$ and R$^{22}$ is independently alkyl, alkenyl, alkynyl, aryl, heteroaryl, or heterocyclyl, each of which is independently substituted or unsubstituted, or hydrogen; and
each R$^{23}$ and R$^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

In some embodiments, R$^1$ is a substituted alkyl. R$^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, R$^1$ is alkyl substituted with an amine group. In some embodiments, R$^1$ is methyl substituted with NR$^{16}$R$^{17}$. In some embodiments, R$^1$ is methyl substituted with NR$^{16}$R$^{17}$, wherein R$^{16}$ is hydrogen, and R$^{17}$ is alkyl, aryl, heteroaryl, an amino group, a carboxyl group, or an ester group, any of which is substituted or unsubstituted. In some embodiments, R$^1$ is methyl substituted with NR$^{16}$R$^{17}$, wherein R$^{16}$ is hydrogen, and R$^{17}$ is substituted or unsubstituted alkyl, aryl, or heteroaryl. In some embodiments, R$^1$ is methyl substituted with NR$^{16}$R$^{17}$, wherein R$^{16}$ is hydrogen, and R$^{17}$ is substituted or unsubstituted phenyl. In some embodiments, R$^1$ is methyl substituted with NR$^{16}$R$^{17}$, wherein R$^{16}$ is hydrogen, and R$^{17}$ is substituted or unsubstituted pyridinyl.

In some embodiments, R$^1$ is —C(O)NR$^{16}$R$^{17}$. In some embodiments, R$^1$ is —C(O)NR$^{16}$R$^{17}$, wherein R$^{16}$ and R$^{17}$ are hydrogen. In some embodiments, R$^1$ is —C(O)NR$^{16}$R$^{17}$, wherein R$^{16}$ is hydrogen, and R$^{17}$ alkyl. In some embodiments, R$^1$ is —C(O)NR$^{16}$R$^{17}$, wherein R$^{16}$ is hydrogen, and R$^{17}$ methyl. In some embodiments, R$^1$ is —C(O)OR$^{16}$. In some embodiments, R$^1$ is —C(O)OH. In some embodiments, R$^1$ is methyl. In some embodiments, R$^1$ is halogen. In some embodiments, R$^1$ is chloro or fluoro.

In some embodiments, n is 0, 1, 2, or 3. In some embodiments, n is 1. In some embodiments, n is 2. In some embodiments, n is 0.

In some embodiments, Q$^1$ is C=O, C=S, C=CR$^{14}$R$^{15}$, C=NR$^{14}$, alkylene, alkenylene, or alkynylene, each of which is independently substituted or unsubstituted, or a bond. In some embodiments, Q$^1$ is alkylene, alkenylene, or alkynylene. In some embodiments, Q$^1$ is a bond. In some embodiments, Q$^1$ is C$_1$-alkylene.

In some embodiments, R$^2$ is hydrogen or alkyl. In some embodiments, R$^{13}$ is alkyl, alkenyl, hydrogen, or halogen. In some embodiments, R$^2$ is alkyl, and R$^{13}$ is alkyl. In some embodiments, R$^2$ is hydrogen, and R$^{13}$ is alkyl. In some embodiments, R$^2$ is methyl, ethyl, propyl, iso-propyl, butyl, or tert-butyl. In some embodiments, R$^{13}$ is methyl, ethyl, propyl, iso-propyl, butyl or tert-butyl. In some embodiments, R$^2$ is hydrogen, and R$^{13}$ is hydrogen. In some embodiments, R$^2$ is trifluoroethyl, and R$^{13}$ is hydrogen.

In some embodiments, R$^3$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen, and R$^4$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen.

In some embodiments, R$^3$ is H, and R$^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, R$^3$ is H, and R$^4$ is alkyl, alkenyl, alkynyl, aryl, heteroaryl, or heterocyclyl, each of which is independently substituted or unsubstituted, or hydrogen. In some embodiments, R$^4$ is heterocyclyl. In some embodiments, R$^4$ is piperidinyl, piperazinyl, tetahydropyranyl, morpholinyl, or pyrrolidinyl, each of which is independently substituted or unsubstituted.

In some embodiments, $R^4$ is a ring that is:

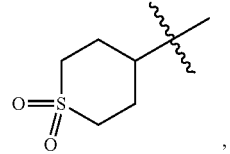,

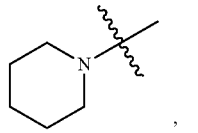,

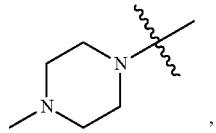,

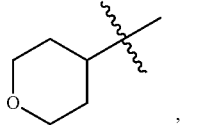,

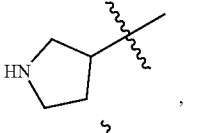,

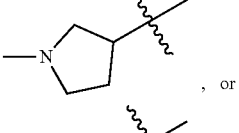, or

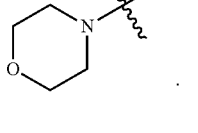

wherein the ring is substituted or unsubstituted. In some embodiments, $R^3$ is H, and $R^4$ is a ring that is

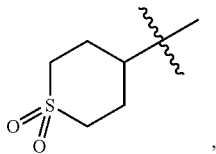 [SMILES: *C1CCS(=O)(=O)CC1]

wherein the ring is substituted or unsubstituted. In some embodiments, $R^a$ is alkylene. In some embodiments, $R^a$ is methyl. In some embodiments, $R^3$ is H, and $R^4$ is a ring that is

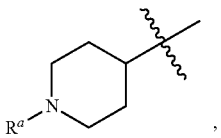

wherein the ring is substituted or unsubstituted. In some embodiments, $R^3$ is H, and $R^4$ is a ring that is

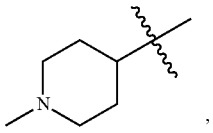 [SMILES: *C1CCN(C)CC1]

wherein the ring is substituted or unsubstituted. In some embodiments, $R^3$ is H, and $R^4$ is a ring that is

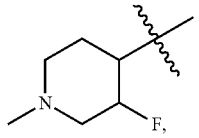

wherein the ring is substituted or unsubstituted. In some embodiments, $R^3$ is H, and $R^4$ is a ring that is

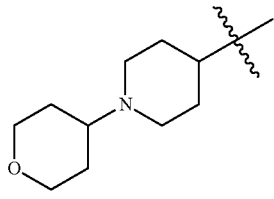.

In some embodiments, the disclosure provides a compound of the formula:

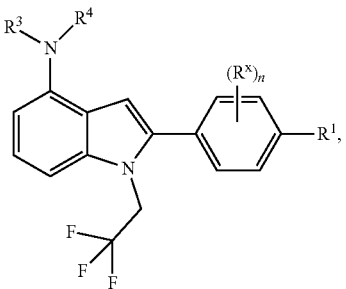

or a pharmaceutically-acceptable salt thereof, wherein the variables are as defined above.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with $NR^{16}R^{17}$. In some embodiments, $R^1$ is methyl substituted with $NR^{16}R^{17}$, wherein $R^{16}$ is hydrogen, and $R^{17}$ is alkyl, aryl, heteroaryl, an amino group, a carboxyl group, or an ester group, any of which is substituted or unsubstituted.

In some embodiments, $R^1$ is methyl substituted with $NR^{16}R^{17}$, wherein $R^{16}$ is hydrogen, and $R^{17}$ is substituted or unsubstituted alkyl, aryl, or heteroaryl. In some embodiments, $R^1$ is methyl substituted with $NR^{16}R^{17}$, wherein $R^{16}$ is hydrogen, and $R^{17}$ is substituted or unsubstituted phenyl. In some embodiments, $R^1$ is methyl substituted with $NR^{16}R^{17}$, wherein $R^{16}$ is hydrogen, and $R^{17}$ is substituted or unsubstituted pyridinyl.

In some embodiments, $R^1$ is $-C(O)NR^{16}R^{17}$. In some embodiments, $R^1$ is $-C(O)NR^{16}R^{17}$, wherein $R^{16}$ and $R^{17}$ are hydrogen. In some embodiments, $R^1$ is $-C(O)NR^{16}R^{17}$, wherein $R^{16}$ is hydrogen, and $R^{17}$ alkyl. In some embodiments, $R^1$ is $-C(O)NR^{16}R^{17}$, wherein $R^{16}$ is hydrogen, and $R^{17}$ methyl. In some embodiments, $R^1$ is $-C(O)OR^{16}$. In some embodiments, $R^1$ is $-C(O)OH$. In some embodiments, $R^1$ is methyl. In some embodiments, $R^1$ is halogen. In some embodiments, $R^1$ is chloro or fluoro.

In some embodiments, n is 1, 2, or 3. In some embodiments, n is 1. In some embodiments, n is 2. In some embodiments, n is 0.

In some embodiments, $R^3$ is $-C(O)R^{19}$, $-C(O)OR^{19}$, alkyl, alkenyl, alkynyl, aryl, heteroaryl, or heterocyclyl, each of which is independently substituted or unsubstituted, or hydrogen, and $R^4$ is $-C(O)R^{19}$, $-C(O)OR^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is $-C(O)R^{19}$, $-C(O)OR^{19}$, $-C(O)NR^{19}R^{20}$, $-SOR^{19}$, $-SO_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^3$ is H, and $R^4$ is a ring that is:

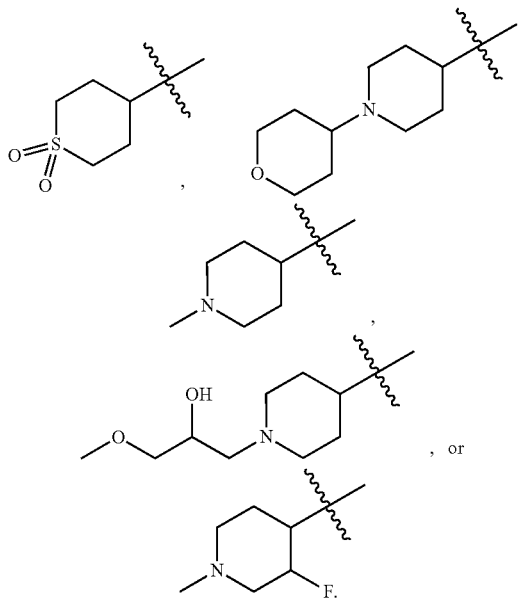

In some embodiments, $R^3$ is H, and $R^4$ is a ring that is

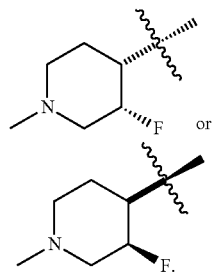 or

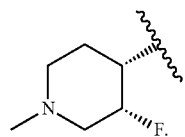

In some embodiments, $R^3$ is H, and $R^4$ is a ring that is

Non-limiting examples of compounds of the disclosure include compounds of any of the following formulae:

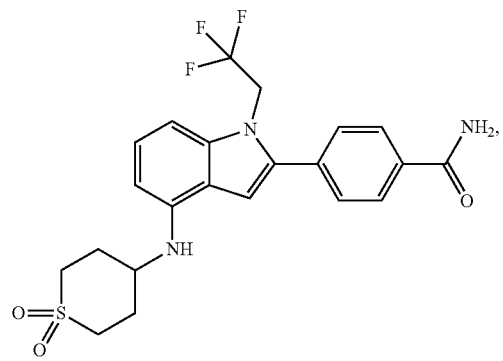

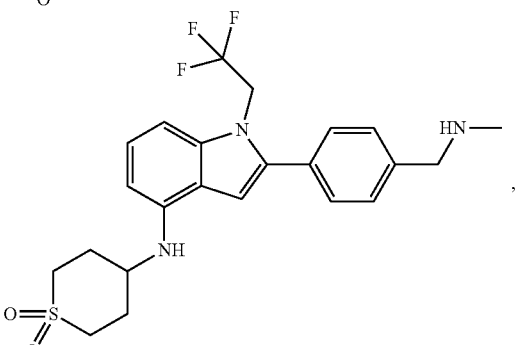

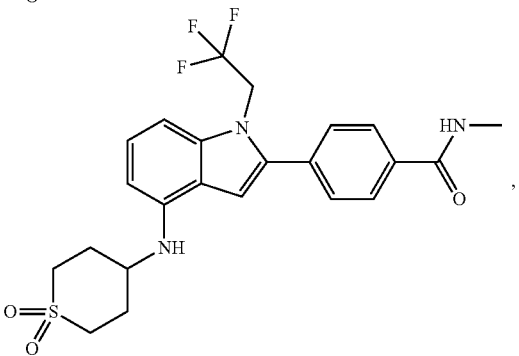

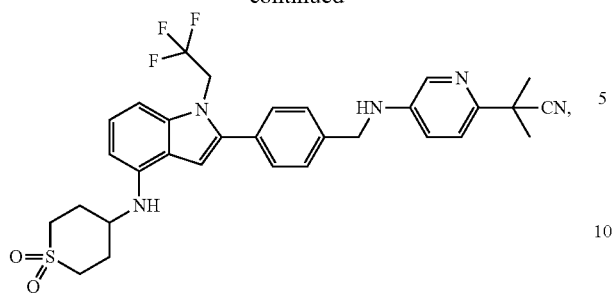
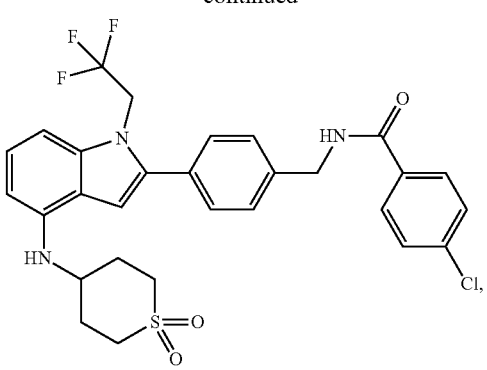

151
-continued

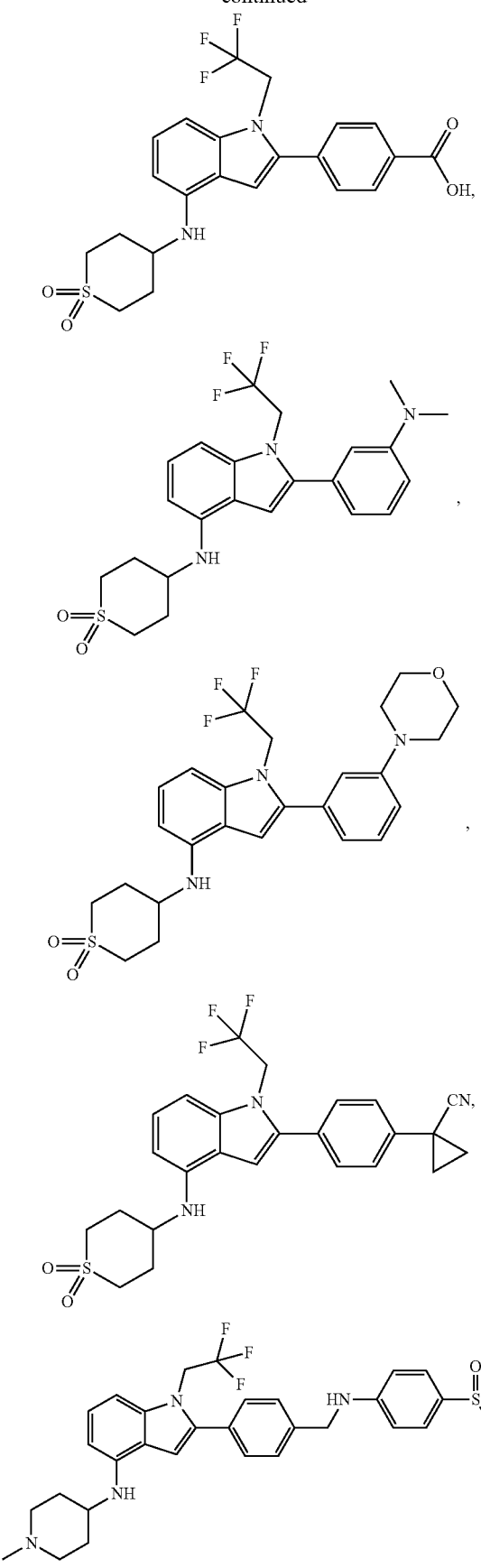

152
-continued

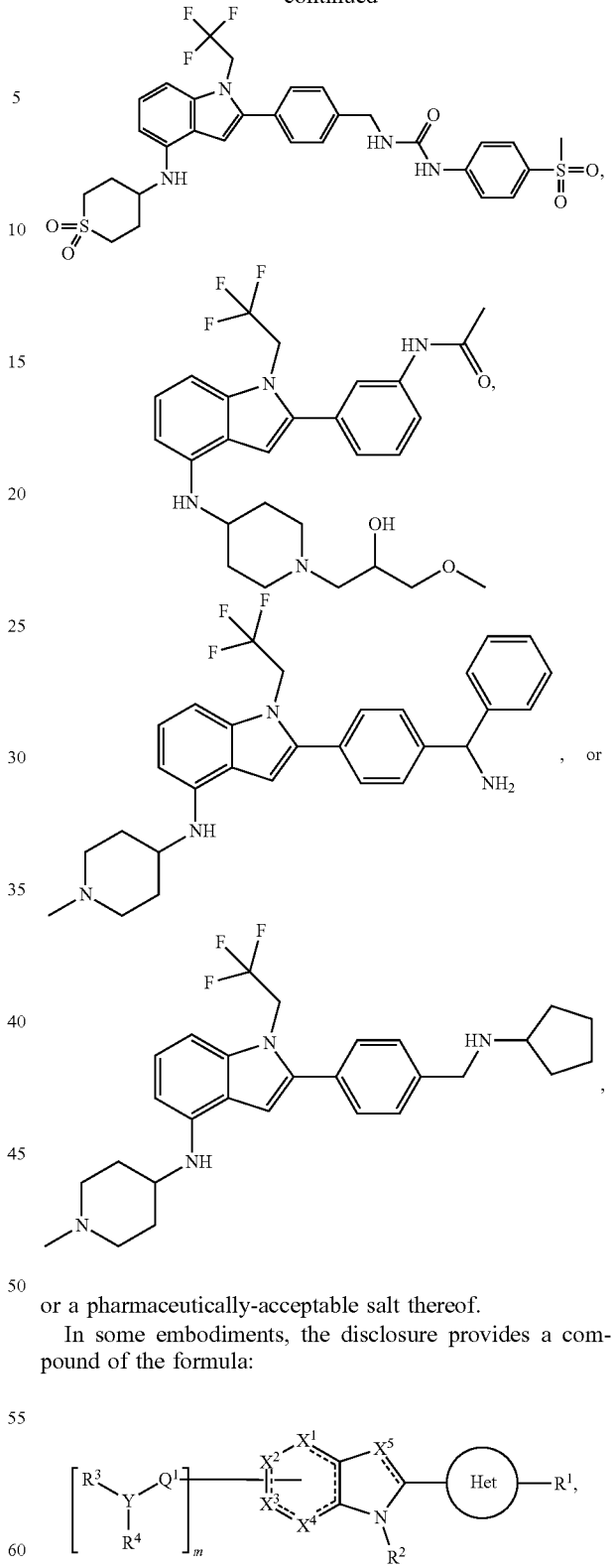

or a pharmaceutically-acceptable salt thereof.

In some embodiments, the disclosure provides a compound of the formula:

$$\left[R^3\underset{R^4}{\overset{}{Y}}Q^1\right]_m\begin{array}{c}X^2{=}X^1\\X^3{-}X^4\end{array}\begin{array}{c}X^5\\\underset{R^2}{\overset{}{N}}\end{array}\text{—Het—}R^1,$$

wherein:
each ----- is independently a single bond or a double bond;
$X^1$ is $CR^5$, $CR^5R^6$, N, $NR^5$, O, S, C=O, C=S, or a carbon atom connected to $Q^1$;

X² is CR⁷, CR⁷R⁸, N, NR⁷, O, S, C=O, C=S, or a carbon atom connected to Q¹;
X³ is CR⁹, CR⁹R¹⁰, N, NR⁹, O, S, C=O, C=S, or a carbon atom connected to Q¹;
X⁴ is CR¹¹, CR¹¹R¹², N, NR¹¹, O, S, C=O, C=S, or a carbon atom connected to Q¹;
X⁵ is CR¹³, N, or NR¹³;
wherein at least one of X¹, X², X³, and X⁴ is a carbon atom connected to Q¹;
Het is substituted or unsubstituted heteroaryl;
Q¹ is C=O, C=S, C=CR¹⁴R¹⁵, C=NR¹⁴, alkylene, alkenylene, or alkynylene, each of which is independently substituted or unsubstituted, or a bond;
m is 1, 2, 3, or 4;
Y is N, O, or absent;
R¹ is —C(O)R¹⁶, —C(O)OR¹⁶, —C(O)NR¹⁶R¹⁷, —OR¹⁶, —SR¹⁶, —NR¹⁶R¹⁷, —NR¹⁶C(O)R¹⁶, —OC(O)R¹⁶, —SiR¹⁶R¹⁷R¹⁸, alkyl, alkenyl, alkynyl, alkoxy, aryl, heteroaryl, heterocyclyl, or halo, each of which is independently substituted or unsubstituted, or hydrogen;
each R³ and R⁴ is independently —C(O)R¹⁹, —C(O)OR¹⁹, —C(O)NR¹⁹R²⁰, —SOR¹⁹, —SO₂R¹⁹, alkyl, alkenyl, alkynyl, aryl, heteroaryl, or heterocyclyl, each of which is independently substituted or unsubstituted, or hydrogen, or R³ and R⁴ together with the nitrogen atom to which R³ and R⁴ are bound form a ring, wherein the ring is substituted or unsubstituted, or R³ is absent;
each R², R⁵, R⁶, R⁷, R⁸, R⁹, R¹⁰, R¹¹, R¹², R¹³, R¹⁴, R¹⁵, R¹⁶, R¹⁷, and R¹⁸ is independently —C(O)R²¹, —C(O)OR²¹, —C(O)NR²¹R²², —OR²¹, —SR²¹, —NR²¹R²², —NR²¹C(O)R²², —OC(O)R²¹, alkyl, alkenyl, alkynyl, aryl, heteroaryl, or heterocyclyl, each of which is independently substituted or unsubstituted, or hydrogen or halogen;
each R¹⁹ and R²⁰ is —C(O)R²³, —C(O)OR²³, —C(O)NR²³R²⁴, —OR²³, —SR²³, —NR²³R²⁴, —NR²³C(O)R²⁴, —OC(O)R²³, alkyl, alkenyl, alkynyl, aryl, heteroaryl, or heterocyclyl, each of which is independently substituted or unsubstituted, or hydrogen or halogen;
each R²¹ and R²² is independently alkyl, alkenyl, alkynyl, aryl, heteroaryl, or heterocyclyl, each of which is independently substituted or unsubstituted, or hydrogen; and
each R²³ and R²⁴ is independently alkyl, alkenyl, alkynyl, aryl, heteroaryl, or heterocyclyl, each of which is independently substituted or unsubstituted, or hydrogen,
or a pharmaceutically-acceptable salt thereof.

The pattern of dashed bonds can be chosen to provide an aromatic system, for example, an indole, an indolene, a pyrrolopyridine, a pyrrolopyrimidine, or a pyrrolopyrazine. In some embodiments, X¹ is CR⁵, CR⁵R⁶, or a carbon atom connected to Q¹. In some embodiments, X² is CR⁷, CR⁷R⁸, or a carbon atom connected to Q¹. In some embodiments, X³ is CR⁹, CR⁹R¹⁰, or a carbon atom connected to Q¹. In some embodiments, X⁴ is CR¹¹, CR¹¹R¹², or a carbon atom connected to Q¹. In some embodiments, X⁵ is CR¹³, N, or NR¹³. In some embodiments, X¹ is a carbon atom connected to Q¹. In some embodiments, X² is a carbon atom connected to Q¹. In some embodiments, X³ is a carbon atom connected to Q¹. In some embodiments, X⁴ is a carbon atom connected to Q¹. In some embodiments, X⁵ is N.

In some embodiments, Het is an aromatic 5-membered, 6-membered, 7-membered, or 8-membered monocyclic ring system comprising 1, 2, or 3 heteroatoms as ring members, wherein each heteroatom is independently selected from O, N, or S. In some embodiments, Het is an aromatic 8-membered, 9-membered, 10-membered, 11-membered, or 12-membered bicyclic ring system comprising 1, 2, 3, 4, 5, or 6 heteroatoms, wherein each heteroatom is independently selected from O, N, or S. In some embodiments, Het is an aromatic 5-membered, 6-membered, 7-membered, or 8-membered monocyclic ring system comprising 1, 2, or 3 heteroatoms, and the aromatic 5-membered, 6-membered, 7-membered, or 8-membered monocyclic ring system is substituted. In some embodiments, Het is an 8-membered, 9-membered, 10-membered, 11-membered, or 12-membered bicyclic ring system having 1, 2, 3, 4, 5, or 6 heteroatoms, and the 8-membered, 9-membered, 10-membered, 11-membered, or 12-membered bicyclic ring system is substituted.

In some embodiments, Het is pyridinyl, pyrimidinyl, thiadiazolyl, thiazolyl, pyrazolyl, thiophenyl, or oxadiazolyl, each of which is independently substituted or unsubstituted. In some embodiments, Het is 1,3,5-thiadiazol-2-yl. In some embodiments, Het is 1,3,4-oxadiazol-2-yl or 1,2,4-oxadiazol-2-yl. In some embodiments, Het is 1,3,4-oxadiazol-2-yl.

In some embodiments, R¹ is —C(O)R¹⁶, —C(O)OR¹⁶, —C(O)NR¹⁶R¹⁷, —OR¹⁶, —SR¹⁶, —NR¹⁶R¹⁷, —NR¹⁶C(O)R¹⁶, —OC(O)R¹⁶, —SiR¹⁶R¹⁷R¹⁸, alkyl, alkenyl, alkynyl, alkoxy, aryl, heteroaryl, or heterocyclyl, each of which is independently substituted or unsubstituted, or hydrogen. In some embodiments, R¹ is alkyl, alkylene, alkoxy, —NR²¹R²², or aryl, each of which is independently substituted or unsubstituted; halo or hydrogen. In some embodiments, R¹ is methyl, cyclohexyl, methylene, methoxy, or benzyl. In some embodiments, R¹ is fluoro or chloro. In some embodiments, R¹ is phenyl. In some embodiments, R¹ is hydrogen.

In some embodiments, R¹ is a substituted alkyl or alkylene. R¹ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, R¹ is substituted alkyl. In some embodiments, R¹ is alkyl substituted with NR¹⁶R¹⁷. In some embodiments, R¹ is methyl substituted with NR¹⁶R¹⁷, wherein each R¹⁶ and R¹⁷ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, R¹ is methyl substituted with NR¹⁶R¹⁷, wherein R¹⁶ is hydrogen, and R¹⁷ is a substituted carboxyl group.

In some embodiments, m is 1, 2, 3, or 4. In some embodiments, m is 1. In some embodiments, X¹ is carbon atom connected to Q¹, and m is 1. In some embodiments, X² is carbon atom connected to Q¹, and m is 1.

In some embodiments, Q¹ is C=O, C=S, C=CR¹⁴R¹⁵, C=NR¹⁴, alkylene, alkenylene, or alkynylene, each of which is independently substituted or unsubstituted, or a bond. In some embodiments, Q¹ is alkylene, alkenylene, or alkynylene. In some embodiments, Q¹ is C₁-alkylene. In some embodiments, each R¹⁶ and R¹⁷ is independently alkyl, alkenyl, aryl, heteroaryl, heterocyclyl, or hydrogen. In some embodiments, $Q^1$ is a bond.

In some embodiments, $Q^1$ is $C_1$-alkylene, $R^{16}$ is aryl, and $R^{17}$ is alkyl. In some embodiments, $Q^1$ is $C_1$-alkylene, $R^{16}$ is aryl, and $R^{17}$ is hydrogen. In some embodiments, $Q^1$ is $C_1$-alkylene, $R^{16}$ is heteroaryl, and $R^{17}$ is alkyl. In some embodiments, $Q^1$ is $C_1$-alkylene, $R^{16}$ is heteroaryl, and $R^{17}$ is hydrogen. In some embodiments, $Q^1$ is $C_1$-alkylene, $R^{16}$ is substituted heteroaryl, and $R^{17}$ is hydrogen. In some embodiments, $Q^1$ is $C_1$-alkylene, $R^{16}$ is substituted alkyl, and $R^{17}$ is hydrogen. In some embodiments, $R^{17}$ is aryl, heteroaryl, or heterocyclyl, each of which is independently substituted or unsubstituted with halogen, alkyl, or hydroxyl. In some embodiments, $R^{16}$ is hydrogen, and $R^{17}$ is aryl or heteroaryl, substituted or unsubstituted with halogen or alkyl. In some embodiments, $R^{16}$ is alkyl, and $R^{17}$ is heteroaryl substituted with halogen or alkyl. In some embodiments, $R^{17}$ is aryl, heteroaryl, or heterocyclyl, each of which is independently substituted or unsubstituted with alkyl. In some embodiments, $R^{17}$ is aryl or heteroaryl, each of which is independently substituted with alkyl, wherein the alkyl is optionally substituted with fluorine, chlorine, bromine, iodine, or cyano.

In some embodiments, $R^2$ is hydrogen or alkyl. In some embodiments, $R^2$ is substituted alkyl. In some embodiments, $R^2$ is trifluoroethyl. In some embodiments, $R^{13}$ is alkyl, alkenyl, hydrogen, or halogen. In some embodiments, $R^{13}$ is methyl, ethyl, propyl, iso-propyl, butyl or tert-butyl. In some embodiments, $R^2$ is trifluoroethyl, and $R^{13}$ is hydrogen.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen; and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

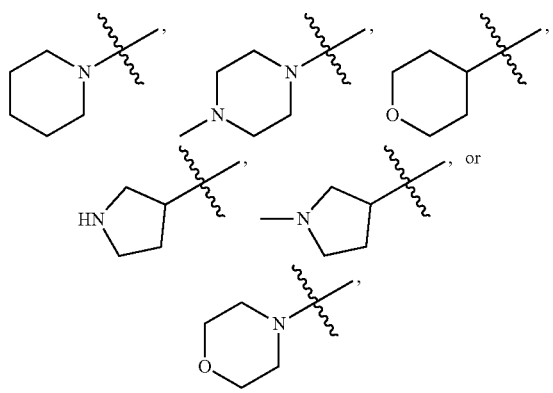

wherein the ring is substituted or unsubstituted. In some embodiments, $R^3$ is H, and $R^4$ is a ring that is

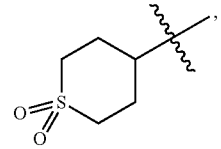 [SMILES: *C1CCS(=O)(=O)CC1]

wherein the ring is substituted or unsubstituted. In some embodiments, $R^3$ is H, and $R^4$ is a ring that is

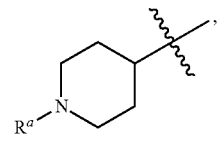

wherein the ring is substituted or unsubstituted. In some embodiments, $R^a$ is alkylene. In some embodiments, $R^a$ is methyl. In some embodiments, $R^3$ is H, and $R^4$ is a ring that is

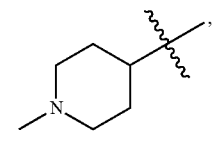 [SMILES: *C1CCN(C)CC1]

wherein the ring is substituted or unsubstituted. In some embodiments, $R^3$ is H, and $R^4$ is a ring that is

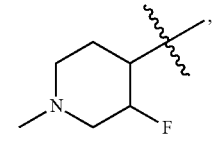

wherein the ring is substituted or unsubstituted.

In some embodiments, $R^3$ and $R^4$ together with the nitrogen atom to which $R^3$ and $R^4$ are bound form a ring, wherein the ring is substituted or unsubstituted. In some embodiments, $R^3$ and $R^4$ together with the nitrogen atom to which $R^3$ and $R^4$ are bound form a substituted heterocycle. In some embodiments, $R^3$ and $R^4$ together with the nitrogen atom to which $R^3$ and $R^4$ are bound form a heterocycle substituted with a hydroxyl group, halogen, amino group, or alkyl group. In some embodiments, $R^3$ and $R^4$ together with the nitrogen atom to which $R^3$ and $R^4$ are bound form a heterocycle, wherein the heterocycle is substituted by a substituted or unsubstituted heterocycle.

In some embodiments, the disclosure provides a compound of the formula:

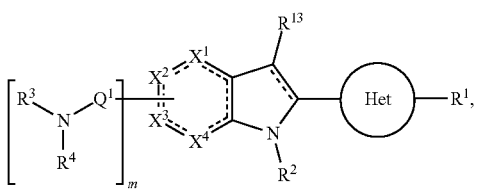

or a pharmaceutically-acceptable salt thereof, wherein the variables are as defined above.

In some embodiments, the disclosure provides a compound of the formula:

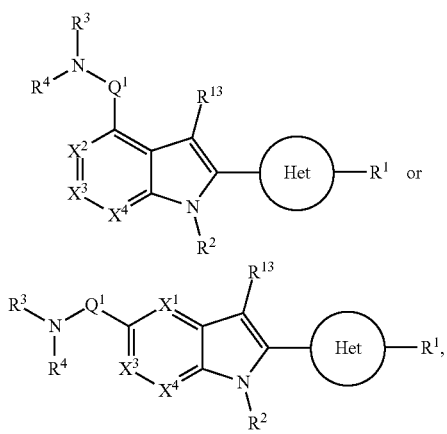

or a pharmaceutically-acceptable salt thereof, wherein the variables are as defined above.

In some embodiments, the compound is of the formula:

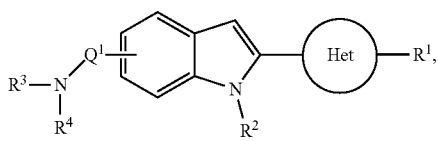

or a pharmaceutically-acceptable salt thereof, wherein the variables are as defined above.

In some embodiments, the disclosure provides a compound of the formula:

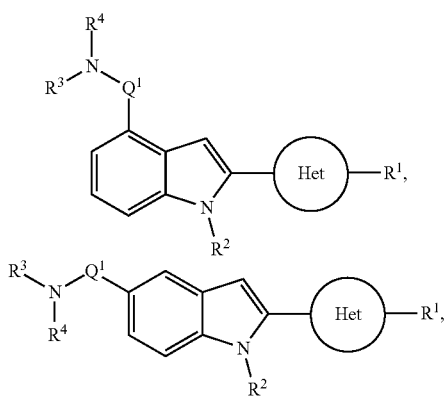

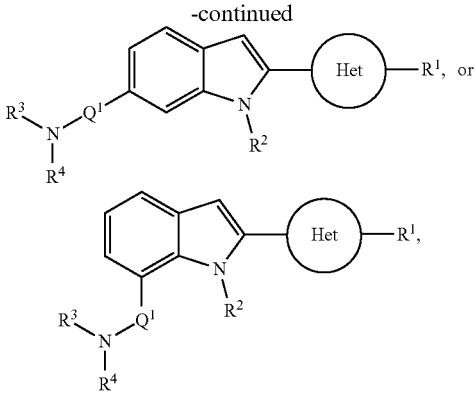

or a pharmaceutically-acceptable salt thereof, wherein the variables are as defined above.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —N$R^{21}R^{22}$, or aryl, each of which is independently substituted or unsubstituted; halo or hydrogen.

In some embodiments, $R^1$ is substituted alkyl. In some embodiments, $R^1$ is alkyl substituted with N$R^{16}R^{17}$. In some embodiments, $R^1$ is methyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with N$R^{16}R^{17}$, wherein $R^{16}$ is hydrogen, and $R^{17}$ is a substituted carboxyl group.

In some embodiments, $R^2$ is hydrogen or alkyl. In some embodiments, $R^2$ is substituted alkyl. In some embodiments, $R^2$ is trifluoroethyl.

In some embodiments, $Q^1$ is C=O, C=S, C=C$R^{14}R^{15}$, C=N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

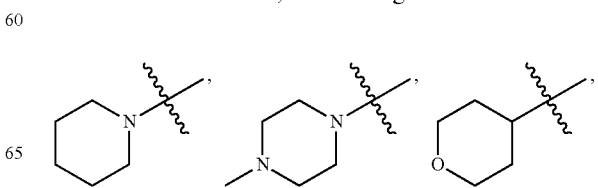

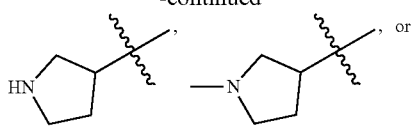

wherein the ring is substituted or unsubstituted. In some embodiments, $R^3$ is H, and $R^4$ is a ring that is

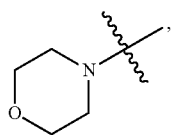

wherein the ring is substituted or unsubstituted. In some embodiments, $R^3$ is H, and $R^4$ is a ring that is

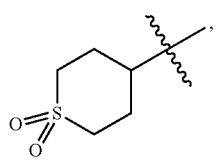

wherein the ring is substituted or unsubstituted. In some embodiments, $R^a$ is alkylene. In some embodiments, $R^a$ is methyl. In some embodiments, $R^3$ is H, and $R^4$ is a ring that is

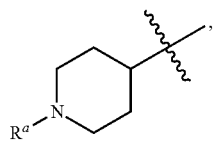

wherein the ring is substituted or unsubstituted. In some embodiments, $R^3$ is H, and $R^4$ is a ring that is

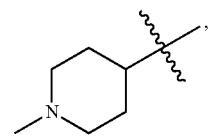

wherein the ring is substituted or unsubstituted.

In some embodiments, the disclosure provides a compound of the formula:

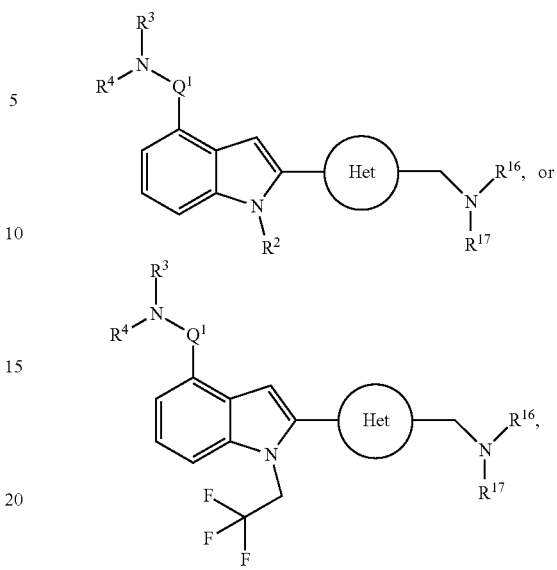

or a pharmaceutically-acceptable salt thereof, wherein the variables are as defined above.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

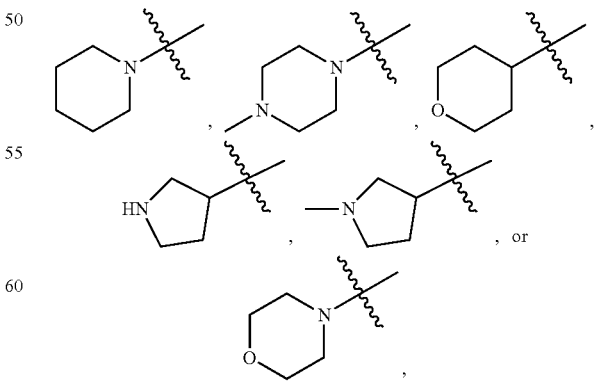

wherein the ring is substituted or unsubstituted. In some embodiments, $R^3$ is H, and $R^4$ is a ring that is

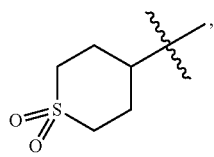

wherein the ring is substituted or unsubstituted. In some embodiments, $R^3$ is H, and $R^4$ is a ring that is wherein the ring is substituted or unsubstituted. In some embodiments, $R^a$ is alkylene. In some embodiments, $R^a$ is methyl. In some embodiments, $R^3$ is H, and $R^4$ is a ring that is wherein the ring is substituted or unsubstituted. In some embodiments, $R^3$ is H, and $R^4$ is a ring that is wherein the ring is substituted or unsubstituted.

In some embodiments, each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group.

In some embodiments, the compound is of the formula:

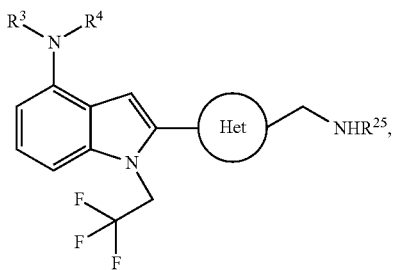

wherein $R^{25}$ is —C(O)R$^{16}$, —C(O)NR$^{16}$R$^{17}$, alkyl, alkenyl, alkynyl, aryl, heteroaryl, or heterocyclyl, each of which is independently substituted or unsubstituted, or hydrogen. In some embodiments, $R^{25}$ is aryl that is substituted or unsubstituted. In some embodiments, $R^{25}$ is substituted phenyl. In some embodiments, $R^{25}$ is —C(O)R$^{16}$, wherein $R^{16}$ is alkyl, aryl, heteroaryl, or heterocyclyl. In some embodiments, $R^{25}$ is —C(O)R$^{16}$, wherein $R^{16}$ is substituted phenyl; or a pharmaceutically-acceptable salt thereof, In some embodiments, the compound is of the formula:

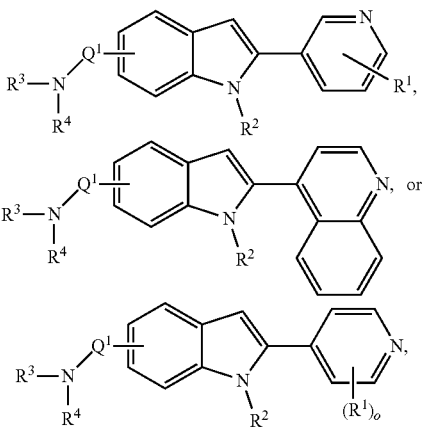

wherein:
$Q^1$ is C=O, C=S, C=CR$^{14}$R$^{15}$, C=NR$^{14}$, alkylene, alkenylene, or alkynylene, each of which is independently substituted or unsubstituted, or a bond;

$R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof, the variables are as defined above, and wherein o is 1, 2, 3, or 4.

In some embodiments, the compound is of the formula:

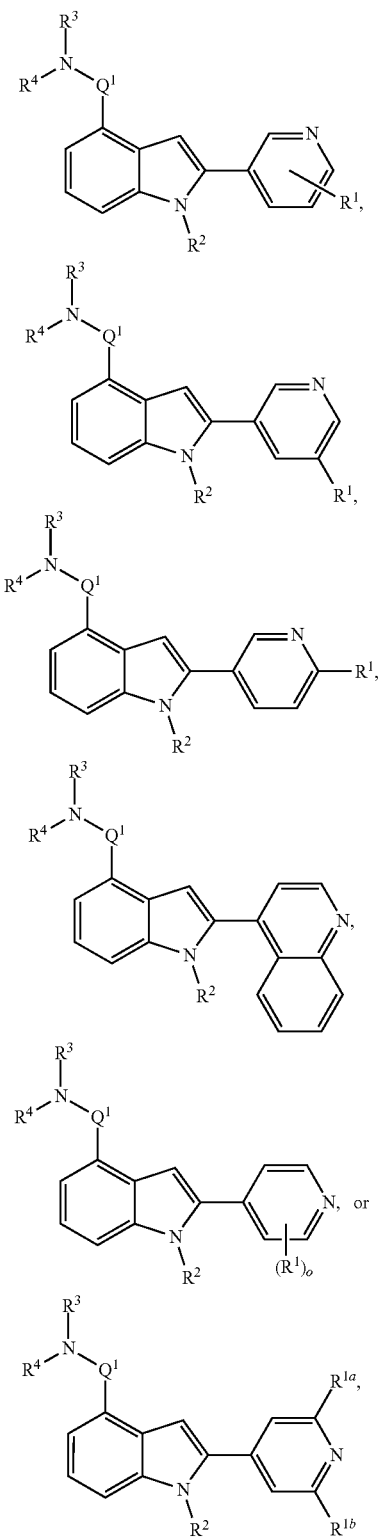

wherein:

Q$^1$ is C=O, C=S, C=CR$^{14}$R$^{15}$, C=NR$^{14}$, alkylene, alkenylene, or alkynylene, each of which is independently substituted or unsubstituted, or a bond;

each R$^1$, R$^{1a}$, and R$^{1b}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;

is 0, 1, 2, 3, or 4;

each R$^2$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, each R$^{1a}$ and R$^{1b}$ is independently alkyl, alkoxy, aryl, heteroaryl, heterocyclyl, or NR$^{16}$R$^{17}$. In some embodiments, R$^{1a}$ is unsubstituted phenyl, and R$^{1b}$ is amino.

In some embodiments, the compound is of the formula:

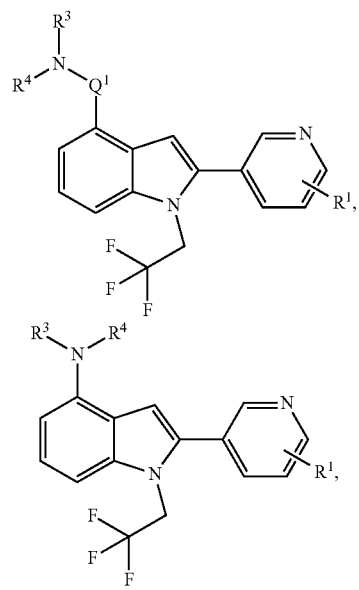

-continued
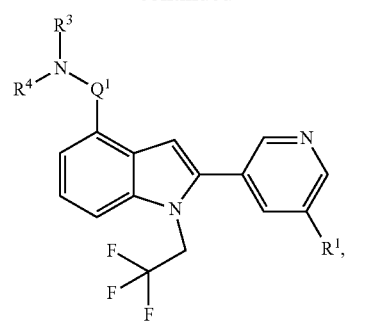
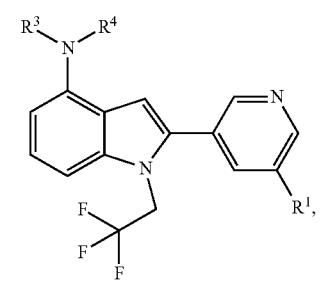
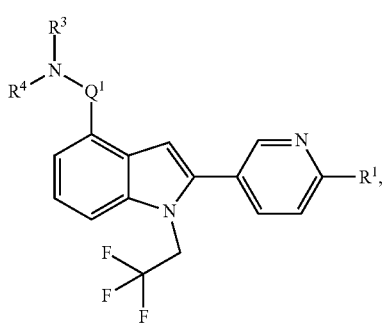
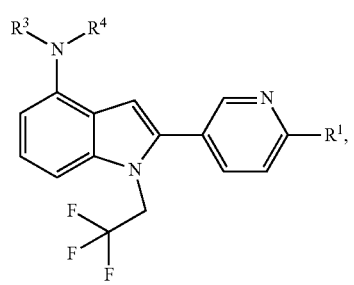
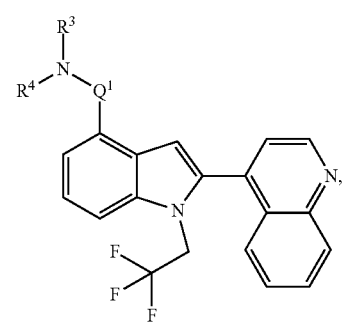
-continued
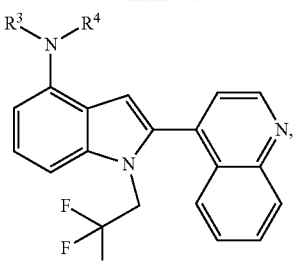
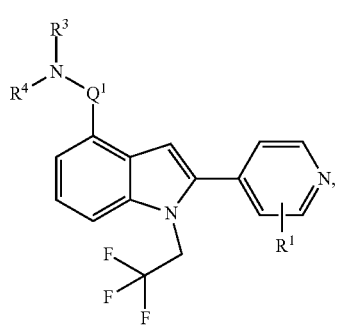
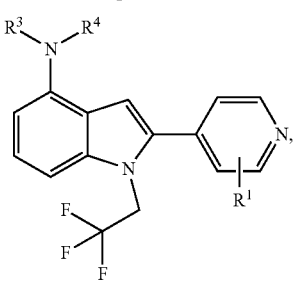
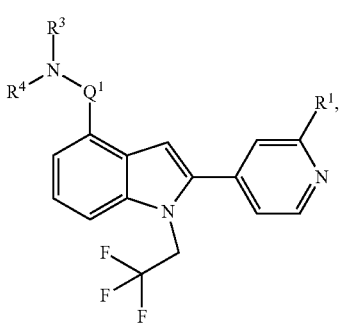
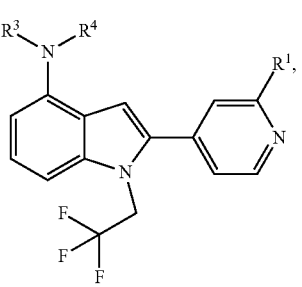

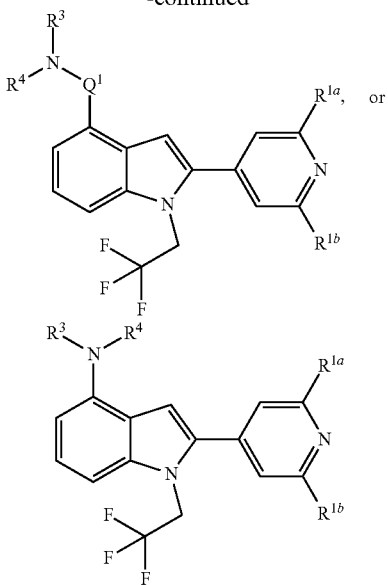

or a pharmaceutically-acceptable salt thereof, wherein the variables are as defined above.

In some embodiments, $R^1$ is —C(O)NR$^{16}$R$^{17}$, alkyl, alkenyl, alkynyl, alkoxy, aryl, heteroaryl, heterocyclyl, or halo, each of which is independently substituted or unsubstituted, or hydrogen. In some embodiments, $R^1$ is alkyl, alkoxy, aryl, or halo. In some embodiments, $R^1$ is methoxy, methyl, or phenyl. In some embodiments, each $R^{1a}$ and $R^{1b}$ is independently alkyl, alkoxy, aryl, heteroaryl, heterocyclyl, or NR$^{16}$R$^{17}$. In some embodiments, $R^{1a}$ is unsubstituted phenyl, and $R^{1b}$ is amino.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

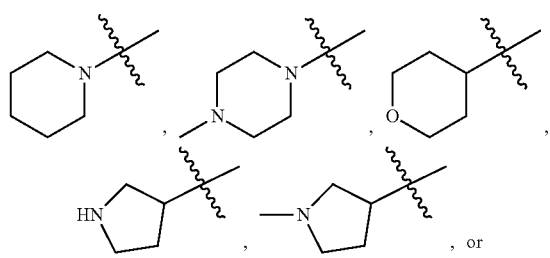

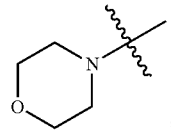

wherein the ring is substituted or unsubstituted. In some embodiments, $R^3$ is H, and $R^4$ is a ring that is

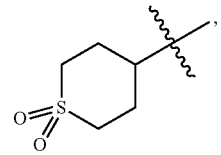 [SMILES: *C1CCS(=O)(=O)CC1]

wherein the ring is substituted or unsubstituted. In some embodiments, $R^3$ is H, and $R^4$ is a ring that is

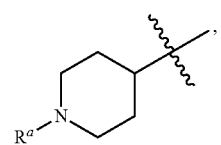

wherein the ring is substituted or unsubstituted. In some embodiments, $R^a$ is alkylene. In some embodiments, $R^a$ is methyl. In some embodiments, $R^3$ is H, and $R^4$ is a ring that is

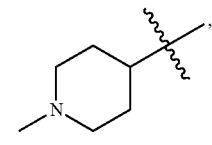

wherein the ring is substituted or unsubstituted. In some embodiments, $R^3$ is H, and $R^4$ is a ring that is

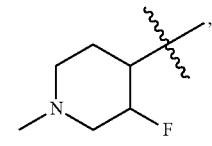 [SMILES: *C1CCN(C)CC1F]

wherein the ring is substituted or unsubstituted.

In some embodiments, each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group.

In some embodiments, the compound is of the formula:

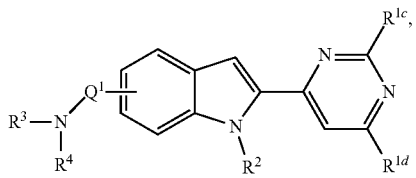

wherein:
- $Q^1$ is C=O, C=S, C=CR$^{14}$R$^{15}$, C=NR$^{14}$, alkylene, alkenylene, or alkynylene, each of which is independently substituted or unsubstituted, or a bond;
- each R$^{1c}$ and R$^{1d}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;
- each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;
- each R$^2$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;
- each R$^{19}$ and R$^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;
- each R$^{21}$ and R$^{22}$ is independently alkyl, alkenyl, alkynyl, aryl, heteroaryl, or heterocyclyl, each of which is independently substituted or unsubstituted, or hydrogen; and
- each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, each R$^{1c}$ and R$^{1d}$ is independently —OR$^{16}$, —NR$^{16}$R$^{17}$, —NR$^{16}$C(O)R$^{16}$, alkyl, alkenyl, alkynyl, alkoxy, aryl, heteroaryl, or heterocyclyl, each of which is independently substituted or unsubstituted, or hydrogen.

In some embodiments, the compound is of the formula:

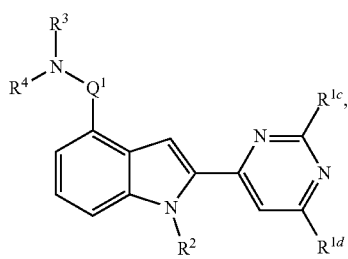

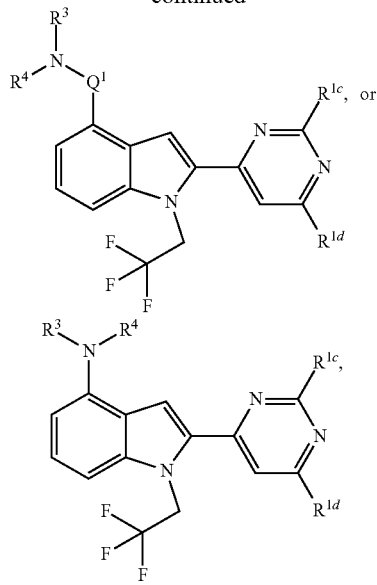

or a pharmaceutically-acceptable salt thereof, wherein the variables are as defined above.

In some embodiments, each R$^{1c}$ and R$^{1d}$ is independently C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen. In some embodiments, R$^{1c}$ is amino, and R$^{1d}$ is phenyl. In some embodiments, R$^{1c}$ is amino, and R$^{1d}$ is cycloalkenyl.

In some embodiments, the compound is of the formula:

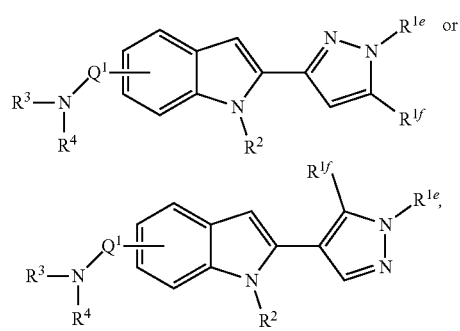

wherein:
- $Q^1$ is C=O, C=S, C=CR$^{14}$R$^{15}$, C=NR$^{14}$, alkylene, alkenylene, or alkynylene, each of which is independently substituted or unsubstituted, or a bond;
- each R$^{1e}$ and R$^{1f}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;
- each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R³ and R⁴ are bound form a ring, wherein the ring is substituted or unsubstituted, or R³ is absent;

each R², R¹⁴, R¹⁵, R¹⁶, R¹⁷, and R¹⁸ is independently —C(O)R²¹, —C(O)OR²¹, —C(O)NR²¹R²², —OR²¹, —SR²¹, —NR²¹R²², —NR²¹C(O)R²², —OC(O)R²¹, alkyl, alkenyl, alkynyl, aryl, heteroaryl, or heterocyclyl, each of which is independently substituted or unsubstituted, or hydrogen or halogen;

each R¹⁹ and R²⁰ is —C(O)R²³, —C(O)OR²³, —C(O)NR²³R²⁴, —OR²³, —SR²³, —NR²³R²⁴, —NR²³C(O)R²⁴, —OC(O)R²³, alkyl, alkenyl, alkynyl, aryl, heteroaryl, or heterocyclyl, each of which is independently substituted or unsubstituted, or hydrogen or halogen;

each R²¹ and R²² is independently alkyl, alkenyl, alkynyl, aryl, heteroaryl, or heterocyclyl, each of which is independently substituted or unsubstituted, or hydrogen; and each R²³ and R²⁴ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

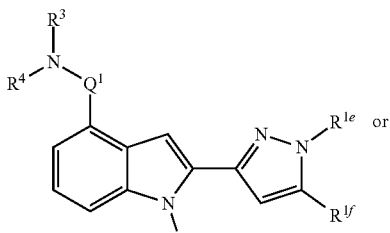

or

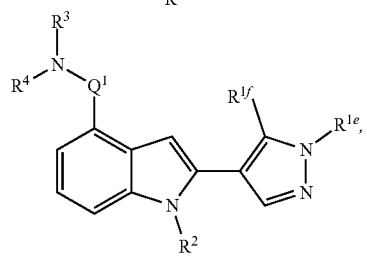

or a pharmaceutically-acceptable salt thereof, wherein the variables are as defined above.

In some embodiments, the compound is of the formula:

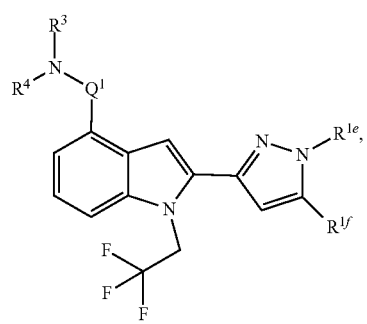

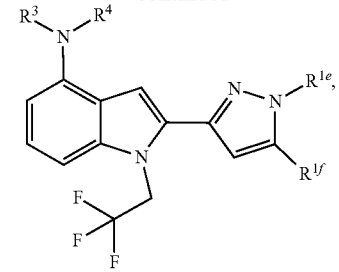

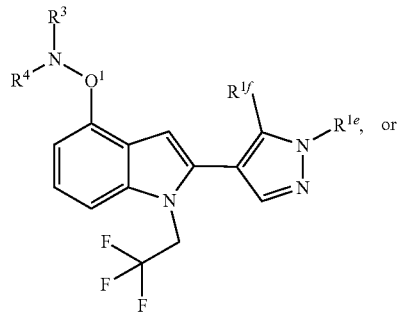

or

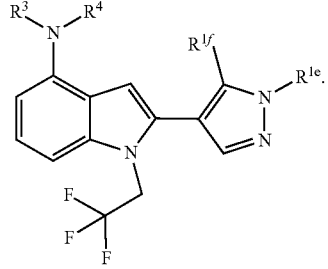

or a pharmaceutically-acceptable salt thereof, wherein the variables are as defined above.

In some embodiments, Q¹ is C=O, C=S, C=CR¹⁴R¹⁵, C=NR¹⁴, alkylene, alkenylene, or alkynylene, each of which is independently substituted or unsubstituted, or a bond. In some embodiments, Q¹ is alkylene, alkenylene, or alkynylene. In some embodiments, Q¹ is C₁-alkylene. In some embodiments, each R¹⁶ and R¹⁷ is independently alkyl, alkenyl, aryl, heteroaryl, heterocyclyl, or hydrogen. In some embodiments, Q¹ is a bond.

In some embodiments, R³ is H, and R⁴ is —C(O)R¹⁹, —C(O)OR¹⁹, —C(O)NR¹⁹R²⁰, —SOR¹⁹, —SO₂R¹⁹, alkyl, alkenyl, alkynyl, aryl, heteroaryl, or heterocyclyl, each of which is independently substituted or unsubstituted; or hydrogen. In some embodiments, R³ is H, and R⁴ is alkyl, alkenyl, alkynyl, aryl, heteroaryl, or heterocyclyl, each of which is independently substituted or unsubstituted, or hydrogen. In some embodiments, R⁴ is heterocyclyl. In some embodiments, R⁴ is piperidinyl, piperazinyl, tetahydropyranyl, morpholinyl, or pyrrolidinyl, each of which is independently substituted or unsubstituted.

In some embodiments, R⁴ is a ring that is:

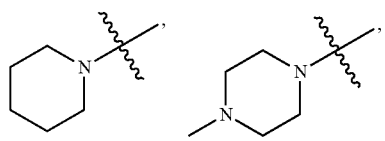

-continued

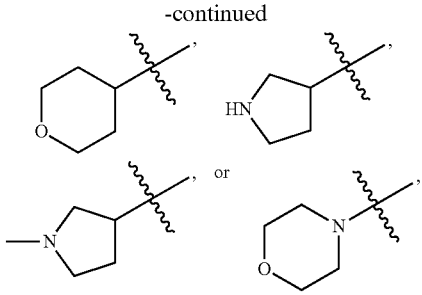

wherein the ring is substituted or unsubstituted. In some embodiments, $R^3$ is H, and $R^4$ is a ring that is

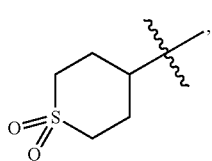 [SMILES: *C1CCS(=O)(=O)CC1]

wherein the ring is substituted or unsubstituted. In some embodiments, $R^3$ is H, and $R^4$ is a ring that is

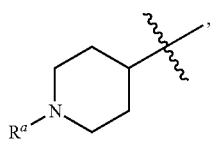

wherein the ring is substituted or unsubstituted. In some embodiments, $R^a$ is alkylene. In some embodiments, $R^a$ is methyl. In some embodiments, $R^3$ is H, and $R^4$ is a ring that is

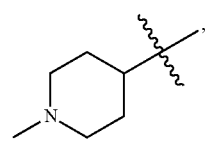 [SMILES: *C1CCN(C)CC1]

wherein the ring is substituted or unsubstituted. In some embodiments, $R^3$ is H, and $R^4$ is a ring that is

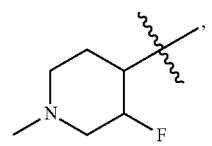 [SMILES: *C1CCN(C)CC1F]

wherein the ring is substituted or unsubstituted.

In some embodiments, each $R^{1e}$ and $R^{1f}$ is independently alkyl, $NR^{16}R^{17}$, aryl, heteroaryl, or heterocyclyl, each of which is independently substituted or unsubstituted, or hydrogen. In some embodiments, $R^{1e}$ is substituted alkyl, and $R^{1f}$ is hydrogen. In some embodiments, $R^{1e}$ is hydrogen, and $R^{1f}$ is $NR^{16}R^{17}$, wherein each $R^{16}$ and $R^{17}$ is independently alkyl, alkenyl, aryl, heteroaryl, or heterocyclyl, each of which is independently substituted or unsubstituted, or hydrogen. In some embodiments, $R^{1e}$ is hydrogen, and $R^{1f}$ is $NR^{16}R^{17}$, wherein $R^{16}$ is hydrogen, and $R^{17}$ is alkyl. In some embodiments, $R^{1e}$ is hydrogen, and $R^{1f}$ is $NR^{16}R^{17}$, wherein $R^{16}$ is hydrogen, and $R^{17}$ is phenyl. In some embodiments, $R^{1e}$ is hydrogen, and $R^{1f}$ is amino.

In some embodiments, the compound is of the formula:

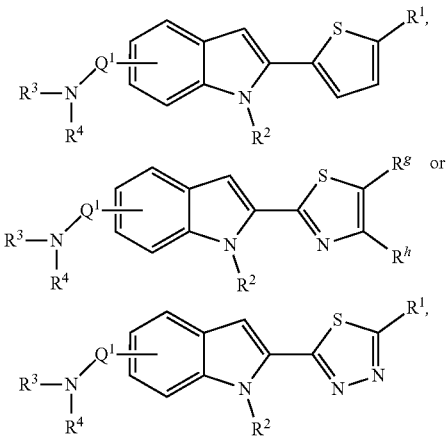

wherein:
Q$^1$ is C=O, C=S, C=CR$^{14}$R$^{15}$, C=NR$^{14}$, alkylene, alkenylene, or alkynylene, each of which is independently substituted or unsubstituted, or a bond;

each R$^1$, R$^{1g}$, and R$^{1h}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;

each R$^2$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

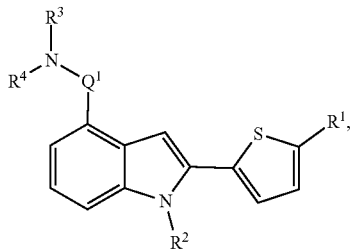

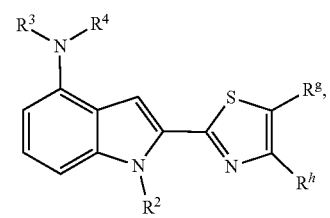

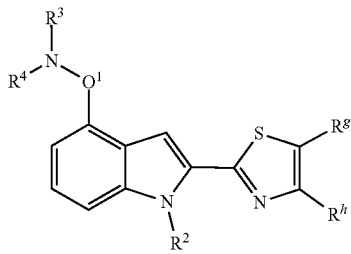

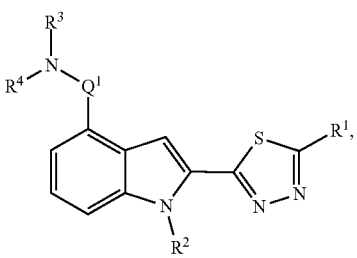

or a pharmaceutically-acceptable salt thereof, wherein the variables are as defined above.

In some embodiments, the compound is of the formula:

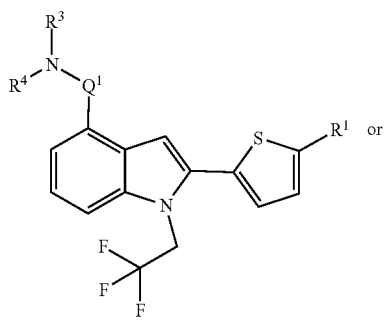

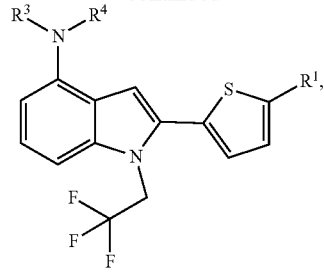

or a pharmaceutically-acceptable salt thereof, wherein the variables are as defined above.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is C$_1$-alkylene. In some embodiments, each R$^{16}$ and R$^{17}$ is independently alkyl, alkenyl, aryl, heteroaryl, heterocyclyl, or hydrogen. In some embodiments, $Q^1$ is a bond.

In some embodiments, R$^3$ is H, and R$^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, R$^3$ is H, and R$^4$ is alkyl, alkenyl, alkynyl, aryl, heteroaryl, or heterocyclyl, each of which is independently substituted or unsubstituted, or hydrogen. In some embodiments, R$^4$ is heterocyclyl. In some embodiments, R$^4$ is piperidinyl, piperazinyl, tetahydropyranyl, morpholinyl, or pyrrolidinyl, each of which is independently substituted or unsubstituted.

In some embodiments, R$^4$ is a ring that is:

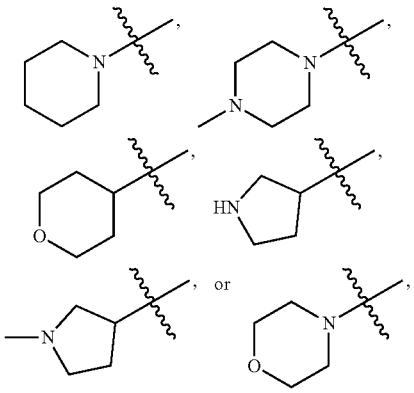

or wherein the ring is substituted or unsubstituted. In some embodiments, R$^3$ is H, and R$^4$ is a ring that is

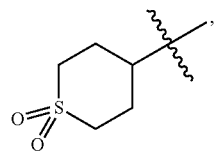 [SMILES: *C1CCS(=O)(=O)CC1]

wherein the ring is substituted or unsubstituted. In some embodiments, R$^3$ is H, and R$^4$ is a ring that is

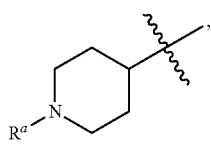

wherein the ring is substituted or unsubstituted. In some embodiments, $R^a$ is alkylene. In some embodiments, $R^a$ is methyl. In some embodiments, $R^3$ is H, and $R^4$ is a ring that is

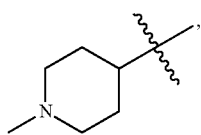 [SMILES: *C1CCN(C)CC1]

wherein the ring is substituted or unsubstituted. In some embodiments, $R^3$ is H, and $R^4$ is a ring that is

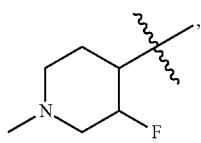 [SMILES: *C1CCN(C)CC1F]

wherein the ring is substituted or unsubstituted.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen. In some embodiments, $R^1$ is substituted alkyl. In some embodiments, $R^1$ is alkyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group. In some embodiments, $R^{16}$ is hydrogen, and $R^{17}$ is carboxyl substituted with alkyl or aryl. In some embodiments, $R^{16}$ is hydrogen, and $R^{17}$ is carboxyl substituted with cycloalkyl or phenyl. In some embodiments, $R^{16}$ and $R^{17}$ are hydrogen.

In some embodiments, the compound is of the formula:

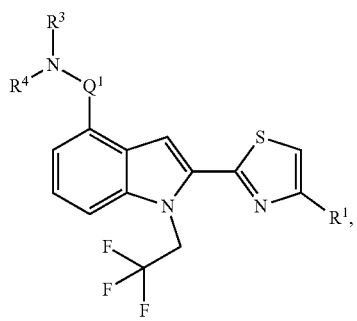

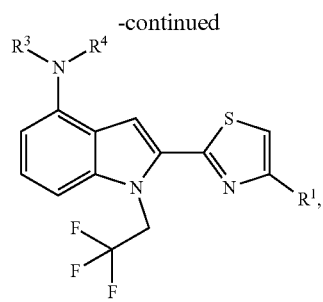

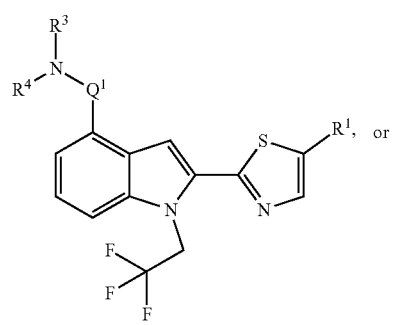

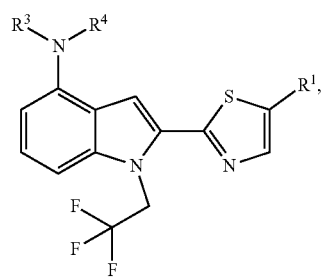

or a pharmaceutically-acceptable salt thereof, wherein the variables are as defined above.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen. In some embodiments, $R^1$ is substituted alkyl. In some embodiments, $R^1$ is alkyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group. In some embodiments, $R^{16}$ is hydrogen, and $R^{17}$ is carboxyl substituted with alkyl or aryl. In some embodiments, $R^{16}$ is hydrogen, and $R^{17}$ is carboxyl substituted with cycloalkyl or phenyl. In some embodiments, $R^{16}$ and $R^{17}$ are hydrogen.

In some embodiments, the compounds if of the formula:

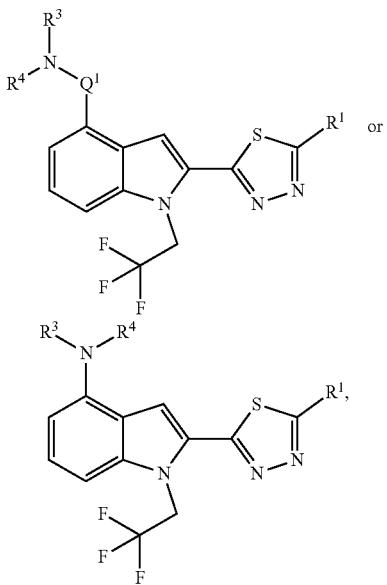

or a pharmaceutically-acceptable salt thereof, wherein the variables are as defined above.

In some embodiments, $Q^1$ is C=O, C=S, C=$CR^{14}R^{15}$, C=$NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

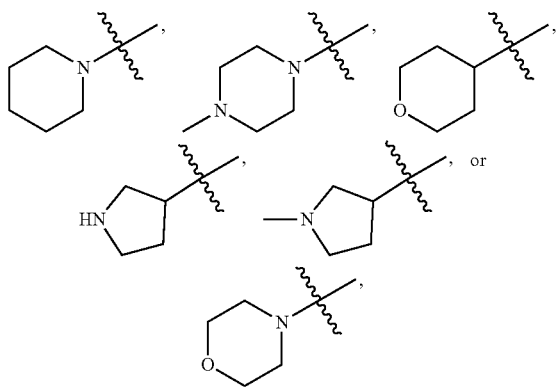

or wherein the ring is substituted or unsubstituted. In some embodiments, $R^3$ is H, and $R^4$ is a ring that is

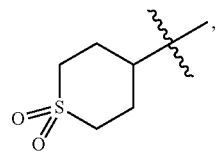

wherein the ring is substituted or unsubstituted. In some embodiments, $R^3$ is H, and $R^4$ is a ring that is

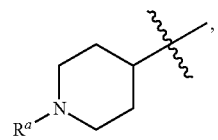

wherein the ring is substituted or unsubstituted. In some embodiments, $R^a$ is alkylene. In some embodiments, $R^a$ is methyl. In some embodiments, $R^3$ is H, and $R^4$ is a ring that is

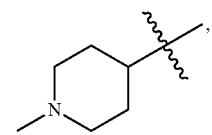 [SMILES: *C1CCN(C)CC1]

wherein the ring is substituted or unsubstituted. In some embodiments, $R^3$ is H, and $R^4$ is a ring that is

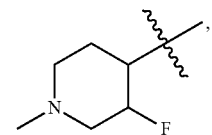 [SMILES: *C1CCN(C)CC1F]

wherein the ring is substituted or unsubstituted.

In some embodiments, $R^1$ is —$C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, heterocyclyl, or halo, each of which is independently substituted or unsubstituted, or hydrogen. In some embodiments $R^1$ is substituted alkyl. In some embodiments, $R^1$ is alkyl substituted with $NR^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is aryl, heteroaryl, carboxyl, or hydrogen. In some embodiments, $R^{16}$ is hydrogen, and $R^{17}$ is carboxyl substituted with aryl, heteroaryl, cycloalkyl, or alkyl. In some embodiments, $R^{16}$ and $R^{17}$ are hydrogen.

In some embodiments, the compound is of the formula:

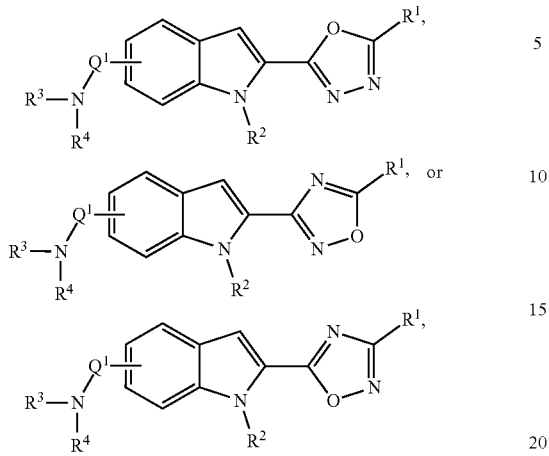

wherein:
- Q$^1$ is C═O, C═S, C═CR$^{14}$R$^{15}$, C═NR$^{14}$, alkylene, alkenylene, or alkynylene, each of which is independently substituted or unsubstituted, or a bond;
- R$^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;
- each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;
- each R$^2$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;
- each R$^{19}$ and R$^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;
- each R$^{21}$ and R$^{22}$ is independently alkyl, alkenyl, alkynyl, aryl, heteroaryl, or heterocyclyl, each of which is independently substituted or unsubstituted, or hydrogen; and
- each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

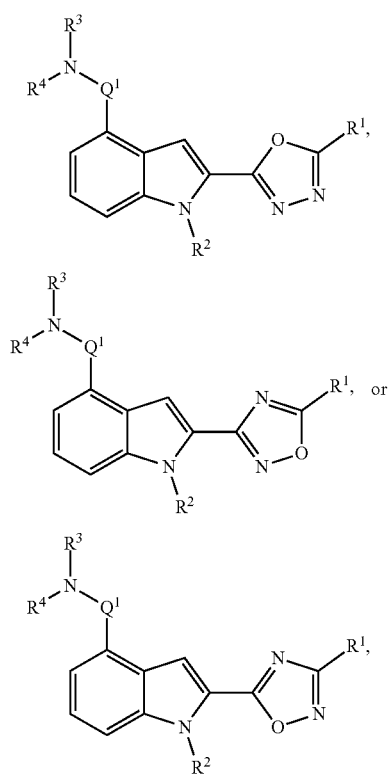

or a pharmaceutically-acceptable salt thereof, wherein the variables are as defined above.

In some embodiments, the compound is of the formula:

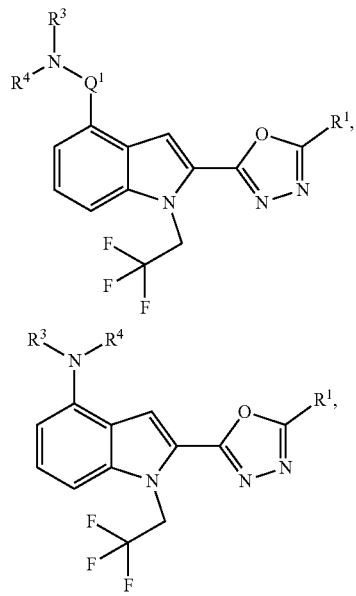

-continued

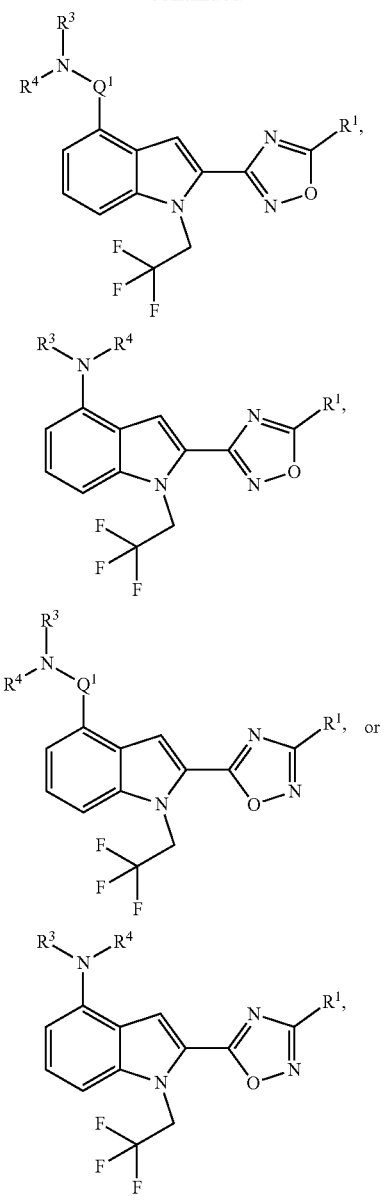

or a pharmaceutically-acceptable salt thereof, wherein the variables are as defined above.

In some embodiments, the compound is of the formula:

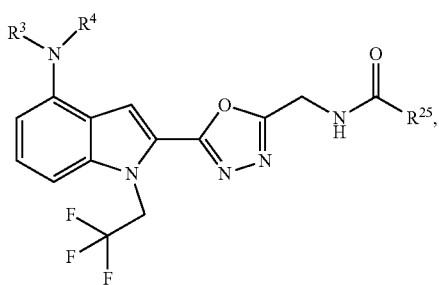

-continued

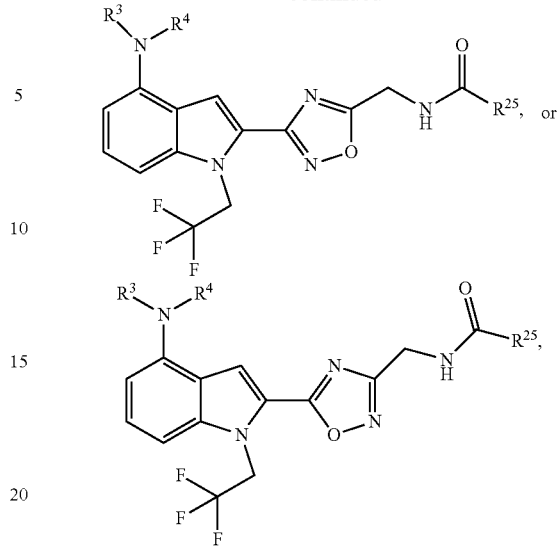

wherein:
Q$^1$ is C=O, C=S, C=CR$^{14}$R$^{15}$, C=NR$^{14}$, alkylene, alkenylene, or alkynylene, each of which is independently substituted or unsubstituted, or a bond;

each R$^{1c}$ and R$^{1d}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;

each R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, R$^{25}$ is alkyl, alkenyl, alkynyl, aryl, heteroaryl, or heterocyclyl, each of which is independently substituted or unsubstituted, or hydrogen;

or a pharmaceutically-acceptable salt thereof.

In some embodiments, R$^{25}$ is heterocyclyl, cycloalkyl, aryl, each of which is substituted or unsubstituted. In some embodiments, $R^{25}$ is phenyl or cyclopropyl, each of which is substituted or unsubstituted. In some embodiments, $R^{25}$ is substituted cyclopropyl. In some embodiments, $R^{25}$ is heteroaryl or heterocyclyl, each of which is substituted or unsubstituted. In some embodiments, $R^{25}$ is thiophenyl, indolenyl, or pyrrolyl, each of which is substituted or unsubstituted.

Non-limiting examples of compounds of the disclosure include compounds of any of the following formulae:

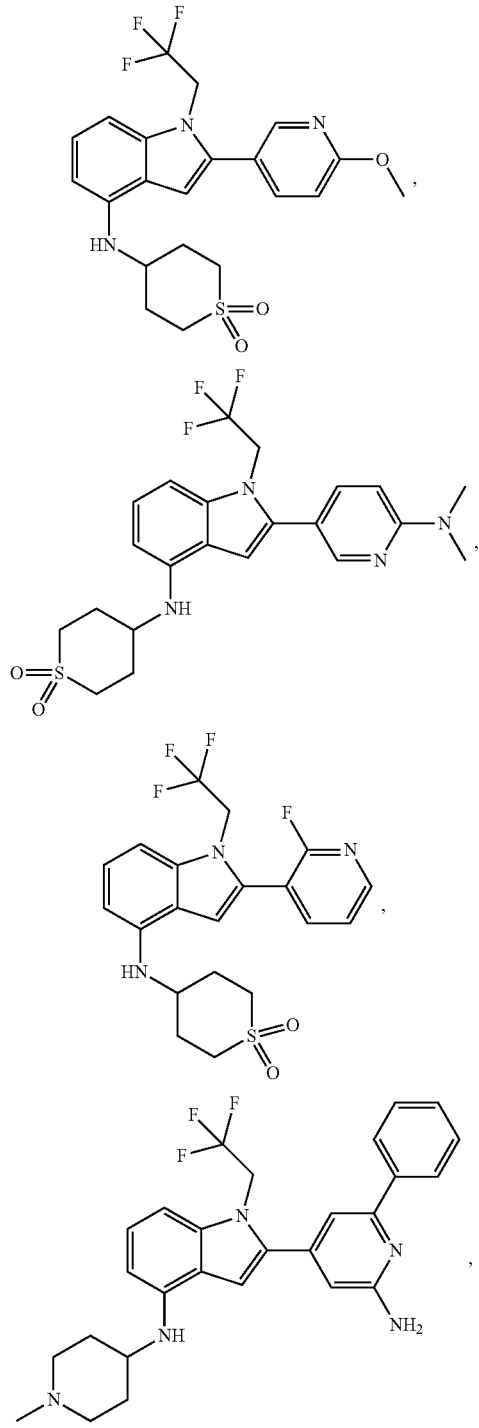

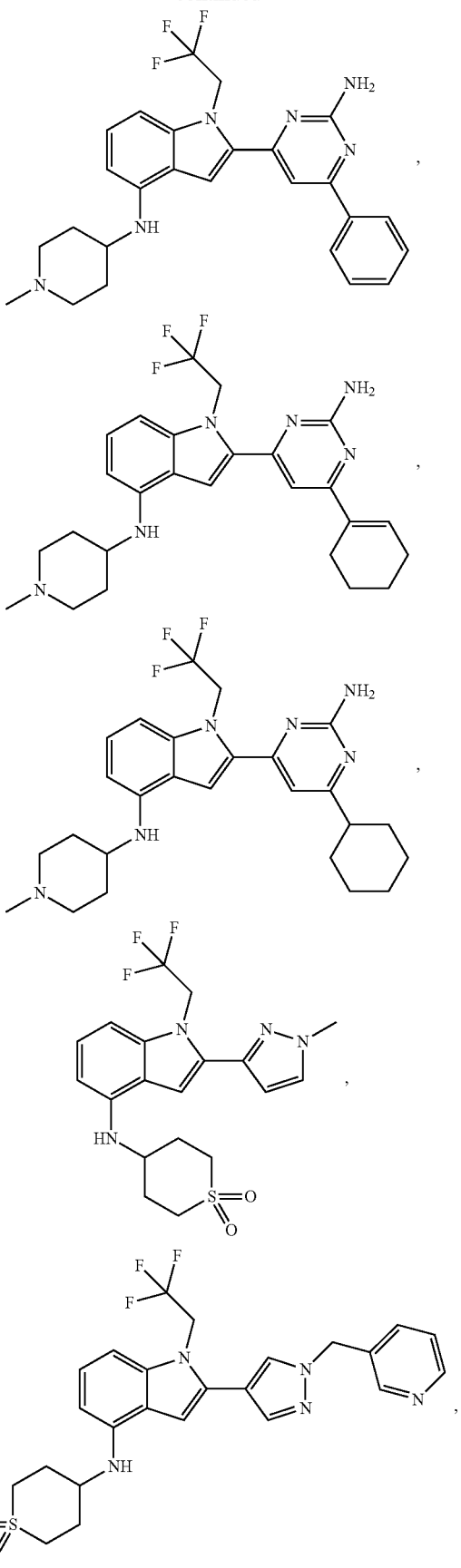

187
-continued
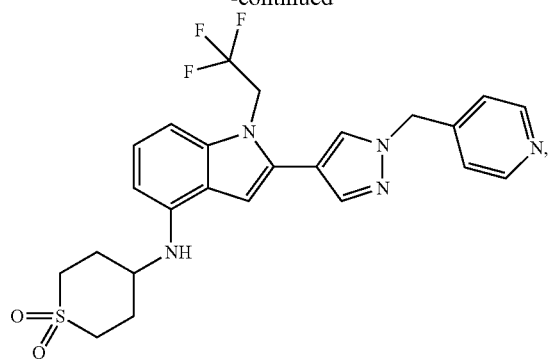
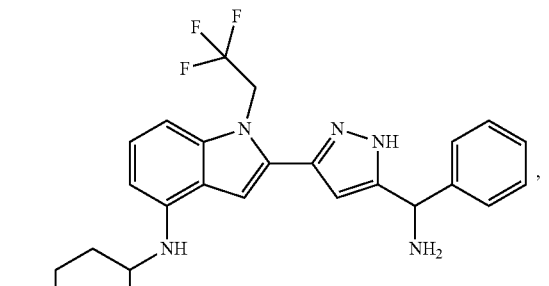
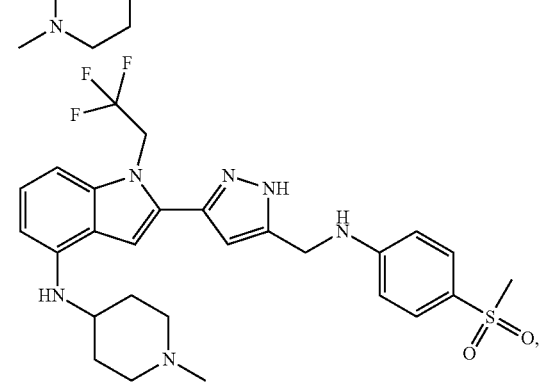
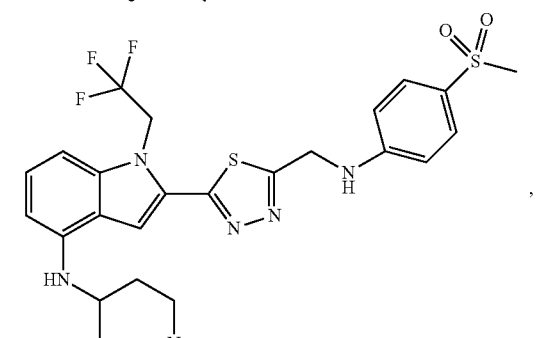
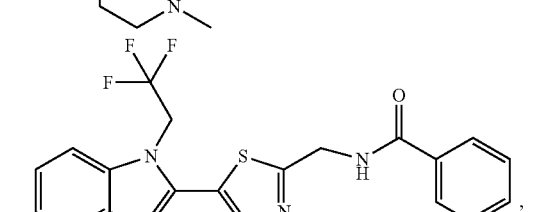
188
-continued
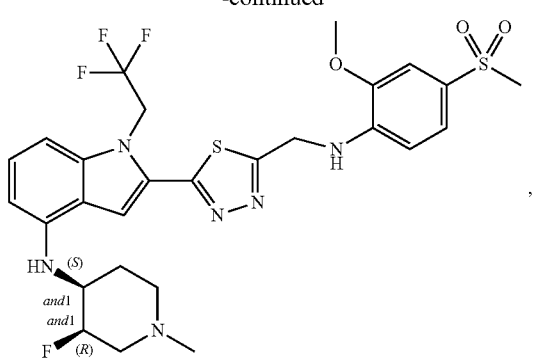
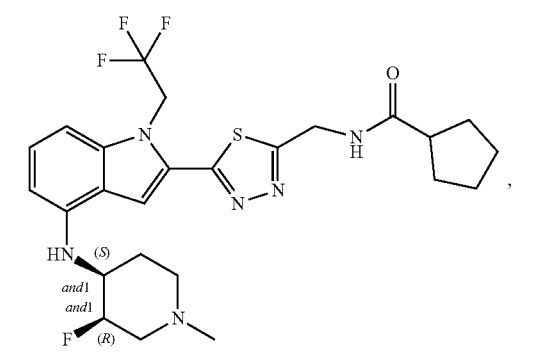
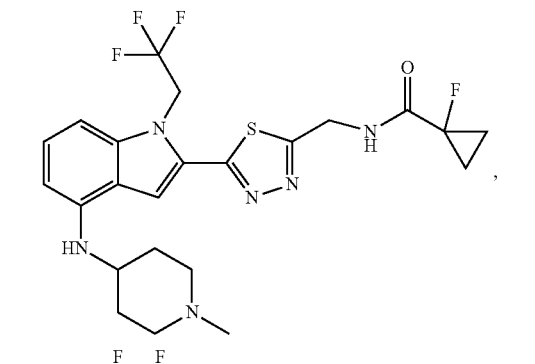
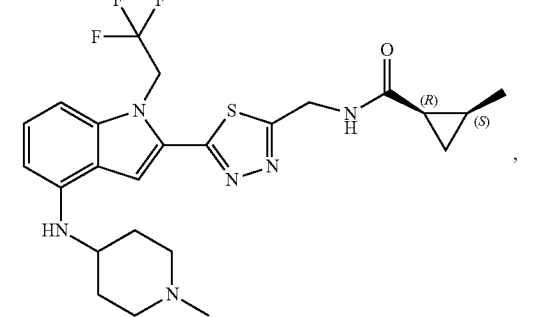
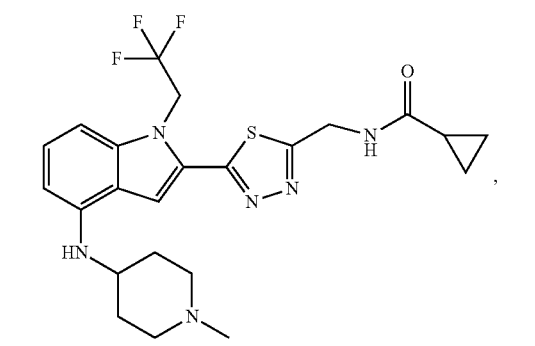

189
-continued
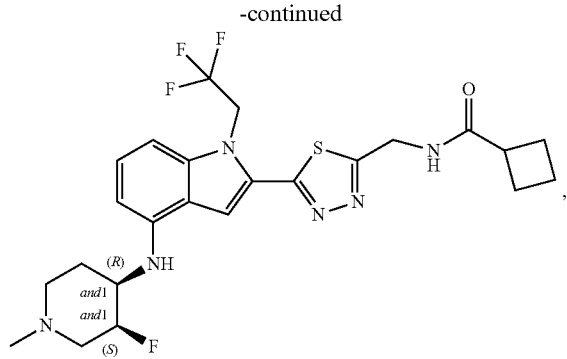
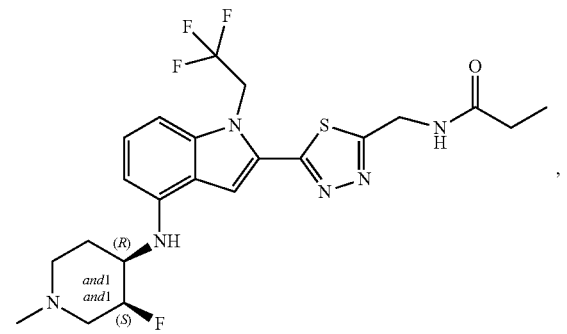
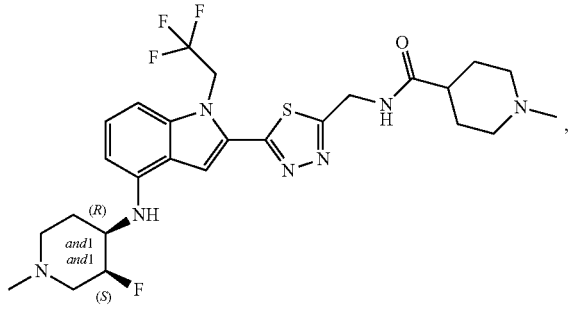
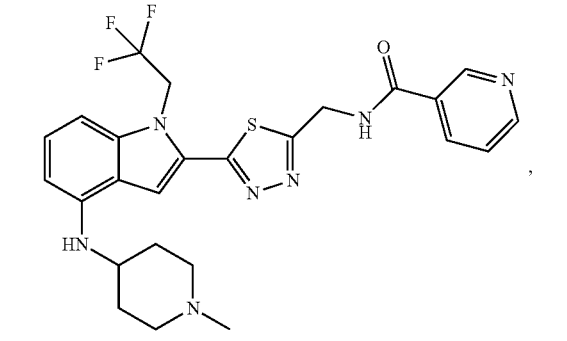
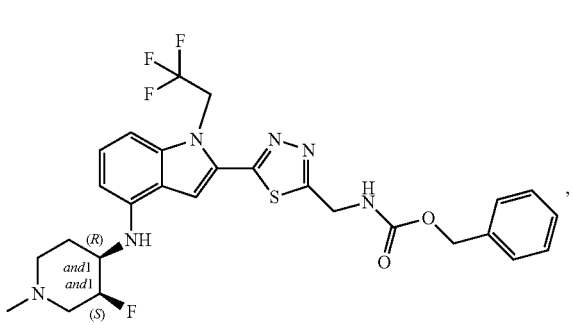
190
-continued
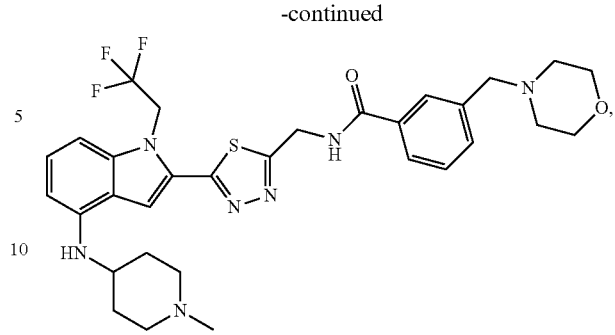
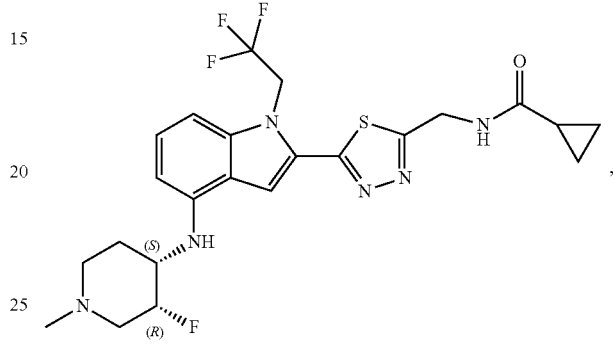
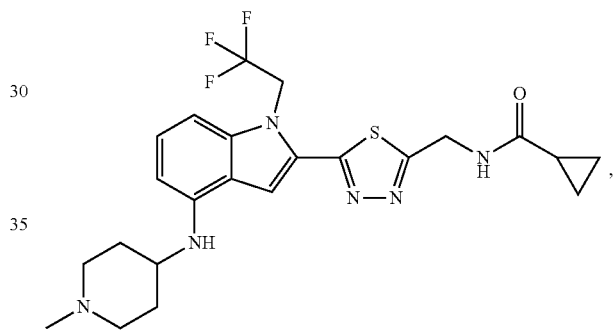
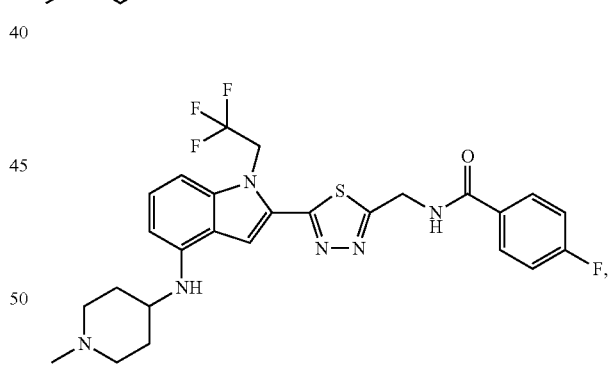
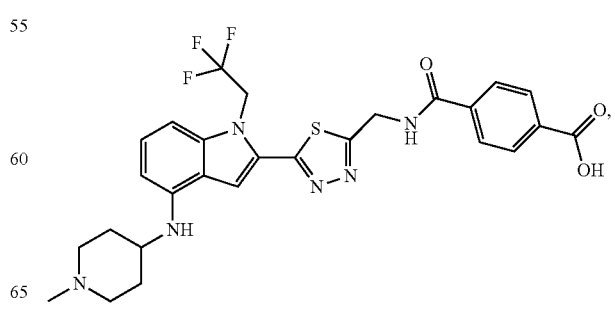

191
-continued
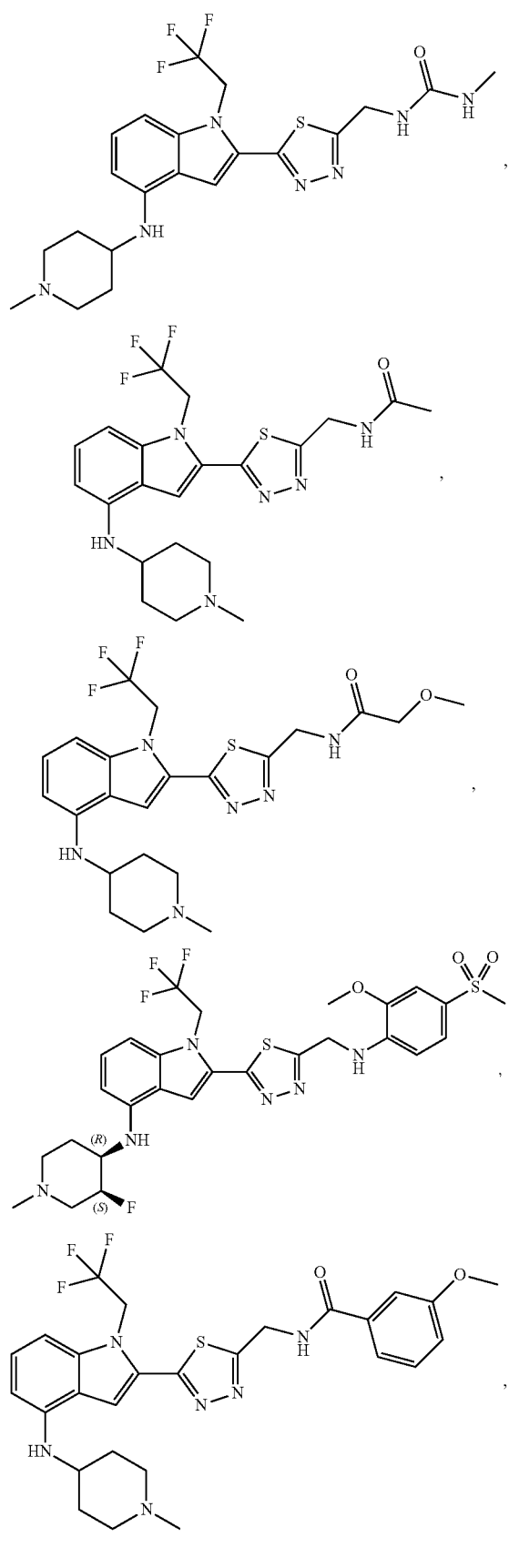
192
-continued
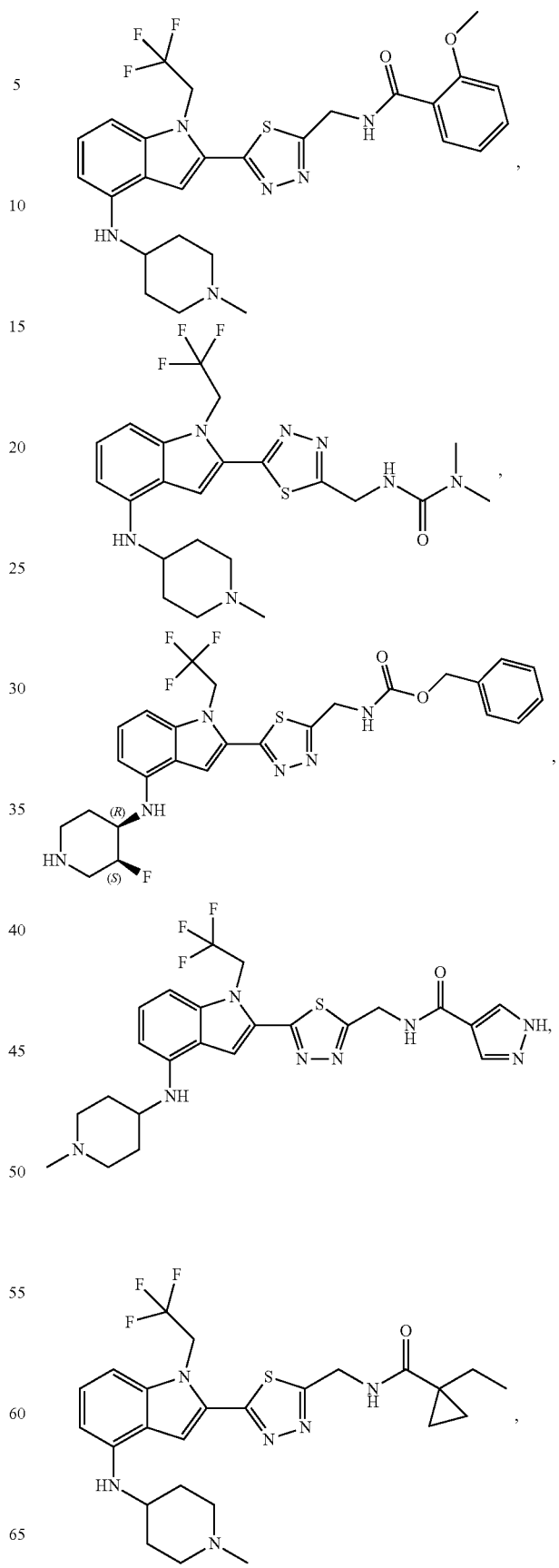

193
-continued
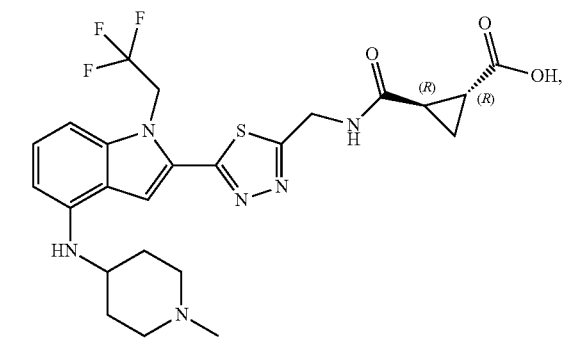
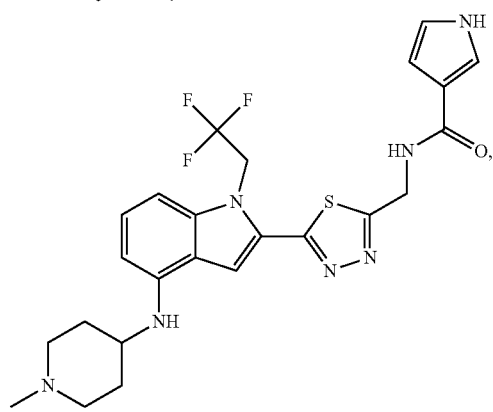
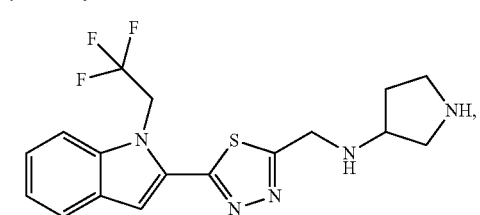
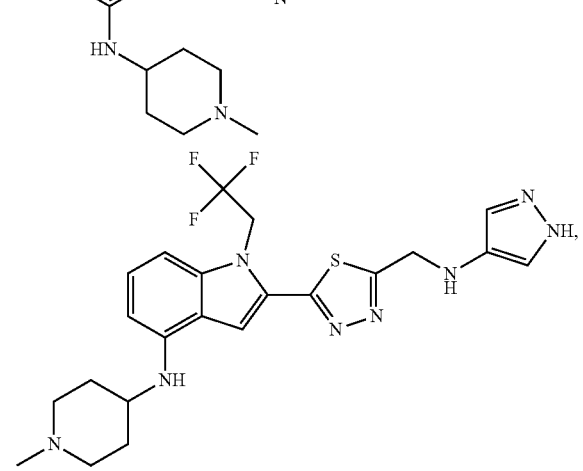
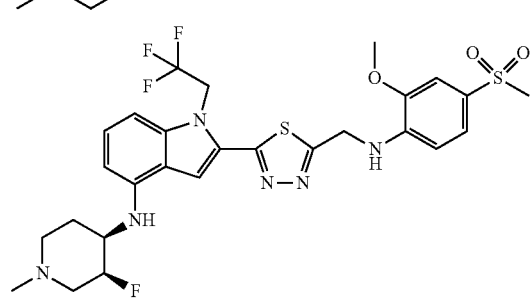, or
194
-continued
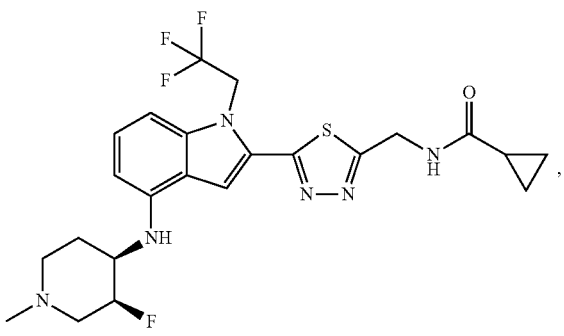
or a pharmaceutically-acceptable salt thereof.
Non-limiting examples of compounds of the disclosure include compounds of any of the following formulae:
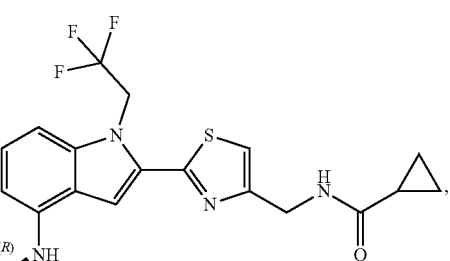
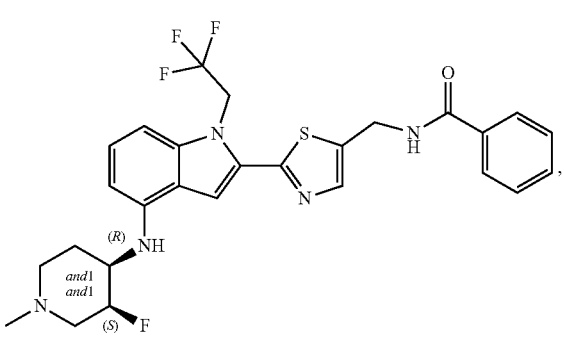
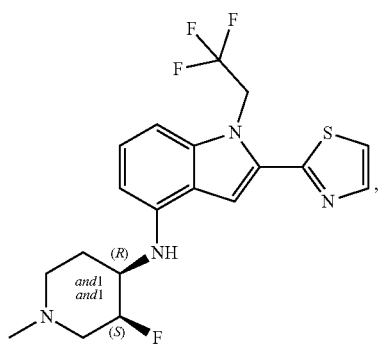

195
-continued
196
-continued
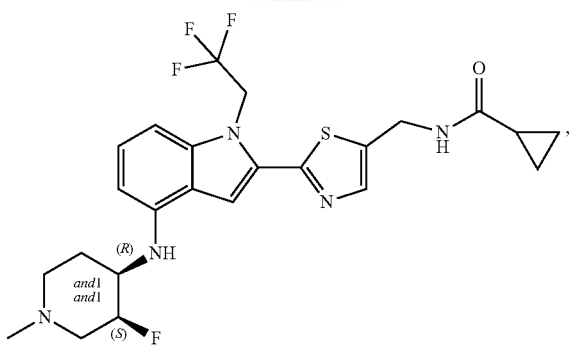
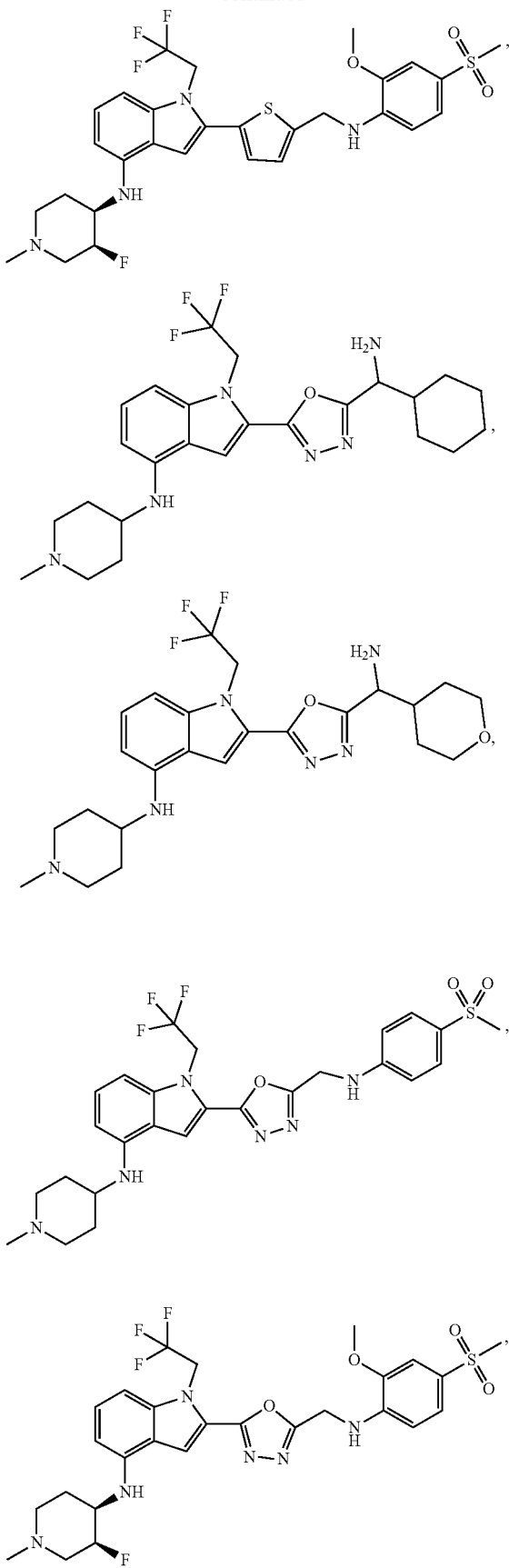

197
-continued
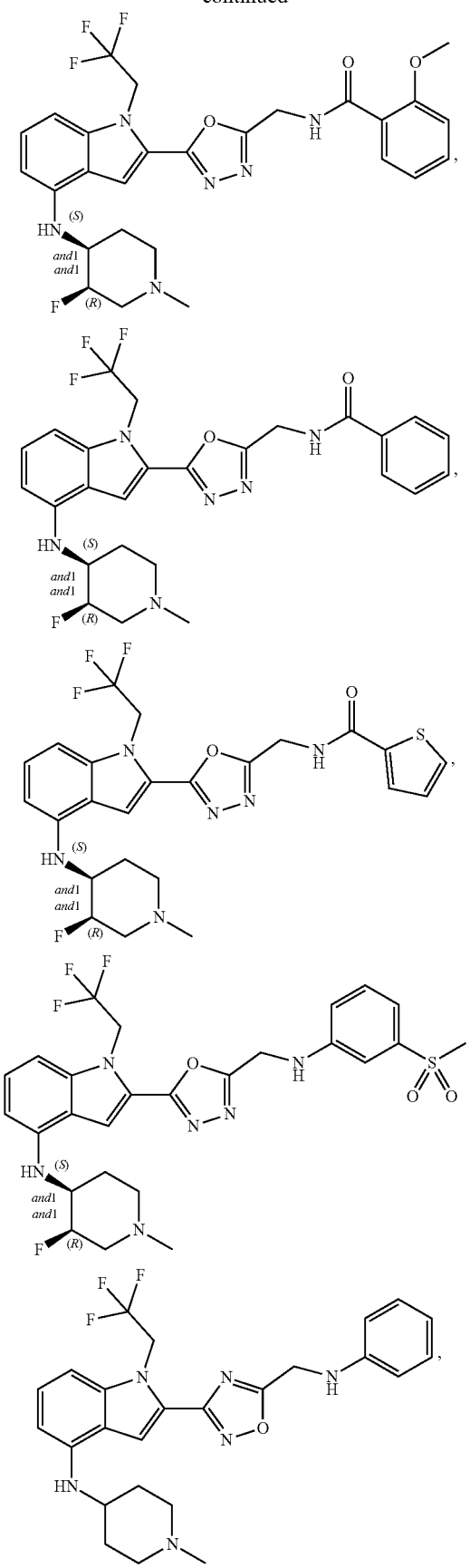
198
-continued
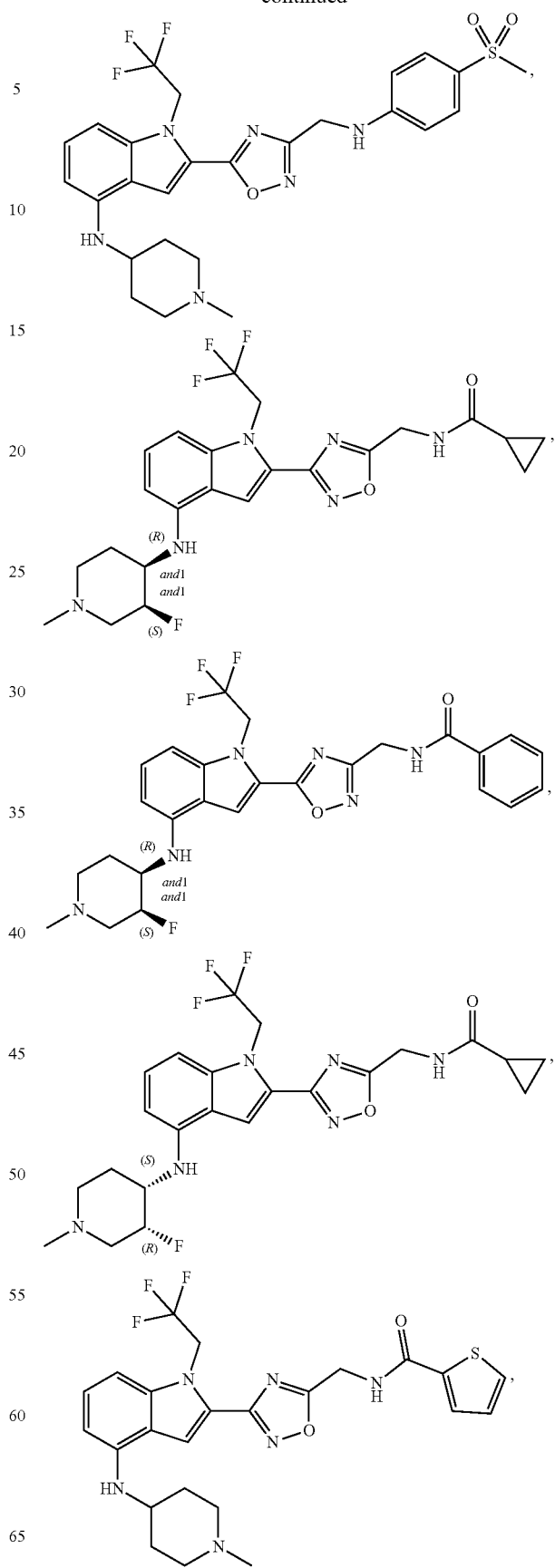

199
-continued
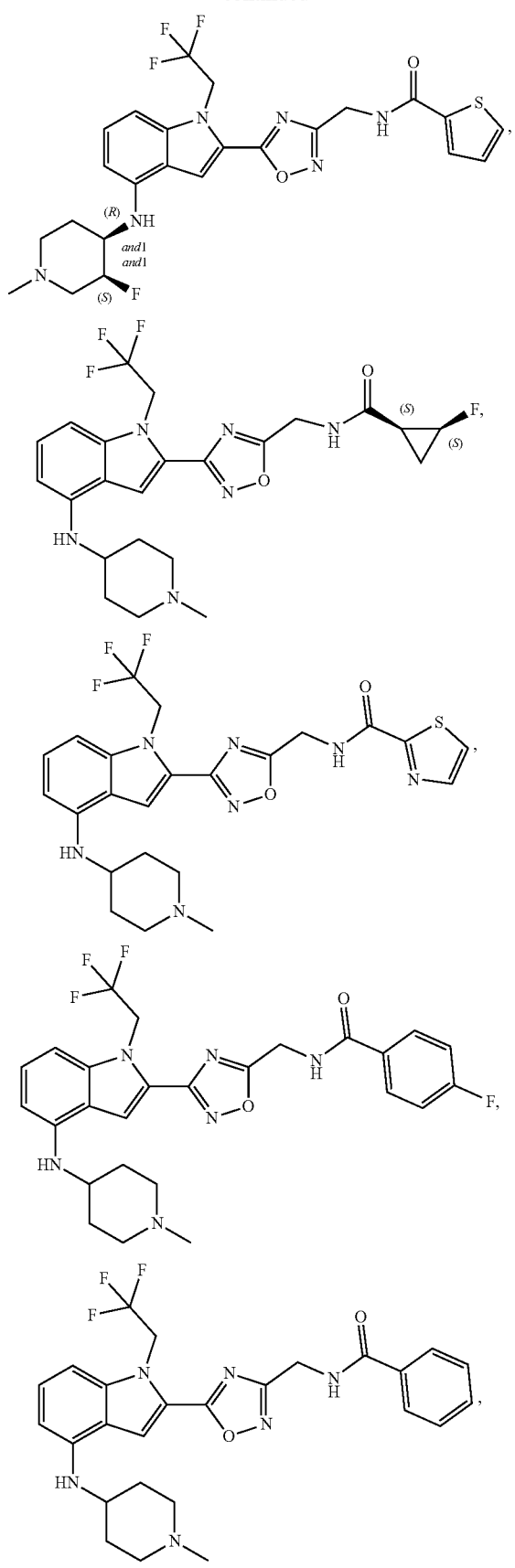
200
-continued
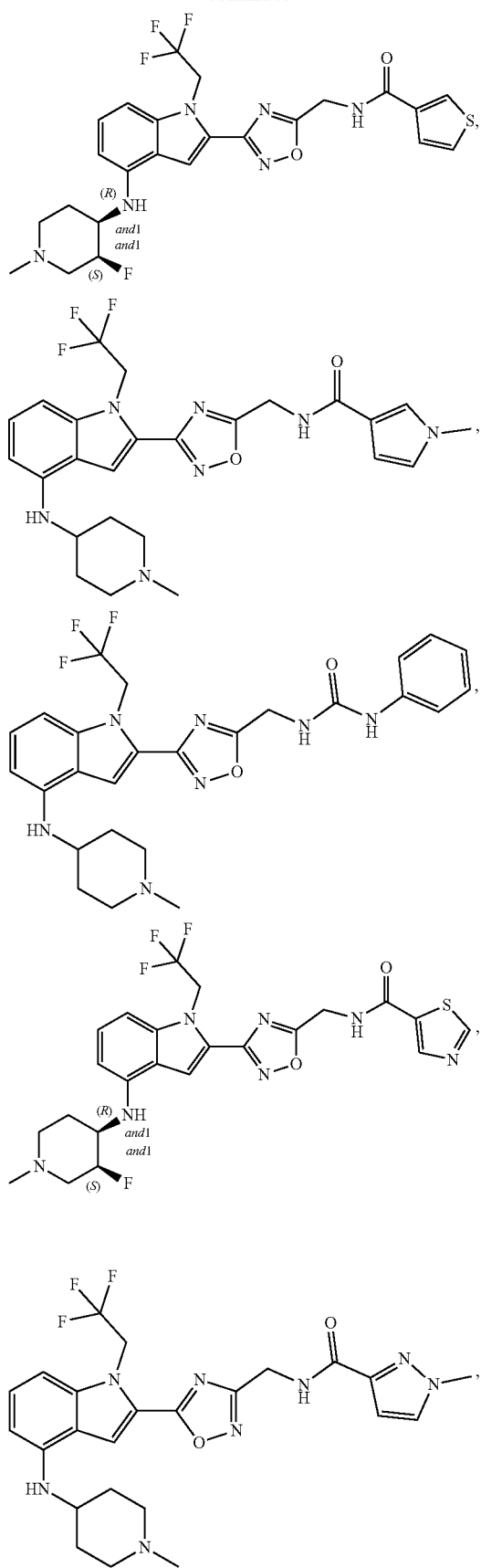

201
-continued
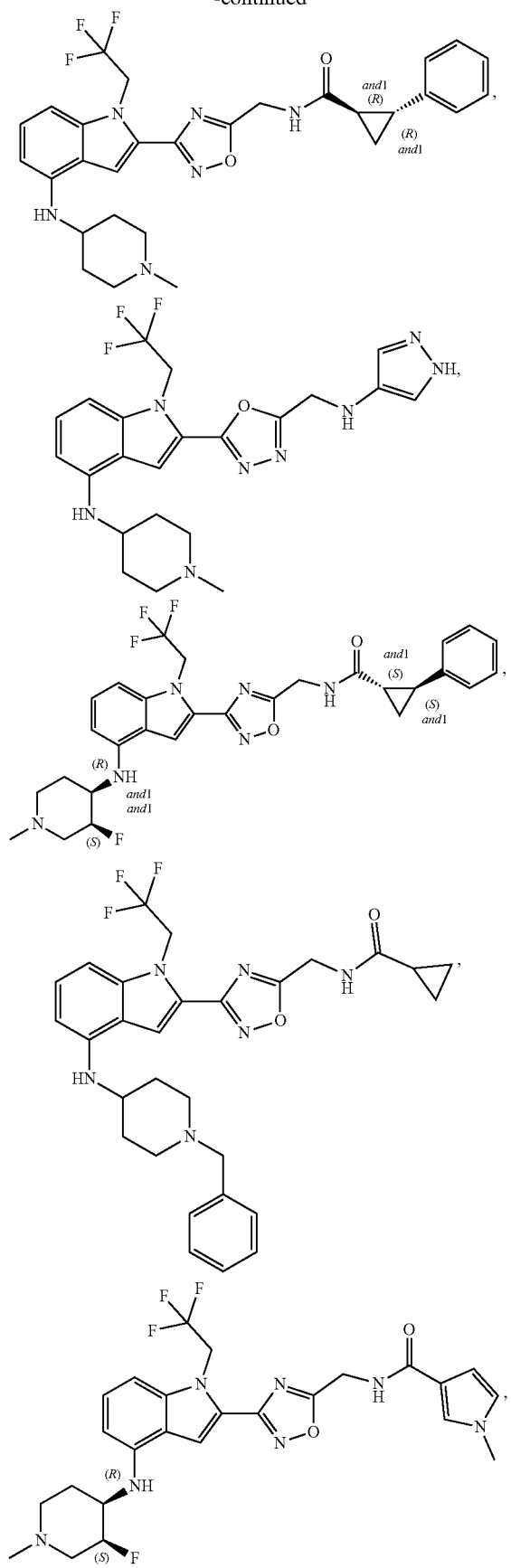
202
-continued
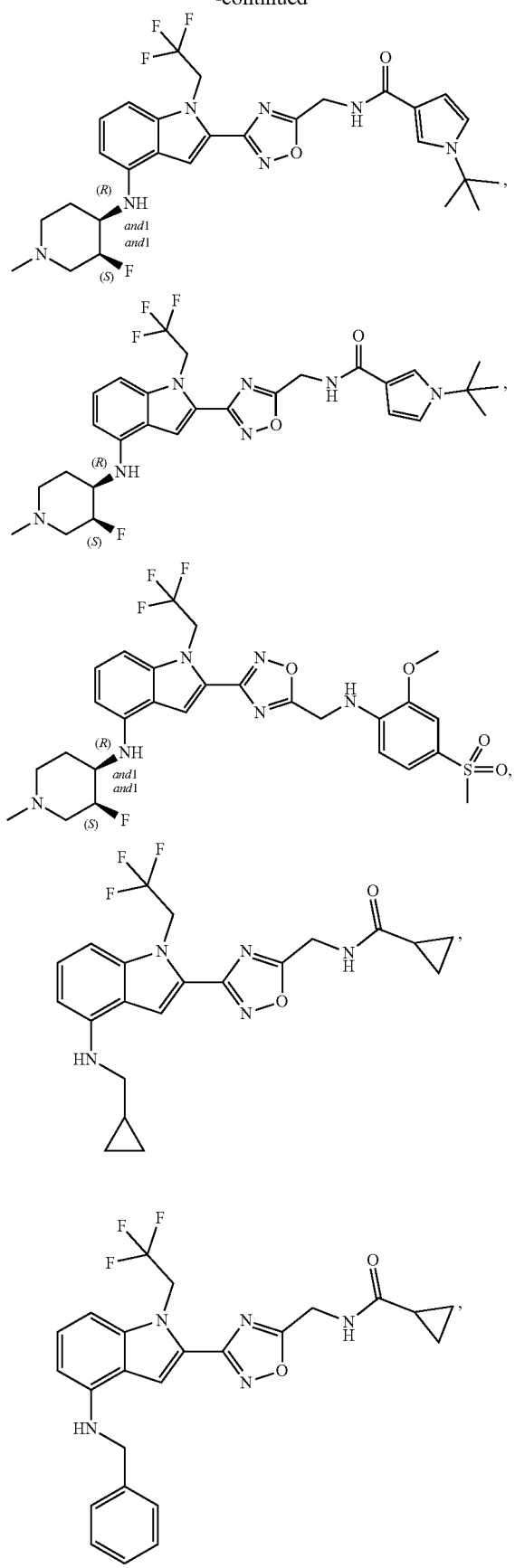

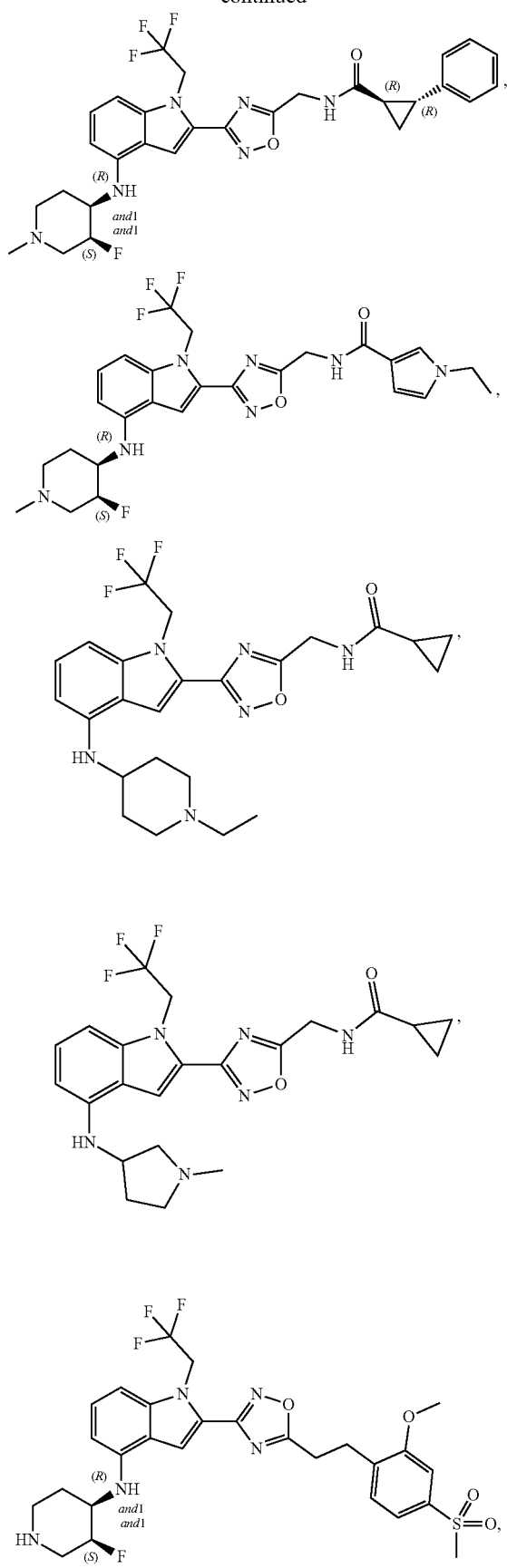
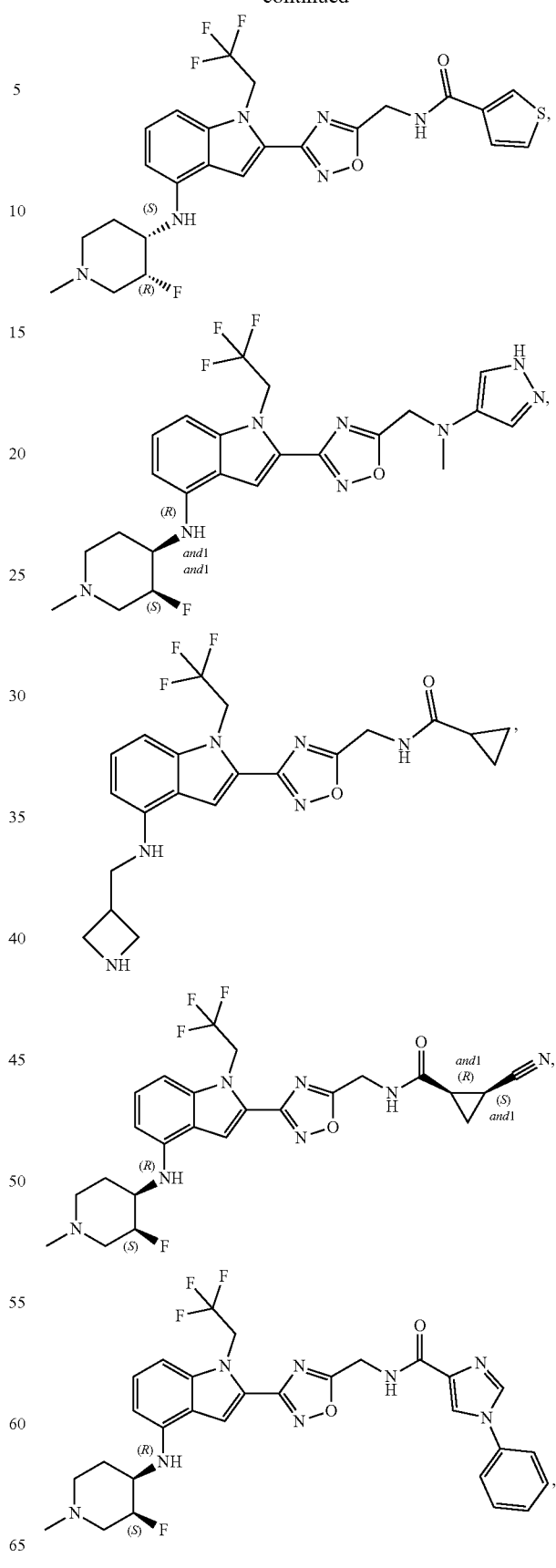

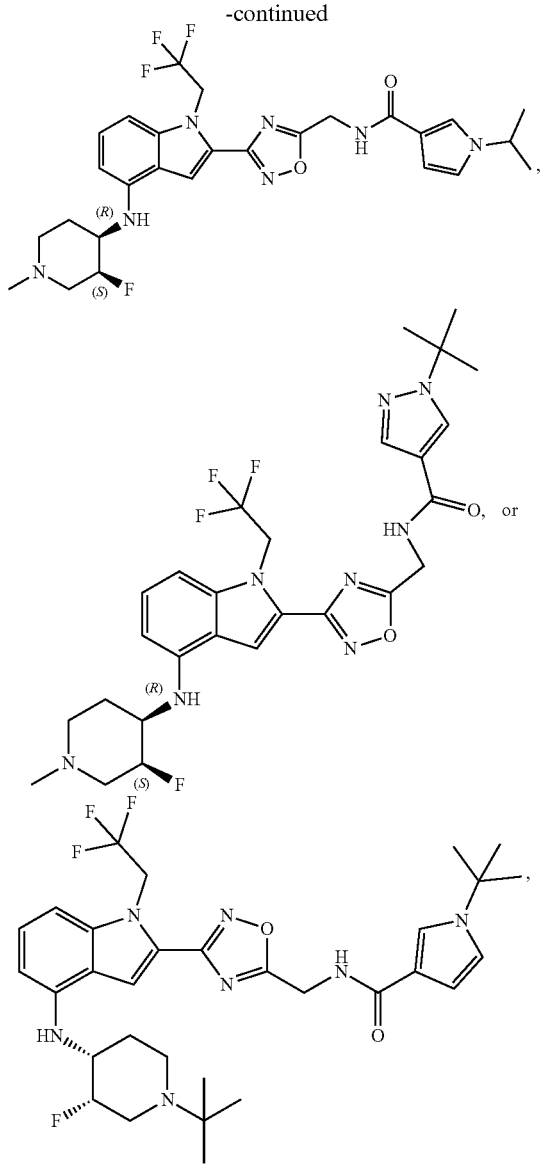

or a pharmaceutically-acceptable salt thereof.

Compounds herein can include all stereoisomers, enantiomers, diastereomers, mixtures, racemates, atropisomers, and tautomers thereof.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxy ethyl, 1,2-difluoroethyl, and 3-carboxypropyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, compounds of the invention can be used to treat cancer in a subject. A compound of the invention can, for example, slow the proliferation of cancer cell lines, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, the compounds of the invention show non-lethal toxicity.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Compositions of the Invention.

A pharmaceutical composition of the invention can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the invention can be applied topically to the skin, or a body cavity, for example, oral, vaginal, bladder, cranial, spinal, thoracic, or pelvic cavity of a subject. The compounds of the invention can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MILV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

Combination Treatment

Combination therapy with a compound of the disclosure and at least one additional therapeutic agent, for example, any additional therapeutic agent described herein, can be used to treat a condition. In some embodiments, the combination therapy can produce a significantly better therapeutic result than the additive effects achieved by each individual constituent when administered alone at a therapeutic dose. In some embodiments, the dosage of the compound or additional therapeutic agent, for example, any additional therapeutic agent described herein, in combination therapy can be reduced as compared to monotherapy with each agent, while still achieving an overall therapeutic effect. In some embodiments, a compound and an additional therapeutic agent, for example, any additional therapeutic agent described herein, can exhibit a synergistic effect. In some embodiments, the synergistic effect of a compound and additional therapeutic agent, for example, any additional therapeutic agent described herein, can be used to reduce the total amount drugs administered to a subject, which decrease side effects experienced by the subject.

The compounds of the disclosure can be used in combination with at least one additional pharmaceutically-active agent, for example, any additional therapeutic agent described herein. In some embodiments, the at least one additional pharmaceutically-active agent, for example, any additional therapeutic agent described herein, can modulate the same or a different target as the compounds of the disclosure. In some embodiments, the at least one additional pharmaceutically-active agent, for example, any additional therapeutic agent described herein, can modulate the same target as the compounds of the disclosure, or other components of the same pathway, or overlapping sets of target enzymes. In some embodiments, the at least one additional pharmaceutically-active agent, for example, any additional therapeutic agent described herein, can modulate a different target from the compounds of the disclosure.

Accordingly, in one aspect, the present disclosure provides a method for treating cancer, the method comprising administering to a subject in need thereof (a) an effective amount of a compound of the disclosure and (b) an effective amount of at least one additional pharmaceutically active agent, for example, any additional therapeutic agent described herein, to provide a combination therapy. In some embodiments, the combination therapy may have an enhanced therapeutic effect compared to the effect of the compound and the at least one additional pharmaceutically active agent each administered alone. According to certain exemplary embodiments, the combination therapy has a synergistic therapeutic effect. According to this embodiment, the combination therapy produces a significantly better therapeutic result (e.g., anti-cancer, cell growth arrest, apoptosis, induction of differentiation, cell death, etc.) than the additive effects achieved by each individual constituent when administered alone at a therapeutic dose.

Combination therapy includes but is not limited to the combination of compounds of the disclosure with chemotherapeutic agents, therapeutic antibodies, or radiation treatment, to provide a synergistic therapeutic effect. In some embodiments, the compounds of the disclosure are used in combination with one or more anti-cancer (antineoplastic or cytotoxic) chemotherapy drug. Suitable chemotherapeutic agents for use in the combinations of the present disclosure include, but are not limited to, alkylating agents, antibiotic agents, antimetabolic agents, hormonal agents, plant-derived agents, anti-angiogenic agents, differentiation inducing agents, cell growth arrest inducing agents, apoptosis inducing agents, cytotoxic agents, agents affecting cell bioenergetics, biologic agents, e.g., monoclonal antibodies, kinase inhibitors and inhibitors of growth factors and their receptors, gene therapy agents, cell therapy, or any combination thereof.

a. Combination Treatment with Estrogen Receptor Antagonists

In some embodiments, a compound of the disclosure is used in combination with an estrogen receptor antagonist. In some embodiments, a compound of the disclosure is used in combination with toremifene (Fareston®), fulvestrant (Faslodex®), or tamoxifen citrate (Soltamox®).

Fulvestrant is a selective estrogen receptor degrader (SERD) and is indicated for the treatment of hormone receptor positive metastatic breast cancer in postmenopausal women with disease progression following anti-estrogen therapy. Fulvestrant is a complete estrogen receptor antagonist with little to no agonist effects and accelerates the proteasomal degradation of the estrogen receptor. Fulvestrant has poor oral bioavailability and is administered via intramuscular injection. Fulvestrant-induced expression of ErbB3 and ErbB4 receptors sensitizes estrogen receptor-positive breast cancer cells to heregulin beta1. In some embodiments, a compound of the disclosure is used in combination with fulvestrant.

b. Combination Treatment with Aromatase Inhibitors

In some embodiments, a compound of the disclosure is used in combination with an aromatase inhibitor. Aromatase inhibitors are used in the treatment of breast cancer in post-menopausal women and gynecomastia in men. Aromatase inhibitors can be used off-label to reduce estrogen conversion when using external testosterone. Aromatase inhibitors can also be used for chemoprevention in high-risk women.

In some embodiments, a compound of the disclosure is used in combination with a non-selective aromatase inhibitor. In some embodiments, a compound of the disclosure is used in combination with a non-selective aromatase inhibitor, such as aminoglutethimide or testolactone (Teslac®). In some embodiments, a compound of the disclosure is used in combination with a selective aromatase inhibitor. In some embodiments, a compound of the disclosure is used in combination with a selective aromatase inhibitor, such as anastrozole (Arimidex®), letrozole (Femara®), exemestane (Aromasin®), vorozole (Rivizor®), formestane (Lentaron®), or fadrozole (Afema®). In some embodiments, a compound of the disclosure is used in combination with exemestane. In some embodiments, a compound of the disclosure is used in combination with an aromatase inhibitor such as 1,4,6-androstatrien-3,17-dione (ATD) or 4-androstene-3,6,17-trione.

c. Combination Treatment with mTOR Inhibitors

In some embodiments, a compound of the disclosure is used in combination with an mTOR inhibitor. mTOR inhibitors are drugs that inhibit the mechanistic target of rapamycin (mTOR), which is a serine/threonine-specific protein kinase that belongs to the family of phosphatidylinositol-3 kinase (PI3K)-related kinases (PIKKs). mTOR regulates cellular metabolism, growth, and proliferation by forming and signaling through the protein complexes mTORC1 and mTORC2.

In some embodiments, a compound of the disclosure is used in combination with an mTOR inhibitor, such as rapamycin, temsirolimus (CCI-779), everolimus (RAD001), ridaforolimus (AP-23573). In some embodiments, a compound of the disclosure is used in combination with everolimus (Afinitor®). Everolimus affects the mTORC1 protein complex and can lead to hyper-activation of the kinase AKT, which can lead to longer survival in some cell types. Everolimus binds to FKBP12, a protein receptor which directly interacts with mTORC1 and inhibits downstream signaling. mRNAs that codify proteins implicated in the cell cycle and in the glycolysis process are impaired or altered as a result, inhibiting tumor growth and proliferation.

In some embodiments, a compound of the disclosure is used in combination with a mTOR inhibitor and an aromatase inhibitor. For example, a compound of the disclosure is used in combination with everolimus and exemestane.

d. Combination Treatment with Antimetabolites

Antimetabolites are chemotherapy treatments that are similar to normal substances within the cell. When cells incorporate the antimetabolites into the cellular metabolism, the cells are unable to divide. Antimetabolites are cell-cycle specific and attack cells at specific phases in the cell cycle.

In some examples, a compound of the disclosure is used in combination with one or more antimetabolites, such as a folic acid antagonist, pyrimidine antagonist, purine antagonist, or an adenosine deaminase inhibitor. In some embodiments, a compound of the disclosure is used in combination with an antimetabolite, such as methotrexate, 5-fluorouracil, foxuridine, cytarabine, capecitabine, gemcitabine, 6-mercaptopurine, 6-thioguanine, cladribine, fludarabine, nelarabine, or pentostatin. In some embodiments, a compound of the disclosure is used in combination with capecitabine (Xeloda®), gemcitabine (Gemzar®), or cytarabine (Cytosar-U®).

e. Combination Treatment with Plant Alkaloids

In some embodiments, a compound of the disclosure is used in combination with a plant alkaloid. In some embodiments, a compound of the disclosure is used in combination with a plant alkaloid, such as *vinca* alkaloids, taxanes, podophyllotoxins, or camptothecan analogues. In some embodiments, a compound of the disclosure is used in combination with plant alkaloids, such as vincristine, vinblastine, vinorelbine, paclitaxel, docetaxel, etoposide, tenisopide, irinotecan, or topotecan.

In some embodiments, a compound of the disclosure is used in combination with a taxane, such as paclitaxel (Abraxane® or Taxol®) and docetaxel (Taxotere®). In some embodiments, a compound of the disclosure is used in combination with paclitaxel. In some embodiments, a compound of the disclosure is used in combination with docetaxel.

f. Combination Treatment with Therapeutic Antibodies

In some embodiments, a compound of the disclosure is used in combination with therapeutic antibodies. In some embodiments, a compound of the disclosure is used in combination with naked monoclonal antibodies, such as alemtuzumab (Campath®) or trastuzumab (Herceptin®). In some embodiments, a compound of the disclosure is used in combination with conjugated monoclonal antibodies, such as radiolabeled antibodies or chemolabeled antibodies. In some embodiments, a compound of the disclosure is used in combination with conjugated monoclonal antibodies, such as ibritumomab tiuxetan (Zevalin®), brentuximab vedotin (Adcetris®), ado-trastuzumab emtansine (Kadcyla®), or denileukin diftitox (Ontak®). In some embodiments, a compound of the disclosure is used in combination with bispecific monoclonal antibodies, such as blinatumomab (Blincyto®).

In some embodiments, a compound of the disclosure is used in combination with an anti-CD20 antibody, such as rituximab (Mabthera®/Rituxan®), obinutuzumab (Gazyva®), ibritumomab tiuxetan, tositumomab, ofatumumab (Genmab®), ocaratuzumab, ocrelizumab, TRU-015, or veltuzumab. Other antibodies that can be used in combination with a compound of the disclosure include antibodies against the programed cell death (PD-1) receptor, for example pembrolizumab (Keytruda®) or nivolumba (Opdivo®).

g. Combination Treatment with PD-L1 and/or PD-1 Antagonists

The PD-1 pathway comprises the immune cell co-receptor Programmed Death-1 (PD-1) and the PD-1 ligands PD-L1 and PD-L2. The PD-1 pathway mediates local immunosuppression in the tumor microenvironment. PD-1 and PD-L1 antagonists suppress the immune system. In some embodiments, a PD-1 or PD-L1 antagonist is a monoclonal antibody or antigen binding fragment thereof that specifically binds to, blocks, or downregulates PD-1 or PD-L1, respectively. In some embodiments, a PD-1 or PD-L1 antagonist is a compound or biological molecule that specifically binds to, blocks, or downregulates PD-1 or PD-L1, respectively.

In some embodiments, the compounds of the disclosure are used in combination with a PD-1 or PD-L1 antagonist. In some embodiments, the compounds of the disclosure are used in combination with a PD-1/PD-L1 antagonist, for example, MK-3475, nivolumab (Opdivo®), pembrolizumab (Keytruda®), humanized antibodies (i.e., h409A1 1, h409A16 and h409A17), AMP-514, BMS-936559, MEDI0680, MEDI4736, MPDL3280A, MSB0010718C, MDX-1105, MDX-1106, or pidilzumab. In some embodiments, the compounds of the disclosure are used in combination with a PD-1/PD-L1 antagonist that is an immunoadhesion molecule, such as AMP-224. In some embodiments, the compounds of the disclosure are used in combination with a PD-1/PD-L1 antagonist to treat cancer cells or a tumor that overexpresses PD-1 or PD-L1. In some embodiments, the compounds of the disclosure are used in combination with a PD-1/PD-L1 antagonist to treat cancer cells or a tumor that overexpresses miR-34.

h. Combination Treatment with Anti-Hormone Therapy

Anti-hormone therapy uses an agent to suppress selected hormones or the effects. Anti-hormone therapy is achieved by antagonizing the function of hormones with a hormone antagonist and/or by preventing the production of hormones. In some embodiments, the suppression of hormones can be beneficial to subjects with certain cancers that grow in response to the presence of specific hormones. In some embodiments, a compound of the disclosure is used in combination with a hormone antagonist.

In some embodiments, a compound of the disclosure is used in combination with anti-androgens, anti-estrogens, aromatase inhibitors, or luteinizing hormone-releasing hormone (LHRH) agonists. In some embodiments, a compound of the disclosure is used in combination with anti-androgens, such as bicalutamide (Casodex®), cyproterone (Androcur®), flutamide (Euflex®), or nilutamide (Anandron®). In some embodiments, a compound of the disclosure is used in combination with anti-estrogens, such as fulvestrant (Faslodex®), raloxifene (Evista®), or tamoxifen (Novaladex®, Tamofen®). In some embodiments, a compound of the disclosure is used in combination with LHRH agonists, such as buserelin (Suprefact®), goserelin (Zoladex®), or leuprolide (Lupron®, Lupron Depot®, Eligard®).

i. Combination Treatment with Hypomethylating (Demethylating) Agents

Hypomethylating (demethylating) agents inhibit DNA methylation, which affects cellular function through successive generations of cells without changing the underlying DNA sequence. Hypomethylating agents can block the activity of DNA methyltransferase. In some embodiments, a compound of the disclosure is used in combination with hypomethylating agents, such as azacitidine (Vidaza®, Azadine®) or decitabine (Dacogen®).

j. Combination Treatment with Anti-Inflammatory Agents

In some embodiments, a compound of the disclosure is used in combination with nonsteroidal anti-inflammatory drugs (NSAIDs), specific COX-2 inhibitors, or corticosteroids. In some embodiments, a compound of the disclosure is used in combination with NSAIDs, such as aspirin, ibuprofen, naproxen, celecoxib, ketorolac, or diclofenac. In some embodiments, a compound of the disclosure is used in combination with specific COX-2 inhibitors, such as celecoxib (Celebrex®), rofecoxib, or etoricoxib. In some embodiments, a compound of the disclosure is used in combination with corticosteroids, such as dexamethasone or glucosteroids (e.g., hydrocortisone and prednisone).

k. Combination Treatment with HDAC Inhibitors

Histone deacetylase (HDAC) inhibitors are chemical compounds that inhibit histone deacetylase. HDAC inhibitors can induce p21 expression, a regulator of p53 activity. In some embodiments, a compound of the disclosure is used in combination with an HDAC inhibitor. In some embodiments, a compound of the disclosure is used in combination with an HDAC inhibitor, such as vorinostat, romidepsin (Istodax®), chidamide, panobinostat (Farydak®), belinostat (PDX101), panobinostat (LBH589), valproic acid, mocetinostat (MGCD0103), abexinostat (PCI-24781), entinostat (MS-275), SB939, resminostat (4SC-201), givinostat (ITF2357), quisinostat (JNJ-26481585), HBI-8000, kevetrin, CUDC-101, AR-42, CHR-2845, CHR-3996, 4SC-202, CG200745, ACY-1215, ME-344, sulforaphane, or trichostatin A.

l. Combination Treatment with Platinum-Based Antineoplastic Drugs

Platinum-based antineoplastic drugs are coordinated complex of platinum. In some embodiments, a compound of the disclosure is used in combination with a platinum-based antineoplastic drug, such as cisplatin, oxaliplatin, carboplatin, nedaplatin, triplatin tetranitrate, phenanthriplatin, picoplatin, or satraplatin. In some embodiments, a compound of the disclosure is used in combination with cisplatin or carboplatin. In some embodiments, a compound of the disclosure is used in combination with cisplatinum, platamin, neoplatin, cismaplat, cis-diamminedichloroplatinum (II), or CDDP; Platinol®) and carboplatin (also known as cis-diammine(1,1-cyclobutanedicarboxylato)platinum(II); tradenames Paraplatin® and Paraplatin-AQ®).

m. Combination Treatment with Kinase Inhibitors

Abnormal activation of protein phosphorylation is frequently either a driver of direct consequence of cancer. Kinase signaling pathways are involved in the phenotypes of tumor biology, including proliferation, survival, motility, metabolism, angiogenesis, and evasion of antitumor immune responses.

MEK inhibitors: MEK inhibitors are drugs that inhibit the mitogen-activated protein kinase enzymes MEK1 and/or MEK2. In some embodiments, a compound of the disclosure is used in combination with a MEK1 inhibitor. In some embodiments, a compound of the disclosure is used in combination with a MEK2 inhibitor. In some embodiments, a compound of the disclosure is used in combination with an agent that can inhibit MEK1 and MEK2. In some embodiments, a compound of the disclosure is used in combination with a MEK1/MEK2 inhibitor, such as trametinib (Mekinist®), cobimetinib, binimetinib, selumetinib (AZD6244), pimasertibe (AS-703026), PD-325901, CI-1040, PD035901, or TAK-733. In some embodiments, a compound of the disclosure is used in combination with trametinib. In some embodiments, a compound of the disclosure is used in combination with cobimetinib.

BRAF inhibitors: BRAF inhibitors are drugs that inhibit the serine/threonine-protein kinase B-raf (BRAF) protein. In some embodiments, a compound of the disclosure is used in combination with a BRAF inhibitor. In some embodiments, a compound of the disclosure is used in combination with a BRAF inhibitor that can inhibit wild type BRAF. In some embodiments, a compound of the disclosure is used in combination with a BRAF inhibitor that can inhibit mutated BRAF. In some embodiments, a compound of the disclosure is used in combination with a BRAF inhibitor that can inhibit V600E mutated BRAF. In some embodiments, a compound of the disclosure is used in combination with a BRAF inhibitor, such as vemurafenib (Zelboraf®), dabrafenib (Tafinlar®), C-1, NVP-LGX818, or sorafenib (Nexavar®).

KRAS inhibitors: KRAS is a gene that acts as an on/off switch in cell signaling. In some embodiments, a compound of the disclosure is used in combination with a KRAS inhibitor. In some embodiments, a compound of the disclosure is used in combination with a wild type KRAS inhibitor. In some embodiments, a compound of the disclosure is used in combination with a mutated KRAS inhibitor.

BTK inhibitors: Bruton's tyrosine kinase (BTK) is a non-receptor tyrosine kinase of the Tec kinase family that is involved in B-cell receptor signaling. In some embodiments, a compound of the disclosure is used in combination with a BTK inhibitor. In some embodiments, a compound of the disclosure is used in combination with a BTK inhibitor, such as ibrutinib or acalabrutinib.

CDK inhibitors: CDK4 and CDK6 are cyclin-dependent kinases that control the transition between the G1 and S phases of the cell cycle. CDK4/CDK6 activity is deregulated and overactive in cancer cells. Selective CDK4/CDK6 inhibitors can block cell-cycle progression in the mid-G1 phase of the cell cycle, causing arrest and preventing the proliferation of cancer cells. In some embodiments, a compound of the disclosure is used in combination with a CDK4/CDK6 inhibitor. In some embodiments, a compound of the disclosure is used in combination with a CDK4/CDK6 inhibitor, such as palbociclib (Ibrance®), ribociclib, trilaciclib, seliciclib, dinaciclib, milciclib, roniciclib, atuveciclib, briciclib, riviciclib, voruciclib, or abemaciclib. In some embodiments, a compound of the disclosure is used in combination with palbociclib. In some embodiments, a compound of the disclosure is used in combination with ribociclib. In some embodiments, a compound of the disclosure is used in combination with abemaciclib.

In some examples, a compound of the disclosure is used in combination with an inhibitor of CDK4 and/or CDK6 and with an agent that reinforces the cytostatic activity of CDK4/6 inhibitors and/or with an agent that converts reversible cytostasis into irreversible growth arrest or cell death. Examples of cancer subtypes include NSCLC, melanoma, neuroblastoma, glioblastoma, liposarcoma, and mantle cell lymphoma. In some examples, a compound of the disclosure is used in combination with at least one additional pharmaceutically active agent that alleviates CDKN2A (cyclin-dependent kinase inhibitor 2A) deletion. In some examples, a compound of the disclosure is used in combination with at least one additional pharmaceutically active agent that alleviates CDK9 (cyclin-dependent kinase 9) abnormality.

In some embodiments, a compound of the disclosure is used in combination with a CDK2, CDK7, and/or CDK9 inhibitor. In some embodiments, a compound of the disclosure is used in combination with a CDK2, CDK7, or CDK9 inhibitor, such as seliciclib, voruciclib, or milciclib. In some embodiments, a compound of the disclosure is used in combination with a CDK inhibitor, such as dinaciclib, roniciclib (Kisqali®), or briciclib. In some examples, a compound of the disclosure is used in combination with at least one additional pharmaceutically-active agent that alleviates CDKN2A (cyclin-dependent kinase inhibitor 2A) deletion.

ATM regulators: A compound of the disclosure can be used in combination with one or more pharmaceutically-active agent that regulates the ATM (upregulate or down-regulate). In some embodiments the compounds described herein can synergize with one or more ATM regulators. In some embodiments one or more of the compounds described herein can synergize with all ATM regulators.

AKT inhibitors: In some embodiments, a compound of the disclosure is used in combination with one or more pharmaceutically-active agent that inhibits the AKT (protein kinase B (PKB)). In some embodiments the compounds described herein can synergize with one or more AKT inhibitors.

n. Combination Treatment with Other Pharmaceutically-Active Agents

In some examples, a compound of the disclosure is used in combination with at least one additional pharmaceutically-active agent that alleviates PTEN (phosphatase and tensin homolog) deletion. In some examples, a compound of the disclosure is used in combination with at least one additional pharmaceutically-active agent that alleviates Wip-1Alpha over expression. In some examples, a compound of the disclosure is used in combination with at least one additional pharmaceutically-active agent that is a Nucleoside metabolic inhibitor. Examples of nucleoside metabolic inhibitors include capecitabine, gemcitabine and cytarabine (Arac).

The table below lists suitable additional pharmaceutically-active agents for use with the methods described herein.

| Cancer Type | Drug name | Brand name |
| --- | --- | --- |
| ALL | ABT-199 | none |
| ALL | clofarabine | Clofarex |
| ALL | cyclophosphamide | Clafen, Cytoxan, Neosar |
| ALL | cytarabine | Cytosar-U, Tarabine PFS |
| ALL | doxorubicin | Adriamycin |
| ALL | imatinib mesylate | Gleevec |
| ALL | methotrexate | Abitrexate, Mexate, Folex |
| ALL | prednisone | Deltasone, Medicorten |
| ALL | romidepsin | Istodax |
| ALL | vincristine | Vincasar |
| AML | ABT-199 | none |
| AML | azacitadine | Vidaza |
| AML | cyclophosphamide | Clafen, Cytoxan, Neosar |
| AML | cytarabine | Cytosar-U, Tarabine PFS |
| AML | decitabine | Dacogen |
| AML | doxorubicin | Adriamycin |
| AML | etoposide | Etopophos, Vepesid |
| AML | vincristine | Vincasar |
| bone | doxorubicin | Adriamycin |
| bone | methotrexate | Abitrexate, Mexate, Folex |
| breast | capecitabine | Xeloda |
| breast | cyclophosphamide | Clafen, Cytoxan, Neosar |
| breast | docetaxel | Taxotere |
| breast | doxorubicin | Adriamycin |
| breast | eribulin mesylate | Haliben |
| breast | everolimus | Afinitor |
| breast | exemestane | Aromasin |
| breast | fluorouracil | Adrucil, Efudex |
| breast | fulvestrant | Faslofex |
| breast | gemcitabine | Gemzar |
| breast | goserelin acetate | Zoladex |
| breast | letrozole | Femara |
| breast | megestrol acetate | Megace |
| breast | methotrexate | Abitrexate, Mexate, Folex |
| breast | paclitaxel | Abraxane ®, Taxol |
| breast | palbociclib | Ibrance |
| breast | pertuzumab | Perjeta |
| breast | tamoxifen citrate | Nolvadex |
| breast | trastuzumab | Herceptin, Kadcyla |
| colon | capecitabine | Xeloda |
| colon | cetuximab | Erbitux |
| colon | fluorouracil | Adrucil, Efudex |
| colon | irinotecan | camptosar |
| colon | ramucirumab | Cyramza |
| endometrial | carboplatin | Paraplatin, Paraplat |
| endometrial | cisplatin | Platinol |
| endometrial | doxorubicin | Adriamycin |
| endometrial | megestrol acetate | Megace |
| endometrial | paclitaxel | Abraxane ®, Taxol |
| gastric | docetaxel | Taxotere |
| gastric | doxorubicin | Adriamycin |
| gastric | fluorouracil | Adrucil, Efudex |
| gastric | ramucirumab | Cyramza |
| gastric | trastuzumab | Herceptin |
| kidney | axitinib | Inlyta |
| kidney | everolimus | Afinitor |
| kidney | pazopanib | Votrient |
| kidney | sorafenib tosylate | Nexavar |
| liver | sorafenib tosylate | Nexavar |
| melanoma | dacarbazine | DTIC, DTIC-Dome |
| melanoma | paclitaxel | Abraxane ®, Taxol |
| melanoma | trametinib | Mekinist |
| melanoma | vemurafenib | Zelboraf |
| melanoma | dabrafenib | Taflinar |
| mesothelioma | cisplatin | Platinol |
| mesothelioma | pemetrexed | Alimta |
| NHL | ABT-199 | none |
| NHL | bendamustine | Treanda |
| NHL | bortezomib | Velcade |
| NHL | brentuximab vedotin | Adcetris |
| NHL | chlorambucil | Ambochlorin, Leukeran, Linfolizin |
| NHL | cyclophosphamide | Clafen, Cytoxan, Neosar |
| NHL | dexamethasone | Decadrone, Dexasone |
| NHL | doxorubicin | Adriamycin |
| NHL | Ibrutinib | Imbruvica |
| NHL | lenalidomide | Revlimid |
| NHL | methotrexate | Abitrexate, Mexate, Folex |
| NHL | obinutuzumab | Gazyva |
| NHL | prednisone | Deltasone, Medicorten |
| NHL | romidepsin | Istodax |
| NHL | rituximab | Rituxan |
| NHL | vincristine | Vincasar |
| NSCLC | afatinib Dimaleate | Gilotrif |
| NSCLC | carboplatin | Paraplatin, Paraplat |
| NSCLC | cisplatin | Platinol |
| NSCLC | crizotinib | Xalkori |
| NSCLC | docetaxel | Taxotere |
| NSCLC | erlotinib | Tarceva |
| NSCLC | gemcitabine | Gemzar |
| NSCLC | methotrexate | Abitrexate, Mexate, Folex |
| NSCLC | paclitaxel | Abraxane ®, Taxol |
| NSCLC | palbociclib | Ibrance |
| NSCLC | pemetrexed | Alimta |
| NSCLC | ramucirumab | Cyramza |
| ovarian | carboplatin | Paraplatin, Paraplat |
| ovarian | cisplatin | Platinol |
| ovarian | cyclophosphamide | Clafen, Cytoxan, Neosar |
| ovarian | gemcitabine | Gemzar |
| ovarian | olaparib | Lynparza |
| ovarian | paclitaxel | Abraxane ®, Taxol |
| ovarian | topotecan | Hycamtin |
| prostate | abiraterone | Zytiga |
| prostate | cabazitaxel | Jevtana |
| prostate | docetaxel | Taxotere |
| prostate | enzalutamide | Xtandi |
| prostate | goserelin acetate | Zoladex |
| prostate | prednisone | Deltasone, Medicorten |
| soft tissue sarcoma | doxorubicin | Adriamycin |
| soft tissue sarcoma | imatinib mesylate | Gleevec |
| soft tissue sarcoma | pazopanib | Votrient |
| T-cell lymphoma | romidepsin | Istodax |

Administration of Combination Treatment

A compound of the disclosure or a pharmaceutical composition comprising a compound of the disclosure and at least one additional pharmaceutically-active agent or a pharmaceutical composition comprising at least one additional pharmaceutically-active agent can be administered simultaneously (i.e., simultaneous administration) or sequentially (i.e., sequential administration).

In some embodiments, a compound of the disclosure and the at least one additional pharmaceutically-active agent, for example, any additional therapeutic agent described herein, are administered simultaneously, either in the same composition or in separate compositions. When the drugs are administered simultaneously, the compound and the at least one additional pharmaceutically-active agent, for example, any additional therapeutic agent described herein, may be contained in the same composition (e.g., a composition comprising both the compound and the at least additional pharmaceutically-active agent) or in separate compositions (e.g., the compound is contained in one composition and the at least additional pharmaceutically-active agent is contained in another composition).

In some embodiments, the compound and the at least one additional pharmaceutically-active agent, for example, any additional therapeutic agent described herein, are administered sequentially, i.e., the compound is administered either prior to or after the administration of the additional pharmaceutically-active agent. In some embodiments, the compound is administered before the additional pharmaceutically-active agent, for example, any additional therapeutic agent described herein. In some embodiments, the pharmaceutically-active agent, for example, any additional therapeutic agent described herein, is administered before the compound. The compound and the additional pharmaceutically-active agent, for example, any additional therapeutic agent described herein, are contained in separate compositions, which may be contained in the same or different packages.

In some embodiments, the administration of the compounds and the additional pharmaceutically-active agent, for example, any additional therapeutic agent described herein, are concurrent, i.e., the administration period of the compounds and that of the agent overlap with each other. In some embodiments, the administration of the compounds and the additional pharmaceutically-active agent, for example, any additional therapeutic agent described herein, are non-concurrent. For example, in some embodiments, the administration of the compound is terminated before the additional pharmaceutically-active agent, for example, any additional therapeutic agent described herein, is administered. In some embodiments, the administration of the additional pharmaceutically-active agent, for example, any additional therapeutic agent described herein, is terminated before the compound is administered. The time period between these two non-concurrent administrations can range from being days apart to being weeks apart.

The dosing frequency of the compound and the at least one additional pharmaceutically-active agent, for example, any additional therapeutic agent described herein, may be adjusted over the course of the treatment, based on the judgment of the administering physician. When administered separately, the compound and the at least one additional pharmaceutically-active agent, for example, any additional therapeutic agent described herein, can be administered at different dosing frequency or intervals. For example, the compound can be administered weekly, while the at least one additional pharmaceutically-active agent, for example, any additional therapeutic agent described herein, can be administered more or less frequently. Or, the compound can be administered twice weekly, while the at least one additional pharmaceutically-active agent, for example, any additional therapeutic agent described herein, can be administered more or less frequently. In addition, the compound and the at least one additional pharmaceutically-active agent, for example, any additional therapeutic agent described herein, can be administered using the same route of administration or using different routes of administration.

A therapeutically-effective amount of a compound and/or the additional pharmaceutically-active agent, for example, any additional therapeutic agent described herein, for use in therapy can vary with the nature of the condition being treated, the length of treatment time desired, the age and the condition of the patient, and can be determined by the attending physician.

In some embodiments, when a compound of the disclosure is administered in combination with at least one additional pharmaceutically-active agent, for example, any additional therapeutic agent described herein, the dosage of the compound can be given a lower dosage than when the compound is administered alone. In some embodiments, the dosage of a compound of the disclosure in combination therapy can be from about 5 mg/kg to about 1000 mg/kg; from about 50 mg/kg to about 600 mg/kg; from about 150 mg/kg to about 600 mg/kg; or from about 300 mg/kg to about 600 mg/kg. In some embodiments, the dosage of a compound of the disclosure in combination therapy can be from about 5 mg/kg to about 25 mg/kg; from about 25 mg/kg to about 50 mg/kg; from about 50 mg/kg to about 75 mg/kg; from about 75 mg/kg to about 100 mg/kg; from about 100 mg/kg to about 125 mg/kg; from about 125 mg/kg to about 150 mg/kg; from about 150 mg/kg to about 200 mg/kg; from about 200 mg/kg to about 250 mg/kg; from about 250 mg/kg to about 300 mg/kg; from about 300 mg/kg to about 350 mg/kg; from about 350 mg/kg to about 400 mg/kg; from about 400 mg/kg to about 450 mg/kg; from about 450 mg/kg to about 500 mg/kg; from about 500 mg/kg to about 550 mg/kg; from about 550 mg/kg to about 600 mg/kg; from about 600 mg/kg to about 700 mg/kg; from about 700 mg/kg to about 800 mg/kg; from about 800 mg/kg to about 900 mg/kg; or from about 900 mg/kg to about 1000 mg/kg. In some embodiments, the dosage of a compound of the disclosure in combination therapy can be from about 50 mg/kg to about 75 mg/kg. In some embodiments, the dosage of a compound of the disclosure in combination therapy can be from about 75 mg/kg to about 150 mg/kg. In some embodiments, the dosage of a compound of the disclosure in combination therapy can be from about 150 mg/kg to about 300 mg/kg. In some embodiments, the dosage of a compound of the disclosure in combination therapy can be from about 300 mg/kg to about 600 mg/kg.

In some embodiments, the dosage of a compound of the disclosure in combination therapy can be in an amount of about 5 mg/kg; about 25 mg/kg; about 50 mg/kg; about 75 mg/kg; about 100 mg/kg; about 125 mg/kg; about 150 mg/kg; about 175 mg/kg; about 200 mg/kg; about 250 mg/kg; about 300 mg/kg; about 350 mg/kg; about 400 mg/kg; about 450 mg/kg; about 500 mg/kg; about 550 mg/kg; about 600 mg/kg; about 700 mg/kg; about 800 mg/kg; about 900 mg/kg; or about 1000 mg/kg. In some embodiments, the dosage of a compound of the disclosure in combination therapy can be in an amount of about 50 mg/kg. In some embodiments, the dosage of a compound of the disclosure in combination therapy can be in an amount of about 75 mg/kg. In some embodiments, the dosage of a compound of the disclosure in combination therapy can be in an amount of about 150 mg/kg. In some embodiments, the dosage of a compound of the disclosure in combination therapy can be in an amount of about 300 mg/kg. In some embodiments, the dosage of a compound of the disclosure in combination therapy can be in an amount of about 600 mg/kg.

In some embodiments, when a compound of the disclosure is administered in combination with at least one additional pharmaceutically-active agent, for example, any additional therapeutic agent described herein, the dosage of the at least one additional pharmaceutically-active agent can be given a lower dosage than when the compound is administered alone. In some embodiments, the dosage of the at least one additional pharmaceutically-active agent in combination therapy can be from about 50 µg to about 100 µg; from about 100 µg to about 150 µg; from about 150 µg to about 200 µg; from about 200 µg to about 250 µg; from about 250 µg to about 300 µg; from about 300 µg to about 350 µg; from about 350 µg to about 400 µg; from about 400 µg to about 450 µg; from about 450 µg to about 500 µg; from about 500 µg to about 600 µg; from about 600 µg to about 700 µg; from about 700 µg to about 800 µg; from about 800 µg to about 900 µg; or from about 900 µg to about 1000 µg. In some embodiments, the dosage of the at least one additional pharmaceutically-active agent in combination therapy can be from about 100 µg to about 150 µg. In some embodiments, the dosage of the at least one additional pharmaceutically-active agent in combination therapy can be from about 150 µg to about 200 µg. In some embodiments, the dosage of the at least one additional pharmaceutically-active agent in combination therapy can be from about 200 µg to about 250 µg.

In some embodiments, the dosage of the at least one additional pharmaceutically-active agent in combination therapy can be in an amount of about 50 µg; about 100 µg; about 150 µg; about 200 µg; about 250 µg; about 300 µg; about 350 µg; about 400 µg; about 450 µg; or about 500 µg. In some embodiments, the dosage of the at least one additional pharmaceutically-active agent in combination therapy can be in an amount of about 200 µg.

In some embodiments, the dosage of the at least one additional pharmaceutically-active agent in combination therapy can be from about 1 mg/kg to about 5 mg/kg; from about 5 mg/kg to about 25 mg/kg; from about 25 mg/kg to about 50 mg/kg; from about 50 mg/kg to about 75 mg/kg; from about 75 mg/kg to about 100 mg/kg; from about 100 mg/kg to about 150 mg/kg; from about 150 mg/kg to about 200 mg/kg; from about 200 mg/kg to about 250 mg/kg; from about 250 mg/kg to about 300 mg/kg; from about 300 mg/kg to about 350 mg/kg; from about 350 mg/kg to about 400 mg/kg; from about 400 mg/kg to about 450 mg/kg; from about 450 mg/kg to about 500 mg/kg; from about 500 mg/kg to about 600 mg/kg; from about 600 mg/kg to about 700 mg/kg; from about 700 mg/kg to about 800 mg/kg; from about 800 mg/kg to about 900 mg/kg; or from about 900 mg/kg to about 1000 mg/kg. In some embodiments, the dosage of the at least one additional pharmaceutically-active agent in combination therapy can be from about 1 mg/kg to about 5 mg/kg. In some embodiments, the dosage of the at least one additional pharmaceutically-active agent in combination therapy can be from about 100 mg/kg to about 150 mg/kg. In some embodiments, the dosage of the at least one additional pharmaceutically-active agent in combination therapy can be from about 200 mg/kg to about 250 mg/kg.

In some embodiments, the dosage of the compound of the disclosure administered in combination therapy can be from about 50 mg/kg to about 600 mg/kg; and the dosage of the at least one additional pharmaceutically-active agent in combination therapy can be from about 1 mg/kg to about 500 mg/kg. In some embodiments, the dosage of the compound of the disclosure administered in combination therapy can be from about 50 mg/kg to about 150 mg/kg; and the dosage of the at least one additional pharmaceutically-active agent in combination therapy can be from about 1 mg/kg to about 250 mg/kg. In some embodiments, the dosage of the compound of the disclosure administered in combination therapy can be from about 150 mg/kg to about 600 mg/kg; and the dosage of the at least one additional pharmaceutically-active agent in combination therapy can be from about 1 mg/kg to about 500 mg/kg.

In some embodiments, the dosage of the compound of the disclosure administered in combination therapy can be about 50 mg/kg; and the dosage of the at least one additional pharmaceutically-active agent in combination therapy can about 5 mg/kg. In some embodiments, the dosage of the compound of the disclosure administered in combination therapy can be about 75 mg/kg; and the dosage of the at least one additional pharmaceutically-active agent in combination therapy can about 5 mg/kg. In some embodiments, the dosage of the compound of the disclosure administered in combination therapy can be about 150 mg/kg; and the dosage of the at least one additional pharmaceutically-active agent in combination therapy can about 5 mg/kg. In some embodiments, the dosage of the compound of the disclosure administered in combination therapy can be about 300 mg/kg; and the dosage of the at least one additional pharmaceutically-active agent in combination therapy can about 5 mg/kg. In some embodiments, the dosage of the compound of the disclosure administered in combination therapy can be about 600 mg/kg; and the dosage of the at least one additional pharmaceutically-active agent in combination therapy can about 5 mg/kg.

In some embodiments, the dosage of the compound of the disclosure administered in combination therapy can be from about 50 mg/kg to about 600 mg/kg; and the dosage of the at least one additional pharmaceutically-active agent in combination therapy can be from about 100 µg to about 500 µg. In some embodiments, the dosage of the compound of the disclosure administered in combination therapy can be from about 50 mg/kg to about 150 mg/kg; and the dosage of the at least one additional pharmaceutically-active agent in combination therapy can be from about 100 µg to about 500 µg. In some embodiments, the dosage of the compound of the disclosure administered in combination therapy can be from about 150 mg/kg to about 300 mg/kg; and the dosage of the at least one additional pharmaceutically-active agent in combination therapy can be from about 100 µg to about 500 µg. In some embodiments, the dosage of the compound of the disclosure administered in combination therapy can be from about 300 mg/kg to about 600 mg/kg; and the dosage of the at least one additional pharmaceutically-active agent in combination therapy can be from about 100 µg to about 500 µg.

In some embodiments, the dosage of the compound of the disclosure administered in combination therapy can be about 50 mg/kg; and the dosage of the at least one additional pharmaceutically-active agent in combination therapy is about 200 µg. In some embodiments, the dosage of the compound of the disclosure administered in combination therapy is be about 75 mg/kg; and the dosage of the at least one additional pharmaceutically-active agent in combination therapy is about 200 µg. In some embodiments, the dosage of the compound of the disclosure administered in combination therapy is be about 150 mg/kg; and the dosage of the at least one additional pharmaceutically-active agent in combination therapy is about 200 µg. In some embodiments, the dosage of the compound of the disclosure administered in combination therapy is be about 300 mg/kg; and the dosage of the at least one additional pharmaceutically-active agent in combination therapy is about 200 µg. In some embodiments, the dosage of the compound of the disclosure administered in combination therapy is be about 600 mg/kg; and the dosage of the at least one additional pharmaceutically-active agent in combination therapy is about 200 µg.

In some embodiments, the dosage of the compound of the disclosure administered in combination therapy can be from about 50 mg/kg to about 600 mg/kg; and the dosage of anti-PD-1 as an additional pharmaceutically-active agent in combination therapy is about 200 µg. In some embodiments, the dosage of the compound of the disclosure administered in combination therapy can be from about 50 mg/kg to about 150 mg/kg; and the dosage of anti-PD-1 as an additional pharmaceutically-active agent in combination therapy is about 200 µg. In some embodiments, the dosage of the compound of the disclosure administered in combination therapy can be from about 150 mg/kg to about 300 mg/kg; and the dosage of anti-PD-1 as an additional pharmaceutically-active agent in combination therapy is about 200 µg. In some embodiments, the dosage of the compound of the disclosure administered in combination therapy can be from about 300 mg/kg to about 600 mg/kg; and the dosage of anti-PD-1 as an additional pharmaceutically-active agent in combination therapy is about 200 μg.

In some embodiments, the dosage of the compound of the disclosure administered in combination therapy is about 50 mg/kg; and the dosage of anti-PD-1 as an additional pharmaceutically-active agent in combination therapy is about 200 μg. In some embodiments, the dosage of the compound of the disclosure administered in combination therapy is about 75 mg/kg; and the dosage of anti-PD-1 as an additional pharmaceutically-active agent in combination therapy is about 200 μg. In some embodiments, the dosage of the compound of the disclosure administered in combination therapy is about 150 mg/kg; and the dosage of anti-PD-1 as an additional pharmaceutically-active agent in combination therapy is about 200 μg. In some embodiments, the dosage of the compound of the disclosure administered in combination therapy is about 300 mg/kg; and the dosage of anti-PD-1 as an additional pharmaceutically-active agent in combination therapy is about 200 μg. In some embodiments, the dosage of the compound of the disclosure administered in combination therapy is about 600 mg/kg; and the dosage of anti-PD-1 as an additional pharmaceutically-active agent in combination therapy is about 200 μg.

In some embodiments, a pharmaceutically-acceptable amount of a compound of the disclosure can be administered to a subject 1, 2, 3, 4, or 5 times a day. In some embodiments, a pharmaceutically-acceptable amount of a compound of the disclosure can be administered to a subject once a day. In some embodiments, a pharmaceutically-acceptable amount of a compound of the disclosure can be administered to a subject twice a day. In some embodiments, a pharmaceutically-acceptable amount of a compound of the disclosure can be administered to a subject three times a day.

In some embodiments, a pharmaceutically-acceptable amount of a compound of the disclosure can be administered to a subject 1, 2, 3, 4, or 5 times a day once every 1, 2, 3, 4, 5, 6, or 7 days. In some embodiments, a pharmaceutically-acceptable amount of a compound of the disclosure can be administered to a subject once a day once every 3 days. In some embodiments, a pharmaceutically-acceptable amount of a compound of the disclosure can be administered to a subject twice a day once every 3 days. In some embodiments, a pharmaceutically-acceptable amount of a compound of the disclosure can be administered to a subject 1, 2, 3, 4, or 5 times a day once every 7 days. In some embodiments, a pharmaceutically-acceptable amount of a compound of the disclosure can be administered to a subject once a day once every 7 days. In some embodiments, a pharmaceutically-acceptable amount of a compound of the disclosure can be administered to a subject twice a day once every 7 days.

In some embodiments, a pharmaceutically-acceptable amount of a compound of the disclosure can be administered to a subject 1, 2, 3, 4, or 5 times a day once every 1, 2, 3, 4, 5, 6, or 7 days for 1 to 50 doses. In some embodiments, a pharmaceutically-acceptable amount of a compound of the disclosure can be administered to a subject 1, 2, 3, 4, or 5 times a day once every 1, 2, 3, 4, 5, 6, or 7 days for about 5 doses. In some embodiments, a pharmaceutically-acceptable amount of a compound of the disclosure can be administered to a subject 1, 2, 3, 4, or 5 times a day once every 1, 2, 3, 4, 5, 6, or 7 days for about 10 doses. In some embodiments, a pharmaceutically-acceptable amount of a compound of the disclosure can be administered to a subject 1, 2, 3, 4, or 5 times a day once every 1, 2, 3, 4, 5, 6, or 7 days for about 15 doses. In some embodiments, a pharmaceutically-acceptable amount of a compound of the disclosure can be administered to a subject 1, 2, 3, 4, or 5 times a day once every 1, 2, 3, 4, 5, 6, or 7 days for about 20 doses. In some embodiments, a pharmaceutically-acceptable amount of a compound of the disclosure can be administered to a subject 1, 2, 3, 4, or 5 times a day once every 1, 2, 3, 4, 5, 6, or 7 days for about 25 doses. In some embodiments, a pharmaceutically-acceptable amount of a compound of the disclosure can be administered to a subject 1, 2, 3, 4, or 5 times a day once every 1, 2, 3, 4, 5, 6, or 7 days for about 30 doses. In some embodiments, a pharmaceutically-acceptable amount of a compound of the disclosure can be administered to a subject 1, 2, 3, 4, or 5 times a day once every 1, 2, 3, 4, 5, 6, or 7 days for about 35 doses.

In some embodiments, a pharmaceutically-acceptable amount of a compound of the disclosure can be administered to a subject once a day every 7 days for about 5 doses. In some embodiments, a pharmaceutically-acceptable amount of a compound of the disclosure can be administered to a subject once a day every 7 days for about 10 doses. In some embodiments, a pharmaceutically-acceptable amount of a compound of the disclosure can be administered to a subject twice a day every 7 days for about 15 doses. In some embodiments, a pharmaceutically-acceptable amount of a compound of the disclosure can be administered to a subject once a day every 3 days for about 20 doses. In some embodiments, a pharmaceutically-acceptable amount of a compound of the disclosure can be administered to a subject once a day every 3 days for about 35 doses.

In some embodiments, a pharmaceutically-acceptable amount of a compound of the disclosure can be administered to a subject twice a day every 7 days for about 5 doses. In some embodiments, a pharmaceutically-acceptable amount of a compound of the disclosure can be administered to a subject twice a day every 7 days for about 15 doses.

Pharmaceutical Compositions for Combination Treatment

According to certain embodiments, the compounds and the additional pharmaceutically-active agent, for example, any additional therapeutic agent described herein, are administered within a single pharmaceutical composition. In some embodiments, the compounds of the disclosure and the additional pharmaceutically-active agent, for example, any additional therapeutic agent described herein, can be provided in a single unit dosage form for being taken together. According to some embodiments, the pharmaceutical composition further comprises pharmaceutically-acceptable diluents or carrier. According to certain embodiments, the compounds of the disclosure and the additional pharmaceutically-active agent, for example, any additional therapeutic agent described herein, are administered within different pharmaceutical composition. In some embodiments, the compounds of the disclosure and the additional pharmaceutically-active agent, for example, any additional therapeutic agent described herein, can be provided in a single unit dosage as separate entities (e.g., in separate containers) to be administered simultaneously or with a certain time difference.

In some embodiments, the compounds of the disclosure and the additional pharmaceutically-active agent, for example, any additional therapeutic agent described herein, can be administered via the same route of administration. In some embodiments, the compounds of the disclosure and the additional pharmaceutically-active agent, for example, any additional therapeutic agent described herein, can be administered via the different route of administration. In some embodiments, a compound of the disclosure and the additional pharmaceutically-active agent are administered orally. In some embodiments, a compound of the disclosure is administered orally, and the additional pharmaceutically-acceptable agent is not administered orally. In some embodiments, a compound of the disclosure is not administered orally, and the additional pharmaceutically-acceptable agent is administered orally.

Treatment of a condition by administering a compound of the disclosure in combination with an additional anti-cancer agent can increase a median survival time of a subject compared to subjects who do not receive combination therapy with a compound of the disclosure and the additional anti-cancer agent. In some embodiments, a median survival time of a first patient population receiving combination therapy with a compound of the disclosure and an additional anti-cancer agent can be greater than a median survival time of a second patient population that does not receive any cancer therapy. In some embodiments, a median survival time of a first patient population receiving combination therapy with a compound of the disclosure and an additional anti-cancer agent can be greater than a median survival time of a second patient population that receives therapy with a compound of the disclosure alone. In some embodiments, a median survival time of a first patient population receiving combination therapy with a compound of the disclosure and an additional anti-cancer agent can be greater than a median survival time of a second patient population that receives therapy with the additional anti-cancer agent alone.

In some embodiments, a median survival time of a first patient population receiving combination therapy with a compound of the disclosure and an additional anti-cancer agent can be greater than a median survival time of a second patient population not receiving combination therapy by at least about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%. In some embodiments, a median survival time of a first patient population receiving combination therapy with a compound of the disclosure and an additional anti-cancer agent can be greater than a median survival time of a second patient population not receiving combination therapy by at least about 50%. In some embodiments, a median survival time of a first patient population receiving combination therapy with a compound of the disclosure and an additional anti-cancer agent can be greater than a median survival time of a second patient population not receiving combination therapy by at least about 100%. In some embodiments, a median survival time of a first patient population receiving combination therapy with a compound of the disclosure and an additional anti-cancer agent can be greater than a median survival time of a second patient population not receiving combination therapy by at least about 150%. In some embodiments, a median survival time of a first patient population receiving combination therapy with a compound of the disclosure and an additional anti-cancer agent can be greater than a median survival time of a second patient population not receiving combination therapy by at least about 200%.

Methods of Treatment

Provided herein is a method of treating cancer in a subject in need thereof, the method comprising: (i) administering to the subject a therapeutically-effective amount of a compound, wherein the compound binds to a mutant p53 protein and reconforms the mutant p53 protein to a conformation of p53 that exhibits anti-cancer activity; and (ii) administering to the subject a therapeutically-effective amount of an anti-cancer agent that functions through a pathway other than p53-induced apoptosis.

Also provided herein is a method of treating cancer in a subject in need thereof, the method comprising: (i) administering to the subject a therapeutically-effective amount of a compound that increases anti-cancer activity of a mutant p53 protein in the subject; and (ii) administering to the subject a therapeutically-effective amount of an anti-cancer agent that functions through a pathway other than p53-induced apoptosis.

In some embodiments, the compound binds to the mutant p53 protein and reconforms the mutant p53 protein to a conformation of p53 that exhibits anti-cancer activity.

Further provided herein is a method of treating cancer, the method comprising: (i) administering to a subject in need thereof a therapeutically-effective amount of a compound that binds to a mutant p53 protein and reconforms the mutant p53 protein to a conformation of p53 that exhibits anti-cancer activity; and (ii) administering to the subject a therapeutically-effective amount of an additional anti-cancer agent that functions through a pathway other than p53-induced apoptosis, wherein if in a controlled study of treatment of the cancer in a first patient population and a second patient population: (a) a first median survival time of the first patient population is determined, wherein the first patient population is treated with the therapeutically-effective amount of the compound that binds to a mutant p53 protein and reconforms the mutant p53 protein to a conformation of p53 that exhibits anti-cancer activity; and (b) a second median survival time of the second patient population is determined, wherein the second patient population is treated with the therapeutically-effective amount of the compound that binds to a mutant p53 protein and reconforms the mutant p53 protein to a conformation of p53 that exhibits anti-cancer activity and the therapeutically-effective amount of the additional therapeutic agent; then the second median survival time is at least about 50% greater than is the first median survival time.

In some embodiments, the second median survival time is at least about 100% greater than the first median survival time. In some embodiments, the second median survival time is at least about 200% greater than the first median survival time.

In some embodiments, the compound increases a stability of the mutant p53 protein. In some embodiments, the cancer expresses a mutant p53 protein. In some embodiments, the mutant p53 protein has a mutation at amino acid 220. In some embodiments, the mutant p53 protein is p53 Y220C. In some embodiments, the compound selectively binds the mutant p53 protein as compared to a wild type p53. In some embodiments, the cancer is ovarian cancer. In some embodiments, the cancer is breast cancer. In some embodiments, the cancer is lung cancer. In some embodiments, the subject is human.

In some embodiments, the administering of the compound is oral. In some embodiments, the administering of the compound is subcutaneous. In some embodiments, the administering of the compound is topical. In some embodiments, the therapeutically-effective amount of the compound is from about 1 mg/kg to about 500 mg/kg. In some embodiments, the therapeutically-effective amount of the compound is from about 100 mg to about 5000 mg. In some embodiments, the therapeutically-effective amount of the compound is from about 500 mg to about 2000 mg. In some embodiments, the therapeutically-effective amount of the compound is about 250 mg, about 500 mg, about 750 mg, about 1000 mg, about 1250 mg, about 1500 mg, about 1750 mg, about 2000 mg, about 2250 mg, or about 2500 mg. In some embodiments, the therapeutically-effective amount of the compound is about 150 mg. In some embodiments, the therapeutically-effective amount of the compound is about 300 mg. In some embodiments, the therapeutically-effective amount of the compound is about 500 mg. In some embodiments, the therapeutically-effective amount of the compound is about 600 mg. In some embodiments, the therapeutically-effective amount of the compound is about 1200 mg. In some embodiments, the therapeutically-effective amount of the compound is about 1500 mg. In some embodiments, the therapeutically-effective amount of the compound is about 2000 mg.

In some embodiments, the anti-cancer agent is a small molecule. In some embodiments, the anti-cancer agent is an antibody. In some embodiments, the anti-cancer agent is an immune checkpoint inhibitor. In some embodiments, the immune checkpoint inhibitor is an anti-PD-1 agent. In some embodiments, the anti-PD-1 agent is nivolumab. In some embodiments, the anti-PD-1 agent is pembrolizumab. In some embodiments, the anti-PD-1 agent is cemiplimab. In some embodiments, the immune checkpoint inhibitor is an anti-PD-L1 agent. In some embodiments, the anti-PD-L1 agent is atezolizumab. In some embodiments, the anti-PD-L1 agent is avelumab. In some embodiments, the anti-PD-L1 agent is durvalumab. In some embodiments, the administering of the anti-cancer agent is oral. In some embodiments, the administering of the anti-cancer agent is subcutaneous. In some embodiments, the administering of the anti-cancer agent is topical. In some embodiments, the therapeutically-effective amount of the anti-cancer agent is from about 5 mg/kg to about 500 mg/kg. In some embodiments, the therapeutically-effective amount of the anti-cancer agent is from about 10 µg to about 500 µg. In some embodiments, the therapeutically-effective amount of the anti-cancer agent is about 200 µg.

Pharmacokinetic and pharmacodynamic data can be obtained by various experimental techniques. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined, for example, by calculating the average of all subject's measurements for each parameter measured. A dose can be modulated to achieve a desired pharmacokinetic or pharmacodynamics profile, such as a desired or effective blood profile, as described herein.

The pharmacodynamic parameters can be any parameters suitable for describing compositions of the invention. For example, the pharmacodynamic profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing a compound. The $C_{max}$ can be, for example, not less than about 1 ng/mL; not less than about 5 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; or any other $C_{max}$ appropriate for describing a pharmacokinetic profile of a compound described herein. The $C_{max}$ can be, for example, about 1 ng/mL to about 5,000 ng/mL; about 1 ng/mL to about 4,500 ng/mL; about 1 ng/mL to about 4,000 ng/mL; about 1 ng/mL to about 3,500 ng/mL; about 1 ng/mL to about 3,000 ng/mL; about 1 ng/mL to about 2,500 ng/mL; about 1 ng/mL to about 2,000 ng/mL; about 1 ng/mL to about 1,500 ng/mL; about 1 ng/mL to about 1,000 ng/mL; about 1 ng/mL to about 900 ng/mL; about 1 ng/mL to about 800 ng/mL; about 1 ng/mL to about 700 ng/mL; about 1 ng/mL to about 600 ng/mL; about 1 ng/mL to about 500 ng/mL; about 1 ng/mL to about 450 ng/mL; about 1 ng/mL to about 400 ng/mL; about 1 ng/mL to about 350 ng/mL; about 1 ng/mL to about 300 ng/mL; about 1 ng/mL to about 250 ng/mL; about 1 ng/mL to about 200 ng/mL; about 1 ng/mL to about 150 ng/mL; about 1 ng/mL to about 125 ng/mL; about 1 ng/mL to about 100 ng/mL; about 1 ng/mL to about 90 ng/mL; about 1 ng/mL to about 80 ng/mL; about 1 ng/mL to about 70 ng/mL; about 1 ng/mL to about 60 ng/mL; about 1 ng/mL to about 50 ng/mL; about 1 ng/mL to about 40 ng/mL; about 1 ng/mL to about 30 ng/mL; about 1 ng/mL to about 20 ng/mL; about 1 ng/mL to about 10 ng/mL; about 1 ng/mL to about 5 ng/mL; about 10 ng/mL to about 4,000 ng/mL; about 10 ng/mL to about 3,000 ng/mL; about 10 ng/mL to about 2,000 ng/mL; about 10 ng/mL to about 1,500 ng/mL; about 10 ng/mL to about 1,000 ng/mL; about 10 ng/mL to about 900 ng/mL; about 10 ng/mL to about 800 ng/mL; about 10 ng/mL to about 700 ng/mL; about 10 ng/mL to about 600 ng/mL; about 10 ng/mL to about 500 ng/mL; about 10 ng/mL to about 400 ng/mL; about 10 ng/mL to about 300 ng/mL; about 10 ng/mL to about 200 ng/mL; about 10 ng/mL to about 100 ng/mL; about 10 ng/mL to about 50 ng/mL; about 25 ng/mL to about 500 ng/mL; about 25 ng/mL to about 100 ng/mL; about 50 ng/mL to about 500 ng/mL; about 50 ng/mL to about 100 ng/mL; about 100 ng/mL to about 500 ng/mL; about 100 ng/mL to about 400 ng/mL; about 100 ng/mL to about 300 ng/mL; or about 100 ng/mL to about 200 ng/mL.

The $T_{max}$ of a compound described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of a compound described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours. In some embodiments, the $T_{max}$ of a compound of the disclosure is about 2 hours. In some embodiments, the $T_{max}$ of a compound of the disclosure is about 4 hours. In some embodiments, the $T_{max}$ of a compound of the disclosure is about 6 hours. In some embodiments, the $T_{max}$ of a compound of the disclosure is about 8 hours.

The $AUC_{(0-inf)}$ or $AUC_{(last)}$ of a compound described herein can be, for example, not less than about 1 ng·hr/mL, not less than about 5 ng·hr/mL, not less than about 10 ng·hr/mL, not less than about 20 ng·hr/mL, not less than about 30 ng·hr/mL, not less than about 40 ng·hr/mL, not less than about 50 ng·hr/mL, not less than about 100 ng·hr/mL, not less than about 150 ng·hr/mL, not less than about 200 ng·hr/mL, not less than about 250 ng·hr/mL, not less than about 300 ng·hr/mL, not less than about 350 ng·hr/mL, not less than about 400 ng·hr/mL, not less than about 450 ng·hr/mL, not less than about 500 ng·hr/mL, not less than about 600 ng·hr/mL, not less than about 700 ng·hr/mL, not less than about 800 ng·hr/mL, not less than about 900 ng·hr/mL, not less than about 1000 ng·hr/mL, not less than about 1250 ng·hr/mL, not less than about 1500 ng·hr/mL, not less than about 1750 ng·hr/mL, not less than about 2000 ng·hr/mL, not less than about 2500 ng·hr/mL, not less than about 3000 ng·hr/mL, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, not less than about 10,000 ng·hr/mL, or any other $AUC_{(0-inf)}$ or $AUC_{(last)}$ appropriate for describing a pharmacokinetic profile of a compound described herein. In some embodiments, the $AUC_{(0-inf)}$ or $AUC_{(last)}$ of a compound described herein can be, for example, not less than about 10,000 ng·hr/mL, not less than about 11,000 ng·hr/mL, not less than about 12,000 ng·hr/mL, not less than about 13,000 ng·hr/mL, not less than about 14,000 ng·hr/mL, not less than about 15,000 ng·hr/mL, not less than about 16,000 ng·hr/mL, not less than about 17,000 ng·hr/mL, not less than about 18,000 ng·hr/mL, not less than about 19,000 ng·hr/mL, not less than about 20,000 ng·hr/mL, not less than about 21,000 ng·hr/mL, not less than about 22,000 ng·hr/mL, not less than about 23,000 ng·hr/mL, not less than about 24,000 ng·hr/mL, or not less than about 25,000 ng·hr/mL.

The $AUC_{(0-inf)}$ or $AUC_{(last)}$ of a compound can be, for example, about 1 ng·hr/mL to about 10,000 ng·hr/mL; about 1 ng·hr/mL to about 10 ng·hr/mL; about 10 ng·hr/mL to about 25 ng·hr/mL; about 25 ng·hr/mL to about 50 ng·hr/mL; about 50 ng·hr/mL to about 100 ng·hr/mL; about 100 ng·hr/mL to about 200 ng·hr/mL; about 200 ng·hr/mL to about 300 ng·hr/mL; about 300 ng·hr/mL to about 400 ng·hr/mL; about 400 ng·hr/mL to about 500 ng·hr/mL; about 500 ng·hr/mL to about 600 ng·hr/mL; about 600 ng·hr/mL to about 700 ng·hr/mL; about 700 ng·hr/mL to about 800 ng·hr/mL; about 800 ng·hr/mL to about 900 ng·hr/mL; about 900 ng·hr/mL to about 1,000 ng·hr/mL; about 1,000 ng·hr/mL to about 1,250 ng·hr/mL; about 1,250 ng·hr/mL to about 1,500 ng·hr/mL; about 1,500 ng·hr/mL to about 1,750 ng·hr/mL; about 1,750 ng·hr/mL to about 2,000 ng·hr/mL; about 2,000 ng·hr/mL to about 2,500 ng·hr/mL; about 2,500 ng·hr/mL to about 3,000 ng·hr/mL; about 3,000 ng·hr/mL to about 3,500 ng·hr/mL; about 3,500 ng·hr/mL to about 4,000 ng·hr/mL; about 4,000 ng·hr/mL to about 4,500 ng·hr/mL; about 4,500 ng·hr/mL to about 5,000 ng·hr/mL; about 5,000 ng·hr/mL to about 5,500 ng·hr/mL; about 5,500 ng·hr/mL to about 6,000 ng·hr/mL; about 6,000 ng·hr/mL to about 6,500 ng·hr/mL; about 6,500 ng·hr/mL to about 7,000 ng·hr/mL; about 7,000 ng·hr/mL to about 7,500 ng·hr/mL; about 7,500 ng·hr/mL to about 8,000 ng·hr/mL; about 8,000 ng·hr/mL to about 8,500 ng·hr/mL; about 8,500 ng·hr/mL to about 9,000 ng·hr/mL; about 9,000 ng·hr/mL to about 9,500 ng·hr/mL; or about 9,500 ng·hr/mL to about 10,000 ng·hr/mL. In some embodiments, the $AUC_{(0-inf)}$ or $AUC_{(last)}$ of a compound described herein can be, for example, about 10,000 ng·hr/mL, about 11,000 ng·hr/mL, about 12,000 ng·hr/mL, about 13,000 ng·hr/mL, about 14,000 ng·hr/mL, about 15,000 ng·hr/mL, about 16,000 ng·hr/mL, about 17,000 ng·hr/mL, about 18,000 ng·hr/mL, about 19,000 ng·hr/mL, about 20,000 ng·hr/mL, about 21,000 ng·hr/mL, about 22,000 ng·hr/mL, about 23,000 ng·hr/mL, about 24,000 ng·hr/mL, or about 25,000 ng·hr/mL.

The plasma concentration of a compound described herein can be, for example, not less than about 1 ng/mL, not less than about 5 ng/mL, not less than about 10 ng/mL, not less than about 15 ng/mL, not less than about 20 ng/mL, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a compound described herein. The plasma concentration can be, for example, about 1 ng/mL to about 2,000 ng/mL; about 1 ng/mL to about 5 ng/mL; about 5 ng/mL to about 10 ng/mL; about 10 ng/mL to about 25 ng/mL; about 25 ng/mL to about 50 ng/mL; about 50 ng/mL to about 75 ng/mL; about 75 ng/mL to about 100 ng/mL; about 100 ng/mL to about 150 ng/mL; about 150 ng/mL to about 200 ng/mL; about 200 ng/mL to about 250 ng/mL; about 250 ng/mL to about 300 ng/mL; about 300 ng/mL to about 350 ng/mL; about 350 ng/mL to about 400 ng/mL; about 400 ng/mL to about 450 ng/mL; about 450 ng/mL to about 500 ng/mL; about 500 ng/mL to about 600 ng/mL; about 600 ng/mL to about 700 ng/mL; about 700 ng/mL to about 800 ng/mL; about 800 ng/mL to about 900 ng/mL; about 900 ng/mL to about 1,000 ng/mL; about 1,000 ng/mL to about 1,100 ng/mL; about 1,100 ng/mL to about 1,200 ng/mL; about 1,200 ng/mL to about 1,300 ng/mL; about 1,300 ng/mL to about 1,400 ng/mL; about 1,400 ng/mL to about 1,500 ng/mL; about 1,500 ng/mL to about 1,600 ng/mL; about 1,600 ng/mL to about 1,700 ng/mL; about 1,700 ng/mL to about 1,800 ng/mL; about 1,800 ng/mL to about 1,900 ng/mL; or about 1,900 ng/mL to about 2,000 ng/mL.

In some embodiments, the plasma concentration can be about 2,500 ng/mL, about 3,000 ng/mL, about 3,500 ng/mL, about 4,000 ng/mL, about 4,500 ng/mL, about 5,000 ng/mL, about 5,500 ng/mL, about 6,000 ng/mL, about 6,500 ng/mL, about 7,000 ng/mL, about 7,500 ng/mL, about 8,000 ng/mL, about 8,500 ng/mL, about 9,000 ng/mL, about 9,500 ng/mL, or about 10,000 ng/mL. In some embodiments, the plasma concentration can be about 10,000 ng/mL, about 15,000 ng/mL, about 20,000 ng/mL, about 25,000 ng/mL, about 30,000 ng/mL, about 35,000 ng/mL, about 40,000 ng/mL, about 45,000 ng/mL, about 50,000 ng/mL, about 55,000 ng/mL, about 60,000 ng/mL, about 65,000 ng/mL, about 70,000 ng/mL, or about 75,000 ng/mL.

The pharmacodynamic parameters can be any parameters suitable for describing compositions of the disclosure. For example, the pharmacodynamic profile can exhibit decreases in viability phenotype for the tumor cells or tumor size reduction in tumor cell lines or xenograft studies, for example, about 24 hours, about 48 hours, about 72 hours, or 1 week.

EXAMPLES

Example 1: Compounds of the Disclosure

Indole compounds with alkynyl, aryl, and heteroaryl linkers were prepared. Alkynyl-linked indole compounds are shown in TABLE 1. Aryl-linked indole compounds are shown in TABLE 2. Heteroaryl-linked indole compounds are shown in TABLE 3.

TABLE 1

Alkynyl indole compounds of the disclosure.

| Mol # | IUPAC name |
|---|---|
| 1. | 1-Anilino-3-{1-ethyl-5-[(1-methyl-4-piperidylamino)methyl]-1H-indol-2-yl}-2-propyne |
| 2. | 1-Anilino-3-{1-ethyl-5-[(methylamino)methyl]-1H-indol-2-yl}-2-propyne |
| 3. | 1-Anilino-3-{1-ethyl-5-[(tetrahydro-2H-pyran-4-ylamino)methyl]-1H-indol-2-yl}-2-propyne |
| 4. | 1-Anilino-3-[5-(benzylaminomethyl)-1-ethyl-1H-indol-2-yl]-2-propyne |
| 5. | 3-{1-Ethyl-5-[(methylamino)methyl]-1H-indol-2-yl}-1-(p-fluorophenylamino)-2-propyne |
| 6. | 3-{1-Ethyl-5-[(tetrahydro-2H-pyran-4-ylmino)methyl]-1H-indol-2-yl}-1-(p-fluorophenylamino)-2-propyne |
| 7. | 1-(p-Chlorophenylamino)-3-{1-ethyl-5-[(1-methyl-4-piperidylamino)methyl]-1H-indol-2-yl}-2-propyne |
| 8. | 3-{1-Ethyl-5-[(tetrahydro-2H-pyran-4-ylamino)methyl]-1H-indol-2-yl}-1-(6-methyl-3-pyridylamino)-2-propyne |
| 9. | 3-{1-Ethyl-5-[(methylamino)methyl]-1H-indol-2-yl}-1-(6-methyl-3-pyridylamino)-2-propyne |
| 10. | 3-{1-Ethyl-5-[(1-methyl-4-piperidylamino)methyl]-1H-indol-2-yl}-1-(2-methyl-4-pyridylamino)-2-propyne |
| 11. | 3-[5-(Benzylaminomethyl)-1-ethyl-1H-indol-2-yl]-1-(2-methyl-4-pyridylamino)-2-propyne |
| 12. | N-(3-{5-[(Diethylamino)methyl]-1-ethyl-1H-indol-2-yl}prop-2-yn-1-yl)aniline |
| 13. | 4-Chloro-N-(3-{5-[(diethylamino)methyl]-1-ethyl-1H-indol-2-yl}prop-2-yn-1-yl)aniline |
| 14. | N-({1-Ethyl-2-[3-(phenylamino)prop-1-yn-1-yl]-1H-indol-5-yl}methyl)oxetan-3-amine |
| 15. | N-[3-(1-Ethyl-5-{[(2-methylpropyl)amino]methyl}-1H-indol-2-yl)prop-2-yn-1-yl]aniline |
| 16. | N-[3-(1-Ethyl-5-{[(2-methoxyethyl)amino]methyl}-1H-indol-2-yl)prop-2-yn-1-yl]aniline |
| 17. | N-({1-ethyl-2-[3-(phenylamino)prop-1-yn-1-yl]-1H-indol-5-yl}methyl)-1-methanesulfonylpiperidin-4-amine |
| 18. | N-(3-{1-Ethyl-5-[(ethylamino)methyl]-1H-indol-2-yl}prop-2-yn-1-yl)aniline |
| 19. | N-{3-[5-({[2-(Dimethylamino)ethyl]amino}methyl)-1-ethyl-1H-indol-2-yl]prop-2-yn-1-yl}aniline |
| 20. | 6-tert-Butyl-N-[3-(1-ethyl-5-{[(1-methylpiperidin-4-yl)amino]methyl}-1H-indol-2-yl)prop-2-yn-1-yl]pyridin-3-amine |
| 21. | N-[(2-{3-[(4-Chlorophenyl)amino]prop-1-yn-1-yl}-1-ethyl-1H-indol-5-yl)methyl]oxan-4-amine |
| 22. | 6-tert-Butyl-N-(3-{1-ethyl-5-[(methylamino)methyl]-1H-indol-2-yl}prop-2-yn-1-yl)pyridin-3-amine |
| 23. | 4-[(3-{1-Ethyl-5-[(methylamino)methyl]-1H-indol-2-yl}prop-2-yn-1-yl)amino]benzonitrile |
| 24. | 4-tert-Butyl-N-(3-{1-ethyl-5-[(methylamino)methyl]-1H-indol-2-yl}prop-2-yn-1-yl)benzamide |
| 25. | 4-Chloro-N-(3-{1-ethyl-5-[(methylamino)methyl]-1H-indol-2-yl}prop-2-yn-1-yl)-3-fluorobenzamide |
| 26. | 4-Cyano-N-({1-ethyl-2-[3-(phenylformamido)prop-1-yn-1-yl]-1H-indol-5-yl}methyl)-N-methylbenzamide |

TABLE 1-continued

Alkynyl indole compounds of the disclosure.

| Mol # | IUPAC name |
|---|---|
| 27. | 3-(3-{1-Ethyl-5-[(methylamino)methyl]-1H-indol-2-yl}prop-2-yn-1-yl)-1-[4-(trifluoromethyl)phenyl]urea |
| 28. | N-{[1-(2-Chloroethyl)-2-{3-[(4-chlorophenyl)amino]prop-1-yn-1-yl}-1H-indol-5-yl]methyl}oxan-4-amine |
| 29. | 2-(4-{[3-(1-Ethyl-5-{[(1-methylpiperidin-4-yl)amino]methyl}-1H-indol-2-yl)prop-2-yn-1-yl]amino}phenyl)-2-methylpropanenitrile |
| 30. | 4-Cyano-N-(3-{1-ethyl-5-[(methylamino)methyl]-1H-indol-2-yl}prop-2-yn-1-yl)benzamide |
| 31. | N-(3-{1-Ethyl-5-[(methylamino)methyl]-1H-indol-2-yl}prop-2-yn-1-yl)-6-methylpyridine-3-carboxamide |
| 32. | 3-[3-(1-Ethyl-5-{[(1-methylpiperidin-4-yl)amino]methyl}-1H-indol-2-yl)prop-2-yn-1-yl]-1-phenylurea |
| 33. | N-[(2-{3-[(4-Chloro-3-fluorophenyl)amino]prop-1-yn-1-yl}-1-ethyl-1H-indol-5-yl)methyl]-1-methylpiperidin-4-amine |
| 34. | 2-(5-{[3-(1-Ethyl-5-{[(1-methylpiperidin-4-yl)amino]methyl}-1H-indol-2-yl)prop-2-yn-1-yl]amino}pyridin-2-yl)-2-methylpropanenitrile |
| 35. | N-{[1-(2-Chloroethyl)-2-{3-[(4-chlorophenyl)amino]prop-1-yn-1-yl}-1H-indol-5-yl]methyl}-1-methylpiperidin-4-amine |
| 36. | 6-tert-Butyl-N-[3-(1-ethyl-5-{[(1-methanesulfonylpiperidin-4-yl)amino]methyl}-1H-indol-2-yl)prop-2-yn-1-yl]pyridin-3-amine |
| 37. | 2-(4-{[3-(1-Ethyl-5-{[(1-methylpiperidin-4-yl)amino]methyl}-1H-indol-2-yl)prop-2-yn-1-yl]amino}phenyl)-2-methylpropanoic acid |
| 38. | 3-(1-Ethyl-5-{[(1-methylpiperidin-4-yl)amino]methyl}-1H-indol-2-yl)-N-methylprop-2-ynamide |
| 39. | Ethyl 2-(4-{[3-(1-ethyl-5-{[(1-methylpiperidin-4-yl)amino]methyl}-1H-indol-2-yl)prop-2-yn-1-yl]amino}phenyl)-2-methylpropanoate |
| 40. | 2-(5-{[3-(1-Ethyl-5-{[(oxan-4-yl)amino]methyl}-1H-indol-2-yl)prop-2-yn-1-yl]amino}pyridin-2-yl)-2-methylpropanenitrile |
| 41. | N-[(1-Ethyl-2-{3-[(4-methylphenyl)amino]prop-1-yn-1-yl}-1H-indol-5-yl)methyl]-1-methylpiperidin-4-amine |
| 42. | 4-{[3-(1-Ethyl-5-{[(1-methylpiperidin-4-yl)amino]methyl}-1H-indol-2-yl)prop-2-yn-1-yl]amino}benzonitrile |
| 43. | 3-(1-Ethyl-5-{[(1-methylpiperidin-4-yl)amino]methyl}-1H-indol-2-yl)-N-phenylprop-2-ynamide |
| 44. | N-[(2-{3-[(4-Chlorophenyl)amino]prop-1-yn-1-yl}-1-ethyl-1H-indol-5-yl)methyl]-1-methanesulfonylpiperidin-4-amine |
| 45. | 1-(4-{[(2-{3-[(4-Chlorophenyl)amino]prop-1-yn-1-yl}-1-ethyl-1H-indol-5-yl)methyl]amino}piperidin-1-yl)ethan-1-one |
| 46. | 6-tert-Butyl-N-[3-(1-ethyl-5-{[(1-methylpiperidin-4-yl)amino]methyl}-1H-indol-2-yl)prop-2-yn-1-yl]pyridine-3-carboxamide |
| 47. | N-(3-{1-Ethyl-5-[(methylamino)methyl]-1H-indol-2-yl}prop-2-yn-1-yl)-4-(trifluoromethyl)aniline |
| 48. | N-[(1-Ethyl-2-{3-[(4-methylphenyl)amino]prop-1-yn-1-yl}-1H-indol-5-yl)methyl]oxan-4-amine |
| 49. | N-(3-{1-ethyl-4-[(methylamino)methyl]-1H-indol-2-yl}prop-2-yn-1-yl)aniline |
| 50. | N-[3-(1-ethyl-4-{[4-(pyrrolidin-1-yl)piperidin-1-yl]methyl}-1H-indol-2-yl)prop-2-yn-1-yl]aniline |
| 51. | N-({1-ethyl-2-[3-(phenylamino)prop-1-yn-1-yl]-1H-indol-4-yl}methyl)-1-methylpiperidin-4-amine |
| 52. | 1-[(2-{3-[(4-chlorophenyl)arnino]prop-1-yn-1-yl}-1-ethyl-1H-indol-4-yl)methyl]piperidin-4-ol |
| 53. | 4-Chloro-N-[3-(1-ethyl-4-{[4-(pyrrolidin-1-yl)piperidin-1-yl]methyl}-1H-indol-2-yl)prop-2-yn-1-yl]aniline |
| 54. | 1-[(2-{3-[(4-chlorophenyl)amino]prop-1-yn-1-yl}-1-ethyl-1H-indol-4-yl)methyl]-N,N-dimethylpiperidin-4-amine |
| 55. | 4-Chloro-N-(3-{1-ethyl-4-[(4-methylpiperazin-1-yl)methyl]-1H-indol-2-yl}prop-2-yn-1-yl)aniline |
| 56. | 1-{1-[(2-{3-[(4-Chlorophenyl)amino]prop-1-yn-1-yl}-1-ethyl-1H-indol-4-yl)methyl]piperidin-4-yl}piperidin-4-ol |
| 57. | 2-(5-{[3-(4-{[4-(4-Aminopiperidin-1-yl)piperidin-1-yl]methyl}-1-ethyl-1H-indol-2-yl)prop-2-yn-1-yl]amino}pyridin-2-yl)-2-methylpropanenitrile |
| 58. | 1-[(1-ethyl-2-{3-[(4-fluorophenyl)amino]prop-1-yn-1-yl}-1H-indol-5-yl)methyl]-N,N-dimethylpiperidin-4-amine |
| 59. | 4-N-({1-ethyl-2-[3-(phenylamino)prop-1-yn-1-yl]-1H-indol-5-yl}methyl)-1-N,1-N-dimethylcyclohexane-1,4-diamine |
| 60. | 4-chloro-N-(3-{1-ethyl-5-[(methylamino)methyl]-1H-indol-2-yl}prop-2-yn-1-yl)-3-fluoroaniline |
| 61. | 6-tert-butyl-N-(3-{1-ethyl-5-[(methylamino)methyl]-1H-indol-2-yl}prop-2-yn-1-yl)pyridine-3-carboxamide |
| 62. | N-(3-{1-ethyl-5-[(methylamino)methyl]-1H-indol-2-yl}prop-2-yn-1-yl)benzamide |
| 63. | 3-(3-{1-ethyl-5-[(methylamino)methyl]-1H-indol-2-yl}prop-2-yn-1-yl)-1-(4-methylphenyl)urea |
| 64. | 4-chloro-N-(3-{1-ethyl-5-[(methylamino)methyl]-1H-indol-2-yl}prop-2-yn-1-yl)aniline |
| 65. | 4-{[3-(1-ethyl-5-{[(oxan-4-yl)amino]methyl}-1H-indol-2-yl)prop-2-yn-1-yl]amino}benzonitrile |
| 66. | N-[(2-{3-[(4-chloro-3-fluorophenyl)amino]prop-1-yn-1-yl}-1-ethyl-1H-indol-5-yl)methyl]oxan-4-amine |

TABLE 1-continued

Alkynyl indole compounds of the disclosure.

| Mol # | IUPAC name |
|---|---|
| 67. | 3-[3-(1-ethyl-5-{[(oxan-4-yl)amino]methyl}-1H-indol-2-yl)prop-2-yn-1-yl]-1-phenylurea |
| 68. | 6-tert-butyl-N-[3-(1-ethyl-5-{[(oxan-4-yl)amino]methyl}-1H-indol-2-yl)prop-2-yn-1-yl]pyridin-3-amine |
| 69. | 4-{[(2-{3-[(4-chlorophenyl)amino]prop-1-yn-1-yl}-1-ethyl-1H-indol-5-yl)methyl]amino}-1$\lambda^6$-thiane-1,1-dione |
| 70. | N-[(2-{3-[(4-chlorophenyl)amino]prop-1-yn-1-yl}-1-ethyl-1H-indol-5-yl)methyl]-1-(2-methanesulfonylethyl)piperidin-4-amine |
| 71. | 1-(4-{[(2-{3-[(4-chlorophenyl)amino]prop-1-yn-1-yl}-1-ethyl-1H-indol-5-yl)methyl]amino}piperidin-1-yl)-2-(dimethylamino)ethan-1-one |
| 72. | 2-(4-{[(2-{3-[(4-chlorophenyl)amino]prop-1-yn-1-yl}-1-ethyl-1H-indol-5-yl)methyl]amino}piperidin-1-yl)-N,N-dimethylacetamide |
| 73. | 2-tert-butyl-N-[3-(1-ethyl-5-{[(1-methylpiperidin-4-yl)amino]methyl}-1H-indol-2-yl)prop-2-yn-1-yl]pyrimidin-5-amine |
| 74. | 2-methyl-2-(5-{[3-(5-{[(oxan-4-yl)amino]methyl}-1-(2,2,2-trifluoroethyl)-1H-indol-2-yl)prop-2-yn-1-yl]amino}pyridin-2-yl)propanenitrile |
| 75. | 2-[5-({3-[1-(2-fluoroethyl)-5-{[(oxan-4-yl)amino]methyl}-1H-indol-2-yl]prop-2-yn-1-yl}amino)pyridin-2-yl]-2-methylpropanenitrile |
| 76. | 3-(1-ethyl-5-{[(1-methylpiperidin-4-yl)amino]methyl}-1H-indol-2-yl)prop-2-yn-1-ol |
| 77. | 2-[5-({3-[1-(2-chloroethyl)-5-{[(oxan-4-yl)amino]methyl}-1H-indol-2-yl]prop-2-yn-1-yl}amino)pyridin-2-yl]-2-methylpropanenitrile |
| 78. | 2-[5-({3-[1-(2,2-difluoroethyl)-5-{[(oxan-4-yl)amino]methyl}-1H-indol-2-yl]prop-2-yn-1-yl}amino)pyridin-2-yl]-2-methylpropanenitrile |
| 79. | 6-chloro-N-[3-(1-ethyl-5-{[(1-methylpiperidin-4-yl)amino]methyl}-1H-indol-2-yl)prop-2-yn-1-yl]pyridin-3-amine |
| 80. | tert-butyl N-({3-ethyl-2-[3-(phenylamino)prop-1-yn-1-yl]-1H-indol-6-yl}methyl)-N-(oxan-4-yl)carbamate |
| 81. | 6-Chloro-N-[3-(1-ethyl-4-{[4-(pyrrolidin-1-yl)piperidin-1-yl]methyl}-1H-indol-2-yl)prop-2-yn-1-yl]pyridin-3-amine |
| 82. | 3-(1-ethyl-5-{[(1-methylpiperidin-4-yl)amino]methyl}-1H-indol-2-yl)prop-2-yn-1-yl benzoate |
| 83. | 2-[5-({3-[1-(2-chloroethyl)-5-{[(1-methylpiperidin-4-yl)amino]methyl}-1H-indol-2-yl]prop-2-yn-1-yl}amino)pyridin-2-yl]-2-methylpropanenitrile |
| 84. | N-(6-chloropyridin-3-yl)-3-(1-ethyl-5-{[(1-methylpiperidin-4-yl)amino]methyl}-1H-indol-2-yl)prop-2-ynamide |
| 85. | N-[6-(1-cyano-1-methylethyl)pyridin-3-yl]-3-(1-ethyl-5-{[(1-methylpiperidin-4-yl)amino]methyl}-1H-indol-2-yl)prop-2-ynamide |
| 86. | N-({3-ethyl-2-[3-(phenylamino)prop-1-yn-1-yl]-1H-indol-6-yl}methyl)oxan-4-amine |
| 87. | 2-[5-({3-[1-(2-chloroethyl)-4-{[4-(pyrrolidin-1-yl)piperidin-1-yl]methyl}-1H-indol-2-yl]prop-2-yn-1-yl}amino)pyridin-2-yl]-2-methylpropanenitrile |
| 88. | 2-(5-{[3-(5-{[(1-methanesulfonylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 89. | 2-[5-({3-[5-({[1-(2-methanesulfonylethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 90. | 2-(5-{[3-(5-{[(1-acetylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 91. | 2-{5-[(3-{5-[({1-[2-(dimethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 92. | 2-methyl-2-(5-{[3-(5-{[(1-methylpiperidin-4-yl)amino]methyl}-1-(2,2,2-trifluoroethyl)-1H-indol-2-yl)prop-2-yn-1-yl]amino}pyridin-2-yl)propanenitrile |
| 93. | 2-methyl-2-{5-[(3-{5-[(methylamino)methyl]-1-(2,2,2-trifluoroethyl)-1H-indol-2-yl}prop-2-yn-1-yl)amino]pyridin-2-yl}propanenitrile |
| 94. | 6-Chloro-N-[3-(5-{[(1-methylpiperidin-4-yl)amino]methyl}-1-(2,2,2-trifluoroethyl)-1H-indol-2-yl)prop-2-yn-1-yl]pyridin-3-amine |
| 95. | 6-chloro-N-[3-(5-{[(oxan-4-yl)amino]methyl}-1-(2,2,2-trifluoroethyl)-1H-indol-2-yl)prop-2-yn-1-yl]pyridin-3-amine |
| 96. | 2-[5-({3-[1-(cyclopropylmethyl)-5-{[(oxan-4-yl)amino]methyl}-1H-indol-2-yl]prop-2-yn-1-yl}amino)pyridin-2-yl]-2-methylpropanenitrile |
| 97. | 2-(5-{[3-(4-{[4-(diethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 98. | 2-methyl-2-{5-[(3-{4-[(4-methylpiperazin-1-yl)methyl]-1-(2,2,2-trifluoroethyl)-1H-indol-2-yl}prop-2-yn-1-yl)amino]pyridin-2-yl}propanenitrile |
| 99. | 2-(5-{[3-(1-ethyl-7-fluoro-4-{[4-(pyrrolidin-1-yl)piperidin-1-yl]methyl}-1H-indol-2-yl)prop-2-yn-1-yl]amino}pyridin-2-yl)-2-methylpropanenitrile |
| 100. | 2-methyl-2-(5-{[3-(4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)propanenitrile |
| 101. | 2-(5-{[3-(4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 102. | N-(6-cyanopyridin-3-yl)-3-(1-ethyl-5-{[(1-methylpiperidin-4-yl)amino]methyl}-1H-indol-2-yl)prop-2-ynamide |
| 103. | N-[6-(1-cyano-1-methylethyl)pyridin-3-yl]-3-(5-{[(oxan-4-yl)amino]methyl}-1-(2,2,2-trifluoroethyl)-1H-indol-2-yl)prop-2-ynamide |
| 104. | N-[6-(1-cyano-1-methylethyl)pyridin-3-yl]-3-(5-{[(1-methylpiperidin-4-yl)amino]methyl}-1-(2,2,2-trifluoroethyl)-1H-indol-2-yl)prop-2-ynamide |
| 105. | 2-methyl-2-(5-{[3-(5-{[(oxan-4-yl)amino]methyl}-1-(oxiran-2-ylmethyl)-1H-indol-2-yl)prop-2-yn-1-yl]amino}pyridin-2-yl)propanenitrile |
| 106. | 2-(5-{[3-(5-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile |

TABLE 1-continued

Alkynyl indole compounds of the disclosure.

| Mol # | IUPAC name |
|---|---|
| 107. | 2-methyl-2-[5-({3-[5-({[2-(morpholin-4-yl)ethyl]amino}methyl)-1-(2,2,2-trifluoroethyl)-1H-indol-2-yl]prop-2-yn-1-yl}amino)pyridin-2-yl]propanenitrile |
| 108. | 2-methyl-2-(5-{[3-(4-{[(1-methylpiperidin-4-yl)amino]methyl}-1-(2,2,2-trifluoroethyl)-1H-indol-2-yl)prop-2-yn-1-yl]amino}pyridin-2-yl)propanenitrile |
| 109. | 2-methyl-2-(5-{[3-(4-{[(oxan-4-yl)amino]methyl}-1-(2,2,2-trifluoroethyl)-1H-indol-2-yl)prop-2-yn-1-yl]amino}pyridin-2-yl)propanenitrile |
| 110. | 2-[5-({3-[5-({[2-(dimethylamino)ethyl]amino}methyl)-1-(2,2,2-trifluoroethyl)-1H-indol-2-yl]prop-2-yn-1-yl}amino)pyridin-2-yl]-2-methylpropanenitrile |
| 111. | 2-(5-{[3-(7-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 112. | 2-methyl-2-[5-({3-[1-(2,2,2-trifluoroethyl)-5-{[(2,2,2-trifluoroethyl)amino]methyl}-1H-indol-2-yl]prop-2-yn-1-yl}amino)pyridin-2-yl]propanenitrile |
| 113. | 2-[5-({3-[5-({[1-(2-hydroxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 114. | 2-[5-({3-[5-({[1-(2-methoxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 115. | 2-[5-({3-[5-({[4-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile |
| 116. | 2-methyl-2-{5-[(3-{5-[({1-[2-(morpholin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 117. | 2-(5-{[3-(4-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile |
| 118. | 2-methyl-2-{5-[(3-{4-[(methylamino)methyl]-1-(2,2,2-trifluoroethyl)-1H-indol-2-yl}prop-2-yn-1-yl)amino]pyridin-2-yl}propanenitrile |
| 119. | 2-{5-[(3-{4-[(4-acetylpiperazin-1-yl)methyl]-1-(2,2,2-trifluoroethyl)-1H-indol-2-yl}prop-2-yn-1-yl)amino]pyridin-2-yl}-2-methylpropanenitrile |
| 120. | 2-methyl-2-(5-{[3-[4-(morpholin-4-ylmethyl)-1-(2,2,2-trifluoroethyl)-1H-indol-2-yl]prop-2-yn-1-yl]amino}pyridin-2-yl)propanenitrile |
| 121. | 2-(5-{[3-(4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 122. | 2-[5-({3-[4-(hydroxymethyl)-1-(2,2,2-trifluoroethyl)-1H-indol-2-yl]prop-2-yn-1-yl}amino)pyridin-2-yl]-2-methylpropanenitrile |
| 123. | 2-methyl-2-[5-({3-[4-({4-[2-(morpholin-4-yl)-2-oxoethyl]piperazin-1-yl}methyl)-1-(2,2,2-trifluoroethyl)-1H-indol-2-yl]prop-2-yn-1-yl}amino)pyridin-2-yl]propanenitrile |
| 124. | 2-(5-{[3-(3-ethyl-7-{[4-(pyrrolidin-1-yl)piperidin-1-yl]methyl}-1H-indol-2-yl)prop-2-yn-1-yl]amino}pyridin-2-yl)-2-methylpropanenitrile |
| 125. | methyl 5-{[3-(5-{[(oxan-4-yl)amino]methyl}-1-(2,2,2-trifluoroethyl)-1H-indol-2-yl)prop-2-yn-1-yl]amino}pyridine-2-carboxylate |
| 126. | N-methyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 127. | N-(2-hydroxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 128. | N-(2-methoxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 129. | 2-[(5-{[3-(5-{[(oxan-4-yl)amino]methyl}-1-(2,2,2-trifluoroethyl)-1H-indol-2-yl)prop-2-yn-1-yl]amino}pyridin-2-yl)formamido]acetic acid |
| 130. | 5-{[3-(5-{[(oxan-4-yl)amino]methyl}-1-(2,2,2-trifluoroethyl)-1H-indol-2-yl)prop-2-yn-1-yl]amino}pyridine-2-carboxylic acid |
| 131. | N-(2-methanesulfonylethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 132. | 2-[5-({3-[1-(cyanomethyl)-5-{[(oxan-4-yl)amino]methyl}-1H-indol-2-yl]prop-2-yn-1-yl}amino)pyridin-2-yl]-2-methylpropanenitrile |
| 133. | 2-methyl-2-[5-({3-[1-(2-methylpropyl)-5-{[(oxan-4-yl)amino]methyl}-1H-indol-2-yl]prop-2-yn-1-yl}amino)pyridin-2-yl]propanenitrile |
| 134. | 2-methyl-2-{5-[(3-{4-[(oxan-4-yl)amino]-1-(2,2,2-trifluoroethyl)-1H-indol-2-yl}prop-2-yn-1-yl)amino]pyridin-2-yl}propanenitrile |
| 135. | 5-{[3-(5-{[(oxan-4-yl)amino]methyl}-1-(2,2,2-trifluoroethyl)-1H-indol-2-yl)prop-2-yn-1-yl]amino}pyridine-2-carbonitrile |
| 136. | N,N-dimethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 137. | N-(oxan-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 138. | 2-tert-butyl-N-[3-(5-{[(oxan-4-yl)amino]methyl}-1-(2,2,2-trifluoroethyl)-1H-indol-2-yl)prop-2-yn-1-yl]pyrimidin-5-amine |
| 139. | N-(1-methylpiperidin-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 140. | N-[6-(1-cyano-1-methylethyl)pyridin-3-yl]-3-[1-(2-fluoroethyl)-5-{[(oxan-4-yl)amino]methyl}-1H-indol-2-yl]prop-2-ynamide |
| 141. | 2-(5-{[3-(7-chloro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 142. | 2-(5-{[3-(6-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 143. | 2-(5-{[3-(1-ethyl-5-{[(oxan-4-yl)amino]methyl}-1H-pyrrolo[2,3-c]pyridin-2-yl)prop-2-yn-1-yl]amino}pyridin-2-yl)-2-methylpropanenitrile |
| 144. | 2-methyl-2-(5-{[3-(5-{[(oxan-4-yl)amino]methyl}-1-(2,2,2-trifluoroethyl)-1H-pyrrolo[2,3-c]pyridin-2-yl)prop-2-yn-1-yl]amino}pyridin-2-yl)propanenitrile |

TABLE 1-continued

Alkynyl indole compounds of the disclosure.

| Mol # | IUPAC name |
|---|---|
| 145. | 2-(5-{[3-(5-{[4-(dimethylamino)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile |
| 146. | 2-(5-{[3-(7-chloro-4-{[4-(pyrrolidin-1-yl)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile |
| 147. | 2-(5-{[3-(4-{[4-(dimethylamino)-piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile |
| 148. | 2-(5-{[3-(4-{[4-(diethylamino)piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile |
| 149. | 2-(5-{[3-(6-fluoro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 150. | 2-(5-{[3-(6-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 151. | 2-(5-{[3-(5-{[(1-acetylpiperidin-4-yl)amino]methyl}-6-fluoro-1-(2,2,2-trifluoroethyl)-1H-indol-2-yl)prop-2-yn-1-yl]amino}pyridin-2-yl)-2-methylpropanenitrile |
| 152. | 2-(5-{[3-(6-chloro-4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 153. | 2-(5-{[3-(6-chloro-4-{[4-(diethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 154. | 2-(5-{[3-(6-chloro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 155. | 2-(5-{[3-(4-{[4-(2-methanesulfonyl-ethyl)piperazin-1-yl]methyl}-1-(2,2,2-trifluoroethyl)-1H-indol-2-yl)prop-2-yn-1-yl]amino}pyridin-2-yl)-2-methylpropanenitrile |
| 156. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)-N,N-dimethylacetamide |
| 157. | 2-methyl-2-{5-[(3-{4-[(3-oxopiperazin-1-yl]methyl}-1-(2,2,2-trifluoroethyl)-1H-indol-2-yl}prop-2-yn-1-yl)amino]pyridin-2-yl}propanenitrile |
| 158. | 2-methyl-2-[5-({3-[4-({4-[2-(morpholin-4-yl)-2-oxoethyl]piperidin-1-yl}methyl)-1-(2,2,2-trifluoroethyl)-1H-indol-2-yl]prop-2-yn-1-yl}amino)pyridin-2-yl]propanenitrile |
| 159. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)acetamide |
| 160. | N-[6-(1-cyano-1-methylethyl)pyridin-3-yl]-3-(4-{[4-(pyrrolidin-1-yl)piperidin-1-yl]methyl}-1-(2,2,2-trifluoroethyl)-1H-indol-2-yl)prop-2-ynamide |
| 161. | 2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperidin-4-yl)acetamide |
| 162. | 2-(5-{[3-(4-{[4-(2-aminoethyl)-piperazin-1-yl]methyl}-1-(2,2,2-trifluoroethyl)-1H-indol-2-yl)prop-2-yn-1-yl]amino}pyridin-2-yl)-2-methylpropanenitrile |
| 163. | 2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperidin-4-yl)-N,N-dimethylacetamide |
| 164. | 2-methyl-2-(5-{[3-(4-{[4-(morpholin-4-yl)piperidin-1-yl]methyl}-1-(2,2,2-trifluoroethyl)-1H-indol-2-yl)prop-2-yn-1-yl]amino}pyridin-2-yl)propanenitrile |
| 165. | 2-(5-{[3-(4-{[4-(4-aminopiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 166. | 2-methyl-2-[5-({3-[1-(oxiran-2-ylmethyl)-4-{[4-(pyrrolidin-1-yl)piperidin-1-yl]methyl}-1H-indol-2-yl]prop-2-yn-1-yl}amino)pyridin-2-yl]propanenitrile |
| 167. | 2-(5-{[3-(3-ethyl-6-{[(oxan-4-yl)amino]methyl}-1H-indol-2-yl)prop-2-yn-1-yl]amino}pyridin-2-yl)-2-methylpropanenitrile |
| 168. | 2-methyl-2-(5-{[3-(6-{[(oxan-4-yl)amino]methyl}-3-(2,2,2-trifluoroethyl)-1H-indol-2-yl)prop-2-yn-1-yl]amino}pyridin-2-yl)propanenitrile |
| 169. | 2-(5-{[3-(1-acetyl-3-ethyl-6-{[(oxan-4-yl)amino]methyl}-1H-indol-2-yl)prop-2-yn-1-yl]amino}pyridin-2-yl)-2-methylpropanenitrile |
| 170. | 2-(5-{[3-(3-ethyl-6-{[(1-methylpiperidin-4-yl)amino]methyl}-1H-indol-2-yl)prop-2-yn-1-yl]amino}pyridin-2-yl)-2-methylpropanenitrile |
| 171. | 2-methyl-2-(5-{[3-(6-{[(1-methylpiperidin-4-yl)amino]methyl}-3-(2,2,2-trifluoroethyl)-1H-indol-2-yl)prop-2-yn-1-yl]amino}pyridin-2-yl)propanenitrile |
| 172. | 2-{5-[(3-{6-chloro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 173. | 2-(3-{[6-(1-cyano-1-methylethyl)pyridin-3-yl]amino}prop-1-yn-1-yl)-6-fluoro-N-(1-methylpiperidin-4-yl)-1-(2,2,2-trifluoroethyl)-1H-indole-4-carboxamide |
| 174. | 2-[5-({3-[6-fluoro-4-(4-methylpiperazine-1-carbonyl)-1-(2,2,2-trifluoroethyl)-1H-indol-2-yl]prop-2-yn-1-yl}amino)pyridin-2-yl]-2-methylpropanenitrile |
| 175. | 6-fluoro-2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine |
| 176. | 2-{5-[(3-{6-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 177. | 5-[(3-{6-fluoro-4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide |
| 178. | 2-methyl-2-(5-{[3-(5-{[(oxan-4-yl)amino]methyl}-1-(2,2,2-trifluoroethyl)-1H-pyrrolo[2,3-b]pyridin-2-yl)prop-2-yn-1-yl]amino}pyridin-2-yl)propanenitrile |
| 179. | 2-methyl-2-{5-[(3-{4-[(1-methylpiperidin-4-yl)amino]-1-(2,2,2-trifluoroethyl)-1H-pyrrolo[2,3-b]pyridin-2-yl}prop-2-yn-1-yl)amino]pyridin-2-yl}propanenitrile |
| 180. | 2-(5-{[3-(7-chloro-1-ethyl-4-{[4-(pyrrolidin-1-yl)piperidin-1-yl]methyl}-1H-indol-2-yl)prop-2-yn-1-yl]amino}pyridin-2-yl)-2-methylpropanenitrile |
| 181. | 2-(5-{[3-(7-chloro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |

TABLE 1-continued

Alkynyl indole compounds of the disclosure.

| Mol # | IUPAC name |
|---|---|
| 182. | 2-(5-{[3-(7-chloro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 183. | 2-{5-[(3-{7-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 184. | 2-(5-{[3-(7-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 185. | 2-(5-{[3-(7-fluoro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 186. | 2-methyl-2-(5-{[3-(5-{[(oxan-4-yl)amino]methyl}-1-(2,2,2-trifluoroethyl)-1H-1,3-benzodiazol-2-yl)prop-2-yn-1-yl]amino}pyridin-2-yl)propanenitrile |
| 187. | N-{[2-(2-phenylethynyl)-1-(2,2,2-trifluoroethyl)-1H-1,3-benzodiazol-5-yl]methyl}oxan-4-amine |
| 188. | 2-methyl-2-(5-{[3-(5-{[(oxan-4-yl)amino]methyl}-1-(2,2,2-trifluoroethyl)-1H-pyrrolo[3,2-b]pyridin-2-yl)prop-2-yn-1-yl]amino}pyridin-2-yl)propanenitrile |
| 189. | 2-{3-[(4-methanesulfonylphenyl)amino]prop-1-yn-1-yl}-5-methyl-N-(1-methylpiperidin-4-yl)-1-(2,2,2-trifluoroethyl)-1H-indol-4-amine |
| 190. | 4-[(2-{3-[(4-methanesulfonylphenyl)amino]prop-1-yn-1-yl}-5-methyl-1-(2,2,2-trifluoroethyl)-1H-indol-4-yl)amino]-1λ⁶-thiane-1,1-dione |
| 191. | 2-methyl-2-{5-[(3-{5-methyl-4-[(1-methylpiperidin-4-yl)amino]-1-(2,2,2-trifluoroethyl)-1H-indol-2-yl}prop-2-yn-1-yl)amino]pyridin-2-yl}propanenitrile |
| 192. | N-[1-(2-methanesulfonylethyl)piperidin-4-yl]-2-{3-[(4-methanesulfonylphenyl)amino]prop-1-yn-1-yl}-5-methyl-1-(2,2,2-trifluoroethyl)-1H-indol-4-amine |
| 193. | 4-[(3-{5-methyl-4-[(piperidin-4-yl)amino]-1-(2,2,2-trifluoroethyl)-1H-indol-2-yl}prop-2-yn-1-yl)amino]benzene-1-sulfonamide |
| 194. | 2-{3-[(4-methanesulfonylphenyl)amino]prop-1-yn-1-yl}-5-methyl-N-[1-(oxan-4-yl)piperidin-4-yl]-1-(2,2,2-trifluoroethyl)-1H-indol-4-amine |
| 195. | 2-{4-[(2-{3-[(4-methanesulfonylphenyl)amino]prop-1-yn-1-yl}-5-methyl-1-(2,2,2-trifluoroethyl)-1H-indol-4-yl)amino]piperidin-1-yl}ethan-1-ol |
| 196. | 2-[5-({3-[4-(methoxymethyl)-1-(2,2,2-trifluoroethyl)-1H-indol-2-yl]prop-2-yn-1-yl}amino)pyridin-2-yl]-2-methylpropanenitrile |
| 197. | 2-[5-({3-[4-(cyanomethyl)-1-(2,2,2-trifluoroethyl)-1H-indol-2-yl]prop-2-yn-1-yl}amino)pyridin-2-yl]-2-methylpropanenitrile |
| 198. | 2-methyl-2-[5-({3-[5-(morpholine-4-carbonyl)-1-(2,2,2-trifluoroethyl)-1H-indol-2-yl]prop-2-yn-1-yl}amino)pyridin-2-yl]propanenitrile |
| 199. | 2-methyl-2-[5-({3-[5-(4-methylpiperazine-1-carbonyl)-1-(2,2,2-trifluoroethyl)-1H-indol-2-yl]prop-2-yn-1-yl}amino)pyridin-2-yl]propanenitrile |
| 200. | 2-{5-[(3-{5-[4-(dimethylamino)piperidine-1-carbonyl]-1-(2,2,2-trifluoroethyl)-1H-indol-2-yl}prop-2-yn-1-yl)amino]pyridin-2-yl}-2-methylpropanenitrile |
| 201. | 2-(3-{[6-(1-cyano-1-methylethyl)pyridin-3-yl]amino}prop-1-yn-1-yl)-N-{1-[2-(dimethylamino)acetyl]piperidin-4-yl}-1-(2,2,2-trifluoroethyl)-1H-indole-5-carboxamide |
| 202. | 2-(3-{[6-(1-cyano-1-methylethyl)pyridin-3-yl]amino}prop-1-yn-1-yl)-N-(oxan-4-yl)-1-(2,2,2-trifluoroethyl)-1H-indole-5-carboxamide |
| 203. | 2-methyl-2-(5-{[3-(5-{1-[(oxan-4-yl)amino]ethyl}-1-(2,2,2-trifluoroethyl)-1H-indol-2-yl)prop-2-yn-1-yl]amino}pyridin-2-yl)propanenitrile |
| 204. | 2-methyl-2-{5-[(3-{4-[(1-methylpiperidin-4-yl)amino]-1-(2,2,2-trifluoroethyl)-1H-pyrrolo[3,2-c]pyridin-2-yl}prop-2-yn-1-yl)amino]pyridin-2-yl}propanenitrile |
| 205. | 2-methyl-2-[5-({3-[5-(morpholin-4-ylmethyl)-1-(2,2,2-trifluoroethyl)-1H-indol-2-yl]prop-2-yn-1-yl}amino)pyridin-2-yl]propanenitrile |
| 206. | 2-[5-({3-[5-({[1-(2-cyanoethyl)-piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 207. | 2-methyl-2-(5-{[3-(5-{[(1-methylazetidin-3-yl)amino]methyl}-1-(2,2,2-trifluoroethyl)-1H-indol-2-yl)prop-2-yn-1-yl]amino}pyridin-2-yl)propanenitrile |
| 208. | 2-methyl-2-(5-{[3-(5-{[(oxetan-3-yl)amino]methyl}-1-(2,2,2-trifluoroethyl)-1H-indol-2-yl)prop-2-yn-1-yl]amino}pyridin-2-yl)propanenitrile |
| 209. | 2-(5-{[3-(5-{[4-(dimethylamino)-piperidin-1-yl]methyl}-1-(2,2,2-trifluoroethyl)-1H-indol-2-yl)prop-2-yn-1-yl]amino}pyridin-2-yl)-2-methylpropanenitrile |
| 210. | 2-methyl-2-{5-[(3-{5-[({1-[2-(4-methylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 211. | 2-(5-{[3-(5-{[(1-methoxypropan-2-yl)amino]methyl}-1-(2,2,2-trifluoroethyl)-1H-indol-2-yl)prop-2-yn-1-yl]amino}pyridin-2-yl)-2-methylpropanenitrile |
| 212. | 2-methyl-2-(5-{[3-(5-{[(pyridin-4-ylmethyl)amino]methyl}-1-(2,2,2-trifluoroethyl)-1H-indol-2-yl)prop-2-yn-1-yl]amino}pyridin-2-yl)propanenitrile |
| 213. | 2-methyl-2-(5-{[3-(5-{[(pyridin-3-ylmethyl)amino]methyl}-1-(2,2,2-trifluoroethyl)-1H-indol-2-yl)prop-2-yn-1-yl]amino}pyridin-2-yl)propanenitrile |
| 214. | 2-[5-({3-[5-({[1-(dimethylamino)-propan-2-yl]amino}methyl)-1-(2,2,2-trifluoroethyl)-1H-indol-2-yl]prop-2-yn-1-yl}amino)pyridin-2-yl]-2-methylpropanenitrile |
| 215. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(oxan-4-yl)acetamide |
| 216. | 2-[5-({3-[5-({[1-(2-methoxyacetyl)-piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 217. | 2-methyl-2-{5-[(3-{5-[({1-[2-(oxan-4-yl)acetyl]piperidin-4-yl}amino)-methyl]-1-(2,2,2-trifluoroethyl)-1H-indol-2-yl}prop-2-yn-1-yl)amino]-pyridin-2-yl}propanenitrile |

TABLE 1-continued

Alkynyl indole compounds of the disclosure.

| Mol # | IUPAC name |
|---|---|
| 218. | 2-methyl-2-{5-[(3-{5-[({1-[2-(pyridin-3-yl)acetyl]piperidin-4-yl}amino)-methyl]-1-(2,2,2-trifluoroethyl)-1H-indol-2-yl}prop-2-yn-1-yl)amino]-pyridin-2-yl}propanenitrile |
| 219. | 2-methyl-2-(5-{[3-(5-{[(1-{2-[(oxan-4-yl)amino]acetyl}piperidin-4-yl)amino]methyl]-1-(2,2,2-trifluoroethyl)-1H-indol-2-yl)prop-2-yn-1-yl]amino}pyridin-2-yl)-propanenitrile |
| 220. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-methyl-N-(propan-2-yl)acetamide |
| 221. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(2-methoxyethyl)-N-methylacetamide |
| 222. | 6-methanesulfonyl-N-[3-(5-{[(oxan-4-yl)amino]methyl}-1-(2,2,2-trifluoroethyl)-1H-indol-2-yl)prop-2-yn-1-yl]pyridin-3-amine |
| 223. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N,N-dimethylacetamide |
| 224. | 2-methyl-2-{5-[(3-{5-[({1-[2-oxo-2-(pyrrolidin-1-yl)ethyl]piperidin-4-yl}amino)methyl]-1-(2,2,2-trifluoroethyl)-1H-indol-2-yl}prop-2-yn-1-yl)amino]pyridin-2-yl}propanenitrile |
| 225. | 4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-N,N-dimethylpiperidine-1-carboxamide |
| 226. | 2-{5-[(3-{5-[({1-[2-(azetidin-1-yl)-2-oxoethyl]piperidin-4-yl}amino)-methyl]-1-(2,2,2-trifluoroethyl)-1H-indol-2-yl}prop-2-yn-1-yl)amino]-pyridin-2-yl}-2-methylpropanenitrile |
| 227. | 2-methyl-2-{5-[(3-{5-[({1-[2-(pyrrolidin-1-yl)acetyl]piperidin-4-yl}amino)methyl]-1-(2,2,2-trifluoroethyl)-1H-indol-2-yl}prop-2-yn-1-yl)amino]pyridin-2-yl}-propanenitrile |
| 228. | 2-(5-{[3-(5-{[(1-{2-[4-(dimethylamino)piperidin-1-yl]acetyl}piperidin-4-yl)amino]-methyl}-1-(2,2,2-trifluoroethyl)-1H-indol-2-yl)prop-2-yn-1-yl]amino}pyridin-2-yl)-2-methylpropanenitrile |
| 229. | 2-{5-[(3-{5-[({1-[2-(diethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 230. | 2-methyl-2-(5-{[3-(5-{[(1-{2-[methyl(propan-2-yl)amino]acetyl}piperidin-4-yl)amino]methyl}-1-(2,2,2-trifluoroethyl)-1H-indol-2-yl)prop-2-yn-1-yl]amino}pyridin-2-yl)propanenitrile |
| 231. | 2-methyl-2-{5-[(3-{5-[({1-[2-(pyridin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 232. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-4-yl)acetamide |
| 233. | 2-methyl-2-{5-[(3-{5-[({1-[2-(morpholin-4-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile |
| 234. | 2-methyl-2-{5-[(3-{5-[({1-[2-(4-methylpiperazin-1-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile |
| 235. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-3-yl)acetamide |
| 236. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(1-methylpiperidin-4-yl)acetamide |
| 237. | 2-methyl-2-[5-({3-[5-({[4-(morpholin-4-yl)cyclohexyl]amino}methyl)-1-(2,2,2-trifluoroethyl)-1H-indol-2-yl]prop-2-yn-1-yl}amino)pyridin-2-yl]propanenitrile |
| 238. | 2-{5-[(3-{5-[({1-[2-(4-hydroxypiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 239. | 2-{5-[(3-{5-[({1-[2-(4-acetylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 240. | 2-(5-{[3-(5-{[(1,1-dioxo-1$\lambda^6$-thian-4-yl)amino]methyl}-1-(2,2,2-trifluoroethyl)-1H-indol-2-yl)prop-2-yn-1-yl]amino}pyridin-2-yl)-2-methylpropanenitrile |
| 241. | 2-{5-[(3-{5-[({1-[2-(1,1-dioxo-1$\lambda^6$,4-thiomorpholin-4-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 242. | 2-[5-({3-[5-({[1-(4-acetylpiperazine-1-carbonyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 243. | 2-(5-{[3-(5-{[(1-{2-[bis(2-hydroxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 244. | 2-methyl-2-{5-[(3-{5-[({1-[2-(3-oxopiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 245. | 2-methyl-2-[5-({3-[5-({[1-(morpholine-4-carbonyl)piperidin-4-yl]amino}-methyl)-1-(2,2,2-trifluoroethyl)-1H-indol-2-yl]prop-2-yn-1-yl}amino)pyridin-2-yl]propanenitrile |
| 246. | 2-methyl-2-(5-{[3-(5-{[(1-methylpiperidin-3-yl)amino]methyl}-1-(2,2,2-trifluoroethyl)-1H-indol-2-yl)prop-2-yn-1-yl]amino}pyridin-2-yl)propanenitrile |
| 247. | N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]acetamide |
| 248. | 2-{5-[(3-{5-[({1-[2-(1H-imidazol-1-yl)acetyl]piperidin-4-yl}amino)-methyl]-1-(2,2,2-trifluoroethyl)-1H-indol-2-yl}prop-2-yn-1-yl)amino]pyridin-2-yl}-2-methylpropanenitrile |
| 249. | 2-(5-{[3-(5-{[(1-{2-[(2-methoxyethyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |

TABLE 1-continued

Alkynyl indole compounds of the disclosure.

| Mol # | IUPAC name |
|---|---|
| 250. | N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]methanesulfonamide |
| 251. | 2-methyl-2-(5-{[3-(5-{[(1-methyl-6-oxopiperidin-3-yl)amino]methyl}-1-(2,2,2-trifluoroethyl)-1H-indol-2-yl)prop-2-yn-1-yl]amino}pyridin-2-yl)propanenitrile |
| 252. | 2-[5-({3-[5-({[3-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile |
| 253. | 2-methyl-2-[5-({3-[5-({[1-(4-methylpiperazine-1-carbonyl)piperidin-4-yl]amino}methyl)-1-(2,2,2-trifluoroethyl)-1H-indol-2-yl]prop-2-yn-1-yl}amino)pyridin-2-yl]propanenitrile |
| 254. | 2-{5-[(3-{5-[({1-[4-(dimethylamino)piperidine-1-carbonyl]piperidin-4-yl}amino)-methyl]-1-(2,2,2-trifluoroethyl)-1H-indol-2-yl}prop-2-yn-1-yl)amino]pyridin-2-yl}-2-methylpropanenitrile |
| 255. | 2-{5-[(3-{5-[({1-[2-(3-hydroxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 256. | 2-{5-[(3-{5-[({1-[2-(3-methoxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 257. | 2-methyl-2-[5-({3-[5-({[1-(2-{2-oxa-8-azaspiro[4.5]decan-8-yl}acetyl)-piperidin-4-yl]amino}methyl)-1-(2,2,2-trifluoroethyl)-1H-indol-2-yl]prop-2-yn-1-yl}amino)pyridin-2-yl]propanenitrile |
| 258. | 2-{5-[(3-{5-[({1-[2-(4-hydroxy-4-methylpiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 259. | 2-(5-{[3-(5-{[(1-{2-[bis(2-methoxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 260. | 2-(5-{[3-(5-{[(1-{2-[methoxy(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 261. | 2-(5-{[3-(5-{[(1-{2-[(2,3-dihydroxypropyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 262. | 2-methyl-2-(5-{[3-(5-{[((1-methyl-2-oxopiperidin-4-yl)amino]methyl}-1-(2,2,2-trifluoroethyl)-1H-indol-2-yl)prop-2-yn-1-yl]amino}pyridin-2-yl)propanenitrile |
| 263. | 2-methyl-2-(5-{[3-(5-{[(1-{2-[methyl(1-methylpiperidin-4-yl)amino]acetyl}piperidin-4-yl)amino]methyl}-1-(2,2,2-trifluoroethyl)-1H-indol-2-yl)prop-2-yn-1-yl]amino}pyridin-2-yl)propanenitrile |
| 264. | 2-methyl-2-[5-({3-[5-({[1-(2-{9-methyl-3,9-diazaspiro[5.5]undecan-3-yl}acetyl)piperidin-4-yl]amino}methyl)-1-(2,2,2-trifluoroethyl)-1H-indol-2-yl]prop-2-yn-1-yl}amino)pyridin-2-yl]propanenitrile |
| 265. | 2-(5-{[3-(5-{[(1-{2-[3-(dimethyl-amino)pyrrolidin-1-yl]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 266. | N-[3-(5-{[(oxan-4-yl)amino]methyl}-1-(2,2,2-trifluoroethyl)-1H-indol-2-yl)prop-2-yn-1-yl]-6-(pyrrolidine-1-carbonyl)pyridin-3-amine |
| 267. | 6-(morpholine-4-carbonyl)-N-[3-(5-{[(oxan-4-yl)amino]methyl}-1-(2,2,2-trifluoroethyl)-1H-indol-2-yl)prop-2-yn-1-yl]pyridin-3-amine |
| 268. | 2-chloro-N-[3-(5-{[(oxan-4-yl)amino]-methyl}-1-(2,2,2-trifluoroethyl)-1H-indol-2-yl)prop-2-yn-1-yl]pyrimidin-5-amine |
| 269. | 5-{[3-(5-{[(oxan-4-yl)amino]methyl}-1-(2,2,2-trifluoroethyl)-1H-indol-2-yl)prop-2-yn-1-yl]amino}-N-phenylpyridine-2-carboxamide |
| 270. | N-methyl-5-{[3-(5-{[(oxan-4-yl)amino]methyl}-1-(2,2,2-trifluoroethyl)-1H-indol-2-yl)prop-2-yn-1-yl]amino]-N-(propan-2-yl)pyridine-2-carboxamide |
| 271. | 5-{[3-(5-{[(oxan-4-yl)amino]methyl}-1-(2,2,2-trifluoroethyl)-1H-indol-2-yl)prop-2-yn-1-yl]amino}-N-(pyridin-4-yl)pyridine-2-carboxamide |
| 272. | 5-{[3-(5-{[(oxan-4-yl)amino]methyl}-1-(2,2,2-trifluoroethyl)-1H-indol-2-yl)prop-2-yn-1-yl]amino}-N-(pyridin-3-yl)pyridine-2-carboxamide |
| 273. | N-(1-methylazetidin-3-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 274. | N,N-diethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 275. | 5-{[3-(5-{[(oxan-4-yl)amino]methyl}-1-(2,2,2-trifluoroethyl)-1H-indol-2-yl)prop-2-yn-1-yl]amino}-N-(oxetan-3-yl)pyridine-2-carboxamide |
| 276. | 1-(4-{[(2-{3-[(2-tert-butylpyrimidin-5-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 277. | 1-(4-{[(2-{3-[(6-chloropyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 278. | 5-[(3-{5-[({1-[2-(dimethylamino)-acetyl]piperidin-4-yl}amino)methyl]-1-(2,2,2-trifluoroethyl)-1H-indol-2-yl}prop-2-yn-1-yl)amino]-N-(1-methylpiperidin-4-yl)pyridine-2-carboxamide |
| 279. | 1-(4-{[(2-{3-[(4-chloro-3-fluorophenyl)amino]prop-1-yn-1-yl}-1-(2,2,2-trifluoroethyl)-1H-indol-5-yl)methyl]amino}piperidin-1-yl)-2-(dimethylamino)ethan-1-one |
| 280. | 2-(dimethylamino)-1-(4-{[(2-{3-[(6-methylpyridin-3-yl)amino]prop-1-yn-1-yl}-1-(2,2,2-trifluoroethyl)-1H-indol-5-yl)methyl]amino}piperidin-1-yl)ethan-1-one |
| 281. | 1-(4-{[(2-{3-[(6-tert-butylpyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one |

TABLE 1-continued

Alkynyl indole compounds of the disclosure.

| Mol # | IUPAC name |
|---|---|
| 282. | N-[6-(1-cyano-1-methylethyl)pyridin-3-yl]-3-[1-(2-fluoroethyl)-5-{[(1-methylpiperidin-4-yl)amino]methyl}-1H-indol-2-yl]prop-2-ynamide |
| 283. | 2-{5-[(3-{5-[({1-[2-(dimethylamino)acetyl]piperidin-4-yl}amino)methyl]-1-ethyl-1H-indol-2-yl}prop-2-yn-1-yl)amino]pyridin-2-yl}-2-methylpropanenitrile |
| 284. | 2-[5-({3-[1-(2,2-difluoroethyl)-5-[({1-[2-(dimethylamino)acetyl]piperidin-4-yl}amino)methyl]-1H-indol-2-yl]prop-2-yn-1-yl}amino)pyridin-2-yl]-2-methylpropanenitrile |
| 285. | 2-{5-[(3-{5-[({1-[2-(dimethylamino)acetyl]piperidin-4-yl}amino)methyl]-1-(2-fluoroethyl)-1H-indol-2-yl}prop-2-yn-1-yl)amino]pyridin-2-yl}-2-methylpropanenitrile |
| 286. | N-(6-chloropyridin-3-yl)-3-(5-{[(1-methylpiperidin-4-yl)amino]methyl}-1-(2,2,2-trifluoroethyl)-1H-indol-2-yl)prop-2-ynamide |
| 287. | 2-(5-{[3-(5-{[(1-acetylpiperidin-4-yl)amino]methyl}-1-(oxiran-2-ylmethyl)-1H-indol-2-yl)prop-2-yn-1-yl]amino}pyridin-2-yl)-2-methylpropanenitrile |
| 288. | 2-methyl-2-{5-[(3-{5-[(oxan-4-yl)amino]-1-(2,2,2-trifluoroethyl)-1H-indol-2-yl}prop-2-yn-1-yl)amino]pyridin-2-yl}propanenitrile |
| 289. | 2-{5-[(3-{4-[(1-acetylpiperidin-4-yl)amino]-1-(2,2,2-trifluoroethyl)-1H-indol-2-yl}prop-2-yn-1-yl)amino]pyridin-2-yl}-2-methylpropanenitrile |
| 290. | 2-methyl-2-{5-[(3-{4-[(propan-2-yl)amino]-1-(2,2,2-trifluoroethyl)-1H-indol-2-yl}prop-2-yn-1-yl)amino]pyridin-2-yl}propanenitrile |
| 291. | 2-methyl-2-{5-[(3-{4-[(piperidin-4-yl)amino]-1-(2,2,2-trifluoroethyl)-1H-indol-2-yl}prop-2-yn-1-yl)amino]pyridin-2-yl}propanenitrile |
| 292. | 2-(5-{[3-(4-{[1-(2-methoxyethyl)-piperidin-4-yl]amino}-1-(2,2,2-trifluoroethyl)-1H-indol-2-yl)prop-2-yn-1-yl]amino}pyridin-2-yl)-2-methylpropanenitrile |
| 293. | 2-{5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridin-2-yl}-2-methylpropanenitrile |
| 294. | 3-[2-(3-{[6-(1-cyano-1-methylethyl)-pyridin-3-yl]amino}prop-1-yn-1-yl)-1-(2,2,2-trifluoroethyl)-1H-indol-4-yl]-1-(oxan-4-yl)urea |
| 295. | 3-[2-(3-{[6-(1-cyano-1-methylethyl)-pyridin-3-yl]amino}prop-1-yn-1-yl)-1-(2,2,2-trifluoroethyl)-1H-indol-4-yl]-1-(1-methylpiperidin-4-yl)urea |
| 296. | 2-(4-{[2-(3-{[6-(1-cyano-1-methylethyl)-pyridin-3-yl]amino}prop-1-yn-1-yl)-1-(2,2,2-trifluoroethyl)-1H-indol-4-yl]amino}piperidin-1-yl)-N,N-dimethylacetamide |
| 297. | 2-methyl-2-(5-{[3-(4-{[1-(propan-2-yl)piperidin-4-yl]amino}-1-(2,2,2-trifluoroethyl)-1H-indol-2-yl)prop-2-yn-1-yl]amino}pyridin-2-yl)propanenitrile |
| 298. | 2-methyl-2-(5-{[3-(4-{[1-(1-methylpiperidin-4-yl)piperidin-4-yl]amino}-1-(2,2,2-trifluoroethyl)-1H-indol-2-yl)prop-2-yn-1-yl]amino}pyridin-2-yl)propanenitrile |
| 299. | 4-{[2-(3-{[6-(1-cyano-1-methylethyl)-pyridin-3-yl]amino}prop-1-yn-1-yl)-1-(2,2,2-trifluoroethyl)-1H-indol-4-yl]amino}-N,N-dimethylpiperidine-1-carboxamide |
| 300. | N-[2-(3-{[6-(1-cyano-1-methylethyl)-pyridin-3-yl]amino}prop-1-yn-1-yl)-1-(2,2,2-trifluoroethyl)-1H-indol-4-yl]-4-methylpiperazine-1-carboxamide |
| 301. | 1-[2-(3-{[6-(1-cyano-1-methylethyl)pyridin-3-yl]amino}prop-1-yn-1-yl)-1-(2,2,2-trifluoroethyl)-1H-indol-4-yl]-3,3-dimethylurea |
| 302. | N-[2-(3-{[6-(1-cyano-1-methylethyl)-pyridin-3-yl]amino}prop-1-yn-1-yl)-1-(2,2,2-trifluoroethyl)-1H-indol-4-yl]morpholine-4-carboxamide |
| 303. | 2-{5-[(3-{4-[(4-hydroxycyclohexyl)-amino]-1-(2,2,2-trifluoroethyl)-1H-indol-2-yl}prop-2-yn-1-yl)amino]pyridin-2-yl}-2-methylpropanenitrile |
| 304. | 2-methyl-2-[5-({3-[4-({1-[2-(4-methylpiperazin-1-yl)-2-oxoethyl]-piperidin-4-yl}amino)-1-(2,2,2-trifluoroethyl)-1H-indol-2-yl]prop-2-yn-1-yl}amino)pyridin-2-yl]propanenitrile |
| 305. | 2-methyl-2-{5-[(3-{4-[(oxan-4-ylmethyl)amino]-1-(2,2,2-trifluoroethyl)-1H-indol-2-yl}prop-2-yn-1-yl)amino]pyridin-2-yl}propanenitrile |
| 306. | 2-{5-[(3-{4-[(1-ethylpiperidin-4-yl)amino]-1-(2,2,2-trifluoroethyl)-1H-indol-2-yl}prop-2-yn-1-yl)amino]pyridin-2-yl}-2-methylpropanenitrile |
| 307. | 2-(5-{[3-(4-{[1-(2-hydroxyethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 308. | 2-{5-[(3-{4-[(1-methanesulfonylpiperidin-4-yl)amino]-1-(2,2,2-trifluoroethyl)-1H-indol-2-yl}prop-2-yn-1-yl)amino]pyridin-2-yl}-2-methylpropanenitrile |
| 309. | 2-(5-{[3-(4-{[1-(2-methanesulfonyl-ethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 310. | 2-methyl-2-(5-{[3-(4-{[(1R,4R)-4-hydroxycyclohexyl]amino}-1-(2,2,2-trifluoroethyl)-1H-indol-2-yl)prop-2-yn-1-yl]amino}pyridin-2-yl)propanenitrile |
| 311. | 2-methyl-2-(5-{[3-(4-{[(1S,4S)-4-hydroxycyclohexyl]amino}-1-(2,2,2-trifluoroethyl)-1H-indol-2-yl)prop-2-yn-1-yl]amino}pyridin-2-yl)propanenitrile |
| 312. | 2-methyl-2-[5-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)pyridin-2-yl]propanenitrile |
| 313. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N,N-bis(2-methoxyethyl)acetamide |
| 314. | 2-methyl-2-{5-[(3-{4-[(pyrrolidin-3-yl)amino]-1-(2,2,2-trifluoroethyl)-1H-indol-2-yl}prop-2-yn-1-yl)amino]pyridin-2-yl}propanenitrile |
| 315. | 2-methyl-2-{5-[(3-{4-[(1-methylpyrrolidin-3-yl)amino]-1-(2,2,2-trifluoroethyl)-1H-indol-2-yl}prop-2-yn-1-yl)amino]pyridin-2-yl}propanenitrile |
| 316. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetamide |
| 317. | methyl 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetate |

TABLE 1-continued

Alkynyl indole compounds of the disclosure.

| Mol # | IUPAC name |
|---|---|
| 318. | 2-[5-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 319. | 2-methyl-2-{5-[(3-{4-[(2-methylpiperidin-4-yl)amino]-1-(2,2,2-trifluoroethyl)-1H-indol-2-yl}prop-2-yn-1-yl)amino]pyridin-2-yl}propanenitrile |
| 320. | 2-{5-[(3-{4-[(1,1-dioxo-1$\lambda^6$-thiolan-3-yl)amino]-1-(2,2,2-trifluoroethyl)-1H-indol-2-yl}prop-2-yn-1-yl)amino]pyridin-2-yl}-2-methylpropanenitrile |
| 321. | 2-methyl-2-[5-({3-[4-({1-[2-oxo-2-(pyrrolidin-1-yl)ethyl]piperidin-4-yl}amino)-1-(2,2,2-trifluoroethyl)-1H-indol-2-yl]prop-2-yn-1-yl}amino)pyridin-2-yl]propanenitrile |
| 322. | 2-{5-[(3-{4-[(1-{2-[4-(dimethylamino)piperidin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 323. | 2-[5-({3-[4-({1-[2-(dimethylamino)acetyl]piperidin-4-yl}amino)-1-(2,2,2-trifluoroethyl)-1H-indol-2-yl]prop-2-yn-1-yl}amino)pyridin-2-yl]-2-methylpropanenitrile |
| 324. | 2-(5-{[3-(4-{[1-(1,1-dioxo-1$\lambda^6$-thian-4-yl)piperidin-4-yl]amino]-1-(2,2,2-trifluoroethyl)-1H-indol-2-yl)prop-2-yn-1-yl]amino}pyridin-2-yl)-2-methylpropanenitrile |
| 325. | 2-(5-{[3-(4-{[1-(cyanomethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 326. | 2-methyl-2-[5-({3-[1-(2,2,2-trifluoroethyl)-4-{[1-(2,2,2-trifluoroethyl)piperidin-4-yl]amino}-1H-indol-2-yl]prop-2-yn-1-yl}amino)pyridin-2-yl]propanenitrile |
| 327. | 2-{5-[(3-{4-[(1-{2-[4-(2-methanesulfonylethyl)piperazin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 328. | 2-[5-({3-[4-({1-[2-(1,1-dioxo-1$\lambda^6$,4-thiomorpholin-4-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 329. | 2-(5-{[3-(4-{[1-(1-methanesulfonylpiperidin-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 330. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N-(2,3-dihydroxypropyl)-N-methylacetamide |
| 331. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N-(2,3-dihydroxypropyl)acetamide |
| 332. | 2-[5-({3-[4-({1-[2-(4-methanesulfonylpiperazin-1-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 333. | 2-{5-[(3-{4-[(1-{2-[4-(2-hydroxyethyl)piperazin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 334. | 2-methyl-2-(5-{[3-(4-{[1-(oxan-4-yl)piperidin-4-yl]amino}-1-(2,2,2-trifluoroethyl)-1H-indol-2-yl)prop-2-yn-1-yl]amino}pyridin-2-yl)propanenitrile |
| 335. | 2-[5-({3-[4-({1-[1-(2-methanesulfonylethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 336. | 2-[5-({3-[4-({1-[1-(2-methoxyethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 337. | 2-[5-({3-[4-({1-[1-(2-hydroxyethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 338. | 2-[5-({3-[4-({1-[2-(dimethylamino)ethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 339. | 2-(5-{[3-(4-{[1-(1-acetylpiperidin-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 340. | 2-methyl-2-[5-({3-[4-({1-[(1R,4R)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile |
| 341. | 2-methyl-2-[5-({3-[4-({1-[(1S,4S)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile |
| 342. | N-(1-methylpiperidin-4-yl)-2-{3-[(6-methylpyridin-3-yl)amino]prop-1-yn-1-yl}-1-(2,2,2-trifluoroethyl)-1H-indol-4-amine |
| 343. | 2-methyl-2-{5-[(3-{4-[(1-methylpiperidin-4-yl)amino]-1-(2,2,2-trifluoroethyl)-1H-indol-2-yl}prop-2-yn-1-yl)amino]pyridin-2-yl}propanenitrile |
| 344. | 5-[(3-{4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide |
| 345. | 5-[(3-{4-[(1-methylpiperidin-4-yl)amino]-1-(2,2,2-trifluoroethyl)-1H-indol-2-yl}prop-2-yn-1-yl)amino]pyridine-2-carbonitrile |
| 346. | N-[6-(1-cyano-1-methylethyl)pyridin-3-yl]-3-{4-[(1-methylpiperidin-4-yl)amino]-1-(2,2,2-trifluoroethyl)-1H-indol-2-yl}prop-2-ynamide |
| 347. | 2-{3-[(2-fluorophenyl)amino]prop-1-yn-1-yl}-N-(1-methylpiperidin-4-yl)-1-(2,2,2-trifluoroethyl)-1H-indol-4-amine |
| 348. | 2-{3-[(3-fluorophenyl)amino]prop-1-yn-1-yl}-N-(1-methylpiperidin-4-yl)-1-(2,2,2-trifluoroethyl)-1H-indol-4-amine |
| 349. | 4-amino-N-(3-{4-[(1-methylpiperidin-4-yl)amino]-1-(2,2,2-trifluoroethyl)-1H-indol-2-yl}prop-2-yn-1-yl)benzene-1-sulfonamide |
| 350. | 2-{3-[(6-tert-butylpyridin-3-yl)amino]prop-1-yn-1-yl}-N-(1-methylpiperidin-4-yl)-1-(2,2,2-trifluoroethyl)-1H-indol-4-amine |
| 351. | 2-{3-[(4-fluorophenyl)amino]prop-1-yn-1-yl}-N-(1-methylpiperidin-4-yl)-1-(2,2,2-trifluoroethyl)-1H-indol-4-amine |

TABLE 1-continued

Alkynyl indole compounds of the disclosure.

| Mol # | IUPAC name |
|---|---|
| 352. | N,N-dimethyl-5-[(3-{4-[(1-methylpiperidin-4-yl)amino]-1-(2,2,2-trifluoroethyl)-1H-indol-2-yl}prop-2-yn-1-yl)amino]pyridine-2-carboxamide |
| 353. | 5-[(3-{4-[(1-methylpiperidin-4-yl)amino]-1-(2,2,2-trifluoroethyl)-1H-indol-2-yl}prop-2-yn-1-yl)amino]-N-(propan-2-yl)pyridine-2-carboxamide |
| 354. | N-(pyridin-3-yl)-5-{[3-(4-{[(1R,4R)-4-(dimethylamino)cyclohexyl]amino}-1-(2,2,2-trifluoroethyl)-1H-indol-2-yl)prop-2-yn-1-yl]amino}pyridine-2-carboxamide |
| 355. | N-(pyridin-3-yl)-5-{[3-(4-{[(1S,4S)-4-(dimethylamino)cyclohexyl]amino}-1-(2,2,2-trifluoroethyl)-1H-indol-2-yl)prop-2-yn-1-yl]amino}pyridine-2-carboxamide |
| 356. | 2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine |
| 357. | 6-tert-butyl-N-(3-{4-[(1-methylpiperidin-4-yl)amino]-1-(2,2,2-trifluoroethyl)-1H-indol-2-yl}prop-2-yn-1-yl)pyridine-3-carboxamide |
| 358. | 2-{3-[(6-chloropyridin-3-yl)amino]prop-1-yn-1-yl}-N-(1-methylpiperidin-4-yl)-1-(2,2,2-trifluoroethyl)-1H-indol-4-amine |
| 359. | 2-{4-[(3-{4-[(1-methylpiperidin-4-yl)amino]-1-(2,2,2-trifluoroethyl)-1H-indol-2-yl}prop-2-yn-1-yl)amino]phenyl}propan-2-ol |
| 360. | 6-methyl-N-(3-{4-[(1-methylpiperidin-4-yl)amino]-1-(2,2,2-trifluoroethyl)-1H-indol-2-yl}prop-2-yn-1-yl)pyridine-3-carboxamide |
| 361. | N-(1-methylpiperidin-4-yl)-1-(2,2,2-trifluoroethyl)-2-(3-{[6-(trifluoromethyl)pyridin-3-yl]amino}prop-1-yn-1-yl)-1H-indol-4-amine |
| 362. | 3-(3-{4-[(1-methylpiperidin-4-yl)amino]-1-(2,2,2-trifluoroethyl)-1H-indol-2-yl}prop-2-yn-1-yl)-1-phenylurea |
| 363. | 2-{3-[(4-tert-butyl-2-fluorophenyl)-amino]prop-1-yn-1-yl}-N-(1-methylpiperidin-4-yl)-1-(2,2,2-trifluoroethyl)-1H-indol-4-amine |
| 364. | 2-{3-fluoro-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile |
| 365. | 4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 366. | 2-{3-[(2,6-difluoro-4-methane-sulfonylphenyl)amino]prop-1-yn-1-yl}-N-(1-methylpiperidin-4-yl)-1-(2,2,2-trifluoroethyl)-1H-indol-4-amine |
| 367. | N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 368. | 2-{3-[(4-methanesulfonyl-3-methoxyphenyl)amino]prop-1-yn-1-yl}-N-(1-methylpiperidin-4-yl)-1-(2,2,2-trifluoroethyl)-1H-indol-4-amine |
| 369. | 2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 370. | 2-{3-[(5-methanesulfonylpyridin-2-yl)amino]prop-1-yn-1-yl}-N-(1-methylpiperidin-4-yl)-1-(2,2,2-trifluoroethyl)-1H-indol-4-amine |
| 371. | 2-{3-[(4-methanesulfonyl-2-methylphenyl)amino]prop-1-yn-1-yl}-N-(1-methylpiperidin-4-yl)-1-(2,2,2-trifluoroethyl)-1H-indol-4-amine |
| 372. | methyl 3-methoxy-4-[(3-{4-[(1-methylpiperidin-4-yl)amino]-1-(2,2,2-trifluoroethyl)-1H-indol-2-yl}prop-2-yn-1-yl)amino]benzoate |
| 373. | N-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}methanesulfonamide |
| 374. | 3-methoxy-4-[(3-{4-[(1-methylpiperidin-4-yl)amino]-1-(2,2,2-trifluoroethyl)-1H-indol-2-yl}prop-2-yn-1-yl)amino]benzonitrile |
| 375. | 3-methoxy-4-[(3-{4-[(1-methylpiperidin-4-yl)amino]-1-(2,2,2-trifluoroethyl)-1H-indol-2-yl}prop-2-yn-1-yl)amino]benzoic acid |
| 376. | 2-{3-[(2,4-dimethoxyphenyl)amino]prop-1-yn-1-yl}-N-(1-methylpiperidin-4-yl)-1-(2,2,2-trifluoroethyl)-1H-indol-4-amine |
| 377. | 2-{3-[(2-methoxypyridin-3-yl)amino]prop-1-yn-1-yl}-N-(1-methylpiperidin-4-yl)-1-(2,2,2-trifluoroethyl)-1H-indol-4-amine |
| 378. | 2-{3-[(5-fluoro-2-methoxyphenyl)-amino]prop-1-yn-1-yl}-N-(1-methylpiperidin-4-yl)-1-(2,2,2-trifluoroethyl)-1H-indol-4-amine |
| 379. | 2-{3-[(2-ethoxy-4-methane-sulfonylphenyl)amino]prop-1-yn-1-yl}-N-(1-methylpiperidin-4-yl)-1-(2,2,2-trifluoroethyl)-1H-indol-4-amine |
| 380. | 2-{3-[(3-fluoro-2-methoxyphenyl)-amino]prop-1-yn-1-yl}-N-(1-methylpiperidin-4-yl)-1-(2,2,2-trifluoroethyl)-1H-indol-4-amine |
| 381. | 3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 382. | 2-{3-[(4-fluoro-2-methoxyphenyl)-amino]prop-1-yn-1-yl}-N-(1-methylpiperidin-4-yl)-1-(2,2,2-trifluoroethyl)-1H-indol-4-amine |
| 383. | 3-methoxy-4-[(3-{4-[(1-methylpiperidin-4-yl)amino]-1-(2,2,2-trifluoroethyl)-1H-indol-2-yl}prop-2-yn-1-yl)amino]-benzamide |
| 384. | 2-{3-[(2-fluoro-6-methoxyphenyl)-amino]prop-1-yn-1-yl}-N-(1-methylpiperidin-4-yl)-1-(2,2,2-trifluoroethyl)-1H-indol-4-amine |
| 385. | 2-{3-[(4-tert-butyl-2-methoxyphenyl)-amino]prop-1-yn-1-yl}-N-(1-methylpiperidin-4-yl)-1-(2,2,2-trifluoroethyl)-1H-indol-4-amine |
| 386. | 4-methoxy-3-[(3-{4-[(1-methylpiperidin-4-yl)amino]-1-(2,2,2-trifluoroethyl)-1H-indol-2-yl}prop-2-yn-1-yl)amino]-benzonitrile |
| 387. | 2-{3-[(5-tert-butyl-2-methoxyphenyl)-amino]prop-1-yn-1-yl}-N-(1-methylpiperidin-4-yl)-1-(2,2,2-trifluoroethyl)-1H-indol-4-amine |
| 388. | N-(1-methylpiperidin-4-yl)-2-[3-(phenylamino)prop-1-yn-1-yl]-1-(2,2,2-trifluoroethyl)-1H-indol-4-amine |
| 389. | 5-methanesulfonyl-2-[(3-{4-[(1-methylpiperidin-4-yl)amino]-1-(2,2,2-trifluoroethyl)-1H-indol-2-yl}prop-2-yn-1-yl)amino]benzonitrile |

TABLE 1-continued

Alkynyl indole compounds of the disclosure.

| Mol # | IUPAC name |
|---|---|
| 390. | 2-(3-{[2-(2-fluoroethoxy)-4-methanesulfonylphenyl]amino}prop-1-yn-1-yl)-N-(1-methylpiperidin-4-yl)-1-(2,2,2-trifluoroethyl)-1H-indol-4-amine |
| 391. | 2-{3-[(3-methoxypyridin-4-yl)amino]prop-1-yn-1-yl}-N-(1-methylpiperidin-4-yl)-1-(2,2,2-trifluoroethyl)-1H-indol-4-amine |
| 392. | 2-{3-[(2-chloro-4-methanesulfonyl-phenyl)amino]prop-1-yn-1-yl}-N-(1-methylpiperidin-4-yl)-1-(2,2,2-trifluoroethyl)-1H-indol-4-amine |
| 393. | 2-{3-[(4-methoxyphenyl)amino]prop-1-yn-1-yl}-N-(1-methylpiperidin-4-yl)-1-(2,2,2-trifluoroethyl)-1H-indol-4-amine |
| 394. | 2-(3-{[4-methanesulfonyl-2-(2-methoxyethoxy)phenyl]amino}prop-1-yn-1-yl)-N-(1-methylpiperidin-4-yl)-1-(2,2,2-trifluoroethyl)-1H-indol-4-amine |
| 395. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridine-2-carbonitrile |
| 396. | 4-{[2-(3-{[6-(morpholine-4-carbonyl)pyridin-3-yl]amino}prop-1-yn-1-yl)-1-(2,2,2-trifluoroethyl)-1H-indol-4-yl]amino}-1$\lambda^6$-thiane-1,1-dione |
| 397. | 4-{[2-(3-{[6-(4-methylpiperazine-1-carbonyl)pyridin-3-yl]amino}prop-1-yn-1-yl)-1-(2,2,2-trifluoroethyl)-1H-indol-4-yl]amino}-1$\lambda^6$-thiane-1,1-dione |
| 398. | 4-[(2-{3-[(quinolin-3-yl)amino]prop-1-yn-1-yl}-1-(2,2,2-trifluoroethyl)-1H-indol-4-yl)amino]-1$\lambda^6$-thiane-1,1-dione |
| 399. | 4-[(2-{3-[(quinoxalin-6-yl)amino]prop-1-yn-1-yl}-1-(2,2,2-trifluoroethyl)-1H-indol-4-yl)amino]-1$\lambda^6$-thiane-1,1-dione |
| 400. | 4-[(2-{3-[(4-methanesulfonylphenyl)-amino]prop-1-yn-1-yl}-1-(2,2,2-trifluoroethyl)-1H-indol-4-yl)amino]-1$\lambda^6$-thiane-1,1-dione |
| 401. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridine-2-carboxamide |
| 402. | 4-[(2-{3-[(6-methoxypyridin-3-yl)amino]prop-1-yn-1-yl}-1-(2,2,2-trifluoroethyl)-1H-indol-4-yl)amino]-1$\lambda^6$-thiane-1,1-dione |
| 403. | 4-{[2-(3-{[6-(4-hydroxypiperidine-1-carbonyl)pyridin-3-yl]amino}prop-1-yn-1-yl)-1-(2,2,2-trifluoroethyl)-1H-indol-4-yl]amino}-1$\lambda^6$-thiane-1,1-dione |
| 404. | 4-[(2-{3-[(1-methyl-2-oxo-1,2-dihydropyridin-4-yl)amino]prop-1-yn-1-yl}-1-(2,2,2-trifluoroethyl)-1H-indol-4-yl)amino]-1$\lambda^6$-thiane-1,1-dione |
| 405. | 4-[(2-{3-[(2-methoxypyridin-4-yl)amino]prop-1-yn-1-yl}-1-(2,2,2-trifluoroethyl)-1H-indol-4-yl)amino]-1$\lambda^6$-thiane-1,1-dione |
| 406. | 2-{4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-fluorophenyl}-2-methylpropanenitrile |
| 407. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(1-methylpiperidin-4-yl)pyridine-2-carboxamide |
| 408. | 4-[(2-{3-[(2-fluoro-4-methanesulfonyl-phenyl)amino]prop-1-yn-1-yl}-1-(2,2,2-trifluoroethyl)-1H-indol-4-yl)amino]-1$\lambda^6$-thiane-1,1-dione |
| 409. | 4-{[2-(3-{[4-(ethanesulfonyl)-phenyl]amino}prop-1-yn-1-yl)-1-(2,2,2-trifluoroethyl)-1H-indol-4-yl]amino}-1$\lambda^6$-thiane-1,1-dione |
| 410. | 4-[(2-{3-[(2-tert-butylpyrimidin-5-yl)amino]prop-1-yn-1-yl}-1-(2,2,2-trifluoroethyl)-1H-indol-4-yl)amino]-1$\lambda^6$-thiane-1,1-dione |
| 411. | 3-{4-[(1,1-dioxo-1$\lambda^6$-thian-4-yl)amino]-1-(2,2,2-trifluoroethyl)-1H-indol-2-yl}-N-(4-methanesulfonyl-phenyl)-prop-2-ynamide |
| 412. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(oxan-4-yl)pyridine-2-carboxamide |
| 413. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(pyridin-3-yl)pyridine-2-carboxamide |
| 414. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-methylpyridine-2-carboxamide |
| 415. | 4-[(2-{3-[(3-chloro-4-methanesulfonylphenyl)amino]prop-1-yn-1-yl}-1-(2,2,2-trifluoroethyl)-1H-indol-4-yl)amino]-1$\lambda^6$-thiane-1,1-dione |
| 416. | N-(2,3-dihydroxypropyl)-5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridine-2-carboxamide |
| 417. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-hydroxypyridine-2-carboxamide |
| 418. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(2-hydroxyethyl)pyridine-2-carboxamide |
| 419. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-hydroxy-N-methylpyridine-2-carboxamide |
| 420. | 4-amino-N-(3-{4-[(1,1-dioxo-1$\lambda^6$-thian-4-yl)amino]-1-(2,2,2-trifluoroethyl)-1H-indol-2-yl}prop-2-yn-1-yl)benzene-1-sulfonamide |
| 421. | 4-({2-[3-({pyrido[2,3-b]pyrazin-7-yl}amino)prop-1-yn-1-yl]-1-(2,2,2-trifluoroethyl)-1H-indol-4-yl}amino)-1$\lambda^6$-thiane-1,1-dione |
| 422. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-benzamide |
| 423. | 4-{[2-(3-{[2-(methylsulfanyl)pyrimidin-5-yl]amino}prop-1-yn-1-yl)-1-(2,2,2-trifluoroethyl)-1H-indol-4-yl]amino}-1$\lambda^6$-thiane-1,1-dione |
| 424. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]benzene-1-sulfonamide |
| 425. | 4-{[2-(3-{[4-(2-methylpropane-2-sulfonyl)phenyl]amino}prop-1-yn-1-yl)-1-(2,2,2-trifluoroethyl)-1H-indol-4-yl]amino}-1$\lambda^6$-thiane-1,1-dione |
| 426. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-N,N-dimethylbenzene-1-sulfonamide |
| 427. | 4-{[1-(2,2,2-trifluoroethyl)-2-[2-(trimethylsilyl)ethynyl]-1H-indol-4-yl]amino}-1$\lambda^6$-thiane-1,1-dione |

TABLE 1-continued

Alkynyl indole compounds of the disclosure.

| Mol # | IUPAC name |
|---|---|
| 428. | 4-[(2-{3-[(5-methanesulfonylpyridin-2-yl)amino]prop-1-yn-1-yl}-1-(2,2,2-trifluoroethyl)-1H-indol-4-yl)amino]-1$\lambda^6$-thiane-1,1-dione |
| 429. | 4-[(2-{3-[(4-methanesulfonyl-2-methoxyphenyl)amino]prop-1-yn-1-yl}-1-(2,2,2-trifluoroethyl)-1H-indol-4-yl)amino]-1$\lambda^6$-thiane-1,1-dione |
| 430. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-methylbenzene-1-sulfonamide |
| 431. | 4-{[2-ethynyl-1-(2,2,2-trifluoroethyl)-1H-indol-4-yl]amino}-1$\lambda^6$-thiane-1,1-dione |
| 432. | N-{4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxyphenyl}methanesulfonamide |
| 433. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzoic acid |
| 434. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzonitrile |
| 435. | 4-[(2-{3-[(5-fluoro-2-methoxyphenyl)amino]prop-1-yn-1-yl}-1-(2,2,2-trifluoroethyl)-1H-indol-4-yl)amino]-1$\lambda^6$-thiane-1,1-dione |
| 436. | 4-[(2-{3-[(2-methoxy-6-methylpyridin-3-yl)amino]prop-1-yn-1-yl}-1-(2,2,2-trifluoroethyl)-1H-indol-4-yl)amino]-1$\lambda^6$-thiane-1,1-dione |
| 437. | 4-[(2-{3-[(2-hydroxy-6-methylpyridin-3-yl)amino]prop-1-yn-1-yl}-1-(2,2,2-trifluoroethyl)-1H-indol-4-yl)amino]-1$\lambda^6$-thiane-1,1-dione |
| 438. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzamide |
| 439. | 4-[(2-{3-[(2-methoxypyridin-3-yl)amino]prop-1-yn-1-yl}-1-(2,2,2-trifluoroethyl)-1H-indol-4-yl)amino]-1$\lambda^6$-thiane-1,1-dione |
| 440. | 4-[(2-{3-[(4-fluoro-2-methoxyphenyl)amino]prop-1-yn-1-yl}-1-(2,2,2-trifluoroethyl)-1H-indol-4-yl)amino]-1$\lambda^6$-thiane-1,1-dione |
| 441. | 4-[(2-{3-[(5-tert-butyl-2-methoxyphenyl)amino]prop-1-yn-1-yl}-1-(2,2,2-trifluoroethyl)-1H-indol-4-yl)amino]-1$\lambda^6$-thiane-1,1-dione |
| 442. | 4-[(2-{3-[(2-ethoxy-4-methanesulfonylphenyl)amino]prop-1-yn-1-yl}-1-(2,2,2-trifluoroethyl)-1H-indol-4-yl)amino]-1$\lambda^6$-thiane-1,1-dione |
| 443. | 4-[(2-{3-[(3-fluoro-2-methoxyphenyl)-amino]prop-1-yn-1-yl}-1-(2,2,2-trifluoroethyl)-1H-indol-4-yl)amino]-1$\lambda^6$-thiane-1,1-dione |
| 444. | 4-({2-[3-(methylamino)prop-1-yn-1-yl]-1-(2,2,2-trifluoroethyl)-1H-indol-4-yl}amino)-1$\lambda^6$-thiane-1,1-dione |
| 445. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzene-1-sulfonamide |
| 446. | 4-[(2-{3-[(2-fluoro-6-methoxyphenyl)-amino]prop-1-yn-1-yl}-1-(2,2,2-trifluoroethyl)-1H-indol-4-yl)amino]-1$\lambda^6$-thiane-1,1-dione |
| 447. | 3-[(3-{4-[(1,1-dioxo-1$\lambda^6$-thian-4-yl)amino]-1-(2,2,2-trifluoroethyl)-1H-indol-2-yl}prop-2-yn-1-yl)amino]-4-methoxybenzonitrile |
| 448. | 4-[(2-{3-[(4-tert-butyl-2-methoxy-phenyl)amino]prop-1-yn-1-yl}-1-(2,2,2-trifluoroethyl)-1H-indol-4-yl)amino]-1$\lambda^6$-thiane-1,1-dione |
| 449. | 4-({2-[3-(phenylamino)prop-1-yn-1-yl]-1-(2,2,2-trifluoroethyl)-1H-indol-4-yl}amino)-1$\lambda^6$-thiane-1,1-dione |
| 450. | 4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}-1$\lambda^6$-thiane-1,1-dione |
| 451. | 2-[(3-{4-[(1,1-dioxo-1$\lambda^6$-thian-4-yl)amino]-1-(2,2,2-trifluoroethyl)-1H-indol-2-yl}prop-2-yn-1-yl)amino]-5-methanesulfonylbenzonitrile |
| 452. | 4-[(2-{3-[(2-chloro-4-methanesulfonyl-phenyl)amino]prop-1-yn-1-yl}-1-(2,2,2-trifluoroethyl)-1H-indol-4-yl)amino]-1$\lambda^6$-thiane-1,1-dione |
| 453. | 4-[(2-{3-[(4-methoxyphenyl)amino]prop-1-yn-1-yl}-1-(2,2,2-trifluoroethyl)-1H-indol-4-yl)amino]-1$\lambda^6$-thiane-1,1-dione |
| 454. | 4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}-1$\lambda^6$-thiane-1,1-dione |
| 455. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-N,N-dimethylacetamide |
| 456. | 2-methyl-2-(5-{[3-(4-{[(1R,4R)-4-(dimethylamino)cyclohexyl]amino}-1-(2,2,2-trifluoroethyl)-1H-indol-2-yl)prop-2-yn-1-yl]amino}pyridin-2-yl)propanenitrile |
| 457. | 2-(5-((3-(4-(((1S,4S)-4-(dimethylamino)-cyclohexyl)amino)-1-(2,2,2-trifluoroethyl)-1H-indol-2-yl)prop-2-yn-1-yl)amino)pyridin-2-yl)-2-methylpropanenitrile |
| 458. | N-[1-(2-methanesulfonylethyl)piperidin-4-yl]-2-{3-[(4-methanesulfonylphenyl)-amino]prop-1-yn-1-yl}-1-(2,2,2-trifluoroethyl)-1H-indol-4-amine |
| 459. | 5-({3-[4-({1-[(dimethylcarbamoyl)methyl]piperidin-4-yl}amino)-1-(2,2,2-trifluoroethyl)-1H-indol-2-yl]prop-2-yn-1-yl}amino)pyridine-2-carboxamide |
| 460. | 5-{[3-(4-{[1-(2-methanesulfonylethyl)piperidin-4-yl]amino}-1-(2,2,2-trifluoroethyl)-1H-indol-2-yl)prop-2-yn-1-yl]amino}pyridine-2-carboxamide |
| 461. | 5-[(3-{4-[(piperidin-4-yl)amino]-1-(2,2,2-trifluoroethyl)-1H-indol-2-yl}prop-2-yn-1-yl)amino]pyridine-2-carboxamide |
| 462. | 5-{[3-(4-{[1-(carbamoylmethyl)piperidin-4-yl]amino}-1-(2,2,2-trifluoroethyl)-1H-indol-2-yl)prop-2-yn-1-yl]amino}pyridine-2-carboxamide |
| 463. | 5-{[3-(4-{[1-(2-hydroxyethyl)piperidin-4-yl]amino}-1-(2,2,2-trifluoroethyl)-1H-indol-2-yl)prop-2-yn-1-yl]amino}pyridine-2-carboxamide |
| 464. | 5-{[3-(4-{[1-(oxan-4-yl)piperidin-4-yl]amino}-1-(2,2,2-trifluoroethyl)-1H-indol-2-yl)prop-2-yn-1-yl]amino}pyridine-2-carboxamide |

TABLE 1-continued

Alkynyl indole compounds of the disclosure.

| Mol # | IUPAC name |
|---|---|
| 465. | 5-{[3-(4-{[(1R,4R)-4-(dimethylamino)-cyclohexyl]amino}-1-(2,2,2-trifluoroethyl)-1H-indol-2-yl)prop-2-yn-1-yl]amino}pyridine-2-carboxamide |
| 466. | 4-{[3-(4-{[1-(2-methanesulfonyl-ethyl)piperidin-4-yl]amino}-1-(2,2,2-trifluoroethyl)-1H-indol-2-yl)prop-2-yn-1-yl]amino}benzene-1-sulfonamide |
| 467. | 4-{[3-(4-{[1-(2-methoxyethyl)piperidin-4-yl]amino}-1-(2,2,2-trifluoroethyl)-1H-indol-2-yl)prop-2-yn-1-yl]amino}benzene-1-sulfonamide |
| 468. | 5-{[3-(4-{[(1S,4S)-4-(dimethylamino)-cyclohexyl]amino}-1-(2,2,2-trifluoroethyl)-1H-indol-2-yl)prop-2-yn-1-yl]amino}pyridine-2-carboxamide |
| 469. | N,N-dimethyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 470. | 4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 471. | 2-{4-[(2-{3-[(4-sulfamoylphenyl)-amino]prop-1-yn-1-yl}-1-(2,2,2-trifluoroethyl)-1H-indol-4-yl)amino]-piperidin-1-yl}acetamide |
| 472. | 4-{[3-(4-{[1-(2-methoxyethyl)piperidin-4-yl]amino}-1-(2,2,2-trifluoroethyl)-1H-indol-2-yl)prop-2-yn-1-yl]amino}-N,N-dimethylbenzene-1-sulfonamide |
| 473. | 4-[(3-{4-[(oxan-4-yl)amino]-1-(2,2,2-trifluoroethyl)-1H-indol-2-yl}prop-2-yn-1-yl)amino]benzene-1-sulfonamide |
| 474. | 4-{[3-(4-{[1-(2-hydroxypropyl)piperidin-4-yl]amino}-1-(2,2,2-trifluoroethyl)-1H-indol-2-yl)prop-2-yn-1-yl]amino}benzene-1-sulfonamide |
| 475. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}benzene-1-sulfonamide |
| 476. | 4-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 477. | methyl 2-{4-[(2-{3-[(4-sulfamoylphenyl)-amino]prop-1-yn-1-yl}-1-(2,2,2-trifluoro-ethyl)-1H-indol-4-yl)amino]piperidin-1-yl}acetate |
| 478. | 4-{[3-(4-{[1-(2-hydroxyethyl)piperidin-4-yl]amino}-1-(2,2,2-trifluoroethyl)-1H-indol-2-yl)prop-2-yn-1-yl]amino}benzene-1-sulfonamide |
| 479. | 4-({3-[4-({1-[2-(2-hydroxyethoxy)ethyl]piperidin-4-yl}amino)-1-(2,2,2-trifluoroethyl)-1H-indol-2-yl]prop-2-yn-1-yl}amino)benzene-1-sulfonamide |
| 480. | N,N-dimethyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide |
| 481. | 4-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 482. | 2-{4-[(2-{3-[(4-sulfamoylphenyl)amino]prop-1-yn-1-yl}-1-(2,2,2-trifluoroethyl)-1H-indol-4-yl)amino]piperidin-1-yl}acetic acid |
| 483. | 4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 484. | N-methyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide |
| 485. | N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 486. | 4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide |
| 487. | N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 488. | 2-(dimethylamino)ethyl 2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetate |
| 489. | 2-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 490. | 2-chloro-4-[(3-{4-[(oxan-4-yl)amino]-1-(2,2,2-trifluoroethyl)-1H-indol-2-yl}prop-2-yn-1-yl)amino]benzene-1-sulfonamide |
| 491. | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 492. | 4-{[3-(4-{[1-(2,3-dihydroxypropyl)-piperidin-4-yl]amino}-1-(2,2,2-trifluoro-ethyl)-1H-indol-2-yl)prop-2-yn-1-yl]amino}-3-methoxybenzene-1-sulfonamide |
| 493. | 3-methoxy-4-[(3-{4-[(piperidin-4-yl)amino]-1-(2,2,2-trifluoroethyl)-1H-indol-2-yl}prop-2-yn-1-yl)amino]benzene-1-sulfonamide |
| 494. | 3-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 495. | 3-methoxy-4-[(3-{4-[(oxan-4-yl)amino]-1-(2,2,2-trifluoroethyl)-1H-indol-2-yl}prop-2-yn-1-yl)amino]benzamide |
| 496. | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzamide |
| 497. | 4-{[3-(4-{[1-(2,3-dihydroxypropyl)-piperidin-4-yl]amino}-1-(2,2,2-trifluoroethyl)-1H-indol-2-yl)prop-2-yn-1-yl]amino}-3-methoxybenzamide |
| 498. | 2-[5-({3-[1-(cyanomethyl)-4-[(1-methylpiperidin-4-yl)amino]-1H-indol-2-yl]prop-2-yn-1-yl}amino)pyridin-2-yl]-2-methylpropanenitrile |
| 499. | 2-[5-({3-[1-(3-methoxypropyl)-4-[(1-methylpiperidin-4-yl)amino]-1H-indol-2-yl]prop-2-yn-1-yl}amino)pyridin-2-yl]-2-methylpropanenitrile |
| 500. | 2-[5-({3-[1-(2-chloroethyl)-4-[(1-methylpiperidin-4-yl)amino]-1H-indol-2-yl]prop-2-yn-1-yl}amino)pyridin-2-yl]-2-methylpropanenitrile |
| 501. | 2-methyl-2-{5-[(3-{4-[(1-methylpiperidin-4-yl)amino]-1-(propan-2-yl)-1H-indol-2-yl}prop-2-yn-1-yl)amino]pyridin-2-yl}propanenitrile |
| 502. | 2-{5-[(3-{1-cyclopentyl-4-[(1-methylpiperidin-4-yl)amino]-1H-indol-2-yl}prop-2-yn-1-yl)amino]pyridin-2-yl}-2-methylpropanenitrile |

TABLE 1-continued

Alkynyl indole compounds of the disclosure.

| Mol # | IUPAC name |
|---|---|
| 503. | 2-methyl-2-{5-[(3-{4-[(1-methylpiperidin-4-yl)amino]-1-(3,3,3-trifluoropropyl)-1H-indol-2-yl}prop-2-yn-1-yl)amino]pyridin-2-yl}propanenitrile |
| 504. | 1-(2-chloroethyl)-N-(1-methylpiperidin-4-yl)-2-{3-[(6-methylpyridin-3-yl)amino]-prop-1-yn-1-yl}-1H-indol-4-amine |
| 505. | 1-(2-chloroethyl)-N-(1-methylpiperidin-4-yl)-2-{3-[(6-methylpyridin-3-yl)amino]-prop-1-yn-1-yl}-1H-indol-4-amine |
| 506. | 1-(2-chloroethyl)-2-{3-[(4-chlorophenyl)-amino]prop-1-yn-1-yl}-N-(1-methylpiperidin-4-yl)-1H-indol-4-amine |
| 507. | 2-[5-({3-[1-(1-cyanoethyl)-4-[(1-methylpiperidin-4-yl)amino]-1H-indol-2-yl]prop-2-yn-1-yl}amino)pyridin-2-yl]-2-methylpropanenitrile |
| 508. | 2-[5-({3-[1-(cyanomethyl)-4-[(1,1-dioxo-1λ$^6$-thian-4-yl)amino]-1H-indol-2-yl]prop-2-yn-1-yl}amino)pyridin-2-yl]-2-methylpropanenitrile |
| 509. | 4-[(2-{3-[(4-methanesulfonylphenyl)amino]prop-1-yn-1-yl}-1-(oxiran-2-ylmethyl)-1H-indol-4-yl)amino]-1λ$^6$-thiane-1,1-dione |
| 510. | 2-{3-[(4-methanesulfonylphenyl)-amino]prop-1-yn-1-yl}-N-[1-(oxan-4-yl)piperidin-4-yl]-1-(oxiran-2-ylmethyl)-1H-indol-4-amine |
| 511. | 4-[(2-{3-[(4-methanesulfonyl-2-methoxyphenyl)amino]prop-1-yn-1-yl}-1-(oxiran-2-ylmethyl)-1H-indol-4-yl)amino]-1λ$^6$-thiane-1,1-dione |
| 512. | 2-{3-[(4-methanesulfonyl-2-methoxy-phenyl)amino]prop-1-yn-1-yl}-N-[1-(oxan-4-yl)piperidin-4-yl]-1-(oxiran-2-ylmethyl)-1H-indol-4-amine |
| 513. | 1-[6-(1-cyano-1-methylethyl)pyridin-3-yl]-3-(3-{4-[(1-methylpiperidin-4-yl)amino]-1-(2,2,2-trifluoroethyl)-1H-indol-2-yl}prop-2-yn-1-yl)urea |
| 514. | 1-(6-methanesulfonylpyridin-3-yl)-3-(3-{4-[(1-methylpiperidin-4-yl)amino]-1-(2,2,2-trifluoroethyl)-1H-indol-2-yl}prop-2-yn-1-yl)urea |
| 515. | 1-[6-(1-cyano-1-methylethyl)pyridin-3-yl]-3-(3-{4-[(1,1-dioxo-1λ$^6$-thian-4-yl)amino]-1-(2,2,2-trifluoroethyl)-1H-indol-2-yl}prop-2-yn-1-yl)urea |
| 516. | 3-(3-{4-[(1,1-dioxo-1λ$^6$-thian-4-yl)amino]-1-(2,2,2-trifluoroethyl)-1H-indol-2-yl}prop-2-yn-1-yl)-1-(6-methanesulfonylpyridin-3-yl)urea |
| 517. | 1-(6-cyanopyridin-3-yl)-3-(3-{4-[(1-methylpiperidin-4-yl)amino]-1-(2,2,2-trifluoroethyl)-1H-indol-2-yl}prop-2-yn-1-yl)urea |
| 518. | 1-(6-cyanopyridin-3-yl)-3-(3-{4-[(1,1-dioxo-1λ$^6$-thian-4-yl)amino]-1-(2,2,2-trifluoroethyl)-1H-indol-2-yl}prop-2-yn-1-yl)urea |
| 519. | 3-(3-{4-[(1,1-dioxo-1λ$^6$-thian-4-yl)amino]-1-(2,2,2-trifluoroethyl)-1H-indol-2-yl}prop-2-yn-1-yl)-1-(quinoxalin-6-yl)urea |
| 520. | N-(3-{4-[(1,1-dioxo-1λ$^6$-thian-4-yl)amino]-1-(2,2,2-trifluoroethyl)-1H-indol-2-yl}prop-2-yn-1-yl)-4-methylpiperazine-1-carboxamide |
| 521. | N-(3-{4-[(1,1-dioxo-1λ$^6$-thian-4-yl)amino]-1-(2,2,2-trifluoroethyl)-1H-indol-2-yl}prop-2-yn-1-yl)morpholine-4-carboxamide |
| 522. | 4-[(2-{3-[(6-methanesulfonylpyridin-3-yl)amino]prop-1-yn-1-yl}-1-(2,2,2-trifluoroethyl)-1H-indol-4-yl)amino]-1λ$^6$-thiane-1,1-dione |
| 523. | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-N,N-dimethylacetamide |
| 524. | N-(1-ethylpiperidin-4-yl)-2-{3-[(6-methanesulfonylpyridin-3-yl)amino]prop-1-yn-1-yl}-1-(2,2,2-trifluoroethyl)-1H-indol-4-amine |
| 525. | N-[1-(2-methanesulfonylethyl)piperidin-4-yl]-2-{3-[(6-methanesulfonylpyridin-3-yl)amino]prop-1-yn-1-yl}-1-(2,2,2-trifluoroethyl)-1H-indol-4-amine |
| 526. | 2-{3-[(6-methanesulfonylpyridin-3-yl)amino]prop-1-yn-1-yl}-N-[1-(1-methylpiperidin-4-yl)piperidin-4-yl]-1-(2,2,2-trifluoroethyl)-1H-indol-4-amine |
| 527. | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}ethan-1-ol |
| 528. | 4-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-1λ$^6$-thiane-1,1-dione |
| 529. | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 530. | 2-{3-[(4-methanesulfonylphenyl)amino]prop-1-yn-1-yl}-N-(oxan-4-yl)-1-(2,2,2-trifluoroethyl)-1H-indol-4-amine |
| 531. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}ethan-1-ol |
| 532. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 533. | 2-{3-[(4-methanesulfonylphenyl)amino]prop-1-yn-1-yl}-N-[1-(1-methylpiperidin-4-yl)piperidin-4-yl]-1-(2,2,2-trifluoroethyl)-1H-indol-4-amine |
| 534. | N-(2,3-dihydroxypropyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}-N-methylacetamide |
| 535. | 4-N-(2-{3-[(4-methanesulfonylphenyl)-amino]prop-1-yn-1-yl}-1-(2,2,2-trifluoroethyl)-1H-indol-4-yl)-1-N,1-N-dimethylcyclohexane-1,4-diamine |
| 536. | (1S,4S)-4-N-(2-{3-[(4-methanesulfonyl-phenyl)amino]prop-1-yn-1-yl}-1-(2,2,2-trifluoroethyl)-1H-indol-4-yl)-1-N,1-N-dimethylcyclohexane-1,4-diamine |
| 537. | 2-{3-[(4-methanesulfonylphenyl)-amino]prop-1-yn-1-yl}-N-[1-(oxan-4-yl)piperidin-4-yl]-1-(2,2,2-trifluoroethyl)-1H-indol-4-amine |
| 538. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(morpholin-4-yl)ethan-1-one |
| 539. | 1-(4-hydroxypiperidin-1-yl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}ethan-1-one |
| 540. | 2-{3-[(4-methanesulfonylphenyl)-amino]prop-1-yn-1-yl}-N-(piperidin-4-yl)-1-(2,2,2-trifluoroethyl)-1H-indol-4-amine |

TABLE 1-continued

Alkynyl indole compounds of the disclosure.

| Mol # | IUPAC name |
|---|---|
| 541. | N-{1-[1-(2-methanesulfonylethyl)piperidin-4-yl]piperidin-4-yl}-2-{3-[(4-methanesulfonylphenyl)amino]prop-1-yn-1-yl}-1-(2,2,2-trifluoroethyl)-1H-indol-4-amine |
| 542. | 2-{3-[(4-methanesulfonylphenyl)-amino]prop-1-yn-1-yl}-N-[1-(2-methoxyethyl)piperidin-4-yl]-1-(2,2,2-trifluoroethyl)-1H-indol-4-amine |
| 543. | 3-{4-[(2-{3-[(4-methane-sulfonylphenyl)-amino]prop-1-yn-1-yl}-1-(2,2,2-trifluoroethyl)-1H-indol-4-yl)amino]piperidin-1-yl}propanenitrile |
| 544. | 2-{3-[(4-methanesulfonylphenyl)-amino]prop-1-yn-1-yl}-N-(1-methylpiperidin-4-yl)-1-(2,2,2-trifluoroethyl)-1H-indol-4-amine |
| 545. | 2-{4-[(2-{3-[(4-methane-sulfonylphenyl)-amino]prop-1-yn-1-yl}-1-(2,2,2-trifluoroethyl)-1H-indol-4-yl)amino]piperidin-1-yl}acetamide |
| 546. | 4-{4-[(2-{3-[(4-methane-sulfonylphenyl)-amino]prop-1-yn-1-yl}-1-(2,2,2-trifluoroethyl)-1H-indol-4-yl)amino]piperidin-1-yl]-1$\lambda^6$-thiane-1,1-dione |
| 547. | 2-{4-[(2-{3-[(4-methane-sulfonylphenyl)amino]prop-1-yn-1-yl}-1-(2,2,2-trifluoroethyl)-1H-indol-4-yl)amino]piperidin-1-yl}-N-methylacetamide |
| 548. | 2-(3-{[4-(ethanesulfonyl)phenyl]amino}prop-1-yn-1-yl)-N-(1-methylpiperidin-4-yl)-1-(2,2,2-trifluoroethyl)-1H-indol-4-amine |
| 549. | 2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}ethan-1-ol |
| 550. | 2-{3-[(2-fluoro-4-methane-sulfonylphenyl)-amino]prop-1-yn-1-yl}-N-[1-(2-methanesulfonylethyl)-piperidin-4-yl]-1-(2,2,2-trifluoroethyl)-1H-indol-4-amine |
| 551. | 2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}acetamide |
| 552. | 2-{3-[(2-fluoro-4-methane-sulfonylphenyl)-amino]prop-1-yn-1-yl}-N-(1-methylpiperidin-4-yl)-1-(2,2,2-trifluoroethyl)-1H-indol-4-amine |
| 553. | 1-{4-[(2-{3-[(4-methanesulfonyl-phenyl)amino]prop-1-yn-1-yl}-1-(2,2,2-trifluoroethyl)-1H-indol-4-yl)amino]piperidin-1-yl}-2-methoxyethan-1-one |
| 554. | 2-{3-[(4-methanesulfonyl-phenyl)amino]prop-1-yn-1-yl}-N-(1-methylpyrrolidin-3-yl)-1-(2,2,2-trifluoroethyl)-1H-indol-4-amine |
| 555. | N-hydroxy-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide |
| 556. | 3-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propane-1,2-diol |
| 557. | 2-{3-[(2-fluoro-4-methanesulfonyl-phenyl)amino]prop-1-yn-1-yl}-N-[1-(1-methylpiperidin-4-yl)piperidin-4-yl]-1-(2,2,2-trifluoroethyl)-1H-indol-4-amine |
| 558. | 2-(3-{[4-(ethanesulfonyl)phenyl]amino}prop-1-yn-1-yl)-N-[1-(1-methylpiperidin-4-yl)piperidin-4-yl]-1-(2,2,2-trifluoroethyl)-1H-indol-4-amine |
| 559. | 2-{3-[(2-fluoro-4-methanesulfonyl-phenyl)amino]prop-1-yn-1-yl}-N-(oxan-4-yl)-1-(2,2,2-trifluoroethyl)-1H-indol-4-amine |
| 560. | 2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethan-1-ol |
| 561. | 1-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propan-2-ol |
| 562. | 2-(3-{[4-(ethanesulfonyl)-phenyl]amino}prop-1-yn-1-yl)-N-[1-(2-methanesulfonylethyl)piperidin-4-yl]-1-(2,2,2-trifluoroethyl)-1H-indol-4-amine |
| 563. | 4-{[1-(2,2,2-trifluoroethyl)-2-{3-[(4-trifluoromethanesulfonylphenyl)amino]prop-1-yn-1-yl}-1H-indol-4-yl]amino}-1$\lambda^6$-thiane-1,1-dione |
| 564. | 2-(4-{[1-(2,2,2-trifluoroethyl)-2-{3-[(4-trifluoromethanesulfonylphenyl)amino]prop-1-yn-1-yl}-1H-indol-4-yl]amino}piperidin-1-yl)ethan-1-ol |
| 565. | N-(1-methylpiperidin-4-yl)-1-(2,2,2-trifluoroethyl)-2-{3-[(4-trifluoromethanesulfonylphenyl)amino]prop-1-yn-1-yl}-1H-indol-4-amine |
| 566. | 2-{3-[(4-methanesulfonyl-phenyl)amino]prop-1-yn-1-yl}-N-[1-(1-methylpyrrolidin-3-yl)piperidin-4-yl]-1-(2,2,2-trifluoroethyl)-1H-indol-4-amine |
| 567. | 2-{3-[(4-methanesulfonyl-phenyl)amino]prop-1-yn-1-yl}-N-[1-(3-methanesulfonylpropyl)piperidin-4-yl]-1-(2,2,2-trifluoroethyl)-1H-indol-4-amine |
| 568. | 2-(3-{[4-(ethanesulfonyl)-phenyl]amino}prop-1-yn-1-yl)-N-[1-(2-methoxyethyl)piperidin-4-yl]-1-(2,2,2-trifluoroethyl)-1H-indol-4-amine |
| 569. | 4-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)-1$\lambda^6$-thiane-1,1-dione |
| 570. | 2-(3-{[4-(ethanesulfonyl)-phenyl]amino}prop-1-yn-1-yl)-N-[1-(oxan-4-yl)piperidin-4-yl]-1-(2,2,2-trifluoroethyl)-1H-indol-4-amine |
| 571. | N-[1-(2-methanesulfonylethyl)-piperidin-4-yl]-1-(2,2,2-trifluoroethyl)-2-{3-[(4-trifluoromethane-sulfonylphenyl)amino]prop-1-yn-1-yl}-1H-indol-4-amine |
| 572. | N-[1-(oxan-4-yl)piperidin-4-yl]-1-(2,2,2-trifluoroethyl)-2-{3-[(4-trifluoromethanesulfonylphenyl)amino]prop-1-yn-1-yl}-1H-indol-4-amine |
| 573. | N-[1-(1-methylpiperidin-4-yl)piperidin-4-yl]-1-(2,2,2-trifluoroethyl)-2-{3-[(4-trifluoromethanesulfonylphenyl)amino]prop-1-yn-1-yl}-1H-indol-4-amine |
| 574. | 2-{3-[(2-fluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine |
| 575. | 2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetonitrile |
| 576. | 2-{3-[(2-fluoro-4-methanesulfonylphenyl)amino]prop-1-yn-1-yl}-N-[1-(2-methoxyethyl)piperidin-4-yl]-1-(2,2,2-trifluoroethyl)-1H-indol-4-amine |
| 577. | 2-{3-[(3-chloro-4-methanesulfonylphenyl)amino]prop-1-yn-1-yl}-N-[1-(oxan-4-yl)piperidin-4-yl]-1-(2,2,2-trifluoroethyl)-1H-indol-4-amine |
| 578. | 2-{3-[(2,6-difluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine |

TABLE 1-continued

Alkynyl indole compounds of the disclosure.

| Mol # | IUPAC name |
|---|---|
| 579. | 2-{3-[(3-chloro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine |
| 580. | 2-{4-[(2-{3-[(3-chloro-4-methanesulfonylphenyl)amino]prop-1-yn-1-yl}-1-(2,2,2-trifluoroethyl)-1H-indol-4-yl)amino]piperidin-1-yl}ethan-1-ol |
| 581. | (2S)-3-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propane-1,2-diol |
| 582. | N-(5-aminopentyl)-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide |
| 583. | 2-{3-[(2,6-difluoro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine |
| 584. | 2-(3-{[4-(ethanesulfonyl)phenyl]-amino}prop-1-yn-1-yl)-N-(oxan-4-yl)-1-(2,2,2-trifluoroethyl)-1H-indol-4-amine |
| 585. | 2-(4-{[2-(3-{[4-(ethanesulfonyl)phenyl]amino}prop-1-yn-1-yl)-1-(2,2,2-trifluoroethyl)-1H-indol-4-yl]amino}piperidin-1-yl)acetonitrile |
| 586. | 2-(3-{[4-(2-methylpropane-2-sulfonyl)phenyl]amino}prop-1-yn-1-yl)-N-[1-(oxan-4-yl)piperidin-4-yl]-1-(2,2,2-trifluoroethyl)-1H-indol-4-amine |
| 587. | 2-(2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}ethoxy)ethan-1-ol |
| 588. | 1-{4-[(2-{3-[(2-fluoro-4-methane-sulfonylphenyl)amino]prop-1-yn-1-yl}-1-(2,2,2-trifluoroethyl)-1H-indol-4-yl)amino]piperidin-1-yl}propan-2-ol |
| 589. | 3-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}propane-1,2-diol |
| 590. | (1S,4S)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine |
| 591. | 3-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propane-1,2-diol |
| 592. | 2-(3-{[4-(ethanesulfonyl)-phenyl]amino}prop-1-yn-1-yl)-N-[1-(3-methanesulfonylpropyl)-piperidin-4-yl]-1-(2,2,2-trifluoroethyl)-1H-indol-4-amine |
| 593. | 1-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propan-2-ol |
| 594. | 2-[2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethoxy]ethan-1-ol |
| 595. | (1R,4R)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethyl-cyclohexane-1,4-diamine |
| 596. | 2-{3-[(2,6-difluoro-4-methanesulfonylphenyl)amino]prop-1-yn-1-yl}-N-[1-(2-methanesulfonylethyl)piperidin-4-yl]-1-(2,2,2-trifluoroethyl)-1H-indol-4-amine |
| 597. | 4-{4-[(2-{3-[(2,6-difluoro-4-methanesulfonylphenyl)amino]prop-1-yn-1-yl}-1-(2,2,2-trifluoroethyl)-1H-indol-4-yl)amino]piperidin-1-yl}-1$\lambda^6$-thiane-1,1-dione |
| 598. | 2-{3-[(4-methanesulfonyl-3-methoxyphenyl)amino]prop-1-yn-1-yl}-N-[1-(oxan-4-yl)piperidin-4-yl]-1-(2,2,2-trifluoroethyl)-1H-indol-4-amine |
| 599. | 2-{3-[(4-methanesulfonyl-3-methoxyphenyl)amino]prop-1-yn-1-yl}-N-[1-(2-methoxyethyl)piperidin-4-yl]-1-(2,2,2-trifluoroethyl)-1H-indol-4-amine |
| 600. | 4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine |
| 601. | 2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetic acid |
| 602. | 2-hydroxyethyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate |
| 603. | 2-{3-[(4-methanesulfonylphenyl)-amino]prop-1-yn-1-yl}-N-(2-methylpiperidin-4-yl)-1-(2,2,2-trifluoroethyl)-1H-indol-4-amine |
| 604. | 2-{4-[(2-{3-[(4-methanesulfonyl-3-methoxyphenyl)amino]prop-1-yn-1-yl}-1-(2,2,2-trifluoroethyl)-1H-indol-4-yl)amino]piperidin-1-yl}ethan-1-ol |
| 605. | (2S)-2-(2-{4-[(2-{3-[(4-methane-sulfonylphenyl)amino]prop-1-yn-1-yl}-1-(2,2,2-trifluoroethyl)-1H-indol-4-yl)amino]piperidin-1-yl}acetamido)pentanedioic acid |
| 606. | 1,5-dimethyl (2S)-2-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentanedioate |
| 607. | N-(4-carbamimidamidobutyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetamide |
| 608. | 2-{3-[(4-methanesulfonyl-2-methoxyphenyl)amino]prop-1-yn-1-yl}-N-(oxan-4-yl)-1-(2,2,2-trifluoroethyl)-1H-indol-4-amine |
| 609. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-ol |
| 610. | 2-{3-[(5-methanesulfonylpyridin-2-yl)amino]prop-1-yn-1-yl}-N-(oxan-4-yl)-1-(2,2,2-trifluoroethyl)-1H-indol-4-amine |
| 611. | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |
| 612. | 4-[(2-{3-[(2,4-dimethoxyphenyl)-amino]prop-1-yn-1-yl}-1-(2,2,2-trifluoroethyl)-1H-indol-4-yl)amino]-1$\lambda^6$-thiane-1,1-dione |
| 613. | methyl 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzoate |
| 614. | 2-{3-[(4-methanesulfonyl-2-methoxyphenyl)amino]prop-1-yn-1-yl}-N-[1-(2-methanesulfonylethyl)-piperidin-4-yl]-1-(2,2,2-trifluoroethyl)-1H-indol-4-amine |
| 615. | 2-{3-[(4-methanesulfonyl-2-methoxyphenyl)amino]prop-1-yn-1-yl}-N-[1-(2-methoxyethyl)piperidin-4-yl]-1-(2,2,2-trifluoroethyl)-1H-indol-4-amine |
| 616. | (1S,4S)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine |

TABLE 1-continued

Alkynyl indole compounds of the disclosure.

| Mol # | IUPAC name |
|---|---|
| 617. | (1R,4R)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine |
| 618. | 2-{3-[(4-methanesulfonyl-2-methoxyphenyl)amino]prop-1-yn-1-yl}-N-[1-(oxan-4-yl)piperidin-4-yl]-1-(2,2,2-trifluoroethyl)-1H-indol-4-amine |
| 619. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-o |
| 620. | 2-{3-[(4-methanesulfonyl-2-methoxyphenyl)amino]prop-1-yn-1-yl}-N-[1-(1-methylpyrrolidin-3-yl)piperidin-4-yl]-1-(2,2,2-trifluoroethyl)-1H-indol-4-amine |
| 621. | 2-{3-[(4-methanesulfonyl-2-methoxyphenyl)amino]prop-1-yn-1-yl}-N-(2-methylpiperidin-4-yl)-1-(2,2,2-trifluoroethyl)-1H-indol-4-amine |
| 622. | 2-{3-[(4-methanesulfonyl-2-methoxyphenyl)amino]prop-1-yn-1-yl}-N-(piperidin-4-yl)-1-(2,2,2-trifluoroethyl)-1H-indol-4-amine |
| 623. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 624. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetamide |
| 625. | 2-{3-[(4-methanesulfonyl-2-methoxyphenyl)amino]prop-1-yn-1-yl}-N-[1-(1-methylpiperidin-4-yl)piperidin-4-yl]-1-(2,2,2-trifluoroethyl)-1H-indol-4-amine |
| 626. | 1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}piperidin-4-ol |
| 627. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(morpholin-4-yl)ethan-1-one |
| 628. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-N,N-dimethylacetamide |
| 629. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetonitrile |
| 630. | methyl 2-{4-[(2-{3-[(4-methane-sulfonyl-2-methoxyphenyl)amino]prop-1-yn-1-yl}-1-(2,2,2-trifluoroethyl)-1H-indol-4-yl)amino]piperidin-1-yl}acetate |
| 631. | 1-(4-hydroxypiperidin-1-yl)-2-{4-[(2-{3-[(4-methanesulfonyl-2-methoxy-phenyl)amino]prop-1-yn-1-yl}-1-(2,2,2-trifluoroethyl)-1H-indol-4-yl)amino]piperidin-1-yl}ethan-1-one |
| 632. | 2-(2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethan-1-ol |
| 633. | -[(1R,4R)-4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl]piperidin-4-ol |
| 634. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetic acid |
| 635. | (1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 636. | (1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 637. | 2-{3-[(4-methanesulfonyl-2-methoxyphenyl)amino]prop-1-yn-1-yl}-1-(2,2,2-trifluoroethyl)-1H-indol-4-amine |
| 638. | 1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}-3-methylpyrrolidin-3-ol |
| 639. | (3R,4R)-1-{4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl}-pyrrolidine-3,4-diol |
| 640. | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboximidamide |
| 641. | 1-[(1S,4S)-4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl]piperidin-4-ol |
| 642. | 4-[(2-{3-[(3-methoxypyridin-4-yl)amino]prop-1-yn-1-yl}-1-(2,2,2-trifluoroethyl)-1H-indol-4-yl)amino]-1$\lambda^6$-thiane-1,1-dione |
| 643. | 2-{3-[(4-methanesulfonyl-2-methoxyphenyl)amino]prop-1-yn-1-yl}-N-[(1S,4S)-4-(morpholin-4-yl)cyclohexyl]-1-(2,2,2-trifluoroethyl)-1H-indol-4-amine |
| 644. | 2-{3-[(4-methanesulfonyl-2-methoxyphenyl)amino]prop-1-yn-1-yl}-N-[(1R,4R)-4-(morpholin-4-yl)cyclohexyl]-1-(2,2,2-trifluoroethyl)-1H-indol-4-amine |
| 645. | 2-(3-{[2-(2-fluoroethoxy)-4-methanesulfonylphenyl]amino}prop-1-yn-1-yl)-N-[1-(oxan-4-yl)piperidin-4-yl]-1-(2,2,2-trifluoroethyl)-1H-indol-4-amine |
| 646. | 4-{[2-(3-{[4-methanesulfonyl-2-(trifluoromethyl)phenyl]amino}prop-1-yn-1-yl)-1-(2,2,2-trifluoroethyl)-1H-indol-4-yl]amino}-1$\lambda^6$-thiane-1,1-dione |
| 647. | 2-(3-{[4-methanesulfonyl-2-(trifluoromethyl)phenyl]amino}prop-1-yn-1-yl)-N-(1-methylpiperidin-4-yl)-1-(2,2,2-trifluoroethyl)-1H-indol-4-amine |
| 648. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 649. | 3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzene-1-sulfonamide |
| 650. | 3-methoxy-4-[(3-{4-[(piperidin-4-yl)amino]-1-(2,2,2-trifluoroethyl)-1H-indol-2-yl}prop-2-yn-1-yl)amino]-benzamide |
| 651. | 3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzamide |
| 652. | 3-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)propane-1,2-diol |
| 653. | 3-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)propane-1,2-diol |

TABLE 1-continued

Alkynyl indole compounds of the disclosure.

| Mol # | IUPAC name |
|---|---|
| 654. | 2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)acetamide |
| 655. | 2-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)-1-(4-methylpiperazin-1-yl)ethan-1-one |
| 656. | 2-(3-{[2-(2-fluoroethoxy)-4-methanesulfonylphenyl]amino}prop-1-yn-1-yl)-N-(oxan-4-yl)-1-(2,2,2-trifluoroethyl)-1H-indol-4-amine |
| 657. | 2-(3-{[2-(2-fluoroethoxy)-4-methanesulfonylphenyl]amino}prop-1-yn-1-yl)-N-[1-(1-methylpiperidin-4-yl)piperidin-4-yl]-1-(2,2,2-trifluoroethyl)-1H-indol-4-amine |
| 658. | 4-[(2-{3-[(4-methoxypyridin-3-yl)amino]prop-1-yn-1-yl}-1-(2,2,2-trifluoroethyl)-1H-indol-4-yl)amino]-1λ$^6$-thiane-1,1-dione |
| 659. | S-{4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxyphenyl}-2-hydroxyethane-1-sulfonamido |
| 660. | 2-hydroxy-S-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}ethane-1-sulfonamido |
| 661. | 2-methyl-2-[5-({3-[4-(morpholin-4-yl)-1-(2,2,2-trifluoroethyl)-1H-indol-2-yl]prop-2-yn-1-yl}amino)pyridin-2-yl]propanenitrile |
| 662. | -{4-[(2-{3-[(4-methanesulfonylphenyl)amino]prop-1-yn-1-yl}-1-(2,2,2-trifluoroethyl)-1H-indol-4-yl)amino]piperidin-1-yl}-N-[5-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentyl]acetamide |
| 663. | 6-[(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetyl)oxy]hexyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate |
| 664. | 3-methoxy-4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 665. | 2-{5-methanesulfonyl-2-[(3-{4-[(1-methylpiperidin-4-yl)amino]-1-(2,2,2-trifluoroethyl)-1H-indol-2-yl}prop-2-yn-1-yl)amino]phenoxy}acetamide |
| 666. | 2-(3-{[4-methanesulfonyl-2-(2-methoxyethoxy)phenyl]amino}prop-1-yn-1-yl)-N-[1-(oxan-4-yl)piperidin-4-yl]-1-(2,2,2-trifluoroethyl)-1H-indol-4-amine |
| 667. | 2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)ethan-1-ol |
| 668. | 3-methoxy-4-[(3-{4-[(oxan-4-yl)amino]-1-(2,2,2-trifluoroethyl)-1H-indol-2-yl}prop-2-yn-1-yl)amino]benzoic acid |
| 669. | 2-{2-[(3-{4-[(1,1-dioxo-1λ$^6$-thian-4-yl)amino]-1-(2,2,2-trifluoroethyl)-1H-indol-2-yl}prop-2-yn-1-yl)amino]-5-methanesulfonylphenoxy}acetamide |
| 670. | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboxamide |
| 671. | 2-{3-[(4-methoxypyridin-3-yl)amino]prop-1-yn-1-yl}-N-(1-methylpiperidin-4-yl)-1-(2,2,2-trifluoroethyl)-1H-indol-4-amine |
| 672. | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carbothioamide |
| 673. | 4-[(2-{3-[(6-methanesulfonyl-4-methoxypyridin-3-yl)amino]prop-1-yn-1-yl}-1-(2,2,2-trifluoroethyl)-1H-indol-4-yl)amino]-1λ$^6$-thiane-1,1-dione |
| 674. | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}benzene-1-sulfonamide |
| 675. | 4-{[2-(3-{[4-(ethanesulfonyl)-2-methoxyphenyl]amino}prop-1-yn-1-yl)-1-(2,2,2-trifluoroethyl)-1H-indol-4-yl]amino}-1λ$^6$-thiane-1,1-dione |
| 676. | 2-(3-{[4-(ethanesulfonyl)-2-methoxyphenyl]amino}prop-1-yn-1-yl)-N-[1-(oxan-4-yl)piperidin-4-yl]-1-(2,2,2-trifluoroethyl)-1H-indol-4-amine |
| 677. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoic acid |
| 678. | methyl 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoate |
| 679. | methyl 3-methoxy-4-[(3-{4-[(oxan-4-yl)amino]-1-(2,2,2-trifluoroethyl)-1H-indol-2-yl}prop-2-yn-1-yl)amino]benzoate |
| 680. | 3-methoxy-4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzamide |
| 681. | 4-[(2-{3-[(4-methanesulfonyl-2-methoxyphenyl)amino]prop-1-yn-1-yl}-1-(2,2,2-trifluoroethyl)-1H-indol-4-yl)amino]-N-methylpiperidine-1-carboximidamide |
| 682. | 2-{3-[(6-methanesulfonyl-4-methoxypyridin-3-yl)amino]prop-1-yn-1-yl}-N-(1-methylpiperidin-4-yl)-1-(2,2,2-trifluoroethyl)-1H-indol-4-amine |
| 683. | 2-{3-[(4-methanesulfonyl-2-methoxyphenyl)amino]prop-1-yn-1-yl}-N-[1-(pyridin-4-yl)piperidin-4-yl]-1-(2,2,2-trifluoroethyl)-1H-indol-4-amine |
| 684. | 3-(4-{[2-(3-{[4-(ethanesulfonyl)-2-methoxyphenyl]amino}prop-1-yn-1-yl)-1-(2,2,2-trifluoroethyl)-1H-indol-4-yl]amino}piperidin-1-yl)propane-1,2-diol |
| 685. | 2-(3-{[4-(ethanesulfonyl)-2-methoxyphenyl]amino}prop-1-yn-1-yl)-N-(1-methylpiperidin-4-yl)-1-(2,2,2-trifluoroethyl)-1H-indol-4-amine |
| 686. | 2-hydroxy-S-{3-methoxy-4-[(3-{4-[(oxan-4-yl)amino]-1-(2,2,2-trifluoroethyl)-1H-indol-2-yl}prop-2-yn-1-yl)amino]phenyl}ethane-1-sulfonamido |
| 687. | 2-(3-{[4-methanesulfonyl-2-(2,2,2-trifluoroethoxy)phenyl]amino}prop-1-yn-1-yl)-N-(1-methylpiperidin-4-yl)-1-(2,2,2-trifluoroethyl)-1H-indol-4-amine |
| 688. | 4-{[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]amino}-1λ$^6$-thiane-1,1-dione |

TABLE 1-continued

Alkynyl indole compounds of the disclosure.

| Mol # | IUPAC name |
|---|---|
| 689. | 2-hydroxy-S-(3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}phenyl)ethane-1-sulfonamido |
| 690. | S-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxyphenyl)-2-hydroxyethane-1-sulfonamido |
| 691. | 2-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile |
| 692. | 3-methoxy-4-{[3-(4-{[(1S,4S)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 693. | 3-methoxy-4-{[3-(4-{[(1R,4R)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 694. | 3-methoxy-4-{[3-(4-{[(1S,4S)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide |
| 695. | 3-methoxy-4-{[3-(4-{[(1R,4R)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide |
| 696. | 2-{4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxyphenyl}-2-methylpropanenitrile |
| 697. | 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 698. | 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 699. | (3S,4S)-1-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]pyrrolidine-3,4-diol |
| 700. | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 701. | 3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 702. | 2-{3-[(4-methanesulfonyl-2-methoxyphenyl)amino]prop-1-yn-1-yl}-N,N-dimethyl-1-(2,2,2-trifluoroethyl)-1H-indol-4-amine |
| 703. | 3-methoxy-4-[(3-{4-[(2-methoxyethyl)amino]-1-(2,2,2-trifluoroethyl)-1H-indol-2-yl}prop-2-yn-1-yl)amino]benzene-1-sulfonamide |
| 704. | 2-[(2-{3-[(2-methoxy-4-sulfamoylphenyl)amino]prop-1-yn-1-yl}-1-(2,2,2-trifluoroethyl)-1H-indol-4-yl)amino]acetamide |
| 705. | 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide |
| 706. | N-(2-{3-[(4-methanesulfonyl-2-methoxyphenyl)amino]prop-1-yn-1-yl}-1-(2,2,2-trifluoroethyl)-1H-indol-4-yl)acetamide |
| 707. | 3-(2-{3-[(4-methanesulfonyl-2-methoxyphenyl)amino]prop-1-yn-1-yl}-1-(2,2,2-trifluoroethyl)-1H-indol-4-yl)-1-(1-methylpiperidin-4-yl)urea |
| 708. | 3-methoxy-4-{[3-(4-{[(1-methylpiperidin-4-yl)carbamoyl]amino}-1-(2,2,2-trifluoroethyl)-1H-indol-2-yl)prop-2-yn-1-yl]amino}benzamide |
| 709. | N-(2-{3-[(4-methanesulfonyl-2-methoxyphenyl)amino]prop-1-yn-1-yl}-1-(2,2,2-trifluoroethyl)-1H-indol-4-yl)-4-methylpiperazine-1-carboxamide |
| 710. | N-(2-{3-[(4-carbamoyl-2-methoxyphenyl)amino]prop-1-yn-1-yl}-1-(2,2,2-trifluoroethyl)-1H-indol-4-yl)-4-methylpiperazine-1-carboxamide |
| 711. | 3-(2-{3-[(4-methanesulfonyl-2-methoxyphenyl)amino]prop-1-yn-1-yl}-1-(2,2,2-trifluoroethyl)-1H-indol-4-yl)-1-[(1S,4S)-4-(dimethylamino)cyclohexyl]urea |
| 712. | 1-(2-(3-((2-methoxy-4-(methylsulfonyl)phenyl)amino)prop-1-yn-1-yl)-1-(2,2,2-trifluoroethyl)-1H-indol-4-yl)-3-(pyridin-4-yl)urea |
| 713. | 3-(2-{3-[(4-methanesulfonyl-2-methoxyphenyl)amino]prop-1-yn-1-yl}-1-(2,2,2-trifluoroethyl)-1H-indol-4-yl)-1-[(1R,4R)-4-(dimethylamino)cyclohexyl]urea |
| 714. | 3-(2-{3-[(4-methanesulfonyl-2-methoxyphenyl)amino]prop-1-yn-1-yl}-1-(2,2,2-trifluoroethyl)-1H-indol-4-yl)-1-[1-(2-methoxyethyl)piperidin-4-yl]urea |
| 715. | 3-(2-{3-[(4-methanesulfonyl-2-methoxyphenyl)amino]prop-1-yn-1-yl}-1-(2,2,2-trifluoroethyl)-1H-indol-4-yl)-1-[1-(oxan-4-yl)piperidin-4-yl]urea |
| 716. | 1-[1-(2,3-dihydroxypropyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea |
| 717. | 2-(4-{[(2-{3-[(4-methanesulfonyl-2-methoxyphenyl)amino]prop-1-yn-1-yl}-1-(2,2,2-trifluoroethyl)-1H-indol-4-yl)carbamoyl]amino}piperidin-1-yl)acetamide |
| 718. | 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide |
| 719. | [1-(chloromethyl)-3-[(2-{3-[(4-methanesulfonyl-2-methoxyphenyl)amino]prop-1-yn-1-yl}-1-(2,2,2-trifluoroethyl)-1H-indol-4-yl)amino]cyclobutyl]methanol |
| 720. | 2-{3-[(4-methanesulfonyl-2-methoxyphenyl)amino]prop-1-yn-1-yl}-N-{2-oxaspiro[3.3]heptan-6-yl}-1-(2,2,2-trifluoroethyl)-1H-indol-4-amine |
| 721. | 4-({3-[4-({2-azaspiro[3.3]heptan-6-yl}amino)-1-(2,2,2-trifluoroethyl)-1H-indol-2-yl]prop-2-yn-1-yl}amino)-3-methoxybenzene-1-sulfonamide |
| 722. | N-{2-azaspiro[3.3]heptan-6-yl}-2-{3-[(4-methanesulfonyl-2-methoxyphenyl)amino]prop-1-yn-1-yl}-1-(2,2,2-trifluoroethyl)-1H-indol-4-amine |
| 723. | 3-methoxy-N-methyl-4-{[3-(4-{[(1R,4R)-4-(methylamino)cyclohexyl]amino}-1-(2,2,2-trifluoroethyl)-1H-indol-2-yl)prop-2-yn-1-yl]amino}benzamide |
| 724. | 3-methoxy-N-methyl-4-{[3-(4-{[(1R,4R)-4-aminocyclohexyl]amino}-1-(2,2,2-trifluoroethyl)-1H-indol-2-yl)prop-2-yn-1-yl]amino}benzamide |
| 725. | 3-methoxy-N-methyl-4-{[3-(4-{[(1S,4S)-4-aminocyclohexyl]amino}-1-(2,2,2-trifluoroethyl)-1H-indol-2-yl)prop-2-yn-1-yl]amino}benzamide |

TABLE 1-continued

Alkynyl indole compounds of the disclosure.

| Mol # | IUPAC name |
|---|---|
| 726. | rel-(1R,3R)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 727. | rac-(1R,3S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 728. | (1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamineQ |
| 729. | rac-(1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine |
| 730. | rel-(1R,3S)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 731. | 3-methoxy-N-methyl-4-{[3-(4-{[(1R,4R)-4-hydroxy-4-methylcyclohexyl]amino}-1-(2,2,2-trifluoroethyl)-1H-indol-2-yl)prop-2-yn-1-yl]amino}benzamide |
| 732. | 3-methoxy-N-methyl-4-{[3-(4-{[(1S,4S)-4-hydroxy-4-methylcyclohexyl]amino}-1-(2,2,2-trifluoroethyl)-1H-indol-2-yl)prop-2-yn-1-yl]amino}benzamide |
| 733. | 4-[(3-{4-[(4-cyanocyclohexyl)amino]-1-(2,2,2-trifluoroethyl)-1H-indol-2-yl}prop-2-yn-1-yl)amino]-3-methoxy-N-methylbenzamide |
| 734. | 3-methoxy-N-methyl-4-{[3-(4-{[(1R,4R)-4-cyanocyclohexyl]amino}-1-(2,2,2-trifluoroethyl)-1H-indol-2-yl)prop-2-yn-1-yl]amino}benzamide |
| 735. | 3-methoxy-N-methyl-4-{[3-(4-{[(1S,4S)-4-cyanocyclohexyl]amino}-1-(2,2,2-trifluoroethyl)-1H-indol-2-yl)prop-2-yn-1-yl]amino}benzamide |
| 736. | 3-[(2-{3-[(4-methanesulfonyl-2-methoxyphenyl)amino]prop-1-yn-1-yl}-1-(2,2,2-trifluoroethyl)-1H-indol-4-yl)amino]cyclohexane-1-carboxylic acid |
| 737. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 738. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 739. | 2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)-$N^4$-methylcyclohexane-1,4-diamine |
| 740. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$-methylcyclohexane-1,4-diamine |
| 741. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 742. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 743. | (3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 744. | 3-methoxy-4-{[3-(4-{[(1R,4R)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 745. | 3-methoxy-4-{[3-(4-{[(1S,4S)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 746. | 4-((3-(4-(((1R,4R)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 747. | 4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 748. | 3-methoxy-N-(1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 749. | 3-methoxy-N-(oxan-4-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 750. | 3-methoxy-N-(1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 751. | 3-methoxy-N-(oxan-4-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 752. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 753. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 754. | 3-methoxy-N-(5-methyl-1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 755. | 3-methoxy-N-(5-methyl-1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 756. | (1S,4S)-$N^4$-(2-{3-[(4-methanesulfonyl-2-methoxyphenyl)amino]prop-1-yn-1-yl}-1-(2,2,2-trifluoroethyl)-1H-indol-4-yl)-$N^1$-(2-methoxyethyl)-$N^1$-methylcyclohexane-1,4-diamine |
| 757. | (1R,4R)-$N^4$-(2-{3-[(4-methanesulfonyl-2-methoxyphenyl)amino]prop-1-yn-1-yl}-1-(2,2,2-trifluoroethyl)-1H-indol-4-yl)-$N^1$-(2-methoxyethyl)-$N^1$-methylcyclohexane-1,4-diamine |
| 758. | 3-methoxy-4-{[3-(4-{[(1S,4S)-4-[(3S,4S)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 759. | 4-((3-(4-(((1R,4R)-4-((3R,4R)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 760. | 4-((3-(4-(((1R,4S)-4-((3S,4S)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |

TABLE 1-continued

Alkynyl indole compounds of the disclosure.

| Mol # | IUPAC name |
|---|---|
| 761. | 3-methoxy-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 762. | 3-methoxy-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 763. | 4-({3-[4-({1,4-dioxaspiro[4.5]decan-8-yl}amino)-1-(2,2,2-trifluoroethyl)-1H-indol-2-yl]prop-2-yn-1-yl}amino)-3-methoxybenzene-1-sulfonamide |
| 764. | N-{1,4-dioxaspiro[4.5]decan-8-yl}-2-{3-[(4-methanesulfonyl-2-methoxyphenyl)amino]prop-1-yn-1-yl}-1-(2,2,2-trifluoroethyl)-1H-indol-4-amine |
| 765. | 3-methoxy-4-[(3-{4-[(4-oxocyclohexyl)amino]-1-(2,2,2-trifluoroethyl)-1H-indol-2-yl}prop-2-yn-1-yl)amino]benzene-1-sulfonamide |
| 766. | 4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-one |
| 767. | (1R,4R)-$N^4$-[2-(3-{[2-methoxy-4-(morpholine-4-sulfonyl)phenyl]amino}prop-1-yn-1-yl)-1-(2,2,2-trifluoroethyl)-1H-indol-4-yl]-$N^1,N^1$-dimethylcyclohexane-1,4-diamine |
| 768. | (1S,4S)-$N^4$-[2-(3-{[2-methoxy-4-(morpholine-4-sulfonyl)phenyl]amino}prop-1-yn-1-yl)-1-(2,2,2-trifluoroethyl)-1H-indol-4-yl]-$N^1,N^1$-dimethylcyclohexane-1,4-diamine |
| 769. | N,N-bis(2-hydroxyethyl)-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 770. | N,N-bis(2-hydroxyethyl)-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 771. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 772. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 773. | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 774. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 775. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 776. | (1R,4R)-$N^4$-{2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}-$N^1,N^1$-dimethylcyclohexane-1,4-diamine |
| 777. | (1R,4R)-$N^4$-(2-{3-[(4-methanesulfonyl-2-methoxyphenyl)amino]prop-1-yn-1-yl}-1-[(oxiran-2-yl)methyl]-1H-indol-4-yl)-$N^1,N^1$-dimethylcyclohexane-1,4-diamine |
| 778. | 2-[(2-{3-[(4-methanesulfonyl-2-methoxyphenyl)amino]prop-1-yn-1-yl}-4-{[(1R,4R)-4-(dimethylamino)cyclohexyl]amino}-1H-indol-1-yl)methyl]prop-2-enenitrile |
| 779. | 5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenol |
| 780. | 5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenol |
| 781. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)acetonitrile |
| 782. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)acetonitrile |
| 783. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)acetamide |
| 784. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)acetamide |
| 785. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)propanamide |
| 786. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)propanamide |
| 787. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)ethan-1-ol |
| 788. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)ethan-1-ol |
| 789. | (1R,4R)-$N^4$-[2-(3-{[4-methanesulfonyl-2-(2-methoxyethoxy)phenyl]amino}prop-1-yn-1-yl)-1-(2,2,2-trifluoroethyl)-1H-indol-4-yl]-$N^1,N^1$-dimethylcyclohexane-1,4-diamine |
| 790. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 791. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 792. | (1R,4R)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1,N^1$-dimethylcyclohexane-1,4-diamine |
| 793. | (1S,4S)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1,N^1$-dimethylcyclohexane-1,4-diamine |
| 794. | (1S,4S)-$N^4$-{2-[3-(2-amino-4-methanesulfonylphenoxy)prop-1-yn-1-yl]-1-(2,2,2-trifluoroethyl)-1H-indol-4-yl}-$N^1,N^1$-dimethylcyclohexane-1,4-diamine |
| 795. | (1R,4R)-$N^4$-(2-{3-[(2-ethoxy-4-methanesulfonylphenyl)amino]prop-1-yn-1-yl}-1-(2,2,2-trifluoroethyl)-1H-indol-4-yl)-$N^1,N^1$-dimethylcyclohexane-1,4-diamine |
| 796. | (1S,4S)-$N^4$-(2-{3-[(2-ethoxy-4-methanesulfonylphenyl)amino]prop-1-yn-1-yl}-1-(2,2,2-trifluoroethyl)-1H-indol-4-yl)-$N^1,N^1$-dimethylcyclohexane-1,4-diamine |
| 797. | 3-hydroxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |

TABLE 1-continued

Alkynyl indole compounds of the disclosure.

| Mol # | IUPAC name |
|---|---|
| 798. | 3-hydroxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 799. | 3-(2-methoxyethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 800. | (1R,4R)-$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine |
| 801. | N-ethyl-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 802. | N-ethyl-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 803. | 3-(2-methoxyethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 804. | 3-(2-fluoroethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 805. | 3-(2-fluoroethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 806. | 3-(fluoromethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 807. | 3-(fluoromethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 808. | (1S,4S)-$N^4$-(2-{3-[4-methanesulfonyl-2-(methylamino)phenoxy]prop-1-yn-1-yl}-1-(2,2,2-trifluoroethyl)-1H-indol-4-yl)-$N^1$,$N^1$-dimethylcyclohexane-1,4-diamine |
| 809. | (1R,4R)-$N^4$-(2-{3-[4-methanesulfonyl-2-(methylamino)phenoxy]prop-1-yn-1-yl}-1-(2,2,2-trifluoroethyl)-1H-indol-4-yl)-$N^1$,$N^1$-dimethylcyclohexane-1,4-diamine |
| 810. | 3-methoxy-N-methyl-4-{[3-(4-{[(1S,4S)-4-(methylamino)cyclohexyl]amino}-1-(2,2,2-trifluoroethyl)-1H-indol-2-yl)prop-2-yn-1-yl]amino}benzamide |
| 811. | (1S,4S)-$N^4$-(2-{3-[2-(dimethylamino)-4-methanesulfonylphenoxy]prop-1-yn-1-yl}-1-(2,2,2-trifluoroethyl)-1H-indol-4-yl)-$N^1$,$N^1$-dimethylcyclohexane-1,4-diamine |
| 812. | (1R,4R)-$N^4$-(2-{3-[2-(dimethylamino)-4-methanesulfonylphenoxy]prop-1-yn-1-yl}-1-(2,2,2-trifluoroethyl)-1H-indol-4-yl)-$N^1$,$N^1$-dimethylcyclohexane-1,4-diamine |
| 813. | 3-(cyanomethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 814. | 3-(2-cyanoethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 815. | N-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]oxy}phenyl)acetamide |
| 816. | N-(2-((3-(4-(((1S,4S)-4-(dimethylamino)cyclohexyl)amino)-1-(2,2,2-trifluoroethyl)-1H-indol-2-yl)prop-2-yn-1-yl)oxy)-5-(methylsulfonyl)phenyl)acetamide |
| 817. | (1R,4R)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 818. | (1S,4S)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 819. | (1R,4R)-$N^4$-[2-(3-{[4-(ethanesulfonyl)-2-methoxyphenyl]amino}prop-1-yn-1-yl)-1-(2,2,2-trifluoroethyl)-1H-indol-4-yl]-$N^1$,$N^1$-dimethylcyclohexane-1,4-diamine |
| 820. | (1S,4S)-$N^4$-[2-(3-{[4-(ethanesulfonyl)-2-methoxyphenyl]amino}prop-1-yn-1-yl)-1-(2,2,2-trifluoroethyl)-1H-indol-4-yl]-$N^1$,$N^1$-dimethylcyclohexane-1,4-diamine |
| 821. | 2-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}phenyl)-2-methylpropanenitrile |
| 822. | 2-(4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxyphenyl)-2-methylpropanenitrile |
| 823. | 3-(cyanomethoxy)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 824. | 3-(cyanomethoxy)-4-((3-(4-(((1S,4S)-4-(dimethylamino)cyclohexyl)amino)-1-(2,2,2-trifluoroethyl)-1H-indol-2-yl)prop-2-yn-1-yl)amino)benzenesulfonamide |
| 825. | 3-(3-(4-(((1R,4R)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 826. | 3-(3-(4-(((1S,4S)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 827. | 3-methoxy-N,N-dimethyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 828. | (1R,4R)-$N^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-$N^4$,$N^4$-dimethylcyclohexane-1,4-diamine |
| 829. | (1S,4S)-$N^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-$N^4$,$N^4$-dimethylcyclohexane-1,4-diamine |
| 830. | (1R,4R)-$N^4$-(2-{3-[(4-chloro-2-methoxyphenyl)amino]prop-1-yn-1-yl}-1-(2,2,2-trifluoroethyl)-1H-indol-4-yl)-$N^1$,$N^1$-dimethylcyclohexane-1,4-diamine |
| 831. | (1S,4S)-$N^1$-(2-(3-((4-chloro-2-methoxyphenyl)amino)prop-1-yn-1-yl)-1-(2,2,2-trifluoroethyl)-1H-indol-4-yl)-$N^4$,$N^4$-dimethylcyclohexane-1,4-diamine |
| 832. | 4-((3-(4-(((1R,4R)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 833. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 834. | (1R,4R)-$N^4$-[2-(3-{[2-methoxy-4-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |

TABLE 1-continued

Alkynyl indole compounds of the disclosure.

| Mol # | IUPAC name |
|---|---|
| 835. | (1S,4S)-N$^1$-(2-(3-((2-methoxy-4-(trifluoromethyl)phenyl)amino)prop-1-yn-1-yl)-1-(2,2,2-trifluoroethyl)-1H-indol-4-yl)-N$^4$,N$^4$-dimethylcyclohexane-1,4-diamine |
| 836. | 2-fluoro-5-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 837. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxy-N-methylbenzamide |
| 838. | (1S,4S)-N$^4$-[2-(3-{[4-methanesulfonyl-2-(trifluoromethyl)phenyl]amino}prop-1-yn-1-yl)-1-(2,2,2-trifluoroethyl)-1H-indol-4-yl]-N$^1$,N$^1$-dimethylcyclohexane-1,4-diamine |
| 839. | (1R,4R)-N$^4$-[2-(3-{[4-methanesulfonyl-2-(trifluoromethyl)phenyl]amino}prop-1-yn-1-yl)-1-(2,2,2-trifluoroethyl)-1H-indol-4-yl]-N$^1$,N$^1$-dimethylcyclohexane-1,4-diamine |
| 840. | (1R,4R)-N$^4$-(2-{3-[(4-methanesulfonyl-2-methylphenyl)amino]prop-1-yn-1-yl}-1-(2,2,2-trifluoroethyl)-1H-indol-4-yl)-N$^1$,N$^1$-dimethylcyclohexane-1,4-diamine |
| 841. | (1S,4S)-N$^1$,N$^1$-dimethyl-N$^4$-(2-(3-((2-methyl-4-(methylsulfonyl)phenyl)amino)prop-1-yn-1-yl)-1-(2,2,2-trifluoroethyl)-1H-indol-4-yl)cyclohexane-1,4-diamine |
| 842. | (1R,4R)-N$^4$-[2-(3-{[4-methanesulfonyl-2-(trifluoromethoxy)phenyl]amino}prop-1-yn-1-yl)-1-(2,2,2-trifluoroethyl)-1H-indol-4-yl]-N$^1$,N$^1$-dimethylcyclohexane-1,4-diamine |
| 843. | (1S,4S)-N$^1$,N$^1$-dimethyl-N$^4$-(2-(3-((4-(methylsulfonyl)-2-(trifluoromethoxy)phenyl)amino)prop-1-yn-1-yl)-1-(2,2,2-trifluoroethyl)-1H-indol-4-yl)cyclohexane-1,4-diamine |
| 844. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzamide |
| 845. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxy-N-methylbenzamide |
| 846. | 3-methoxy-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 847. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxybenzenesulfonamide |
| 848. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 849. | 2-(5-methanesulfonyl-2-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 850. | 2-(5-methanesulfonyl-2-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 851. | 3-methoxy-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 852. | 3-methoxy-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 853. | N-ethyl-3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 854. | N-ethyl-3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzamide |
| 855. | (1R,4R)-N$^1$-(2-(3-((2-(fluoromethoxy)-4-(methylsulfonyl)phenyl)amino)prop-1-yn-1-yl)-1-(2,2,2-trifluoroethyl)-1H-indol-4-yl)-N$^4$-(2-methoxyethyl)-N$^4$-methylcyclohexane-1,4-diamine |
| 856. | (1S,4S)-N$^1$-(2-(3-((2-(fluoromethoxy)-4-(methylsulfonyl)phenyl)amino)prop-1-yn-1-yl)-1-(2,2,2-trifluoroethyl)-1H-indol-4-yl)-N$^4$-(2-methoxyethyl)-N$^4$-methylcyclohexane-1,4-diamine |
| 857. | 3-(fluoromethoxy)-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 858. | 3-(fluoromethoxy)-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 859. | 3-(fluoromethoxy)-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)-N-methylbenzamide |
| 860. | 3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 861. | 3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzenesulfonamide |
| 862. | (1R,4R)-N$^1$,N$^1$-diethyl-N$^4$-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine |
| 863. | (1S,4S)-N$^1$,N$^1$-diethyl-N$^4$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 864. | 3-(cyanomethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 865. | 3-(cyanomethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 866. | 3-(fluoromethoxy)-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 867. | 3-(fluoromethoxy)-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 868. | 3-(fluoromethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 869. | 3-(fluoromethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 870. | 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 871. | 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |
| 872. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 873. | 3-methoxy-N-methyl-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |
| 874. | 2-(2-{3-[(4-methanesulfonyl-2-methoxyphenyl)amino]prop-1-yn-1-yl}-4-{[(1R,4R)-4-(morpholin-4-yl)cyclohexyl]amino}-1H-indol-1-yl)acetonitrile |
| 875. | 4-({3-[1-(2-fluoroethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 876. | 1-(2-fluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 877. | 4-({3-[1-(cyanomethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 878. | 2-{3-[(4-methanesulfonyl-2-methoxyphenyl)amino]prop-1-yn-1-yl}-1-propyl-N-[(1R,4R)-4-(morpholin-4-yl)cyclohexyl]-1H-indol-4-amine |
| 879. | 2-{3-[(4-methanesulfonyl-2-methoxyphenyl)amino]prop-1-yn-1-yl}-1-(2-methylpropyl)-N-[(1R,4R)-4-(morpholin-4-yl)cyclohexyl]-1H-indol-4-amine |
| 880. | 1-(2,2-difluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 881. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 882. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 883. | N-ethyl-3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 884. | N-ethyl-3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzamide |
| 885. | 2-(5-methanesulfonyl-2-{[3-(4-{[(1R,4R)-4-(morpholin-4-yl)cyclohexyl]amino}-1-(2,2,2-trifluoroethyl)-1H-indol-2-yl)prop-2-yn-1-yl]amino}phenoxy)acetonitrile |
| 886. | 2-(5-methanesulfonyl-2-{[3-(4-{[(1S,4S)-4-(morpholin-4-yl)cyclohexyl]amino}-1-(2,2,2-trifluoroethyl)-1H-indol-2-yl)prop-2-yn-1-yl]amino}phenoxy)acetonitrile |
| 887. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 888. | 2-{3-[(4-methanesulfonyl-2-methoxyphenyl)amino]prop-1-yn-1-yl}-N-[(1R,4R)-4-(3-methanesulfonylazetidin-1-yl)cyclohexyl]-1-(2,2,2-trifluoroethyl)-1H-indol-4-amine |
| 889. | 2-(3-((2-methoxy-4-(methylsulfonyl)phenyl)amino)prop-1-yn-1-yl)-N-((1S,4S)-4-(3-(methylsulfonyl)azetidin-1-yl)cyclohexyl)-1-(2,2,2-trifluoroethyl)-1H-indol-4-amine |
| 890. | 3-methoxy-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzene-1-sulfonamide |
| 891. | 3-methoxy-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzenesulfonamide |
| 892. | 3-methoxy-N-methyl-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzamide |
| 893. | 3-methoxy-N-methyl-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzamide |
| 894. | 2-{3-[(4-methanesulfonyl-2-methoxyphenyl)amino]prop-1-yn-1-yl}-N-[(1R,4R)-4-{2-azaspiro[3.3]heptan-2-yl}cyclohexyl]-1-(2,2,2-trifluoroethyl)-1H-indol-4-amine |
| 895. | N-((1S,4S)-4-(2-azaspiro[3.3]heptan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 896. | 3-methoxy-N-methyl-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzamide |
| 897. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxy-N-methylbenzamide |
| 898. | 3-methoxy-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzene-1-sulfonamide |
| 899. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxybenzenesulfonamide |
| 900. | 2-(3-((2-methoxy-4-(methylsulfonyl)phenyl)amino)prop-1-yn-1-yl)-N-(2-azaspiro[3.3]heptan-6-yl)-1-(2,2,2-trifluoroethyl)-1H-indol-4-amine |

TABLE 1-continued

Alkynyl indole compounds of the disclosure.

| Mol # | IUPAC name |
|---|---|
| 901. | 4-((3-(4-((2-azaspiro[3.3]heptan-6-yl)amino)-1-(2,2,2-trifluoroethyl)-1H-indol-2-yl)prop-2-yn-1-yl)amino)-3-methoxybenzenesulfonamide |
| 902. | 2-{3-[(4-methanesulfonyl-2-methoxyphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 903. | 2-{3-[(4-methanesulfonyl-2-methoxyphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 904. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 905. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 906. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 907. | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 908. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 909. | N-(3-methoxy-4-{[3-(4-{[(1S,4S)-4-}2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 910. | N-((1R,4R)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 911. | N-((1S,4S)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 912. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 913. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 914. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 915. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 916. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 917. | N-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 918. | N-(2-hydroxy-4-methanesulfonylphenyl)-2-methyl-N-[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]propanamide |
| 919. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 920. | 2-(3-{[4-methanesulfonyl-2-(2-methoxyethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 921. | 2-(3-{[4-methanesulfonyl-2-(2-methoxyethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 922. | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 923. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 924. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 925. | 2-(5-methanesulfonyl-2-([3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 926. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 927. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)acetamide |
| 928. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 929. | 3-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 930. | 3-methoxy-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |

TABLE 1-continued

Alkynyl indole compounds of the disclosure.

| Mol # | IUPAC name |
|---|---|
| 931. | 2-(3-{[4-methanesulfonyl-2-(2,2,2-trifluoroethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 932. | 2-(3-{[4-methanesulfonyl-2-(2,2,2-trifluoroethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 933. | 2-[3-(2-amino-4-methanesulfonylphenoxy)prop-1-yn-1-yl]-N-[(1S,4S)-4-{2-oxa-6-azaspiro[3.3]heptan-6-yl}cyclohexyl]-1-(2,2,2-trifluoroethyl)-1H-indol-4-amine |
| 934. | 2-{3-[(2-ethoxy-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 935. | 2-{3-[(2-ethoxy-4-methanesulfonylphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 936. | 3-(2-methoxyethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 937. | 3-(2-methoxyethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 938. | N-ethyl-3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 939. | N-ethyl-3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 940. | 3-(2-fluoroethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 941. | 3-(2-fluoroethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 942. | 3-(cyanomethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 943. | 3-(cyanomethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 944. | 2-{3-[4-methanesulfonyl-2-(methylamino)phenoxy]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 945. | 2-{3-[4-methanesulfonyl-2-(methylamino)phenoxy]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 946. | 2-[3-(2-amino-4-methanesulfonylphenoxy)prop-1-yn-1-yl]-N-[(1R,4R)-4-{2-oxa-6-azaspiro[3.3]heptan-6-yl}cyclohexyl]-1-(2,2,2-trifluoroethyl)-1H-indol-4-amine |
| 947. | N-((1R,4R)-4-(2-oxa-6-azaspiro[3.3]heptan-6-yl)cyclohexyl)-2-(3-(2-amino-4-(methylsulfonyl)phenoxy)prop-1-yn-1-yl)-1-(2,2,2-trifluoroethyl)-1H-indol-4-amine |
| 948. | 3-hydroxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 949. | 3-methoxy-4-[(3-{4-[(4-{2-oxa-6-azaspiro[3.3]heptan-6-yl}cyclohexyl)amino]-1-(2,2,2-trifluoroethyl)-1H-indol-2-yl}prop-2-yn-1-yl)amino]benzonitrile |
| 950. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzonitrile |
| 951. | 2-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl)-2-methylpropanenitrile |
| 952. | 2-(4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 953. | 3-(fluoromethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 954. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(fluoromethoxy)-N-methylbenzamide |
| 955. | 3-(2-cyanoethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 956. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(2-cyanoethoxy)-N-methylbenzamide |
| 957. | 2-(3-{[2-(fluoromethoxy)-4-methanesulfonylphenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 958. | N-((1S,4S)-4-(2-oxa-6-azaspiro[3.3]heptan-6-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 959. | 3-(cyanomethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 960. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(cyanomethoxy)benzenesulfonamide |
| 961. | 3-(fluoromethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 962. | 3-(fluoromethoxy)-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 963. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 964. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 965. | N-((1R,4R)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |

TABLE 1-continued

Alkynyl indole compounds of the disclosure.

| Mol # | IUPAC name |
|---|---|
| 966. | N-((1S,4S)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 967. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 968. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 969. | N-((1R,4R)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 970. | N-((1S,4S)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 971. | N-((1R,4R)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 972. | N-((1S,4S)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 973. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 974. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzamide |
| 975. | 2-fluoro-5-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 976. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxy-N-methylbenzamide |
| 977. | 2-(3-{[2-methoxy-4-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 978. | N-((1S,4S)-4-(2-oxa-6-azaspiro[3.3]heptan-6-yl)cyclohexyl)-2-(3-((2-methoxy-4-(trifluoromethyl)phenyl)amino)prop-1-yn-1-yl)-1-(2,2,2-trifluoroethyl)-1H-indol-4-amine |
| 979. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 980. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 981. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzoic acid |
| 982. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzoic acid |
| 983. | 2-{3-[(4-methanesulfonyl-2-methylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 984. | N-((1S,4S)-4-(2-oxa-6-azaspiro[3.3]heptan-6-yl)cyclohexyl)-2-(3-((2-methyl-4-(methylsulfonyl)phenyl)amino)prop-1-yn-1-yl)-1-(2,2,2-trifluoroethyl)-1H-indol-4-amine |
| 985. | 2-(3-{[4-methanesulfonyl-2-(trifluoromethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 986. | N-((1S,4S)-4-(2-oxa-6-azaspiro[3.3]heptan-6-yl)cyclohexyl)-2-(3-((4-(methylsulfonyl)-2-(trifluoromethoxy)phenyl)amino)prop-1-yn-1-yl)-1-(2,2,2-trifluoroethyl)-1H-indol-4-amine |
| 987. | 2-(3-{[4-methanesulfonyl-2-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 988. | N-((1S,4S)-4-(2-oxa-6-azaspiro[3.3]heptan-6-yl)cyclohexyl)-2-(3-((4-(methylsulfonyl)-2-(trifluoromethyl)phenyl)amino)prop-1-yn-1-yl)-1-(2,2,2-trifluoroethyl)-1H-indol-4-amine |
| 989. | 2-{3-[(2-chloro-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 990. | N-((1S,4S)-4-(2-oxa-6-azaspiro[3.3]heptan-6-yl)cyclohexyl)-2-(3-((2-chloro-4-(methylsulfonyl)phenyl)amino)prop-1-yn-1-yl)-1-(2,2,2-trifluoroethyl)-1H-indol-4-amine |
| 991. | 3-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 992. | 3-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 993. | 2-{3-[(4-methanesulfonyl-2-methoxyphenyl)amino]prop-1-yn-1-yl}-N-[(1S,4S)-4-{7-oxa-2-azaspiro[3.5]nonan-2-yl}cyclohexyl]-1-(2,2,2-trifluoroethyl)-1H-indol-4-amine |
| 994. | 2-{3-[(4-methanesulfonyl-2-methoxyphenyl)amino]prop-1-yn-1-yl}-N-[(1R,4R)-4-{7-oxa-2-azaspiro[3.5]nonan-2-yl}cyclohexyl]-1-(2,2,2-trifluoroethyl)-1H-indol-4-amine |
| 995. | 3-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 996. | 3-methoxy-N-methyl-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 997. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 998. | 3-methoxy-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 999. | 3-(cyanomethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 1000. | 3-(cyanomethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1001. | 2-(3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenyl)-2-methylpropanenitrile |
| 1002. | 2-(4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 1003. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1004. | 2-(5-methanesulfonyl-2-{[3-(4-([[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1005. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1006. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1007. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1008. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1009. | methyl 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetate |
| 1010. | methyl 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate |
| 1011. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetic acid |
| 1012. | 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetic acid |
| 1013. | 2-{3-[(4-methanesulfonyl-2-methoxyphenyl)amino]prop-1-yn-1-yl}-N-[(1R,4R)-4-{2-oxa-7-azaspiro[3.5]nonan-7-yl}cyclohexyl]-1-(2,2,2-trifluoroethyl)-1H-indol-4-amine |
| 1014. | 2-(3-{[4-(ethanesulfonyl)-2-methoxyphenyl]amino}prop-1-yn-1-yl)-N-[(1R,4R)-4-{7-oxa-2-azaspiro[3.5]nonan-2-yl}cyclohexyl]-1-(2,2,2-trifluoroethyl)-1H-indol-4-amine |
| 1015. | 2-(3-{[4-(ethanesulfonyl)-2-methoxyphenyl]amino}prop-1-yn-1-yl)-N-[(1S,4S)-4-{7-oxa-2-azaspiro[3.5]nonan-2-yl}cyclohexyl]-1-(2,2,2-trifluoroethyl)-1H-indol-4-amine |
| 1016. | 3-(fluoromethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1017. | 3-(fluoromethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1018. | 3-methoxy-N-methyl-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1019. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzamide |
| 1020. | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1021. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzenesulfonamide |
| 1022. | 2-{3-[(4-methanesulfonyl-2-methoxyphenyl)amino]prop-1-yn-1-yl}-N-[(1R,4R)-4-{6-oxa-2-azaspiro[3.5]nonan-2-yl}cyclohexyl]-1-(2,2,2-trifluoroethyl)-1H-indol-4-amine |
| 1023. | N-((1S,4S)-4-(6-oxa-2-azaspiro[3.5]nonan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1024. | N-((1R,4R)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1025. | N-((1S,4S)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1026. | 4-(3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)-7-(methylsulfonyl)-2H-benzo[b][1,4]oxazin-3(4H)-one |
| 1027. | 4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |
| 1028. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |

TABLE 1-continued

Alkynyl indole compounds of the disclosure.

| Mol # | IUPAC name |
|---|---|
| 1029. | N-((1R,4R)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1030. | N-((1S,4S)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1031. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1032. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1033. | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1034. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1035. | 2-fluoro-5-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1036. | 2-(3-((2-methoxy-4-(methylsulfonyl)phenyl)amino)prop-1-yn-1-yl)-N-((1R,4R)-4-(3-methoxypyrrolidin-1-yl)cyclohexyl)-1-(2,2,2-trifluoroethyl)-1H-indol-4-amine |
| 1037. | 2-(3-((2-methoxy-4-(methylsulfonyl)phenyl)amino)prop-1-yn-1-yl)-N-((1S,4S)-4-(3-methoxypyrrolidin-1-yl)cyclohexyl)-1-(2,2,2-trifluoroethyl)-1H-indol-4-amine |
| 1038. | 3-methoxy-4-((3-(4-(((1R,4R)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1039. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1040. | 2-(3-{[2-(fluoromethoxy)-4-methanesulfonylphenyl]amino}prop-1-yn-1-yl)-N-[(1R,4R)-4-(morpholin-4-yl)cyclohexyl]-1-(2,2,2-trifluoroethyl)-1H-indol-4-amine |
| 1041. | 2-(3-{[2-(fluoromethoxy)-4-methanesulfonylphenyl]amino}prop-1-yn-1-yl)-N-[(1S,4S)-4-(morpholin-4-yl)cyclohexyl]-1-(2,2,2-trifluoroethyl)-1H-indol-4-amine |
| 1042. | 3-(cyanomethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1043. | 3-(cyanomethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1044. | 3-(fluoromethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1045. | 3-(fluoromethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1046. | 2-(3-((2-ethoxy-4-(methylsulfonyl)phenyl)amino)prop-1-yn-1-yl)-N-((1R,4R)-4-morpholinocyclohexyl)-1-(2,2,2-trifluoroethyl)-1H-indol-4-amine |
| 1047. | 2-(3-((2-ethoxy-4-(methylsulfonyl)phenyl)amino)prop-1-yn-1-yl)-N-((1S,4S)-4-morpholinocyclohexyl)-1-(2,2,2-trifluoroethyl)-1H-indol-4-amine |
| 1048. | 2-{3-[(4-methanesulfonyl-2-methoxyphenyl)amino]prop-1-yn-1-yl}-N-[(1R,4R)-4-(3-methoxypiperidin-1-yl)cyclohexyl]-1-(2,2,2-trifluoroethyl)-1H-indol-4-amine |
| 1049. | 2-(3-((2-methoxy-4-(methylsulfonyl)phenyl)amino)prop-1-yn-1-yl)-N-((1S,4S)-4-(3-methoxypiperidin-1-yl)cyclohexyl)-1-(2,2,2-trifluoroethyl)-1H-indol-4-amine |
| 1050. | 2-{3-[(4-methanesulfonyl-2-methoxyphenyl)amino]prop-1-yn-1-yl}-N-[(1R,4R)-4-(4-methoxypiperidin-1-yl)cyclohexyl]-1-(2,2,2-trifluoroethyl)-1H-indol-4-amine |
| 1051. | 2-(3-((2-methoxy-4-(methylsulfonyl)phenyl)amino)prop-1-yn-1-yl)-N-((1S,4S)-4-(4-methoxypiperidin-1-yl)cyclohexyl)-1-(2,2,2-trifluoroethyl)-1H-indol-4-amine |
| 1052. | 3-methoxy-N-methyl-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzamide |
| 1053. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)-N-methylbenzamide |
| 1054. | 3-methoxy-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1055. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)benzenesulfonamide |
| 1056. | 3-methoxy-N-methyl-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzamide |
| 1057. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)-N-methylbenzamide |
| 1058. | 3-methoxy-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1059. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)benzenesulfonamide |
| 1060. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 1061. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 1062. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^6$-thiomorpholine-1,1-dione |
| 1063. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1,1-dioxide |

TABLE 1-continued

Alkynyl indole compounds of the disclosure.

Mol # IUPAC name 1064. 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ⁴-thiomorpholin-1-one
1065. 4-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ⁴-thiomorpholin-1-one
1066. 4-((3-(4-(((1R,4R)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide
1067. 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide
1068. 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1-oxide
1069. 3-methoxy-N-methyl-4-{[3-(4-{[(1R,4R)-4-(1-oxo-1λ⁴-thiomorpholin-4-yl)cyclohexyl]amino}-1-(2,2,2-trifluoroethyl)-1H-indol-2-yl)prop-2-yn-1-yl]amino}benzamide
1070. 3-methoxy-4-{[3-(4-{[(1R,4R)-4-(1-oxo-1λ⁴-thiomorpholin-4-yl)cyclohexyl]amino}-1-(2,2,2-trifluoroethyl)-1H-indol-2-yl)prop-2-yn-1-yl]amino}benzene-1-sulfonamide
1071. 3-methoxy-4-((3-(4-(((1S,4S)-4-(1-oxidothiomorpholino)cyclohexyl)amino)-1-(2,2,2-trifluoroethyl)-1H-indol-2-yl)prop-2-yn-1-yl)amino)benzenesulfonamide
1072. 3-methoxy-4-{[3-(4-{[(1R,4R)-4-(1,1-dioxo-1λ⁶-thiomorpholin-4-yl)cyclohexyl]amino}-1-(2,2,2-trifluoroethyl)-1H-indol-2-yl)prop-2-yn-1-yl]amino}benzene-1-sulfonamide
1073. 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxybenzenesulfonamide
1074. 2-{3-[(4-methanesulfonyl-2-methoxyphenyl)amino]prop-1-yn-1-yl}-N-[(1S,4S)-4-{2-oxa-7-azaspiro[3.5]nonan-7-yl}cyclohexyl]-1-(2,2,2-trifluoroethyl)-1H-indol-4-amine
1075. 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide
1076. 3-methoxy-N-methyl-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide
1077. 3-methoxy-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1078. 4-((3-(4-(((1S,4S)-4-(2-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide
1079. 3-(cyanomethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1080. 3-(cyanomethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1081. 3-(fluoromethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1082. 3-(fluoromethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1083. 2-{3-[(4-methanesulfonyl-2-methoxyphenyl)amino]prop-1-yn-1-yl}-N-[(1R,4R)-4-{1-oxa-7-azaspiro[3.5]nonan-7-yl}cyclohexyl]-1-(2,2,2-trifluoroethyl)-1H-indol-4-amine
1084. N-((1S,4S)-4-(1-oxa-7-azaspiro[3.5]nonan-7-yl)cyclohexyl)-2-(3-((2-methoxy-4-(methylsulfonyl)phenyl)amino)prop-1-yn-1-yl)-1-(2,2,2-trifluoroethyl)-1H-indol-4-amine
1085. 3-methoxy-N-methyl-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzamide
1086. 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxy-N-methylbenzamide
1087. 3-methoxy-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1088. 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide
1089. 2-(5-methanesulfonyl-2-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile
1090. 2-(5-methanesulfonyl-2-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile
1091. 2-(3-{[2-(fluoromethoxy)-4-methanesulfonylphenyl]amino}prop-1-yn-1-yl)-N-[(1R,4R)-4-{2-oxa-7-azaspiro[3.5]nonan-7-yl}cyclohexyl]-1-(2,2,2-trifluoroethyl)-1H-indol-4-amine
1092. 2-(3-{[2-(fluoromethoxy)-4-methanesulfonylphenyl]amino}prop-1-yn-1-yl)-N-[(1S,4S)-4-{2-oxa-7-azaspiro[3.5]nonan-7-yl}cyclohexyl]-1-(2,2,2-trifluoroethyl)-1H-indol-4-amine
1093. N-((1R,4R)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine
1094. N-((1S,4S)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine
1095. 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide TABLE 1-continued Alkynyl indole compounds of the disclosure.

| Mol # | IUPAC name |
|---|---|
| 1096. | N-((1R,4R)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1097. | N-((1S,4S)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1098. | 2-{3-[(4-methanesulfonyl-2-methoxyphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1099. | 2-{3-[(4-methanesulfonyl-2-methoxyphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1100. | 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |
| 1101. | 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |
| 1102. | 3-methoxy-N-methyl-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1103. | 3-methoxy-N-methyl-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1104. | 2-{3-[(2-ethoxy-4-methanesulfonylphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1105. | 2-{3-[(2-ethoxy-4-methanesulfonylphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1106. | N-ethyl-3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1107. | 2-(5-methanesulfonyl-2-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}phenoxy)acetonitrile |
| 1108. | 2-(2-((3-(4-(((1S,4S)-4-(6-oxa-3-azabicyclo[3.1.1]heptan-3-yl)cyclohexyl)amino)-1-(2,2,2-trifluoroethyl)-1H-indol-2-yl)prop-2-yn-1-yl)amino)-5-(methylsulfonyl)phenoxy)acetonitrile |
| 1109. | 3-methoxy-N-methyl-4-{[3-(4-{[(1R,4R)-4-[2-oxa-8-azaspiro[4.5]decan-8-yl}cyclohexyl]amino}-1-(2,2,2-trifluoroethyl)-1H-indol-2-yl)prop-2-yn-1-yl]amino}benzamide |
| 1110. | 2-{3-[(4-methanesulfonyl-2-methoxyphenyl)amino]prop-1-yn-1-yl}-N-[(1R,4R)-4-{2-oxa-8-azaspiro[4.5]decan-8-yl}cyclohexyl]-1-(2,2,2-trifluoroethyl)-1H-indol-4-amine |
| 1111. | 3-methoxy-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzene-1-sulfonamide |
| 1112. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1113. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1114. | 2-{3-[(4-methanesulfonyl-2-methoxyphenyl)amino]prop-1-yn-1-yl}-N-[(1R,4R)-4-{3-oxa-9-azaspiro[5.5]undecan-9-yl}cyclohexyl]-1-(2,2,2-trifluoroethyl)-1H-indol-4-amine |
| 1115. | N-((1S,4S)-4-(3-oxa-9-azaspiro[5.5]undecan-9-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1116. | 3-methoxy-N-methyl-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzamide |
| 1117. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxy-N-methylbenzamide |
| 1118. | 3-methoxy-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzene-1-sulfonamide |
| 1119. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxybenzenesulfonamide |
| 1120. | 3-methoxy-N-methyl-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzamide |
| 1121. | 3-methoxy-N-methyl-4-((3-(4-(((1S,4S)-4-(pyrrolidin-1-yl)cyclohexyl)amino)-1-(2,2,2-trifluoroethyl)-1H-indol-2-yl)prop-2-yn-1-yl)amino)benzamide |
| 1122. | 3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide |
| 1123. | 3-methoxy-4-((3-(4-(((1S,4S)-4-(pyrrolidin-1-yl)cyclohexyl)amino)-1-(2,2,2-trifluoroethyl)-1H-indol-2-yl)prop-2-yn-1-yl)amino)benzenesulfonamide |
| 1124. | 2-{3-[(4-methanesulfonyl-2-methoxyphenyl)amino]prop-1-yn-1-yl}-N-[(1R,4R)-4-(pyrrolidin-1-yl)cyclohexyl]-1-(2,2,2-trifluoroethyl)-1H-indol-4-amine |
| 1125. | 2-(3-((2-methoxy-4-(methylsulfonyl)phenyl)amino)prop-1-yn-1-yl)-N-((1S,4S)-4-(pyrrolidin-1-yl)cyclohexyl)-1-(2,2,2-trifluoroethyl)-1H-indol-4-amine |
| 1126. | -{3-[(4-methanesulfonyl-2-methoxyphenyl)amino]prop-1-yn-1-yl}-N-[(1R,4R)-4-(3-methoxypyrrolidin-1-yl)cyclohexyl]-1-(2,2,2-trifluoroethyl)-1H-indol-4-amine |
| 1127. | 3-methoxy-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 1128. | 3-methoxy-N-methyl-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzamide |
| 1129. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)-N-methylbenzamide |
| 1130. | 3-methoxy-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzene-1-sulfonamide |
| 1131. | 3-methoxy-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzenesulfonamide |
| 1132. | 2-{3-[(4-methanesulfonyl-2-methoxyphenyl)amino]prop-1-yn-1-yl}-N-[(1R,4R)-4-{hexahydro-1H-furo[3,4-c]pyrrol-5-yl}cyclohexyl]-1-(2,2,2-trifluoroethyl)-1H-indol-4-amine |
| 1133. | 2-(3-((2-methoxy-4-(methylsulfonyl)phenyl)amino)prop-1-yn-1-yl)-N-((1R,4R)-4-(tetrahydro-1H-furo[3,4-c]pyrrol-5(3H)-yl)cyclohexyl)-1-(2,2,2-trifluoroethyl)-1H-indol-4-amine |
| 1134. | 3-methoxy-N-methyl-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzamide |
| 1135. | 3-methoxy-N-methyl-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzamide |
| 1136. | 2-{3-[(4-methanesulfonyl-2-methoxyphenyl)amino]prop-1-yn-1-yl}-N-[(1R,4R)-4-[4-(trifluoromethyl)piperidin-1-yl]cyclohexyl]-1-(2,2,2-trifluoroethyl)-1H-indol-4-amine |
| 1137. | 2-(3-((2-methoxy-4-(methylsulfonyl)phenyl)amino)prop-1-yn-1-yl)-1-(2,2,2-trifluoroethyl)-N-((1S,4S)-4-(4-(trifluoromethyl)piperidin-1-yl)cyclohexyl)-1H-indol-4-amine |
| 1138. | 3-methoxy-N-methyl-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzamide |
| 1139. | 3-methoxy-N-methyl-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzamide |
| 1140. | 3-methoxy-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzene-1-sulfonamide |
| 1141. | 3-methoxy-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzenesulfonamide |
| 1142. | 2-{3-[(4-methanesulfonyl-2-methoxyphenyl)amino]prop-1-yn-1-yl}-N-[(1R,4R)-4-(4-methanesulfonylpiperidin-1-yl)cyclohexyl]-1-(2,2,2-trifluoroethyl)-1H-indol-4-amine |
| 1143. | 2-(3-((2-methoxy-4-(methylsulfonyl)phenyl)amino)prop-1-yn-1-yl)-N-((1S,4S)-4-(4-(methylsulfonyl)piperidin-1-yl)cyclohexyl)-1-(2,2,2-trifluoroethyl)-1H-indol-4-amine |
| 1144. | 3-methoxy-N-methyl-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzamide |
| 1145. | 3-methoxy-N-methyl-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzamide |
| 1146. | 3-methoxy-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzene-1-sulfonamide |
| 1147. | 3-methoxy-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzenesulfonamide |
| 1148. | 1-[(1S,3R)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-4,5-dihydro-1H-1,2,3,4-tetrazol-5-one |
| 1149. | 2-(3-((2-methoxy-4-(methylsulfonyl)phenyl)amino)prop-1-yn-1-yl)-N-((1R,4R)-4-morpholinocyclohexyl)-1-(oxiran-2-ylmethyl)-1H-indol-4-amine |
| 1150. | 2-((2-(3-((2-methoxy-4-(methylsulfonyl)phenyl)amino)prop-1-yn-1-yl)-4-(((1R,4R)-4-morpholinocyclohexyl)amino)-1H-indol-1-yl)methyl)acrylonitrile |
| 1151. | N-((1R,4R)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1152. | N-((1S,4S)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1153. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1154. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1155. | 1-[1-(2-hydroxyethyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea |
| 1156. | 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide |
| 1157. | [1-(chloromethyl)-3-[(2-{3-[(4-methanesulfonyl-2-methoxyphenyl)amino]prop-1-yn-1-yl}-1-(2,2,2-trifluoroethyl)-1H-indol-4-yl)amino]cyclobutyl]methanol |

TABLE 1-continued

Alkynyl indole compounds of the disclosure.

| Mol # | IUPAC name |
|---|---|
| 1158. | 2-{3-[(4-methanesulfonyl-2-methoxyphenyl)amino]prop-1-yn-1-yl}-N-{2-oxaspiro[3.3]heptan-6-yl}-1-(2,2,2-trifluoroethyl)-1H-indol-4-amine |
| 1159. | 4-({3-[4-({2-azaspiro[3.3]heptan-6-yl}amino)-1-(2,2,2-trifluoroethyl)-1H-indol-2-yl]prop-2-yn-1-yl}amino)-3-methoxybenzene-1-sulfonamide |
| 1160. | N-{2-azaspiro[3.3]heptan-6-yl}-2-{3-[(4-methanesulfonyl-2-methoxyphenyl)amino]prop-1-yn-1-yl}-1-(2,2,2-trifluoroethyl)-1H-indol-4-amine |
| 1161. | 3-methoxy-N-methyl-4-{[3-(4-{[(1R,4R)-4-(methylamino)cyclohexyl]amino}-1-(2,2,2-trifluoroethyl)-1H-indol-2-yl)prop-2-yn-1-yl]amino}benzamide |
| 1162. | 3-methoxy-N-methyl-4-{[3-(4-{[(1R,4R)-4-aminocyclohexyl]amino}-1-(2,2,2-trifluoroethyl)-1H-indol-2-yl)prop-2-yn-1-yl]amino}benzamide |
| 1163. | 3-methoxy-N-methyl-4-{[3-(4-{[(1S,4S)-4-aminocyclohexyl]amino}-1-(2,2,2-trifluoroethyl)-1H-indol-2-yl)prop-2-yn-1-yl]amino}benzamide |
| 1164. | rel-(1R,3R)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 1165. | rac-(1R,3S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 1166. | (1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine |
| 1167. | rac-(1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine |
| 1168. | rel-(1R,3S)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 1169. | 3-methoxy-N-methyl-4-{[3-(4-{[(1R,4R)-4-hydroxy-4-methylcyclohexyl]amino}-1-(2,2,2-trifluoroethyl)-1H-indol-2-yl)prop-2-yn-1-yl]amino}benzamide |
| 1170. | 3-methoxy-N-methyl-4-{[3-(4-{[(1S,4S)-4-hydroxy-4-methylcyclohexyl]amino}-1-(2,2,2-trifluoroethyl)-1H-indol-2-yl)prop-2-yn-1-yl]amino}benzamide |
| 1171. | 4-[(3-{4-[(4-cyanocyclohexyl)amino]-1-(2,2,2-trifluoroethyl)-1H-indol-2-yl}prop-2-yn-1-yl)amino]-3-methoxy-N-methylbenzamide |
| 1172. | 3-methoxy-N-methyl-4-{[3-(4-{[(1R,4R)-4-cyanocyclohexyl]amino}-1-(2,2,2-trifluoroethyl)-1H-indol-2-yl)prop-2-yn-1-yl]amino}benzamide |
| 1173. | 3-methoxy-N-methyl-4-{[3-(4-{[(1S,4S)-4-cyanocyclohexyl]amino}-1-(2,2,2-trifluoroethyl)-1H-indol-2-yl)prop-2-yn-1-yl]amino}benzamide |
| 1174. | 3-[(2-{3-[(4-methanesulfonyl-2-methoxyphenyl)amino]prop-1-yn-1-yl}-1-(2,2,2-trifluoroethyl)-1H-indol-4-yl)amino]cyclohexane-1-carboxylic acid |
| 1175. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 1176. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 1177. | 2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)-$N^4$-methylcyclohexane-1,4-diamine |
| 1178. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$-methylcyclohexane-1,4-diamine |
| 1179. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 1180. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 1181. | (3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 1182. | 3-methoxy-4-{[3-(4-{[(1R,4R)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 1183. | 3-methoxy-4-{[3-(4-{[(1S,4S)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 1184. | 4-((3-(4-(((1R,4R)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 1185. | 4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 1186. | 3-methoxy-N-(1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1187. | 3-methoxy-N-(oxan-4-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1188. | 3-methoxy-N-(1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1189. | 3-methoxy-N-(oxan-4-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1190. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1191. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1192. | 3-methoxy-N-(5-methyl-1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1193. | 3-methoxy-N-(5-methyl-1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 1194. | (1S,4S)-N$^4$-(2-{3-[(4-methanesulfonyl-2-methoxyphenyl)amino]prop-1-yn-1-yl}-1-(2,2,2-trifluoroethyl)-1H-indol-4-yl)-N$^1$-(2-methoxyethyl)-N$^1$-methylcyclohexane-1,4-diamine |
| 1195. | (1R,4R)-N$^4$-(2-{3-[(4-methanesulfonyl-2-methoxyphenyl)amino]prop-1-yn-1-yl}-1-(2,2,2-trifluoroethyl)-1H-indol-4-yl)-N$^1$-(2-methoxyethyl)-N$^1$-methylcyclohexane-1,4-diamine |
| 1196. | 3-methoxy-4-{[3-(4-{[(1S,4S)-4-[(3S,4S)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 1197. | 4-((3-(4-(((1R,4R)-4-((3R,4R)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 1198. | 4-((3-(4-(((1R,4S)-4-((3S,4S)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 1199. | 3-methoxy-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1200. | 3-methoxy-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1201. | 4-({3-[4-({1,4-dioxaspiro[4.5]decan-8-yl}amino)-1-(2,2,2-trifluoroethyl)-1H-indol-2-yl]prop-2-yn-1-yl}amino)-3-methoxybenzene-1-sulfonamide |
| 1202. | N-{1,4-dioxaspiro[4.5]decan-8-yl}-2-{3-[(4-methanesulfonyl-2-methoxyphenyl)amino]prop-1-yn-1-yl}-1-(2,2,2-trifluoroethyl)-1H-indol-4-amine |
| 1203. | 3-methoxy-4-[(3-{4-[(4-oxocyclohexyl)amino]-1-(2,2,2-trifluoroethyl)-1H-indol-2-yl}prop-2-yn-1-yl)amino]benzene-1-sulfonamide |
| 1204. | 4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-one |
| 1205. | (1R,4R)-N$^4$-[2-(3-{[2-methoxy-4-(morpholine-4-sulfonyl)phenyl]amino}prop-1-yn-1-yl)-1-(2,2,2-trifluoroethyl)-1H-indol-4-yl]-N$^1$,N$^1$-dimethylcyclohexane-1,4-diamine |
| 1206. | (1S,4S)-N$^4$-[2-(3-{[2-methoxy-4-(morpholine-4-sulfonyl)phenyl]amino}prop-1-yn-1-yl)-1-(2,2,2-trifluoroethyl)-1H-indol-4-yl]-N$^1$,N$^1$-dimethylcyclohexane-1,4-diamine |
| 1207. | N,N-bis(2-hydroxyethyl)-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1208. | N,N-bis(2-hydroxyethyl)-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1209. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1210. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1211. | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1212. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1213. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1214. | (1R,4R)-N$^4$-{2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}-N$^1$,N$^1$-dimethylcyclohexane-1,4-diamine |
| 1215. | (1R,4R)-N$^4$-(2-{3-[(4-methanesulfonyl-2-methoxyphenyl)amino]prop-1-yn-1-yl}-1-[(oxiran-2-yl)methyl]-1H-indol-4-yl)-N$^1$,N$^1$-dimethylcyclohexane-1,4-diamine |
| 1216. | 2-[(2-{3-[(4-methanesulfonyl-2-methoxyphenyl)amino]prop-1-yn-1-yl}-4-{[(1R,4R)-4-(dimethylamino)cyclohexyl]amino}-1H-indol-1-yl)methyl]prop-2-enenitrile |
| 1217. | 5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenol |
| 1218. | 5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenol |
| 1219. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)acetonitrile |
| 1220. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)acetonitrile |
| 1221. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)acetamide |
| 1222. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)acetamide |
| 1223. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)propanamide |
| 1224. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)propanamide |
| 1225. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)ethan-1-ol |
| 1226. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)ethan-1-ol |
| 1227. | (1R,4R)-N$^4$-[2-(3-{[4-methanesulfonyl-2-(2-methoxyethoxy)phenyl]amino}prop-1-yn-1-yl)-1-(2,2,2-trifluoroethyl)-1H-indol-4-yl]-N$^1$,N$^1$-dimethylcyclohexane-1,4-diamine |
| 1228. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 1229. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 1230. | (1R,4R)-N$^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-N$^1$,N$^1$-dimethylcyclohexane-1,4-diamine |

TABLE 1-continued

Alkynyl indole compounds of the disclosure.

| Mol # | IUPAC name |
|---|---|
| 1231. | (1S,4S)-N$^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-N$^1$,N$^1$-dimethylcyclohexane-1,4-diamine |
| 1232. | (1S,4S)-N$^4$-{2-[3-(2-amino-4-methanesulfonylphenoxy)prop-1-yn-1-yl]-1-(2,2,2-trifluoroethyl)-1H-indol-4-yl}-N$^1$,N$^1$-dimethylcyclohexane-1,4-diamine |
| 1233. | (1R,4R)-N$^4$-(2-{3-[(2-ethoxy-4-methanesulfonylphenyl)amino]prop-1-yn-1-yl}-1-(2,2,2-trifluoroethyl)-1H-indol-4-yl)-N$^1$,N$^1$-dimethylcyclohexane-1,4-diamine |
| 1234. | (1S,4S)-N$^4$-(2-{3-[(2-ethoxy-4-methanesulfonylphenyl)amino]prop-1-yn-1-yl}-1-(2,2,2-trifluoroethyl)-1H-indol-4-yl)-N$^1$,N$^1$-dimethylcyclohexane-1,4-diamine |
| 1235. | 3-hydroxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1236. | 3-hydroxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1237. | 3-(2-methoxyethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1238. | (1R,4R)-N$^4$-{2-[3-(2-amino-4-methanesulfonylphenoxy)prop-1-yn-1-yl]-1-(2,2,2-trifluoroethyl)-1H-indol-4-yl}-N$^1$,N$^1$-dimethylcyclohexane-1,4-diamine |
| 1239. | N-ethyl-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1240. | N-ethyl-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1241. | 3-(2-methoxyethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1242. | 3-(2-fluoroethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1243. | 3-(2-fluoroethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1244. | 3-(fluoromethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1245. | 3-(fluoromethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1246. | (1S,4S)-N$^4$-(2-{3-[4-methanesulfonyl-2-(methylamino)phenoxy]prop-1-yn-1-yl}-1-(2,2,2-trifluoroethyl)-1H-indol-4-yl)-N$^1$,N$^1$-dimethylcyclohexane-1,4-diamine |
| 1247. | (1R,4R)-N$^4$-(2-{3-[4-methanesulfonyl-2-(methylamino)phenoxy]prop-1-yn-1-yl}-1-(2,2,2-trifluoroethyl)-1H-indol-4-yl)-N$^1$,N$^1$-dimethylcyclohexane-1,4-diamine |
| 1248. | 3-methoxy-N-methyl-4-{[3-(4-{[(1S,4S)-4-(methylamino)cyclohexyl]amino}-1-(2,2,2-trifluoroethyl)-1H-indol-2-yl)prop-2-yn-1-yl]amino}benzamide |
| 1249. | (1S,4S)-N$^4$-(2-{3-[2-(dimethylamino)-4-methanesulfonylphenoxy]prop-1-yn-1-yl}-1-(2,2,2-trifluoroethyl)-1H-indol-4-yl)-N$^1$,N$^1$-dimethylcyclohexane-1,4-diamine |
| 1250. | (1R,4R)-N$^4$-(2-{3-[2-(dimethylamino)-4-methanesulfonylphenoxy]prop-1-yn-1-yl}-1-(2,2,2-trifluoroethyl)-1H-indol-4-yl)-N$^1$,N$^1$-dimethylcyclohexane-1,4-diamine |
| 1251. | 3-(cyanomethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1252. | 3-(2-cyanoethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1253. | N-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]oxy}phenyl)acetamide |
| 1254. | N-(2-((3-(4-(((1S,4S)-4-(dimethylamino)cyclohexyl)amino)-1-(2,2,2-trifluoroethyl)-1H-indol-2-yl)prop-2-yn-1-yl)oxy)-5-(methylsulfonyl)phenyl)acetamide |
| 1255. | (1R,4R)-N$^1$-(2-(3-((2-(fluoromethoxy)-4-(methylsulfonyl)phenyl)amino)prop-1-yn-1-yl)-1-(2,2,2-trifluoroethyl)-1H-indol-4-yl)-N$^4$,N$^4$-dimethylcyclohexane-1,4-diamine |
| 1256. | (1S,4S)-N$^1$-(2-(3-((2-(fluoromethoxy)-4-(methylsulfonyl)phenyl)amino)prop-1-yn-1-yl)-1-(2,2,2-trifluoroethyl)-1H-indol-4-yl)-N$^4$,N$^4$-dimethylcyclohexane-1,4-diamine |
| 1257. | (1R,4R)-N$^4$-[2-(3-{[4-(ethanesulfonyl)-2-methoxyphenyl]amino}prop-1-yn-1-yl)-1-(2,2,2-trifluoroethyl)-1H-indol-4-yl]-N$^1$,N$^1$-dimethylcyclohexane-1,4-diamine |
| 1258. | (1S,4S)-N$^4$-[2-(3-{[4-(ethanesulfonyl)-2-methoxyphenyl]amino}prop-1-yn-1-yl)-1-(2,2,2-trifluoroethyl)-1H-indol-4-yl]-N$^1$,N$^1$-dimethylcyclohexane-1,4-diamine |
| 1259. | 2-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}phenyl)-2-methylpropanenitrile |
| 1260. | 2-(4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxyphenyl)-2-methylpropanenitrile |
| 1261. | 3-(cyanomethoxy)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1262. | 3-(cyanomethoxy)-4-((3-(4-(((1S,4S)-4-(dimethylamino)cyclohexyl)amino)-1-(2,2,2-trifluoroethyl)-1H-indol-2-yl)prop-2-yn-1-yl)amino)benzenesulfonamide |
| 1263. | 3-(3-(4-(((1R,4R)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1264. | 3-(3-(4-(((1S,4S)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1265. | 3-methoxy-N,N-dimethyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1266. | (1R,4R)-N$^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-N$^4$,N$^4$-dimethylcyclohexane-1,4-diamine |
| 1267. | (1S,4S)-N$^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-N$^4$,N$^4$-dimethylcyclohexane-1,4-diamine |

TABLE 1-continued

Alkynyl indole compounds of the disclosure.

| Mol # | IUPAC name |
|---|---|
| 1268. | (1R,4R)-N$^4$-(2-{3-[(4-chloro-2-methoxyphenyl)amino]prop-1-yn-1-yl}-1-(2,2,2-trifluoroethyl)-1H-indol-4-yl)-N$^1$,N$^1$-dimethylcyclohexane-1,4-diamine |
| 1269. | (1S,4S)-N$^1$-(2-(3-((4-chloro-2-methoxyphenyl)amino)prop-1-yn-1-yl)-1-(2,2,2-trifluoroethyl)-1H-indol-4-yl)-N$^4$,N$^4$-dimethylcyclohexane-1,4-diamine |
| 1270. | 4-((3-(4-((((1R,4R)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 1271. | 4-((3-(4-((((1S,4S)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 1272. | (1R,4R)-N$^4$-[2-(3-{[2-methoxy-4-(trifluoromethyl)phenyl]amino}prop-1-yn-1-yl)-1-(2,2,2-trifluoroethyl)-1H-indol-4-yl]-N$^1$,N$^1$-dimethylcyclohexane-1,4-diamine |
| 1273. | (1S,4S)-N$^1$-(2-(3-((2-methoxy-4-(trifluoromethyl)phenyl)amino)prop-1-yn-1-yl)-1-(2,2,2-trifluoroethyl)-1H-indol-4-yl)-N$^4$,N$^4$-dimethylcyclohexane-1,4-diamine |
| 1274. | 2-fluoro-5-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1275. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxy-N-methylbenzamide |
| 1276. | (1S,4S)-N$^4$-[2-(3-{[4-methanesulfonyl-2-(trifluoromethyl)phenyl]amino}prop-1-yn-1-yl)-1-(2,2,2-trifluoroethyl)-1H-indol-4-yl]-N$^1$,N$^1$-dimethylcyclohexane-1,4-diamine |
| 1277. | (1R,4R)-N$^4$-[2-(3-{[4-methanesulfonyl-2-(trifluoromethyl)phenyl]amino}prop-1-yn-1-yl)-1-(2,2,2-trifluoroethyl)-1H-indol-4-yl]-N$^1$,N$^1$-dimethylcyclohexane-1,4-diamine |
| 1278. | (1R,4R)-N$^4$-(2-{3-[(4-methanesulfonyl-2-methylphenyl)amino]prop-1-yn-1-yl}-1-(2,2,2-trifluoroethyl)-1H-indol-4-yl)-N$^1$,N$^1$-dimethylcyclohexane-1,4-diamine |
| 1279. | (1S,4S)-N$^1$,N$^1$-dimethyl-N$^4$-(2-(3-((2-methyl-4-(methylsulfonyl)phenyl)amino)prop-1-yn-1-yl)-1-(2,2,2-trifluoroethyl)-1H-indol-4-yl)cyclohexane-1,4-diamine |
| 1280. | (1R,4R)-N$^4$-[2-(3-{[4-methanesulfonyl-2-(trifluoromethoxy)phenyl]amino}prop-1-yn-1-yl)-1-(2,2,2-trifluoroethyl)-1H-indol-4-yl]-N$^1$,N$^1$-dimethylcyclohexane-1,4-diamine |
| 1281. | (1S,4S)-N$^1$,N$^1$-dimethyl-N$^4$-(2-(3-((4-(methylsulfonyl)-2-(trifluoromethoxy)phenyl)amino)prop-1-yn-1-yl)-1-(2,2,2-trifluoroethyl)-1H-indol-4-yl)cyclohexane-1,4-diamine |
| 1282. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzamide |
| 1283. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxy-N-methylbenzamide |
| 1284. | 3-methoxy-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 1285. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxybenzenesulfonamide |
| 1286. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 1287. | 2-(5-methanesulfonyl-2-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 1288. | 2-(5-methanesulfonyl-2-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 1289. | 3-methoxy-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1290. | 3-methoxy-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1291. | N-ethyl-3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1292. | N-ethyl-3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzamide |
| 1293. | (1R,4R)-N$^1$-(2-(3-((2-(fluoromethoxy)-4-(methylsulfonyl)phenyl)amino)prop-1-yn-1-yl)-1-(2,2,2-trifluoroethyl)-1H-indol-4-yl)-N$^4$-(2-methoxyethyl)-N$^4$-methylcyclohexane-1,4-diamine |
| 1294. | (1S,4S)-N$^1$-(2-(3-((2-(fluoromethoxy)-4-(methylsulfonyl)phenyl)amino)prop-1-yn-1-yl)-1-(2,2,2-trifluoroethyl)-1H-indol-4-yl)-N$^4$-(2-methoxyethyl)-N$^4$-methylcyclohexane-1,4-diamine |
| 1295. | 3-(fluoromethoxy)-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1296. | 3-(fluoromethoxy)-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1297. | 3-(fluoromethoxy)-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)-N-methylbenzamide |
| 1298. | 3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1299. | 3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzenesulfonamide |
| 1300. | (1R,4R)-N$^1$,N$^1$-diethyl-N$^4$-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine |

TABLE 1-continued

Alkynyl indole compounds of the disclosure.

Mol #    IUPAC name 1301. (1S,4S)-N$^1$,N$^1$-diethyl-N$^4$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine 1302. 3-(cyanomethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide 1303. 3-(cyanomethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide 1304. 3-(fluoromethoxy)-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide 1305. 3-(fluoromethoxy)-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide 1306. 3-(fluoromethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide 1307. 3-(fluoromethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide 1308. 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide 1309. 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide 1310. 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide 1311. 3-methoxy-N-methyl-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide 1312. 2-(2-{3-[(4-methanesulfonyl-2-methoxyphenyl)amino]prop-1-yn-1-yl}-4-{[(1R,4R)-4-(morpholin-4-yl)cyclohexyl]amino}-1H-indol-1-yl)acetonitrile 1313. 4-({3-[1-(2-fluoroethyl)-4-{[(1R,4R)-4-(morpholin-4-yl)cyclohexyl]amino}-1H-indol-2-yl]prop-2-yn-1-yl}amino)-3-methoxy-N-methylbenzamide 1314. 1-(2-fluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine 1315. 4-({3-[1-(cyanomethyl)-4-{[(1R,4R)-4-(morpholin-4-yl)cyclohexyl]amino}-1H-indol-2-yl]prop-2-yn-1-yl}amino)-3-methoxy-N-methylbenzamide 1316. 2-{3-[(4-methanesulfonyl-2-methoxyphenyl)amino]prop-1-yn-1-yl}-1-propyl-N-[(1R,4R)-4-(morpholin-4-yl)cyclohexyl]-1H-indol-4-amine 1317. 2-{3-[(4-methanesulfonyl-2-methoxyphenyl)amino]prop-1-yn-1-yl}-1-(2-methylpropyl)-N-[(1R,4R)-4-(morpholin-4-yl)cyclohexyl]-1H-indol-4-amine 1318. 1-(2,2-difluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine 1319. 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide 1320. 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide 1321. N-ethyl-3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide 1322. N-ethyl-3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzamide 1323. 2-(5-methanesulfonyl-2-{[3-(4-{[(1R,4R)-4-(morpholin-4-yl)cyclohexyl]amino}-1-(2,2,2-trifluoroethyl)-1H-indol-2-yl)prop-2-yn-1-yl]amino}phenoxy)acetonitrile 1324. 2-(5-methanesulfonyl-2-{[3-(4-{[(1S,4S)-4-(morpholin-4-yl)cyclohexyl]amino}-1-(2,2,2-trifluoroethyl)-1H-indol-2-yl)prop-2-yn-1-yl]amino}phenoxy)acetonitrile 1325. 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide 1326. 2-{3-[(4-methanesulfonyl-2-methoxyphenyl)amino]prop-1-yn-1-yl}-N-[(1R,4R)-4-(3-methanesulfonylazetidin-1-yl)cyclohexyl]-1-(2,2,2-trifluoroethyl)-1H-indol-4-amine 1327. 2-(3-((2-methoxy-4-(methylsulfonyl)phenyl)amino)prop-1-yn-1-yl)-N-((1S,4S)-4-(3-(methylsulfonyl)azetidin-1-yl)cyclohexyl)-1-(2,2,2-trifluoroethyl)-1H-indol-4-amine 1328. 3-methoxy-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzene-1-sulfonamide 1329. 3-methoxy-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzenesulfonamide 1330. 3-methoxy-N-methyl-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzamide 1331. 3-methoxy-N-methyl-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzamide 1332. 2-{3-[(4-methanesulfonyl-2-methoxyphenyl)amino]prop-1-yn-1-yl}-N-[(1R,4R)-4-{2-azaspiro[3.3]heptan-2-yl}cyclohexyl]-1-(2,2,2-trifluoroethyl)-1H-indol-4-amine 1333. N-((1S,4S)-4-(2-azaspiro[3.3]heptan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine 1334. 3-methoxy-N-methyl-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzamide TABLE 1-continued Alkynyl indole compounds of the disclosure.

| Mol # | IUPAC name |
|---|---|
| 1335. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxy-N-methylbenzamide |
| 1336. | 3-methoxy-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzene-1-sulfonamide |
| 1337. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxybenzenesulfonamide |
| 1338. | 2-(3-((2-methoxy-4-(methylsulfonyl)phenyl)amino)prop-1-yn-1-yl)-N-(2-azaspiro[3.3]heptan-6-yl)-1-(2,2,2-trifluoroethyl)-1H-indol-4-amine |
| 1339. | 4-((3-(4-((2-azaspiro[3.3]heptan-6-yl)amino)-1-(2,2,2-trifluoroethyl)-1H-indol-2-yl)prop-2-yn-1-yl)amino)-3-methoxybenzenesulfonamide |
| 1340. | 2-{3-[(4-methanesulfonyl-2-methoxyphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1341. | 2-{3-[(4-methanesulfonyl-2-methoxyphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 1342. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1343. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1344. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 1345. | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 1346. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 1347. | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 1348. | N-((1R,4R)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 1349. | N-((1S,4S)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 1350. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1351. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1352. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 1353. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 1354. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1355. | N-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1356. | N-(2-hydroxy-4-methanesulfonylphenyl)-2-methyl-N-[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]propanamide |
| 1357. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 1358. | 2-(3-{[4-methanesulfonyl-2-(2-methoxyethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1359. | 2-(3-{[4-methanesulfonyl-2-(2-methoxyethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 1360. | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 1361. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 1362. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 1363. | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |

TABLE 1-continued

Alkynyl indole compounds of the disclosure.

| Mol # | IUPAC name |
|---|---|
| 1364. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 1365. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)acetamide |
| 1366. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 1367. | 3-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1368. | 3-methoxy-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1369. | 2-(3-{[4-methanesulfonyl-2-(2,2,2-trifluoroethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1370. | 2-(3-{[4-methanesulfonyl-2-(2,2,2-trifluoroethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 1371. | 2-[3-(2-amino-4-methanesulfonylphenoxy)prop-1-yn-1-yl]-N-[(1S,4S)-4-{2-oxa-6-azaspiro[3.3]heptan-6-yl}cyclohexyl]-1-(2,2,2-trifluoroethyl)-1H-indol-4-amine |
| 1372. | 2-{3-[(2-ethoxy-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1373. | 2-{3-[(2-ethoxy-4-methanesulfonylphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 1374. | 3-(2-methoxyethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1375. | 3-(2-methoxyethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1376. | N-ethyl-3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1377. | N-ethyl-3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1378. | 3-(2-fluoroethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1379. | 3-(2-fluoroethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1380. | 3-(cyanomethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1381. | 3-(cyanomethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1382. | 2-{3-[4-methanesulfonyl-2-(methylamino)phenoxy]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 1383. | 2-{3-[4-methanesulfonyl-2-(methylamino)phenoxy]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1384. | 2-[3-(2-amino-4-methanesulfonylphenoxy)prop-1-yn-1-yl]-N-[(1R,4R)-4-{2-oxa-6-azaspiro[3.3]heptan-6-yl}cyclohexyl]-1-(2,2,2-trifluoroethyl)-1H-indol-4-amine |
| 1385. | N-((1R,4R)-4-(2-oxa-6-azaspiro[3.3]heptan-6-yl)cyclohexyl)-2-(3-(2-amino-4-(methylsulfonyl)phenoxy)prop-1-yn-1-yl)-1-(2,2,2-trifluoroethyl)-1H-indol-4-amine |
| 1386. | 3-hydroxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1387. | 3-methoxy-4-[(3-{4-[(4-{2-oxa-6-azaspiro[3.3]heptan-6-yl}cyclohexyl)amino]-1-(2,2,2-trifluoroethyl)-1H-indol-2-yl}prop-2-yn-1-yl)amino]benzonitrile |
| 1388. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzonitrile |
| 1389. | 2-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl)-2-methylpropanenitrile |
| 1390. | 2-(4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxyphenyl)-2-methylpropanenitrile |

TABLE 1-continued

Alkynyl indole compounds of the disclosure.

| Mol # | IUPAC name |
|---|---|
| 1391. | 3-(fluoromethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1392. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(fluoromethoxy)-N-methylbenzamide |
| 1393. | 3-(2-cyanoethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1394. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(2-cyanoethoxy)-N-methylbenzamide |
| 1395. | 2-(3-{[2-(fluoromethoxy)-4-methanesulfonylphenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1396. | N-((1S,4S)-4-(2-oxa-6-azaspiro[3.3]heptan-6-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1397. | 3-(cyanomethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1398. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(cyanomethoxy)benzenesulfonamide |
| 1399. | 3-(fluoromethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1400. | 3-(fluoromethoxy)-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1401. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 1402. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 1403. | N-((1R,4R)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 1404. | N-((1S,4S)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 1405. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 1406. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 1407. | N-((1R,4R)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1408. | N-((1S,4S)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1409. | N-((1R,4R)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 1410. | N-((1S,4S)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 1411. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1412. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzamide |
| 1413. | 2-fluoro-5-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1414. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxy-N-methylbenzamide |
| 1415. | 2-(3-{[2-methoxy-4-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1416. | N-((1S,4S)-4-(2-oxa-6-azaspiro[3.3]heptan-6-yl)cyclohexyl)-2-(3-((2-methoxy-4-(trifluoromethyl)phenyl)amino)prop-1-yn-1-yl)-1-(2,2,2-trifluoroethyl)-1H-indol-4-amine |
| 1417. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 1418. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 1419. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzoic acid |

TABLE 1-continued

Alkynyl indole compounds of the disclosure.

| Mol # | IUPAC name |
|---|---|
| 1420. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzoic acid |
| 1421. | 2-{3-[(4-methanesulfonyl-2-methylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1422. | N-((1S,4S)-4-(2-oxa-6-azaspiro[3.3]heptan-6-yl)cyclohexyl)-2-(3-((2-methyl-4-(methylsulfonyl)phenyl)amino)prop-1-yn-1-yl)-1-(2,2,2-trifluoroethyl)-1H-indol-4-amine |
| 1423. | 2-(3-{[4-methanesulfonyl-2-(trifluoromethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1424. | N-((1S,4S)-4-(2-oxa-6-azaspiro[3.3]heptan-6-yl)cyclohexyl)-2-(3-((4-(methylsulfonyl)-2-(trifluoromethoxy)phenyl)amino)prop-1-yn-1-yl)-1-(2,2,2-trifluoroethyl)-1H-indol-4-amine |
| 1425. | 2-(3-{[4-methanesulfonyl-2-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1426. | N-((1S,4S)-4-(2-oxa-6-azaspiro[3.3]heptan-6-yl)cyclohexyl)-2-(3-((4-(methylsulfonyl)-2-(trifluoromethyl)phenyl)amino)prop-1-yn-1-yl)-1-(2,2,2-trifluoroethyl)-1H-indol-4-amine |
| 1427. | 2-{3-[(2-chloro-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1428. | N-((1S,4S)-4-(2-oxa-6-azaspiro[3.3]heptan-6-yl)cyclohexyl)-2-(3-((2-chloro-4-(methylsulfonyl)phenyl)amino)prop-1-yn-1-yl)-1-(2,2,2-trifluoroethyl)-1H-indol-4-amine |
| 1429. | 3-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1430. | 3-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1431. | 2-{3-[(4-methanesulfonyl-2-methoxyphenyl)amino]prop-1-yn-1-yl}-N-[(1S,4S)-4-{7-oxa-2-azaspiro[3.5]nonan-2-yl}cyclohexyl]-1-(2,2,2-trifluoroethyl)-1H-indol-4-amine |
| 1432. | 2-{3-[(4-methanesulfonyl-2-methoxyphenyl)amino]prop-1-yn-1-yl}-N-[(1R,4R)-4-{7-oxa-2-azaspiro[3.5]nonan-2-yl}cyclohexyl]-1-(2,2,2-trifluoroethyl)-1H-indol-4-amine |
| 1433. | 3-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1434. | 3-methoxy-N-methyl-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1435. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1436. | 3-methoxy-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1437. | 3-(cyanomethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1438. | 3-(cyanomethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1439. | 2-(3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenyl)-2-methylpropanenitrile |
| 1440. | 2-(4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 1441. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1442. | 2-(5-methanesulfonyl-2-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1443. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1444. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1445. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1446. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1447. | methyl 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetate |
| 1448. | methyl 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate |
| 1449. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetic acid |

TABLE 1-continued

Alkynyl indole compounds of the disclosure.

| Mol # | IUPAC name |
|---|---|
| 1450. | 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetic acid |
| 1451. | 2-{3-[(4-methanesulfonyl-2-methoxyphenyl)amino]prop-1-yn-1-yl}-N-[(1R,4R)-4-{2-oxa-7-azaspiro[3.5]nonan-7-yl}cyclohexyl]-1-(2,2,2-trifluoroethyl)-1H-indol-4-amine |
| 1452. | 2-(3-{[4-(ethanesulfonyl)-2-methoxyphenyl]amino}prop-1-yn-1-yl)-N-[(1R,4R)-4-{7-oxa-2-azaspiro[3.5]nonan-2-yl}cyclohexyl]-1-(2,2,2-trifluoroethyl)-1H-indol-4-amine |
| 1453. | 2-(3-{[4-(ethanesulfonyl)-2-methoxyphenyl]amino}prop-1-yn-1-yl)-N-[(1S,4S)-4-{7-oxa-2-azaspiro[3.5]nonan-2-yl}cyclohexyl]-1-(2,2,2-trifluoroethyl)-1H-indol-4-amine |
| 1454. | 3-(fluoromethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1455. | 3-(fluoromethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1456. | 3-methoxy-N-methyl-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1457. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzamide |
| 1458. | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1459. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzenesulfonamide |
| 1460. | 2-{3-[(4-methanesulfonyl-2-methoxyphenyl)amino]prop-1-yn-1-yl}-N-[(1R,4R)-4-{6-oxa-2-azaspiro[3.5]nonan-2-yl}cyclohexyl]-1-(2,2,2-trifluoroethyl)-1H-indol-4-amine |
| 1461. | N-((1S,4S)-4-(6-oxa-2-azaspiro[3.5]nonan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1462. | N-((1R,4R)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1463. | N-((1S,4S)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1464. | 4-(3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)-7-(methylsulfonyl)-2H-benzo[b][1,4]oxazin-3(4H)-one |
| 1465. | 4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |
| 1466. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |
| 1467. | N-((1R,4R)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1468. | N-((1S,4S)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1469. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1470. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1471. | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1472. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1473. | 2-fluoro-5-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1474. | 2-(3-((2-methoxy-4-(methylsulfonyl)phenyl)amino)prop-1-yn-1-yl)-N-((1R,4R)-4-(3-methoxypyrrolidin-1-yl)cyclohexyl)-1-(2,2,2-trifluoroethyl)-1H-indol-4-amine |
| 1475. | 2-(3-((2-methoxy-4-(methylsulfonyl)phenyl)amino)prop-1-yn-1-yl)-N-((1S,4S)-4-(3-methoxypyrrolidin-1-yl)cyclohexyl)-1-(2,2,2-trifluoroethyl)-1H-indol-4-amine |
| 1476. | 3-methoxy-4-((3-(4-(((1R,4R)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1477. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1478. | 2-(3-{[2-(fluoromethoxy)-4-methanesulfonylphenyl]amino}prop-1-yn-1-yl)-N-[(1R,4R)-4-(morpholin-4-yl)cyclohexyl]-1-(2,2,2-trifluoroethyl)-1H-indol-4-amine |
| 1479. | 2-(3-{[2-(fluoromethoxy)-4-methanesulfonylphenyl]amino}prop-1-yn-1-yl)-N-[(1S,4S)-4-(morpholin-4-yl)cyclohexyl]-1-(2,2,2-trifluoroethyl)-1H-indol-4-amine |
| 1480. | 3-(cyanomethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1481. | 3-(cyanomethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1482. | 3-(fluoromethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1483. | 3-(fluoromethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1484. | 2-(3-((2-ethoxy-4-(methylsulfonyl)phenyl)amino)prop-1-yn-1-yl)-N-((1R,4R)-4-morpholinocyclohexyl)-1-(2,2,2-trifluoroethyl)-1H-indol-4-amine |

TABLE 1-continued

Alkynyl indole compounds of the disclosure.

| Mol # | IUPAC name |
|---|---|
| 1485. | 2-(3-((2-ethoxy-4-(methylsulfonyl)phenyl)amino)prop-1-yn-1-yl)-N-((1S,4S)-4-morpholinocyclohexyl)-1-(2,2,2-trifluoroethyl)-1H-indol-4-amine |
| 1486. | 2-{3-[(4-methanesulfonyl-2-methoxyphenyl)amino]prop-1-yn-1-yl}-N-[(1R,4R)-4-(3-methoxypiperidin-1-yl)cyclohexyl]-1-(2,2,2-trifluoroethyl)-1H-indol-4-amine |
| 1487. | 2-(3-((2-methoxy-4-(methylsulfonyl)phenyl)amino)prop-1-yn-1-yl)-N-((1S,4S)-4-(3-methoxypiperidin-1-yl)cyclohexyl)-1-(2,2,2-trifluoroethyl)-1H-indol-4-amine |
| 1488. | 2-{3-[(4-methanesulfonyl-2-methoxyphenyl)amino]prop-1-yn-1-yl}-N-[(1R,4R)-4-(4-methoxypiperidin-1-yl)cyclohexyl]-1-(2,2,2-trifluoroethyl)-1H-indol-4-amine |
| 1489. | 2-(3-((2-methoxy-4-(methylsulfonyl)phenyl)amino)prop-1-yn-1-yl)-N-((1S,4S)-4-(4-methoxypiperidin-1-yl)cyclohexyl)-1-(2,2,2-trifluoroethyl)-1H-indol-4-amine |
| 1490. | 3-methoxy-N-methyl-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzamide |
| 1491. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)-N-methylbenzamide |
| 1492. | 3-methoxy-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1493. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)benzenesulfonamide |
| 1494. | 3-methoxy-N-methyl-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzamide |
| 1495. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)-N-methylbenzamide |
| 1496. | 3-methoxy-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1497. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)benzenesulfonamide |
| 1498. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 1499. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 1500. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^6$-thiomorpholine-1,1-dione |
| 1501. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1,1-dioxide |
| 1502. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^4$-thiomorpholin-1-one |
| 1503. | 4-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^4$-thiomorpholin-1-one |
| 1504. | 4-((3-(4-(((1R,4R)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1505. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1506. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1-oxide |
| 1507. | 3-methoxy-N-methyl-4-{[3-(4-{[(1R,4R)-4-(1-oxo-1$\lambda^4$-thiomorpholin-4-yl)cyclohexyl]amino}-1-(2,2,2-trifluoroethyl)-1H-indol-2-yl)prop-2-yn-1-yl]amino}benzamide |
| 1508. | 3-methoxy-4-{[3-(4-{[(1R,4R)-4-(1-oxo-1$\lambda^4$-thiomorpholin-4-yl)cyclohexyl]amino}-1-(2,2,2-trifluoroethyl)-1H-indol-2-yl)prop-2-yn-1-yl]amino}benzene-1-sulfonamide |
| 1509. | 3-methoxy-4-((3-(4-(((1S,4S)-4-(1-oxidothiomorpholino)cyclohexyl)amino)-1-(2,2,2-trifluoroethyl)-1H-indol-2-yl)prop-2-yn-1-yl)amino)benzenesulfonamide |
| 1510. | 3-methoxy-4-{[3-(4-{[(1R,4R)-4-(1,1-dioxo-1$\lambda^6$-thiomorpholin-4-yl)cyclohexyl]amino}-1-(2,2,2-trifluoroethyl)-1H-indol-2-yl)prop-2-yn-1-yl]amino}benzene-1-sulfonamide |
| 1511. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxybenzenesulfonamide |
| 1512. | 2-{3-[(4-methanesulfonyl-2-methoxyphenyl)amino]prop-1-yn-1-yl}-N-[(1S,4S)-4-{2-oxa-7-azaspiro[3.5]nonan-7-yl}cyclohexyl]-1-(2,2,2-trifluoroethyl)-1H-indol-4-amine |
| 1513. | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1514. | 3-methoxy-N-methyl-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1515. | 3-methoxy-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1516. | 4-((3-(4-(((1S,4S)-4-(2-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide |
| 1517. | 3-(cyanomethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1518. | 3-(cyanomethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

Mol #    IUPAC name 1519. 3-(fluoromethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1520. 3-(fluoromethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1521. 2-{3-[(4-methanesulfonyl-2-methoxyphenyl)amino]prop-1-yn-1-yl}-N-[(1R,4R)-4-{1-oxa-7-azaspiro[3.5]nonan-7-yl}cyclohexyl]-1-(2,2,2-trifluoroethyl)-1H-indol-4-amine
1522. N-((1S,4S)-4-(1-oxa-7-azaspiro[3.5]nonan-7-yl)cyclohexyl)-2-(3-((2-methoxy-4-(methylsulfonyl)phenyl)amino)prop-1-yn-1-yl)-1-(2,2,2-trifluoroethyl)-1H-indol-4-amine
1523. 3-methoxy-N-methyl-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzamide
1524. 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxy-N-methylbenzamide
1525. 3-methoxy-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1526. 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide
1527. 2-(5-methanesulfonyl-2-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile
1528. 2-(5-methanesulfonyl-2-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile
1529. 2-(3-{[2-(fluoromethoxy)-4-methanesulfonylphenyl]amino}prop-1-yn-1-yl)-N-[(1R,4R)-4-{2-oxa-7-azaspiro[3.5]nonan-7-yl}cyclohexyl]-1-(2,2,2-trifluoroethyl)-1H-indol-4-amine
1530. 2-(3-{[2-(fluoromethoxy)-4-methanesulfonylphenyl]amino}prop-1-yn-1-yl)-N-[(1S,4S)-4-{2-oxa-7-azaspiro[3.5]nonan-7-yl}cyclohexyl]-1-(2,2,2-trifluoroethyl)-1H-indol-4-amine
1531. N-((1R,4R)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine
1532. N-((1S,4S)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine
1533. 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide
1534. N-((1R,4R)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine
1535. N-((1S,4S)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine
1536. 2-{3-[(4-methanesulfonyl-2-methoxyphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine
1537. 2-{3-[(4-methanesulfonyl-2-methoxyphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine
1538. 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide
1539. 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide
1540. 3-methoxy-N-methyl-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide
1541. 3-methoxy-N-methyl-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide
1542. 2-{3-[(2-ethoxy-4-methanesulfonylphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine
1543. 2-{3-[(2-ethoxy-4-methanesulfonylphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine
1544. N-ethyl-3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide
1545. 2-(5-methanesulfonyl-2-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}phenoxy)acetonitrile
1546. 2-(2-((3-(4-(((1S,4S)-4-(6-oxa-3-azabicyclo[3.1.1]heptan-3-yl)cyclohexyl)amino)-1-(2,2,2-trifluoroethyl)-1H-indol-2-yl)prop-2-yn-1-yl)amino)-5-(methylsulfonyl)phenoxy)acetonitrile
1547. 3-methoxy-N-methyl-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzamide
1548. 2-{3-[(4-methanesulfonyl-2-methoxyphenyl)amino]prop-1-yn-1-yl}-N-[(1R,4R)-4-{2-oxa-8-azaspiro[4.5]decan-8-yl}cyclohexyl]-1-(2,2,2-trifluoroethyl)-1H-indol-4-amine
1549. 3-methoxy-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzene-1-sulfonamide TABLE 1-continued Alkynyl indole compounds of the disclosure.

| Mol # | IUPAC name |
|---|---|
| 1550. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1551. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1552. | 2-{3-[(4-methanesulfonyl-2-methoxyphenyl)amino]prop-1-yn-1-yl}-N-[(1R,4R)-4-{3-oxa-9-azaspiro[5.5]undecan-9-yl}cyclohexyl]-1-(2,2,2-trifluoroethyl)-1H-indol-4-amine |
| 1553. | N-((1S,4S)-4-(3-oxa-9-azaspiro[5.5]undecan-9-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1554. | 3-methoxy-N-methyl-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzamide |
| 1555. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxy-N-methylbenzamide |
| 1556. | 3-methoxy-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzene-1-sulfonamide |
| 1557. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxybenzenesulfonamide |
| 1558. | 3-methoxy-N-methyl-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzamide |
| 1559. | 3-methoxy-N-methyl-4-((3-(4-(((1S,4S)-4-(pyrrolidin-1-yl)cyclohexyl)amino)-1-(2,2,2-trifluoroethyl)-1H-indol-2-yl)prop-2-yn-1-yl)amino)benzamide |
| 1560. | 3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide |
| 1561. | 3-methoxy-4-((3-(4-(((1S,4S)-4-(pyrrolidin-1-yl)cyclohexyl]amino)-1-(2,2,2-trifluoroethyl)-1H-indol-2-yl)prop-2-yn-1-yl)amino)benzenesulfonamide |
| 1562. | 2-{3-[(4-methanesulfonyl-2-methoxyphenyl)amino]prop-1-yn-1-yl}-N-[(1R,4R)-4-(pyrrolidin-1-yl)cyclohexyl]-1-(2,2,2-trifluoroethyl)-1H-indol-4-amine |
| 1563. | 2-(3-((2-methoxy-4-(methylsulfonyl)phenyl)amino)prop-1-yn-1-yl)-N-((1S,4S)-4-(pyrrolidin-1-yl)cyclohexyl)-1-(2,2,2-trifluoroethyl)-1H-indol-4-amine |
| 1564. | 2-{3-[(4-methanesulfonyl-2-methoxyphenyl)amino]prop-1-yn-1-yl}-N-[(1R,4R)-4-(3-methoxypyrrolidin-1-yl)cyclohexyl]-1-(2,2,2-trifluoroethyl)-1H-indol-4-amine |
| 1565. | 3-methoxy-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzene-1-sulfonamide |
| 1566. | 3-methoxy-N-methyl-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzamide |
| 1567. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)-N-methylbenzamide |
| 1568. | 3-methoxy-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzene-1-sulfonamide |
| 1569. | 3-methoxy-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzenesulfonamide |
| 1570. | 2-{3-[(4-methanesulfonyl-2-methoxyphenyl)amino]prop-1-yn-1-yl}-N-[(1R,4R)-4-{hexahydro-1H-furo[3,4-c]pyrrol-5-yl}cyclohexyl]-1-(2,2,2-trifluoroethyl)-1H-indol-4-amine |
| 1571. | 2-(3-((2-methoxy-4-(methylsulfonyl)phenyl)amino)prop-1-yn-1-yl)-N-((1R,4R)-4-(tetrahydro-1H-furo[3,4-c]pyrrol-5(3H)-yl)cyclohexyl)-1-(2,2,2-trifluoroethyl)-1H-indol-4-amine |
| 1572. | 3-methoxy-N-methyl-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzamide |
| 1573. | 3-methoxy-N-methyl-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzamide |
| 1574. | 2-{3-[(4-methanesulfonyl-2-methoxyphenyl)amino]prop-1-yn-1-yl}-N-[(1R,4R)-4-[4-(trifluoromethyl)piperidin-1-yl]cyclohexyl]-1-(2,2,2-trifluoroethyl)-1H-indol-4-amine |
| 1575. | 2-(3-((2-methoxy-4-(methylsulfonyl)phenyl)amino)prop-1-yn-1-yl)-1-(2,2,2-trifluoroethyl)-N-((1S,4S)-4-(4-(trifluoromethyl)piperidin-1-yl)cyclohexyl)-1H-indol-4-amine |
| 1576. | 3-methoxy-N-methyl-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzamide |
| 1577. | 3-methoxy-N-methyl-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzamide |
| 1578. | 3-methoxy-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzene-1-sulfonamide |
| 1579. | 3-methoxy-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzenesulfonamide |
| 1580. | 2-{3-[(4-methanesulfonyl-2-methoxyphenyl)amino]prop-1-yn-1-yl}-N-[(1R,4R)-4-(4-methanesulfonylpiperidin-1-yl)cyclohexyl]-1-(2,2,2-trifluoroethyl)-1H-indol-4-amine |
| 1581. | 2-(3-((2-methoxy-4-(methylsulfonyl)phenyl)amino)prop-1-yn-1-yl)-N-((1S,4S)-4-(4-(methylsulfonyl)piperidin-1-yl)cyclohexyl)-1-(2,2,2-trifluoroethyl)-1H-indol-4-amine |

TABLE 1-continued

Alkynyl indole compounds of the disclosure.

| Mol # | IUPAC name |
|---|---|
| 1582. | 3-methoxy-N-methyl-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzamide |
| 1583. | 3-methoxy-N-methyl-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzamide |
| 1584. | 3-methoxy-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzene-1-sulfonamide |
| 1585. | 3-methoxy-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzenesulfonamide |
| 1586. | 1-[(1S,3R)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-4,5-dihydro-1H-1,2,3,4-tetrazol-5-one |
| 1587. | 2-((2-(3-((2-methoxy-4-(methylsulfonyl)phenyl)amino)prop-1-yn-1-yl)-4-(((1R,4R)-4-morpholinocyclohexyl)amino)-1H-indol-1-yl)methyl)acrylonitrile |
| 1588. | N-((1R,4R)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1589. | N-((1S,4S)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1590. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1591. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1592. | 1-{3-[(2-{3-[(4-methanesulfonyl-2-methoxyphenyl)amino]prop-1-yn-1-yl}-1-(2,2,2-trifluoroethyl)-1H-indol-4-yl)amino]pyrrolidin-1-yl}-3-methoxypropan-2-ol |
| 1593. | N-[3-(4-{[1-(2-hydroxy-3-methoxypropyl)pyrrolidin-3-yl]amino}-1-(2,2,2-trifluoroethyl)-1H-indol-2-yl)prop-2-yn-1-yl]benzamide |
| 1594. | 1-{3-[(2-{3-[(4-methanesulfonylphenyl)amino]prop-1-yn-1-yl}-1-(2,2,2-trifluoroethyl)-1H-indol-4-yl)amino]pyrrolidin-1-yl}-3-methoxypropan-2-ol |
| 1595. | 2-{3-[(4-methanesulfonyl-2-methoxyphenyl)amino]prop-1-yn-1-yl}-N-[1-(oxan-4-yl)pyrrolidin-3-yl]-1-(2,2,2-trifluoroethyl)-1H-indol-4-amine |
| 1596. | 2-(3-{[2-methoxy-4-(morpholine-4-sulfonyl)phenyl]amino}prop-1-yn-1-yl)-N-(piperidin-4-yl)-1-(2,2,2-trifluoroethyl)-1H-indol-4-amine |
| 1597. | 3-methoxy-N,N-dimethyl-4-[(3-{4-[(piperidin-4-yl)amino]-1-(2,2,2-trifluoroethyl)-1H-indol-2-yl}prop-2-yn-1-yl)amino]benzene-1-sulfonamide |
| 1598. | 2-{5-methanesulfonyl-2-[(3-{4-[(piperidin-4-yl)amino]-1-(2,2,2-trifluoroethyl)-1H-indol-2-yl}prop-2-yn-1-yl)amino]phenoxy}acetonitrile |
| 1599. | 3-methoxy-4-((3-(4-(piperidin-4-ylamino)-1-(2,2,2-trifluoroethyl)-1H-indol-2-yl)prop-2-yn-1-yl)amino)benzamide |
| 1600. | 2-{3-[(4-methanesulfonyl-2-methoxyphenyl)amino]prop-1-yn-1-yl}-N-[(3R)-piperidin-3-yl]-1-(2,2,2-trifluoroethyl)-1H-indol-4-amine |
| 1601. | 3-methoxy-4-{[3-(4-{[(2S,4S)-2-methylpiperidin-4-yl]amino}-1-(2,2,2-trifluoroethyl)-1H-indol-2-yl)prop-2-yn-1-yl]amino}benzene-1-sulfonamide |
| 1602. | 3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide |
| 1603. | 2-(3-{[4-methanesulfonyl-2-(trifluoromethoxy)phenyl]amino}prop-1-yn-1-yl)-N-(1-methylpiperidin-4-yl)-1-(2,2,2-trifluoroethyl)-1H-indol-4-amine |
| 1604. | N-(1-methylpiperidin-4-yl)-2-(3-((4-(methylsulfonyl)-2-(2,2,2-trifluoroethoxy)phenyl)amino)prop-1-yn-1-yl)-1-(2,2,2-trifluoroethyl)-1H-indol-4-amine |
| 1605. | 2-{4-methoxy-5-[(3-{4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 1606. | 3-methoxy-4-[(3-{4-[(1-methylpiperidin-4-yl)amino]-1-(2,2,2-trifluoroethyl)-1H-indol-2-yl}prop-2-yn-1-yl)amino]-N-(1,2-oxazol-3-yl)benzene-1-sulfonamide |
| 1607. | 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzene-1-sulfonamide |
| 1608. | 3-methoxy-N-(5-methyl-1,2-oxazol-3-yl)-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1609. | N-(2-hydroxyethyl)-3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1610. | 3-methoxy-N,N-dimethyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1611. | 4-[(3-{6-fluoro-4-[(1-methylpiperidin-4-yl)amino]-1-(2,2,2-trifluoroethyl)-1H-indol-2-yl}prop-2-yn-1-yl)amino]-3-methoxybenzene-1-sulfonamide |
| 1612. | 6-fluoro-2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 1613. | 2-(3-((4-methoxy-6-(methylsulfonyl)pyridin-3-yl)amino)prop-1-yn-1-yl)-N-(1-methylpiperidin-4-yl)-1-(2,2,2-trifluoroethyl)-1H-indol-4-amine |
| 1614. | 3-methoxy-N-(2-methoxyethyl)-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1615. | 2-{3-[(4-methanesulfonyl-2-methoxyphenyl)(methyl)amino]prop-1-yn-1-yl}-N-(1-methylpiperidin-4-yl)-1-(2,2,2-trifluoroethyl)-1H-indol-4-amine |

TABLE 1-continued

Alkynyl indole compounds of the disclosure.

| Mol # | IUPAC name |
|---|---|
| 1616. | 1-(4-{3-methoxy-4-[(3-{4-[(1-methylpiperidin-4-yl)amino]-1-(2,2,2-trifluoroethyl)-1H-indol-2-yl}prop-2-yn-1-yl)amino]benzenesulfonyl}piperazin-1-yl)ethan-1-one |
| 1617. | 2-(3-{[2-methoxy-4-(morpholine-4-sulfonyl)phenyl]amino}prop-1-yn-1-yl)-N-(1-methylpiperidin-4-yl)-1-(2,2,2-trifluoroethyl)-1H-indol-4-amine |
| 1618. | 3-methoxy-4-((3-(4-((1-methylpiperidin-4-yl)amino)-1-(2,2,2-trifluoroethyl)-1H-indol-2-yl)prop-2-yn-1-yl)amino)benzoic acid |
| 1619. | 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide |
| 1620. | N,N-bis(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1621. | 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1622. | 2-[3-({2-methoxy-4-[(4-methylpiperazin-1-yl)sulfonyl]phenyl}amino)prop-1-yn-1-yl]-N-(1-methylpiperidin-4-yl)-1-(2,2,2-trifluoroethyl)-1H-indol-4-amine |
| 1623. | 5-methanesulfonyl-2-[(3-{4-[(1-methylpiperidin-4-yl)amino]-1-(2,2,2-trifluoroethyl)-1H-indol-2-yl}prop-2-yn-1-yl)amino]phenol |
| 1624. | 2-{3-[(4-methanesulfonyl-2-methoxyphenyl)amino]prop-1-yn-1-yl}-6-methoxy-N-(1-methylpiperidin-4-yl)-1-(2,2,2-trifluoroethyl)-1H-indol-4-amine |
| 1625. | 2-{3-[2-(dimethylamino)-4-methanesulfonylphenoxy]prop-1-yn-1-yl}-N-(1-methylpiperidin-4-yl)-1-(2,2,2-trifluoroethyl)-1H-indol-4-amine |
| 1626. | 2-{5-methanesulfonyl-2-[(3-{4-[(1-methylpiperidin-4-yl)amino]-1-(2,2,2-trifluoroethyl)-1H-indol-2-yl}prop-2-yn-1-yl)amino]phenoxy}acetonitrile |
| 1627. | 2-(3-{[2-(fluoromethoxy)-4-methanesulfonylphenyl]amino}prop-1-yn-1-yl)-N-(1-methylpiperidin-4-yl)-1-(2,2,2-trifluoroethyl)-1H-indol-4-amine |
| 1628. | 2-(3-{[2-methoxy-4-(morpholine-4-carbonyl)phenyl]amino}prop-1-yn-1-yl)-N-(1-methylpiperidin-4-yl)-1-(2,2,2-trifluoroethyl)-1H-indol-4-amine |
| 1629. | 1-{3-methoxy-4-[(3-{4-[(1-methylpiperidin-4-yl)amino]-1-(2,2,2-trifluoroethyl)-1H-indol-2-yl}prop-2-yn-1-yl)amino]benzoyl}piperidin-4-ol |
| 1630. | 3-(3-(4-((1-methylpiperidin-4-yl)amino)-1-(2,2,2-trifluoroethyl)-1H-indol-2-yl)prop-2-yn-1-yl)-6-(methylsulfonyl)benzo[d]oxazol-2(3H)-one |
| 1631. | 2-(3-{[2-methoxy-4-(5-methoxypyridin-3-yl)phenyl]amino}prop-1-yn-1-yl)-N-(1-methylpiperidin-4-yl)-1-(2,2,2-trifluoroethyl)-1H-indol-4-amine |
| 1632. | 2-{3-[(5-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 1633. | N-(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzamide |
| 1634. | 3-methoxy-N-(2-methoxyethyl)-4-[(3-{4-[(1-methylpiperidin-4-yl)amino]-1-(2,2,2-trifluoroethyl)-1H-indol-2-yl}prop-2-yn-1-yl)amino]benzamide |
| 1635. | 3-methoxy-N-(1-methylpiperidin-4-yl)-4-[(3-{4-[(1-methylpiperidin-4-yl)amino]-1-(2,2,2-trifluoroethyl)-1H-indol-2-yl}prop-2-yn-1-yl)amino]benzamide |
| 1636. | 2-[3-({4-[4-(dimethylamino)piperidine-1-carbonyl]-2-methoxyphenyl}amino)prop-1-yn-1-yl]-N-(1-methylpiperidin-4-yl)-1-(2,2,2-trifluoroethyl)-1H-indol-4-amine |
| 1637. | 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzamide |
| 1638. | 2-(3-{[2-methoxy-4-(4-methylpiperazine-1-carbonyl)phenyl]amino}prop-1-yn-1-yl)-N-(1-methylpiperidin-4-yl)-1-(2,2,2-trifluoroethyl)-1H-indol-4-amine |
| 1639. | 2-{3-[(2-methoxy-4-{2-oxa-6-azaspiro[3.3]heptane-6-carbonyl}phenyl)amino]prop-1-yn-1-yl}-N-(1-methylpiperidin-4-yl)-1-(2,2,2-trifluoroethyl)-1H-indol-4-amine |
| 1640. | 2-(3-{[2-methoxy-4-(pyridin-3-yl)phenyl]amino}prop-1-yn-1-yl)-N-(1-methylpiperidin-4-yl)-1-(2,2,2-trifluoroethyl)-1H-indol-4-amine |
| 1641. | 2-(3-{[2-methoxy-4-(pyridin-4-yl)phenyl]amino}prop-1-yn-1-yl)-N-(1-methylpiperidin-4-yl)-1-(2,2,2-trifluoroethyl)-1H-indol-4-amine |
| 1642. | N-(3-{4-[(1-methylpiperidin-4-yl)amino]-1-(2,2,2-trifluoroethyl)-1H-indol-2-yl}prop-2-yn-1-yl)pyridine-3-carboxamide |
| 1643. | 2-(3-{[2-methoxy-4-(1,3-oxazol-2-yl)phenyl]amino}prop-1-yn-1-yl)-N-(1-methylpiperidin-4-yl)-1-(2,2,2-trifluoroethyl)-1H-indol-4-amine |
| 1644. | 2-{3-[(3-methanesulfonylphenyl)amino]prop-1-yn-1-yl}-N-(1-methylpiperidin-4-yl)-1-(2,2,2-trifluoroethyl)-1H-indol-4-amine |
| 1645. | N-(1-methylpiperidin-4-yl)-2-[3-({4-[(morpholin-4-yl)methyl]phenyl}amino)prop-1-yn-1-yl]-1-(2,2,2-trifluoroethyl)-1H-indol-4-amine |
| 1646. | 2-(3-{[2-methoxy-4-(1,3-thiazol-2-yl)phenyl]amino}prop-1-yn-1-yl)-N-(1-methylpiperidin-4-yl)-1-(2,2,2-trifluoroethyl)-1H-indol-4-amine |
| 1647. | 2-[3-({2-methoxy-4-[1-(2-methoxyethyl)-1H-pyrazol-4-yl]phenyl}amino)prop-1-yn-1-yl]-N-(1-methylpiperidin-4-yl)-1-(2,2,2-trifluoroethyl)-1H-indol-4-amine |
| 1648. | 2-{3-[(2-methoxy-4-{7-oxa-2-azaspiro[3.5]nonane-2-carbonyl}phenyl)amino]prop-1-yn-1-yl}-N-(1-methylpiperidin-4-yl)-1-(2,2,2-trifluoroethyl)-1H-indol-4-amine |
| 1649. | 2-{3-[(4-chloro-2-methoxyphenyl)amino]prop-1-yn-1-yl}-N-(1-methylpiperidin-4-yl)-1-(2,2,2-trifluoroethyl)-1H-indol-4-amine |
| 1650. | 2-(3-(((3S,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine |
| 1651. | 2-fluoro-5-methoxy-4-[(3-{4-[(1-methylpiperidin-4-yl)amino]-1-(2,2,2-trifluoroethyl)-1H-indol-2-yl}prop-2-yn-1-yl)amino]benzamide |
| 1652. | 2-(3-{[2-methoxy-4-(trifluoromethyl)phenyl]amino}prop-1-yn-1-yl)-N-(1-methylpiperidin-4-yl)-1-(2,2,2-trifluoroethyl)-1H-indol-4-amine |
| 1653. | 2-fluoro-5-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide |

TABLE 1-continued

Alkynyl indole compounds of the disclosure.

| Mol # | IUPAC name |
|---|---|
| 1654. | 2-{3-[(4-methanesulfonyl-2-methoxyphenyl)amino]prop-1-yn-1-yl}-N-(1-methylpiperidin-4-yl)-1-[(oxiran-2-yl)methyl]-1H-indol-4-amine |
| 1655. | 2-(3-((2-ethoxy-4-(methylsulfonyl)phenyl)amino)prop-1-yn-1-yl)-N-(1-methylpiperidin-4-yl)-1-(2,2,2-trifluoroethyl)-1H-indol-4-amine |
| 1656. | 2-{3-[(2-fluoro-4-methanesulfonyl-6-methoxyphenyl)amino]prop-1-yn-1-yl}-N-(1-methylpiperidin-4-yl)-1-(2,2,2-trifluoroethyl)-1H-indol-4-amine |
| 1657. | 2-{3-[(4-methanesulfonyl-2-methoxyphenyl)amino]prop-1-yn-1-yl}-3-methyl-N-(1-methylpiperidin-4-yl)-1-(2,2,2-trifluoroethyl)-1H-indol-4-amine |
| 1658. | 2-(3-(((3R,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine |
| 1659. | 2-{3-[(5-fluoro-4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 1660. | 2-{3-[(5-methanesulfonylthiophen-2-yl)amino]prop-1-yn-1-yl}-N-(1-methylpiperidin-4-yl)-1-(2,2,2-trifluoroethyl)-1H-indol-4-amine |
| 1661. | N-methyl-5-[(3-{4-[(1-methylpiperidin-4-yl)amino]-1-(2,2,2-trifluoroethyl)-1H-indol-2-yl}prop-2-yn-1-yl)amino]thiophene-2-carboxamide |
| 1662. | N,N-dimethyl-5-[(3-{4-[(1-methylpiperidin-4-yl)amino]-1-(2,2,2-trifluoroethyl)-1H-indol-2-yl}prop-2-yn-1-yl)amino]thiophene-2-carboxamide |
| 1663. | 5-[(3-{4-[(1-methylpiperidin-4-yl)amino]-1-(2,2,2-trifluoroethyl)-1H-indol-2-yl}prop-2-yn-1-yl)amino]thiophene-2-carboxylic acid |
| 1664. | 2-(3-((4-methoxypyridin-3-yl)amino)prop-1-yn-1-yl)-N-(1-methylpiperidin-4-yl)-1-(2,2,2-trifluoroethyl)-1H-indol-4-amine |
| 1665. | 2-(2-((3-(4-((1-methylpiperidin-4-yl)amino)-1-(2,2,2-trifluoroethyl)-1H-indol-2-yl)prop-2-yn-1-yl)amino)-5-(methylsulfonyl)phenoxy)acetamide |
| 1666. | N-(2-hydroxyethyl)-3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide |
| 1667. | 4-((2-(3-((2-methoxy-4-(methylsulfonyl)phenyl)amino)prop-1-yn-1-yl)-1-(2,2,2-trifluoroethyl)-1H-indol-4-yl)amino)-1-methylpiperidin-2-one |
| 1668. | 2-{3-[(4-methanesulfonyl-2-methoxyphenyl)amino]prop-1-yn-1-yl}-N-[(3R,4S)-3-methoxy-1-methylpiperidin-4-yl]-1-(2,2,2-trifluoroethyl)-1H-indol-4-amine |
| 1669. | 2-{3-[(4-methanesulfonyl-2-methoxyphenyl)amino]prop-1-yn-1-yl}-N-[(3S,4R)-3-methoxy-1-methylpiperidin-4-yl]-1-(2,2,2-trifluoroethyl)-1H-indol-4-amine |
| 1670. | 2-{3-[(4-methanesulfonyl-2-methoxyphenyl)amino]prop-1-yn-1-yl}-N-[(3S,4R)-3-methoxy-1-methylpiperidin-4-yl]-N-methyl-1-(2,2,2-trifluoroethyl)-1H-indol-4-amine |
| 1671. | N-(1-ethylpiperidin-4-yl)-2-(3-{[2-(fluoromethoxy)-4-methanesulfonylphenyl]amino}prop-1-yn-1-yl)-1-(2,2,2-trifluoroethyl)-1H-indol-4-amine |
| 1672. | 4-[(3-{4-[(1-ethylpiperidin-4-yl)amino]-1-(2,2,2-trifluoroethyl)-1H-indol-2-yl}prop-2-yn-1-yl)amino]-3-methoxy-N-methylbenzamide |
| 1673. | 2-{2-[(3-{4-[(1-ethylpiperidin-4-yl)amino]-1-(2,2,2-trifluoroethyl)-1H-indol-2-yl}prop-2-yn-1-yl)amino]-5-methanesulfonylphenoxy}acetonitrile |
| 1674. | N-(1-ethylpiperidin-4-yl)-2-{3-[(4-methanesulfonyl-2-methoxyphenyl)amino]prop-1-yn-1-yl}-1-(2,2,2-trifluoroethyl)-1H-indol-4-amine |
| 1675. | 4-[(3-{4-[(1-ethylpiperidin-4-yl)amino]-1-(2,2,2-trifluoroethyl)-1H-indol-2-yl}prop-2-yn-1-yl)amino]-3-methoxybenzene-1-sulfonamide |
| 1676. | 3-methoxy-N-methyl-4-{[3-(4-{[1-(propan-2-yl)piperidin-4-yl]amino}-1-(2,2,2-trifluoroethyl)-1H-indol-2-yl)prop-2-yn-1-yl]amino}benzamide |
| 1677. | 2-(5-methanesulfonyl-2-{[3-(4-{[1-(propan-2-yl)piperidin-4-yl]amino}-1-(2,2,2-trifluoroethyl)-1H-indol-2-yl)prop-2-yn-1-yl]amino}phenoxy)acetonitrile |
| 1678. | 2-(3-{[2-(fluoromethoxy)-4-methanesulfonylphenyl]amino}prop-1-yn-1-yl)-N-[1-(propan-2-yl)piperidin-4-yl]-1-(2,2,2-trifluoroethyl)-1H-indol-4-amine |
| 1679. | 2-{3-[(4-methanesulfonyl-2-methoxyphenyl)amino]prop-1-yn-1-yl}-N-[1-(propan-2-yl)piperidin-4-yl]-1-(2,2,2-trifluoroethyl)-1H-indol-4-amine |
| 1680. | 3-methoxy-4-{[3-(4-{[1-(propan-2-yl)piperidin-4-yl]amino}-1-(2,2,2-trifluoroethyl)-1H-indol-2-yl)prop-2-yn-1-yl]amino}benzene-1-sulfonamide |
| 1681. | 2-[2-(2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethoxy]ethan-1-ol |
| 1682. | 4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one |
| 1683. | 3-methoxy-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzene-1-sulfonamide |
| 1684. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(1,2-oxazol-3-yl)benzene-1-sulfonamide |
| 1685. | 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzenesulfonamide |
| 1686. | 4-({3-[4-({1-[(2S)-2,3-dihydroxypropyl]piperidin-4-yl}amino)-1-(2,2,2-trifluoroethyl)-1H-indol-2-yl]prop-2-yn-1-yl}amino)-3-methoxybenzene-1-sulfonamide |
| 1687. | 4-({3-[4-({1-[(2R)-2,3-dihydroxypropyl]piperidin-4-yl}amino)-1-(2,2,2-trifluoroethyl)-1H-indol-2-yl]prop-2-yn-1-yl}amino)-3-methoxybenzene-1-sulfonamide |
| 1688. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(5-methyl-1,2-oxazol-3-yl)benzene-1-sulfonamide |
| 1689. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(oxan-4-yl)benzene-1-sulfonamide |
| 1690. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-N-(2-hydroxyethyl)-3-methoxy-N-methylbenzene-1-sulfonamide |

TABLE 1-continued

Alkynyl indole compounds of the disclosure.

| Mol # | IUPAC name |
|---|---|
| 1691. | 2-(5-{[3-(4-{[1-(2,3-dihydroxypropyl)piperidin-4-yl]amino}-1-(2,2,2-trifluoroethyl)-1H-indol-2-yl)prop-2-yn-1-yl]amino}-4-methoxypyridin-2-yl)-2-methylpropanenitrile |
| 1692. | N-(2-hydroxyethyl)-3-methoxy-N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 1693. | 3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propane-1,2-diol |
| 1694. | (2R)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |
| 1695. | (2S)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |
| 1696. | 3-[4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)piperidin-1-yl]propane-1,2-diol |
| 1697. | 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoic acid |
| 1698. | methyl 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoate |
| 1699. | 3-methoxy-4-[(3-{4-[(1-{[(4R)-2-oxo-1,3-dioxolan-4-yl]methyl}piperidin-4-yl)amino]-1-(2,2,2-trifluoroethyl)-1H-indol-2-yl}prop-2-yn-1-yl)amino]benzene-1-sulfonamide |
| 1700. | (4R)-4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one |
| 1701. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide |
| 1702. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}EtOAc |
| 1703. | N-(1-{[(4R)-2,2-dimethyl-1,3-dioxolan-4-yl]methyl}piperidin-4-yl)-2-{3-[(4-methanesulfonyl-2-methoxyphenyl)amino]prop-1-yn-1-yl}-1-(2,2,2-trifluoroethyl)-1H-indol-4-amine |
| 1704. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl acetate |
| 1705. | 4-[(3-{4-[(1-{[(4R)-2,2-dimethyl-1,3-dioxolan-4-yl]methyl}piperidin-4-yl)amino]-1-(2,2,2-trifluoroethyl)-1H-indol-2-yl}prop-2-yn-1-yl)amino]-3-methoxybenzene-1-sulfonamide |
| 1706. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1707. | 1-(4-((2-(3-((4-(ethylsulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol |
| 1708. | 1-ethoxy-3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propan-2-ol |
| 1709. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(2-methoxyethyl)-N-methylbenzene-1-sulfonamide |
| 1710. | 1-(acetyloxy)-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate |
| 1711. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzene-1-sulfonamide |
| 1712. | 3-methoxy-4-{[3-(4-{[1-(2-methoxyacetyl)piperidin-4-yl]amino}-1-(2,2,2-trifluoroethyl)-1H-indol-2-yl)prop-2-yn-1-yl]amino}benzene-1-sulfonamide |
| 1713. | 1-(4-(N-(2-(3-((2-methoxy-4-(methylsulfonyl)phenyl)amino)prop-1-yn-1-yl)-1-(2,2,2-trifluoroethyl)-1H-indol-4-yl)acetamido)piperidin-1-yl)propan-2-yl acetate |
| 1714. | 1-[4-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzenesulfonyl)piperazin-1-yl]ethan-1-one |
| 1715. | (4S)-4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one |
| 1716. | 1-(acetyloxy)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl acetate |
| 1717. | N-[1-(2,3-dimethoxypropyl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1718. | 4-{[3-(4-{[1-(2,3-dimethoxypropyl)piperidin-4-yl]amino}-1-(2,2,2-trifluoroethyl)-1H-indol-2-yl)prop-2-yn-1-yl]amino}-3-methoxybenzene-1-sulfonamide |
| 1719. | 3-(4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}piperidin-1-yl)propane-1,2-diol |
| 1720. | 4-({3-[4-({1-[(2R)-2,3-dihydroxypropyl]piperidin-4-yl}amino)-1-(2,2,2-trifluoroethyl)-1H-indol-2-yl]prop-2-yn-1-yl}amino)-3-methoxybenzamide |
| 1721. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethyl 2-methylpropanoate |
| 1722. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethyl propanoate |
| 1723. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(propanoyloxy)propan-2-yl propanoate |
| 1724. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-(propanoyloxy)propan-2-yl propanoate |

TABLE 1-continued

Alkynyl indole compounds of the disclosure.

| Mol # | IUPAC name |
|---|---|
| 1725. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate |
| 1726. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate |
| 1727. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl propanoate |
| 1728. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl 2-methylpropanoate |
| 1729. | 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl 2-methylpropanoate |
| 1730. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl acetate |
| 1731. | 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl propanoate |
| 1732. | N,N-bis(2-hydroxyethyl)-4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxybenzene-1-sulfonamide |
| 1733. | 4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxy-N-methylbenzamide |
| 1734. | (S)-4-((3-(4-((1-(2-hydroxy-3-methoxypropyl)piperidin-4-yl)amino)-1-(2,2,2-trifluoroethyl)-1H-indol-2-yl)prop-2-yn-1-yl)amino)-3-methoxy-N-methylbenzamide |
| 1735. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl 2-methylpropanoate |
| 1736. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate |
| 1737. | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl 2-methylpropanoate |
| 1738. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzamide |
| 1739. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl propanoate |
| 1740. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate |
| 1741. | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl 2-methylpropanoate |
| 1742. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl propanoate |
| 1743. | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)acetamide |
| 1744. | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)propanamide |
| 1745. | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl propanoate |
| 1746. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzene-1-sulfonamide |
| 1747. | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl propanoate |
| 1748. | (2R)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1749. | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1750. | 3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1751. | 3-methoxy-4-((3-(4-((1-(2-methoxyethyl)piperidin-4-yl)amino)-1-(2,2,2-trifluoroethyl)-1H-indol-2-yl)prop-2-yn-1-yl)amino)benzenesulfonamide |
| 1752. | 2-(3-((2-methoxy-4-(methylsulfonyl)phenyl)amino)prop-1-yn-1-yl)-N-(1-(2-methoxyethyl)piperidin-4-yl)-1-(2,2,2-trifluoroethyl)-1H-indol-4-amine |
| 1753. | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzamide |
| 1754. | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide |
| 1755. | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}EtOAc |
| 1756. | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate |
| 1757. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzamide |
| 1758. | 2-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methanesulfonylphenol |
| 1759. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide |

TABLE 1-continued

Alkynyl indole compounds of the disclosure.

| Mol # | IUPAC name |
|---|---|
| 1760. | 4-({3-[4-({1-[(2R)-3-hydroxy-2-methoxypropyl]piperidin-4-yl}amino)-1-(2,2,2-trifluoroethyl)-1H-indol-2-yl]prop-2-yn-1-yl}amino)-3-methoxybenzene-1-sulfonamide |
| 1761. | N-(4-{[3-(4-{[1-(2-hydroxy-3-methoxypropyl)piperidin-4-yl]amino}-1-(2,2,2-trifluoroethyl)-1H-indol-2-yl]prop-2-yn-1-yl]amino}-3-methoxybenzenesulfonyl)-N-methylpropanamide |
| 1762. | 1-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1763. | 1-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)tetradecan-1-one |
| 1764. | 1-methoxy-3-(4-{[2-(3-{[2-methoxy-4-(propanamidosulfonyl)phenyl]amino}prop-1-yn-1-yl)-1-(2,2,2-trifluoroethyl)-1H-indol-4-yl]amino}piperidin-1-yl)propan-2-yl propanoate |
| 1765. | 1-(4-{[2-(3-{[2-methoxy-4-(propanamidosulfonyl)phenyl]amino}prop-1-yn-1-yl)-1-(2,2,2-trifluoroethyl)-1H-indol-4-yl]amino}piperidin-1-yl)-3-(propanoyloxy)propan-2-yl propanoate |
| 1766. | (2R)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxypropan-1-ol |
| 1767. | (2S)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxypropan-1-ol |
| 1768. | 1-{4-[(2-{3-[(2-ethoxy-4-methanesulfonylphenyl)amino]prop-1-yn-1-yl}-1-(2,2,2-trifluoroethyl)-1H-indol-4-yl)amino]piperidin-1-yl}-3-methoxypropan-2-ol |
| 1769. | 4-({3-[4-({1-[(2S)-3-hydroxy-2-methoxypropyl]piperidin-4-yl}amino)-1-(2,2,2-trifluoroethyl)-1H-indol-2-yl]prop-2-yn-1-yl}amino)-3-methoxybenzene-1-sulfonamide |
| 1770. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-(propan-2-yl)benzamide |
| 1771. | 3-hydroxy-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}benzene-1-sulfonamide |
| 1772. | (2R)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate |
| 1773. | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(N-propionylsulfamoyl)phenyl)propionamide |
| 1774. | 1-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)-3-methoxypropan-2-ol |
| 1775. | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate |
| 1776. | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)acetamide |
| 1777. | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)propionamide |
| 1778. | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)isobutyramide |
| 1779. | 2-(2-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methanesulfonylphenoxy)acetonitrile |
| 1780. | 1-{4-[(2-{3-[(4-methanesulfonyl-2-methoxyphenyl)amino]prop-1-yn-1-yl}-5-methoxy-1-(2,2,2-trifluoroethyl)-1H-indol-4-yl)amino]piperidin-1-yl}-3-methoxypropan-2-ol |
| 1781. | 1-(4-{[2-(3-{[2-(2-hydroxyethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1782. | 1-(4-{[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]amino}piperidin-1-yl)-3-methoxypropan-2-ol |
| 1783. | 1-[4-({2-[3-(2-amino-4-methanesulfonylphenoxy)prop-1-yn-1-yl]-1-(2,2,2-trifluoroethyl)-1H-indol-4-yl}amino)piperidin-1-yl]-3-methoxypropan-2-ol |
| 1784. | 4-({3-[4-({1-[(2R)-2-hydroxy-3-methoxypropyl]piperidin-4-yl}amino)-1-(2,2,2-trifluoroethyl)-1H-indol-2-yl]prop-2-yn-1-yl}amino)-3-methoxy-N-methylbenzamide |
| 1785. | 4-({3-[4-({1-[(2S)-2-hydroxy-3-methoxypropyl]piperidin-4-yl}amino)-1-(2,2,2-trifluoroethyl)-1H-indol-2-yl]prop-2-yn-1-yl}amino)-3-methoxy-N-methylbenzamide |
| 1786. | 4-({3-[4-({1-[(2R)-3-hydroxy-2-methoxypropyl]piperidin-4-yl}amino)-1-(2,2,2-trifluoroethyl)-1H-indol-2-yl]prop-2-yn-1-yl}amino)-3-methoxy-N-methylbenzamide |
| 1787. | 4-({3-[4-({1-[(2S)-3-hydroxy-2-methoxypropyl]piperidin-4-yl}amino)-1-(2,2,2-trifluoroethyl)-1H-indol-2-yl]prop-2-yn-1-yl}amino)-3-methoxy-N-methylbenzamide |
| 1788. | 1-{4-[(2-{3-[4-methanesulfonyl-2-(methylamino)phenoxy]prop-1-yn-1-yl}-1-(2,2,2-trifluoroethyl)-1H-indol-4-yl)amino]piperidin-1-yl}-3-methoxypropan-2-ol |
| 1789. | 3-(2-fluoroethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1790. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-(2-methoxyethoxy)-N-methylbenzamide |
| 1791. | 3-(cyanomethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1792. | N-ethyl-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzamide |
| 1793. | 1-(4-{[2-(3-{[2-methoxy-4-(methylcarbamoyl)phenyl]amino}prop-1-yn-1-yl)-1-(2,2,2-trifluoroethyl)-1H-indol-4-yl]amino}piperidin-1-yl)-3-(propanoyloxy)propan-2-yl propanoate |

TABLE 1-continued

Alkynyl indole compounds of the disclosure.

| Mol # | IUPAC name |
|---|---|
| 1794. | 1-methoxy-3-(4-{[2-(3-{[2-methoxy-4-(methylcarbamoyl)phenyl]amino}prop-1-yn-1-yl)-1-(2,2,2-trifluoroethyl)-1H-indol-4-yl]amino}piperidin-1-yl)propan-2-yl propanoate |
| 1795. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-methylbenzamide |
| 1796. | 3-(2-cyanoethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1797. | 1-ethoxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-ol |
| 1798. | 2-(2-{[3-(4-{[1-(2-hydroxypropyl)piperidin-4-yl]amino}-1-(2,2,2-trifluoroethyl)-1H-indol-2-yl)prop-2-yn-1-yl]amino}-5-methanesulfonylphenoxy)acetonitrile |
| 1799. | 1-(4-{[2-(3-{[4-(ethanesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol |
| 1800. | 3-(fluoromethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1801. | 1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1802. | 2-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxyphenyl)-2-methylpropanenitrile |
| 1803. | (2S)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1804. | (2R)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1805. | 1-(4-{[2-(3-{[2-(difluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1806. | 3-(2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propoxy)propane-1,2-diol |
| 1807. | 1-{4-[(2-{3-[(5-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1808. | 3-(3-(4-((1-(2-hydroxy-3-methoxypropyl)piperidin-4-yl)amino)-1-(2,2,2-trifluoroethyl)-1H-indol-2-yl)prop-2-yn-1-yl)-6-(methylsulfonyl)benzo[d]oxazol-2(3H)-one |
| 1809. | 1-{4-[(2-{3-[(4-methanesulfonylphenyl)amino]prop-1-yn-1-yl}-1-(2,2,2-trifluoroethyl)-1H-indol-4-yl)amino]piperidin-1-yl}-3-methoxypropan-2-ol |
| 1810. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(2,2,2-trifluoroethoxy)propan-2-ol |
| 1811. | 4-hydroxy-9-[(2-{3-[(4-methanesulfonyl-2-methoxyphenyl)amino]prop-1-yn-1-yl}-1-(2,2,2-trifluoroethyl)-1H-indol-4-yl)amino]-2-oxa-6λ⁵-azaspiro[5.5]undecan-6-ylium |
| 1812. | 2-{3-[(4-methanesulfonyl-2-methoxyphenyl)amino]prop-1-yn-1-yl}-N-[1-(3-methoxypropyl)piperidin-4-yl]-1-(2,2,2-trifluoroethyl)-1H-indol-4-amine |
| 1813. | 1-{4-[(2-{3-[(4-methanesulfonyl-2-methoxyphenyl)amino]prop-1-yn-1-yl}-3-methyl-1-(2,2,2-trifluoroethyl)-1H-indol-4-yl)amino]piperidin-1-yl}-3-methoxypropan-2-ol |
| 1814. | 1-{4-[(2-{3-[(5-fluoro-4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1815. | 2-{3-[(4-methanesulfonyl-2-methoxyphenyl)amino]prop-1-yn-1-yl}-N-[1-(oxetan-3-yl)piperidin-4-yl]-1-(2,2,2-trifluoroethyl)-1H-indol-4-amine |
| 1816. | 2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine |
| 1817. | (R)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine |
| 1818. | (S)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine |
| 1819. | 2-(3-((2-methoxy-4-(methylsulfonyl)phenyl)amino)prop-1-yn-1-yl)-N-(1-((tetrahydrofuran-2-yl)methyl)piperidin-4-yl)-1-(2,2,2-trifluoroethyl)-1H-indol-4-amine |
| 1820. | 2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxybenzamide |
| 1821. | 1-methoxy-3-(4-((2-(3-(((3S,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol |
| 1822. | 1-(4-{[2-(3-{[4-(cyclopropanesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol |
| 1823. | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propanenitrile |
| 1824. | 4-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)butanenitrile |
| 1825. | 2-{3-[(4-methanesulfonyl-2-methoxyphenyl)amino]prop-1-yn-1-yl}-N-{1-[(oxolan-2-yl)methyl]piperidin-4-yl}-1-(2,2,2-trifluoroethyl)-1H-indol-4-amine |
| 1826. | 1-methoxy-3-(4-{[2-(3-{[2-methoxy-4-(trifluoromethyl)phenyl]amino}prop-1-yn-1-yl)-1-(2,2,2-trifluoroethyl)-1H-indol-4-yl]amino}piperidin-1-yl)propan-2-ol |
| 1827. | 2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxy-N-methylbenzamide |
| 1828. | 1-(4-{[2-(3-{[4-(benzenesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol |
| 1829. | 2-{3-[(4-methanesulfonyl-2-methoxyphenyl)amino]prop-1-yn-1-yl}-N-[1-(2-methoxy-2-methylpropyl)piperidin-4-yl]-1-(2,2,2-trifluoroethyl)-1H-indol-4-amine |
| 1830. | 2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-ol |

TABLE 1-continued

Alkynyl indole compounds of the disclosure.

| Mol # | IUPAC name |
|---|---|
| 1831. | 1-methoxy-3-(4-{[2-(3-{[2-methoxy-4-(propane-2-sulfonyl)phenyl]amino}prop-1-yn-1-yl)-1-(2,2,2-trifluoroethyl)-1H-indol-4-yl]amino}piperidin-1-yl)propan-2-ol |
| 1832. | 1-{3-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1833. | 1-methoxy-3-(4-((2-(3-(((3R,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol |
| 1834. | 1-{4-[(2-{3-[(4-methanesulfonyl-2-methoxyphenyl)amino]prop-1-yn-1-yl}-1-propyl-1H-indol-4-yl)amino]piperidin-1-yl}-3-methoxypropan-2-ol |
| 1835. | 1-(4-{[1-(2-fluoroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol |
| 1836. | 2-(4-{[1-(2-hydroxy-3-methoxypropyl)piperidin-4-yl]amino}-2-{3-[(4-methanesulfonyl-2-methoxyphenyl)amino]prop-1-yn-1-yl}-1H-indol-1-yl)acetonitrile |
| 1837. | 1-(4-{[1-(2-chloroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol |
| 1838. | rac-1-[(3R,4S)-4-[(2-{3-[(4-methanesulfonyl-2-methoxyphenyl)amino]prop-1-yn-1-yl}-1-(2,2,2-trifluoroethyl)-1H-indol-4-yl)amino]-3-methylpiperidin-1-yl]-3-methoxypropan-2-ol |
| 1839. | rac-1-[(3R,4R)-4-[(2-{3-[(4-methanesulfonyl-2-methoxyphenyl)amino]prop-1-yn-1-yl}-1-(2,2,2-trifluoroethyl)-1H-indol-4-yl)amino]-3-methylpiperidin-1-yl]-3-methoxypropan-2-ol |
| 1840. | 1-{4-[(2-{3-[(4-methanesulfonyl-2-methylphenyl)amino]prop-1-yn-1-yl}-1-(2,2,2-trifluoroethyl)-1H-indol-4-yl)amino]piperidin-1-yl}-3-methoxypropan-2-ol |
| 1841. | 1-[4-({1-[(2,2-difluorocyclopropyl)methyl]-2-{3-[(4-methanesulfonyl-2-methoxyphenyl)amino]prop-1-yn-1-yl}-1H-indol-4-yl}amino)piperidin-1-yl]-3-methoxypropan-2-ol |
| 1842. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzoic acid |
| 1843. | 2-{3-[(4-methanesulfonyl-2-methoxyphenyl)amino]prop-1-yn-1-yl}-N-[1-(3-methanesulfonylpropyl)piperidin-4-yl]-1-(2,2,2-trifluoroethyl)-1H-indol-4-amine |
| 1844. | 4-{[3-(4-{[1-(3-methanesulfonylpropyl)piperidin-4-yl]amino}-1-(2,2,2-trifluoroethyl)-1H-indol-2-yl)prop-2-yn-1-yl]amino}-3-methoxybenzoic acid |
| 1845. | 1-(4-{[2-(3-{[4-methanesulfonyl-2-(trifluoromethyl)phenyl]amino}prop-1-yn-1-yl)-1-(2,2,2-trifluoroethyl)-1H-indol-4-yl]amino}piperidin-1-yl)-3-methoxypropan-2-ol |
| 1846. | 1-(4-{[1-(2,2-difluoroethyl)-2-{3-[(4-methanesulfonyl-2-methoxyphenyl)ino]prop-1-yn-1-yl}-1H-indol-4-yl]amino}piperidin-1-yl)-3-methoxypropan-2-ol |
| 1847. | 1-(4-{[2-(3-{[4-methanesulfonyl-2-(trifluoromethoxy)phenyl]amino}prop-1-yn-1-yl)-1-(2,2,2-trifluoroethyl)-1H-indol-4-yl]amino}piperidin-1-yl)-3-methoxypropan-2-ol |
| 1848. | 1-{4-[(2-{3-[(4-methanesulfonyl-2-methoxyphenyl)amino]prop-1-yn-1-yl}-1-(3,3,3-trifluoropropyl)-1H-indol-4-yl)amino]piperidin-1-yl}-3-methoxypropan-2-ol |
| 1849. | 1-(4-{[1-(2,2-difluoropropyl)-2-{3-[(4-methanesulfonyl-2-methoxyphenyl)amino]prop-1-yn-1-yl}-1H-indol-4-yl]amino}piperidin-1-yl)-3-methoxypropan-2-ol |
| 1850. | 1-{4-[(2-{3-[(2-chloro-4-methanesulfonylphenyl)amino]prop-1-yn-1-yl}-1-(2,2,2-trifluoroethyl)-1H-indol-4-yl)amino]piperidin-1-yl}-3-methoxypropan-2-ol |
| 1851. | 1-{4-[(2-{3-[(2-fluoro-4-methanesulfonyl-6-methoxyphenyl)amino]prop-1-yn-1-yl}-1-(2,2,2-trifluoroethyl)-1H-indol-4-yl)amino]piperidin-1-yl}-3-methoxypropan-2-ol |
| 1852. | 1-(4-((2-(3-((4-((6-oxa-3-azabicyclo[3.1.1]heptan-3-yl)sulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol |
| 1853. | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl propanoate |
| 1854. | 1-{4-[(2-{3-[(4-chloro-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1855. | 2-(2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethoxy)ethan-1-ol |
| 1856. | 4-((3-(4-((1-(2,3-dihydroxypropyl)piperidin-4-yl)amino)-1-(2,2,2-trifluoroethyl)-1H-indol-2-yl)prop-2-yn-1-yl)amino)-N-(2-hydroxyethyl)-3-methoxybenzenesulfonamide |
| 1857. | 2-{3-[(4-methanesulfonyl-2-methoxyphenyl)amino]prop-1-yn-1-yl}-N-[1-(4-methyl-1,3-thiazol-2-yl)piperidin-4-yl]-1-(2,2,2-trifluoroethyl)-1H-indol-4-amine |
| 1858. | N-(1-cyclopropylpiperidin-4-yl)-2-{3-[(4-methanesulfonyl-2-methoxyphenyl)amino]prop-1-yn-1-yl}-1-(2,2,2-trifluoroethyl)-1H-indol-4-amine |
| 1859. | 4-[(3-{4-[(1-cyclopropylpiperidin-4-yl)amino]-1-(2,2,2-trifluoroethyl)-1H-indol-2-yl}prop-2-yn-1-yl)amino]-3-methoxybenzoic acid |
| 1860. | 2-{3-[(4-methanesulfonyl-2-methoxyphenyl)amino]prop-1-yn-1-yl}-N-{1-[(3R)-oxolan-3-yl]piperidin-4-yl}-1-(2,2,2-trifluoroethyl)-1H-indol-4-amine |
| 1861. | 2-{3-[(4-methanesulfonyl-2-methoxyphenyl)amino]prop-1-yn-1-yl}-N-{1-[(3S)-oxolan-3-yl]piperidin-4-yl}-1-(2,2,2-trifluoroethyl)-1H-indol-4-amine |
| 1862. | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzoic acid |
| 1863. | 3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzamide |
| 1864. | N-(2-hydroxyethyl)-3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide |
| 1865. | 3-methoxy-4-((3-(4-((1'-methyl-[1,4'-bipiperidin]-4-yl)amino)-1-(2,2,2-trifluoroethyl)-1H-indol-2-yl)prop-2-yn-1-yl)amino)benzamide |

TABLE 1-continued

Alkynyl indole compounds of the disclosure.

| Mol # | IUPAC name |
|---|---|
| 1866. | 3-methoxy-4-((3-(4-((1-(2-(4-methylpiperazin-1-yl)-2-oxoethyl)piperidin-4-yl)amino)-1-(2,2,2-trifluoroethyl)-1H-indol-2-yl)prop-2-yn-1-yl)amino)benzamide |
| 1867. | 2-{2-[(3-{4-[(1-acetylpiperidin-4-yl)amino]-1-(2,2,2-trifluoroethyl)-1H-indol-2-yl}prop-2-yn-1-yl)amino]-5-methanesulfonylphenoxy}acetonitrile |
| 1868. | 4-{[3-(4-{[1-(2-hydroxyacetyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide |
| 1869. | 2-hydroxy-1-{4-[(2-{3-[(2-hydroxy-4-methanesulfonylphenyl)amino]prop-1-yn-1-yl}-1-(2,2,2-trifluoroethyl)-1H-indol-4-yl)amino]piperidin-1-yl}ethan-1-one |
| 1870. | 2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 1871. | N-((3S,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1872. | N-((3R,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1873. | N-((3R,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1874. | N-((3R,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1875. | N-((3S,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1876. | 1-(4-((2-(3-((2-methoxy-4-(methylsulfonyl)phenyl)amino)prop-1-yn-1-yl)-1-(2,2,2-trifluoroethyl)-1H-indol-4-yl)amino)-2-methylpiperidin-1-yl)ethan-1-one |
| 1877. | 1-{4-[(2-{3-[(4-methanesulfonyl-2-methoxyphenyl)amino]prop-1-yn-1-yl}-1-(2,2,2-trifluoroethyl)-1H-indol-4-yl)amino]-2-methylpiperidin-1-yl}ethan-1-one |
| 1878. | 4-{[3-(4-{[(2S,4S)-1-acetyl-2-methylpiperidin-4-yl]amino}-1-(2,2,2-trifluoroethyl)-1H-indol-2-yl)prop-2-yn-1-yl]amino}-3-methoxybenzene-1-sulfonamide |
| 1879. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxyethan-1-one |
| 1880. | 2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one |
| 1881. | 2-methoxy-1-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-one |
| 1882. | 3-methoxy-4-((3-(4-((1-(2-methoxyacetyl)piperidin-4-yl)amino)-1-(2,2,2-trifluoroethyl)-1H-indol-2-yl)prop-2-yn-1-yl)amino)benzenesulfonamide |
| 1883. | 4-{[3-(4-{[1-(2-hydroxypropanoyl)piperidin-4-yl]amino}-1-(2,2,2-trifluoroethyl)-1H-indol-2-yl)prop-2-yn-1-yl]amino}-3-methoxybenzene-1-sulfonamide |
| 1884. | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-oxopropanenitrile |
| 1885. | 4-{[3-(4-{[1-(2-cyanoacetyl)piperidin-4-yl]amino}-1-(2,2,2-trifluoroethyl)-1H-indol-2-yl)prop-2-yn-1-yl]amino}-3-methoxybenzene-1-sulfonamide |
| 1886. | 4-{[3-(4-{[1-(2-hydroxyacetyl)piperidin-4-yl]amino}-1-(2,2,2-trifluoroethyl)-1H-indol-2-yl)prop-2-yn-1-yl]amino}-3-methoxybenzene-1-sulfonamide |
| 1887. | 4-[(3-{4-[(1-acetylpiperidin-4-yl)amino]-1-(2,2,2-trifluoroethyl)-1H-indol-2-yl}prop-2-yn-1-yl)amino]-3-methoxybenzene-1-sulfonamide |
| 1888. | 2-(dimethylamino)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 1889. | 4-((3-(4-((1-(dimethylglycyl)piperidin-4-yl)amino)-1-(2,2,2-trifluoroethyl)-1H-indol-2-yl)prop-2-yn-1-yl)amino)-3-methoxybenzenesulfonamide |
| 1890. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methylpropan-1-one |
| 1891. | 3-methoxy-4-{[3-(4-{[1-(2-methylpropanoyl)piperidin-4-yl]amino}-1-(2,2,2-trifluoroethyl)-1H-indol-2-yl)prop-2-yn-1-yl]amino}benzene-1-sulfonamide |
| 1892. | 4-((2-(3-((2-methoxy-4-(methylsulfonyl)phenyl)amino)prop-1-yn-1-yl)-1-(2,2,2-trifluoroethyl)-1H-indol-4-yl)amino)-N,N-dimethylpiperidine-1-carboxamide |
| 1893. | 4-[(3-{4-[(1-acetylpiperidin-4-yl)amino]-1-(2,2,2-trifluoroethyl)-1H-indol-2-yl}prop-2-yn-1-yl)amino]-3-methoxy-N,N-dimethylbenzene-1-sulfonamide |
| 1894. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one |
| 1895. | 3-methoxy-4-[(3-{4-[(1-propanoylpiperidin-4-yl)amino]-1-(2,2,2-trifluoroethyl)-1H-indol-2-yl}prop-2-yn-1-yl)amino]benzene-1-sulfonamide |
| 1896. | 1-(4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}piperidin-1-yl)ethan-1-one |
| 1897. | 3-methoxy-4-[(3-{4-[(1-{[(4S)-2-oxo-1,3-dioxolan-4-yl]methyl}piperidin-4-yl)amino]-1-(2,2,2-trifluoroethyl)-1H-indol-2-yl}prop-2-yn-1-yl)amino]benzene-1-sulfonamide |
| 1898. | N-((3-methoxy-4-((3-(4-((1-((2-oxo-1,3-dioxolan-4-yl)methyl)piperidin-4-yl)amino)-1-(2,2,2-trifluoroethyl)-1H-indol-2-yl)prop-2-yn-1-yl)amino)phenyl)sulfonyl)propionamide |
| 1899. | N-[3-methoxy-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzenesulfonyl]acetamide |
| 1900. | 3-methoxy-N-methyl-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzamide |
| 1901. | 2-(3-((2-methoxy-4-(methylsulfonyl)phenyl)amino)prop-1-yn-1-yl)-N-(octahydroindolizin-7-yl)-1-(2,2,2-trifluoroethyl)-1H-indol-4-amine |
| 1902. | N-[(7R,8aS)-octahydroindolizin-7-yl]-2-{3-[(4-methanesulfonyl-2-methoxyphfenyl)amino]prop-1-yn-1-yl}-1-(2,2,2-trifluoroethyl)-1H-indol-4-amine |
| 1903. | N-[(7R,8aR)-octahydroindolizin-7-yl]-2-{3-[(4-methanesulfonyl-2-methoxyphenyl)amino]prop-1-yn-1-yl}-1-(2,2,2-trifluoroethyl)-1H-indol-4-amine |

TABLE 1-continued

Alkynyl indole compounds of the disclosure.

| Mol # | IUPAC name |
|---|---|
| 1904. | rac-(3R,4S)-3-[(2-{3-[(4-methanesulfonyl-2-methoxyphenyl)amino]prop-1-yn-1-yl}-1-(2,2,2-trifluoroethyl)-1H-indol-4-yl)amino]-1-methylpiperidin-4-ol |
| 1905. | rac-(3R,4R)-4-[(2-{3-[(4-methanesulfonyl-2-methoxyphenyl)amino]prop-1-yn-1-yl}-1-(2,2,2-trifluoroethyl)-1H-indol-4-yl)amino]-1-methylpiperidin-3-ol |
| 1906. | 3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide |
| 1907. | rac-N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1908. | N-((3S,4S)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1909. | N-[(3S,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1910. | N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1911. | N-[(3S,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1912. | N-[(3R,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1913. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1914. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1915. | rac-methyl 4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1916. | rac-methyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1917. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1918. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1919. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1920. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1921. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1922. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide |
| 1923. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1924. | 2-fluoro-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide |
| 1925. | 2-fluoro-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide |
| 1926. | 4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1927. | 4-{[3-(4-{[(3S,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1928. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1929. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1930. | methyl 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1931. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1932. | methyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1933. | rac-N-[(3R,4S)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1934. | rac-4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid |
| 1935. | rac-ethyl 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate |
| 1936. | rac-ethyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1937. | (2R)-1-(acetyloxy)-3-[(3RS,4SR)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate |
| 1938. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1939. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide |

TABLE 1-continued

Alkynyl indole compounds of the disclosure.

| Mol # | IUPAC name |
|---|---|
| 1940. | N-[(3S,4R)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1941. | N-[(3R,4S)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1942. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1943. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1944. | rac-2-hydroxypropyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1945. | 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-N-isopropyl-3-methoxybenzamide |
| 1946. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(propan-2-yl)benzamide |
| 1947. | 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid |
| 1948. | 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid |
| 1949. | rac-2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]acetamide |
| 1950. | N-[(3S,4R)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1951. | N-[(3R,4S)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1952. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide |
| 1953. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide |
| 1954. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide |
| 1955. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(propan-2-yl)benzamide |
| 1956. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(oxan-4-yl)benzamide |
| 1957. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(oxan-4-yl)benzamide |
| 1958. | rac-N-[(3R,4S)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1959. | ethyl 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate |
| 1960. | ethyl 4-((3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoate |
| 1961. | ethyl 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoate |
| 1962. | ethyl 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoate |
| 1963. | ethyl 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate |
| 1964. | 2-fluoro-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methoxy-N-methylbenzamide |
| 1965. | 2-fluoro-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methoxy-N-methylbenzamide |
| 1966. | 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoic acid |
| 1967. | 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoic acid |
| 1968. | rac-N-(2-{bis[(pyridin-2-yl)methyl]amino}ethyl)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1969. | rac-N-[(3R,4S)-3-fluoro-1-methylpiperidin-4-yl]-2-{3-[(4-methanesulfonyl-2-methoxyphenyl)amino]prop-1-yn-1-yl}-N-methyl-1-(2,2,2-trifluoroethyl)-1H-indol-4-amine |
| 1970. | rac-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid |
| 1971. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1972. | 2-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methanesulfonylphenol |
| 1973. | 2-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methanesulfonylphenol |
| 1974. | rac-6-fluoro-N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1975. | N-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)acetamide |

TABLE 1-continued

Alkynyl indole compounds of the disclosure.

| Mol # | IUPAC name |
|---|---|
| 1976. | N-(4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)acetamide |
| 1977. | ethyl 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1978. | ethyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1979. | N-[(3R,4S)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine |
| 1980. | N-[(3S,4R)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine |
| 1981. | 2-{3-[(2-ethoxy-4-methanesulfonylphenyl)amino]prop-1-yn-1-yl}-N-[(3S,4R)-3-fluoro-1-methylpiperidin-4-yl]-1-(2,2,2-trifluoroethyl)-1H-indol-4-amine |
| 1982. | 2-{3-[(2-ethoxy-4-methanesulfonylphenyl)amino]prop-1-yn-1-yl}-N-[(3R,4S)-3-fluoro-1-methylpiperidin-4-yl]-1-(2,2,2-trifluoroethyl)-1H-indol-4-amine |
| 1983. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 1984. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 1985. | N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1986. | N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1987. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzamide |
| 1988. | 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzamide |
| 1989. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxy-N-methylbenzamide |
| 1990. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzoic acid |
| 1991. | 2-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol |
| 1992. | 2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol |
| 1993. | 2-(dimethylamino)-1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 1994. | 2-(dimethylamino)-1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 1995. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxy-N-methylbenzamide |
| 1996. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzoic acid |
| 1997. | N-[(3S,4R)-3-fluoro-1-(2-methoxyethyl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1998. | N-[(3R,4S)-3-fluoro-1-(2-methoxyethyl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1999. | 4-{[3-(4-{[(3S,4R)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide |
| 2000. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2001. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2002. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-1-one |
| 2003. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-1-one |
| 2004. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one |
| 2005. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one |
| 2006. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzamide |
| 2007. | 4-{[3-(4-{[(3R,4S)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide |
| 2008. | N-[(7S,8R)-7-fluoro-1,4-dioxaspiro[4.5]decan-8-yl]-2-{3-[(4-methanesulfonyl-2-methoxyphenyl)amino]prop-1-yn-1-yl}-1-(2,2,2-trifluoroethyl)-1H-indol-4-amine |
| 2009. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol |
| 2010. | 1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2011. | 1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |

TABLE 1-continued

Alkynyl indole compounds of the disclosure.

| Mol # | IUPAC name |
|---|---|
| 2012. | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2013. | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2014. | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2015. | 4-((3-(4-(((3S,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2016. | methyl 4-((3-(4-(((3S,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate |
| 2017. | methyl 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate |
| 2018. | (R)-1-((3R,4S)-3-fluoro-4-((2-(3-((2-fluoro-6-methoxy-4-(methylsulfonyl)phenyl)amino)prop-1-yn-1-yl)-1-propyl-1H-indol-4-yl)amino)piperidin-1-yl)-3-methoxypropan-2-ol |
| 2019. | (R)-1-((3R,4S)-4-((1-allyl-2-(3-((2-fluoro-6-methoxy-4-(methylsulfonyl)phenyl)amino)prop-1-yn-1-yl)-1H-indol-4-yl)amino)-3-fluoropiperidin-1-yl)-3-methoxypropan-2-ol |
| 2020. | 4-{[3-(4-{[(3S,4R)-1-[(2R)-2,3-dihydroxypropyl]-3-fluoropiperidin-4-yl]amino}-1-(2,2,2-trifluoroethyl)-1H-indol-2-yl]prop-2-yn-1-yl]amino}-3-methoxybenzene-1-sulfonamide |
| 2021. | 4-{[3-(4-{[(3S,4S)-1-[(2R)-2,3-dihydroxypropyl]-3-fluoropiperidin-4-yl]amino}-1-(2,2,2-trifluoroethyl)-1H-indol-2-yl]prop-2-yn-1-yl]amino}-3-methoxybenzene-1-sulfonamide |
| 2022. | (2R)-1-[(3RS,4SR)-3-fluoro-4-[(2-{3-[(4-methanesulfonyl-2-methoxyphenyl)amino]prop-1-yn-1-yl}-1-propyl-1H-indol-4-yl)amino]piperidin-1-yl]-3-methoxypropan-2-ol |
| 2023. | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2024. | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2025. | 4-((3-(4-(((3R,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2026. | (2R)-1-(acetyloxy)-3-[(3R,4S)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate |
| 2027. | N-[(2R)-2,3-dihydroxypropyl]-4-{[3-(4-{[(3RS,4SR)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide |
| 2028. | (2R)-1-(acetyloxy)-3-[(3S,4R)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate |
| 2029. | rac-N-(2-{bis[(pyridin-2-yl)methyl]amino}ethyl)-2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]acetamide |
| 2030. | 2-amino-1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2031. | 2-amino-1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2032. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol |
| 2033. | 3-(4-(((3S,4R)-3-fluoro-1-methylpiperidin-4-yl)amino)-1-(2,2,2-trifluoroethyl)-1H-indol-2-yl)prop-2-yn-1-ol |
| 2034. | (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)glycine |
| 2035. | methyl 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate |
| 2036. | 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid |
| 2037. | methyl 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate |
| 2038. | methyl 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate |
| 2039. | methyl 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate |
| 2040. | methyl 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate |
| 2041. | methyl 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate |
| 2042. | 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid |
| 2043. | methyl 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate |

TABLE 1-continued

Alkynyl indole compounds of the disclosure.

| Mol # | IUPAC name |
|---|---|
| 2044. | N-[(3S,4R)-3-fluoro-1-methylpiperidin-4-yl]-2-{3-[(2-methoxy-4-{2-oxa-6-azaspiro[3.3]heptane-6-carbonyl}phenyl)amino]prop-1-yn-1-yl}-1-(2,2,2-trifluoroethyl)-1H-indol-4-amine |
| 2045. | N-[(3S,4R)-3-fluoro-1-methylpiperidin-4-yl]-2-{3-[(2-methoxy-4-{7-oxa-2-azaspiro[3.5]nonane-2-carbonyl}phenyl)amino]prop-1-yn-1-yl}-1-(2,2,2-trifluoroethyl)-1H-indol-4-amine |
| 2046. | 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid |
| 2047. | N-[(3S,4R)-3-fluoro-1-methylpiperidin-4-yl]-2-(3-{[2-methoxy-4-(morpholine-4-carbonyl)phenyl]amino}prop-1-yn-1-yl)-1-(2,2,2-trifluoroethyl)-1H-indol-4-amine |
| 2048. | N-[(3S,4R)-3-fluoro-1-methylpiperidin-4-yl]-2-(3-{[2-methoxy-4-(4-methylpiperazine-1-carbonyl)phenyl]amino}prop-1-yn-1-yl)-1-(2,2,2-trifluoroethyl)-1H-indol-4-amine |
| 2049. | 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid |
| 2050. | 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid |
| 2051. | methyl 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoate |
| 2052. | methyl 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoate |
| 2053. | methyl 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate |
| 2054. | 2-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)acetamide |
| 2055. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1,3-thiazol-2-yl)benzamide |
| 2056. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1-methylpiperidin-4-yl)benzamide |
| 2057. | 1-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoyl)piperidin-4-ol |
| 2058. | 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid |
| 2059. | 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid |
| 2060. | tert-butyl (3S,4R)-4-{[2-(3-{[4-(ethanesulfonyl)-2-methoxyphenyl]amino}prop-1-yn-1-yl)-1-(2,2,2-trifluoroethyl)-1H-indol-4-yl]amino}-3-fluoropiperidine-1-carboxylate |
| 2061. | 2-(3-((4-(ethylsulfonyl)-2-methoxyphenyl)amino)prop-1-yn-1-yl)-N-((3S,4R)-3-fluoropiperidin-4-yl)-1-(2,2,2-trifluoroethyl)-1H-indol-4-amine |
| 2062. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[2-(morpholin-4-yl)ethyl]benzamide |
| 2063. | 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid |
| 2064. | 4-{[3-(4-{[(3S,4R)-1-(carbamoylmethyl)-3-fluoropiperidin-4-yl]amino]-1-(2,2,2-trifluoroethyl)-1H-indol-2-yl)prop-2-yn-1-yl]amino}-3-methoxybenzoic acid |
| 2065. | 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid |
| 2066. | tert-butyl (3S,4R)-4-[(2-{3-[(2-ethoxy-4-methanesulfonylphenyl)amino]prop-1-yn-1-yl}-1-(2,2,2-trifluoroethyl)-1H-indol-4-yl)amino]-3-fluoropiperidine-1-carboxylate |
| 2067. | (2S)-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]pentanedioic acid |
| 2068. | (2S)-4-carbamoyl-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]butanoic acid |
| 2069. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonic acid |
| 2070. | 1,5-dimethyl (2S)-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]pentanedioate |
| 2071. | 2-[3-({4-[4-(dimethylamino)piperidine-1-carbonyl]-2-methoxyphenyl}amino)prop-1-yn-1-yl]-N-[(3S,4R)-3-fluoro-1-methylpiperidin-4-yl]-1-(2,2,2-trifluoroethyl)-1H-indol-4-amine |
| 2072. | 4-{[3-(4-{[(3S,4R)-1-(carboxymethyl)-3-fluoropiperidin-4-yl]amino}-1-(2,2,2-trifluoroethyl)-1H-indol-2-yl)prop-2-yn-1-yl]amino}-3-methoxybenzoic acid |
| 2073. | 2-(3-{[4-(ethanesulfonyl)-2-methoxyphenyl]amino}prop-1-yn-1-yl)-N-[(3S,4R)-3-fluoropiperidin-4-yl]-1-(2,2,2-trifluoroethyl)-1H-indol-4-amine |
| 2074. | (1R,2R,4S)-2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine |
| 2075. | (1R,2R,4S)-2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)-$N^4$-methylcyclohexane-1,4-diamine |
| 2076. | (1S,3R,4R)-3-fluoro-$N^4$-(2-{3-[(4-methanesulfonyl-2-methoxyphenyl)amino]prop-1-yn-1-yl}-1-(2,2,2-trifluoroethyl)-1H-indol-4-yl)-$N^1,N^1$-dimethylcyclohexane-1,4-diamine |
| 2077. | 2-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)ethan-1-ol |

TABLE 1-continued

Alkynyl indole compounds of the disclosure.

| Mol # | IUPAC name |
|---|---|
| 2078. | N-ethyl-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2079. | 2-{3-[(2-ethoxy-4-methanesulfonylphenyl)amino]prop-1-yn-1-yl}-N-[(3S,4R)-3-fluoropiperidin-4-yl]-1-(2,2,2-trifluoroethyl)-1H-indol-4-amine |
| 2080. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide |
| 2081. | N-ethyl-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide |
| 2082. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methyl-N-(propan-2-yl)benzamide |
| 2083. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide |
| 2084. | N-[2-(diethylamino)ethyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2085. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxyethyl)-3-methoxybenzamide |
| 2086. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[(2R,3R,4R,5S,6R)-2,4,5-trihydroxy-6-(hydroxymethyl)oxan-3-yl]benzamide |
| 2087. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-(1-hydroxypropan-2-yl)-3-methoxybenzamide |
| 2088. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-[(2R)-1-hydroxypropan-2-yl]-3-methoxybenzamide |
| 2089. | N-[3-(4-{[(3S,4R)-3-fluoro-1-methylpiperidin-4-yl]amino}-1-(2,2,2-trifluoroethyl)-1H-indol-2-yl)prop-2-yn-1-yl]cyclopropanecarboxamide |
| 2090. | (1R,2R)-N-[3-(4-{[(3S,4R)-3-fluoro-1-methylpiperidin-4-yl]amino}-1-(2,2,2-trifluoroethyl)-1H-indol-2-yl)prop-2-yn-1-yl]-2-phenylcyclopropane-1-carboxamide |
| 2091. | N-[3-(4-{[(3S,4R)-3-fluoro-1-methylpiperidin-4-yl]amino}-1-(2,2,2-trifluoroethyl)-1H-indol-2-yl)prop-2-yn-1-yl]-1-methyl-1H-pyrrole-3-carboxamide |
| 2092. | 1-ethyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide |
| 2093. | 1-tert-butyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide |
| 2094. | methyl (2S)-4-carbamoyl-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]butanoate |
| 2095. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-((R)-2-hydroxypropyl)-3-methoxybenzamide |
| 2096. | rac-4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoic acid |
| 2097. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-((S)-2-hydroxypropyl)-3-methoxybenzamide |
| 2098. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide |
| 2099. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-[(2S)-2-hydroxypropyl]-3-methoxybenzamide |
| 2100. | N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2101. | N-[(2R)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2102. | N-[(2S)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2103. | N-(1,5-dihydroxypentan-3-yl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2104. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(3-hydroxy-2-methoxypropyl)-3-methoxybenzamide |
| 2105. | 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-3-[(2-methylpropanoyl)oxy]propan-2-yl 2-methylpropanoate |
| 2106. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[(2-oxo-1,3-dioxolan-4-yl)methyl]benzamide |
| 2107. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-methanesulfonylethyl)-3-methoxybenzamide |
| 2108. | 1-(acetyloxy)-3-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]propan-2-yl acetate |
| 2109. | 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-3-(propanoyloxy)propan-2-yl propanoate |
| 2110. | 2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]propyl 2-methylpropanoate |

TABLE 1-continued

Alkynyl indole compounds of the disclosure.

| Mol # | IUPAC name |
|---|---|
| 2111. | (S)-5-ethoxy-2-(4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamido)-5-oxopentanoic acid |
| 2112. | (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)-L-glutamine |
| 2113. | (S)-2-(4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamido)-5-methoxy-5-oxopentanoic acid |
| 2114. | (S)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2115. | (S)-1-((3R,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2116. | (S)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2117. | (S)-1-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2118. | 1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2119. | 1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2120. | (R)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2121. | (R)-1-((3R,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2122. | (R)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2123. | (R)-1-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2124. | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzenesulfonamide |
| 2125. | 1-(3,3-difluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2126. | 2-{3-[(4-methanesulfonyl-2-methoxyphenyl)amino]prop-1-yn-1-yl}-N-(1-methylazepan-4-yl)-1-(2,2,2-trifluoroethyl)-1H-indol-4-amine |
| 2127. | 1-{4-[2-{3-[(4-methanesulfonyl-2-methoxyphenyl)amino]prop-1-yn-1-yl}-1-(2,2,2-trifluoroethyl)-1H-indol-4-yl)amino]azepan-1-yl}-3-methoxypropan-2-ol |
| 2128. | 2-{3-[(4-methanesulfonyl-2-methoxyphenyl)amino]prop-1-yn-1-yl}-N-{8-methyl-8-azabicyclo[3.2.1]octan-3-yl}-1-(2,2,2-trifluoroethyl)-1H-indol-4-amine |
| 2129. | 2-(3-{[4-methanesulfonyl-2-(trifluoromethoxy)phenyl]amino}prop-1-yn-1-yl)-N-(oxan-4-yl)-1-(2,2,2-trifluoroethyl)-1H-indol-4-amine |
| 2130. | 3-methoxy-4-[(3-{4-[(oxan-4-yl)amino]-1-(2,2,2-trifluoroethyl)-1H-indol-2-yl}prop-2-yn-1-yl)amino]-N-(1,2-oxazol-3-yl)benzene-1-sulfonamide |
| 2131. | 3-methoxy-N-(oxan-4-yl)-4-[(3-{4-[(oxan-4-yl)amino]-1-(2,2,2-trifluoroethyl)-1H-indol-2-yl}prop-2-yn-1-yl)amino]benzene-1-sulfonamide |
| 2132. | 3-methoxy-N-(5-methyl-1,2-oxazol-3-yl)-4-[(3-{4-[(oxan-4-yl)amino]-1-(2,2,2-trifluoroethyl)-1H-indol-2-yl}prop-2-yn-1-yl)amino]benzene-1-sulfonamide |
| 2133. | 2-{4-methoxy-5-[(3-{4-[(oxan-4-yl)amino]-1-(2,2,2-trifluoroethyl)-1H-indol-2-yl}prop-2-yn-1-yl)amino]pyridin-2-yl}-2-methylpropanenitrile |
| 2134. | N-(2-hydroxyethyl)-3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2135. | 6-fluoro-2-{3-[(4-methanesulfonyl-2-methoxyphenyl)amino]prop-1-yn-1-yl}-N-(oxan-4-yl)-1-(2,2,2-trifluoroethyl)-1H-indol-4-amine |
| 2136. | 4-[(3-{6-fluoro-4-[(oxan-4-yl)amino]-1-(2,2,2-trifluoroethyl)-1H-indol-2-yl}prop-2-yn-1-yl)amino]-3-methoxybenzene-1-sulfonamide |
| 2137. | 3-methoxy-N,N-dimethyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2138. | 3-methoxy-N-(2-methoxyethyl)-N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2139. | 1-(4-{3-methoxy-4-[(3-{4-[(oxan-4-yl)amino]-1-(2,2,2-trifluoroethyl)-1H-indol-2-yl}prop-2-yn-1-yl)amino]benzenesulfonyl}piperazin-1-yl)ethan-1-one |
| 2140. | 2-(3-{[2-methoxy-4-(morpholine-4-sulfonyl)phenyl]amino}prop-1-yn-1-yl)-N-(oxan-4-yl)-1-(2,2,2-trifluoroethyl)-1H-indol-4-amine |
| 2141. | 3-methoxy-N-methyl-4-[(3-{4-[(oxan-4-yl)amino]-1-(2,2,2-trifluoroethyl)-1H-indol-2-yl}prop-2-yn-1-yl)amino]benzamide |
| 2142. | 3-methoxy-4-((3-(4-((tetrahydro-2H-pyran-4-yl)amino)-1-(2,2,2-trifluoroethyl)-1H-indol-2-yl)prop-2-yn-1-yl)amino)benzoic acid |
| 2143. | methyl 3-methoxy-4-((3-(4-((tetrahydro-2H-pyran-4-yl)amino)-1-(2,2,2-trifluoroethyl)-1H-indol-2-yl)prop-2-yn-1-yl)amino)benzoate |
| 2144. | 3-methoxy-4-((3-(4-((tetrahydro-2H-pyran-4-yl)amino)-1-(2,2,2-trifluoroethyl)-1H-indol-2-yl)prop-2-yn-1-yl)amino)benzamide |
| 2145. | 3-methoxy-N-(2-methoxyethyl)-N-methyl-4-((3-(4-((tetrahydro-2H-pyran-4-yl)amino)-1-(2,2,2-trifluoroethyl)-1H-indol-2-yl)prop-2-yn-1-yl)amino)benzenesulfonamide |
| 2146. | N,N-bis(2-hydroxyethyl)-3-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 2147. | 3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide |

TABLE 1-continued

Alkynyl indole compounds of the disclosure.

| Mol # | IUPAC name |
|---|---|
| 2148. | 5-methanesulfonyl-2-[(3-{4-[(oxan-4-yl)amino]-1-(2,2,2-trifluoroethyl)-1H-indol-2-yl}prop-2-yn-1-yl)amino]phenol |
| 2149. | 3-methoxy-4-[(3-{5-methoxy-4-[(oxan-4-yl)amino]-1-(2,2,2-trifluoroethyl)-1H-indol-2-yl}prop-2-yn-1-yl)amino]benzene-1-sulfonamide |
| 2150. | 2-[3-({2-methoxy-4-[(4-methylpiperazin-1-yl)sulfonyl]phenyl}amino)prop-1-yn-1-yl]-N-(oxan-4-yl)-1-(2,2,2-trifluoroethyl)-1H-indol-4-amine |
| 2151. | 2-{3-[(4-methanesulfonyl-2-methoxyphenyl)amino]prop-1-yn-1-yl}-5-methoxy-N-(oxan-4-yl)-1-(2,2,2-trifluoroethyl)-1H-indol-4-amine |
| 2152. | 3-methoxy-4-[(3-{6-methoxy-4-[(oxan-4-yl)amino]-1-(2,2,2-trifluoroethyl)-1H-indol-2-yl}prop-2-yn-1-yl)amino]benzene-1-sulfonamide |
| 2153. | 5-methanesulfonyl-2-[(3-{4-[(oxan-4-yl)amino]-1-(2,2,2-trifluoroethyl)-1H-indol-2-yl}prop-2-yn-1-yl)amino]phenyl propanoate |
| 2154. | N-(2-hydroxyethyl)-3-methoxy-4-((3-(4-((tetrahydro-2H-pyran-4-yl)amino)-1-(2,2,2-trifluoroethyl)-1H-indol-2-yl)prop-2-yn-1-yl)amino)benzenesulfonamide |
| 2155. | 2-{3-[(4-methanesulfonyl-2-methoxyphenyl)amino]prop-1-yn-1-yl}-N-[(2S,4R)-2-methyloxan-4-yl]-1-(2,2,2-trifluoroethyl)-1H-indol-4-amine |
| 2156. | 2-{3-[(4-methanesulfonyl-2-methoxyphenyl)amino]prop-1-yn-1-yl}-N-[(2S,4S)-2-methyloxan-4-yl]-1-(2,2,2-trifluoroethyl)-1H-indol-4-amine |
| 2157. | 3-methoxy-4-{[3-(4-{[(2S,4R)-2-methyloxan-4-yl]amino}-1-(2,2,2-trifluoroethyl)-1H-indol-2-yl)prop-2-yn-1-yl]amino}benzene-1-sulfonamide |
| 2158. | 3-methoxy-4-{[3-(4-{[(2S,4S)-2-methyloxan-4-yl]amino}-1-(2,2,2-trifluoroethyl)-1H-indol-2-yl)prop-2-yn-1-yl]amino}benzene-1-sulfonamide |
| 2159. | 3-methoxy-4-{[3-(4-{[(2S,4R)-2-methyloxan-4-yl]amino}-1-(2,2,2-trifluoroethyl)-1H-indol-2-yl)prop-2-yn-1-yl]amino}benzamide |
| 2160. | 3-methoxy-4-{[3-(4-{[(2S,4S)-2-methyloxan-4-yl]amino}-1-(2,2,2-trifluoroethyl)-1H-indol-2-yl)prop-2-yn-1-yl]amino}benzamide |
| 2161. | rac-N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine |
| 2162. | 2-(3-((2-methoxy-4-(methylsulfonyl)phenyl)amino)prop-1-yn-1-yl)-N-((3R,4S)-3-methoxytetrahydro-2H-pyran-4-yl)-1-(2,2,2-trifluoroethyl)-1H-indol-4-amine |
| 2163. | 2-(3-((2-methoxy-4-(methylsulfonyl)phenyl)amino)prop-1-yn-1-yl)-N-((3S,4S)-3-methoxytetrahydro-2H-pyran-4-yl)-1-(2,2,2-trifluoroethyl)-1H-indol-4-amine |
| 2164. | N-[(3S,4S)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine |
| 2165. | N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine |
| 2166. | 2-{3-[(4-methanesulfonyl-2-methoxyphenyl)amino]prop-1-yn-1-yl}-N-[(2R,4R,6S)-2,6-dimethyloxan-4-yl]-1-(2,2,2-trifluoroethyl)-1H-indol-4-amine |
| 2167. | 2-{3-[(4-methanesulfonyl-2-methoxyphenyl)amino]prop-1-yn-1-yl}-N-[(2R,4S,6S)-2,6-dimethyloxan-4-yl]-1-(2,2,2-trifluoroethyl)-1H-indol-4-amine |
| 2168. | 3-methoxy-4-{[3-(4-{[(2R,4R,6S)-2,6-dimethyloxan-4-yl]amino}-1-(2,2,2-trifluoroethyl)-1H-indol-2-yl)prop-2-yn-1-yl]amino}benzamide |
| 2169. | 3-methoxy-4-{[3-(4-{[(2R,4S,6S)-2,6-dimethyloxan-4-yl]amino}-1-(2,2,2-trifluoroethyl)-1H-indol-2-yl)prop-2-yn-1-yl]amino}benzamide |
| 2170. | 3-methoxy-4-{[3-(4-{[(2R,4S,6S)-2,6-dimethyloxan-4-yl]amino}-1-(2,2,2-trifluoroethyl)-1H-indol-2-yl)prop-2-yn-1-yl]amino}benzene-1-sulfonamide |
| 2171. | 3-methoxy-4-{[3-(4-{[(2R,4R,6S)-2,6-dimethyloxan-4-yl]amino}-1-(2,2,2-trifluoroethyl)-1H-indol-2-yl)prop-2-yn-1-yl]amino}benzene-1-sulfonamide |
| 2172. | 4-((2-(3-((4-methoxypyridin-3-yl)amino)prop-1-yn-1-yl)-1-(2,2,2-trifluoroethyl)-1H-indol-4-yl)amino)tetrahydro-2H-thiopyran 1,1-dioxide |
| 2173. | 2-{5-[(3-{4-[(1,1-dioxo-1$\lambda^6$-thian-4-yl)amino]-1-(2,2,2-trifluoroethyl)-1H-indol-2-yl}prop-2-yn-1-yl)amino]-4-methoxypyridin-2-yl}-2-methylpropanenitrile |
| 2174. | 4-{[2-(3-{[4-methanesulfonyl-2-(trifluoromethoxy)phenyl]amino}prop-1-yn-1-yl)-1-(2,2,2-trifluoroethyl)-1H-indol-4-yl]amino}-1$\lambda^6$-thiane-1,1-dione |
| 2175. | 4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}-1$\lambda^6$-thiane-1,1-dione |
| 2176. | 4-({2-[3-({2-[2-(dimethylamino)ethoxy]-4-methanesulfonylphenyl}amino)prop-1-yn-1-yl]-1-(2,2,2-trifluoroethyl)-1H-indol-4-yl}amino)-1$\lambda^6$-thiane-1,1-dione |
| 2177. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(2-hydroxyethyl)-3-methoxy-N-methylbenzene-1-sulfonamide |
| 2178. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxy-N-(1,2-oxazol-3-yl)benzene-1-sulfonamide |
| 2179. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxy-N-(5-methyl-1,2-oxazol-3-yl)benzene-1-sulfonamide |
| 2180. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxy-N-(oxan-4-yl)benzene-1-sulfonamide |
| 2181. | N-(2,3-dihydroxypropyl)-4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzene-1-sulfonamide |
| 2182. | N-[2-(dimethylamino)ethyl]-4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxy-N-methylbenzene-1-sulfonamide |
| 2183. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxy-N,N-dimethylbenzene-1-sulfonamide |
| 2184. | 4-({2-[3-({4-[(4-acetylpiperazin-1-yl)sulfonyl]-2-methoxyphenyl}amino)prop-1-yn-1-yl]-1-(2,2,2-trifluoroethyl)-1H-indol-4-yl}amino)-1$\lambda^6$-thiane-1,1-dione |

TABLE 1-continued

Alkynyl indole compounds of the disclosure.

| Mol # | IUPAC name |
|---|---|
| 2185. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxy-N-(2-methoxyethyl)-N-methylbenzene-1-sulfonamide |
| 2186. | 4-[2-{3-[(2-methoxy-4-{2-oxa-6-azaspiro[3.3]heptane-6-sulfonyl}phenyl)amino]prop-1-yn-1-yl}-1-(2,2,2-trifluoroethyl)-1H-indol-4-yl)amino]-1$\lambda^6$-thiane-1,1-dione |
| 2187. | 4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)-1$\lambda^6$-thiane-1,1-dione |
| 2188. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxy-N-methylbenzamide |
| 2189. | 4-((2-(3-((4-methoxy-6-(methylsulfonyl)pyridin-3-yl)amino)prop-1-yn-1-yl)-1-(2,2,2-trifluoroethyl)-1H-indol-4-yl)amino)tetrahydro-2H-thiopyran 1,1-dioxide |
| 2190. | 4-((2-(3-((4-(methylsulfonyl)-2-(2,2,2-trifluoroethoxy)phenyl)amino)prop-1-yn-1-yl)-1-(2,2,2-trifluoroethyl)-1H-indol-4-yl)amino)tetrahydro-2H-thiopyran 1,1-dioxide |
| 2191. | 2-(2-((3-(4-((1,1-dioxidotetrahydro-2H-thiopyran-4-yl)amino)-1-(2,2,2-trifluoroethyl)-1H-indol-2-yl)prop-2-yn-1-yl)amino)-5-(methylsulfonyl)phenoxy)acetamide |
| 2192. | 2-(2-((3-(4-((1,1-dioxidotetrahydro-2H-thiopyran-4-yl)amino)-1-(2,2,2-trifluoroethyl)-1H-indol-2-yl)prop-2-yn-1-yl)amino)-5-(methylsulfonyl)phenoxy)acetamide |
| 2193. | N-(2,3-dihydroxypropyl)-4-((3-(4-((1,1-dioxidotetrahydro-2H-thiopyran-4-yl)amino)-1-(2,2,2-trifluoroethyl)-1H-indol-2-yl)prop-2-yn-1-yl)amino)-3-methoxybenzenesulfonamide |
| 2194. | 3-methoxy-4-((3-(4-(3-(1-methylpiperidin-4-yl)ureido)-1-(2,2,2-trifluoroethyl)-1H-indol-2-yl)prop-2-yn-1-yl)amino)benzamide |

TABLE 2

Aryl-linked indole compounds of the disclosure.

| Mol # | Structure<br>IUPAC name |
|---|---|
| 2195. | 4-{4-[(1,1-dioxo-1$\lambda^6$-thian-4-yl)amino]-1-(2,2,2-trifluoroethyl)-1H-indol-2-yl}benzamide |
| 2196. | 4-({2-[4-(aminomethyl)phenyl]-1-(2,2,2-trifluoroethyl)-1H-indol-4-yl}amino)-1$\lambda^6$-thiane-1,1-dione |
| 2197. | 4-[(2-{4-[(methylamino)methyl]phenyl}-1-(2,2,2-trifluoroethyl)-1H-indol-4-yl)amino]-1$\lambda^6$-thiane-1,1-dione |
| 2198. | tert-butyl N-[(4-{4-[(1,1-dioxo-1$\lambda^6$-thian-4-yl)amino]-1-(2,2,2-trifluoroethyl)-1H-indol-2-yl}phenyl)methyl]-N-methylcarbamate |
| 2199. | 4-{4-[(1,1-dioxo-1$\lambda^6$-thian-4-yl)amino]-1-(2,2,2-trifluoroethyl)-1H-indol-2-yl}-N-methylbenzamide |
| 2200. | tert-butyl N-[(4-{4-[(1,1-dioxo-1$\lambda^6$-thian-4-yl)amino]-1-(2,2,2-trifluoroethyl)-1H-indol-2-yl}phenyl)methyl]carbamate |
| 2201. | 2-(5-{[(4-{4-[(1,1-dioxo-1$\lambda^6$-thian-4-yl)amino]-1-(2,2,2-trifluoroethyl)-1H-indol-2-yl}phenyl)methyl]amino}pyridin-2-yl)-2-methylpropanenitrile |
| 2202. | 4-{[2-(4-{[(4-methanesulfonylphenyl)amino]methyl}phenyl)-1-(2,2,2-trifluoroethyl)-1H-indol-4-yl]amino}-1$\lambda^6$-thiane-1,1-dione |
| 2203. | 4-[(2-{4-[(phenylamino)methyl]phenyl}-1-(2,2,2-trifluoroethyl)-1H-indol-4-yl)amino]-1$\lambda^6$-thiane-1,1-dione |
| 2204. | 3-{4-[(1,1-dioxo-1$\lambda^6$-thian-4-yl)amino]-1-(2,2,2-trifluoroethyl)-1H-indol-2-yl}benzonitrile |
| 2205. | 4-{[2-(2-fluoro-4-methylphenyl)-1-(2,2,2-trifluoroethyl)-1H-indol-4-yl]amino}-1$\lambda^6$-thiane-1,1-dione |
| 2206. | 4-{[2-(3-chlorophenyl)-1-(2,2,2-trifluoroethyl)-1H-indol-4-yl]amino}-1$\lambda^6$-thiane-1,1-dione |
| 2207. | -{[2-(3-methoxyphenyl)-1-(2,2,2-trifluoroethyl)-1H-indol-4-yl]amino}-1$\lambda^6$-thiane-1,1-dione |
| 2208. | 4-{[2-(4-chlorophenyl)-1-(2,2,2-trifluoroethyl)-1H-indol-4-yl]amino}-1$\lambda^6$-thiane-1,1-dione |
| 2209. | 4-tert-butyl-N-[(4-{4-[(1,1-dioxo-1$\lambda^6$-thian-4-yl)amino]-1-(2,2,2-trifluoroethyl)-1H-indol-2-yl}phenyl)methyl]benzamide |
| 2210. | 4-cyano-N-[(4-{4-[(1,1-dioxo-1$\lambda^6$-thian-4-yl)amino]-1-(2,2,2-trifluoroethyl)-1H-indol-2-yl}phenyl)methyl]benzamide |
| 2211. | 4-chloro-N-[(4-{4-[(1,1-dioxo-1$\lambda^6$-thian-4-yl)amino]-1-(2,2,2-trifluoroethyl)-1H-indol-2-yl}phenyl)methyl]benzamide |
| 2212. | 3-[6-(1-cyano-1-methylethyl)pyridin-3-yl]-1-[(4-{4-[(1,1-dioxo-1$\lambda^6$-thian-4-yl)amino]-1-(2,2,2-trifluoroethyl)-1H-indol-2-yl}phenyl)methyl]urea |
| 2213. | 3-[(4-{4-[(1,1-dioxo-1$\lambda^6$-thian-4-yl)amino]-1-(2,2,2-trifluoroethyl)-1H-indol-2-yl}phenyl)methyl]-1-phenylurea |
| 2214. | 3-{4-[(1,1-dioxo-1$\lambda^6$-thian-4-yl)amino]-1-(2,2,2-trifluoroethyl)-1H-indol-2-yl}benzoic acid |
| 2215. | 4-({2-[3-(dimethylamino)phenyl]-1-(2,2,2-trifluoroethyl)-1H-indol-4-yl}amino)-1$\lambda^6$-thiane-1,1-dione |
| 2216. | 3-{4-[(1,1-dioxo-1$\lambda^6$-thian-4-yl)amino]-1-(2,2,2-trifluoroethyl)-1H-indol-2-yl}-N-methylbenzamide |

TABLE 2-continued

Aryl-linked indole compounds of the disclosure.

| Mol # | Structure IUPAC name |
|---|---|
| 2217. | 4-{4-[(11-dioxo-1$\lambda^6$-thian-4-yl)amino]-1-(2,2,2-trifluoroethyl)-1H-indol-2-yl}benzoic acid |
| 2218. | 4-[(2-{4-[(morpholin-4-yl)methyl]phenyl}-1-(2,2,2-trifluoroethyl)-1H-indol-4-yl)amino]-1$\lambda^6$-thiane-1,1-dione |
| 2219. | methyl N-(3-{4-[(1,1-dioxo-1$\lambda^6$-thian-4-yl)amino]-1-(2,2,2-trifluoroethyl)-1H-indol-2-yl}phenyl)carbamate |
| 2220. | 1-(4-{4-[(1,1-dioxo-1$\lambda^6$-thian-4-yl)amino]-1-(2,2,2-trifluoroethyl)-1H-indol-2-yl}phenyl)cyclopropane-1-carbonitrile |
| 2221. | 4-({2-[4-(hydroxymethyl)phenyl]-1-(2,2,2-trifluoroethyl)-1H-indol-4-yl}amino)-1$\lambda^6$-thiane-1,1-dione |
| 2222. | 1-[(4-{4-[(1,1-dioxo-1$\lambda^6$-thian-4-yl)amino]-1-(2,2,2-trifluoroethyl)-1H-indol-2-yl}phenyl)methyl]-3-(4-methanesulfonylphenyl)urea |
| 2223. | 4-{[2-(4-{[(6-methanesulfonylpyridin-3-yl)amino]methyl(phenyl)-1-(2,2,2-trifluoroethyl)-1H-indol-4-yl]amino}-1$\lambda^6$-thiane-1,1-dione |
| 2224. | 2-(4-{[(4-methanesulfonylphenyl)amino]methyl}phenyl)-N-[1-(oxan-4-yl)piperidin-4-yl]-1-(2,2,2-trifluoroethyl)-1H-indol-4-amine |
| 2225. | 2-(4-{[(6-methylpyridin-3-yl)amino]methyl}phenyl)-N-[1-(oxan-4-yl)piperidin-4-yl]-1-(2,2,2-trifluoroethyl)-1H-indol-4-amine |
| 2226. | 2-(4-{[(4-chlorophenyl)amino]methyl}phenyl)-N-[1-(oxan-4-yl)piperidin-4-yl]-1-(2,2,2-trifluoroethyl)-1H-indol-4-amine |
| 2227. | 2-(4-{[(4-methoxyphenyl)amino]methyl}phenyl)-N-[1-(oxan-4-yl)piperidin-4-yl]-1-(2,2,2-trifluoroethyl)-1H-indol-4-amine |
| 2228. | 2-(4-{[(3-chlorophenyl)amino]methyl}phenyl)-N-[1-(oxan-4-yl)piperidin-4-yl]-1-(2,2,2-trifluoroethyl)-1H-indol-4-amine |
| 2229. | 6-methyl-N-{[4-(5-{[(1-methylpiperidin-4-yl)amino]methyl}-1-(2,2,2-trifluoroethyl)-1H-indol-2-yl)phenyl]methyl}pyridin-3-amine |
| 2230. | N-{[2-(4-{[(4-methanesulfonylphenyl)amino]methyl}phenyl)-1-(2,2,2-trifluoroethyl)-1H-indol-5-yl]methyl}-1-methylpiperidin-4-amine |
| 2231. | 2-(5-amino-[1,1'-biphenyl]-3-yl)-N-(1-methylpiperidin-4-yl)-1-(2,2,2-trifluoroethyl)-1H-indol-4-amine |
| 2232. | 2-{4-[amino(phenyl)methyl]phenyl}-N-(1-methylpiperidin-4-yl)-1-(2,2,2-trifluoroethyl)-1H-indol-4-amine |
| 2233. | 2-(4-(amino(cyclohexyl)methyl)phenyl)-N-(1-methylpiperidin-4-yl)-1-(2,2,2-trifluoroethyl)-1H-indol-4-amine |
| 2234. | 2-{4-[(cyclopentylamino)methyl]phenyl}-N-(1-methylpiperidin-4-yl)-1-(2,2,2-trifluoroethyl)-1H-indol-4-amine |
| 2235. | 2-(4-{1-[(4-methanesulfonylphenyl)amino]ethyl}phenyl)-N-(1-methylpiperidin-4-yl)-1-(2,2,2-trifluoroethyl)-1H-indol-4-amine |
| 2236. | (+/−)-2-{4-[(cyclopropylamino)methyl]phenyl}-N-[(3R,4S)-3-fluoro-1-methylpiperidin-4-yl]-1-(2,2,2-trifluoroethyl)-1H-indol-4-amine |
| 2237. | (+/−)-N-[(3R,4S)-3-fluoro-1-methylpiperidin-4-yl]-2-(4-{[(4-methanesulfonyl-2-methoxyphenyl)amino]methyl}phenyl)-1-(2,2,2-trifluoroethyl)-1H-indol-4-amine |
| 2238. | N-[(3R,4S)-3-fluoro-1-methylpiperidin-4-yl]-2-(4-{[(4-methanesulfonylphenyl)amino]methyl(phenyl)-1-(2,2,2-trifluoroethyl)-1H-indol-4-amine |
| 2239. | (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}benzamide |
| 2240. | (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}cyclopropanecarboxamide |
| 2241. | 1-methoxy-3-(4-{[2-(3-methyl-2H-indazol-6-yl)-1-(2,2,2-trifluoroethyl)-1H-indol-4-yl]amino}piperidin-1-yl)propan-2-ol |
| 2242. | 1-(4-{[2-(2H-indazol-6-yl)-1-(2,2,2-trifluoroethyl)-1H-indol-4-yl]amino}piperidin-1-yl)-3-methoxypropan-2-ol |
| 2243. | 4-{[1-(2-hydroxy-3-methoxypropyl)piperidin-4-yl]amino}-1-(2,2,2-trifluoroethyl)-2',3'-dihydro-1H,1'H-[2,6'-biindol]-2'-one |
| 2244. | 4-(4-((1-(2-hydroxy-3-methoxypropyl)piperidin-4-yl)amino)-1-(2,2,2-trifluoroethyl)-1H-indol-2-yl)isoindolin-1-one |
| 2245. | N-[3-(4-{[1-(2-hydroxy-3-methoxypropyl)piperidin-4-yl]amino}-1-(2,2,2-trifluoroethyl)-1H-indol-2-yl)phenyl]acetamide |

TABLE 3

Heteroaryl-linked indole compounds of the disclosure.

| Mol # | IUPAC name |
|---|---|
| 2246. | 4-((2-(6-methoxypyridin-3-yl)-1-(2,2,2-trifluoroethyl)-1H-indol-4-yl)amino)tetrahydro-2H-thiopyran 1,1-dioxide-indol-4-amine |
| 2247. | 4-((2-(6-methylpyridin-3-yl)-1-(2,2,2-trifluoroethyl)-1H-indol-4-yl)amino)tetrahydro-2H-thiopyran 1,1-dioxide |
| 2248. | 4-((2-(6-(dimethylamino)pyridin-3-yl)-1-(2,2,2-trifluoroethyl)-1H-indol-4-yl)amino)tetrahydro-2H-thiopyran 1,1-dioxide |

TABLE 3-continued

Heteroaryl-linked indole compounds of the disclosure.

| Mol # | IUPAC name |
|---|---|
| 2249. | 4-((2-(quinolin-4-yl)-1-(2,2,2-trifluoroethyl)-1H-indol-4-yl)amino)tetrahydro-2H-thiopyran 1,1-dioxide |
| 2250. | 4-((2-(2-fluoropyridin-3-yl)-1-(2,2,2-trifluoroethyl)-1H-indol-4-yl)amino)tetrahydro-2H-thiopyran 1,1-dioxide |
| 2251. | 1-(4-((2-(5-aminopyridin-3-yl)-1-(2,2,2-trifluoroethyl)-1H-indol-4-yl)amino)piperidin-1-yl)-3-methoxypropan-2-ol |
| 2252. | 2-(2-amino-6-phenylpyridin-4-yl)-N-(1-methylpiperidin-4-yl)-1-(2,2,2-trifluoroethyl)-1H-indol-4-amine |
| 2253. | 5-(4-((1,1-dioxidotetrahydro-2H-thiopyran-4-yl)amino)-1-(2,2,2-trifluoroethyl)-1H-indol-2-yl)-N-methylpicolinamide |
| 2254. | 2-(2-amino-6-phenylpyrimidin-4-yl)-N-(1-methylpiperidin-4-yl)-1-(2,2,2-trifluoroethyl)-1H-indol-4-amine |
| 2255. | 2-(2-amino-6-(cyclohex-1-en-1-yl)pyrimidin-4-yl)-N-(1-methylpiperidin-4-yl)-1-(2,2,2-trifluoroethyl)-1H-indol-4-amine |
| 2256. | 2-(2-amino-6-cyclohexylpyrimidin-4-yl)-N-(1-methylpiperidin-4-yl)-1-(2,2,2-trifluoroethyl)-1H-indol-4-amine |
| 2257. | 2-(2-(methylamino)pyrimidin-4-yl)-N-(1-methylpiperidin-4-yl)-1-(2,2,2-trifluoroethyl)-1H-indol-4-amine |
| 2258. | 2-(2-aminopyrimidin-4-yl)-N-(1-methylpiperidin-4-yl)-1-(2,2,2-trifluoroethyl)-1H-indol-4-amine |
| 2259. | 4-{[2-(1-methyl-1H-pyrazol-3-yl)-1-(2,2,2-trifluoroethyl)-1H-indol-4-yl]amino}-1$\lambda^6$-thiane-1,1-dione |
| 2260. | 4-({2-[1-(2-hydroxyethyl)-1H-pyrazol-4-yl]-1-(2,2,2-trifluoroethyl)-1H-indol-4-yl}amino)-1$\lambda^6$-thiane-1,1-dione |
| 2261. | 4-[(2-{1-[(pyridin-3-yl)methyl]-1H-pyrazol-4-yl}-1-(2,2,2-trifluoroethyl)-1H-indol-4-yl)amino]-1$\lambda^6$-thiane-1,1-dione |
| 2262. | 4-((2-(1-(2-methoxyethyl)-1H-pyrazol-4-yl)-1-(2,2,2-trifluoroethyl)-1H-indol-4-yl)amino)tetrahydro-2H-thiopyran 1,1-dioxide |
| 2263. | 4-[(2-{1-[(pyridin-4-yl)methyl]-1H-pyrazol-4-yl}-1-(2,2,2-trifluoroethyl)-1H-indol-4-yl)amino]-1$\lambda^6$-thiane-1,1-dione |
| 2264. | 2-(5-amino-1-phenyl-1H-pyrazol-3-yl)-N-(1-methylpiperidin-4-yl)-1-(2,2,2-trifluoroethyl)-1H-indol-4-amine |
| 2265. | 2-{5-[amino(phenyl)methyl]-1H-pyrazol-3-yl}-N-(1-methylpiperidin-4-yl)-1-(2,2,2-trifluoroethyl)-1H-indol-4-amine |
| 2266. | 2-(5-amino-1H-pyrazol-3-yl)-N-(1-methylpiperidin-4-yl)-1-(2,2,2-trifluoroethyl)-1H-indol-4-amine |
| 2267. | 2-(5-{[(4-methanesulfonylphenyl)amino]methyl}-1H-pyrazol-3-yl)-N-(1-methylpiperidin-4-yl)-1-(2,2,2-trifluoroethyl)-1H-indol-4-amine |
| 2268. | 2-[5-(methylamino)-1H-pyrazol-3-yl]-N-(1-methylpiperidin-4-yl)-1-(2,2,2-trifluoroethyl)-1H-indol-4-amine |
| 2269. | 2-(5-{[(4-methanesulfonylphenyl)amino]methyl}-1,3,4-thiadiazol-2-yl)-N-(1-methylpiperidin-4-yl)-1-(2,2,2-trifluoroethyl)-1H-indol-4-amine |
| 2270. | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide |
| 2271. | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}benzamide |
| 2272. | (+/−)-N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2273. | (+/−)-N-[(3R,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2274. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopentanecarboxamide |
| 2275. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}thiophene-2-carboxamide |
| 2276. | 1-fluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2277. | (+/−)-2,2-difluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2278. | (+/−)-(1R,2S)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2279. | (+/−)-(1R,2R)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2280. | N-[(5-{4-[(1-methylpiperidin-4-yl)amino]-1-(2,2,2-trifluoroethyl)-1H-indol-2-yl}-1,3,4-thiadiazol-2-yl)methyl]cyclopropanecarboxamide |
| 2281. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}oxetane-3-carboxamide |
| 2282. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclobutanecarboxamide |
| 2283. | (+/−)-methyl N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}carbamate |
| 2284. | methyl 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoate |

TABLE 3-continued

Heteroaryl-linked indole compounds of the disclosure.

| Mol # | IUPAC name |
|---|---|
| 2285. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}-1-methylpiperidine-4-carboxamide |
| 2286. | N-[(5-{4-[(1-methylpiperidin-4-yl)amino]-1-(2,2,2-trifluoroethyl)-1H-indol-2-yl}-1,3,4-thiadiazol-2-yl)methyl]pyridine-2-carboxamide |
| 2287. | N-[(5-{4-[(1-methylpiperidin-4-yl)amino]-1-(2,2,2-trifluoroethyl)-1H-indol-2-yl}-1,3,4-thiadiazol-2-yl)methyl]pyridine-3-carboxamide |
| 2288. | (+/−)-N-[(3R,4S)-3-fluoro-1-methylpiperidin-4-yl]-2-{5-[(methylamino)methyl]-1,3,4-thiadiazol-2-yl}-1-(2,2,2-trifluoroethyl)-1H-indol-4-amine |
| 2289. | (+/−)-benzyl N-{[5-(4-{[(3R,4S)-3-fluoro-1-methylpipendin-4-yl]amino}-1-(2,2,2-trifluoroethyl)-1H-indol-2-yl)-1,3,4-thiadiazol-2-yl]methyl}carbamate |
| 2290. | N-[(5-{4-[(1-methylpiperidin-4-yl)amino]-1-(2,2,2-trifluoroethyl)-1H-indol-2-yl}-1,3,4-thiadiazol-2-yl)methyl]-4-[(morpholin-4-yl)methyl]benzamide |
| 2291. | N-[(5-{4-[(1-methylpiperidin-4-yl)amino]-1-(2,2,2-trifluoroethyl)-1H-indol-2-yl}-1,3,4-thiadiazol-2-yl)methyl]-3-[(morpholin-4-yl)methyl]benzamide |
| 2292. | N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide |
| 2293. | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide |
| 2294. | N-[(5-{4-[(1-methylpiperidin-4-yl)amino]-1-(2,2,2-trifluoroethyl)-1H-indol-2-yl}-1,3,4-thiadiazol-2-yl)methyl]pyridine-4-carboxamide |
| 2295. | 2-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2296. | 3-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2297. | 4-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2298. | (+/−)-(1S,2S)-N-[(5-{4-[(1-methylpiperidin-4-yl)amino]-1-(2,2,2-trifluoroethyl)-1H-indol-2-yl}-1,3,4-thiadiazol-2-yl)methyl]-2-phenylcyclopropane-1-carboxamide |
| 2299. | 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoic acid |
| 2300. | N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-5-carboxamide |
| 2301. | 3-methyl-1-[(5-{4-[(1-methylpiperidin-4-yl)amino]-1-(2,2,2-trifluoroethyl)-1H-indol-2-yl}-1,3,4-thiadiazol-2-yl)methyl]urea |
| 2302. | 2-methyl-N-[(5-{4-[(1-methylpiperidin-4-yl)amino]-1-(2,2,2-trifluoroethyl)-1H-indol-2-yl}-1,3,4-thiadiazol-2-yl)methyl]propanamide |
| 2303. | N-[(5-{4-[(1-methylpiperidin-4-yl)amino]-1-(2,2,2-trifluoroethyl)-1H-indol-2-yl}-1,3,4-thiadiazol-2-yl)methyl]acetamide |
| 2304. | N-[(5-{4-[(1-methylpiperidin-4-yl)amino]-1-(2,2,2-trifluoroethyl)-1H-indol-2-yl}-1,3,4-thiadiazol-2-yl)methyl]-2-phenylacetamide |
| 2305. | 2-methoxy-N-[(5-{4-[(1-methylpiperidin-4-yl)amino]-1-(2,2,2-trifluoroethyl)-1H-indol-2-yl}-1,3,4-thiadiazol-2-yl)methyl]acetamide |
| 2306. | N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2307. | N-[(3S,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2308. | 4-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2309. | 3-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2310. | N-[(5-{4-[(1-methylpiperidin-4-yl)amino]-1-(2,2,2-trifluoroethyl)-1H-indol-2-yl}-1,3,4-thiadiazol-2-yl)methyl]butanamide |
| 2311. | 2-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2312. | 2-[5-(aminomethyl)-1,3,4-thiadiazol-2-yl]-N-(1-methylpiperidin-4-yl)-1-(2,2,2-trifluoroethyl)-1H-indol-4-amine |
| 2313. | 3,3-dimethyl-1-[(5-{4-[(1-methylpiperidin-4-yl)amino]-1-(2,2,2-trifluoroethyl)-1H-indol-2-yl}-1,3,4-thiadiazol-2-yl)methyl]urea |
| 2314. | N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-6-carboxamide |
| 2315. | benzyl N-{[5-(4-{[(3S,4R)-3-fluoropiperidin-4-yl]amino}-1-(2,2,2-trifluoroethyl)-1H-indol-2-yl)-1,3,4-thiadiazol-2-yl]methyl}carbamate |
| 2316. | 1-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2317. | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrazole-4-carboxamide |
| 2318. | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrazole-5-carboxamide |
| 2319. | 1-ethyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2320. | (+/−)-methyl (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylate |

TABLE 3-continued

Heteroaryl-linked indole compounds of the disclosure.

| Mol # | IUPAC name |
|---|---|
| 2321. | (+/−)-(1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid |
| 2322. | 1-methyl-N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrrole-3-carboxamide |
| 2323. | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrrole-3-carboxamide |
| 2324. | N-[(5-{4-[(1-methylpiperidin-4-yl)amino]-1-(2,2,2-trifluoroethyl)-1H-indol-2-yl}-1,3,4-thiadiazol-2-yl)methyl]-2-(thiophen-2-yl)cyclopropane-1-carboxamide |
| 2325. | N-(1-methylpiperidin-4-yl)-2-(5-{[(pyrrolidin-3-yl)amino]methyl}-1,3,4-thiadiazol-2-yl)-1-(2,2,2-trifluoroethyl)-1H-indol-4-amine |
| 2326. | (+/−)-(1R,2S)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid |
| 2327. | N-(1-methylpiperidin-4-yl)-2-(5-{[(1H-pyrazol-4-yl)amino]methyl}-1,3,4-thiadiazol-2-yl)-1-(2,2,2-trifluoroethyl)-1H-indol-4-amine |
| 2328. | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopentanecarboxamide |
| 2329. | N-((3S,4R)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine |
| 2330. | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)benzamide |
| 2331. | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopropanecarboxamide |
| 2332. | 2-(5-((dimethylamino)methyl)-1,3,4-thiadiazol-2-yl)-N-((3S,4R)-3-fluoro-1-methylpiperidin-4-yl)-1-(2,2,2-trifluoroethyl)-1H-indol-4-amine |
| 2333. | N-((3S,4S)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine |
| 2334. | N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}cyclopropanecarboxamide |
| 2335. | N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}benzamide |
| 2336. | (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}benzamide |
| 2337. | N-[(2-{4-[(1-methylpiperidin-4-yl)amino]-1-(2,2,2-trifluoroethyl)-1H-indol-2-yl}-1,3-thiazol-5-yl)methyl]benzamide |
| 2338. | (+/−)-N-[(3R,4S)-3-fluoro-1-methylpiperidin-4-yl]-2-(1,3-thiazol-2-yl)-1-(2,2,2-trifluoroethyl)-1H-indol-4-amine |
| 2339. | N-[(2-{4-[(1-methylpiperidin-4-yl)amino]-1-(2,2,2-trifluoroethyl)-1H-indol-2-yl}-1,3-thiazol-5-yl)methyl]cyclopropanecarboxamide |
| 2340. | (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}cyclopropanecarboxamide |
| 2341. | (+/−)-2-[5-(aminomethyl)-1,3-thiazol-2-yl]-N-[(3R,4S)-3-fluoro-1-methylpiperidin-4-yl]-1-(2,2,2-trifluoroethyl)-1H-indol-4-amine |
| 2342. | 2-(4-(aminomethyl)thiazol-2-yl)-N-((3S,4R)-3-fluoro-1-methylpiperidin-4-yl)-1-(2,2,2-trifluoroethyl)-1H-indol-4-amine |
| 2343. | (+/−)-N-[(3R,4S)-3-fluoro-1-methylpiperidin-4-yl]-2-{5-[(phenylamino)methyl]-1,3-thiazol-2-yl}-1-(2,2,2-trifluoroethyl)-1H-indol-4-amine |
| 2344. | N-[(3S,4R)-3-fluoro-1-methylpiperidin-4-yl]-2-(5-{[(4-methanesulfonyl-2-methoxyphenyl)amino]methyl}-1,3-thiazol-2-yl)-1-(2,2,2-trifluoroethyl)-1H-indol-4-amine |
| 2345. | 2-(5-{[(4-methanesulfonylphenyl)amino]methyl}thiophen-2-yl)-N-(1-methylpiperidin-4-yl)-1-(2,2,2-trifluoroethyl)-1H-indol-4-amine |
| 2346. | (+/−)-N-[(3R,4S)-3-fluoro-1-methylpiperidin-4-yl]-2-(5-{[(4-methanesulfonyl-2-methoxyphenyl)amino]methyl}thiophen-2-yl)-1-(2,2,2-trifluoroethyl)-1H-indol-4-amine |
| 2347. | (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}benzamide |
| 2348. | (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}cyclopropanecarboxamide |
| 2349. | N-(1-methylpiperidin-4-yl)-2-(5-(((4-(methylsulfonyl)phenyl)amino)methyl)thiophen-2-yl)-1-(2,2,2-trifluoroethyl)-1H-indol-4-amine |
| 2350. | N-((5-(4-(((3S,4R)-3-fluoro-1-methylpiperidin-4-yl)amino)-1-(2,2,2-trifluoroethyl)-1H-indol-2-yl)thiophen-2-yl)methyl)benzamide |
| 2351. | N-((3S,4R)-3-fluoro-1-methylpiperidin-4-yl)-2-(5-(((2-methoxy-4-(methylsulfonyl)phenyl)amino)methyl)thiophen-2-yl)-1-(2,2,2-trifluoroethyl)-1H-indol-4-amine |
| 2352. | 2-(5-(amino(cyclohexyl)methyl)-1,3,4-oxadiazol-2-yl)-N-(1-methylpiperidin-4-yl)-1-(2,2,2-trifluoroethyl)-1H-indol-4-amine |
| 2353. | N-(1-methylpiperidin-4-yl)-2-{5-[(phenylamino)methyl]-1,3,4-oxadiazol-2-yl}-1-(2,2,2-trifluoroethyl)-1H-indol-4-amine |
| 2354. | 2-(5-(amino(tetrahydro-2H-pyran-4-yl)methyl)-1,3,4-oxadiazol-2-yl)-N-(1-methylpiperidin-4-yl)-1-(2,2,2-trifluoroethyl)-1H-indol-4-amine |
| 2355. | N-[(5-{4-[(1-methylpiperidin-4-yl)amino]-1-(2,2,2-trifluoroethyl)-1H-indol-2-yl}-1,3,4-oxadiazol-2-yl)methyl]cyclopropanecarboxamide |

TABLE 3-continued

Heteroaryl-linked indole compounds of the disclosure.

| Mol # | IUPAC name |
|---|---|
| 2356. | 2-(5-{[(4-methanesulfonylphenyl)amino]methyl}-1,3,4-oxadiazol-2-yl)-N-(1-methylpiperidin-4-yl)-1-(2,2,2-trifluoroethyl)-1H-indol-4-amine |
| 2357. | N-(1-methylpiperidin-4-yl)-2-(5-{[(1H-pyrazol-4-yl)amino]methyl}-1,3,4-oxadiazol-2-yl)-1-(2,2,2-trifluoroethyl)-1H-indol-4-amine |
| 2358. | 2-(5-(aminomethyl)-1,3,4-oxadiazol-2-yl)-N-(1-methylpiperidin-4-yl)-1-(2,2,2-trifluoroethyl)-1H-indol-4-amine |
| 2359. | (+/−)-N-[(3R,4S)-3-fluoro-1-methylpiperidin-4-yl]-2-(5-{[(4-methanesulfonyl-2-methoxyphenyl)amino]methyl}-1,3,4-oxadiazol-2-yl)-1-(2,2,2-trifluoroethyl)-1H-indol-4-amine |
| 2360. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-2-methoxybenzamide |
| 2361. | (+/−)-2-[5-(aminomethyl)-1,3,4-oxadiazol-2-yl]-N-[(3R,4S)-3-fluoro-1-methylpiperidin-4-yl]-1-(2,2,2-trifluoroethyl)-1H-indol-4-amine |
| 2362. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-4-methoxybenzamide |
| 2363. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}benzamide |
| 2364. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-3-methoxybenzamide |
| 2365. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}thiophene-2-carboxamide |
| 2366. | (+/−)-2-(5-{[(cyclopropylmethyl)amino]methyl}-1,3,4-oxadiazol-2-yl)-N-[(3R,4S)-3-fluoro-1-methylpiperidin-4-yl]-1-(2,2,2-trifluoroethyl)-1H-indol-4-amine |
| 2367. | (+/−)-N-[(3R,4S)-3-fluoro-1-methylpiperidin-4-yl]-2-(5-{[(3-methanesulfonylphenyl)amino]methyl}-1,3,4-oxadiazol-2-yl)-1-(2,2,2-trifluoroethyl)-1H-indol-4-amine |
| 2368. | (+/−)-N-[(3R,4R)-3-fluoro-1-methylpiperidin-4-yl]-2-(5-{[(4-methanesulfonyl-2-methoxyphenyl)amino]methyl}-1,3,4-oxadiazol-2-yl)-1-(2,2,2-trifluoroethyl)-1H-indol-4-amine |
| 2369. | (+/−)-2-(5-((bis(cyclopropylmethyl)amino)methyl)-1,3,4-oxadiazol-2-yl)-N-((3R,4S)-3-fluoro-1-methylpiperidin-4-yl)-1-(2,2,2-trifluoroethyl)-1H-indol-4-amine |
| 2370. | (+/−)-N-((3S,4R)-3-fluoro-1-methylpiperidin-4-yl)-2-(5-(((3-(methylsulfonyl)phenyl)amino)methyl)-1,3,4-oxadiazol-2-yl)-1-(2,2,2-trifluoroethyl)-1H-indol-4-amine |
| 2371. | (+/−)-N-((3S,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine |
| 2372. | (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine |
| 2373. | (+/−)-N-((3S,4S)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine |
| 2374. | N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)benzamide |
| 2375. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)thiophene-2-carboxamide |
| 2376. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-2-methoxybenzamide |
| 2377. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-3-methoxybenzamide |
| 2378. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-4-methoxybenzamide |
| 2379. | (+/−)-2-(5-(((cyclopropylmethyl)amino)methyl)-1,3,4-oxadiazol-2-yl)-N-((3S,4R)-3-fluoro-1-methylpiperidin-4-yl)-1-(2,2,2-trifluoroethyl)-1H-indol-4-amine |
| 2380. | (+/−)-N-((3R,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine |
| 2381. | 2-(3-{[(4-methanesulfonylphenyl)amino]methyl}-1,2,4-oxadiazol-5-yl)-N-(1-methylpiperidin-4-yl)-1-(2,2,2-trifluoroethyl)-1H-indol-4-amine |
| 2382. | N-[(5-{4-[(1-methylpiperidin-4-yl)amino]-1-(2,2,2-trifluoroethyl)-1H-indol-2-yl}-1,2,4-oxadiazol-3-yl)methyl]cyclopropanecarboxamide |
| 2383. | N-[(5-{4-[(1-methylpiperidin-4-yl)amino]-1-(2,2,2-trifluoroethyl)-1H-indol-2-yl}-1,2,4-oxadiazol-3-yl)methyl]benzamide |
| 2384. | N-[(5-{4-[(1-methylpiperidin-4-yl)amino]-1-(2,2,2-trifluoroethyl)-1H-indol-2-yl}-1,2,4-oxadiazol-3-yl)methyl]thiophene-2-carboxamide |
| 2385. | 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-4-carboxamide |
| 2386. | 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-3-carboxamide |
| 2387. | N-(1-methylpiperidin-4-yl)-2-{5-[(phenylamino)methyl]-1,2,4-oxadiazol-3-yl}-1-(2,2,2-trifluoroethyl)-1H-indol-4-amine |
| 2388. | N-[(3-{4-[(1-methylpiperidin-4-yl)amino]-1-(2,2,2-trifluoroethyl)-1H-indol-2-yl}-1,2,4-oxadiazol-5-yl)methyl]thiophene-2-carboxamide |
| 2389. | N-[(3-{4-[(1-methylpiperidin-4-yl)amino]-1-(2,2,2-trifluoroethyl)-1H-indol-2-yl}-1,2,4-oxadiazol-5-yl)methyl]benzamide |

TABLE 3-continued

Heteroaryl-linked indole compounds of the disclosure.

| Mol # | IUPAC name |
|---|---|
| 2390. | (+/−)-(1S,2R)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2391. | N-[(3-{4-[(1-methylpiperidin-4-yl)amino]-1-(2,2,2-trifluoroethyl)-1H-indol-2-yl}-1,2,4-oxadiazol-5-yl)methyl]cyclopropanecarboxamide |
| 2392. | (+/−)-(1S,2S)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2393. | 4-chloro-N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2394. | N-[(3-{4-[(1-methylpiperidin-4-yl)amino]-1-(2,2,2-trifluoroethyl)-1H-indol-2-yl}-1,2,4-oxadiazol-5-yl)methyl]-1,3-thiazole-2-carboxamide |
| 2395. | 4-fluoro-N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2396. | 4-cyano-N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2397. | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrrole-3-carboxamide |
| 2398. | 3-[(3-{4-[(1-methylpiperidin-4-yl)amino]-1-(2,2,2-trifluoroethyl)-1H-indol-2-yl}-1,2,4-oxadiazol-5-yl)methyl]-1-phenylurea |
| 2399. | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-4-carboxamide |
| 2400. | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-3-carboxamide |
| 2401. | (+/−)-(1R,2R)-N-[(3-{4-[(1-methylpiperidin-4-yl)amino]-1-(2,2,2-trifluoroethyl)-1H-indol-2-yl}-1,2,4-oxadiazol-5-yl)methyl]-2-phenylcyclopropane-1-carboxamide |
| 2402. | (+/−)-(1R,2R)-2-methyl-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2403. | (+/−)-(1R,2S)-2-methyl-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2404. | N-[(3-{4-[(oxan-4-yl)amino]-1-(2,2,2-trifluoroethyl)-1H-indol-2-yl}-1,2,4-oxadiazol-5-yl)methyl]cyclopropanecarboxamide |
| 2405. | N-({3-[4-(benzylamino)-1-(2,2,2-trifluoroethyl)-1H-indol-2-yl]-1,2,4-oxadiazol-5-yl}methyl)cyclopropanecarboxamide |
| 2406. | N-[(3-{4-[(1-acetylpiperidin-4-yl)amino]-1-(2,2,2-trifluoroethyl)-1H-indol-2-yl}-1,2,4-oxadiazol-5-yl)methyl]cyclopropanecarboxamide |
| 2407. | N-[(3-{4-[(1,1-dioxo-1λ⁶-thian-4-yl)amino]-1-(2,2,2-trifluoroethyl)-1H-indol-2-yl}-1,2,4-oxadiazol-5-yl)methyl]cyclopropanecarboxamide |
| 2408. | N-[(3-{4-[(1-benzylpiperidin-4-yl)amino]-1-(2,2,2-trifluoroethyl)-1H-indol-2-yl}-1,2,4-oxadiazol-5-yl)methyl]cyclopropanecarboxamide |
| 2409. | N-[(3-{4-[(1-cyclopropylpiperidin-4-yl)amino]-1-(2,2,2-trifluoroethyl)-1H-indol-2-yl}-1,2,4-oxadiazol-5-yl)methyl]cyclopropanecarboxamide |
| 2410. | N-[(3-{4-[(cyclopropylmethyl)amino]-1-(2,2,2-trifluoroethyl)-1H-indol-2-yl}-1,2,4-oxadiazol-5-yl)methyl]cyclopropanecarboxamide |
| 2411. | N-[(3-{4-[(cyclobutylmethyl)amino]-1-(2,2,2-trifluoroethyl)-1H-indol-2-yl}-1,2,4-oxadiazol-5-yl)methyl]cyclopropanecarboxamide |
| 2412. | (+/−)-N-[(3-{4-[(pyrrolidin-3-yl)amino]-1-(2,2,2-trifluoroethyl)-1H-indol-2-yl}-1,2,4-oxadiazol-5-yl)methyl]cyclopropanecarboxamide |
| 2413. | N-[(3-{4-[(1-ethylpiperidin-4-yl)amino]-1-(2,2,2-trifluoroethyl)-1H-indol-2-yl}-1,2,4-oxadiazol-5-yl)methyl]cyclopropanecarboxamide |
| 2414. | (+/−)-N-[(3-{4-[(1-methylpyrrolidin-3-yl)amino]-1-(2,2,2-trifluoroethyl)-1H-indol-2-yl}-1,2,4-oxadiazol-5-yl)methyl]cyclopropanecarboxamide |
| 2415. | N-{[3-(4-{[(1ƛzetidine-3-yl)methyl]amino}-1-(2,2,2-trifluoroethyl)-1H-indol-2-yl)-1,2,4-oxadiazol-5-yl]methyl}cyclopropanecarboxamide |
| 2416. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide |
| 2417. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2418. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide |
| 2419. | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide |
| 2420. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide |
| 2421. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2422. | (+/−)-N-[(3R,4S)-3-fluoro-1-methylpiperidin-4-yl]-2-(5-{[(4-methanesulfonylphenyl)amino]methyl}-1,2,4-oxadiazol-3-yl)-1-(2,2,2-trifluoroethyl)-1H-indol-4-amine |
| 2423. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide |

TABLE 3-continued

Heteroaryl-linked indole compounds of the disclosure.

| Mol # | IUPAC name |
|---|---|
| 2424. | (+/−)-1-ethyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2425. | (+/−)-(1R,2R)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2426. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide |
| 2427. | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide |
| 2428. | (+/−)-N-[(3R,4S)-3-fluoro-1-methylpiperidin-4-yl]-2-(5-{[(4-methanesulfonyl-2-methoxyphenyl)amino]methyl}-1,2,4-oxadiazol-3-yl)-1-(2,2,2-trifluoroethyl)-1H-indol-4-amine |
| 2429. | (+/−)-1-tert-butyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2430. | (+/−)-(1R,2R)-N-{[3-(4-{[(3RS,4SR)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2431. | 1-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2432. | 1-ethyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2433. | (+/−)-N-[(3R,4S)-3-fluoropiperidin-4-yl]-2-(5-{[(4-methanesulfonyl-2-methoxyphenyl)amino]methyl}-1,2,4-oxadiazol-3-yl)-1-(2,2,2-trifluoroethyl)-1H-indol-4-amine |
| 2434. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2435. | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2436. | (+/−)-N-[(3R,4S)-3-fluoropiperidin-4-yl]-2-(5-{[methyl(1H-pyrazol-4-yl)amino]methyl}-1,2,4-oxadiazol-3-yl)-1-(2,2,2-trifluoroethyl)-1H-indol-4-amine |
| 2437. | (+/−)-N-[(3R,4S)-3-fluoro-1-methylpiperidin-4-yl]-2-(5-{[methyl(1H-pyrazol-4-yl)amino]methyl}-1,2,4-oxadiazol-3-yl)-1-(2,2,2-trifluoroethyl)-1H-indol-4-amine |
| 2438. | (1RS,2RS)-2-cyano-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2439. | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2440. | (1RS,2SR)-2-cyano-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2441. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}indolizine-2-carboxamide |
| 2442. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-phenyl-1H-imidazole-4-carboxamide |
| 2443. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide |
| 2444. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-pyrrole-3-carboxamide |
| 2445. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-4-carboxamide |
| 2446. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-2-carboxamide |
| 2447. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide |
| 2448. | N-[(3S,4R)-3-fluoropiperidin-4-yl]-2-(5-{[(1H-pyrazol-4-yl)amino]methyl}-1,2,4-oxadiazol-3-yl)-1-(2,2,2-trifluoroethyl)-1H-indol-4-amine |
| 2449. | benzyl N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamate |
| 2450. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-3-carboxamide |
| 2451. | (1S,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2452. | (1R,2S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2453. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-methylthiophene-3-carboxamide |

TABLE 3-continued

Heteroaryl-linked indole compounds of the disclosure.

| Mol # | IUPAC name |
|---|---|
| 2454. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-methylthiophene-3-carboxamide |
| 2455. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-fluorophenyl)cyclopropane-1-carboxamide |
| 2456. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-methylthiophene-3-carboxamide |
| 2457. | (1s,3r)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methylcyclobutane-1-carboxamide |
| 2458. | 5-chloro-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2459. | N-[(3S,4R)-3-fluoropiperidin-4-yl]-2-(5-{[(1H-pyrazol-5-yl)amino]methyl}-1,2,4-oxadiazol-3-yl)-1-(2,2,2-trifluoroethyl)-1H-indol-4-amine |
| 2460. | 2-chloro-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2461. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyrazolo[1,5-a]pyridine-2-carboxamide |
| 2462. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}imidazo[1,2-a]pyridine-2-carboxamide |
| 2463. | 1-cyclopropyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2464. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,5-dimethyl-1H-pyrrole-3-carboxamide |
| 2465. | 4-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2466. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzenesulfonamide |
| 2467. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclobutanecarboxamide |
| 2468. | (1r,3s)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methylcyclobutane-1-carboxamide |
| 2469. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(2-fluorophenyl)cyclopropane-1-carboxamide |
| 2470. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(1-methyl-1H-pyrazol-4-yl)cyclopropane-1-carboxamide |
| 2471. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(pyridin-2-yl)cyclopropane-1-carboxamide |
| 2472. | N-[(3S,4R)-3-fluoro-1-methylpiperidin-4-yl]-2-(5-{[(1H-pyrazol-4-yl)amino]methyl}-1,2,4-oxadiazol-3-yl)-1-(2,2,2-trifluoroethyl)-1H-indol-4-amine |
| 2473. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}acetamide |
| 2474. | 1-[2-(dimethylamino)ethyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2475. | N-[(3S,4R)-3-fluoro-1-methylpiperidin-4-yl]-2-(5-{[(1H-pyrazol-5-yl)amino]methyl}-1,2,4-oxadiazol-3-yl)-1-(2,2,2-trifluoroethyl)-1H-indol-4-amine |
| 2476. | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide |
| 2477. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-4-carboxamide |
| 2478. | (1S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2,2-dimethylcyclopropane-1-carboxamide |
| 2479. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(4-methylpiperazin-1-yl)methyl]cyclopropane-1-carboxamide |
| 2480. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(3-fluorophenyl)cyclopropane-1-carboxamide |
| 2481. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-1,2,3-triazole-4-carboxamide |
| 2482. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-hydroxypropan-2-yl)-1H-pyrrole-3-carboxamide |
| 2483. | 2-[3-({[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamoyl)-1H-pyrrol-1-yl]acetic acid |

TABLE 3-continued

Heteroaryl-linked indole compounds of the disclosure.

| Mol # | IUPAC name |
|---|---|
| 2484. | (1R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2,2-dimethylcyclopropane-1-carboxamide |
| 2485. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylpropyl)-1H-pyrrole-3-carboxamide |
| 2486. | 1-(cyclopropylmethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2487. | 3-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2488. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-(pyrrolidin-1-yl)benzamide |
| 2489. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxypropyl)-1H-pyrrole-3-carboxamide |
| 2490. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(morpholin-4-yl)methyl]cyclopropane-1-carboxamide |
| 2491. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{[(propan-2-yl)amino]methyl}cyclopropane-1-carboxamide |
| 2492. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(propylamino)methyl]cyclopropane-1-carboxamide |
| 2493. | 3-[3-({[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamoyl)-1H-pyrrol-1-yl]propanoic acid |
| 2494. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxyethyl)-1H-pyrrole-3-carboxamide |
| 2495. | 1-(2,2-difluoroethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2496. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxy-2-methylpropyl)-1H-pyrrole-3-carboxamide |
| 2497. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxy-2-methylpropyl)-1H-pyrrole-3-carboxamide |
| 2498. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxypropyl)-1H-pyrrole-3-carboxamide |
| 2499. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indole-6-carboxamide |
| 2500. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-pyrazole-4-carboxamide |
| 2501. | 4-(4,4-difluoropiperidin-1-yl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2502. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-5-carboxamide |
| 2503. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-indole-5-carboxamide |
| 2504. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indole-5-carboxamide |
| 2505. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-(morpholin-4-yl)benzamide |
| 2506. | 2-[5-(aminomethyl)-1,2,4-oxadiazol-3-yl]-N-[(3S,4R)-3-fluoro-1-methylpiperidin-4-yl]-1-(2,2,2-trifluoroethyl)-1H-indol-4-amine |
| 2507. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(morpholin-4-yl)benzamide |
| 2508. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(pyrrolidin-1-yl)benzamide |
| 2509. | (1R,2R)-2-[(dimethylamino)methyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2510. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(pyrrolidin-1-yl)methyl]cyclopropane-1-carboxamide |
| 2511. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1H-indole-5-carboxamide |
| 2512. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-indole-6-carboxamide |

TABLE 3-continued

Heteroaryl-linked indole compounds of the disclosure.

| Mol # | IUPAC name |
|---|---|
| 2513. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-imidazole-5-carboxamide |
| 2514. | (1R,2R)-2-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2515. | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-5-carboxamide |
| 2516. | (1S,2S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{[(propan-2-yl)amino]methyl}cyclopropane-1-carboxamide |
| 2517. | N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide |
| 2518. | N-{[3-(4-{[(3R,4S)-1-ethyl-3-fluoropiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide |
| 2519. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1H-indole-6-carboxamide |
| 2520. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}cyclopropanecarboxamide |
| 2521. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}benzamide |
| 2522. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-2-carboxamide |
| 2523. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-3-carboxamide |
| 2524. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}-1,3-thiazole-5-carboxamide |
| 2525. | N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)-1-(1-fluoropropan-2-yl)-1H-pyrrole-3-carboxamide |
| 2526. | N-((3-(4-(((3S,4R)-1-ethyl-3-fluoropiperidin-4-yl)amino)-1-(2,2,2-trifluoroethyl)-1H-indol-2-yl)-1,2,4-oxadiazol-5-yl)methyl)-1-(2-fluoroethyl)-1H-pyrrole-3-carboxamide |
| 2527. | N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)-1-(1-methoxypropan-2-yl)-1H-pyrrole-3-carboxamide |

Example 2: Combination of Compound 1 and Anti-PD-1 Agent in Mouse Sarcoma Model (MT373)

Compound 1 is an indole compound substituted with a trifluoroethyl group at the 1-position; propynyl amino-methoxy-N-methylbenzamide group at the 2-position; and a heterocycle-substituted amino group at the 4-position.

The efficacy of Compound 1 was tested as a single agent and in combination with anti-PD-1 in a mouse syngeneic model of sarcoma (MT373). C57Bl/6 mice were implanted with MT373 cells, and tumors were grown to ~80 mm$^3$. The mice were randomized on day 6 post-inoculation into one of six study groups. Mice were dosed orally (PO) with either vehicle control (0.2% HPC, 0.5% Tween 80) twice per day once weekly (2Q7D); anti-PD-1 at 200 µg per mouse once every three days (Q3D×35); Compound 1 at 75 mg/kg or 150 mg/kg twice per day, once weekly, for 6 weeks (2Q7D×6); the combination of Compound 1 at 75 mg/kg+anti-PD-1 twice per day, once weekly (2Q7D×15); or the combination of Compound 1 at 150 mg/kg+anti-PD-1 twice per day, once weekly (2Q7D×15).

Animals: Female C57Bl/6 mice (120 total) were acclimatized for 1 week and were 8-10 weeks old at initiation of the study. Animals were group housed (N=5) in ventilated cages. Fluorescent lighting was provided on a 12-hour cycle (6:30 am-6:30 pm). Temperature and humidity were monitored and recorded daily and maintained between 68-72° F. (20-22.2° C.) and 30-70% humidity, respectively. 18% soy irradiated rodent feed and autoclaved acidified water was provided ad libitum.

Tumor Cell Culture: MT373 cells were cultured in DMEM medium with 10% fetal bovine serum. The cells were washed with PBS and counted at a total of 6.59×10$^8$ cells with 92% viability. Cells were spun by centrifuge and resuspended in 50% PBS:50% Matrigel Matrix at a concentration of 5×10$^6$ viable cells/200 µL.

Implantation of Mice: Cells were prepared for injections by drawing the cell suspension into a 1 mL tuberculin syringe fitted with a 25 G ⅝" needle. Individual mice were manually restrained, the site of injection (right flank) was disinfected with a 70% ethanol swab, and 200 µL of cell suspension was injected subcutaneously.

Randomization and Study Setup: Implanted mice were monitored for palpable tumors. Five days post implant the mice with palpable tumors had their tumor sizes determined via digital caliper. Mice were selected and randomized into six treatment groups according to tumor size. Average tumor volume (mm$^3$) and body weight (g) is reported in TABLE 4A and 4B. Treatment began on the sixth day post-implant to facilitate twice daily dosing.

TABLE 4A

| Group | N | Mean | St Dev | Min | Max |
|---|---|---|---|---|---|
| Group 1- Vehicle Control 2Q7Dx4 | 10 | 77.35 | ±8.61 | 64.488 | 96.246 |
| Group 2- Anti-PD-1 200 µg Q3Dx35 | 10 | 84.08 | ±18.43 | 53.95 | 116.30 |
| Group 3- Compound 1 75 mg/kg 2Q7Dx6 | 10 | 82.46 | ±16.79 | 58.42 | 114.05 |
| Group 4- Compound 1 150 mg/kg 2Q7Dx15 | 10 | 79.04 | ±23.07 | 53.11 | 117.04 |
| Group 5- Compound 1 75 mg/kg 2Q7Dx15 + Anti-PD-1 200 µg Q3Dx35 | 10 | 80.96 | ±15.78 | 51.69 | 106.31 |
| Group 6- Compound 1 150 mg/kg 2Q7Dx15 + Anti-PD-1 200 µg Q3Dx35 | 10 | 79.54 | ±11.10 | 63.56 | 103.10 |

TABLE 4B

| Group | N | Mean | St Dev | Min | Max |
|---|---|---|---|---|---|
| Group 1- Vehicle Control 2Q7Dx4 | 10 | 18.48 | ±0.81 | 17.40 | 19.50 |
| Group 2- Anti-PD-1 200 µg Q3Dx35 | 10 | 18.44 | ±0.83 | 16.70 | 19.40 |
| Group 3- Compound 1 75 mg/kg 2Q7Dx6 | 10 | 18.67 | ±0.82 | 17.30 | 19.90 |
| Group 4- Compound 1 150 mg/kg 2Q7Dx15 | 10 | 18.97 | ±1.12 | 16.90 | 21.00 |
| Group 5- Compound 1 75 mg/kg 2Q7Dx15 + Anti-PD-1 200 µg Q3Dx35 | 10 | 18.48 | ±0.92 | 16.50 | 20.10 |
| Group 6- Compound 1 150 mg/kg 2Q7Dx15 + Anti-PD-1 200 µg Q3Dx35 | 10 | 18.86 | ±0.63 | 17.70 | 20.00 |

Measurements and Calculation of Tumor Volume: Tumor volume was calculated using the following equation: (longest diameter×shortest diameter$^2$)/2. Individual tumor volumes and body weight measurements were taken twice weekly for all groups until the animals reached the humane endpoints. The calculation for percent tumor growth inhibition (TGI) was as follows: $[1-((T_t-T_0/C_t-C_0))]\times 100$, where $C_t$ is the mean tumor volume of the vehicle control group at time t, $C_0$ is the mean tumor volume of the vehicle control group at time 0, and T is the mean tumor volume of the treatment group. Tumor regression was determined with the equation $[(T_0-T_t)/T_0]\times 100$ using the same definitions.

Group 1 animals were dosed PO with vehicle control (2% HPC, 0.500 Tween 80 in water (w/v/v)) twice a day (BID, 8 hours apart), once per week for four doses (2Q7Dx4). Group 2 animals were dosed interperitoneally (IP) with anti-PD-1 at 200 µg for 35 doses (Q3Dx35). Groups 3 and 4 animals were dosed PO twice a day (BTD, 8 hours apart) with Compound 1 at 75 mg/kg for 6 doses (2Q7Dx6) or 150 mg/kg for 15 doses (2Q7Dx15), respectively. Groups 5 and 6 animals were dosed with Compound 1 at 75 and 150 mg/kg for 15 doses (2Q7Dx15) in combination with anti-PD-1 at 200 µg for 15 doses (Q3Dx15), respectively. TABLE 5 shows the efficacy of the six study groups and dosing regimens. All dosing was discontinued on day 102 and the remaining mice with no palatable tumors were monitored for survival. The time for each tumor to reach 2000 mm$^3$ was determined and a median survival time for each dosed group could be calculated. At day 185, the study was terminated, and median survival was calculated across all groups. Some tumors that regressed but re-grew were collected 24 h post dose for subsequent genetic analysis.

TABLE 5

| Group | Treatment | N | Route | Dosing Frequency & Duration | Dose (mg/kg) | Dose Volume (ml/kg) |
|---|---|---|---|---|---|---|
| 1 | Vehicle Control | 10 | PO | 2Q7Dx4 | — | 10 |
| 2 | Anti-PD-1 | 10 | IP | Q3DX35 | 200 µg | 10 |
| 3 | Compound 1 | 10 | PO | 2Q7Dx6 | 75 | 10 |
| 4 | Compound 1 | 10 | PO | 2Q7Dx15 | 150 | 10 |
| 5 | Compound1 + Anti-PD-1 | 10 | PO IP | 2Q7Dx15 Q3DX35 | 75 200 µg | 10 10 |
| 6 | Compound1 + Anti-PD-1 | 10 | PO IP | 2Q7Dx15 Q3DX35 | 150 200 µg | 10 10 |

MT373 mouse syngeneic sarcoma tumors implanted into female C57Bl/6 mice grew from an average of 77.4 mm$^3$ to 2692 mm$^3$ in 27 days with a median survival time of 20.9 days. Group 2 mice treated with anti-PD-1 (200 µg/mouse) Q3Dx35 resulted in 39% TGI by day 27 and a median survival time of 27.14 days. Mice in group 3 received Compound 1 at 75 mg/kg 2Q7Dx6 which resulted in 57% TGI by day 27 and median survival time of 32 days. Compound 1 administration at the higher dose of 150 mg/kg 2Q7Dx15 resulted in 95% TGI and a median survival of 42.9 days. Co-administration of Compound 1 with anti-PD-1 improved efficacy significantly for both dose levels of Compound 1. Mice in the 75 mg/kg Compound 1+anti-PD-1 combination group demonstrated 91% TGI at day 27 with a median survival time of 43.7 days, while the 150 mg/kg Compound 1+anti-PD-1 combination achieved 92% regression by day 27 and extended median survival time to >185 days.

Figure 1:
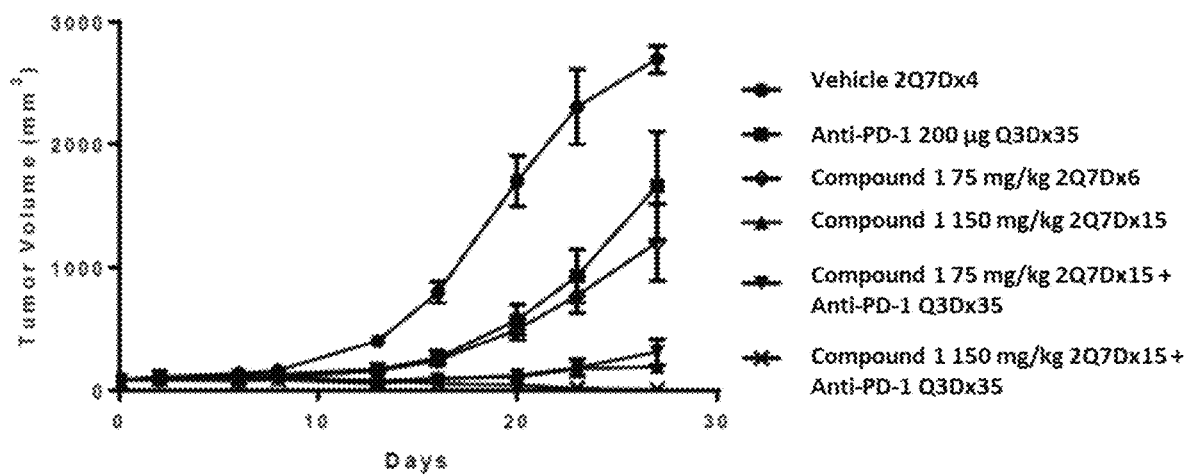
FIG. 1 shows changes in tumor volume ($mm^3$) in a mouse syngeneic model of sarcoma (MT373) over 27 days upon receiving treatment with vehicle (2Q7Dx4); anti-PD-1 200 µg (Q3Dx35); Compound 1, 75 mg/kg (2Q7Dx6); Compound 1, 150 mg/kg (2Q7Dx15); Compound 1, 75 mg/kg (2Q7Dx15)+anti-PD-1 (Q3Dx35); or Compound 1, 150 mg/kg (2Q7Dx15)+anti-PD-1 (Q3Dx35).

At day 27, tumor growth inhibition (TGI) of 39.6%, 57.1%, 95.7%, and 91.2% was observed in animals treated with anti-PD-1, Compound 1 at 75 mg/kg, Compound 1 at 150 mg/kg, and the combination 75 mg/kg+200 µg anti-PD-1, respectively. Tumor regression of 92.3% was observed at day 27 in mice treated with Compound 1 at 150 mg/kg+ anti-PD-1. FIG. 1 shows changes in tumor volume (mm$^3$) in a mouse syngeneic model of sarcoma (MT373) over 27 days upon receiving treatment with vehicle (2Q7D×4); anti-PD-1 200 µg (Q3D×35); Compound 1, 75 mg/kg (2Q7D×6); Compound 1, 150 mg/kg (2Q7D×15); Compound 1, 75 mg/kg (2Q7D×15)+anti-PD-1 (Q3D×35); or Compound 1, 150 mg/kg (2Q7D×15)+anti-PD-1 (Q3D×35).

Figure 2:
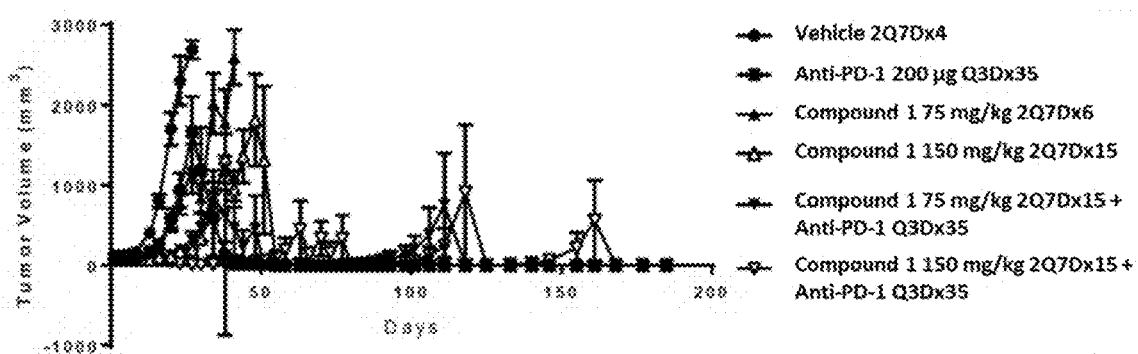
FIG. 2 shows changes in tumor volume ($mm^3$) in a mouse syngeneic model of sarcoma (MT373) over 185 days upon receiving treatment with vehicle (2Q7Dx4); anti-PD-1 200 µg (Q3Dx35); Compound 1, 75 mg/kg (2Q7Dx6); Compound 1, 150 mg/kg (2Q7Dx15); Compound 1, 75 mg/kg (2Q7Dx15)+anti-PD-1 (Q3Dx35); or Compound 1, 150 mg/kg (2Q7Dx15)+anti-PD-1 (Q3Dx35).

FIG. 2 shows changes in tumor volume (mm$^3$) in a mouse syngeneic model of sarcoma (MT373) over 185 days upon receiving treatment with vehicle (2Q7D×4); anti-PD-1 200 µg (Q3D×35); Compound 1, 75 mg/kg (2Q7D×6); Compound 1, 150 mg/kg (2Q7D×15); Compound 1, 75 mg/kg (2Q7D×15)+anti-PD-1 (Q3D×35); or Compound 1, 150 mg/kg (2Q7D×15)+anti-PD-1 (Q3D×35). The median survival time (defined as median time taken for tumors in a group to reach 2000 mm$^3$) was significantly increased in mice receiving the high dose combination of Compound 1 at 150 mg/kg and anti-PD-1 to >185 days, when compared to vehicle control at 20.9 days. Compound 1 was well-tolerated by mice with no significant body weight loss across the course of the study. Mice were dosed on their various group regimens until day 102 after which dosing ceased and mice were monitored for clinical observations, tumor volume, and body weight measurements until day 185.

TABLE 6 and TABLE 7 show average percent tumor growth inhibition (0%) across 27 days of study and 185 days of study, respectively. TABLE 8 shows median survival time in days and increase in survival relative to the vehicle group for the 6 mouse groups.

TABLE 6

| Day of Study | Group 1- Vehicle Control 2Q7D×4 | Group 2- Anti-PD-1 200 µg Q3D×35 | Group 3- Compound 1 75 mg/kg 2Q7D×6 | Group 4- Compound 1 150 mg/kg 2Q7D×15 | Group 5- Compound 1 75 mg/kg 2Q7D×15 + Anti-PD-1 200 µg Q3D×35 | Group 6- Compound 1 150 mg/kg 2Q7D×6 + Anti-PD-1 200 µg Q3D×35 |
|---|---|---|---|---|---|---|
| 2 | 0 | 13.5 | 83.0 | 69.9 | 92.8 | 37.6 |
| 6 | 0 | 47.3 | 87.1 | 95.5 | >100 | 75.2 |
| 8 | 0 | 43.3 | 74.9 | 69.4 | 94.2 | 89.2 |
| 13 | 0 | 73.3 | 76.6 | >100 | >100 | >100 |
| 16 | 0 | 75.3 | 77.9 | 97.4 | 99.0 | >100 |
| 20 | 0 | 69.6 | 74.4 | 98.3 | 97.5 | >100 |
| 23 | 0 | 62.0 | 69.0 | 95.8 | 65.4 | >100 |
| 27 | 0 | 39.6 | 57.1 | 96.7 | 91.2 | >100 |

TABLE 7

(n = 10 unless noted)

| Day of Study | Group 1- Vehicle Control 2Q7D×4 | Group 2- Anti-PD-1 200 µg Q3D×35 | Group 3- Compound 1 75 mg/kg 2Q7D×6 | Group 4- Compound 1 150 mg/kg 2Q7D×6 | Group 5- Compound 1 75 mg/kg 2Q7D×15 + Anti-PD-1 200 µg Q3D×35 | Group 6- Compound 1 150 mg/kg 2Q7D×6 + Anti-PD-1 200 µg Q3D×35 |
|---|---|---|---|---|---|---|
| 2 | 0 | 0 | 0 | 0 | 0 | 0 |
| 6 | 0 | 0 | 0 | 0 | 4.5 | 0 |
| 8 | 0 | 0 | 0 | 0 | 0 | 0 |
| 13 | 0 | 0 | 0 | 4.0 | 33.5 | 0.6 |
| 16 | 0 | 0 | 0 | 0 | 0 | 31.1 |
| 20 | 0 | 0 | 0 | 0 | 0 | 44.6 |
| 23 | 0 (n = 6) | 0 | 0 | 0 | 0 | 80 |
| 27 | 0 (n = 2) | 0 (n = 9) | 0 | 0 | 0 | 92.3 |
| 30 | -NA- | 0 (n = 5) | 0 (=7) | 0 | 0 | 96.9 |
| 34 | -NA- | 0 (n = 3) | 0 (n = 7) | 0 | 0 | 85.0 |
| 38 | -NA- | 0 (n = 3) | 0 (n = 3) | 0 | 0 (n = 7) | 82.9 |
| 41 | -NA- | 93.6 (n = 2) | -NA- | 0 (n = 6) | 0 (n = 6) | 77.8 |
| 44 | -NA- | 94.6 (n = 2) | -NA- | 0 (n = 6) | 0 (n = 6) | 71.8 |
| 48 | -NA- | 93.3 (n = 2) | -NA- | 0 (n = 4) | 0 (n = 6) | 48.3 |
| 51 | -NA- | 92.0 (n = 2) | -NA- | 0 (n = 2) | 100.00 (n = 5) | 23.0 |
| 55 | -NA- | 91.6 (n = 2) | -NA- | 100.00 (n = 1) | 100.00 (n = 4) | 0 |
| 58 | -NA- | 94.8 (n = 2) | -NA- | 100.00 (n = 1) | 100.00 (n = 4) | 0 |
| 63 | -NA- | 95.4 (n = 2) | -NA- | 100.00 (n = 1) | 100.00 (n = 4) | 0 |
| 66 | -NA- | 94.6 (n = 2) | -NA- | 100.00 (n = 1) | 99.3 (n = 4) | 0 (n = 9) |
| 70 | -NA- | 98.0 (n = 2) | -NA- | 100.00 (n = 1) | 95.8 (n = 4) | 0 (n = 9) |
| 73 | -NA- | 97.6 (n = 2) | -NA- | 100.00 (n = 1) | 94.5 (n = 4) | 0 (n = 8) |
| 77 | -NA- | 96.7 (n = 2) | -NA- | 100.00 (n = 1) | 82.0 (n = 4) | 0 (n = 8 |
| 80 | -NA- | 96.9 (n = 2) | -NA- | 100.00 (n = 1) | 76.8 (n = 4) | 89.5 (n = 8) |
| 84 | -NA- | 98.0 (n = 2) | -NA- | 100.00 (n = 1) | 61.3 (n = 4) | 88.0 (n = 7) |
| 87 | -NA- | 97.2 (n = 2) | -NA- | 100.00 (n = -1) | 37.6 (n = 4) | 78.6 (n = 7) |
| 90 | -NA- | 98.5 (n = 2) | -NA- | 100.00 (n = 1) | 4.9 (n = 4) | 69.4 (n = 7) |
| 93 | -NA- | 97.3 (n = 2) | -NA- | 100.00 (n = 1) | 0 (n = 4) | 69.1 (n = 7) |
| 98 | -NA- | 97.6 (n = 2) | -NA- | 100.00 (n = 1) | 0 (n = 4) | 40.9 (n = 7) |
| 101 | -NA- | 96.3 (n = 2) | -NA- | 100.00 (n = 1) | 0 (n = 4) | 32.0 (n = 7) |
| 106 | -NA- | 97.4 (n = 2) | -NA- | 100.00 (n = 1) | -NA- | -NA- |

TABLE 7-continued (n = 10 unless noted)

| Day of Study | Group 1- Vehicle Control 2Q7Dx4 | Group 2- Anti-PD-1 200 μg Q3Dx35 | Group 3- Compound 1 75 mg/kg 2Q7Dx6 | Group 4- Compound 1 150 mg/kg 2Q7Dx6 | Group 5- Compound 1 75 mg/kg 2Q7Dx15 + Anti-PD-1 200 μg Q3Dx35 | Group 6- Compound 1 150 mg/kg 2Q7Dx6 + Anti-PD-1 200 μg Q3Dx35 |
|---|---|---|---|---|---|---|
| 111 | -NA- | 96.8 (n = 2) | -NA- | 100.00 (n = 1) | -NA- | -NA- |
| 118 | -NA- | 97.3 (n = 2) | -NA- | 100.00 (n = 1) | 100.00 (n = 3) | -NA- |
| 125 | -NA- | 96.2 (n = 2) | -NA- | 100.00 (n = 1) | 100.00 (n = 3) | 97.7 (n = 6) |
| 133 | -NA- | 96.8 (n = 2) | -NA- | 100.00 (n = 1) | 100.00 (n = 3) | 92.3 (n = 6) |
| 140 | -NA- | 96.8 (n = 2) | -NA- | 100.00 (n = 1) | 100.00 (n = 3) | 64.8 (n = 6) |
| 146 | -NA- | 98.9 (n = 2) | -NA- | 100.00 (n = 1) | 100.00 (n = 3) | 20.9 (n = 6) |
| 155 | -NA- | 98.1 (n = 2) | -NA- | 100.00 (n = 1) | 100.00 (n = 3) | -NA- |
| 161 | -NA- | 97.6 (n = 2) | -NA- | 100.00 (n = 1) | 100.00 (n = 3) | -NA- |
| 168 | -NA- | 95.5 (n = 2) | -NA- | 100.00 (n = 1) | 100.00 (n = 3) | 98.8 (n = 5) |
| 177 | -NA- | 98.2 (n = 2) | -NA- | 100.00 (n = 1) | 100.00 (n = 3) | 99.0 (n = 5) |
| 185 | -NA- | 97.1 (n = 2) | -NA- | 100.00 (n = 1) | 100.00 (n = 3) | 99.0 (n = 5) |

NA = no mice in the group.

TABLE 8

| Group | n | Range (Days) | Median Survival (Days) | Increase in Survival Relative to Vehicle (Days) |
|---|---|---|---|---|
| Group 1- Vehicle Control 2Q7Dx4 | 10 | 17.74-25.39 | 20.94 | — |
| Group 2- Anti-PD-1 200 μg Q3Dx35 | 10 | 22.68-N/A | 27.14 | 6.20 |
| Group 3- Compound 1 75 mg/kg 2Q7Dx6 | 10 | 23.76-40.59 | 32.00 | 11.06 |
| Group 4- Compound 1 150 mg/kg 2Q7Dx15 | 10 | 35.22-N/A | 42.90 | 21.96 |
| Group 5- Compound 1 75 mg/kg 2Q7Dx15 + Anti-PD-1 200 μg Q3Dx35 | 10 | 32.24-N/A | 43.78 | 22.84 |
| Group 6- Compound 1 150 mg/kg 2Q7Dx15 + Anti-PD-1 200 μg Q3Dx35 | 10 | 58.78-N/A | >185.00 | >164.06 |

Figure 3:
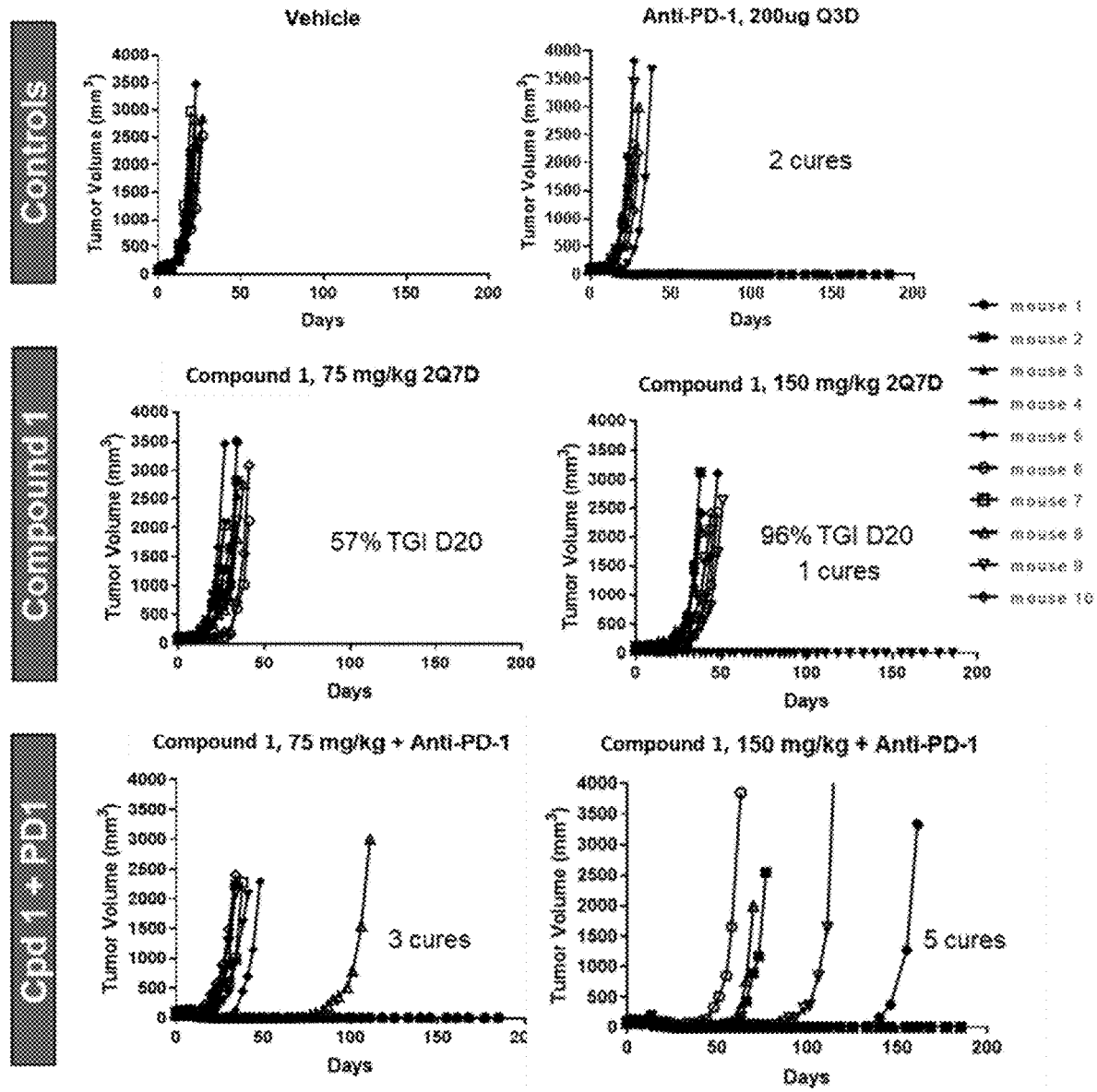
FIG. 3 shows changes in tumor volume ($mm^3$) in individual C57Bl/6 mice implanted with MT373 mouse syngeneic sarcoma tumors upon receiving treatment with vehicle; anti-PD-1 200 µg; Compound 1, 75 mg/kg; Compound 1, 150 mg/kg; Compound 1, 75 mg/kg+anti-PD-1; or Compound 1, 150 mg/kg+anti-PD-1.

FIG. 3 shows changes in tumor volume (mm$^3$) in individual C57Bl/6 mice implanted with MT373 mouse syngeneic sarcoma tumors upon receiving treatment with vehicle; anti-PD-1 200 μg; Compound 1, 75 mg/kg; Compound 1, 150 mg/kg; Compound 1, 75 mg/kg+anti-PD-1; or Compound 1, 150 mg/kg+anti-PD-1. MT373 tumors treated with vehicle control (0.2% HPC, 0.5% Tween 80) displayed consistent growth with all mice reaching ~2000 mm$^3$ between days 20 and 27. Tumors on mice receiving anti-PD-1 Q3D×35 demonstrated consistent growth inhibition through 13 days at which point 8 out of 10 tumors began to regrow at varied rates through day 38. Mice administered Compound 1 at 75 mg/kg 2Q7D×6 displayed consistent tumor growth through 16 days, at which point two tumors (mouse 6 and mouse 10) trended much slower than the remaining mice until reaching 2000 mm$^3$ at day 41. Mice administered Compound 1 at 150 mg/kg 2Q7D×15; Compound 1 75 mg/kg 2Q7D×15+200 μg anti-PD-1 Q3D×35; and 150 mg/kg 2Q7D×15+200 μg anti-PD-1 Q3D×35 showed tumor stasis through day 20, at which point tumors began to escape or regrow at variable rates. At the conclusion of the study, two animals (Group 2 mouse 2, Group 6 mouse 10) had tumor stasis. Several animals (Group 2: n=1, Group 4: n=1, Group 5: n=3, Group 6: n=4) demonstrated complete tumor regression.

Figure 4:
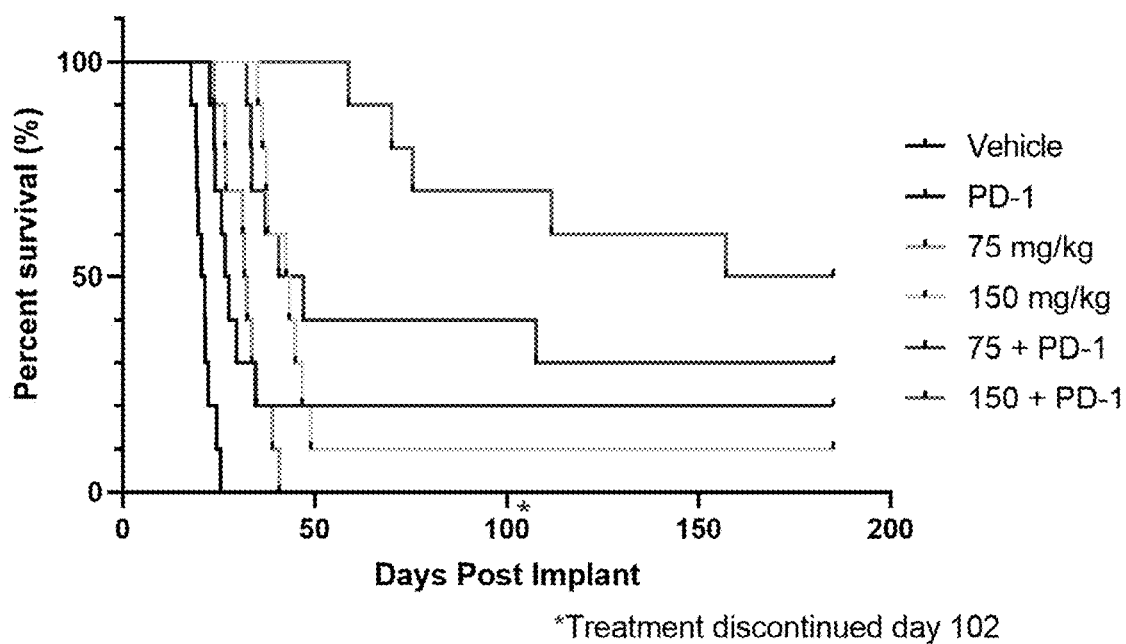
FIG. 4 shows changes in percentage survival of mice upon receiving treatment with vehicle; anti-PD-1; Compound 1, 75 mg/kg; Compound 1, 150 mg/kg; Compound 1, 75 mg/kg+anti-PD-1; or Compound 1, 150 mg/kg+anti-PD-1.

FIG. 4 shows changes in percentage survival of mice upon receiving treatment with vehicle; anti-PD-1; Compound 1, 75 mg/kg; Compound 1, 150 mg/kg; Compound 1, 75 mg/kg+anti-PD-1; or Compound 1, 150 mg/kg+anti-PD-1. TABLE 9 summarizes the median survival times (MST) of the six treatment groups. TABLE 10 and TABLE 11 show individual tumor volumes across study days 0-66 and days 70-185, respectively.

TABLE 9

| Group | MST (Days) |
|---|---|
| Vehicle | 21 |
| Anti-PD-1 200 μg | 27 |
| Compound 1 75 mg/kg 2Q7D | 32 |
| Compound 1 150 mg/kg 2Q7D | 43 |
| PD-1 + Compound 1 75 mg/kg | 44 |
| PD-1 + Compound 1 150 mg/kg | >185 |

TABLE 10

|  | Mouse | \multicolumn{11}{c}{Days} |
|---|---|---|---|---|---|---|---|---|---|---|---|---|

| | Mouse | 0 | 1 | 6 | 8 | 13 | 16 | 20 | 23 | 27 | 30 | 34 |
|---|---|---|---|---|---|---|---|---|---|---|---|---|
| Group 1 | 1 | 70 | 144 | 172 | 164 | 450 | 977 | 2219 | | | | |
| Vehicle | 2 | 78 | 143 | 139 | 144 | 314 | 506 | 1109 | 2299 | | | |
| Control | 3 | 76 | 80 | 112 | 99 | 245 | 465 | 908 | 1583 | 2854 | | |
| 2Q7Dx4 | 4 | 64 | 107 | 170 | 178 | 451 | 830 | 1575 | 2434 | | | |
| | 5 | 79 | 92 | 122 | 183 | 462 | 928 | 1671 | 3473 | | | |
| | 6 | 70 | 93 | 89 | 131 | 256 | 475 | 826 | 1211 | 2529 | | |
| | 7 | 85 | 91 | 137 | 190 | 516 | 1253 | 2973 | | | | |
| | 8 | 83 | 104 | 113 | 146 | 319 | 608 | 1350 | 2814 | | | |
| | 9 | 72 | 100 | 167 | 172 | 541 | 821 | 2102 | | | | |
| | 10 | 96 | 129 | 152 | 190 | 471 | 1101 | 2277 | | | | |
| | Ave | 77 | 108 | 137 | 160 | 403 | 727 | 1701 | 2302 | 2822 | | |
| | SD | 9 | 24 | 27 | 28 | 103 | 262 | 653 | 748 | 163 | | |
| Group 2 | 1 | 54 | 118 | 145 | 153 | 243 | 448 | 1041 | 2113 | | | |
| Anti-PD-1 | 2 | 77 | 95 | 124 | 140 | 76 | 38 | 16 | 7 | 0 | 5 | 18 |
| 200 µg/mse | 3 | 82 | 123 | 141 | 163 | 108 | 83 | 15 | 16 | 0 | 10 | 0 |
| Q3Dx35 | 4 | 70 | 105 | 117 | 120 | 120 | 79 | 99 | 200 | 439 | 752 | 1714 |
| | 5 | 116 | 144 | 132 | 150 | 228 | 490 | 945 | 1493 | 3815 | | |
| | 6 | 107 | 117 | 83 | 108 | 255 | 430 | 889 | 1322 | 2321 | | |
| | 7 | 93 | 93 | 89 | 118 | 288 | 449 | 919 | 1265 | 2064 | | |
| | 8 | 86 | 100 | 102 | 110 | 117 | 204 | 505 | 840 | 1745 | 2989 | |
| | 9 | 94 | 123 | 133 | 140 | 169 | 334 | 831 | 1524 | 3432 | | |
| | 10 | 61 | 91 | 90 | 106 | 107 | 61 | 510 | 520 | 1150 | 2165 | |
| | Ave | 84 | 111 | 118 | 181 | 171 | 262 | 577 | 180 | 1668 | 1188 | 577 |
| | SD | 13 | 16 | 22 | 20 | 72 | 177 | 387 | 688 | 1319 | 1198 | 804 |
| Group 3 | 1 | 80 | 93 | 108 | 105 | 204 | 322 | 687 | 962 | 873 | 986 | 3500 |
| Compound 1 | 2 | 79 | 92 | 87 | 107 | 202 | 326 | 698 | 837 | 1270 | 1642 | 2824 |
| 75 mg/kg | 3 | 58 | 81 | 89 | 103 | 152 | 227 | 385 | 711 | 783 | 1158 | 2566 |
| 2Q7Dx6 | 4 | 114 | 103 | 109 | 133 | 249 | 394 | 844 | 1285 | 2077 | | |
| | 5 | 78 | 96 | 91 | 130 | 173 | 295 | 854 | 1656 | 3460 | | |
| | 6 | 88 | 66 | 77 | 63 | 106 | 86 | 71 | 92 | 118 | 164 | 593 |
| | 7 | 69 | 89 | so | 95 | 193 | 297 | 650 | 1013 | 2045 | | |
| | 8 | 94 | 86 | 85 | 92 | 108 | 170 | 330 | 497 | 574 | 743 | 1813 |
| | 9 | 62 | 74 | 83 | 107 | 112 | 199 | 355 | 532 | 649 | 982 | 2120 |
| | 10 | 103 | 99 | 94 | 97 | 88 | 95 | 105 | 142 | 193 | 191 | 716 |
| | Ave | 83 | 88 | 90 | 103 | 159 | 241 | 498 | 772 | 1204 | 888 | 2019 |
| | SD | 17 | 11 | 10 | 19 | 51 | 98 | 273 | 463 | 988 | 489 | 995 |
| Group 4 | 1 | 68 | 54 | 43 | 73 | 65 | 135 | 128 | 261 | 379 | 653 | 1380 |
| Compound 1 | 2 | 53 | 75 | 63 | 97 | 53 | 113 | 92 | 192 | 231 | 568 | 1508 |
| 150 Mg/kg | 3 | 87 | 143 | 97 | 159 | 207 | 133 | 176 | 337 | 269 | 506 | 1203 |
| 2Q7Dx15 | 4 | 113 | 128 | 85 | 134 | 83 | 34 | 0 | 0 | 0 | 0 | 0 |
| | 5 | 85 | 86 | 77 | 129 | 93 | 136 | 106 | 136 | 58 | 86 | 328 |
| | 6 | 60 | 73 | 101 | 101 | 44 | 53 | 63 | 74 | 93 | 143 | 302 |
| | 7 | 57 | 76 | 92 | 71 | 40 | 43 | 91 | 103 | 187 | 306 | 615 |
| | 8 | 98 | 84 | 109 | 119 | 88 | 195 | 228 | 367 | 432 | 660 | 1067 |
| | 9 | 117 | 107 | 108 | 110 | 55 | 69 | 65 | 107 | 101 | 146 | 289 |
| | 10 | 53 | 58 | 43 | 49 | 32 | 66 | 113 | 158 | 161 | 220 | 590 |
| | Ave | 79 | 88 | 82 | 104 | 76 | 98 | 106 | 174 | 191 | 329 | 728 |
| | SD | 23 | 28 | 23 | 32 | 48 | 50 | 60 | 111 | 132 | 235 | 497 |
| Group 5 | 1 | 76 | 60 | 46 | 44 | 16 | 10 | 5 | 10 | 0 | 0 | 0 |
| Compound 1 | 2 | 106 | 100 | 78 | 144 | 59 | 156 | 166 | 294 | 594 | 888 | 2228 |
| 75 Mg/kg | 3 | 78 | 55 | 58 | 57 | 25 | 22 | 7 | 0 | 0 | 0 | 0 |
| 2Q7Dx15 + | 4 | 88 | 136 | 91 | 104 | 50 | 93 | 129 | 128 | 295 | 407 | 922 |
| anti-PD-1 | 5 | 88 | 91 | 92 | 83 | 25 | 42 | 17 | 18 | 13 | 39 | 137 |
| 200 µg/mse | 6 | 101 | 91 | 94 | 95 | 36 | 42 | 14 | 0 | 0 | 0 | 0 |
| Q3Dx35 | 7 | 85 | 91 | 111 | 100 | 101 | 133 | 157 | 316 | 522 | 591 | 992 |
| | 8 | 52 | 58 | 58 | 47 | 20 | 19 | 0 | 0 | 0 | 0 | 0 |
| | 9 | 72 | 78 | 79 | 85 | 91 | 141 | 332 | 495 | 797 | 1285 | 2096 |
| | 10 | 63 | 72 | 65 | 98 | 115 | 226 | 396 | 583 | 899 | 1489 | 2401 |
| | Ave | 81 | 83 | 77 | 86 | 54 | 88 | 122 | 184 | 312 | 470 | 878 |
| | SD | 16 | 23 | 19 | 29 | 35 | 69 | 137 | 212 | 344 | 545 | 963 |
| Group 6 | 1 | 87 | 134 | 89 | 82 | 40 | 30 | 29 | 0 | 0 | 0 | 0 |
| Compound 1 | 2 | 76 | 139 | 84 | 90 | 207 | 112 | 70 | 0 | 0 | 0 | 0 |
| 150 ng/kg | 3 | 70 | 86 | 140 | 129 | 108 | 64 | 78 | 0 | 0 | 0 | 0 |
| 2Q7Dx15 + | 4 | 82 | 114 | 98 | 88 | 60 | 43 | 20 | 16 | 0 | 0 | 0 |
| anti-PD-1 | 5 | 77 | 52 | 46 | 67 | 0 | 0 | 0 | 0 | 0 | 0 | 0 |
| 200 µg/mse | 6 | 8S | 71 | 119 | 122 | 79 | 65 | 55 | 24 | 9 | 9 | 31 |
| Q3Dx35 | 7 | 103 | 101 | 84 | 68 | 72 | 65 | 42 | 18 | 0 | 0 | 0 |
| | 8 | 64 | 75 | 87 | 68 | 74 | 34 | 20 | 12 | 1 | 1 | 6 |

TABLE 10-continued

|   |   |   |   |   |   |   |   |   |   |   |
|---|---|---|---|---|---|---|---|---|---|---|
| 9 | 85 | 132 | 121 | 118 | 110 | 100 | 100 | 81 | 52 | 15 | 76 |
| 10 | 66 | 85 | 76 | 53 | 40 | 34 | 27 | 8 | 1 | 1 | 7 |
| Ave | 80 | 99 | 94 | 89 | 79 | 55 | 44 | 16 | 6 | 3 | 12 |
| SD | 11 | 28 | 25 | 25 | 53 | 32 | 29 | 23 | 136 | 5 | 23 |

|  |  | Days |  |  |  |  |  |  |  |  |
|---|---|---|---|---|---|---|---|---|---|---|
|  | Mouse | 38 | 41 | 44 | 48 | 51 | 55 | 58 | 63 | 66 |
| Group 1 | 1 |  |  |  |  |  |  |  |  |  |
| Vehicle | 2 |  |  |  |  |  |  |  |  |  |
| Control | 3 |  |  |  |  |  |  |  |  |  |
| 2Q7Dx4 | 4 |  |  |  |  |  |  |  |  |  |
|  | 5 |  |  |  |  |  |  |  |  |  |
|  | 6 |  |  |  |  |  |  |  |  |  |
|  | 7 |  |  |  |  |  |  |  |  |  |
|  | 8 |  |  |  |  |  |  |  |  |  |
|  | 9 |  |  |  |  |  |  |  |  |  |
|  | 10 |  |  |  |  |  |  |  |  |  |
|  | Ave |  |  |  |  |  |  |  |  |  |
|  | SD |  |  |  |  |  |  |  |  |  |
| Group 2 | 1 |  |  |  |  |  |  |  |  |  |
| Anti-PD-1 | 2 | 7 | 11 | 9 | 11 | 14 | 14 | 9 | 8 | 9 |
| 200 μg/mse | 3 | 0 | 0 | 0 | 0 | 0 | 0 | 0 | 0 | 0 |
| Q3Dx35 | 4 | 3655 |  |  |  |  |  |  |  |  |
|  | 5 |  |  |  |  |  |  |  |  |  |
|  | 6 |  |  |  |  |  |  |  |  |  |
|  | 7 |  |  |  |  |  |  |  |  |  |
|  | 8 |  |  |  |  |  |  |  |  |  |
|  | 9 |  |  |  |  |  |  |  |  |  |
|  | 10 |  |  |  |  |  |  |  |  |  |
|  | Ave | 1221 | 5 | 5 | 5 | 7 | 7 | 4 | 4 | 5 |
|  | SD | 1721 | 5 | 5 | 6 | 7 | 7 | 4 | 4 | 5 |
| Group 3 | 1 |  |  |  |  |  |  |  |  |  |
| Compound 1 | 2 |  |  |  |  |  |  |  |  |  |
| 75 mg/kg | 3 |  |  |  |  |  |  |  |  |  |
| 2Q7Dx6 | 4 |  |  |  |  |  |  |  |  |  |
|  | 5 |  |  |  |  |  |  |  |  |  |
|  | 6 | 1022 | 2114 |  |  |  |  |  |  |  |
|  | 7 |  |  |  |  |  |  |  |  |  |
|  | 8 | 2750 |  |  |  |  |  |  |  |  |
|  | 9 |  |  |  |  |  |  |  |  |  |
|  | 10 | 1563 | 3078 |  |  |  |  |  |  |  |
|  | Ave | 1778 | 2596 |  |  |  |  |  |  |  |
|  | SD | 722 | 482 |  |  |  |  |  |  |  |
| Group 4 | 1 | 2406 |  |  |  |  |  |  |  |  |
| Compound 1 | 2 | 3114 |  |  |  |  |  |  |  |  |
| 150 Mg/kg | 3 | 2162 |  |  |  |  |  |  |  |  |
| 2Q7Dx15 | 4 | 0 | 0 | 0 | 0 | 0 | 0 | 0 | 0 | 0 |
|  | 5 | 609 | 990 | 1672 | 3099 |  |  |  |  |  |
|  | 6 | 595 | 843 | 1169 | 2418 |  |  |  |  |  |
|  | 7 | 1003 | 1652 | 2114 |  |  |  |  |  |  |
|  | 8 | 2085 |  |  |  |  |  |  |  |  |
|  | 9 | 449 | 631 | 810 | 1730 | 2622 |  |  |  |  |
|  | 10 | 944 | 1566 | 2407 |  |  |  |  |  |  |
|  | Ave | 1337 | 947 | 1362 | 1312 | 1311 | 0 | 0 | 0 | 0 |
|  | SD | 973 | 561 | 812 | 1153 | 1311 | 0 | 0 | 0 | 0 |
| Group 5 | 1 | 0 | 0 | 0 | 0 | 0 | 0 | 0 | 0 | 0 |
| Compound 1 | 2 |  |  |  |  |  |  |  |  |  |
| 75 Mg/kg | 3 | 0 | 0 | 0 | 0 | 0 | 0 | 0 | 0 | 0 |
| 2Q7Dx15 + | 4 | 1588 | 2068 |  |  |  |  |  |  |  |
| anti-PD-1 | 5 | 440 | 696 | 1143 | 2286 |  |  |  |  |  |
| 200 μg/mse | 6 | 0 | 0 | 0 | 0 | 0 | 0 | 0 | 0 | 0 |
| Q3Dx35 | 7 | 2274 |  |  |  |  |  |  |  |  |
|  | 8 | 0 | 0 | 0 | 0 | 0 | 0 | 0 | 0 | 2 |
|  | 9 |  |  |  |  |  |  |  |  |  |
|  | 10 |  |  |  |  |  |  |  |  |  |
|  | Ave | 615 | 461 | 229 | 457 | 0 | 0 | 0 | 0 | 1 |
|  | SD | 866 | 763 | 457 | 815 | 0 | 0 | 0 | 0 | 1 |
| Group 6 | 1 | 0 | 0 | 0 | 0 | 0 | 0 | 0 | 0 | 0 |
| Compound 1 | 2 | 0 | 0 | 0 | 0 | 0 | 0 | 0 | 136 | 433 |
| 150 ng/kg | 3 | 0 | 0 | 0 | 0 | 0 | 0 | 0 | 0 | 0 |

TABLE 10-continued

|  |  |  |  |  |  |  |  |  |  |  |
|---|---|---|---|---|---|---|---|---|---|---|
| 2Q7Dx15 + | 4 | 0 | 0 | 0 | 0 | 0 | 0 | 0 | 0 | 0 |
| anti-PD-1 | 5 | 0 | 0 | 0 | 0 | 0 | 0 | 0 | 0 | 0 |
| 200 µg/mse | 6 | 76 | 111 | 150 | 343 | 517 | 853 | 1655 | 3853 | |
| Q3Dx35 | 7 | 0 | 0 | 0 | 0 | 0 | 0 | 0 | 0 | 0 |
|  | 8 | 2 | 10 | 8 | 33 | 36 | 68 | 112 | 330 | 765 |
|  | 9 | 47 | 45 | S6 | 29 | 36 | 63 | 76 | 43 | 35 |
|  | 10 | 11 | 11 | 10 | 6 | 23 | 20 | 13 | 11 | 5 |
|  | Ave | 14 | 18 | 23 | 41 | 61 | 100 | 186 | 437 | 1141 |
|  | SD | 25 | 34 | 46 | 102 | 153 | 252 | 491 | 1143 | 259 |

TABLE 11

|  |  | Days | | | | | | | | | | | |
|---|---|---|---|---|---|---|---|---|---|---|---|---|---|
|  | Mouse | 70 | 73 | 77 | 80 | 84 | 87 | 90 | 93 | 98 | 101 | 106 | 111 |
| Group 2 | 1 | | | | | | | | | | | | |
| Anti-PD-1 | 2 | 3 | 4 | 6 | 5 | 3 | 5 | 2 | 5 | 4 | 6 | 4 | 5 |
| 200 µg/mse | 3 | 0 | 0 | 0 | 0 | 0 | 0 | 0 | 0 | 0 | 0 | 0 | 0 |
| Q3Dx35 | 4 | | | | | | | | | | | | |
|  | 5 | | | | | | | | | | | | |
|  | 6 | | | | | | | | | | | | |
|  | 7 | | | | | | | | | | | | |
|  | 8 | | | | | | | | | | | | |
|  | 9 | | | | | | | | | | | | |
|  | 10 | | | | | | | | | | | | |
|  | Ave | 2 | 2 | 3 | 3 | 2 | 2 | 1 | 2 | 2 | 3 | 2 | 3 |
|  | SD | 2 | 2 | 3 | 3 | 2 | 2 | 1 | 2 | 2 | 3 | 2 | 3 |
| Group 4 | 1 | | | | | | | | | | | | |
| Compound 1 | 2 | | | | | | | | | | | | |
| 150 mg/kg | 3 | | | | | | | | | | | | |
| 2Q7Dx15 | 4 | 0 | 0 | 0 | 0 | 0 | 0 | 0 | 0 | 0 | 0 | 0 | 0 |
|  | 5 | | | | | | | | | | | | |
|  | 6 | | | | | | | | | | | | |
|  | 7 | | | | | | | | | | | | |
|  | 8 | | | | | | | | | | | | |
|  | 9 | | | | | | | | | | | | |
|  | 10 | | | | | | | | | | | | |
|  | Ave | 0 | 0 | 0 | 0 | 0 | 0 | 0 | 0 | 0 | 0 | 0 | 0 |
|  | SD | 0 | 0 | 0 | 0 | 0 | 0 | 0 | 0 | 0 | 0 | 0 | 0 |
| Group 5 | 1 | 0 | 0 | 0 | 0 | 0 | 0 | 0 | 0 | 0 | 0 | 0 | 0 |
| Compound 1 | 2 | | | | | | | | | | | | |
| 75 mg/kg | 3 | 0 | 0 | 0 | 0 | 0 | 0 | 0 | 0 | 0 | 0 | 0 | 0 |
| 2Q7Dx15 + | 4 | | | | | | | | | | | | |
| anti-PD-1 | 5 | | | | | | | | | | | | |
| 200 µg/mse | 6 | 0 | 0 | 0 | 0 | 0 | 0 | 0 | 0 | 0 | 0 | 0 | 0 |
| Q3Dx35 | 7 | | | | | | | | | | | | |
|  | 8 | 14 | 18 | 58 | 7 | 125 | 202 | 308 | 359 | 507 | 777 | 1538 | 3000 |
|  | 9 | | | | | | | | | | | | |
|  | 10 | | | | | | | | | | | | |
|  | Ave | 3 | 5 | 15 | 19 | 31 | 51 | 77 | 90 | 127 | 194 | 385 | 750 |
|  | SD | 6 | 8 | 25 | 33 | 54 | 88 | 133 | 156 | 220 | 336 | 666 | 1299 |
| Group 6 | 1 | 0 | 0 | 0 | 0 | 0 | 0 | 0 | 0 | 0 | 0 | 0 | 0 |
| Compound 1 | 2 | 893 | 1170 | 2553 | | | | | | | | | |
| 150 mg/kg | 3 | 0 | 0 | 0 | 0 | 0 | 0 | 0 | 0 | 0 | 0 | 0 | 0 |
| 2Q7Dx15 + | 4 | 0 | 0 | 0 | 0 | 0 | 0 | 0 | 0 | 0 | 0 | 0 | 0 |
| anti-PD-1 | 5 | 0 | 0 | 0 | 0 | 0 | 0 | 0 | 0 | 0 | 0 | 0 | 0 |
| 200 µg/mse | 6 | | | | | | | | | | | | |
| Q3Dx35 | 7 | 0 | 0 | 0 | 0 | 0 | 0 | 0 | 0 | 0 | 0 | 0 | 0 |
|  | 8 | 2002 | | | | | | | | | | | |
|  | 9 | 59 | 40 | 46 | 49 | 55 | 106 | 162 | 164 | 323 | 369 | 843 | 1643 |
|  | 10 | 16 | 13 | 9 | 10 | 12 | 13 | 8 | 8 | 6 | 10 | 6 | 5 |
|  | Ave | 330 | 153 | 326 | 8 | 10 | 17 | 24 | 25 | 47 | 54 | 121 | 235 |
|  | SD | 652 | 385 | 842 | 17 | 19 | 37 | 56 | 57 | 113 | 129 | 295 | 575 |

|  |  | Days | | | | | | | | |
|---|---|---|---|---|---|---|---|---|---|---|
|  | Mouse | 118 | 125 | 133 | 140 | 146 | 155 | 161 | 168 | 177 | 185 |
| Group 2 | 1 | | | | | | | | | |
| Anti-PD-1 | 2 | 4 | 6 | 5 | 5 | 2 | 3 | 4 | 7 | 3 | 5 |
| 200 µg/mse | 3 | 0 | 0 | 0 | 0 | 0 | 0 | 0 | 0 | 0 |
| Q3Dx35 | 4 | | | | | | | | | |
|  | 5 | | | | | | | | | |
|  | 6 | | | | | | | | | |
|  | 7 | | | | | | | | | |
|  | 8 | | | | | | | | | |

TABLE 11-continued

| | | | | | | | | | | | |
|---|---|---|---|---|---|---|---|---|---|---|---|
| | 9 | | | | | | | | | | |
| | 10 | | | | | | | | | | |
| | Ave | 2 | 3 | 3 | 3 | 1 | 2 | 2 | 3 | 1 | 2 |
| | SD | 2 | 3 | 3 | 3 | 1 | 2 | 2 | 3 | 1 | 2 |
| Group 4 Compound 1 150 mg/kg 2Q7Dx15 | 1 | | | | | | | | | | |
| | 2 | | | | | | | | | | |
| | 3 | | | | | | | | | | |
| | 4 | 0 | 0 | 0 | 0 | 0 | 0 | 0 | 0 | 0 | 0 |
| | 5 | | | | | | | | | | |
| | 6 | | | | | | | | | | |
| | 7 | | | | | | | | | | |
| | 8 | | | | | | | | | | |
| | 9 | | | | | | | | | | |
| | 10 | | | | | | | | | | |
| | Ave | 0 | 0 | 0 | 0 | 0 | 0 | 0 | 0 | 0 | 0 |
| | SD | 0 | 0 | 0 | 0 | 0 | 0 | 0 | 0 | 0 | 0 |
| Group 5 Compound 1 75 mg/kg 2Q7Dx15 + anti-PD-1 200 μg/mse Q3Dx35 | 1 | 0 | 0 | 0 | 0 | 0 | 0 | 0 | 0 | 0 | 0 |
| | 2 | | | | | | | | | | |
| | 3 | 0 | 0 | 0 | 0 | 0 | 0 | 0 | 0 | 0 | 0 |
| | 4 | | | | | | | | | | |
| | 5 | | | | | | | | | | |
| | 6 | 0 | 0 | 0 | 0 | 0 | 0 | 0 | 0 | 0 | 0 |
| | 7 | | | | | | | | | | |
| | 8 | | | | | | | | | | |
| | 9 | | | | | | | | | | |
| | 10 | | | | | | | | | | |
| | Ave | 0 | 0 | 0 | 0 | 0 | 0 | 0 | 0 | 0 | 0 |
| | SD | 0 | 0 | 0 | 0 | 0 | 0 | 0 | 0 | 0 | 0 |
| Group 6 Compound 1 150 mg/kg 2Q7Dx15 + anti-PD-1 200 μg/mse Q3Dx35 | 1 | 0 | 0 | 0 | 0 | 0 | 0 | 0 | 0 | 0 | 0 |
| | 2 | | | | | | | | | | |
| | 3 | 0 | 0 | 0 | 0 | 0 | 0 | 0 | 0 | 0 | 0 |
| | 4 | 0 | 0 | 0 | 0 | 0 | 0 | 0 | 0 | 0 | 0 |
| | 5 | 0 | 0 | 0 | 0 | 0 | 0 | 0 | 0 | 0 | 0 |
| | 6 | | | | | | | | | | |
| | 7 | 0 | 0 | 0 | 0 | 0 | 0 | 0 | 0 | 0 | 0 |
| | 8 | | | | | | | | | | |
| | 9 | 6357 | | | | | | | | | |
| | 10 | 11 | 4 | 6 | 5 | 4 | 6 | 10 | 5 | 4 | |
| | Ave | 910 | 2 | 6 | 29 | 65 | 214 | 557 | 1 | 1 | 1 |
| | SD | 2224 | 3 | 12 | 62 | 143 | 475 | 1240 | 2 | 2 | 2 |

Body Weights: Average mouse body weights were well-maintained over the course of the study. Mice dosed with vehicle control were an average of 22.9 g by the end of the study (day 27) with the percentage change varying between 1.3600 early in the study to +27.740%. Mice administered anti-PD-1 lost 1.38% body weight early in the study but recovered and gained an average of 18.15% by Day 27. One mouse (6) lost 16.6% on Day 6 but recovered by day 13 with 1.10% body weight loss. Mice administered Compound 1 (Groups 3-6) also maintained body weight well throughout the study and no individual mouse lost more than 50 body weight. By day 27, Group 3 gained 12.96%, Group 4 gained 10.02%, Group 5 gained 11.65% and Group 6 gained 9.60%.

Figure 5:
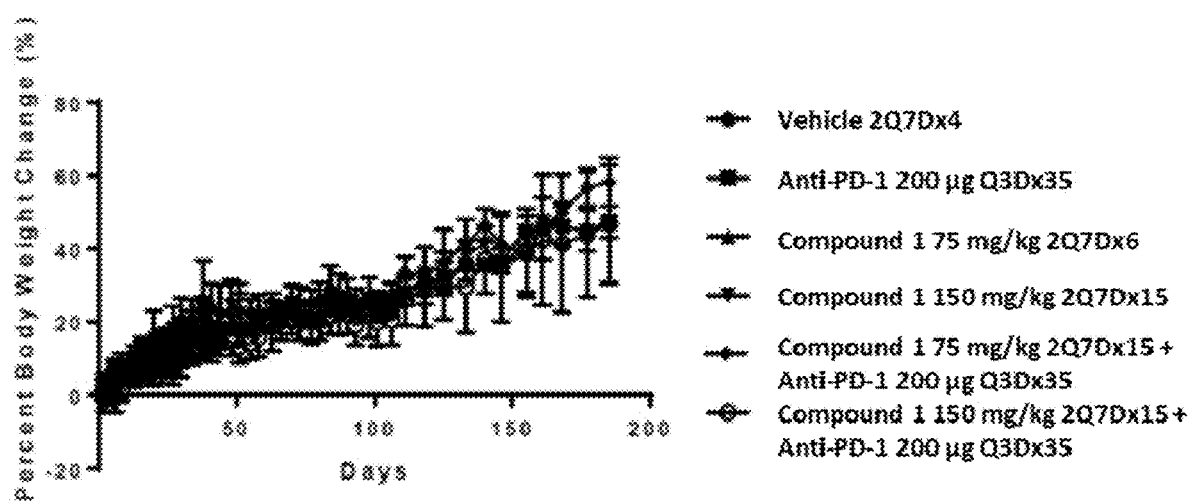
FIG. 5 shows the changes in percent body weight change in female C57Bl/6 mice implanted with MT373 mouse syngeneic sarcoma tumors upon receiving treatment with vehicle (2Q7Dx4); anti-PD-1 200 µg (Q3Dx35); Compound 1, 75 mg/kg (2Q7Dx6); Compound 1, 150 mg/kg (2Q7Dx15); Compound 1, 75 mg/kg (2Q7Dx15)+anti-PD-1 (Q3Dx35); or Compound 1, 150 mg/kg (2Q7Dx15)+anti-PD-1 (Q3Dx35).

TABLE 11 shows the average percent change in mouse body weight across the study (n=10 unless otherwise noted; n/a=no mice in the group). TABLE 12 shows individual mouse body weights across the study from days 0-66. TABLE 13 shows individual mouse body weights across the study from days 70-185. FIG. 5 shows the changes in percent body weight change in female C57Bl/6 mice implanted with MT373 mouse syngeneic sarcoma tumors upon receiving treatment with vehicle (2Q7Dx4); anti-PD-1 200 μg (Q3Dx35); Compound 1, 75 mg/kg (2Q7Dx6); Compound 1, 150 mg/kg (2Q7Dx15); Compound 1, 75 mg/kg (2Q7Dx15)+anti-PD-1 (Q3Dx35); or Compound 1, 150 mg/kg (2Q7Dx25)+anti-PD-1 (Q3Dx35).

TABLE 11

| Day of study | Group 1 Vehicle control 2Q7Dx4 | Group 2 Anti-PD-1 200 μg Q3Dx35 | Group 3 Compound 1 75 mg/kg 2Q7Dx6 | Group 4 Compound 1 150 mg/kg 2Q7Dx6 | Group 5 Compound 1 75 mg/kg 2Q7Dx15 + Anti-PD-1 200 μg Q3Dx35 | Group 6 Compound 1 150 mg/kg 2Q7Dx6 + Anti-PD-1 200 μg Q3Dx35 |
|---|---|---|---|---|---|---|
| 2 | 1.36 ± 2.61 | −1.38 ± 3.28 | 2.05 ± 1.40 | 3.47 ± 2.49 | 3.29 ± 2.67 | 2.28 ± 2.32 |
| 6 | 3.11 ± 3.28 | 2.48 ± 7.18 | 2.90 ± 2.56 | 4.67 ± 4.56 | 4.53 ± 2.60 | 5.62 ± 2.89 |
| 8 | 5.91 ± 3.53 | 5.00 ± 6.47 | 4.29 ± 4.05 | 2.69 ± 4.48 | 6.20 ± 3.41 | 0.94 ± 2.49 |
| 13 | 8.28 ± 2.30 | 7.56 ± 4.24 | 4.88 ± 2.70 | 7.86 ± 5.56 | 6.28 ± 3.51 | 7.74 ± 4.13 |
| 16 | 12.10 ± 3.67 | 9.36 ± 5.45 | 7.06 ± 2.34 | 8.02 ± 3.80 | 10.43 ± 4.02 | 8.00 ± 3.47 |
| 20 | 15.81 ± 7.19 | 10.50 ± 4.51 | 8.75 ± 2.85 | 8.06 ± 4.79 | 8.07 ± 5.72 | 9.05 ± 3.43 |
| 23 | 16.91 ± 1.44 (n = 6) | 11.69 ± 5.38 | 12.43 ± 4.12 | 8.47 ± 5.21 | 10.39 ± 4.54 | 8.04 ± 3.30 |
| 27 | 27.74 ± 2.22 (n = 2) | 18.15 ± 6.10 (n = 9) | 12.96 ± 5.24 | 10.02 ± 7.27 | 11.65 ± 3.45 | 9.60 ± 3.19 |

TABLE 11-continued

| Day of study | Group 1 Vehicle control 2Q7Dx4 | Group 2 Anti-PD-1 200 μg Q3Dx35 | Group 3 Compound 1 75 mg/kg 2Q7Dx6 | Group 4 Compound 1 150 mg/kg 2Q7Dx6 | Group 5 Compound 1 75 mg/kg 2Q7Dx15 + Anti-PD-1 200 μg Q3Dx35 | Group 6 Compound 1 150 mg/kg 2Q7Dx6 + Anti-PD-1 200 μg Q3Dx35 |
|---|---|---|---|---|---|---|
| 30 | n/a | 18.00 ± 8.52 (n = 5) | 11.93 ± 6.80 (n = 7) | 12.48 ± 7.51 | 15.19 ± 4.93 | 11.46 ± 3.80 |
| 34 | n/a | 16.55 ± 6.43 (n = 3) | 18.26 ± 8.13 (n = 7) | 14.88 ± 6.40 | 16.91 ± 3.56 | 13.35 ± 4.23 |
| 38 | n/a | 23.70 ± 13.23 (n = 3) | 22.28 ± 4.13 (n = 3) | 19.05 ± 7.92 | 18.13 ± 5.10 (n = 7) | 14.18 ± 3.30 |
| 41 | n/a | 15.55 ± 1.58 (n = 2) | 25.18 ± 5.26 (n = 2) | 17.97 ± 5.31 (n = 6) | 17.52 ± 5.27 (n = 6) | 13.37 ± 4.43 |
| 44 | n/a | 15.03 ± 2.31 (n = 2) | n/a | 21.56 ± 8.64 (n = 6) | 18.10 ± 4.89 (n = 5) | 15.17 ± 4.59 |
| 48 | n/a | 18.21 ± 0.96 (n = 2) | n/a | 24.55 ± 7.11 (n = 4) | 19.40 ± 2.40 (n = 5) | 14.57 ± 3.66 |
| 51 | n/a | 17.91 ± 0.19 (n = 2) | n/a | 22.20 ± 8.23 (n = 2) | 23.21 ± 4.70 (n = 5) | 13.07 ± 4.28 |
| 55 | n/a | 18.19 ± 0.21 (n = 2) | n/a | 18.08 ± 0 (n = 1) | 22.07 ± 4.40 (0 = 4) | 14.10 ± 4.53 |
| 58 | n/a | 19.54 ± 0.66 (n = 2) | n/a | 19.77 ± 0 (n = 1) | 22.77 ± 4.81 (n = 4) | 15.77 ± 5.39 |
| 63 | n/a | 22.11 ± 2.99 (n = 2) | n/a | 20.90 ± 0 (n = 1) | 21.50 ± 4.48 (n = 4) | 20.06 ± 7.93 |
| 66 | n/a | 21.64 ± 0.75 (n = 2) | n/a | 22.60 ± 0 (n = 1) | 21.66 ± 3.16 (n = 4) | 20.18 ± 5.40 (n = 9) |
| 70 | n/a | 25.37 ± 1.30 (n = 2) | n/a | 23.16 ± 0 (n = 1) | 25.49 ± 4.64 (n = 4) | 20.82 ± 4.16 (n = 9) |
| 73 | n/a | 21.44 ± 1.89 (n = 2) | n/a | 18.08 ± 0 (n = 1) | 25.06 ± 4.50 (n = 4) | 20.20 ± 5.37 (n = 8) |
| 77 | n/a | 20.37 ± 1.83 (n = 2) | n/a | 20.34 ± 0 (n = 1) | 24.48 ± 4.48 (n = 4) | 19.86 ± 5.99 (n = 8) |
| 80 | n/a | 20.86 ± 0.35 (n = 2) | n/a | 23.73 ± 0 (n = 1) | 26.20 ± 4.69 (n = 4) | 20.18 ± 5.19 (n = 7) |
| 84 | n/a | 25.15 ± 0.58 (n = 2) | n/a | 26.55 ± 0 (n = 1) | 28.94 ± 6.62 (n = 4) | 21.82 ± 5.10 (n = 7) |
| 87 | n/a | 25.15 ± 0.58 (n = 2) | n/a | 21.47 ± 0 (n = 1) | 27.35 ± 5.85 (n = 4)) | 22.82 ± 5.99 (n = 7) |
| 90 | n/a | 24.32 ± 0.60 (n = 2) | n/a | 24.29 ± 0 (n = 1) | 27.17 ± 4.70 (n = 4) | 21.94 ± 5.33 (n = 7) |
| 93 | n/a | 23.48 ± 1.78 (n = 2) | n/a | 21.47 ± 0 (n = 1) | 25.70 ± 3.59 (n = 4) | 19.00 ± 5.46 (n = 7) |
| 98 | n/a | 25.60 ± 2.43 (n = 2) | n/a | 23.73 ± 0 (n = 1) | 26.91 ± 5.28 (n = 4) | 21.86 ± 6.19 (n = 7) |
| 101 | n/a | 23.70 ± 3.66 (n = 2) | n/a | 22.60 ± 0 (n = 1) | 24.75 ± 3.99 (n = 4) | 19.90 ± 6.40 (n = 7) |
| 106 | n/a | 24.51 ± 3.24 (n = 2) | n/a | 22.03 ± 0 (n = 1) | 26.44 ± 4.25 (n = 4) | 20.47 ± 6.72 (n = 7) |
| 111 | n/a | 28.24 ± 3.80 (n = 2) | n/a | 26.55 ± 0 (n = 1) | 33.68 ± 4.22 (n = 4) | 26.06 ± 7.03 (n = 7) |
| 118 | n/a | 30.66 ± 3.29 (n = 2) | n/a | 33.33 ± 0 (n = 1) | 32.69 ± 7.76 (n = 3) | 29.52 ± 10.87 (n = 7) |
| 125 | n/a | 32.78 ± 3.94 (n = 2) | n/a | 28.25 ± 0 (n = 1) | 36.44 ± 8.93 (n = 3) | 29.89 ± 9.26 (n = 6) |
| 133 | n/a | 35.72 ± 4.16 (n = 2) | n/a | 38.42 ± 0 (n = 1) | 41.28 ± 6.86 (n = 3) | 29.70 ± 12.70 (n = 6) |
| 140 | n/a | 35.78 ± 1.89 (n = 2) | n/a | 41.24 ± 0 (n = 1) | 46.51 ± 4.41 (n = 3) | 37.02 ± 9.12 (n = 6) |
| 146 | n/a | 36.81 ± 3.35 (n = 2) | n/a | 34.46 ± 0 (n = 1) | 41.30 ± 7.73 (n = 3) | 35.09 ± 15.06 (n = 6) |
| 155 | n/a | 45.08 ± 4.04 (n = 2) | n/a | 42.37 ± 0 (n = 1) | 38.61 ± 10.37 (n = 3) | 38.99 ± 12.02 (n = 6) |
| 161 | n/a | 45.50 ± 8.56 (n = 2) | n/a | 47.46 ± 0 (n = 1) | 46.34 ± 1.29 (n = 3) | 42.41 ± 17.81 (n = 6) |
| 168 | n/a | 46.11 ± 5.50 (n = 2) | n/a | 46.33 ± 0 (n = 1) | 50.03 ± 2.60 (n = 3) | 41.43 ± 18.91 (n = 5) |
| 177 | n/a | 45.04 ± 5.56 (n = 2) | n/a | 44.63 ± 0 (n = 1) | 56.82 ± 5.25 (n = 3) | 43.87 ± 16.97 (n = 5) |
| 185 | n/a | 47.48 ± 4.29 (n = 2) | n/a | 47.46 ± 0 (n = 1) | 58.26 ± 6.54 (n = 3) | 46.83 ± 16.09 (n = 5) |

TABLE 12

| | Mou | \multicolumn{11}{c|}{Days} |
|---|---|---|---|---|---|---|---|---|---|---|---|---|

| | Mou | 0 | 2 | 6 | 8 | 13 | 16 | 20 | 23 | 27 | 30 | 34 |
|---|---|---|---|---|---|---|---|---|---|---|---|---|
| Group 1 | 1 | 18. | 19. | 19. | 19. | 20. | 21. | 22. | | | | |
| Vehicle | 2 | 17. | 17. | 17. | 18. | 18. | 19. | 20. | 20. | | | |
| Control | 3 | 17. | 17. | 18. | 18. | 19. | 19. | 20. | 20. | 22. | | |
| 2Q7Dx4 | 4 | 19. | 19. | 19. | 20. | 20. | 21. | 21. | 22. | | | |
| | 5 | 19. | 19. | 19. | 19. | 20. | 20. | 21. | 22. | | | |
| | 6 | 17. | 18. | 18. | 19. | 19. | 19. | 19. | 20. | 22. | | |
| | 7 | 17. | 18. | 19. | 19. | 19. | 21. | 23. | | | | |
| | 8 | 19. | 19. | 19. | 20. | 20. | 21. | 22. | 23. | | | |
| | 9 | 19. | 19. | 20. | 21. | 21. | 22. | 23. | | | | |
| | 10 | 18. | 17. | 18. | 18. | 19. | 20. | 19. | | | | |
| | Ave | 18. | 18. | 19. | 19. | 20 | 20. | 21. | 21. | 22. | | |
| | SD | 0.8 | 0.6 | 0.7 | 0.8 | 0.7 | 1.0 | 1.4 | 1.1 | 0.3 | | |
| Group 2 | 1 | 19. | 19. | 19. | 20. | 20. | 20. | 21. | 22. | | | |
| Anti-PD-1 | 1 | 19. | 19. | 20. | 20. | 21. | 21. | 21. | 21. | 21. | 20. | 21. |
| 200 µg/mse | 3 | 18. | 18. | 19. | 18. | 19. | 19. | 19. | 19. | 20. | 20. | 20. |
| Q3Dx35 | 4 | 16. | 17. | 18. | 18. | 19. | 19. | 18. | 19. | 20. | 19. | 20. |
| | 5 | 19. | 20. | 21. | 21. | 21. | 22. | 22. | 23. | 23. | | |
| | 6 | 18. | 17. | 15. | 15. | 17. | 17. | 18. | 18. | 20. | | |
| | 7 | 18. | 17. | 19. | 19. | 19. | 20. | 21. | 19. | 22. | | |
| | 8 | 18. | 17. | 19. | 20. | 20. | 20. | 21. | 11. | 22. | 24. | |
| | 9 | 17. | 17. | 17. | 18. | 18. | 19. | 19. | 20. | 22. | | |
| | 10 | 18. | 18. | 19. | 20. | 20. | 20. | 20. | 20. | 22. | 23. | |
| | Ave | 18. | 18. | 18. | 19. | 19. | 20. | 20. | 20. | 21. | 21. | 20. |
| | SD | 0.8 | 0.9 | 1.6 | 1.4 | 1.1 | 1.2 | 1.4 | 1.4 | 1.3 | 1.8 | 0.7 |
| Group 3 | 1 | 18. | 19. | 19. | 20. | 19. | 19. | 20. | 20. | 20. | 22. | 23. |
| Compound 1 | 2 | 19. | 19. | 19. | 20. | 19. | 20. | 21. | 22. | 22. | 22. | 24. |
| 75 mg/kg | 3 | 19. | 19. | 20. | 20. | 20. | 21. | 21. | 22. | 21. | 22. | 23. |
| 2Q7Dx6 | 4 | 18. | 18. | 18. | 18. | 18. | 19. | 19. | 19. | 20. | | |
| | 5 | 17. | 18. | 18. | 18. | 18. | 19. | 19. | 21. | 21. | | |
| | 6 | 19. | 19. | 20. | 20. | 20. | 20. | 20. | 21. | 21. | 20. | 22. |
| | 7 | 17. | 18. | 18. | 18. | 19. | 19. | 20. | 21. | | | |
| | 8 | 19. | 19. | 19. | 19. | 20. | 19. | 20. | 21. | 21. | 21. | 22. |
| | 9 | 19. | 20. | 20. | 21. | 21. | 21. | 21. | 21. | 21. | 21. | 23. |
| | 10 | 17. | 17. | 17. | 16. | 18. | 18. | 18. | 19. | 18. | 17. | 1 |
| | Ave | 18. | 19. | 19. | 19. | 19. | 19. | 20. | 20. | 21. | 21. | 22. |
| | SD | 0.8 | 0.8 | 0.9 | 1.3 | 1.0 | 1.0 | 1.0 | 0.9 | 1.0 | 1.9 | 2.2 |
| Group 4 | 1 | 19. | 20. | 20. | 20. | 21. | 21. | 20. | 21. | 20. | 21. | 21. |
| Compound 1 | 2 | 21. | 21. | 21. | 21. | 21. | 21. | 21. | 22. | 22. | 23. | 24. |
| 150 mg/kg | 3 | 16. | 18. | 19. | 18. | 20. | 19. | 20. | 20. | 21. | 22. | 22. |
| 2Q7Dx15 | 4 | 17. | 18. | 18. | 18. | 18. | 19. | 19. | 19. | 19. | 19. | 20. |
| | 5 | 19. | 20. | 21. | 19. | 21. | 21. | 21. | 20. | 21. | 21. | 22. |
| | 6 | 19. | 19. | 18. | 18. | 19. | 19. | 19. | 19. | 20. | 20. | 20. |
| | 7 | 19. | 19. | 19. | 19. | 20. | 20. | 20. | 20. | 20. | 20. | 21. |
| | 8 | 18. | 19. | 19. | 18. | 20. | 20. | 20. | 19. | 19. | 20. | 21. |
| | 9 | 18. | 19. | 19. | 19. | 20. | 20. | 20. | 19. | 20. | 21. | 21. |
| | 10 | 18. | 20. | 20. | 20. | 21. | 20. | 20. | 21. | 22. | 21. | 21. |
| | Ave | 18. | 19. | 19. | 19. | 20. | 20. | 20. | 20. | 20. | 21. | 21. |
| | SD | 1.1 | 0.9 | 1.0 | 0.9 | 0.9 | 0.8 | 0.8 | 0.9 | 1.0 | 1.0 | 1.1 |
| Group 5 | 1 | 19. | 20. | 19. | 20. | 19. | 20. | 19. | 20. | 20. | 21. | 22. |
| Compound 1 | 2 | 18. | 19. | 19. | 19. | 19. | 20. | 19. | 20. | 20. | 21. | 21. |
| 75 mg/kg | 3 | 18. | 19. | 19. | 20. | 20. | 21. | 20. | 21. | 20. | 20. | 21. |
| 2Q7Dx15 + | 4 | 19. | 2a | 20. | 19. | 20. | 20. | 20. | 21. | 21. | 22. | 22. |
| Anti-PD-1 | 5 | 18. | 18. | 18. | 18. | 18. | 19. | 18. | 19. | 19. | 19. | 20. |
| 200 µg/mse | 6 | 16. | 17. | 18. | 18. | 18. | 19. | 19. | 19. | 19. | 20. | 20. |
| Q3Dx35 | 7 | 20. | 20. | 20. | 21. | 20. | 21. | 19. | 21. | 22. | 22. | 23. |
| | 8 | 17. | 17. | 18. | 19. | 19. | 20. | 20. | 20. | 20. | 20. | 21. |
| | 9 | 18. | 19. | 19. | 19. | 19. | 20. | 20. | 20. | 20. | 21. | 21. |
| | 10 | 18. | 18. | 19. | 19. | 19. | 20. | 21. | 20. | 2a | 21. | 22. |
| | Ave | 18. | 19. | 193 | 19. | 19. | 20. | 19. | 20. | 20. | 21. | 21. |
| | SD | 0.9 | 0.9 | 0.7 | 0.8 | 0.7 | 0.6 | 0.6 | 0.7 | 0.8 | 1.0 | 1.0 |
| Group 6 | 1 | 18. | 19. | 20. | 18. | 20. | 20. | 20. | 20. | 20. | 20. | 21. |
| Compound 1 | 2 | 18. | 18. | 19. | 19. | 20. | 20. | 20. | 20. | 20. | 21. | 21. |
| 150 mg/kg | 3 | 19. | 20. | 20. | 20. | 21. | 21. | 21. | 21. | 21. | 22. | 22. |
| 2Q7Dx15 + | 4 | 18. | 18. | 19. | 18. | 19. | 18. | 19. | 19. | 19. | 19. | 20. |
| anti-PD-1 | 5 | 17. | 17. | 19. | 18. | 19. | 19. | 19. | 19. | 19. | 20. | 20. |
| 200 µg/mse | 6 | 18. | 19. | 20. | 18. | 21. | 20. | 21. | 20. | 21. | 21. | 22. |
| Q3Dx35 | 7 | 18. | 19. | 19. | 18. | 19. | 20. | 19. | 20. | 20. | 20. | 21. |
| | 8 | 19. | 19. | 20. | 19. | 19. | 19. | 19. | 19. | 19. | 70. | 20. |
| | 9 | 18. | 19. | 20. | 18. | 21. | 19. | 20. | 20. | 21. | 20. | 21. |
| | 10 | 20. | 20. | 20. | 19. | 21. | 21. | 22. | 21. | 22. | 22. | 22. |
| | Ave | MU | 19. | 19. | 19. | 20. | 20. | 20. | 20. | 20. | 21. | 21. |
| | SD | 0.6 | 0.8 | 0.5 | 0.6 | 0.8 | 0.9 | 0.7 | 0.1 | 0.8 | 0.1 | 0.9 |

TABLE 12-continued

| | | Days | | | | | | | | |
|---|---|---|---|---|---|---|---|---|---|---|
| | Mou | 38 | 41 | 44 | 48 | 51 | 55 | 58 | 63 | 66 |
| Group 1 | 1 | | | | | | | | | |
| Vehicle | 2 | | | | | | | | | |
| Control | 3 | | | | | | | | | |
| 2Q7Dx4 | 4 | | | | | | | | | |
| | 5 | | | | | | | | | |
| | 6 | | | | | | | | | |
| | 7 | | | | | | | | | |
| | 8 | | | | | | | | | |
| | 9 | | | | | | | | | |
| | 10 | | | | | | | | | |
| | Ave | | | | | | | | | |
| | SD | | | | | | | | | |
| Group 2 | 1 | | | | | | | | | |
| Anti-PD-1 | 1 | 22. | 22. | 22. | 22. | 22. | 22. | 23. | 24. | 13. |
| 200 µg/mse | 3 | 21. | 21. | 21. | 21. | 21. | 21. | 21. | 21. | 21. |
| Q3Dx35 | 4 | 23. | | | | | | | | |
| | 5 | | | | | | | | | |
| | 6 | | | | | | | | | |
| | 7 | | | | | | | | | |
| | 8 | | | | | | | | | |
| | 9 | | | | | | | | | |
| | 10 | | | | | | | | | |
| | Ave | 22. | 21. | 21. | 22. | 22. | 22. | 22. | 22. | 22. |
| | SD | 1.0 | 0.8 | 0.7 | 0.9 | 1.2 | 1.1 | 1.0 | 1.7 | 1.3 |
| Group 3 | 1 | | | | | | | | | |
| Compound 1 | 2 | | | | | | | | | |
| 75 mg/kg | 3 | | | | | | | | | |
| 2Q7Dx6 | 4 | | | | | | | | | |
| | 5 | | | | | | | | | |
| | 6 | 22. | 23. | | | | | | | |
| | 7 | | | | | | | | | |
| | 8 | 24. | | | | | | | | |
| | 9 | | | | | | | | | |
| | 10 | 21. | 22. | | | | | | | |
| | Ave | 22. | 22. | | | | | | | |
| | SD | 1.6 | 0.6 | | | | | | | |
| Group 4 | 1 | 22. | | | | | | | | |
| Compound 1 | 2 | 25. | | | | | | | | |
| 150 mg/kg | 3 | 23. | | | | | | | | |
| 2Q7Dx15 | 4 | 21. | 20. | 20. | 20. | 20. | 20. | 21. | 21. | 21. |
| | 5 | 22. | 22. | 24. | 26. | | | | | |
| | 6 | 21. | 21. | 22. | 23. | | | | | |
| | 7 | 21. | 22. | 21. | | | | | | |
| | 8 | 22. | | | | | | | | |
| | 9 | 22. | 22. | 23. | 23. | 23. | | | | |
| | 10 | 23. | 23. | 25. | | | | | | |
| | Ave | 22. | 22. | 22. | 288 | 21. | 20. | 21. | 21. | 21. |
| | SD | 1.2 | 0.9 | 1.7 | 2.3 | 1.9 | 0.0 | 0.0 | 0.0 | 0.0 |
| Group 5 | 1 | 21. | 21. | 21. | 22. | 23. | 23. | 23. | 23. | 22. |
| Compound 1 | 2 | | | | | | | | | |
| 75 mg/kg | 3 | 21. | 21. | 21. | 22. | 22. | 22. | 22. | 21. | 22. |
| 2Q7Dx15 + | 4 | 23. | 23. | | | | | | | |
| Anti-PD-1 | 5 | 20. | 20. | 20. | 22. | 23. | | | | |
| 200 µg/mse | 6 | 20. | 19. | 20. | 20. | 21. | 21. | 21. | 21. | 20. |
| Q3Dx35 | 7 | 24. | | | | | | | | |
| | 8 | 21. | 21. | 21. | 20. | 20. | 20. | 20. | 20. | 21. |
| | 9 | | | | | | | | | |
| | 10 | | | | | | | | | |
| | Ave | 21. | 21. | 21. | 21. | 22. | 21. | 21. | 21. | 21. |
| | SD | 1.4 | 1.2 | 0.5 | 1.0 | 1.2 | 1.1 | 1.1 | 1.1 | 0.9 |
| Group 6 | 1 | 22. | 21. | 22. | 22. | 21. | 21. | 21. | 22. | 22. |
| Compound 1 | 2 | 21. | 21. | 21. | 21. | 21. | 21. | 21. | 22. | 22. |
| 150 mg/kg | 3 | 22. | 22. | 23. | 22. | 23. | 23. | 22. | 23. | 24. |
| 2Q7Dx15 + | 4 | 20. | 20. | 20. | 20. | 20. | 20. | 21. | 21. | 21. |
| anti-PD-1 | 5 | 21. | 21. | 21. | 20. | 20. | 20. | 21. | 22. | 22. |
| 200 µg/mse | 6 | 21. | 21. | 21. | 22. | 22. | 22. | 23. | 26. | |
| Q3Dx35 | 7 | 20. | 20. | 20. | 20. | 20. | 20. | 20. | 20. | 21. |
| | 8 | 21. | 20. | 20. | 21. | 20. | 20. | 20. | 21. | 22. |
| | 9 | 20. | 22. | 22. | 21. | 20. | 20. | 21. | 21. | 22. |
| | 10 | 23. | 23. | 22. | 22. | 22. | 22. | 22. | 22. | 23. |
| | Ave | 21. | 21. | 21. | 21. | 21. | 21. | 21. | 22. | 22. |
| | SD | 0.8 | 0.8 | 0.8 | 0.8 | 1.0 | 0.9 | 0.9 | 1.4 | 0.8 |

TABLE 13

| | Mouse | \multicolumn{11}{c}{Days} |
|---|---|---|---|---|---|---|---|---|---|---|---|---|
| | | 70 | 73 | 77 | 80 | 84 | 87 | 90 | 93 | 98 | 101 | 106 |
| Group 2 anti-PD-1 200 µg/mse Q3Dx35 | 1 | | | | | | | | | | | |
| | 2 | 24.50 | 23.30 | 23.10 | 23.40 | 24.20 | 24.20 | 24.20 | 24.20 | 24.70 | 24.50 | 24.60 |
| | 3 | 22.40 | 22.10 | 21.90 | 21.80 | 22.60 | 22.60 | 22.30 | 22.00 | 22.30 | 21.80 | 22.00 |
| | 4 | | | | | | | | | | | |
| | 5 | | | | | | | | | | | |
| | 6 | | | | | | | | | | | |
| | 7 | | | | | | | | | | | |
| | 8 | | | | | | | | | | | |
| | 9 | | | | | | | | | | | |
| | 10 | | | | | | | | | | | |
| | Ave | 23.45 | 22.70 | 2250 | 22.60 | 23.40 | 23.40 | 23.25 | 23.10 | 23.50 | 23.15 | 23.30 |
| | SD | 1.48 | 0.85 | 0.85 | 1.13 | 1.13 | 1.13 | 1.34 | 1.56 | 1.70 | 1.91 | 1.84 |
| Group 4 Compound 1 150 mg/kg 2Q7Dx15 | 1 | | | | | | | | | | | |
| | 2 | | | | | | | | | | | |
| | 3 | | | | | | | | | | | |
| | 4 | 21.80 | 20.90 | 21.30 | 21.90 | 22.40 | 21.50 | 22.00 | 21.50 | 21.90 | 21.70 | 21.60 |
| | 5 | | | | | | | | | | | |
| | 6 | | | | | | | | | | | |
| | 7 | | | | | | | | | | | |
| | 8 | | | | | | | | | | | |
| | 9 | | | | | | | | | | | |
| | 10 | | | | | | | | | | | |
| | Ave | 21.80 | 20.90 | 21.30 | 21.90 | 22.40 | 21.50 | 22.00 | 21.50 | 21.90 | 21.70 | 21.60 |
| | SD | 0.00 | 0.00 | 0.00 | 0.00 | 0.00 | 0.00 | 0.00 | 0.00 | 0.00 | 0.00 | 0.00 |
| Group 5 Compound 1 75 mg/kg 2Q7Dx15 + anti-PD-1 200 µg/mse Q3Dx35 | 1 | 23.50 | 23.50 | 23.60 | 23.50 | 23.80 | 23.90 | 23.90 | 23.90 | 23.90 | 23.60 | 23.70 |
| | 2 | | | | | | | | | | | |
| | 3 | 22.60 | 22.50 | 22.30 | 22.80 | 23.00 | 22.50 | 22.70 | 22.70 | 22.50 | 22.40 | 22.60 |
| | 4 | | | | | | | | | | | |
| | 5 | | | | | | | | | | | |
| | 6 | 2180 | 21.70 | 21.60 | 21.90 | 22.80 | 22.30 | 22.00 | 21.60 | 2210 | 21.50 | 21.40 |
| | 7 | | | | | | | | | | | |
| | 8 | 2180 | 2170 | 21.50 | 22.00 | 22.50 | 22.30 | 22.30 | 21.70 | 22.20 | 21.70 | 22.70 |
| | 9 | | | | | | | | | | | |
| | 10 | | | | | | | | | | | |
| | Ave | 22.43 | 22.35 | 22.25 | 22.55 | 23.03 | 22.75 | 22.73 | 22.48 | 22.68 | 22.30 | 22.60 |
| | SD | 0.81 | 0.85 | 0.97 | 0.75 | 0.56 | 0.77 | 0.83 | 1.07 | 0.83 | 0.95 | 0.94 |
| Group 6 Compound 1 150 mg/kg 2Q7Dx15 + anti-PD-1 200 pg/mse Q3Dx35 | 1 | 23.10 | 22.30 | 22.50 | 22.40 | 22.70 | 23.00 | 22.60 | 22.20 | 22.40 | 22.30 | 23.40 |
| | 2 | 23.40 | 23.60 | 22.10 | | | | | | | | |
| | 3 | 24.50 | 24/0 | 25.40 | 24.90 | 24.50 | 25.00 | 25.00 | 24.90 | 25.60 | 24.90 | 24.80 |
| | 4 | 21.80 | 21.10 | 21.20 | 21.40 | 21.30 | 2160 | 21.30 | 20.60 | 2090 | 20.90 | 2100 |
| | 5 | 22.30 | 21.80 | 21.90 | 21.70 | 21.90 | 22.60 | 22.60 | 22.00 | 22.40 | 22.10 | 22.40 |
| | 6 | | | | | | | | | | | |
| | 7 | 21.80 | 21.30 | 21.60 | 21.70 | 21.90 | 21.90 | 22.20 | 22.40 | 22.00 | 21.60 | 22.00 |
| | 8 | 23.70 | | | | | | | | | | |
| | 9 | 21.40 | 23.10 | 22.80 | 22.90 | 23.60 | 23.50 | 23.00 | 21.40 | 22.60 | 23.10 | 22.70 |
| | 10 | 23.10 | 23.30 | 22.70 | 23.10 | 2440 | 23.20 | 23.70 | 23.10 | 24.50 | 22.80 | 22.10 |
| | Ave | 22.79 | 22.59 | 2253 | 22.59 | 22.90 | 22.97 | 22.91 | 22.37 | 22.91 | 22.53 | 22.63 |
| | SD | 1.03 | 1.13 | 1.28 | 1.21 | 1.28 | 1.13 | 1.18 | 1.36 | 1.59 | 1.28 | 1.20 |

| | Mouse | \multicolumn{9}{c}{Days} |
|---|---|---|---|---|---|---|---|---|---|---|
| | | 111 | 118 | 125 | 133 | 140 | 155 | 161 | 168 | 177 | 185 |
| Group 2 anti-PD-1 200 µg/mse Q3Dx35 | 1 | | | | | | | | | | |
| | 2 | 2540 | 25.80 | 26.30 | 26.90 | 26.60 | 27.00 | 28.70 | 29.10 | 28.90 | 29.20 |
| | 3 | 22.60 | 23.10 | 23.40 | 23.90 | 24.20 | 24.20 | 25.60 | 25.60 | 25.40 | 26.00 |
| | 4 | | | | | | | | | | |
| | 5 | | | | | | | | | | |
| | 6 | | | | | | | | | | |
| | 7 | | | | | | | | | | |
| | 8 | | | | | | | | | | |
| | 9 | | | | | | | | | | |
| | 10 | | | | | | | | | | |
| | Ave | 24.00 | 24.45 | 24.85 | 25.40 | 25.40 | 25.60 | 27.15 | 27.35 | 27.15 | 27.60 |
| | SD | 1.98 | 1.91 | 2.05 | 2.12 | 1.70 | 1.98 | 2.19 | 2.47 | 2.47 | 2.26 |
| Group 4 Compound 1 150 mg/kg 2Q7Dx15 | 1 | | | | | | | | | | |
| | 2 | | | | | | | | | | |
| | 3 | | | | | | | | | | |
| | 4 | 2140 | 23.60 | 2270 | 24.50 | 25.00 | 23.80 | 25.20 | 25.90 | 25.60 | 26.10 |
| | 5 | | | | | | | | | | |
| | 6 | | | | | | | | | | |
| | 7 | | | | | | | | | | |
| | 8 | | | | | | | | | | |

TABLE 13-continued

| | | | | | | | | | | | |
|---|---|---|---|---|---|---|---|---|---|---|---|
| | 9 | | | | | | | | | | |
| | 10 | | | | | | | | | | |
| | Ave | 22.40 | 23.60 | 22.70 | 24.50 | 25.00 | 23.80 | 25.20 | 25.90 | 25.60 | 26.10 |
| | SD | 0.00 | 0.00 | 0.00 | 0.00 | 0.00 | 0.00 | 0.00 | 0.00 | 0.00 | 0.00 |
| Group 5 | 1 | 25.50 | 24.20 | 25.00 | 26.60 | 27.20 | 27.80 | 27.60 | 29.10 | 30.20 | 30.90 |
| Compound 1 | 2 | | | | | | | | | | |
| 75 mg/kg | 3 | 23.70 | 24.20 | 24.50 | 25.20 | 27.30 | 24.50 | 26.90 | 27.20 | 28.00 | 27.90 |
| 2Q7Dx15 + | 4 | | | | | | | | | | |
| anti-PD-1 | 5 | | | | | | | | | | |
| 200 µg/mse | 6 | 2270 | 23.30 | 24.20 | 24.60 | 24.80 | 24.20 | 20.90 | 25.00 | 26.70 | 26.90 |
| Q3Dx35 | 7 | | | | | | | | | | |
| | 8 | 2370 | | | | | | | | | |
| | 9 | | | | | | | | | | |
| | 10 | | | | | | | | | | |
| | Ave | 23.90 | 23.90 | 24.57 | 25.47 | 26.43 | 25.50 | 25.13 | 27.10 | 28.30 | 28.57 |
| | SD | 1.17 | 0.52 | 0.40 | 1.03 | 1.42 | 2.00 | 3.68 | 2.05 | 1.77 | 2.08 |
| Group 6 | 1 | 24.10 | 24.50 | 24.80 | 26.60 | 27.40 | 26.50 | 27.70 | | | |
| Compound 1 | 2 | | | | | | | | | | |
| 150 mg/kg | 3 | 26.20 | 26.60 | 28.10 | 26.30 | 28.30 | 28.10 | 29.50 | 30.90 | 31.60 | 32.00 |
| 2Q7Dx15 + | 4 | 2230 | 21.20 | 21.90 | 2260 | 24.50 | 2200 | 2290 | 24.00 | 23.90 | 24.30 |
| anti-PD-1 | 5 | 23.00 | 23.50 | 24.10 | 25.90 | 25.60 | 28.00 | 26.70 | 28.90 | 28.80 | 29.10 |
| 200 pg/mse | 6 | | | | | | | | | | |
| Q3Dx35 | 7 | 22.00 | 23.20 | 2330 | 22.30 | 23.30 | 23.80 | 24.90 | 25.70 | 24.80 | 25.90 |
| | 8 | | | | | | | | | | |
| | 9 | 24.30 | 26.90 | | | | | | | | |
| | 10 | 23.90 | 24.40 | 24.90 | 23.10 | 26.20 | 24.50 | 25.80 | 23.80 | 26.70 | 27.30 |
| | Ave | 23.69 | 24.33 | 24.55 | 24.47 | 25.88 | 25.48 | 26.25 | 26.66 | 27.16 | 27.72 |
| | SD | 1.42 | 1.98 | 2.05 | 2.00 | 1.84 | 2.46 | 2.29 | 3.13 | 3.11 | 2.98 |

Clinical Observations: Compound 1 was well tolerated throughout the study with no clinical observations made on the mice. One mouse (7) in group 2 mice administered anti-PD-1 at 200 µg Q3D displayed a necrotic tumor as well as one mouse (8) in group 5 administered Compound 1 75 mg/kg 2Q7D+anti-PD-1 200 µg Q3D. TABLE 14 shows the date of death of individual mice in the treatment groups and relevant clinical observations.

TABLE 14

| Group | Mouse Number | Date of Death (Study Day) | Method | Clinical Observations |
|---|---|---|---|---|
| Group 1 | 1 | 20 | Euthanasia | None; euthanized for tumor burden |
| Vehicle | 2 | 23 | Euthanasia | None; euthanized for tumor burden |
| 2Q7Dx4 | 3 | 27 | Euthanasia | None; euthanized for tumor burden |
| | 4 | 23 | Euthanasia | None; euthanized for tumor burden |
| | 5 | 23 | Euthanasia | None; euthanized for tumor burden |
| | 6 | 27 | Euthanasia | None; euthanized for tumor burden |
| | 7 | 20 | Euthanasia | None; euthanized for tumor burden |
| | 8 | 23 | Euthanasia | None; euthanized for tumor burden |
| | 9 | 20 | Euthanasia | None; euthanized for tumor burden |
| | 10 | 20 | Euthanasia | None; euthanized for tumor burden |
| Group 2 | 1 | 23 | Euthanasia | None; euthanized for tumor burden |
| Anti-PD-1 | 2 | 185 | Re-enrolled in future study | None; study terminated |
| 200 µg Q3Dx35 | 3 | 185 | Re-enrolled in future study | None; study terminated |
| | 4 | 38 | Euthanasia | None; euthanized for tumor burden |
| | 5 | 27 | Euthanasia | None; euthanized for tumor burden |
| | 6 | 27 | Euthanasia | None; euthanized for tumor burden |
| | 7 | 27 | Euthanasia | Tumor necrotic; euthanized for tumor burden |
| | 8 | 30 | Euthanasia | None; euthanized for tumor burden |
| | 9 | 27 | Euthanasia | None; euthanized for tumor burden |
| | 10 | 30 | Euthanasia | None; euthanized for tumor burden |
| Group 3 | 1 | 34 | Euthanasia | None; euthanized for tumor burden |
| Compound 1 | 2 | 34 | Euthanasia | None; euthanized for tumor burden |
| 75 mg/kg | 3 | 34 | Euthanasia | None; euthanized for tumor burden |
| 2Q7Dx6 | 4 | 27 | Euthanasia | None; euthanized for tumor burden |
| | 5 | 27 | Euthanasia | None; euthanized for tumor burden |
| | 6 | 41 | Euthanasia | None; euthanized for tumor burden |
| | 7 | 27 | Euthanasia | None; euthanized for tumor burden |
| | 8 | 38 | Euthanasia | None; euthanized for tumor burden |
| | 9 | 34 | Euthanasia | None; euthanized for tumor burden |
| | 10 | 41 | Euthanasia | None; euthanized for tumor burden |
| Group 4 | 1 | 34 | Euthanasia | None; euthanized for tumor burden |
| Compound 1 | 2 | 34 | Euthanasia | None; euthanized for tumor burden |
| 150 mg/kg | 3 | 34 | Euthanasia | None; euthanized for tumor burden |

TABLE 14-continued

| Group | Mouse Number | Date of Death (Study Day) | Method | Clinical Observations |
|---|---|---|---|---|
| 2Q7Dx15 | 4 | 185 | Re-enrolled in future study | None; study terminated |
|  | 5 | 48 | Euthanasia | None; tumor Burden collected for 24 H |
|  | 6 | 48 | Euthanasia | None; tumor Burden collected for 24 H |
|  | 7 | 44 | Euthanasia | None; euthanized for tumor burden |
|  | 8 | 34 | Euthanasia | None; euthanized for tumor burden |
|  | 9 | 51 | Euthanasia | None; tumor Burden collected for 24 H |
|  | 10 | 44 | Euthanasia | None; euthanized for tumor burden |
| Group 5 Compound 1 75 mg/kg 2Q7Dx15 + Anti-PD-1 200 µg Q3Dx35 | 1 | 185 | Euthanasia | None; study terminated |
|  | 2 | 34 | Euthanasia | None; euthanized for tumor burden |
|  | 3 | 185 | Euthanasia | None; study terminated |
|  | 4 | 41 | Euthanasia | None; euthanized for tumor burden |
|  | 5 | 48 | Euthanasia | None; euthanized for tumor burden |
|  | 6 | 185 | Re-enrolled in future study | None; study terminated |
|  | 7 | 38 | Euthanasia | None; euthanized for tumor burden |
|  | 8 | 111 | Euthanasia | Tumor necrotic; euthanized for tumor burden |
|  | 9 | 34 | Euthanasia | None; euthanized for tumor burden |
|  | 10 | 34 | Euthanasia | None; euthanized for tumor burden |
| Group 6 Compound 1 150 mg/kg 2Q7Dx15 + Anti-PD-1 200 µg Q3Dx35 | 1 | 161 | Euthanasia | None; tumor Burden collected for sequencing |
|  | 2 | 78 | Euthanasia | None; tumor Burden collected for 24 H |
|  | 3 | 185 | Re-enrolled in future study | None; study terminated |
|  | 4 | 185 | Re-enrolled in future study | None; study terminated |
|  | 5 | 185 | Re-enrolled in future study | None; study terminated |
|  | 6 | 63 | Euthanasia | None; euthanized for tumor burden |
|  | 7 | 185 | Re-enrolled in future study | None; study terminated |
|  | 8 | 70 | Euthanasia | None; tumor Burden collected for 24 H |
|  | 9 | 118 | Euthanasia | None; euthanized for tumor burden |

The dose responsive anti-tumor effect was tested for Compound 1 in combination with anti-PD-1 in a mouse syngeneic model of sarcoma (MT373). Vehicle control treated animals had a median survival time of 20.94 days. Anti-PD-1 was dosed IP at 200 µg per mouse and resulted in 39.6% TGI and a median survival of 27.14 days. Compound 1 was dosed orally at 75 mg/kg or 150 mg/kg, resulting in 57.1% and 95.7% TGI, respectively by day 27 and median survival times of 32 and 42.9 days, respectively. Mice dosed with combination therapy; Compound 1 at 75 mg/kg+200 µg anti-PD-1, and Compound 1 at 150 mg/kg+200 µg anti-PD-1, resulted in 91.2% TGI and 92.3% regression, respectively by day 27 of the study. Combination therapy similarly improved median survival times versus monotherapy with the low dose combination resulting in median survival of 43.78 days (a 22.84 day extension in survival compared to vehicle control). High-dose combination treatment delayed median survival time to >185 days, and a >164 day extension in survival compared to vehicle control. Following cessation of dosing on day 102, mice were continuously monitored until day 185. The anti-PD-1 group had one residual tumor in stasis and 10% cure; the 150 mg/kg Compound 1 2Q7Dx15 group had 10% cure; the Compound 1 75 mg/kg 2Q7Dx15+anti-PD-1 Q3Dx35 group had 30% cures with 1 mouse having a tumor that regrew and had to be euthanized at day 111; and the high dose combination group Compound 1 150 mg/kg 2Q7Dx15+Anti-PD-1 (Q3Dx35) had 40% cures and 1 mouse with a residual tumor in stasis.

Administration of Compound 1 once weekly resulted in dose responsive anti-tumor effect with tumor grow delay. Combination therapy with anti-PD-1 significantly improved the anti-tumor effect demonstrating regression, cures, and a significant increase in median survival time at the highest dose level.

Example 3: Combination of Compound 1 and Anti-PD-1 Agent in Mouse Sarcoma Model (MT245)

The efficacy of Compound 1 was tested as a single agent and in combination with anti-PD-1 in a mouse syngeneic model of sarcoma (MT245). C57Bl/6 mice were implanted with MT245 cells, tumors were grown to ~77 mm$^3$ and randomized on day 7 post-inoculation into one of seven study groups. Mice were dosed orally (PO) with either vehicle control (0.2% HPC, 0.5% Tween 80); dosed intraperitoneally (IP) with anti-PD-1 at 200 µg per mouse, once every three days, for 19 weeks (Q3Dx19); Compound 1 PO at 150 mg/kg, once weekly, for 5 weeks (Q7Dx5); Compound 1 at 300 mg/kg and 600 mg/kg, once weekly, for 9 weeks (Q7Dx9); and combinations of Compound 1 150 mg/kg (Q7Dx9)+anti-PD-1 200 µg (Q3Dx19); and Compound 1 300 mg/kg (Q7Dx9)+anti-PD-1 200 µg (Q3Dx19).

Animals: Female C57Bl/6 mice (90 total) were acclimatized for 1 week and were 8-10 weeks old at initiation of study. Animals were group housed (N=5) in ventilated cages. Fluorescent lighting was provided on a 12-hour cycle (6:30 am-6:30 pm). Temperature and humidity were monitored and recorded daily and maintained between 68-72° F. (20-22.2° C.) and 30-70% humidity, respectively. 18% soy irradiated rodent feed and autoclaved acidified water (pH 2.5-3) was provided ad libitum.

Tumor Cell Culture: MT245 cells were cultured according to the DMEM medium with 10% fetal bovine serum. The cells were washed with PBS and counted at a total of $2.33 \times 10^8$ cells with 85% viability. Cells were centrifuged and resuspended in 50% PBS:50% Matrigel Matrix at a concentration of $1 \times 10^6$ viable cells/100 µL.

Implantation of Mice: Cells were prepared for injections by drawing the cell suspension into a 1 mL tuberculin syringe fitted with a 25 G ⅝" needle. Individual mice were manually restrained, the site of injection (right flank) was disinfected with a 70% ethanol swab, and 100 µL of cell suspension was injected subcutaneously.

Randomization and Study Setup: Implanted mice were monitored for palpable tumors. Six days post implant, the mice with palpable tumors had their tumor sizes determined via digital caliper. Mice were selected and randomized into six treatment groups according to tumor size. Average tumor volume (mm³) and body weight (g) is reported in TABLE 15A and TABLE 15B, respectively. Treatment began on the seventh day post-implant to facilitate twice daily dosing.

TABLE 15

TABLE 15A

| Group | N | Mean | St Dev | Min | Max |
|---|---|---|---|---|---|
| Group 1- Vehicle Control Q7Dx3 | 10 | 77.01 | ±10.33 | 60.03 | 96.80 |
| Group 2- Anti-PD-1 200 µg Q3Dx19 | 10 | 76.88 | ±9.74 | 61.85 | 95.65 |
| Group 3- Compound 1 150 mg/kg Q7Dx5 | 10 | 77.11 | ±9.70 | 62.43 | 95.29 |
| Group 4- Compound 1 300 mg/kg Q7Dx9 | 10 | 76.82 | ±9.19 | 62.42 | 92.60 |
| Group 5- Compound 1 600 mg/kg Q7Dx9 | 10 | 77.00 | ±9.33 | 62.50 | 92.51 |
| Group 6- Compound 1 150 mg/kg + + Anti-PD-1 200 µg Q3Dx19 | 10 | 76.81 | ±9.34 | 62.5 | 91.85 |
| Group 7- Compound 1 300 mg/kg Q7Dx9 + Anti-PD-1 200 µg Q3Dx19 | 10 | 76.79 | ±9.41 | 62.96 | 91.29 |

TABLE 15B

| Group | N | Mean | St Dev | Min | Max |
|---|---|---|---|---|---|
| Group 1- Vehicle Control Q7Dx3 | 10 | 18.33 | ±1.25 | 16.90 | 20.60 |
| Group 2- Anti-PD1 200 µg Q3Dx19 | 10 | 18.57 | ±0.91 | 17.42 | 19.90 |
| Group 3- Compound 1 150 mg/kg Q7Dx5 | 10 | 18.14 | ±0.63 | 17.27 | 18.96 |
| Group 4- Compound 1 300 mg/kg Q7Dx9 | 10 | 17.96 | ±1.20 | 15.60 | 19.80 |
| Group 5- Compound 1 600 mg/kg Q7Dx9 | 10 | 18.34 | ±0.52 | 17.60 | 19.22 |
| Group 6- Compound 1 150 mg/kg Q7Dx9 + Anti-PD1 200 µg Q3Dx19 | 10 | 17.54 | ±1.14 | 15.12 | 18.77 |
| Group 7- Compound 1 300 mg/kg Q7Dx9 + Anti-PD1 200 µg Q3Dx19 | 10 | 18.72 | ±1.32 | 16.28 | 20.84 |

Group 1 animals were dosed PO with vehicle control (20 HPC, 0.50% Tween 80 in water (w/v/v)) once per week for three doses (Q7Dx3). Group 2 animals were dosed IP with anti-PD-1 at 200 jig once every three days for 19 doses (Q3Dx19). Groups 3, 4 and 5 animals were dosed PO once a week with Compound 1 at 150 mg/kg for 5 doses (Q7Dx 5), 300 mg/kg for 9 doses (Q7Dx9) and Compound 1 at 600 mg/kg for 9 doses (Q7Dx9), respectively. Groups 6 and 7 animals were dosed with Compound 1 at 150 and 300 mg/kg for 9 doses (Q7Dx9) in combination with anti-PD-1 at 200 jig for 19 doses (Q3Dx19), respectively. All dosing was terminated on day 55 and the remaining mice were monitored for survival. Mice were euthanized when individual tumors reached an endpoint of −2000 mm³. At Day 157 the study was terminated, and median survival was calculated across all groups TABLE 16 show the seven efficacy study groups and dosing regimens of the study groups. TABLE 17 shows the median survival time in days of the study groups and increases in survival time relative to mice in the vehicle control group. TABLE 18 shows clinical observations of the mice of each study group and dates of death.

TABLE 16

| Group | Treatment | N | Route | Dosing Frequency & Duration | Dose (mg/kg) | Dose Volume (mL/kg) |
|---|---|---|---|---|---|---|
| 1 | Vehicle Control | 10 | PO | Q7Dx3 | NA | 10 |
| 2 | Anti-PD-1 | 10 | IP | Q3Dx19 | 200 µg | 10 |
| 3 | Compound 1 | 10 | PO | Q7Dx5 | 150 | 10 |
| 4 | Compound 1 | 10 | PO | 07Dx9 | 300 | 10 |
| 5 | Compound 1 | 10 | PO | Q7Dx9 | 600 | 10 |
| 6 | Compound 1 | 10 | PO | Q7Dx9 | 150 | 10 |
|   | Anti-PD-1 |   | IP | Q3Dx19 | 200 µg | 10 |
| 7 | Compound 1 | 10 | PO | Q7Dx9 | 300 | 10 |
|   | Anti-PD-1 |   | IP | Q3Dx19 | 200 µg | 10 |

TABLE 17

| Group | N | Range (Days) | Median (Days) | Increase in Survival Relative to Vehicle (Days) |
|---|---|---|---|---|
| Group 1- Vehicle Control Q7Dx3 | 10 | 15.96 to 20.00 | 1930 | — |
| Group 2- Antl-PD-1 200 µg Q3Dx19 | 10 | 17.45 to >157.00 | 24.89 | 5.59 |
| Group 3- Compound 1 150 mg/kg Q7Dx5 | 10 | 18.07 to 27.97 | 25.04 | 5.74 |
| Group 4- Compound 1 300 mg/kg Q7Dx9 | 10 | 31.47 to N157.00 | 41.21 | 21.91 |
| Group 5- Compound 1 600 mg/kg Q7Dx9 | 10 | 78.00 to >157.00 | >157.00 | >138.70 |
| Group 6- Compound 1 150 mg/kg Q7Dx9 + Anti-PD-1 200 µg Q3Dx19 | 10 | 31.28 to >157.00 | >157.00 | >138.70 |
| Group 7- Compound 1 300 mg/kg Q7Dx9 + Anti-PD-1 200 µg Q3Dx19 | 10 | 1'1/A | >157.00 | >138.70 |

TABLE 18

| Group | Mouse | Date of Death (Study Day) | Method | Clinical Observations |
|---|---|---|---|---|
| Group 1- Vehicle Control Q7Dx3 | 1 | 20 | Euthanasia | None; euthanized for tumor burden |
|  | 2 | 20 | Euthanasia | None; euthanized for tumor burden |
|  | 3 | 20 | Euthanasia | Necrotic tumor; taken for humane endpoint |
|  | 4 | 20 | Euthanasia | None; euthanized for tumor burden |
|  | 5 | 20 | Euthanasia | None; euthanized for tumor burden |
|  | 6 | 17 | Euthanasia | None; euthanized for tumor burden |
|  | 7 | 20 | Euthanasia | None; euthanized for tumor burden |
|  | 8 | 20 | Euthanasia | None; euthanized for tumor burden |
|  | 9 | 17 | Euthanasia | None; euthanized for tumor burden |
|  | 10 | 20 | Euthanasia | None; euthanized for tumor burden |
| Group 2- Anti-PD-1 200 µg Q3Dx19 | 1 | 157 | Re-enrolled in future study | None, study terminated |
|  | 2 | 25 | Euthanasia | Necrotic tumor; taken for humane endpoint |
|  | 3 | 20 | Euthanasia | None; euthanized for tumor burden |
|  | 4 | 25 | Euthanasia | None; euthanized for tumor burden |
|  | 5 | 34 | Euthanasia | None; euthanized for tumor burden |
|  | 6 | 19 | Euthanasia | Necrotic tumor; taken for humane endpoint |
|  | 7 | 20 | Euthanasia | None; euthanized for tumor burden |
|  | 8 | 25 | Euthanasia | None; euthanized for tumor burden |
|  | 9 | 34 | Euthanasia | None; euthanized for tumor burden |
|  | 10 | 25 | Euthanasia | None; euthanized for tumor burden |
| Group 3- Compound 1 150 mg/kg Q7Dx5 | 11 | 20 | Euthanasia | Necrotic tumor; animal cold to touch |
|  | 2 | 28 | Euthanasia | None; euthanized for tumor burden |
|  | 3 |  | Euthanasia | None; euthanized for tumor burden |
|  | 4 | 20 | Euthanasia | None; euthanized for tumor burden |
|  | 5 | 25 | Euthanasia | None; euthanized for tumor burden |
|  | 6 | 28 | Euthanasia | None; euthanized for tumor burden |
|  | 7 | 28 | Euthanasia | None; euthanized for tumor burden |
|  | 8 | 28 | Euthanasia | None; euthanized for tumor burden |
|  | 9 | 20 | Euthanasia | None; euthanized for tumor burden |
|  | 10 | 20 | Euthanasia | None; euthanized for tumor burden |
| Group 4- Compound 1 300 mg/kg Q7Dx9 | 1 | 42 | Euthanasia | None; euthanized for tumor burden |
|  | 2 | 42 | Euthanasia | None; euthanized for tumor burden |
|  | 3 | 157 | Re-enrolled in future study | None, study terminated |

TABLE 18-continued

| Group | Mouse | Date of Death (Study Day) | Method | Clinical Observations |
|---|---|---|---|---|
| | 4 | 157 | Re-enrolled in future study | None, study terminated |
| | 5 | 38 | Euthanasia | None; euthanized for tumor burden |
| | 6 | 34 | Euthanasia | None; euthanized for tumor burden |
| | 7 | 157 | Re-enrolled in future study | None, study terminated |
| | 8 | 34 | Euthanasia | None; euthanized for tumor burden |
| | 9 | 157 | Re-enrolled in future study | None, study terminated |
| | 10 | 34 | Euthanasia | None; euthanized for tumor burden |
| Group 5-Compound 1 600 mg/kg Q7Dx9 | 1 | 157 | Re-enrolled in future study | None, study terminated |
| | 2 | 157 | Re-enrolled in future study | None, study terminated |
| | 3 | 157 | Re-enrolled in future study | None, study terminated |
| | 4 | 157 | Re-enrolled in future study | None, study terminated |
| | 5 | 157 | Re-enrolled in future study | None, study terminated |
| | 6 | 78 | Found Dead | Found dead |
| | 7 | 157 | Re-enrolled in future study | None, study terminated |
| | 8 | 157 | Re-enrolled in future study | None, study terminated |
| | 9 | 157 | Re-enrolled in future study | None, study terminated |
| | 10 | 157 | Re-enrolled in future study | None, study terminated |
| Group 6-Compound 1 150 mg/kg Q7Dx9 + Anti-P13-1 200 μg Q3Dx19 | 1 | 42 | Euthanasia | None; euthanized for tumor burden |
| | 2 | 10 | Found Dead | Found Dead, potential dosing error |
| | 3 | 38 | Euthanasia | None; euthanized for tumor burden |
| | 4 | 34 | Euthanasia | None; euthanized for tumor burden |
| | 5 | 157 | Re-enrolled in future study | None, study terminated |
| | 6 | 157 | Re-enrolled in future study | None, study terminated |
| | 7 | 42 | Euthanasia | Chest wound, taken for humane endpoint |
| | 8 | 157 | Re-enrolled in future study | None, study terminated |
| | 9 | 157 | Re-enrolled in future study | None, study terminated |
| | 10 | 157 | Re-enrolled in future study | None, study terminated |
| Group 7-Compound 1 300 mg/kg Q7Dx9 + Anti-PD-1 200 μg Q3Dx19 | 1 | 157 | Re-enrolled in future study | None, study terminated |
| | 2 | 157 | Re-enrolled in future study | None, study terminated |
| | 3 | 157 | Re-enrolled in future study | None, study terminated |
| | 4 | 157 | Re-enrolled in future study | None, study terminated |
| | 5 | 157 | Re-enrolled in future study | None, study terminated |
| | 6 | 157 | Re-enrolled in future study | None, study terminated |
| | 7 | 157 | Re-enrolled in future study | None, study terminated |
| | 8 | 157 | Re-enrolled in future study | None, study terminated |
| | 9 | 157 | Re-enrolled in future study | None, study terminated |
| | 10 | 157 | Re-enrolled in future study | None, study terminated |

Measurements and Calculation of Tumor Volume: Tumor volume was calculated using the following equation: (longest diameter×shortest diameter$^2$)/2. Individual tumor volumes and body weight measurements were taken twice weekly for all groups until the animals reached the humane endpoints. The calculation for percent tumor growth inhibition (TGI) is as follows: $[1-((T_t-T_0/C_t-C_0))]\times 100$, where $C_t$ is the mean tumor volume of the vehicle control group at time t, $C_0$ is the mean tumor volume of the vehicle control group at time 0, and T is the mean tumor volume of the treatment group. Tumor regression was determined with the equation $[(T_0-T_t)/T_0]\times 100$ using the same definitions.

At day 20, tumor growth inhibition (TGI) of 55.19%, 42.62%, 95.58% and 97.34% was observed in animals treated with 200 µg anti-PD-1 Q3D×7; Compound 1 at 150 mg/kg Q7D×3; Compound 1 at 300 mg/kg Q7D×3; and Compound 1 at 150 mg/kg Q7D×3+200 µg anti-PD-1 Q3D× 7, respectively. Tumor regression of 10000 and 99.93% was observed at day 20 in mice treated with Compound 1 at 600 mg/kg Q7D×3; and Compound 1 300 mg/kg Q7D×3+200 µg Anti-PD-1 Q3D×7, respectively. Median Survival Times (MST), defined as median time taken for tumors to reach 2000 mm$^3$, were significantly increased in mice receiving the high dose of Compound 1 and both dose level combinations of Compound 1 and anti-PD-1 to >157 days, when compared to vehicle control at 19.3 days. Compound 1 and the combination with anti-PD-1 was well tolerated by mice with no significant body weight loss across the course of the study. Mice were dosed through day 55 of study and then monitored for clinical observations, tumor volume and body weight measurements.

MT245 mouse syngeneic sarcoma tumors implanted into female C57Bl/6 mice grew from an average of 77 mm$^3$ to 2242 mm$^3$ in 20 days with a median survival of 19.30 days. Tumors on mice administered anti-PD-1 200 µg Q3D×19 showed 55.19% TGI by day 20 with a median survival of 24.89 days. Mice in groups 3, 4 and 5 treated with Compound 1 at 150 mg/kg, 300 mg/kg and 600 mg/kg resulted in 42.62% TGI, 95.58% TGI and 100% regression by day 20, respectively. The median survival for those groups was observed to be 25.04, 41.21, and >157.00 days, respectively. Co-administration of Compound 1 with anti-PD-1 improved efficacy significantly for both dose levels of Compound 1. Mice in the 150 mg/kg combination group demonstrated 97.34% TGI at day 20 with a median survival time of >157.00 days while the 300 mg/kg combination achieved 99.93% regression and extended median survival time to >157.00 days.

Figure 6:
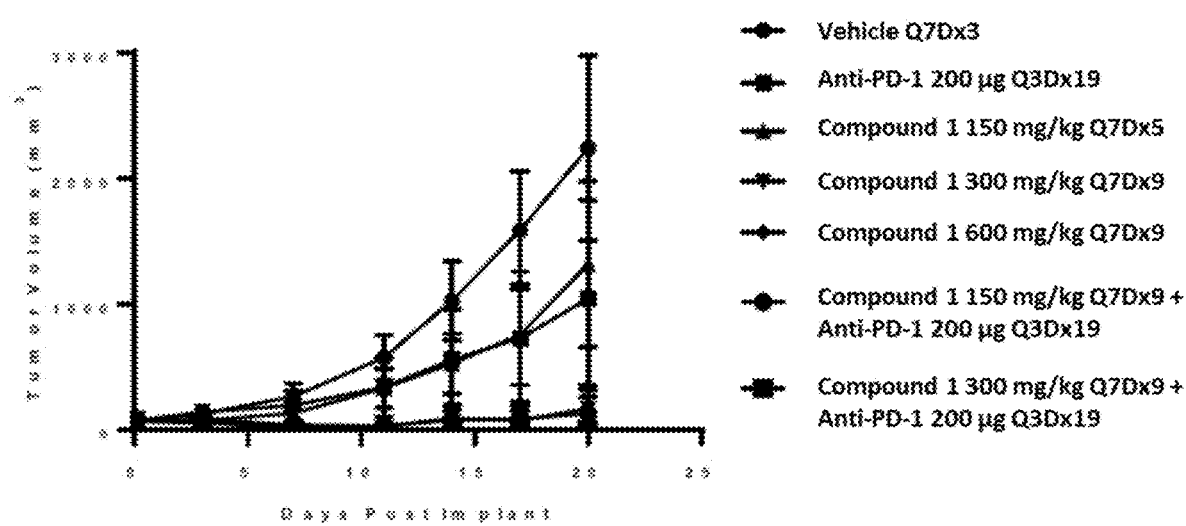
FIG. 6 shows changes in tumor volume ($mm^3$) in female C57Bl/6 mice implanted with MT245 mouse syngeneic sarcoma tumors over 20 days upon receiving treatment with vehicle (Q7Dx3); anti-PD-1 200 µg (Q3Dx19); Compound 1, 150 mg/kg (Q7Dx5); Compound 1, 300 mg/kg (Q7Dx9); Compound 1, 600 mg/kg (Q7Dx9); Compound 1, 150 mg/kg (Q7Dx9)+anti-PD-1 200 µg (Q3Dx19); or Compound 1, 300 mg/kg (Q7Dx9)+anti-PD-1 200 µg (Q3Dx19).

FIG. 6 shows changes in tumor volume (mm$^3$) in female C57Bl/6 mice implanted with MT245 mouse syngeneic sarcoma tumors over 20 days upon receiving treatment with vehicle (Q7D×3); anti-PD-1 200 µg (Q3D×19); Compound 1, 150 mg/kg (Q7D×5); Compound 1, 300 mg/kg (Q7D×9); Compound 1, 600 mg/kg (Q7D×9); Compound 1, 150 mg/kg (Q7D×9)+anti-PD-1 200 µg (Q3D×19); or Compound 1, 300 mg/kg (Q7D×9)+anti-PD-1 200 µg (Q3D×19). TABLE 19 shows average percentage tumor growth inhibition (%) across 20 days of study (n=10 unless noted). TABLE 20 shows average percentage tumor regression (%) across 157 days of study (n=10 unless noted).

TABLE 19

| Day of Study | Group 1 Vehicle Control Q7Dx3 | Group 2 Anti-PD-1 200 µg Q3Dx19 | Group 3 Comp 1 150 mg/kg Q7Dx5 | Group 4 Comp 1 300 mg/kg Q7Dx9 | Group 5 Comp 1 600 mg/kg Q7Dx9 | Group 6 Comp 1 150 mg/kg Q7Dx9 + Anti-PD-1 200 µg Q3Dx19 | Group 7 Comp 1 300 mg/kg Q7Dx9 + Anti-PD-1 200 µg Q3Dx19 |
|---|---|---|---|---|---|---|---|
| 0 | 0.00 | 0.00 | 0.00 | 0.00 | 0.00 | 0.00 | 0.00 |
| 3 | 0.00 | 0.00 | 96.72 | >100 | >100 | 77.22 | >100 |
| 7 | 0.00 | 36.54 | 68.93 | >100 | >100 | >100 | >100 |
| 11 | 0.00 | 46.98 | 48.26 | >100 | >100 | >100 (n = 9) | >100 |
| 14 | 0.00 | 49.22 | 52.39 | 98.02 | >100 | 99.43 (n = 9) | >100 |
| 17 | 0.00 | 56.76 | 54.96 | 99.83 | >100 | 99.05 (n = 9) | >100 |
| 20 | 0.00 (n = 8) | 55.19 (n = 9) | 42.62 | 95.58 | >100 | 97.34 (n = 9) | >100 |

TABLE 20

| Day of Study | Group 1 Vehicle Control Q7Dx3 | Group 2 Anti-PD-1 200 µg Q3Dx19 | Group 3 Comp 1 150 mg/kg Q7Dx5 | Group 4 Comp 1 300 mg/kg Q7Dx9 | Group 5 Comp 1 600 mg/kg Q7Dx9 | Group 6 Comp 1 150 mg/kg Q7Dx9 + Anti-PD-1 200 µg Q3Dx19 | Group 7 Comp 1 300 mg/kg Q7Dx9 + Anti-PD-1 200 µg Q3Dx19 |
|---|---|---|---|---|---|---|---|
| 0 | 0.00 | 0.00 | 0.00 | 0.00 | 0.00 | 0.00 | 0.00 |
| 3 | 0.00 | 0.00 | 0.00 | 24.34 | 10.04 | 0.00 | 6.33 |
| 7 | 0.00 | 0.00 | 0.00 | 45.41 | 87.69 | 42.47 | 87.56 |
| 11 | 0.00 | 0.00 | 0.00 | 58.23 | 97.92 | 52.67 (n = 9) | 99.16 |
| 14 | 0.00 | 0.00 | 0.00 | 0.00 | 99.94 | 0.00 (n = 9) | 99.87 |
| 17 | 0.00 | 0.00 | 0.00 | 0.00 | 100.00 | 0.00 (n = 9) | 99.93 |
| 20 | 0.00 (n = 8) | 0.00 (n = 9) | 0.00 | 0.00 | 100.00 | 0.00 (n = 9) | 99.93 |
| 25 | n/a | 0.00 (n = 7) | 0.00 (n = 6) | 0.00 | 100.00 | 0.00 (n = 9) | 100.00 |
| 28 | n/a | 0.00 (n = 3) | 0.00 (n = 5) | 0.00 | 100.00 | 0.00 (n = 9) | 100.00 |
| 31 | n/a | 0.00 (n = 3) | n/a | 0.00 | 100.00 | 0.00 (n = 9) | 100.00 |
| 34 | n/a | 0.00 (n = 3) | n/a | 0.00 | 100.00 | 0.00 (n = 9) | 100.00 |
| 38 | n/a | 100.00 (n = 1) | n/a | 0.00 (n = 7) | 100.00 | 0.00 (n = 8) | 100.00 |
| 42 | n/a | 100.00 n = 1 | n/a | 0.00 n = 6 | 100.00 | 0.00 n = 6 | 100.00 |
| 46 | n/a | 100.00 (n = 1) | n/a | 100.00 (n = 4) | 100.00 | 100.00 (n = 5) | 100.00 |
| 49 | n/a | 100.00 (n = 1) | n/a | 100.00 (n = 4) | 100.00 | 100.00 (n = 5) | 100.00 |
| 53 | n/a | 100.00 (n = 1) | n/a | 100.00 (n = 4) | 100.00 | 100.00 (n = 5) | 100.00 |
| 56 | n/a | 100.00 (n = 1) | n/a | 100.00 (n = 4) | 100.00 | 100.00 (n = 5) | 100.00 |
| 59 | n/a | 100.00 (n = 1) | n/a | 100.00 (n = 4) | 100.00 | 100.00 (n = 5) | 100.00 |
| 63 | n/a | 100.00 (n = 1) | n/a | 100.00 (n = 4) | 100.00 | 100.00 (n = 5) | 100.00 |
| 67 | n/a | 100.00 (n = 1) | n/a | 100.00 (n = 4) | 100.00 | 100.00 (n = 5) | 100.00 |
| 73 | n/a | 100.00 n = 1 | n/a | 100.00 n = 4 | 100.00 | 100.00 n = 5 | 100.00 |
| 80 | n/a | 100.00 (n = 1) | n/a | 100.00 (n = 4) | 100.00 (n = 9) | 100.00 (n = 5) | 100.00 |

TABLE 20-continued

| Day of Study | Group 1 Vehicle Control Q7Dx3 | Group 2 Anti-PD-1 200 μg Q3Dx19 | Group 3 Comp 1 150 mg/kg Q7Dx5 | Group 4 Comp 1 300 mg/kg Q7Dx9 | Group 5 Comp 1 600 mg/kg Q7Dx9 | Group 6 Comp 1 150 mg/kg Q7Dx9 + Anti-PD-1 200 μg Q3Dx19 | Group 7 Comp 1 300 mg/kg Q7Dx9 + Anti-PD-1 200 μg Q3Dx19 |
|---|---|---|---|---|---|---|---|
| 87 | n/a | 100.00 (n = 1) | n/a | 100.00 (n = 4) | 100.00 (n = 9) | 100.00 (n = 5) | 100.00 |
| 94 | n/a | 100.00 (n = 1) | n/a | 100.00 (n = 4) | 100.00 (n = 9) | 100.00 (n = 5) | 100.00 |
| 102 | n/a | 100.00 (n = 1) | n/a | 100.00 (n = 4) | too.00 (n = 9) | 100.00 (n = 5) | 100.00 |
| 109 | n/a | 100.00 (n = 1) | n/a | 100.00 (n = 4) | 100.00 (n = 9) | 100.00 (n = 5) | 100.00 |
| 116 | n/a | 100.00 (n = 1) | n/a | 100.00 (n = 4) | 100.00 (n = 9) | 100.00 (n = 5) | 100.00 |
| 123 | n/a | 100.00 (n = 1) | n/a | 100.00 (n = 4) | 100.00 (n = 9) | 100.00 (n = 5) | 100.00 |
| 157 | n/a | 100.00 (n = 1) | n/a | 100.00 (n = 4) | 100.00 (n = 9) | 100.00 (n = 5) | 100.00 |

MT245 tumors treated with vehicle control (2% HPC, 0.5% Tween 80) displayed consistent growth with animals reaching ~2000 mm³ by Day 20 and were euthanized due to tumor burden. Tumors on mice receiving anti-PD-1 Q3Dx19 demonstrated consistent growth inhibition through 20 days, after which 9 out of 10 tumors began to regrow at varied rates through day 34. One tumor (1), remained a cure to the end of the study. Mice administered Compound 1 150 mg/kg Q7Dx5 displayed maximal TGI at day 3 with 96.72% but all tumors thereafter began to grow and mice were euthanized due to tumor burden between days 20 and 28. Mice administered with Compound 1 300 mg/kg Q7Dx9; Compound 1 600 mg/kg Q7Dx9; Compound 1 150 mg/kg Q7Dx9+200 μg anti-PD-1 Q3Dx19; and 300 mg/kg Q7Dx9+200 μg anti-PD-1 Q3Dx19 showed maximal tumor control early in the study. At the end of study, several mice had complete tumor regression (Group 4: n=4, Group 5: n=9, Group 6: n=5, Group 7: n=10).

Figure 7:
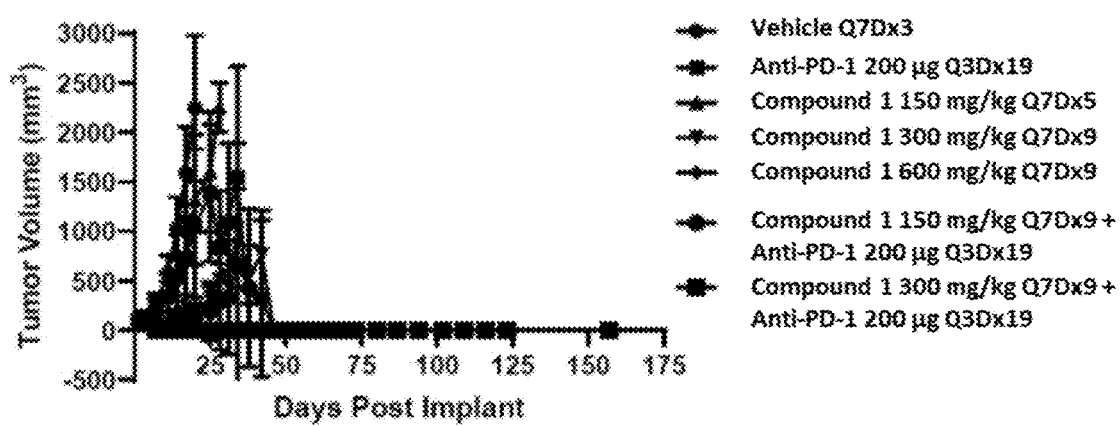
FIG. 7 shows changes in tumor volume ($mm^3$) in female C57Bl/6 mice implanted with MT245 mouse syngeneic sarcoma tumors over 157 days upon receiving treatment with vehicle (Q7Dx3); anti-PD-1 200 µg (Q3Dx19); Compound 1, 150 mg/kg (Q7Dx5); Compound 1, 300 mg/kg (Q7Dx9); Compound 1, 600 mg/kg (Q7Dx9); Compound 1, 150 mg/kg (Q7Dx9)+anti-PD-1 200 µg (Q3Dx19); or Compound 1, 300 mg/kg (Q7Dx9)+anti-PD-1 200 µg (Q3Dx19).
Figure 8:
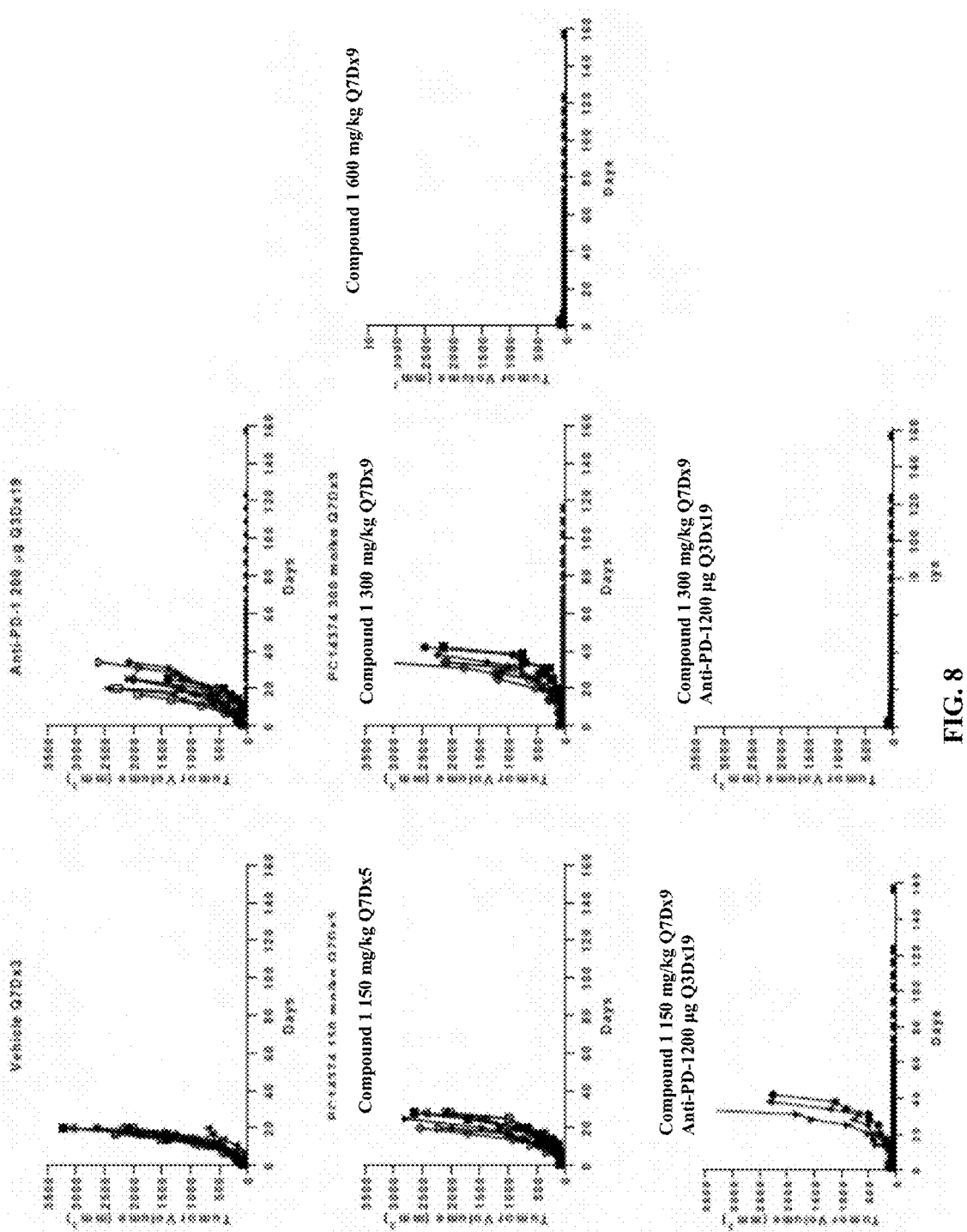
FIG. 8 shows changes in tumor volume ($mm^3$) in individual C57Bl/6 mice implanted with MT245 mouse syngeneic sarcoma tumors upon receiving treatment with vehicle (Q7Dx3); anti-PD-1 200 µg (Q3Dx19); Compound 1, 150 mg/kg (Q7Dx5); Compound 1, 300 mg/kg (Q7Dx9); Compound 1, 600 mg/kg (Q7Dx9); Compound 1, 150 mg/kg (Q7Dx9)+anti-PD-1 200 µg (Q3Dx19); or Compound 1, 300 mg/kg (Q7Dx9)+anti-PD-1 200 µg (Q3Dx19).

FIG. 7 shows changes in tumor volume (mm³) in female C57Bl/6 mice implanted with MT245 mouse syngeneic sarcoma tumors over 157 days upon receiving treatment with vehicle (Q7Dx3); anti-PD-1 200 μg (Q3Dx19); Compound 1, 150 mg/kg (Q7Dx5); Compound 1, 300 mg/kg (Q7Dx9); Compound 1, 600 mg/kg (Q7Dx9); Compound 1, 150 mg/kg (Q7Dx9)+anti-PD-1 200 μg (Q3Dx19); or Compound 1, 300 mg/kg (Q7Dx9)+anti-PD-1 200 μg (Q3Dx19). FIG. 8 shows changes in tumor volume (mm³) in individual C57Bl/6 mice implanted with MT245 mouse syngeneic sarcoma tumors upon receiving treatment with vehicle (Q7Dx3); anti-PD-1 200 μg (Q3Dx19); Compound 1, 150 mg/kg (Q7Dx5); Compound 1, 300 mg/kg (Q7Dx9); Compound 1, 600 mg/kg (Q7Dx9); Compound 1, 150 mg/kg (Q7Dx9)+anti-PD-1 200 μg (Q3Dx19); or Compound 1, 300 mg/kg (Q7Dx9)+anti-PD-1 200 μg (Q3Dx19). FIG. 9 provides a Kaplan-Meier survival curve of C57Bl/6 mice implanted with MT245 mouse syngeneic sarcoma tumors upon receiving treatment with vehicle (Q7Dx3); anti-PD-1 200 μg (Q3Dx19); Compound 1, 150 mg/kg (Q7Dx5); Compound 1, 300 mg/kg (Q7Dx9); Compound 1, 600 mg/kg (Q7Dx9); Compound 1, 150 mg/kg (Q7Dx9)+anti-PD-1 200 μg (Q3Dx19); or Compound 1, 300 mg/kg (Q7Dx9)+anti-PD-1 200 μg (Q3Dx19). TABLE 21 shows individual tumor volumes across the study for days 0-67. TABLE 22 shows individual tumor volumes across the study for days 73-157.

TABLE 21

| | | Days | | | | | | | | | |
|---|---|---|---|---|---|---|---|---|---|---|---|
| | Mouse | 0 | 3 | 7 | 11 | 14 | 17 | 20 | 25 | 28 | 31 |
| Group 1 | 1 | 60 | 108 | 291 | 676 | 1096 | 1613 | 2635 | | | |
| Vehicle | 2 | 67 | 113 | 272 | 542 | 1414 | 1872 | 3225 | | | |
| Control | 3 | 67 | 84 | 57 | 202 | 426 | 621 | 696 | | | |
| Q7Dx3 | 4 | 74 | 171 | 348 | 644 | 1311 | 1585 | 2013 | | | |
| | 5 | 74 | 81 | 187 | 462 | 874 | 1244 | 2112 | | | |
| | 6 | 80 | 180 | 317 | 653 | 982 | 2313 | | | | |
| | 7 | 80 | 75 | 148 | 462 | 651 | 1418 | 2013 | | | |
| | 8 | 85 | 153 | 289 | 918 | 978 | 1504 | 3072 | | | |
| | 9 | 86 | 148 | 338 | 690 | 1499 | 2267 | | | | |
| | 10 | 97 | 206 | 438 | 532 | 1064 | 1441 | 2171 | | | |
| | Ave | 77 | 132 | 268 | 578 | 1030 | 1588 | 2242 | | | |
| | SD | 11 | 46 | 110 | 188 | 332 | 492 | 786 | | | |
| Group 2 | 1 | 62 | 104 | 16 | 13 | 4 | 0 | 0 | 0 | 0 | 0 |
| Anti-PD-1 | 2 | 66 | 155 | 55 | 71 | 167 | 293 | 429 | 1397 | | |
| 200 μg | 3 | 68 | 150 | 375 | 605 | 1140 | 1306 | 2450 | | | |
| Q3Dx19 | 4 | 74 | 172 | 188 | 394 | 522 | 857 | 1137 | 2079 | | |
| | 5 | 74 | 129 | 128 | 130 | 252 | 633 | 671 | 1145 | 1252 | 1381 |
| | 6 | 79 | 176 | 387 | 809 | 1339 | 1913 | | | | |
| | 7 | 79 | 147 | 212 | 416 | 613 | 580 | 2266 | | | |
| | 8 | 85 | 123 | 275 | 379 | 676 | 963 | 1210 | 2034 | | |
| | 9 | 86 | 151 | 101 | 185 | 259 | 295 | 504 | 1051 | 1222 | 1887 |
| | 10 | 96 | 159 | 246 | 426 | 632 | 463 | 755 | 2005 | | |
| | Ave | 77 | 147 | 198 | 343 | 561 | 730 | 1047 | 1387 | 825 | 1089 |
| | SD | 10 | 22 | 126 | 248 | 424 | 560 | 828 | 750 | 714 | 977 |

TABLE 21-continued

| Group | Mouse | | | | | | | | | |
|---|---|---|---|---|---|---|---|---|---|---|
| Group 3 | 1 | 62 | 95 | 140 | 342 | 476 | 537 | 1154 | | |
| Compound 1 | 2 | 66 | 48 | 36 | 131 | 222 | 415 | 699 | 1695 | 2644 |
| 150 mg/kg | 3 | 68 | 82 | 176 | 499 | 861 | 1023 | 2020 | | |
| Q7Dx5 | 4 | 73 | 100 | 158 | 405 | 714 | 995 | 1437 | 2782 | |
| | 5 | 75 | 97 | 110 | 260 | 343 | 502 | 872 | 1732 | 2084 |
| | 6 | 79 | 51 | 61 | 161 | 233 | 362 | 649 | 982 | 2009 |
| | 7 | 81 | 41 | 55 | 224 | 466 | 420 | 721 | 986 | 2078 |
| | 8 | 85 | 96 | 122 | 529 | 379 | 634 | 915 | 1420 | 2455 |
| | 9 | 86 | 95 | 311 | 591 | 686 | 984 | 2195 | | |
| | 10 | 95 | 82 | 196 | 223 | 925 | 1704 | 2533 | | |
| | Ave | 77 | 79 | 137 | 336 | S31 | 758 | 1319 | 1600 | 2254 |
| | SD | 10 | 23 | 81 | 162 | 252 | 421 | 693 | 666 | 279 |
| Group 4 | 1 | 62 | 57 | 23 | 19 | 19 | 35 | 76 | 261 | 475 | 388 |
| Compound 1 | 2 | 66 | 63 | 23 | 28 | 93 | 79 | 144 | 231 | 348 | 274 |
| 300 mg/kg | 3 | 68 | 70 | 9 | 0.5 | 0.5 | 0.5 | 0 | 0 | 0 | 0 |
| Q7Dx9 | 4 | 72 | 54 | 6 | 0.5 | 0.5 | 0 | 0 | 0 | 0 | 0 |
| | 5 | 76 | 58 | 87 | 48 | 184 | 130 | 400 | 501 | 752 | 781 |
| | 6 | 79 | 71 | 107 | 117 | 285 | 216 | 359 | 626 | 1161 | 1011 |
| | 7 | 81 | 57 | 8 | 10 | 0 | 0 | 0 | 0 | 0 | 0 |
| | 8 | 85 | 52 | 38 | 31 | 106 | 115 | 226 | 506 | 1168 | 936 |
| | 9 | 87 | 52 | 5 | 0 | 0 | 0 | 0 | 0 | 0 | 0 |
| | 10 | 93 | 50 | 113 | 68 | 269 | 218 | 520 | 1171 | 1266 | 1774 |
| | Ave | 77 | 58 | 42 | 32 | 96 | 79 | 173 | 330 | 517 | 516 |
| | SD | 10 | 7 | 43 | 37 | 114 | 87 | 194 | 381 | 533 | 598 |
| Group 5 | 1 | 63 | 39 | 10 | 10 | 0 | 0 | 0 | 0 | 0 | 0 |
| Compound 1 | 2 | 66 | 74 | 9 | 0.5 | 0 | 0 | 0 | 0 | 0 | 0 |
| 600 mg/kg | 3 | 68 | 50 | 10 | 05 | 0 | 0 | 0 | 0 | 0 | 0 |
| Q7Dx9 | 4 | 72 | 73 | 10 | 0 | 0 | 0 | 0 | 0 | 0 | 0 |
| | 5 | 76 | 62 | 7 | 5 | 0.5 | 0 | 0 | 0 | 0 | 0 |
| | 6 | 7 | 103 | 12 | 0 | 0 | 0 | 0 | 0 | 0 | 0 |
| | 7 | 85 | 43 | 5 | 0 | 0 | 0 | 0 | 0 | 0 | 0 |
| | 8 | 83 | 91 | 3 | 0 | 0 | 0 | 0 | 0 | 0 | 0 |
| | 9 | 87 | 96 | 28 | 0 | 0 | 0 | 0 | 0 | 0 | 0 |
| | 10 | 93 | 61 | 0.5 | 0 | 0 | 0 | 0 | 0 | 0 | 0 |
| | Ave | 77 | 69 | 9 | 2 | 0.05 | 0 | 0 | 0 | 0 | 0 |
| | SD | 10 | 22 | 7 | 3 | 0.2 | 0 | 0 | 0 | 0 | 0 |
| Group 6 | 1 | 63 | 95 | 68 | 75 | 133 | 173 | 287 | 318 | 491 | 499 |
| Compound 1 | 2 | 66 | 79 | 83 | | | | | | | |
| 150 mg/kg | 3 | 69 | 56 | 63 | 107 | 255 | 247 | 425 | 528 | 778 | 691 |
| Q7Dx9 + | 4 | 71 | 90 | 86 | 121 | 350 | 399 | 497 | 879 | 1540 | 1807 |
| Anti-PD-1 | 5 | 77 | 52 | 9 | 0.5 | 0 | 0 | 0 | 0 | 0 | 0 |
| 200 µg | 6 | 77 | 121 | 46 | 9 | 0.5 | 0 | 0 | 0 | 0 | 0 |
| Q3Dx19 | 7 | 8 | 130 | 19 | 0 | 0 | 0 | 0 | 0 | | |
| | 8 | 83 | 55 | 6 | 0.5 | 0 | 0 | 0 | 0 | 0 | 0 |
| | 9 | 89 | 128 | 48 | 9 | 0.5 | 0 | 0 | 0 | 0 | 0 |
| | 10 | 92 | 87 | 14 | 6 | 0.5 | 0.5 | 0 | 0 | 0 | 0 |
| | Ave | 77 | 89 | 44 | 36 | 82 | 91 | 134 | 192 | 312 | 333 |
| | SD | 10 | 30 | 31 | 50 | 134 | 148 | 209 | 320 | 541 | 612 |
| Group 7 | 1 | 63 | 102 | 8 | 0 | 0 | 0 | 0 | 0 | 0 | 0 |
| Compound 1 | 2 | 64 | 69 | 15 | 6 | 0.5 | 0.5 | 0 | 0 | 0 | 0 |
| 300 mg/kg | 3 | 70 | 51 | 0 | 0 | 0 | 0 | 0 | 0 | 0 | 0 |
| Q7Dx9 + | 4 | 71 | 75 | 11 | 0 | 0 | 0 | 0 | 0 | 0 | 0 |
| Anti-PD-1 | 5 | 77 | 65 | 17 | 0 | 0 | 0 | 0 | 0 | 0 | 0 |
| 200 µg | 6 | 77 | 65 | 0.5 | 0 | 0 | 0 | 0 | 0 | 0 | 0 |
| Q3Dx19 | 7 | 83 | 104 | 15 | 0.5 | 0.5 | 0.5 | 0 | 0 | 0 | 0 |
| | 8 | 83 | 72 | 10 | 0 | 0 | 0 | 0 | 0 | 0 | 0 |
| | 9 | 89 | 23 | 0.5 | 0 | 0 | 0 | 0 | 0 | 0 | 0 |
| | 10 | 91 | 94 | 18 | 0 | 0 | 0 | 0 | 0 | 0 | 0 |
| | Ave | 77 | 72 | 10 | 0.6 | 0.1 | 0.1 | 0.1 | 0 | 0 | 0 |
| | SD | 10 | 24 | 7 | 2 | 0.2 | 0.2 | 0.2 | 0 | 0 | 0 |

| | | Days | | | | | | | | |
|---|---|---|---|---|---|---|---|---|---|---|
| | Mouse | 34 | 38 | 42 | 46 | 49 | 53 | 56 | 59 | 63 | 67 |
| Group 1 | 1 | | | | | | | | | | |
| Vehicle | 2 | | | | | | | | | | |
| Control | 3 | | | | | | | | | | |
| Q7Dx3 | 4 | | | | | | | | | | |
| | 5 | | | | | | | | | | |
| | 6 | | | | | | | | | | |
| | 7 | | | | | | | | | | |
| | 8 | | | | | | | | | | |
| | 9 | | | | | | | | | | |
| | 10 | | | | | | | | | | |
| | Ave | | | | | | | | | | |
| | SD | | | | | | | | | | |

TABLE 21-continued

| Group | # | | | | | | | | | | |
|---|---|---|---|---|---|---|---|---|---|---|---|
| Group 2 Anti-PD-1 200 µg Q3Dx19 | 1 | 0 | 0 | 0 | 0 | 0 | 0 | 0 | 0 | 0 | 0 |
| | 2 | | | | | | | | | | |
| | 3 | | | | | | | | | | |
| | 4 | | | | | | | | | | |
| | 5 | 2075 | | | | | | | | | |
| | 6 | | | | | | | | | | |
| | 7 | | | | | | | | | | |
| | 8 | | | | | | | | | | |
| | 9 | 2577 | | | | | | | | | |
| | 10 | | | | | | | | | | |
| | Ave | 1550 | | | | | | | | | |
| | SD | 1366 | | | | | | | | | |
| Group 3 Compound 1 150 mg/kg Q7Dx5 | 1 | | | | | | | | | | |
| | 2 | | | | | | | | | | |
| | 3 | | | | | | | | | | |
| | 4 | | | | | | | | | | |
| | 5 | | | | | | | | | | |
| | 6 | | | | | | | | | | |
| | 7 | | | | | | | | | | |
| | 8 | | | | | | | | | | |
| | 9 | | | | | | | | | | |
| | 10 | | | | | | | | | | |
| | Ave | | | | | | | | | | |
| | SD | | | | | | | | | | |
| Group 4 Compound 1 300 mg/kg Q7Dx9 | 1 | 757 | 917 | 2459 | | | | | | | |
| | 2 | 707 | 763 | 2137 | | | | | | | |
| | 3 | 0 | 0 | 0 | 0 | 0 | 0 | 0 | 0 | 0 | 0 |
| | 4 | 0 | 0 | 0 | 0 | 0 | 0 | 0 | 0 | 0 | 0 |
| | 5 | 1371 | 2233 | | | | | | | | |
| | 6 | 2093 | | | | | | | | | |
| | 7 | 0 | 0 | 0 | 0 | 0 | 0 | 0 | 0 | 0 | 0 |
| | 8 | 2097 | | | | | | | | | |
| | 9 | 0 | 0 | 0 | 0 | 0 | 0 | 0 | 0 | 0 | 0 |
| | 10 | 3221 | | | | | | | | | |
| | Ave | 1025 | 559 | 766 | 0 | 0 | 0 | 0 | 0 | 0 | 0 |
| | SD | 1136 | 839 | 1191 | 0 | 0 | 0 | 0 | 0 | 0 | 0 |
| Group 5 Compound 1 600 mg/kg Q7Dx9 | 1 | 0 | 0 | 0 | 0 | 0 | 0 | 0 | 0 | 0 | 0 |
| | 2 | 0 | 0 | 0 | 0 | 0 | 0 | 0 | 0 | 0 | 0 |
| | 3 | 0 | 0 | 0 | 0 | 0 | 0 | 0 | 0 | 0 | 0 |
| | 4 | 0 | 0 | 0 | 0 | 0 | 0 | 0 | 0 | 0 | 0 |
| | 5 | 0 | 0 | 0 | 0 | 0 | 0 | 0 | 0 | 0 | 0 |
| | 6 | 0 | 0 | 0 | 0 | 0 | 0 | 0 | 0 | 0 | 0 |
| | 7 | 0 | 0 | 0 | 0 | 0 | 0 | 0 | 0 | 0 | 0 |
| | 8 | 0 | 0 | 0 | 0 | 0 | 0 | 0 | 0 | 0 | 0 |
| | 9 | 0 | 0 | 0 | 0 | 0 | 0 | 0 | 0 | 0 | 0 |
| | 10 | 0 | 0 | 0 | 0 | 0 | 0 | 0 | 0 | 0 | 0 |
| | Ave | 0 | 0 | 0 | 0 | 0 | 0 | 0 | 0 | 0 | 0 |
| | SD | 0 | 0 | 0 | 0 | 0 | 0 | 0 | 0 | 0 | 0 |
| Group 6 Compound 1 150 mg/kg Q7Dx9 + Anti-PD-1 200 µg Q3Dx19 | 1 | 910 | 1113 | 2260 | | | | | | | |
| | 2 | | | | | | | | | | |
| | 3 | 1221 | 2314 | | | | | | | | |
| | 4 | 3878 | | | | | | | | | |
| | 5 | 0 | 0 | 0 | 0 | 0 | 0 | 0 | 0 | 0 | 0 |
| | 6 | 0 | 0 | 0 | 0 | 0 | 0 | 0 | 0 | 0 | 0 |
| | 7 | | | | | | | | | | |
| | 8 | 0 | 0 | 0 | 0 | 0 | 0 | 0 | 0 | 0 | 0 |
| | 9 | 0 | 0 | 0 | 0 | 0 | 0 | 0 | 0 | 0 | 0 |
| | 10 | 0 | 0 | 0 | 0 | 0 | 0 | 0 | 0 | 0 | 0 |
| | Ave | 668 | 428 | 377 | 0 | 0 | 0 | 0 | 0 | 0 | 0 |
| | SD | 1292 | 856 | 922 | 0 | 0 | 0 | 0 | 0 | 0 | 0 |
| Group 7 Compound 1 300 mg/kg Q7Dx9 + Anti-PD-1 200 µg Q3Dx19 | 1 | 0 | 0 | 0 | 0 | 0 | 0 | 0 | 0 | 0 | 0 |
| | 2 | 0 | 0 | 0 | 0 | 0 | 0 | 0 | 0 | 0 | 0 |
| | 3 | 0 | 0 | 0 | 0 | 0 | 0 | 0 | 0 | 0 | 0 |
| | 4 | 0 | 0 | 0 | 0 | 0 | 0 | 0 | 0 | 0 | 0 |
| | 5 | 0 | 0 | 0 | 0 | 0 | 0 | 0 | 0 | 0 | 0 |
| | 6 | 0 | 0 | 0 | 0 | 0 | 0 | 0 | 0 | 0 | 0 |
| | 7 | 0 | 0 | 0 | 0 | 0 | 0 | 0 | 0 | 0 | 0 |
| | 8 | 0 | 0 | 0 | 0 | 0 | 0 | 0 | 0 | 0 | 0 |
| | 9 | 0 | 0 | 0 | 0 | 0 | 0 | 0 | 0 | 0 | 0 |
| | 10 | 0 | 0 | 0 | 0 | 0 | 0 | 0 | 0 | 0 | 0 |
| | Ave | 0 | 0 | 0 | 0 | 0 | 0 | 0 | 0 | 0 | 0 |
| | SD | 0 | 0 | 0 | 0 | 0 | 0 | 0 | 0 | 0 | 0 |

TABLE 22

Individual tumor volumes across study (Days 73-157)

| | Mouse | 73 | 80 | 87 | 94 | 102 | 109 | 116 | 123 | 157 |
|---|---|---|---|---|---|---|---|---|---|---|
| Group 2 | 1 | 0 | 0 | 0 | 0 | 0 | 0 | 0 | 0 | 0 |
| Anti-PD-1 | 3 | | | | | | | | | |
| 200 µg | 4 | | | | | | | | | |
| Q3Dx19 | 5 | | | | | | | | | |
| | 6 | | | | | | | | | |
| | 7 | | | | | | | | | |
| | S | | | | | | | | | |
| | 9 | | | | | | | | | |
| | 10 | | | | | | | | | |
| | Ave | 0 | 0 | 0 | 0 | 0 | 0 | 0 | 0 | 0 |
| | SD | 0 | 0 | 0 | 0 | 0 | 0 | 0 | 0 | 0 |
| Group 4 | 1 | | | | | | | | | |
| Compound 1 | 2 | | | | | | | | | |
| 300 mg/kg | 3 | 0 | 0 | 0 | 0 | 0 | 0 | 0 | 0 | 0 |
| Q7Dx9 | 4 | 0 | 0 | 0 | 0 | 0 | 0 | 0 | 0 | 0 |
| | 5 | | | | | | | | | |
| | 6 | | | | | | | | | |
| | 7 | 0 | 0 | 0 | 0 | 0 | 0 | 0 | 0 | 0 |
| | 8 | | | | | | | | | |
| | 9 | 0 | 0 | 0 | 0 | 0 | 0 | 0 | | |
| | 10 | | | | | | | | | |
| | Ave | 0 | 0 | 0 | 0 | 0 | 0 | 0 | 0 | |
| | SD | 0 | 0 | 0 | 0 | 0 | 0 | 0 | 0 | |
| Group 5 | 1 | 0 | 0 | 0 | 0 | 0 | 0 | 0 | 0 | |
| Compound 1 | | 0 | 0 | 0 | 0 | 0 | 0 | 0 | 0 | |
| 600 mg/kg | 3 | 0 | 0 | 0 | 0 | 0 | 0 | 0 | 0 | |
| Q7Dx9 | 4 | 0 | 0 | 0 | 0 | 0 | 0 | 0 | 0 | |
| | S | 0 | 0 | 0 | 0 | 0 | 0 | 0 | 0 | |
| | 6 | 0 | | | | | | | | |
| | 7 | 0 | 0 | 0 | 0 | 0 | 0 | 0 | 0 | |
| | 8 | 0 | 0 | 0 | 0 | 0 | 0 | 0 | 0 | |
| | 9 | 0 | 0 | 0 | 0 | 0 | 0 | 0 | 0 | |
| | 10 | 0 | 0 | 0 | 0 | 0 | 0 | 0 | 0 | |
| | Ave | 0 | 0 | 0 | 0 | 0 | 0 | 0 | 0 | |
| | SD | 0 | 0 | 0 | 0 | 0 | 0 | 0 | 0 | |
| Group 6 | 1 | | | | | | | | | |
| Compound 1 | 2 | | | | | | | | | |
| 150 mg/kg | 3 | | | | | | | | | |
| Q7Dx9 + | 4 | | | | | | | | | |
| Anti-PD-1 | 5 | 0 | 0 | 0 | 0 | 0 | 0 | 0 | 0 | 0 |
| 200 µg | 6 | 0 | 0 | 0 | 0 | 0 | 0 | 0 | 0 | 0 |
| Q3Dx19 | 7 | | | | | | | | | |
| | 8 | 0 | 0 | 0 | 0 | 0 | 0 | 0 | 0 | 0 |
| | 9 | 0 | 0 | 0 | 0 | 0 | 0 | 0 | 0 | 0 |
| | 10 | 0 | 0 | 0 | 0 | 0 | 0 | 0 | 0 | 0 |
| | Ave | 0 | 0 | 0 | 0 | 0 | 0 | 0 | 0 | 0 |
| | SD | 0 | 0 | 0 | 0 | 0 | D | 0 | 0 | 0 |
| Group 7 | 1 | 0 | 0 | 0 | 0 | 0 | 0 | 0 | 0 | 0 |
| Compound 1 | 2 | 0 | 0 | 0 | 0 | 0 | 0 | 0 | 0 | 0 |
| 300 mg/kg | 3 | 0 | 0 | 0 | 0 | 0 | 0 | 0 | 0 | 0 |
| Q7Dx9 + | 4 | 0 | 0 | 0 | 0 | 0 | 0 | 0 | 0 | 0 |
| Anti-PD-1 | 5 | 0 | 0 | 0 | 0 | 0 | 0 | 0 | 0 | 0 |
| 200 µg | 6 | 0 | 0 | 0 | 0 | 0 | 0 | 0 | 0 | 0 |
| Q3Dx19 | 7 | 0 | 0 | 0 | 0 | 0 | 0 | 0 | 0 | 0 |
| | 8 | 0 | 0 | 0 | 0 | 0 | 0 | 0 | 0 | 0 |
| | 9 | 0 | 0 | 0 | 0 | 0 | 0 | 0 | 0 | 0 |
| | 10 | 0 | 0 | 0 | 0 | 0 | 0 | 0 | 0 | 0 |
| | Ave | 0 | 0 | 0 | 0 | 0 | 0 | 0 | 0 | 0 |
| | SD | 0 | 0 | 0 | 0 | 0 | 0 | 0 | 0 | 0 |

Body Weights: Mouse body weights were well maintained over the course of the study (5). Mice dosed with vehicle control were an average of 20.33 g by the end of the study (day 20) with the percentage change varying between −0.28% early in the study to +11.69%. Mice administered anti-PD-1 consistently gained body weight through the study and by day 34 gained 16.65%. One mouse (7) began to lose weight at day 14 and by day 17 had a weight change of −9.5% and was euthanized for tumor burden on day 20. Two mice (1 and 9) that received Compound 1 150 mg/kg had a body weight change of −5.9% and −7.5% at day 20 when the mice were euthanized for tumor burden, all other mice in that group lost no more than 5% body weight. By day 123, Group 4 gained 26.82%, Group 5 gained 23.017, Group 6 gained 24.82 and Group 7 gained 25.66%. In Group 5, one mouse (5) had body weight loss>50% early but recovered by day 17 and one mouse in Group 6 (10) had body weight loss>5% around day 31 but also recovered.

FIG. 10 shows changes in percent body weight C57Bl/6 mice implanted with MT245 mouse syngeneic sarcoma tumors upon receiving treatment with vehicle (Q7Dx3);

anti-PD-1 200 μg (Q3D×19); Compound 1, 150 mg/kg (Q7D×5); Compound 1, 300 mg/kg (Q7D×9); Compound 1, 600 mg/kg (Q7D×9); Compound 1, 150 mg/kg (Q7D×9)+ anti-PD-1 200 μg (Q3D×19); or Compound 1, 300 mg/kg (Q7D×9)+anti-PD-1 200 μg (Q3D×39). TABLE 23 shows average percentage changes in body weight of mice across the study (n=10 unless noted). TABLE 24 shows individual body weights of mice across the study from days 0-67. TABLE 25 shows individual body weights of mice across the study from days 73-157.

TABLE 23

| Day of Study | Group 1 Vehicle Control Q713x3 | Group 2 Anti-PD 1 200 μg Q3Dx19 | Group 3 Compound 1 300 mg/kg Q7Dx5 | Group 4 Compound 1 300 mg/kg Q7Dx9 | Group 5 Compound 1 600 mg/kg Q7Dx9 | Group 6 Compound 1 150 mg/kg QDx9 + Anti-PD-1 200 μg Q3Dx19 | Group 7 Compound 1 300 mg/kg Q7Dx9 + Anti-PD-1 200 μg Q3Dx19 |
|---|---|---|---|---|---|---|---|
| 0 | 0.00 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 3 | −0.28 ± 2.42 | 0.58 ± 2.10 | 0.38 ± 1.57 | 1 28 ± 3.05 | −0.99 ± 3.49 | 1.23 ± 1.43 | 074 ± 4.93 |
| 7 | 2.60 ± 2.99 | 2.41 ± 2.18 | 1.47 ± 2.53 | 1.09 ± 2.31 | 0.18 ± 2.44 | 2.22 ± 1.92 | 2.46 ± 3.59 |
| 11 | 4.32 ± 2 30 | 1.50 ± 3.54 | 2.20 ± 4.34 | 3.75 ± 3.20 | 1.90 ± 1.99 | 3.00 ± 2.50 | 1.50 ± 3 62 |
| 14 | 3.33 ± 5.47 | 0.20 ± 3.88 | 0.60 ± 5.42 | 1.14 ± 3.00 | −1.04 ± 2.34 | 2.31 ± 5.26 (n = 9) | 1.64 ± 3.47 |
| 17 | 7.81 ± 7.20 | 4.05 ± 9.80 | 4.10 ± 6.98 | 3.52 ± 3.85 | 2.40 ± 2.23 | 3.20 ± 2.43 (n = 9) | 2.09 ± 4.93 |
| 20 | 11.69 ± 9.95 (n = 8) | 4.43 ± 5.88 (n = 9) | 5.89 ± 7.37 | 4.59 ± 5.47 | 3.17 ± 2.17 | 4.17 ± 3.01 (n = 9) | 3.37 ± 2.92 |
| 25 | | 6.84 ± 6.20 (n = 7) | 13.07 ± 9.84 {n = 6) | 6.84 ± 4.84 | 5.86 ± 3.36 | 6.35 ± 4.30 (n = 9)' | 585 ± 4.37 |
| 28 | | 11.64 ± 4.39 (n = 3) | 15.76 ± 8.25 (n = 5) | 4.57 ± 2.09 | 4.57 ± 2.09 | 8.87 ± 4.53 | 7.82 ± 3.77 |
| 31 | | 13.74 ± 5.08 (n = 3) | | 10.24 ± 7.54 | 6.75 ± 2.62 | 8.88 ± 8.61 (n = 9) | 9.88 ± 4.25 |
| 34 | | 16.65 ± 7.79 (n = 3) | | 13.27 ± 9.37 | 5.59 ± 2.70 | 11.69 ± 8.42 (n = 9) | 9.25 ± 4.28 |
| 38 | | 11.98 ± 0.00 (n = 1) | | 14.77 ± 8.41 (n = 7) | 9.99 ± 3.67 | 13.07 ± 7.25 (n = 8) | 11.17 ± 4.84 |
| 42 | | 12.58 ± 0.00 (n = 1) | | 15.13 ± 5.68 (n = 6) | 10.70 ± 3.70 | 14.06 ± 5.30 (n = 7) | 12.54 ± 6.54 |
| 46 | | 18.54 ± 0.00 (n = 1) | | 15.21 ± 5.27 (n = 4) | 13.47 ± 3.25 | 14.68 ± 2.68 (n = 5) | 10.82 ± 5.33 |
| 49 | | 18.05 ± 0.00 (n = 1) | | 14.89 ± 3.60 (n = 4) | 13.47 ± 3.25 | 14.68 ± 2.68 (n = 5) | 10.82 ± 5.33 |
| 53 | | 20.03 ± 0.00 | | 14.69 ± 4.37 (n = 4) | 13.38 ± 3.06 | 14.44 ± 4.49 (n = 5) | 14.91 ± 5.07 |
| 56 | | 19.21 ± 0.00 (n = 1) | | 14.83 ± 4.40 (n = 4) | 13.57 3.48 | 15.04 ± 5.00 (n = 5) | 15.57 ± 5.64 |
| 59 | | 20.42 ± 0.00 (n = 1) | | 15.60 ± 4.59 (n = 4) | 13.51 ± 3.23 | 15.76 ± 5.60 (n = 5) | 15.26 ± 5.92 |
| 63 | | 19.59 ± 0.00 (n = 1) | | 17.01 ± 5.52 (n = 4) | 14.33 ± 2.85 | 16.89 ± 4.25 (n = 5) | 15.56 ± 5.31 |
| 67 | | 19.37 ± 0.00 (n = 1) | | 18.81 ± 7.85 (n = 4) | 14.15 ± 3.15 | 16.05 ± 4.81 (n = 5) | 20.30 ± 5.47 |
| 73 | | 21.41 ± 0.00 (n = 1) | | 20.86 ± 4.41 (n = 4) | 16.24 ± 3.31 | 19.80 ± 6.40 (n = 5) | 20.30 ± 5.47 |
| 80 | | 22.52 ± 0.00 (n = 1) | | 20.04 ± 4.95 (n = 4) | 16.41 ± 1.92 (n = 9) | 17.85 ± 6.51 (n = 5) | 19.36 ± 3.93 |
| 87 | | 26.93 ± 0.00 (n = 1) | | 21.66 ± 5.39 (n = 4) | 17.90 ± 3.37 (n = 9) | 18.06 ± 5.75 (n = 5) | 21.38 ± 4.39 |
| 94 | | 25.50 ± 0.00 (n = 1) | | 20.68 ± 4.41 (n = 4) | 18.17 ± 2.96 (n = 9) | 18.01 ± 6.67 (n = 5) | 21.00 ± 3.97 |
| 102 | | 26.93 ± 0.00 (n = 1) | | 24.86 ± 5.93 (n = 4) | 19.66 ± 3.78 (n = 9) | 25.79 ± 4.19 (n = 5) | 26.33 ± 4.18 |
| 109 | | 25.28 ± 0.00 (n = 1) | | 25.06 ± 6.31 (n = 4) | 22.72 ± 5.31 (n = 9) | 23.45 ± 4.10 (n = 5) | 25.33 ± 5.22 |
| 116 | | 27.48 ± 0.00 (n = 1) | | 27.02 ± 6.13 (n = 4) | 22.71 ± 5.56 (n = 9) | 24.84 ± 4.18 (n = 5) | 26.41 ± 5.16 |
| 123 | | 28.59 ± 0.00 (n = 1) | | 26.82 ± 5.88 (n = 4) | 23.01 ± 6.31 (n = 9) | 24.82 ± 4.17 (n = 5) | 25.66 ± 4.91 |
| 157 | | 27.48 ± 0.00 (n = 1) | | 32.14 ± 8.58 (n = 4) | 20.76 ± 3.23 (n = 9) | 29.44 ± 8.13 (n = 5) | 26.22 ± 4.19 |

TABLE 24

| | Mouse | Days | | | | | | | | | |
|---|---|---|---|---|---|---|---|---|---|---|---|
| | | 0 | 3 | 7 | 11 | 14 | 17 | 20 | 25 | 28 | 31 | 34 |
| Group 1 Vehicle | 1 | 20.60 | 20.20 | 21.02 | 21.09 | 20.53 | 21.07 | 20.46 | | | | |
| | 2 | 18.10 | 17.80 | 18.60 | 18.70 | 18.58 | 19.20 | 19.70 | | | | |

TABLE 24-continued

| | | | | | | | | | | | | |
|---|---|---|---|---|---|---|---|---|---|---|---|---|
| Control Q7Dx3 | 3 | 19.70 | 19.38 | 20.30 | 19.95 | 18.04 | 18.56 | 19.25 | | | | |
| | 4 | 19.20 | 18.90 | 19.05 | 19.6 | 20.05 | 20.60 | 22.57 | | | | |
| | 5 | 17.50 | 17.78 | 18.22 | 18.40 | 18.57 | 19.45 | 19.70 | | | | |
| | 6 | 18.03 | 17.83 | 18.50 | 19.12 | 18.57 | 19.65 | | | | | |
| | 7 | 17.09 | 17.00 | 17.40 | 18.09 | 18.20 | 18.74 | 20.05 | | | | |
| | 8 | 17.17 | 16.62 | 16.65 | 17.26 | 17.12 | 17.82 | 19.24 | | | | |
| | 9 | 19.00 | 19.85 | 20.33 | 20.57 | 20.83 | 21.51 | | | | | |
| | 10 | 16.90 | 17.36 | 17.98 | 18.30 | 18.60 | 20.53 | 21.65 | | | | |
| | Ave | 18.33 | 18.27 | 18.81 | 19.11 | 18.91 | 19.71 | 20.33 | | | | |
| | SD | 1.25 | 1.23 | 1.39 | 1.19 | 1.18 | 1.19 | 1.20 | | | | |
| Group 2 Anti-PD-1 200 μg Q3Dx19 | 1 | 18.12 | 18.3 | 18.5 | 18.14 | 18.50 | 23.00 | 19.10 | 19.65 | 19.68 | 20.45 | 20.38 |
| | 2 | 17.42 | 17.73 | 17.87 | 17.82 | 18.48 | 18.75 | 19.25 | 18.50 | | | |
| | 3 | 17.80 | 17.84 | 18.12 | 17.16 | 16.54 | 17.18 | 18.62 | | | | |
| | 4 | 19.90 | 19.54 | 20.05 | 20.63 | 19.96 | 19.90 | 19.15 | 18.81 | | | |
| | 5 | 18.60 | 19.09 | 19.18 | 19.76 | 19.20 | 20.35 | 20.70 | 21.20 | 21.70 | 22.17 | 23.37 |
| | 6 | 17.59 | 17.90 | 17.85 | 16.90 | 17.08 | 17.34 | | | | | |
| | 7 | 18.13 | 18.80 | 19.40 | 19.00 | 17.42 | 16.40 | 16.98 | | | | |
| | 8 | 19.26 | 19.06 | 19.50 | 19.76 | 19.85 | 19.86 | 20.50 | 21.09 | | | |
| | 9 | 19.00 | 19.14 | 19.91 | 19.80 | 19.13 | 20.19 | 20.07 | 21.00 | 20.83 | 20.74 | 21.25 |
| | 10 | 19.88 | 19.24 | 19.73 | 19.60 | 19.96 | 20.20 | 21.10 | 20.82 | | | |
| | Ave | 18.57 | 18.66 | 19.01 | 18.86 | 18.61 | 19.32 | 19.50 | 20.15 | 20.74 | 21.12 | 21.67 |
| | SD | 0.91 | 0.66 | 0.85 | 1.27 | 1.24 | 1.95 | 1.26 | 1.15 | 1.01 | 0.92 | 1.54 |
| Group 3 Compound 1 150 mg/kg Q7Dx5 | 1 | 18.33 | 18.40 | 18.70 | 18.5 | 17.44 | 17.56 | 17.25 | | | | |
| | 2 | 18.69 | 18.30 | 18.70 | 18.70 | 18.52 | 18.35 | 19.50 | 20.00 | 20.83 | | |
| | 3 | 18.23 | 18.20 | 18.46 | 19.20 | 19.00 | 18.93 | 19.84 | | | | |
| | 4 | 17.56 | 17.50 | 17.20 | 18.26 | 18.78 | 19.70 | 20.25 | 22.75 | | | |
| | 5 | 17.40 | 17.40 | 17.50 | 18.20 | 18.16 | 18.95 | 19.20 | 20.47 | 21.29 | | |
| | 6 | 17.60 | 18.00 | 18.00 | 17.90 | 17.73 | 18.75 | 19.00 | 18.90 | 20.54 | | |
| | 7 | 18.80 | 18.77 | 18.40 | 19.45 | 18.35 | 19.57 | 19.81 | 19.20 | 19.56 | | |
| | 8 | 18.96 | 18.90 | 19.40 | 19.62 | 18.93 | 20.27 | 20.45 | 21.75 | 23.56 | | |
| | 9 | 18.60 | 18.70 | 19.50 | 17.00 | 16.81 | 17.05 | 17.20 | | | | |
| | 10 | 17.27 | 17.9 | 18.22 | 18.50 | 18.60 | 19.50 | 19.40 | | | | |
| | Ave | 18.14 | 18.20 | 18.41 | 18.53 | 18.23 | 18.86 | 19.19 | 20.51 | 21.16 | | |
| | SD | 0.63 | 0.51 | 0.73 | 0.78 | 0.71 | 0.99 | 1.13 | 1.49 | 1.49 | | |
| Group 4 Compound 1 300 mg/kg Q7Dx9 | 1 | 19.80 | 19.20 | 20.20 | 20.45 | 20.41 | 20.85 | 20.97 | 21.57 | 20.92 | 20.77 | 21.00 |
| | 2 | 17.76 | 18.20 | 18.22 | 17.84 | 17.89 | 18.26 | 18.53 | 18.81 | 19.16 | 19.80 | 19.90 |
| | 3 | 15.60 | 16.07 | 16.00 | 16.50 | 16.37 | 16.92 | 17.50 | 17.55 | 17.82 | 18.12 | 18.20 |
| | 4 | 17.20 | 17.06 | 17.30 | 17.89 | 17.36 | 17.25 | 17.87 | 18.34 | 18.36 | 18.20 | 19.10 |
| | 5 | 17.34 | 17.66 | 18.02 | 18.60 | 17.87 | 18.97 | 19.50 | 18.60 | 19.85 | 20.20 | 21.82 |
| | 6 | 17.75 | 18.46 | 17.60 | 18.32 | 17.98 | 17.24 | 16.94 | 17.88 | 16.90 | 17.30 | 18.58 |
| | 7 | 19.15 | 18.96 | 18.60 | 19.06 | 18.40 | 19.40 | 19.30 | 19.47 | 19.96 | 20.37 | 20.40 |
| | 8 | 19.20 | 20.20 | 19.50 | 21.00 | 19.35 | 20.00 | 20.00 | 20.91 | 21.33 | 21.86 | 21.21 |
| | 9 | 17.86 | 17.30 | 17.50 | 17.86 | 17.20 | 17.96 | 17.60 | 18.00 | 18.53 | 19.00 | 19.00 |
| | 10 | 17.9 | 18.65 | 18.5 | 18.73 | 18.66 | 18.94 | 19.36 | 20.6 | 21.87 | 22.11 | 23.8 |
| | Ave | 17.96 | 18.18 | 18.14 | 18.63 | 18.15 | 18.58 | 18.76 | 19.17 | 19.47 | 19.77 | 20.30 |
| | SD | 1.20 | 1.19 | 1.18 | 1.31 | 1.14 | 1.29 | 1.28 | 1.40 | 1.61 | 1.61 | 1.72 |
| Group 5 Compound 1 600 mg/kg 2Q7Dx9 | 1 | 17.90 | 18.50 | 18.70 | 18.30 | 18.10 | 18.36 | 18.56 | 19.20 | 18.20 | 19.20 | 18.80 |
| | 2 | 18.50 | 18.21 | 18.50 | 18.40 | 18.20 | 18.32 | 18.60 | 18.72 | 19.00 | 19.00 | 18.75 |
| | 3 | 18.80 | 18.71 | 18.80 | 19.21 | 18.76 | 19.51 | 19.16 | 20.15 | 19.65 | 19.96 | 20.00 |
| | 4 | 18.30 | 17.90 | 18.57 | 19.28 | 18.20 | 18.85 | 19.26 | 19.90 | 19.09 | 19.66 | 19.76 |
| | 5 | 18.60 | 17.50 | 18.40 | 18.62 | 18.00 | 18.41 | 18.70 | 18.80 | 19.08 | 19.50 | 19.00 |
| | 6 | 18.70 | 19.30 | 19.00 | 19.16 | 19.09 | 19.35 | 19.77 | 20.80 | 20.20 | 20.60 | 19.90 |
| | 7 | 17.98 | 18.17 | 18.50 | 18.77 | 18.28 | 18.42 | 18.86 | 19.35 | 19.15 | 19.80 | 19.90 |
| | 8 | 17.60 | 17.30 | 17.20 | 18.04 | 17.30 | 18.69 | 18.35 | 18.80 | 18.87 | 19.12 | 18.65 |
| | 9 | 19.22 | 19.16 | 18.60 | 19.40 | 18.70 | 19.92 | 19.52 | 20.18 | 20.10 | 20.60 | 20.00 |
| | 10 | 17.76 | 16.62 | 17.40 | 17.64 | 16.82 | 17.92 | 18.05 | 18.20 | 18.40 | 18.30 | 18.81 |
| | Ave | 18.34 | 18.16 | 18.37 | 18.6820 | 18.15 | 18.78 | 18.9130 | 19.41 | 19.17 | 19.57 | 19.36 |
| | SD | 0.52 | 0.87 | 0.59 | 0.59 | 0.67 | 0.62 | 0.51 | 0.82 | 0.65 | 0.71 | 0.59 |
| Group 6 Compound 1 150 mg/kg 2Q7Dx9 + Anti-PD-1 200 μg Q3Dx19 | 1 | 18.30 | 18.44 | 18.58 | 18.60 | 18.70 | 18.76 | 19.30 | 20.40 | 21.00 | 20.70 | 21.30 |
| | 2 | 15.12 | 15.36 | 15.65 | | | | | | | | |
| | 3 | 16.52 | 16.44 | 17.10 | 17.60 | 17.40 | 17.18 | 17.40 | 18.75 | 18.86 | 19.56 | 20.23 |
| | 4 | 18.50 | 18.91 | 18.80 | 19.10 | 18.85 | 19.04 | 19.00 | 19.90 | 20.40 | 21.30 | 22.96 |
| | 5 | 18.30 | 18.40 | 18.50 | 18.40 | 18.11 | 18.22 | 18.30 | 18.80 | 18.50 | 19.28 | 19.26 |
| | 6 | 17.50 | 17.48 | 17.65 | 17.96 | 18.20 | 18.26 | 18.47 | 18.50 | 19.46 | 19.52 | 19.50 |
| | 7 | 17.80 | 18.14 | 18.70 | 18.88 | 17.26 | 19.00 | 19.29 | 19.50 | 19.16 | 19.30 | 19.26 |
| | 8 | 16.30 | 17.20 | 17.40 | 17.43 | 18.96 | 17.60 | 17.86 | 17.80 | 17.88 | 18.50 | 18.50 |
| | 9 | 18.00 | 17.90 | 18.20 | 18.40 | 17.86 | 18.50 | 18.40 | 18.94 | 19.74 | 19.45 | 19.60 |
| | 10 | 18.77 | 19.30 | 18.60 | 18.60 | 18.40 | 18.75 | 18.83 | 18.68 | 19.40 | 16.60 | 18.22 |
| | Ave | 17.54 | 17.76 | 17.92 | 18.33 | 18.19 | 18.37 | 18.54 | 19.03 | 19.38 | 19.36 | 19.87 |
| | SD | 1.14 | 1.18 | 0.99 | 0.56 | 0.61 | 0.63 | 0.64 | 0.78 | 0.95 | 1.32 | 1.47 |
| Group 7 Compound 1 300 mg/kg 2Q7Dx9 + Anti-PD-1 200 μg Q3Dx19 | 1 | 17.60 | 18.00 | 18.30 | 18.70 | 18.10 | 19.00 | 18.84 | 19.40 | 19.73 | 20.26 | 20.00 |
| | 2 | 18.95 | 19.30 | 19.40 | 18.75 | 18.97 | 19.32 | 19.30 | 19.60 | 19.85 | 20.46 | 20.40 |
| | 3 | 19.57 | 20.11 | 19.56 | 19.80 | 19.89 | 20.00 | 20.36 | 21.00 | 21.06 | 20.90 | 21.08 |
| | 4 | 16.28 | 16.80 | 17.46 | 16.95 | 17.06 | 14.75 | 17.27 | 18.60 | 18.40 | 19.30 | 19.00 |
| | 5 | 19.60 | 19.29 | 19.31 | 19.40 | 18.84 | 19.24 | 19.30 | 19.80 | 20.32 | 20.64 | 20.20 |
| | 6 | 18.00 | 18.50 | 19.00 | 18.27 | 18.50 | 18.74 | 18.20 | 18.80 | 19.23 | 19.60 | 19.80 |
| | 7 | 20.84 | 18.30 | 19.90 | 19.60 | 20.09 | 20.90 | 20.76 | 20.80 | 21.30 | 21.95 | 21.44 |
| | 8 | 18.50 | 18.60 | 19.10 | 18.99 | 19.40 | 19.40 | 19.54 | 19.45 | 19.78 | 20.12 | 20.20 |
| | 9 | 19.85 | 21.03 | 20.97 | 21.00 | 21.14 | 21.00 | 20.82 | 21.60 | 22.34 | 22.00 | 21.91 |
| | 10 | 17.97 | 18.30 | 18.44 | 18.24 | 18.03 | 18.87 | 18.86 | 18.70 | 19.51 | 20.00 | 20.00 |

TABLE 24-continued

| | Ave | 18.72 | 18.82 | 19.14 | 18.97 | 19.00 | 19.12 | 19.33 | 19.78 | 20.15 | 20.52 | 20.40 |
|---|---|---|---|---|---|---|---|---|---|---|---|---|
| | SD | 1.32 | 1.18 | 0.96 | 1.09 | 1.18 | 1.73 | 1.12 | 1.04 | 1.14 | 0.90 | 0.85 |

| | | Days | | | | | | | | |
|---|---|---|---|---|---|---|---|---|---|---|
| | Mouse | 38 | 42 | 46 | 49 | 53 | 56 | 59 | 63 | 67 |
| Group 1 | 1 | | | | | | | | | |
| Vehicle | 2 | | | | | | | | | |
| Control | 3 | | | | | | | | | |
| Q7Dx3 | 4 | | | | | | | | | |
| | 5 | | | | | | | | | |
| | 6 | | | | | | | | | |
| | 7 | | | | | | | | | |
| | 8 | | | | | | | | | |
| | 9 | | | | | | | | | |
| | 10 | | | | | | | | | |
| | Ave | | | | | | | | | |
| | SD | | | | | | | | | |
| Group 2 | 1 | 20.29 | 20.40 | 21.48 | 21.39 | 21.75 | 21.60 | 21.82 | 21.67 | 21.63 |
| Anti-PD-1 | 2 | | | | | | | | | |
| 200 μg | 3 | | | | | | | | | |
| Q3Dx19 | 4 | | | | | | | | | |
| | 5 | | | | | | | | | |
| | 6 | | | | | | | | | |
| | 7 | | | | | | | | | |
| | 8 | | | | | | | | | |
| | 9 | | | | | | | | | |
| | 10 | | | | | | | | | |
| | Ave | | | | | | | | | |
| | SD | | | | | | | | | |
| Group 3 | 1 | | | | | | | | | |
| Compound 1 | 2 | | | | | | | | | |
| 150 mg/kg | 3 | | | | | | | | | |
| Q7Dx5 | 4 | | | | | | | | | |
| | 5 | | | | | | | | | |
| | 6 | | | | | | | | | |
| | 7 | | | | | | | | | |
| | 8 | | | | | | | | | |
| | 9 | | | | | | | | | |
| | 10 | | | | | | | | | |
| | Ave | | | | | | | | | |
| | SD | | | | | | | | | |
| Group 4 | 1 | 21.16 | 23.02 | | | | | | | |
| Compound 1 | 2 | 20.88 | 21.72 | | | | | | | |
| 300 mg/kg | 3 | 18.90 | 18.53 | 18.70 | 18.32 | 18.76 | 18.80 | 19.00 | 19.52 | 20.36 |
| Q7Dx9 | 4 | 19.34 | 20.06 | 20.58 | 20.33 | 19.91 | 19.87 | 19.88 | 19.90 | 19.95 |
| | 5 | 22.39 | | | | | | | | |
| | 6 | | | | | | | | | |
| | 7 | 21.20 | 21.00 | 21.08 | 21.16 | 21.58 | 21.68 | 21.87 | 21.85 | 21.80 |
| | 8 | | | | | | | | | |
| | 9 | 18.85 | 19.14 | 19.87 | 20.26 | 19.66 | 19.66 | 19.79 | 20.20 | 20.52 |
| | 10 | | | | | | | | | |
| | Ave | 20.39 | 20.58 | 20.06 | 20.02 | 19.98 | 20.00 | 20.14 | 20.37 | 20.66 |
| | SD | 1.37 | 1.67 | 1.03 | 1.20 | 1.18 | 1.21 | 1.22 | 1.03 | 0.80 |
| Group 5 | 1 | 19.30 | 19.78 | 19.49 | 18.96 | 19.87 | 19.90 | 19.91 | 20.00 | 20.50 |
| Compound 1 | 2 | 19.30 | 19.44 | 20.35 | 19.60 | 19.99 | 20.12 | 20.10 | 20.97 | 20.57 |
| 600 mg/kg | 3 | 20.69 | 21.41 | 21.65 | 20.37 | 20.85 | 20.85 | 21.00 | 21.20 | 2120 |
| 2Q7Dx9 | 4 | 20.90 | 20.89 | 20.92 | 20.63 | 21.32 | 21.43 | 21.00 | 21.10 | 20.92 |
| | 5 | 19.90 | 20.15 | 20.67 | 19.78 | 21.08 | 21.11 | 21.00 | 21.07 | 20.93 |
| | 6 | 21.16 | 20.60 | 21.35 | 20.65 | 21.86 | 21.75 | 22.02 | 22.20 | 21.98 |
| | 7 | 20.81 | 21.21 | 21.52 | 20.26 | 20.96 | 20.89 | 20.80 | 20.90 | 21.51 |
| | 8 | 19.60 | 19.37 | 20.55 | 20.63 | 20.45 | 21.00 | 20.89 | 20.91 | 20.68 |
| | 9 | 21.10 | 20.90 | 21.56 | 20.90 | 21.68 | 21.20 | 21.20 | 21.23 | 21.23 |
| | 10 | 18.90 | 19.20 | 19.97 | 19.80 | 19.81 | 19.91 | 20.14 | 20.00 | 19.73 |
| | Ave | 20.17 | 20.30 | 20.80 | 20.16 | 20.79 | 20.82 | 20.81 | 20.96 | 20.93 |
| | SD | 0.86 | 0.81 | 0.73 | 0.61 | 0.74 | 0.64 | 0.62 | 0.63 | 0.62 |
| Group 6 | 1 | 21.82 | 21.72 | | | | | | | |
| Compound 1 | 2 | | | | | | | | | |
| 150 mg/kg | 3 | 20.60 | | | | | | | | |
| 2Q7Dx9 + | 4 | | | | | | | | | |
| Anti-PD-1 | 5 | 19.80 | 20.52 | 21.06 | 19.67 | 20.08 | 20.00 | 20.10 | 21.00 | 20.19 |
| 200 μg | 6 | 19.87 | 20.30 | 20.33 | 19.80 | 20.24 | 20.25 | 20.40 | 20.76 | 21.02 |
| Q3Dx19 | 7 | 20.44 | 21.30 | | | | | | | |
| | 8 | 18.70 | 19.34 | 19.52 | 19.83 | 19.97 | 20.20 | 20.65 | 20.44 | 20.14 |
| | 9 | 20.00 | 19.98 | 20.53 | 20.86 | 20.95 | 21.15 | 20.90 | 20.89 | 20.94 |
| | 10 | 18.82 | 19.60 | 20.74 | 20.40 | 20.67 | 20.84 | 21.00 | 21.00 | 21.05 |
| | Ave | 20.01 | 20.39 | 20.44 | 20.11 | 20.38 | 20.49 | 20.61 | 20.82 | 20.67 |
| | SD | 1.00 | 0.87 | 0.58 | 0.50 | 0.41 | 0.48 | 0.37 | 0.23 | 0.46 |

TABLE 24-continued

| | | | | | | | | | | |
|---|---|---|---|---|---|---|---|---|---|---|
| Group 7 | 1 | 19.98 | 19.90 | 20.04 | 20.5 | 20.84 | 21.20 | 21.23 | 21.20 | 21.16 |
| Compound 1 | 2 | 20.55 | 20.13 | 20.52 | 21.4 | 21.20 | 21.4 | 21.37 | 21.24 | 21.13 |
| 300 mg/kg | 3 | 21.57 | 22.89 | 22.10 | 23.16 | 23.26 | 23.85 | 23.64 | 23.27 | 22.57 |
| 2Q7Dx9 + | 4 | 19.70 | 19.47 | 19.56 | 20.06 | 20.20 | 20.2 | 20.17 | 20.30 | 20.57 |
| Anti-PD-1 | 5 | 20.60 | 21.57 | 21.10 | 21.64 | 22.06 | 22.11 | 22.00 | 21.73 | 21.40 |
| 200 µg | 6 | 20.48 | 21.00 | 19.95 | 20.70 | 20.76 | 20.79 | 20.91 | 20.70 | 20.48 |
| Q3Dx19 | 7 | 21.68 | 20.51 | 20.70 | 21.09 | 21.85 | 21.70 | 21.37 | 22.00 | 22.42 |
| | 8 | 20.53 | 21.70 | 20.61 | 20.60 | 21.09 | 21.10 | 21.15 | 21.35 | 21.67 |
| | 9 | 22.05 | 21.85 | 21.92 | 22.45 | 22.56 | 22.63 | 22.57 | 23.12 | 23.38 |
| | 10 | 20.40 | 21.04 | 20.36 | 20.03 | 20.76 | 20.82 | 20.76 | 20.88 | 20.99 |
| | Ave | 20.75 | 21.01 | 20.69 | 21.16 | 21.46 | 21.58 | 21.52 | 21.58 | 21.58 |
| | SD | 0.76 | 1.04 | 0.82 | 1.02 | 0.95 | 1.06 | 0.99 | 0.98 | 0.94 |

TABLE 25

| | | Days | | | | | | | | |
|---|---|---|---|---|---|---|---|---|---|---|
| | Mouse | 73 | 80 | 87 | 94 | 102 | 109 | 116 | 123 | 157 |
| Group 2 | 1 | 22.00 | 22.20 | 23.00 | 22.74 | 23.00 | 22.70 | 23.10 | 23.30 | 23.10 |
| Anti-PD-1 | 2 | | | | | | | | | |
| 200 µg | 3 | | | | | | | | | |
| Q3Dx19 | 4 | | | | | | | | | |
| | 5 | | | | | | | | | |
| | 6 | | | | | | | | | |
| | 7 | | | | | | | | | |
| | 8 | | | | | | | | | |
| | 9 | | | | | | | | | |
| | 10 | | | | | | | | | |
| | Ave | 22.00 | 22.20 | 23.00 | 22.74 | 21.00 | 22.70 | 23.10 | 23.30 | 23.10 |
| | SD | 0 | 0 | 0 | 0 | 0 | 0 | 0 | 0 | 0 |
| Group 4 | 1 | | | | | | | | | |
| Compound 1 | 2 | | | | | | | | | |
| 300 mg/kg | 3 | 19.66 | 19.78 | 20.01 | 19.65 | 20.85 | 20.96 | 21.20 | 21.12 | 20.85 |
| Q7Dx19 | 4 | 21.37 | 20.76 | 21.30 | 21.10 | 20.80 | 21.25 | 21.50 | 21.57 | 20.80 |
| | 5 | | | | | | | | | |
| | 6 | | | | | | | | | |
| | 7 | 22.18 | 22.30 | 22.50 | 22.45 | 23.32 | 23.30 | 24.00 | 23.83 | 25.32 |
| | 8 | | | | | | | | | |
| | 9 | 20.96 | 20.76 | 20.90 | 20.87 | 21.98 | 21.55 | 21.76 | 21.80 | 25.32 |
| | 10 | | | | | | | | | |
| | Ave | 21.04 | 20.90 | 21.18 | 21.02 | 21.7 | 21.8 | 22.1 | 22.08 | 23.07 |
| | SD | 1.05 | 1.04 | 1.03 | 1.15 | 1.19 | 1.05 | 1.28 | 1.20 | 2.60 |
| Group 5 | 1 | 20.62 | 20.80 | 20.80 | 21.20 | 20.78 | 22.13 | 22.18 | 22.20 | 20.79 |
| Compound 1 | 2 | 21.60 | 21.20 | 22.10 | 22.40 | 22.03 | 23.30 | 23.20 | 23.32 | 22.13 |
| 600 mg/kg | 3 | 22.50 | 21.45 | 21.75 | 21.63 | 22.36 | 24.60 | 24.65 | 25.12 | 22.36 |
| Q7Dx9 | 4 | 21.20 | 21.80 | 23 | 22.45 | 22.76 | 23.00 | 22.93 | 23.18 | 22.65 |
| | 5 | 21.30 | 22.02 | 21.89 | 22.20 | 21.34 | 21.62 | 21.54 | 21.39 | 22.34 |
| | 6 | 21.60 | | | | | | | | |
| | 7 | 21.51 | 21.18 | 21.00 | 21.36 | 22.09 | 22.51 | 22.50 | 21.37 | 22.16 |
| | 8 | 21.40 | 20.75 | 21.03 | 21.00 | 22.11 | 21.88 | 22.11 | 22.08 | 22.05 |
| | 9 | 21.72 | 22.12 | 22.10 | 21.97 | 22.65 | 22.69 | 22.73 | 22.70 | 21.43 |
| | 10 | 19.65 | 20.34 | 20.44 | 20.34 | 20.85 | 20.34 | 20.21 | 20.20 | 21.85 |
| | Ave | 21.31 | 21.30 | 21.57 | 21.62 | 21.89 | 22.45 | 22.45 | 22.51 | 22.08 |
| | SD | 0.75 | 0.61 | 0.81 | 0.71 | 0.73 | 1.19 | 1.21 | 1.36 | 0.54 |
| Group 6 | 1 | | | | | | | | | |
| Compound 1 | 2 | | | | | | | | | |
| 150 mg/kg | 3 | | | | | | | | | |
| Q7Dx9 + | 4 | | | | | | | | | |
| Anti-PD-1 | 5 | 21.23 | 20.24 | 20.76 | 20.5 | 21.53 | 22.22 | 22.45 | 22.34 | 22.45 |
| Q3Dx19 | 6 | 21.16 | 21.32 | 21.17 | 21.22 | 23.13 | 22 | 21.98 | 21.87 | 23.91 |
| | 7 | | | | | | | | | |
| | 8 | 21.64 | 20.94 | 20.9 | 21.12 | 20.75 | 21.12 | 21.27 | 21.33 | 23.12 |
| | 9 | 20.56 | 21.33 | 21.3 | 21.3 | 22.91 | 22.62 | 21.22 | 23.25 | 22.91 |
| | 10 | 22.05 | 21.06 | 20.96 | 20.87 | 22.78 | 22 | 22.3 | 22.41 | 22.78 |
| | Ave | 21.33 | 20.98 | 21.02 | 21.00 | 22.42 | 21.99 | 22.24 | 22.24 | 23.03 |
| | SD | 0.56 | 0.45 | 0.22 | 0.32 | 0.96 | 0.55 | 0.71 | 0.71 | 0.55 |
| Group 7 | 1 | 22.40 | 22.00 | 22.37 | 21.93 | 21.65 | 23.12 | 23.21 | 23.23 | 22.76 |
| Compound 1 | 2 | 22.33 | 22.36 | 22.79 | 23.01 | 23.30 | 22.78 | 22.94 | 23.02 | 23.37 |
| 300 mg/kg | 3 | 24.00 | 23.80 | 24.32 | 24.22 | 24.45 | 23.67 | 24.55 | 24.43 | 24.54 |
| Q7Dx9 + | 4 | 20.97 | 20.12 | 20.20 | 20.17 | 20.34 | 20.54 | 20.55 | 20.61 | 20.22 |
| Anti-PD-1 | 5 | 22.05 | 21.82 | 21.90 | 21.89 | 23.48 | 22.76 | 22.90 | 22.83 | 2334 |
| Q3Dx19 | 6 | 21.60 | 21.42 | 22.47 | 22.40 | 23.06 | 22.16 | 22.43 | 22.31 | 23.26 |
| | 7 | 23.40 | 24.50 | 25.00 | 24.87 | 2558 | 26.74 | 26.43 | 25.87 | 25.54 |
| | 8 | 22.80 | 22.29 | 22.67 | 22.60 | 23.46 | 23.35 | 23.62 | 23.23 | 23.42 |
| | 9 | 23.57 | 24.00 | 24.13 | 23.99 | 25.15 | 26.37 | 26.87 | 26.52 | 25.60 |
| | 10 | 21.50 | 20.86 | 21.10 | 21.17 | 22.89 | 23.00 | 23.04 | 23.00 | 24.00 |

TABLE 25-continued

| | Days | | | | | | | | |
|---|---|---|---|---|---|---|---|---|---|
| Mouse | 73 | 80 | 87 | 94 | 102 | 109 | 116 | 123 | 157 |
| Ave | 22.46 | 22.32 | 21.70 | 22.63 | 23.44 | 23.45 | 23.65 | 21.51 | 23.61 |
| SO | 0.98 | 1.41 | 1.47 | 1.45 | 1.46 | 1.85 | 1.87 | 1.71 | 1.53 |

The dose responsive anti-tumor effect of Compound 1 as a single agent and in combination with anti-PD-1 was tested in a mouse syngeneic model of sarcoma (MT245). Vehicle control treated animals had a median survival time of 19.30 days. Anti-PD-1 was dosed IP at 200 µg per mouse and resulted in 55.19% TGI at day 20 and a median survival of 24.89 days. Compound 1 was dosed PO as a single agent at 150 mg/kg Q7D×5, 300 mg/kg Q7D×9, and 600 mg/kg Q7D×9, resulting in 42.62% TGI, 95.58% TGI and 100% regression respectively by day 20 of the study. Increase in median survival in the monotherapy groups compared to vehicle were 25.04, 41.21, and >157 days, respectively. Mice dosed with Compound 1 150 mg/kg Q7D×9+200 µg Anti-PD-1 Q7D×19, and Compound 1 600 mg/kg Q7D×9+200 µg Anti-PD-1 Q7D×19 resulted in 97.34% TGI and 99.93% regression, respectively by day 20 of the study and exhibited increases in median survival>157 days.

Following cessation of dosing on day 55 mice were continuously monitored until day 157. Mice with tumors that were not palatable or cured did not show signs of tumor re-growth during the 157 days. The anti-PD-1 Q3D×9 group had one cure, the Compound 1 300 mg/kg group Q7D×9 had 4 cures, the Compound 1 600 mg/kg group Q7D×9 had 9 cures, the Compound 1 150 mg/kg Q7D×9+anti-PD-1 Q3D×19 group had 5 cures, and the Compound 1 300 mg/kg Q7D×9+anti-PD-1 Q3D×19 group had 10 cures.

Compound 1 was well tolerated throughout the dosing period and only minimal weight loss (<10%) in several mice across the groups were reported early in the study (up to day 25). Mice were euthanized when tumors reached ~2000 mm³ or if tumors were necrotic. One mouse in Group 5 (6) was found dead due to unknown reasons, one mouse in Group 6 (2) was found dead early in the study most likely due to a dosing error, and one mouse in Group 6 (7) had an unrelated chest wound that required euthanasia. TABLE 26 below provides the median survival time (MST).

TABLE 26

| Group | MST (Days) |
|---|---|
| Vehicle | 18 |
| Anti-PD-1 200 µg | 24 |
| Compound 1 150 mg/kg Q7D | 24 |
| Compound 1 300 mg/kg Q7D | 40 |
| Compound 1 600 mg/kg Q7D | >108 |
| PD1 + Compound 1 150 mg/kg | >108 |
| PD1 + Compound 1 300 mg/kg | >108 |

Administration of Compound 1 once weekly resulted in dose responsive anti-tumor effect with tumor grow delay at lower doses and complete regression at the higher dose and a dose responsive increase in median survival time. Combination therapy with anti-PD-1 significantly improved the anti-tumor effect at lower doses of Compound 1 demonstrating regression, cures, and a significant increase in median survival time. FIG. 11 shows changes in tumor volume (mm³) of C57Bl/6 mice implanted with MT245 mouse syngeneic sarcoma tumors upon receiving treatment with Vehicle; Compound 1, 150 mg/kg (Q7D×2); Compound 1, 300 mg/kg (Q7D×2); or Compound 1, 600 mg/kg (Q7D×2).

Example 4: Combination of Compound 2 with an Anti-PD-1 Agent in Mouse Sarcoma (MT373) Model Compound 2 is an indole compound substituted with a trifluoroethyl group at the 1-position; propynyl aminomethoxy-methylsulfonyl phenyl group at the 2-position; and a heterocycle-substituted amino group at the 4-position.

The efficacy of Compound 2 at various dose levels and regimens and in combination with one dose regimen of Anti-PD-1 in a subcutaneous mouse syngeneic model of sarcoma (MT373). Immunocompetent mice (C57Bl/6) were implanted subcutaneously with MT373 cells and randomized into study groups on day 6 post-implantation when tumors were ~75 mm³. Group 1 mice were dosed PO with vehicle control (0.2% HPC) twice a day (2Q7D×4, 8 hours apart), once per week for four doses (2Q7D×4). Group 2 mice were dosed interperitoneally (IP) with Anti-PD-1 at 200 µg every three days for 7 doses (Q3D×7). Groups 3 and 4 mice were dosed PO daily (QD) with Compound 2 at 50 mg/kg for 44 doses (QD×44) or 100 mg/kg for 71 doses (QD×71), respectively. Groups 5 and 6 mice were dosed with Compound 2 at 150 and 300 mg/kg for 10 doses (2Q7D×10) or 11 doses (2Q7D×11), respectively. In Groups 7 and 8, mice were dosed with Compound 2 at 50 mg/kg for 71 doses (QD×71) and 150 mg/kg for 11 doses (2Q7D×11) in combination with Anti-PD-1 at 200 µg for 24 doses (Q3D×24), respectively.

Animals: Female C57Bl/6 mice (120 total) were acclimatized for 1 week and were 8-10 weeks at initiation of study. Animals were group housed (N=5) in ventilated cages. Fluorescent lighting was provided on a 12-hour cycle (6:30 am-6:30 pm). Temperature and humidity were monitored and recorded daily and maintained between 68-72° F. (20-22.2° C.) and 30-70% humidity, respectively. 18% soy irradiated rodent feed and autoclaved, acidified water (pH 2.5-3) was provided ad libitum.

Tumor Cell Culture: MT373 cells were cultured in DMEM medium with 10% fetal bovine serum. The cells were washed with PBS and counted at a total of $5.67 \times 10^8$ cells with 93.5% viability. Cells were centrifuged and resuspended in 50% PBS:50% Matrigel Matrix at a concentration of $5 \times 10^6$ viable cells/200 µL.

Implantation of Mice: Cells were prepared for injections by drawing the cell suspension into a 1 mL tuberculin syringe fitted with a 25 G ⅝" needle. Individual mice were manually restrained, the site of injection (right flank) was disinfected with a 70% ethanol swab, and 200 µL of cell suspension was injected subcutaneously.

Randomization and Study Setup: Implanted mice were monitored for palpable tumors. Five days post implant the mice with palpable tumors had their tumor sizes determined via digital caliper. Mice were selected and randomized into six treatment groups according to tumor size. Average tumor volume (mm³) and body weight (g) is reported in TABLE 27A and TABLE 27B. Treatment began on the sixth day post-implant to facilitate twice daily dosing.

TABLE 27A

| Group | N | Mean | St Dev | Min | Max |
|---|---|---|---|---|---|
| Group 1 - Vehicle Control 2Q7Dx4 | 10 | 75.9 | 13.1 | 59.2 | 108.8 |
| Group 2 - Anti-PD-1 200 μg Q3Dx7 | 10 | 75.7 | 12.5 | 59.2 | 106.3 |
| Group 3 - Compound 2 50 mg/kg QDx44 | 10 | 75.3 | 11.3 | 59.6 | 101.1 |
| Group 4 - Compound 2 100 mg/kg QDx71 | 10 | 75.2 | 11.2 | 59.8 | 100.2 |
| Group 5 - Compound 2 150 mg/kg 2Q7Dx44 | 10 | 74.8 | 10.3 | 60.7 | 96.1 |
| Group 6 - Compound 2 300 mg/kg 2Q7Dx11 | 10 | 74.5 | 9.4 | 61.8 | 92.1 |
| Group 7 - Compound 2 150 mg/kg QDx71 + Anti-PD-1 200 μg Q3Dx24 | 10 | 74.2 | 9.1 | 61.9 | 89.8 |
| Group 8 - Compound 2 150 mg/kg 2Q7Dx11 + Anti-PD-1 200 μg Q3Dx24 | 10 | 74.3 | 8.8 | 62.7 | 88.2 |

TABLE 27B

| Group | N | Mean | St Dev | Min | Max |
|---|---|---|---|---|---|
| Group 1 - Vehicle Control 2Q7Dx4 | 10 | 18.3 | 0.68 | 17.3 | 19.2 |
| Group 2 - Anti-PD-1 200μ Q3Dx7 | 10 | 18.0 | 0.82 | 16.8 | 19.3 |
| Group 3 - Compound 2 50 mg/kg QDx44 | 10 | 17.3 | 1.4 | 15.8 | 19.6 |
| Group 4 - Compound 2 100 mg/kg QDx71 | 10 | 18.1 | 0.80 | 17.0 | 19.3 |
| Group 5 - Compound 2 150 mg/kg 2Q7Dx44 | 10 | 18.3 | 1.1 | 16.8 | 19.8 |
| Group 6 - Compound 2 300 mg/kg 2Q7Dx11 | 10 | 17.7 | 0.97 | 16.1 | 19.1 |
| Group 7 - Compound 2 150 mg/kg QDx71 + Anti-PD-1 200 μg Q3Dx24 | 10 | 17.7 | 0.48 | 16.6 | 18.4 |
| Group 8- Compound 2 150 mg/kg 2Q7Dx11 + Anti-PD-1 200 μg Q3Dx24 | 10 | 17.0 | 1.1 | 15.6 | 18.6 |

Measurements and Calculation of Tumor Volume: Tumor volume was calculated using the following equation: (longest diameter×shortest diameter$^2$)/2. Individual tumor volumes and body weight measurements were collected twice weekly for all groups until the animals reached the humane endpoints. The calculation for percent tumor growth inhibition (TGI) is as follows: $[1-((T_t-T_0/C_t-C_0))] \times 100$, where $C_t$ is the mean tumor volume of the vehicle control group at time t, $C_0$ is the mean tumor volume of the vehicle control group at time 0, and T is the mean tumor volume of the treatment group. Tumor regression was determined with the equation $[(T_0-T_t)/T_0] \times 100$ using the same definitions.

The study was continued until all actively growing tumors reached 2000 mm$^3$ so that a median survival time could be calculated for all groups. All dosing was discontinued on day 70, after the last actively growing tumor reached 2000 mm$^3$, and the remaining mice with no palatable tumors or small tumors (<100 mm3) that remained in stasis were monitored for survival. The time for each tumor to reach 2000 mm$^3$ was determined and a median survival time for each study group was calculated. At day 182, the study was terminated, and median survival was calculated across all groups.

Mice that received the vehicle control survived 17.3 days, while mice dosed with Anti-PD-1 survived 24 days. Mice dosed with Compound 2 as a single agent at 50 or 100 mg/kg daily survived 28 and >182 days, respectively; while the twice daily once weekly regimens of 150 and 300 mg/kg resulted in 30.8 and 47.8 days median survival. For the 100 mg/kg daily group, 71% of mice survived until termination of the study, while 20% survived in the 300 mg/kg 2Q7D group. A significant increase in median survival was measured when the sub-efficacious doses of Compound 2, 50 mg/kg QD and 150 mg/kg 2Q7D, were combined with Anti-PD-1 resulting in >182 median survival for both groups. For the Compound 2 50 mg/kg QD+Anti-PD-1 group at 182 days, 89% of mice survived. 78% of the mice survived in the 150 mg/kg 2Q7D+Anti-PD-1 group.

By day 20 of the study, mice administered Compound 2 alone exhibited dose responsive single agent activity of 74% TGI (50 mg/kg QDx44), 40% regression (100 mg/kg QDx71), 92% TGI (150 mg/kg 2Q7Dx10), and 99% TGI (300 mg/kg 2Q7Dx11). Anti-PD-1 alone resulted in 72% TGI by day 20 of study. The combination of Anti-PD-1 with Compound 2 administered at either 50 mg/kg QDx71 or 150 mg/kg 2Q7Dx11 resulted in regression of 39% and 24%, respectively, at day 20 compared to vehicle control.

TABLE 28 shows the 9 study groups that were treated with varying doses of vehicle, anti-PD-1, Compound 2, and Compound 2 in combination with Anti-PD-1. TABLE 29 shows survival time of mice at the termination point (182 days).

TABLE 28

| Group | Treatment | N | Route | Dosing Frequency & Duration | Dose (mg/Kg) | Dose Volume (mL/kg) |
|---|---|---|---|---|---|---|
| 1 | Vehicle Control | 10 | PO | 2Q7Dx4 | — | 10 |
| 2 | Anti-PD-1 | 10 | IP | Q3DX7 | 200 μg | 0.2* |
| 3 | Compound 2 | 10 | PO | QDx44 | 50 | 10 |
| 4 | Compound 2 | 10 | PO | QDx71 | 100 | 10 |
| 5 | Compound 2 | 10 | PO | 2Q7Dx10 | 150 | 10 |
| 6 | Compound 2 | 10 | PO | 2Q7Dx11 | 300 | 10 |

TABLE 28-continued

| Group | Treatment | N | Route | Dosing Frequency & Duration | Dose (mg/Kg) | Dose Volume (mL/kg) |
|---|---|---|---|---|---|---|
| 7 | Compound 2 + Anti-PD-1 | 10 | PO IP | QDx71 QD3X24 | 50 200 μg | 10 0.2* |
| 9 | Compound 2 + Anti-PD-1 | 10 | PO IP | 2Q7Dx11 Q3DX24 | 150 200 μg | 10 0.2* |

*mL/mouse

TABLE 29

| Group | N | Range (Days) | Median Survival (Days) | Increase in Survival Relative to Vehicle (Days) | % Survival of Mice at 182 days |
|---|---|---|---|---|---|
| Group 1 Vehicle Control 2Q7Dx4 | 10 | 15.53-21.93 | 17.27 | NA | NA |
| Group 2 Anti-PD-1 200 μg Q3Dx7 | 10 | 20.85-36.52 | 24.01 | 6.74 | NA |
| Group 3 Compound 2 50 mg/kg QDx44 | 9 | 20.85-42.63 | 28.00 | 10.73 | NA |
| Group 4 Compound 2 100 mg/kg QDx71 | 7 | 48.74-NA | >182.00 | >164.73 | 71% (5/7) |
| Group 5 Compound 2 150 mg/kg 2QDx10 | 9 | 26.27-64.45 | 30.81 | 14.54 | NA |
| Group 6 Compound 2 300 mg/kg 2QDx11 | 10 | 33.01-NA | 47.77 | 30.50 | 20% (8/9) |
| Group 7 Compound 2 150 mg/kg QDx71 + Anti-PD-1 200 μg Q3Dx24 | 9 | 33.96-NA | >182.00 | >164.73 | 89% (8/9) |
| Group 8 Compound 2 150 mg/kg 2Q7Dx11 + Anti-PD-1 200 μg Q3Dx24 | 9 | 30.82-NA | >182.00 | >164.73 | 78% (7/9) |

MT373 mouse sarcoma tumors implanted into female C57Bl/6 mice grew from an average of 75.9 mm³ to 2815.4 mm³ in 20 days. Day 20 was the last day with a significant number of vehicle controls remaining on study (N=8). Mice in groups 3-6 were administered Compound 2 as a single agent. In two daily dosing regimens, mice in group 3 received Compound 2 at 50 mg/kg QDx44 that resulted in 74.0% TGI by day 20 and mice in group 4 received Compound 2 at 100 mg/kg QDx71 which exhibited 39.9% regression by day 20. Compound 2 administration twice daily once per week of 150 mg/kg 2Q7Dx10 exhibited 92% TGI and 300 mg/kg 2Q7Dx11 exhibited 99. % TGI by Day 20 of study. Mice in group 2 were administered 200 μg Anti-PD-1 alone and in groups 7 and 8 in combination with Compound 2 at 50 mg/kg QDx71 and 150 mg/kg 2Q7Dx11. Mice administered Anti-PD-1 at 200 μg Q3Dx7 showed 72.3% TGI by day 20. Mice administered the combination of Compound 2 and Anti-PD-1 showed an increase in efficacy over either single agent in both dosing regimens tested. Mice in group 7 administered Compound 2 at 50 mg/kg QDx71 and 200 μg of Anti-PD-1 Q3Dx24 exhibited 38.6% regression compared to single agents, 74% TGI and 72.3% TGI, respectively, by day 20. Mice in group 8 administered Compound 2 at 150 mg/kg 2Q7Dx11 and 200 μg of Anti-PD-1 Q3Dx24 exhibited 23.5% regression compared to single agents, 92% TGI and 72.3% TGI, respectively by day 20.

FIG. 12 shows changes in tumor volume (mm³) for C57Bl/6 mice implanted with MT373 mouse sarcoma tumors over 20 days upon receiving treatment with vehicle (2Q7Dx4); anti-PD-1 200 μg (Q3Dx7); Compound 2, 50 mg/kg (QDx44); Compound 2, 100 mg/kg (QDx71); Compound 2, 150 mg/kg (2Q7Dx10); Compound 2, 300 mg/kg (2Q7Dx11); Compound 2 50 mg/kg (QDx71)+anti-PD-1 200 μg (Q3Dx24); or Compound 2, 150 mg/kg (2Q7Dx11)+anti-PD-1 200 μg (Q3Dx24). TABLE 30 shows individual tumor volumes across the study for days 0-69. TABLE 31 shows individual tumor volumes across the study for days 72-182. Only mice left in the study are shown for groups 4 and 6-8. TABLE 32 shows average percent growth inhibition (%) across 23 days of study (n=10 unless noted). TABLE 33 shows average percentage tumor regression (%) across 182 days of study (n=10 unless noted).

TABLE 30

| Days | Mouse | 0 | 2 | 6 | 8 | 13 | 16 | 20 | 23 | 28 | 31 | 34 |
|---|---|---|---|---|---|---|---|---|---|---|---|---|
| Group 1 Vehicle Control 2Q7Dx4 | 1 | 59.2 | 95.7 | 162.6 | 181.3 | 470.6 | 1096.4 | 2200.5 | | | | |
| | 2 | 65.3 | 97.8 | 141.0 | 153.5 | 301.5 | 589.0 | 1442.8 | 2310.4 | | | |
| | 3 | 65.4 | 103.8 | 148.9 | 248.6 | 542.2 | 1138.0 | 3039.9 | | | | |
| | 4 | 70.9 | 97.7 | 157.2 | 254.5 | 875.3 | 1198.1 | 2363.0 | | | | |
| | 5 | 71.1 | 110.5 | 104.8 | 174.4 | 755.9 | 1386.5 | 3170.5 | | | | |
| | 6 | 76.9 | 100.2 | 168.9 | 317.5 | 846.8 | 1699.0 | 3647.5 | | | | |
| | 7 | 82.6 | 92.7 | 104.6 | 258.8 | 570.3 | 1409.3 | 3439.9 | | | | |
| | 8 | 81.8 | 116.1 | 181.4 | 339.9 | 954.1 | 2193.0 | | | | | |
| | 9 | 77.1 | 91.2 | 157.2 | 280.0 | 825.1 | 2151.7 | | | | | |
| | 10 | 108.8 | 123.1 | 139.5 | 243.3 | 894.0 | 1746.6 | 3219.5 | | | | |
| | Ave | 75.9 | 102.9 | 146.6 | 245.2 | 703.6 | 1460.7 | 2815.4 | 2310.4 | | | |
| | SD | 13.8 | 10.5 | 25.4 | 60.7 | 217.6 | 497.3 | 745.4 | | | | |

TABLE 30-continued

| | | | | | | | | | | | |
|---|---|---|---|---|---|---|---|---|---|---|---|
| Group 2 Anti PD 1 200 µg Q3Dx7 | 1 | 59.2 | 86.0 | 81.8 | 120.4 | 189.5 | 426.5 | 1126.8 | 2262.2 | | |
| | 2 | 65.1 | 102.1 | 103.7 | 178.4 | 327.0 | 793.7 | 1089.7 | 1836.1 | 5150.8 | |
| | 3 | 66.1 | 74.9 | 65.9 | 125.0 | 195.0 | 342.2 | 625.9 | 887.7 | 2073.0 | |
| | 4 | 69.6 | 91.6 | 103.8 | 156.8 | 398.4 | 945.3 | 1650.4 | 2877.0 | | |
| | 5 | 71.2 | 109.3 | 128.1 | 185.9 | 352.1 | 669.1 | 1321.3 | 2323.2 | | |
| | 6 | 76.9 | 99.2 | 123.2 | 148.8 | 247.6 | 494.0 | 879.4 | 1385.4 | 3593.3 | |
| | 7 | 77.7 | 72.5 | 66.4 | 106.7 | 79.1 | 121.8 | 330.4 | 552.9 | 1145.7 | 2032.9 |
| | 8 | 81.7 | 84.5 | 96.7 | 174.7 | 176.1 | 298.3 | 946.9 | 1739.5 | 3797.1 | |
| | 9 | 82.9 | 81.4 | 118.2 | 115.4 | 61.6 | 41.6 | 175.0 | 318.8 | 547.7 | 971.5 | 1272.9 |
| | 10 | 106.3 | 170.0 | 163.8 | 190.7 | 68.0 | 49.6 | 194.2 | 195.7 | 302.6 | 733.2 | 1499.7 |
| | Ave | 75.7 | 97.2 | 105.2 | 150.3 | 209.4 | 418.2 | 834.0 | 1437.9 | 2372.9 | 1245.9 | 1386.3 |
| | SD | 13.2 | 28.2 | 30.0 | 31.6 | 121.1 | 311.5 | 495.6 | 923.1 | 1846.1 | 691.9 | 160.4 |
| Group 3 Compound 2 50 mg/kg QDx44 | 1 | 59.6 | 71.4 | 65.9 | 126.8 | 92.7 | 202.9 | 441.1 | 812.8 | 1573.0 | 2208.5 | |
| | 2 | 64.8 | 83.9 | 80.9 | 121.0 | 74.3 | 157.4 | 483.6 | 947.9 | 2140.0 | | |
| | 3 | 66.2 | 76.4 | 84.5 | 74.5 | 49.4 | 46.2 | 23.7 | 38.5 | 175.7 | 318.5 | 791.8 |
| | 4 | 69.3 | 95.4 | 80.9 | 110.4 | | | | | | | |
| | 5 | 71.2 | 75.2 | 79.8 | 113.2 | 73.0 | 68.6 | 386.0 | 690.2 | 1322.0 | 2366.7 | |
| | 6 | 76.8 | 108.5 | 117.2 | 145.4 | 289.2 | 939.7 | 1872.5 | 2324.6 | | | |
| | 7 | 78.2 | 78.7 | 63.1 | 81.3 | 111.3 | 149.0 | 345.8 | 509.6 | 1265.9 | 2314.7 | |
| | 8 | 81.5 | 92.0 | 112.1 | 171.0 | 297.8 | 742.9 | 1681.2 | 3126.1 | | | |
| | 9 | 83.9 | 84.5 | 95.0 | 102.7 | 65.5 | 108.2 | 289.3 | 502.7 | 2000.5 | | |
| | 10 | 101.1 | 115.0 | 119.6 | 205.1 | 402.0 | 902.4 | 1577.0 | 2664.7 | | | |
| | Ave | 75.3 | 88.1 | 89.9 | 125.1 | 161.7 | 368.6 | 788.9 | 1290.8 | 1412.9 | 1802.1 | 791.8 |
| | SD | 11.9 | 14.6 | 20.4 | 39.8 | 131.0 | 376.4 | 707.1 | 1108.5 | 701.5 | 991.3 | |
| Group 4 Compound 2 100 mg/kg QDx71 | 1 | 59.8 | 97.1 | 58.3 | 78.0 | 75.2 | 38.2 | 74.2 | 57.3 | 105.9 | 130.6 | 160.5 |
| | 2 | 64.2 | 66.7 | 45.2 | | | | | | | | |
| | 3 | 66.4 | 66.7 | 41.8 | 67.8 | 23.6 | 19.5 | 65.8 | 38.9 | 67.5 | 43.4 | 57.4 |
| | 4 | 69.1 | 66.6 | 41.8 | 56.1 | 41.7 | 32.4 | 42.4 | 24.7 | 30.6 | 32.5 | 23.4 |
| | 5 | 71.4 | 62.3 | 65.0 | 60.6 | 22.0 | 17.6 | 14.5 | 15.1 | 16.1 | 19.8 | 13.0 |
| | 6 | 76.3 | 108.0 | 93.3 | 78.7 | 63.2 | 24.4 | 0.5 | 8.3 | 0.5 | 0.0 | 0.0 |
| | 7 | 78.8 | 70.2 | 65.0 | 76.2 | 52.6 | 52.4 | 97.0 | 95.2 | 82.4 | 123.0 | 105.2 |
| | 8 | 81.1 | 75.3 | 62.4 | 48.7 | 17.9 | 25.0 | 22.1 | 38.3 | 40.6 | 43.8 | 26.9 |
| | 9 | 85.0 | 84.8 | | | | | | | | | |
| | 10 | 100.2 | 76.2 | | | | | | | | | |
| | Ave | 75.2 | 77.4 | 59.1 | 66.6 | 42.3 | 29.9 | 45.2 | 39.7 | 49.1 | 56.1 | 55.2 |
| | SD | 11.8 | 14.9 | 17.1 | 11.8 | 22.3 | 12.2 | 35.2 | 29.S | 37.7 | 50.6 | 58.1 |
| Group 5 Compound 2 150 mg/kg 2Q7Dx10 | 1 | 60.7 | 68.9 | 93.4 | 135.1 | 129.6 | 147.6 | 408.8 | 693.7 | 1549.6 | 2029.9 | |
| | 2 | 63.7 | 75.4 | 84.6 | 56.5 | 112.2 | 110.2 | 209.8 | 330.5 | 835.1 | 1443.0 | 2585.1 |
| | 3 | 66.5 | 75.8 | 106.1 | 111.2 | 94.9 | 86.0 | 160.9 | 294.5 | 809.3 | 1368.8 | 2450.0 |
| | 4 | 69.0 | 77.0 | 67.9 | 94.3 | 135.7 | 171.6 | 483.7 | 694.1 | 2691.2 | | |
| | 5 | 71.5 | 67.8 | 87.1 | 114.4 | 104.1 | 127.6 | 259.1 | 306.4 | 1357.6 | 2052.6 | |
| | 6 | 75.2 | 76.4 | 118.6 | 105.5 | 71.8 | 83.8 | 185.5 | 352.6 | 1238.5 | 1549.6 | 2911.5 |
| | 7 | 79.0 | 80.5 | 136.1 | 198.3 | 248.3 | | | | | | |
| | 8 | 81.0 | 75.9 | 90.4 | 146.0 | 111.4 | 266.6 | 663.2 | 1226.9 | 2378.7 | | |
| | 9 | 85.4 | 89.8 | 105.5 | 130.9 | 94.0 | 61.1 | 0.0 | 0.0 | 7.2 | 28.3 | 89.5 |
| | 10 | 96.1 | 92.1 | 91.8 | 151.4 | 119.3 | 108.6 | 274.7 | 483.7 | 1497.4 | 2623.3 | |
| | Ave | 74.8 | 78.0 | 98.1 | 124.4 | 122.1 | 129.2 | 294.0 | 486.9 | 1373.9 | 1585.1 | 2009.0 |
| | SD | 10.8 | 7.8 | 19.2 | 38.0 | 48.0 | 61.6 | 196.9 | 350.4 | 812.9 | 815.1 | 1294.2 |
| Group 6 Compound 2 300 mg/kg 2Q7Dx11 | 1 | 61.8 | 68.6 | 70.5 | 94.7 | 73.5 | 110.5 | 143.1 | 212.2 | 521.4 | 651.0 | 1181.0 |
| | 2 | 63.3 | 52.0 | 60.7 | 98.3 | 75.8 | 127.1 | 337.2 | 446.8 | 1077.2 | 1449.2 | 2273.0 |
| | 3 | 67.5 | 62.0 | 88.1 | 98.8 | 71.2 | 56.8 | 81.3 | 133.9 | 313.5 | 396.3 | 779.7 |
| | 4 | 68.5 | 63.2 | 57.6 | 48.9 | 35.8 | 42.3 | 44.2 | 64.7 | 228.0 | 275.8 | 444.3 |
| | 5 | 71.7 | 99.3 | 106.7 | 113.1 | 89.9 | 41.0 | 51.5 | 36.6 | 0.5 | 0.5 | 38.0 |
| | 6 | 73.4 | 90.7 | 62.6 | 86.8 | 43.6 | 20.7 | 16.4 | 12.3 | 48.5 | 52.3 | 68.1 |
| | 7 | 79.7 | 103.3 | 115.7 | 163.6 | 69.0 | 50.5 | 80.6 | 41.2 | 49.7 | 42.4 | 0.5 |
| | 8 | 80.8 | 64.2 | 76.2 | 86.5 | 67.8 | 62.4 | 68.9 | 97.1 | 87.3 | 112.9 | 87.3 |
| | 9 | 86.0 | 81.4 | 77.5 | 83.5 | 48.2 | 34.5 | 0.5 | 8.9 | 38.3 | 43.0 | 71.7 |
| | 10 | 92.1 | 105.8 | 94.1 | 121.1 | 76.7 | 73.3 | 140.4 | 162.3 | 585.6 | 633.8 | 1094.4 |
| | Ave | 74.5 | 79.1 | 81.0 | 99.5 | 65.1 | 61.9 | 96.4 | 121.6 | 295.0 | 365.7 | 603.8 |
| | SD | 9.9 | 19.6 | 19.8 | 29.7 | 17.0 | 33.6 | 96.4 | 132.5 | 344.7 | 452.2 | 740.7 |
| Group 7 Compound 2 50 mg/kg QDx71 + Anti-PD-1 200 µg Q3Dx24 | 1 | 61.9 | 69.9 | 50.2 | 49.9 | 19.0 | 12.2 | 0.5 | 0 | 0 | 0 | 0 |
| | 2 | 63.0 | 78.2 | 58.3 | 41.2 | 17.8 | 13.8 | 16.5 | 9.1 | 11.1 | 10.0 | 13.8 |
| | 3 | 67.7 | 85.9 | 76.6 | 70.2 | 59.6 | 31.8 | 225.5 | 372.7 | 877.9 | 1077.2 | 2013.2 |
| | 4 | 68.0 | 71.9 | 68.1 | 64.1 | 71.5 | 31.9 | 23.4 | 15.1 | 21.3 | 13.7 | 20.5 |
| | 5 | 72.5 | 111.1 | 49.3 | 62.5 | 39.8 | 27.6 | 0.5 | 0.0 | 0.0 | 0.0 | 0.0 |
| | 6 | 73.0 | 0 | 0 | 0 | 0 | 0 | 0 | 0 | 0 | 0 | 0 |
| | 7 | 79.8 | 87.3 | 88.3 | 80.9 | 43.9 | 46.5 | 53.7 | 33.3 | 0.5 | 0 | 0 |
| | 8 | 80.6 | 92.3 | 49.8 | 40.3 | 40.6 | 8.5 | 10.7 | 12.4 | 0.0 | 0 | 0 |
| | 9 | 86.1 | 67.2 | 42.9 | 48.2 | 34.2 | 29.3 | 37.6 | 35.6 | 34.4 | 35.0 | 26.1 |
| | 10 | 89.8 | 85.6 | 125.9 | 100.3 | 88.0 | 69.4 | 31.3 | 44.5 | 44.7 | 60.5 | 0.5 |
| | Ave | 74.2 | 83.3 | 67.7 | 62.0 | 46.0 | 30.1 | 45.2 | 58.1 | 110.0 | 132.9 | 230.5 |
| | SD | 9.5 | 13.6 | 26.4 | 19.8 | 23.3 | 19.0 | 73.5 | 119.0 | 288.5 | 354.7 | 668.6 |
| Group 8 Compound 2 150 mg/kg 2Q7Dx11 200 µg Q3Dx24 | 1 | 62.7 | 69.8 | 70.2 | 53.6 | 30.8 | 12.4 | 21.2 | 21.8 | 8.3 | 12.3 | 0.5 |
| | 2 | 63.0 | 52.1 | 53.7 | 29.1 | 13.5 | 0.5 | 0.0 | 0.5 | 0.5 | 0.5 | 0.5 |
| | 3 | 68.0 | 73.3 | 81.8 | 78.7 | 78.9 | 65.5 | 274.1 | 394.8 | 1288.6 | 2044.6 | 0 |
| | 4 | 68.0 | 61.1 | 60.9 | 47.6 | 38.1 | 38.6 | 20.7 | 26.4 | 0.5 | 0.5 | 0 |
| | 5 | 72.9 | 78.2 | 66.3 | 100.8 | 73.6 | 0 | 0 | 0 | 0 | 0 | 0 |
| | 6 | 73.0 | 74.8 | 88.5 | 87.9 | 57.7 | 47.7 | 85.0 | 136.3 | 345.0 | 544.4 | 824.3 |
| | 7 | 80.1 | 108.8 | 112.7 | 81.5 | 59.0 | 48.0 | 0.5 | 0.5 | 0.5 | 0.0 | 0.5 |
| | 8 | 80.3 | 70.2 | 53.1 | 59.9 | 34.8 | 20.9 | 27.3 | 30.1 | 30.8 | 45.6 | 59.1 |

TABLE 30-continued

| | | | | | | | | | | | |
|---|---|---|---|---|---|---|---|---|---|---|---|
| 9 | 87.0 | 70.9 | 100.1 | 75.6 | 75.0 | 55.1 | 29.4 | 29.6 | 13.4 | 0.5 | 0 |
| 10 | 88.2 | 76.4 | 88.0 | 108.5 | 70.3 | 53.1 | 53.5 | 42.6 | 26.1 | 15.8 | 19.9 |
| Ave | 74.3 | 73.6 | 77.5 | 72.3 | 53.2 | 38.0 | 56.9 | 75.8 | 190.4 | 296.0 | 113.1 |
| SD | 9.3 | 14.6 | 20.0 | 24.7 | 22.5 | 21.9 | 85.6 | 126.2 | 426.5 | 679.2 | 288.1 |

| Days | Mouse | 37 | 41 | 44 | 47 | 51 | 55 | 62 | 65 | 69 |
|---|---|---|---|---|---|---|---|---|---|---|
| Group 1 | 1 | | | | | | | | | |
| Vehicle | 2 | | | | | | | | | |
| Control | 3 | | | | | | | | | |
| 2Q7Dx4 | 4 | | | | | | | | | |
| | 5 | | | | | | | | | |
| | 6 | | | | | | | | | |
| | 7 | | | | | | | | | |
| | 8 | | | | | | | | | |
| | 9 | | | | | | | | | |
| | 10 | | | | | | | | | |
| | Ave | | | | | | | | | |
| | SD | | | | | | | | | |
| Group 2 | 1 | | | | | | | | | |
| Anti PD 1 | 2 | | | | | | | | | |
| 200 µg | 3 | | | | | | | | | |
| Q3Dx7 | 4 | | | | | | | | | |
| | 5 | | | | | | | | | |
| | 6 | | | | | | | | | |
| | 7 | | | | | | | | | |
| | 8 | | | | | | | | | |
| | 9 | 2137.9 | | | | | | | | |
| | 10 | 2998.2 | | | | | | | | |
| | Ave | 2568.1 | | | | | | | | |
| | SD | 608.3 | | | | | | | | |
| Group 3 | 1 | | | | | | | | | |
| Compound 2 | 2 | | | | | | | | | |
| 50 mg/kg | 3 | 1048.6 | 1533.4 | 2391.1 | | | | | | |
| QDx44 | 4 | | | | | | | | | |
| | 5 | | | | | | | | | |
| | 6 | | | | | | | | | |
| | 7 | | | | | | | | | |
| | 8 | | | | | | | | | |
| | 9 | | | | | | | | | |
| | 10 | | | | | | | | | |
| | Ave | 1048.6 | 1533.4 | 2391.1 | | | | | | |
| | SD | | | | | | | | | |
| Group 4 | 1 | 224.7 | 425.1 | 730.2 | 1527.3 | 2613.7 | | | | |
| Compound 2 | 2 | | | | | | | | | |
| 100 mg/kg | 3 | 70.0 | 47.5 | 44.0 | 34.5 | 34.8 | 20.6 | 45.4 | 25.3 | 21.2 |
| QDx71 | 4 | 23.0 | 8.3 | 22.2 | 16.1 | 9.7 | 0.5 | 0.5 | 0.0 | 0.0 |
| | 5 | 20.5 | 6.3 | 0.5 | 0.5 | 0.5 | 0.5 | 0.5 | 0.5 | 7.1 |
| | 6 | 0.0 | 0.0 | 0.0 | 0.0 | 0.0 | 0.0 | 0.0 | 0.0 | 0.0 |
| | 7 | 127.6 | 123.3 | 156.7 | 126.2 | 131.1 | 105.1 | 139.4 | 98.4 | 123.3 |
| | 8 | 28.4 | 27.5 | 48.9 | 38.4 | 39.9 | 36.5 | 33.5 | 29.3 | 35.5 |
| | 9 | | | | | | | | | |
| | 10 | | | | | | | | | |
| | Ave | 70.6 | 91.1 | 143.2 | 249.0 | 404.2 | 27.2 | 36.6 | 25.6 | 31.2 |
| | SD | 80.2 | 153.2 | 264.3 | 565.3 | 975.3 | 40.9 | 54.0 | 38.1 | 47.2 |
| Group 5 | 1 | | | | | | | | | |
| Compound 2 | 2 | | | | | | | | | |
| 150 mg/kg | 3 | | | | | | | | | |
| 2Q7Dx10 | 4 | | | | | | | | | |
| | 5 | | | | | | | | | |
| | 6 | | | | | | | | | |
| | 7 | | | | | | | | | |
| | 8 | | | | | | | | | |
| | 9 | 143.5 | 199.4 | 274.2 | 359.3 | 458.6 | 655.4 | 1657.6 | 2076.3 | |
| | 10 | | | | | | | | | |
| | Ave | 143.5 | 199.4 | 274.2 | 359.3 | 458.6 | 655.4 | 1657.6 | 2076.3 | |
| | SD | | | | | | | | | |
| Group 6 | 1 | 1626.2 | 2400.9 | | | | | | | |
| Compound 2 | 2 | | | | | | | | | |
| 300 mg/kg | 3 | 1104.7 | 2004.8 | | | | | | | |
| 2Q7Dx11 | 4 | 648.0 | 1145.6 | 1353.2 | 1885.3 | 332.2 | | | | |
| | 5 | 38.7 | 59.6 | 62.9 | 125.6 | 189.2 | 332.1 | 1235.4 | 1779.2 | 3034.8 |
| | 6 | 176.7 | 410.7 | 687.1 | 1226.1 | 2660.7 | 0 | 0 | 0 | 0.0 |
| | 7 | 0.0 | 0.0 | 0.0 | 0.0 | 0.0 | 0.0 | 0.0 | 0.0 | 0.0 |
| | 8 | 103.0 | 81.3 | 87.6 | 94.4 | 99.7 | 79.1 | 131.6 | 80.7 | 99.2 |
| | 9 | 116.8 | 359.3 | 721.4 | 1494.1 | 3158.8 | | | | |
| | 10 | 1530.5 | 2822.0 | | | | | | | |
| | Ave | 593.9 | 1031.6 | 485.4 | 804.3 | 1571.9 | 137.1 | 455.7 | 620.0 | 1044.7 |
| | SD | 662.4 | 1106.2 | 533.3 | 828.7 | 1632.3 | 173.5 | 678.4 | 1004.7 | 1724.2 |

TABLE 30-continued

| | | | | | | | | | | |
|---|---|---|---|---|---|---|---|---|---|---|
| Group 7 | 1 | 0 | 0 | 0 | 0 | 0 | 0 | 0 | 0 | 0 |
| Compound 2 | 2 | 15.9 | 9.5 | 0.5 | 0.5 | 0 | 0 | 0 | 0 | 0 |
| 50 mg/kg | 3 | 0 | 0 | 0 | 0 | 0 | 0 | 0 | 0 | 0 |
| QDx71 + | 4 | 24.0 | 12.4 | 17.0 | 8.8 | 0.5 | 0.5 | 0.0 | 0.0 | 0.0 |
| Anti-PD-1 | 5 | 0.0 | 0.0 | 0.0 | 0.0 | 0.0 | 0.0 | 0.0 | 0.0 | 0.0 |
| 200 µg | 6 | 0 | 0 | 0 | 0 | 0 | 0 | 0 | 0 | 0 |
| Q3Dx24 | 7 | 0 | 0 | 0 | 0 | 0 | 0 | 0 | 0 | 0 |
| | 8 | 0 | 0 | 0 | 0 | 0 | 0 | 0 | 0 | 0 |
| | 9 | 28.9 | 26.9 | 22.7 | 16.6 | 11.9 | 16.5 | 18.6 | 23.6 | 26.7 |
| | 10 | 0.5 | 29.4 | 23.4 | 56.7 | 45.3 | 42.5 | 40.5 | 25.1 | 30.5 |
| | Ave | 8.7 | 9.8 | 8.0 | 10.3 | 7.2 | 7.4 | 7.4 | 6.1 | 7.1 |
| | SD | 12.3 | 12.3 | 11.0 | 19.7 | 15.9 | 15.3 | 14.9 | 11.3 | 13.3 |
| Group 8 | 1 | 0.5 | 0 | 0 | 0 | 0 | 0 | 0 | 0 | 0 |
| Compound 2 | 2 | 0 | 0 | 0 | 0 | 0 | 0 | 0 | 0 | 0 |
| 150 mg/kg | 3 | 0 | 0 | 0 | 0 | 0 | 0 | 0 | 0 | 0 |
| 2Q7Dx11 | 4 | 0 | 0 | 0 | 0 | 0 | 0 | 0 | 0 | 0 |
| 200 µg | 5 | 0 | 0 | 0 | 0 | 0 | 0 | 0 | 0 | 0 |
| Q3Dx24 | 6 | 1324.8 | 2078.0 | 0 | 0 | 0 | 0 | 0 | 0 | 0 |
| | 7 | 0 | 0 | 0 | 0 | 0.5 | 0.5 | 0 | 0 | 0 |
| | 8 | 55.1 | 38.5 | 39.4 | 33.4 | 26.7 | 25.7 | 14.6 | 13 4 | 16.0 |
| | 9 | 0 | 0 | 0 | 0 | 0 | 0 | 0 | 0 | 0 |
| | 10 | 16.3 | 0.5 | 0.5 | 0 | 0 | 0 | 0 | 0 | 0 |
| | Ave | 174.6 | 264.6 | 5.7 | 4.8 | 3.8 | 3.7 | 2.2 | 1.9 | 2.3 |
| | SD | 465.2 | 732.8 | 14.9 | 12.6 | 10.1 | 9.7 | 5.5 | 5.1 | 6.0 |

TABLE 31

| Days | Mouse | 72 | 76 | 84 | 93 | 100 | 107 | 115 | 121 | 129 | 135 | 143 | 149 | 156 | 164 | 170 | 182 |
|---|---|---|---|---|---|---|---|---|---|---|---|---|---|---|---|---|---|
| Group 4 | 3 | 26.8 | 37.5 | 13.6 | 31.2 | 31.4 | 34.9 | 21.7 | 23.7 | 31.5 | 40.2 | 22.4 | 40.8 | 30.6 | 49.5 | 42.3 | 37.0 |
| Compound 2 | 4 | 0 | 0 | 0 | 0 | 0 | 0 | 0 | 0 | 0 | 0 | 0 | 0 | 0 | 0 | 0 | 0 |
| 100 mg/kg | 5 | 8.3 | 20.1 | 0.5 | 8.8 | 7.2 | 8.7 | 6.2 | 9.6 | 14.4 | 11.8 | 7.4 | 4.7 | 12.4 | 10.0 | 13.9 | 6.3 |
| QDx71 | 6 | 0 | 0 | 0 | 0 | 0 | 0 | 0 | 0 | 0 | 0 | 0 | 0 | 0 | 0 | 0 | 0 |
| | 7 | 128.0 | 154.6 | 65.8 | 126.5 | 184.4 | 430.2 | 1172.0 | 1534.9 | 3168.5 | | | | | | | |
| | 8 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 | 0.0 |
| | Ave | 27.3 | 35.5 | 13.4 | 27.8 | 37.2 | 79.1 | 200.1 | 261.4 | 535.8 | 10.5 | 6.1 | 9.2 | 8.7 | 12.0 | 11.3 | 8.7 |
| | SD | 50.4 | 60.3 | 26.2 | 49.8 | 73.1 | 172.6 | 476.2 | 623.9 | 1289.8 | 17.4 | 9.6 | 17.8 | 13.3 | 21.4 | 18.3 | 16.1 |
| Group 6 | 7 | 0 | 0 | 0 | 0 | 0 | 0 | 0 | 0 | 0 | 0 | 0 | 0 | 0 | 0 | 0 | 0 |
| Compound 2 | 8 | 83.1 | 66.4 | 53.9 | 56.0 | 51.6 | 61.8 | 42.8 | 31.5 | 27.7 | 19.8 | 14.9 | 28.4 | 37.0 | 41.6 | 33.8 | 18.8 |
| 300 mg/kg | Ave | 41.6 | 33.2 | 26.9 | 28.0 | 25.8 | 30.9 | 21.4 | 15.7 | 13.9 | 9.9 | 7.5 | 14.2 | 18.5 | 20.8 | 16.9 | 9.4 |
| 2Q7Dx11 | SD | 58.8 | 47.0 | 38.1 | 39.6 | 36.5 | 43.7 | 30.3 | 22.2 | 19.6 | 14.0 | 10.5 | 20.1 | 26.2 | 29.4 | 23.9 | 13.3 |
| Group 7 | 1 | e | 0 | 0 | 0 | 0 | 0 | 0 | 0 | 0 | 0 | 0 | 0 | 0 | 0 | 0 | 0 |
| Compound 2 | 2 | 0 | 0 | 0 | 0 | 0 | 0 | 0 | 0 | 0 | 0 | 0 | 0 | 0 | 0 | 0 | 0 |
| 50 mg/kg | 4 | 0 | 0 | 0 | 0 | 0 | 0 | 0 | 0 | 0 | 0 | 0 | 0 | 0 | 0 | 0 | 0 |
| QDx71 + | 5 | 0 | 0 | 0 | 0 | 0 | 0 | 0 | 0 | 0 | 0 | 0 | 0 | 0 | 0 | 0 | 0 |
| Anti-PD-1 | 7 | 0 | 0 | 0 | 0 | 0 | 0 | 0 | 0 | 0 | 0 | 0 | 0 | 0 | 0 | 0 | 0 |
| 200 µg | 8 | 0 | 0 | 0 | 0 | 0 | 0 | 0 | 0 | 0 | 0 | 0 | 0 | 0 | 0 | 0 | 0 |
| Q3Dx24 | 9 | 21.9 | 15.4 | 8.2 | 13.7 | 21.1 | 21.4 | 27.9 | 11.4 | 13.6 | 10.4 | 6.7 | 13.3 | 9.5 | 14.6 | 14.7 | 18.0 |
| | 10 | 57.0 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| | Ave | 9.9 | 2.0 | 1.1 | 1.8 | 2.7 | 2.7 | 3.6 | 1.5 | 1.8 | 1.4 | 0.9 | 1.7 | 1.2 | 1.9 | 1.9 | 2.3 |
| | SD | 20.5 | 5.4 | 2.9 | 4.8 | 7.4 | 7.5 | 9.9 | 4.0 | 4.8 | 3.6 | 2.4 | 4.7 | 3.3 | 5.1 | 5.2 | 6.3 |
| Group 8 | 1 | 0 | 0 | 0 | 0 | 0 | 0 | 0 | 0 | 0 | 0 | 0 | 0 | 0 | 0 | 0 | 0 |
| Compound 2 | 2 | 0 | 0 | 0 | 0 | 0 | 0 | 0 | 0 | 0 | 0 | 0 | 0 | 39.3 | 34.4 | 60.6 | 53.3 |
| 150 mg/kg | 4 | 0 | 0 | 0 | 0 | 0 | 0 | 0 | 0 | 0 | 0 | 0 | 0 | 0 | 0 | 0 | 0 |
| 2Q7Dx11 + | 7 | 0 | 0 | 0 | 0 | 0 | 0 | 0 | 0 | 0 | 0 | 0 | 0 | 0 | 0 | 0 | 0 |
| Anti-PD-1 | 8 | 20.9 | 24.5 | 0.5 | 12.5 | 8.3 | 15.5 | 10.3 | 9.6 | 9.8 | 4.4 | 8.6 | 9.4 | 10.3 | 16.5 | 21.8 | 11.9 |
| 200 µg | 9 | 0 | 0 | 0 | 0 | 0 | 0 | 0 | 0 | 0 | 0 | 0 | 0 | 0 | 0 | 0 | 0 |
| Q3Dx24 | 10 | 0 | 0 | 0 | 0 | 0 | 0 | 0 | 0 | 0 | 0 | 0 | 0 | 0 | 0 | 0 | 0 |
| | Ave | 3.0 | 3.5 | 0.1 | 1.8 | 1.2 | 2.2 | 1.5 | 1.4 | 1.4 | 0.6 | 0.6 | 1.2 | 1.3 | 7.1 | 7.3 | 11.8 |
| | SD | 0 | 0 | 0 | 0 | 0 | 0 | 0 | 0 | 0 | 0 | 1.7 | 3.3 | 3.5 | 14.7 | 13.4 | 23.0 |

TABLE 32

| Day of Study | Group 1- Vehicle Control 2Q7Dx4 | Group 2- Anti-PD-1 200 µg Q3Dx7 | Group 3- Compound 2 50 mg/kg QDx44 | Group 4- Compound 2 100 mg/kg QDx71 | Group 5- Compound 2 150 mg/kg 2Q7Dx10 | Group 6- Compound 2 300 mg/kg 2Q7Dx11 | Group 7- Compound 2 50 mg/kg QDx71 + Anti-PD-1 200 µg Q3Dx24 | Group 8- Compound 2 150 mg/kg 2QDx11 + Anti-PD-1 200 µg Q3Dx24 |
|---|---|---|---|---|---|---|---|---|
| 2 | 0 | 20.2 | 52.4 | 92.0 | 88.3 | 83.0 | 66.5 (N = 9) | >100 |
| 6 | 0 | 58.3 | 79.3 | >100 (N = 8) | 67.0 | 90.8 | >100 (N = 9) | 95.4 |
| 8 | 0 | 55.9 | 70.5 | >100 (N = 7) | 70.7 | 85.2 | >100 (N = 9) | >100 |
| 13 | 0 | 78.7 | 86.2 (N = 9) | >100 (N = 7) | 92.5 | >100 | >100 (N = 9) | >100 |
| 16 | 0 | 75.3 | 78.8 (N = 9) | >100 (N = 7) | 96.1 (N = 9) | >100 | >100 (N = 9) | >100 (N = 9) |
| 20 | 0 (N = 8) | 72.3 | 74.0 (N = 9) | >100 (N = 7) | 92.0 (N = 9) | 99.2 | >100 (N = 9) | >100 (N = 9) |
| 23 | 0 (N = 1) | 39.0 | 45.6 (N = 9) | >100 (N = 7) | 81.6 (N = 9) | 97.9 | >100 (N = 9) | 99.9 (N = 9) |

TABLE 33

| Day of Study | Group 1- Vehicle Control 2Q7Dx4 | Group 2- Anti-PD-1 200 µg Q3Dx7 | Group 3- Compound 2 50 mg/kg QDx44 | Group 4- Compound 2 100 mg/kg QDx71 | Group 5- Compound 2 150 mg/kg 2Q7Dx10 | Group 6- Compound 2 300 mg/kg 2Q7Dx11 | Group 7- Compound 2 50 mg/kg QDx71 + Anti-PD-1 200 µg Q3Dx24 | Group 8- Compound 2 150 mg/kg 2QDx11 + Anti-PD-1 200 µg Q3Dx24 |
|---|---|---|---|---|---|---|---|---|
| 2 | 0 | 0 | 0 | 0 | 0 | 0 | 0 | 1.0 |
| 6 | 0 | 0 | 0 | 21.4 | 0 | 0 | 8.8 (N = 9) | 0 |
| 8 | 0 | 0 | 0 | 11.5 (N = 8) | 0 | 0 | 16.5 (N = 9) | 2.7 |
| 13 | 0 | 0 | 0 | 43.7 (N = 9) | 0 (N = 7) | 12.6 | 38.0 (N = 9) | 28.5 |
| 16 | 0 | 0 | 0 | 60.2 (N = 9) | 0 (N = 7) | 16.9 (N = 9) | 59.4 (N = 9) | 48.9 (N = 9) |
| 20 | 0 | 0 | 0 | 39.9 (N = 9) | 0 (N = 7) | 0 (N = 9) | 38.6 (N = 9) | 23.5 (N = 9) |
| 23 | 0 | 0 | 0 | 47.2 (N = 9) | 0 (N = 7) | 0 (N = 9) | 21.8 (N = 9) | 0 (N = 9) |
| 28 | 0 (NA) | 0 (N = 7) | 0 (N = 6) | 34.7 (N = 7) | 0 (N = 9) | 0 | 0 (N = 9) | 0 (N = 9) |
| 31 | 0 (NA) | 0 (N = 3) | 0 (N = 4) | 25.4 (N = 7) | 0 (N = 7) | 0 | 0 (N = 9) | 0 (N = 9) |
| 34 | 0 (NA) | 0 (N = 2) | 0 (N = 1) | 26.6 (N = 7) | 0 (N = 4) | 0 | 0 (N = 9) | 0 (N = 8) |
| 37 | 0 (NA) | 0 (N = 2) | 0 (N = 1) | 6.1 (N = 7) | 0 (N = 1) | 0 (N = 9) | 88.3 (N = 8) | 0 (N = 8) |
| 41 | 0 (NA) | 0 (NA) | 0 (N = 1) | 0 (N = 7) | 0 (N = 1) | 0 (N = 9) | 86.8 (N = 8) | 0 (N = 8) |
| 44 | 0 (NA) | 0 (NA) | 0 (N = 1) | 0 (N = 7) | 0 (N = 1) | 0 (N = 6) | 89.3 (N = 8) | 92.3 (N = 7) |
| 47 | 0 (NA) | 0 (NA) | 0 (NA) | 0 (N = 7) | 0 (N = 1) | 0 (N = 6) | 86.1 (N = 8) | 93.6 (N = 7) |
| 51 | 0 (NA) | 0 (NA) | 0 (NA) | 0 (N = 7) | 0 (N = 1) | 0 (N = 6) | 90.3 (N = 8) | 94.9 (N = 7) |
| 55 | 0 (NA) | 0 (NA) | 0 (NA) | 63.8 (N = 6) | 0 (N = 1) | 0 (N = 3) | 90.0 (N = 8) | 95.0 (N = 7) |
| 62 | 0 (NA) | 0 (NA) | 0 (NA) | 51.4 (N = 6) | 0 (N = 1) | 0 (N = 3) | 90.0 (N = 8) | 97.1 (N = 7) |
| 65 | 0 (NA) | 0 (NA) | 0 (NA) | 66.0 (N = 6) | 0 (N = 1) | 0 (N = 3) | 91.8 (N = 8) | 97.4 (N = 7) |

TABLE 33-continued

| Day of Study | Group 1- Vehicle Control 2Q7Dx4 | Group 2- Anti-PD-1 200 µg Q3Dx7 | Group 3- Compound 2 50 mg/kg QDx44 | Group 4- Compound 2 100 mg/kg QDx71 | Group 5- Compound 2 150 mg/kg 2Q7Dx10 | Group 6- Compound 2 300 mg/kg 2Q7Dx11 | Group 7- Compound 2 50 mg/kg QDx71 + Anti-PD-1 200 µg Q3Dx24 | Group 8- Compound 2 150 mg/kg 2QDx11 + Anti-PD-1 200 µg Q3Dx24 |
|---|---|---|---|---|---|---|---|---|
| 69 | 0 (NA) | 0 (NA) | 0 (NA) | 58.5 (N = 6) | 0 (NA) | 0 (N = 3) | 90.4 (N = 8) | 96.9 (N = 7) |
| 72 | 0 (NA) | 0 (NA) | 0 (NA) | 63.8 (N = 6) | 0 (NA) | 44.2 (N = 2) | 86.7 (N = 8) | 96.0 (N = 7) |
| 76 | 0 (NA) | 0 (NA) | 0 (NA) | 52.9 (N = 6) | 0 (NA) | 55.4 (N = 2) | 97.3 (N = 8) | 95.3 (N = 7) |
| 84 | 0 (NA) | 0 (NA) | 0 (NA) | 82.2 (N = 6) | 0 (NA) | 63.8 (N = 2) | 98.5 (N = 8) | 99.9 (N = 7) |
| 93 | 0 (NA) | 0 (NA) | 0 (NA) | 63.0 (N = 6) | 0 (NA) | 62.4 (N = 2) | 97.6 (N = 8) | 97.6 (N = 7) |
| 100 | 0 (NA) | 0 (NA) | 0 (NA) | 50.5 (N = 6) | 0 (NA) | 65.4 (N = 2) | 96.4 (N = 8) | 98.4 (N = 7) |
| 107 | 0 (NA) | 0 (NA) | 0 (NA) | 0 (N = 6) | 0 (NA) | 58.5 (N = 2) | 96.3 (N = 8) | 97.0 (N = 7) |
| 115 | 0 (NA) | 0 (NA) | 0 (NA) | 0 (N = 6) | 0 (NA) | 71.3 (N = 2) | 95.2 (N = 8) | 98.0 (N = 7) |
| 121 | 0 (NA) | 0 (NA) | 0 (NA) | 0 (N = 6) | 0 (NA) | 78.9 (N = 2) | 98.0 (N = 8) | 98.2 (N = 7) |
| 129 | 0 (NA) | 0 (NA) | 0 (NA) | 0 (N = 6) | 0 (NA) | 81.4 (N = 2) | 97.6 (N = 8) | 98.1 (N = 7) |
| 135 | 0 (NA) | 0 (NA) | 0 (NA) | 86.0 (N = 5) | 0 (NA) | 86.7 (N = 2) | 98.2 (N = 8) | 99.1 (N = 7) |
| 143 | 0 (NA) | 0 (NA) | 0 (NA) | 91.9 (N = 5) | 0 (NA) | 90.0 (N = 2) | 98.8 (N = 8) | 98.3 (N = 7) |
| 149 | 0 (NA) | 0 (NA) | 0 (NA) | 87.8 (N = 5) | 0 (NA) | 81.0 (N = 2) | 97.7 (N = 8) | 98.2 (N = 7) |
| 156 | 0 (NA) | 0 (NA) | 0 (NA) | 88.4 (N = 5) | 0 (NA) | 75.1 (N = 2) | 98.3 (N = 8) | 90.5 (N = 7) |
| 160 | 0 (NA) | 0 (NA) | 0 (NA) | 84.0 (N = 5) | 0 (NA) | 72.0 (N = 2) | 97.5 (N = 8) | 90.2 (N = 7) |
| 170 | 0 (NA) | 0 (NA) | 0 (NA) | 84.9 (N = 5) | 0 (NA) | 77.3 (N = 2) | 97.4 (N = 8) | 84.2 (N = 7) |
| 182 | 0 (NA) | 0 (NA) | 0 (NA) | 88.5 (N = 5) | 0 (NA) | 87.4 (N = 2) | 96.9 (N = 8) | 87.5 (N = 7) |

NA = no mice in the group

The study was continued after the vehicle control mice succumbed and were euthanized due to tumor burden (2000 mm³). Individual mice in treatment groups were dosed and monitored until the tumor burden achieved the endpoint. FIG. 13 shows changes in tumor volume (mm³) for C57Bl/6 mice implanted with MT373 mouse sarcoma tumors over 182 days upon receiving treatment with vehicle (2Q7Dx4); anti-PD-1 200 µg (Q3Dx7); Compound 2, 50 mg/kg (QDx44); Compound 2, 100 mg/kg (QDx71); Compound 2, 150 mg/kg (2Q7Dx10); Compound 2, 300 mg/kg (2Q7Dx11); Compound 2 50 mg/kg (QDx71)+anti-PD-1 200 µg (Q3Dx24); or Compound 2, 150 mg/kg (2Q7Dx11)+anti-PD-1 200 µg (Q3Dx24). FIG. 14 shows changes in tumor volume (mm³) of individual C57Bl/6 mice implanted with MT373 mouse sarcoma tumors upon receiving treatment with vehicle (2Q7Dx4); anti-PD-1 200 µg (Q3Dx7); Compound 2, 50 mg/kg (QDx44); Compound 2, 100 mg/kg (QDx71); Compound 2, 150 mg/kg (2Q7Dx10); Compound 2, 300 mg/kg (2Q7Dx11); Compound 2 50 mg/kg (QDx71)+anti-PD-1 200 µg (Q3Dx24); or Compound 2, 150 mg/kg (2Q7Dx11)+anti-PD-1 200 µg (Q3Dx24). MT373 tumors administered vehicle control (0.2% HPC) displayed consistent growth with all mice reaching ~2000 mm³ between days 16 and 23. Mice administered Compound 2 at 50 mg/kg QDx44 displayed consistent tumor growth and reached ~2000 mm³ between 23 and 44 days. Mice administered Compound 2 at 100 mg/kg QDx71 had an extended survival time with Mouse #1 reaching ~2000 mm³ at 51 days and Mouse #7 at 129 days. Five other mice in this group had tumor regression that persisted until the study ended at day 182.

Median survival was calculated for the single agents dosing groups, where the vehicle control group had a median survival of 17.3 days. For mice administered Compound 2 on the daily dosing regimen at 50 mg/kg QDx44 and 100 mg/kg QDx71, the median survival was 28 days and >182.0 days, respectively. The 100 mg/kg QDx71 group had 71% mice (2 tumor stasis and 3 cures, i.e., no palpable tumors under the skin) surviving by termination of the study. Administration of Compound 2 at 100 mg/kg QDx71 also showed a >164-day extension in survival compared to vehicle control. For mice administered Compound 2 on the twice daily, once a week dosing regimen at 150 mg/kg 2Q7Dx10 and 300 mg/kg 2Q7Dx11, the median survival was 30.8 days and 47.8 days, respectively. The 300 mg/kg 2Q7Dx11 group had 20% mice surviving by termination of the study (1 tumor stasis and 1 cure).

Median survival was also calculated for both combination groups compared to single agent. Mice in group 2 were administered Anti-PD-1 alone and had only a slight increase in median survival time of 24 days compared to 17.3 days in the vehicle control group. For both the combination groups, co-administration of Compound 2 and Anti-PD-1 exhibited an increase in survival compared to either single agent. Mice in group 7 administered Compound 2 at 50 mg/kg QDx71 and 200 µg of Anti-PD-1 Q3Dx24 showed a median survival of >182 days as compared to single agents, 28 days and 24 days, respectively. Mice in group 8 administered Compound 2 at 150 mg/kg 2Q7D×11 and 200 µg of Anti-PD-1 Q3D×24 showed a median survival of >182 days compared to single agents, 30.8 and 24 days, respectively. In both combination groups a >164-day extension in survival compared to vehicle control was observed. The group that received Compound 2 at 50 mg/kg QD×71 and 200 µg of Anti-PD-1 Q3D×24 group had 89% of mice (2 tumor stasis and 6 cures) surviving at the termination of study. The group that received Compound 2 at 150 mg/kg 2Q7D×11 and 200 µg of Anti-PD-1 Q3D×24 group had 78% surviving (2 tumor stasis and 5 cures) mice at the end of the study.

FIG. 15 shows changes in percent survival of C57Bl/6 mice implanted with MT373 mouse sarcoma tumors upon receiving treatment with vehicle (2Q7D×4); anti-PD-1 200 µg (Q3D×7); Compound 2, 50 mg/kg (QD×44); Compound 2, 100 mg/kg (QD×71); Compound 2, 150 mg/kg (2Q7D×10); Compound 2, 300 mg/kg (2Q7D×11); Compound 2 50 mg/kg (QD×71)+anti-PD-1 200 µg (Q3D×24); or Compound 2, 150 mg/kg (2Q7D×11)+anti-PD-1 200 µg (Q3D×24). TABLE 34 shows clinical observations of the mice of each study group and dates of death. TABLE 35 shows the MST for the animals.

TABLE 34

| Group | Mouse Number | Date of Death (Study Day) | Method | Clinical Observations |
|---|---|---|---|---|
| Group 1 | 1 | 20 | Euthanasia | None; euthanized for tumor burden |
| Vehicle | 2 | 23 | Euthanasia | None; euthanized for tumor burden |
| Control | 3 | 20 | Euthanasia | None; euthanized for tumor burden |
| 2Q7D×4 | 4 | 20 | Euthanasia | None; euthanized for tumor burden |
|  | 5 | 20 | Euthanasia | None; euthanized for tumor burden |
|  | 6 | 20 | Euthanasia | None; euthanized for tumor burden |
|  | 7 | 20 | Euthanasia | None; euthanized for tumor burden |
|  | 8 | 16 | Euthanasia | None; euthanized for tumor burden |
|  | 9 | 16 | Euthanasia | None; euthanized for tumor burden |
|  | 10 | 20 | Euthanasia | None; euthanized for tumor burden |
| Group 2 | 1 | 23 | Euthanasia | None; euthanized for tumor burden |
| Anti-PD-1 | 2 | 28 | Euthanasia | None; euthanized for tumor burden |
| 200 µg | 3 | 28 | Euthanasia | None; euthanized for tumor burden |
| Q3D×7 | 4 | 23 | Euthanasia | None; euthanized for tumor burden |
|  | 5 | 23 | Euthanasia | None; euthanized for tumor burden |
|  | 6 | 28 | Euthanasia | None; euthanized for tumor burden |
|  | 7 | 31 | Euthanasia | None; euthanized for tumor burden |
|  | 8 | 28 | Euthanasia | None; euthanized for tumor burden |
|  | 9 | 37 | Euthanasia | None; euthanized for tumor burden |
|  | 10 | 37 | Euthanasia | None; euthanized for tumor burden |
| Group 3 | 1 | 31 | Euthanasia | None; euthanized for tumor burden |
| Compound 2 | 2 | 28 | Euthanasia | None; euthanized for tumor burden |
| 50 mg/kg | 3 | 44 | Euthanasia | None; euthanized for tumor burden |
| QD×44 | 4 | 8 | Euthanasia | Animal found moribund Oct. 9, 2019 |
|  | 5 | 31 | Euthanasia | None; euthanized for tumor burden |
|  | 6 | 23 | Euthanasia | None; euthanized for tumor burden |
|  | 7 | 31 | Euthanasia | None; euthanized for tumor burden |
|  | 8 | 23 | Euthanasia | None; euthanized for tumor burden |
|  | 9 | 28 | Euthanasia | None; euthanized for tumor burden |
|  | 10 | 23 | Euthanasia | None; euthanized for tumor burden |
| Group 4 | 1 | 51 | Euthanasia | None; euthanized for tumor burden |
| Compound 2 | 2 | 8 | Found Dead | Lab accident |
| 100 mg/kg | 3 | 182 | Re-enrolled in future study | None; study termination |
| QD×71 | 4 | 182 | Re-enrolled in future study | None; study termination |
|  | 5 | 182 | Re-enrolled in future study | None; study termination |
|  | 6 | 182 | Re-enrolled in future study | None; study termination |
|  | 7 | 129 | Euthanasia | None; euthanized for tumor burden |
|  | 8 | 182 | Re-enrolled in future study | None; study termination |
|  | 9 | 3 | Found Dead | Found Dead- 9% body weight loss Oct. 3, 2019, likely lab accident |
|  | 10 | 3 | Found Dead | Found Dead- 9% body weight loss Oct. 3, 2019, likely lab accident |
| Group 5 | 1 | 31 | Euthanasia | None; euthanized for tumor burden |
| Compound 2 | 2 | 34 | Euthanasia | None; euthanized for tumor burden |
| 150 mg/kg | 3 | 34 | Euthanasia | None; euthanized for tumor burden |
| 2Q7D×10 | 4 | 28 | Euthanasia | None; euthanized for tumor burden |
|  | 5 | 31 | Euthanasia | None; euthanized for tumor burden |
|  | 6 | 34 | Euthanasia | None; euthanized for tumor burden |
|  | 7 | 15 | Found Dead | Lab accident |
|  | 8 | 28 | Euthanasia | None; euthanized for tumor burden |
|  | 9 | 65 | Euthanasia | None; euthanized for tumor burden |
|  | 10 | 31 | Euthanasia | None; euthanized for tumor burden |

TABLE 34-continued

| Group | Mouse Number | Date of Death (Study Day) | Method | Clinical Observations |
|---|---|---|---|---|
| Group 6 | 1 | 41 | Euthanasia | None; euthanized for tumor burden |
| Compound 2 | 2 | 34 | Euthanasia | None; euthanized for tumor burden |
| 300 mg/kg | 3 | 41 | Euthanasia | None; euthanized for tumor burden |
| 2Q7Dx11 | 4 | 51 | Euthanasia | None; euthanized for tumor burden |
|  | 5 | 69 | Euthanasia | None; euthanized for tumor burden |
|  | 6 | 51 | Euthanasia | None; euthanized for tumor burden |
|  | 7 | 182 | Re-enrolled in future study | None; study termination |
|  | 8 | 182 | Re-enrolled in future study | None; study termination |
|  | 9 | 51 | Euthanasia | None; euthanized for tumor burden |
|  | 10 | 41 | Euthanasia | None; euthanized for tumor burden |
| Group 7 | 1 | 182 | Re-enrolled in future study | None; study termination |
| Compound 2 |  |  |  |  |
| 50 mg/kg | 2 | 182 | Re-enrolled in future study | None; study termination |
| QDx71 + |  |  |  |  |
| Anti-PD-1 | 3 | 34 | Euthanasia | None; euthanized for tumor burden |
| 200 µg | 4 | 182 | Re-enrolled in future study | None; study termination |
| Q3Dx24 |  |  |  |  |
|  | 5 | 182 | Re-enrolled in future study | None; study termination |
|  | 6 | 2 | Found Dead | Lab accident |
|  | 7 | 182 | Re-enrolled in future study | None; study termination |
|  | 8 | 182 | Re-enrolled in future study | None; study termination |
|  | 9 | 182 | Re-enrolled in future study | None; study termination |
|  | 10 | 182 | Re-enrolled in future study | None; study termination |
| Group 8 | 1 | 182 | Re-enrolled in future study | None; study termination |
| Compound 2 |  |  |  |  |
| 150 mg/kg | 2 | 182 | Re-enrolled in future study | None; study termination |
| 2Q7Dx11 + |  |  |  |  |
| Anti-PD-1 | 3 | 31 | Euthanasia | None; euthanized for tumor burden |
| 200 µg | 4 | 182 | Re-enrolled in future study | None; study termination |
| Q3Dx24 |  |  |  |  |
|  | 5 | 16 | Found Dead | Lab Accident |
|  | 6 | 41 | Euthanasia | None; euthanized for tumor burden |
|  | 7 | 182 | Re-enrolled in future study | None; study termination |
|  | 8 | 182 | Re-enrolled in future study | None; study termination |
|  | 9 | 182 | Re-enrolled in future study | None; study termination |
|  | 10 | 182 | Re-enrolled in future study | None; study termination |

TABLE 35

| Group | MST (Days) |
|---|---|
| Vehicle | 17 |
| Anti-PD-1 200 µg | 24 |
| Compound 2 50 mg/kg QD | 28 |
| Compound 2 100 mg/kg QD | >156 |
| PD-1 + Compound 2 50 mg/kg | >156 |

Body Weights: Average mouse body weights were well maintained over the course of the study. Mice dosed with vehicle control were an average of 21.9-22.4 g by the end of the study, day 20-23, with the percentage change varying between 0.33% early in the study to +18.13-22.4% by the study end. One mouse (#10) lost>10% on day 2 but recovered by day 16. Mice administered Anti-PD-1 gained an average of 11.8% by day 20. Mice in Group 4, 5, and 8 did not experience any body weight loss over 10% and gained an average of 4.6%, 3.9% and 5.6% at day 20, respectively. While in Group 3, one mouse (#10) lost>10% body weight on day 2 but recovered on day 13, in Group 6, one mouse (#1) lost>10% body weight on day 2 and recovered by day 6 and in Group 7, one mouse (#9) lost>10% body weight on day 6 and recovered by day 23. By day 23 on average, Group 3 gained 9.7%, Group 6 gained 7.5%, and Group 7 gained 5.5%.

FIG. 16 shows changes in percent survival of C57Bl/6 mice implanted with MT373 mouse sarcoma tumors upon receiving treatment with vehicle; anti-PD-1; Compound 2, 50 mg/kg (QD); Compound 2, 100 mg/kg (QD); or Compound 2, 50 mg/kg (QD)+anti-PD-1. FIG. 17 shows changes in percentage body weight of C57Bl/6 mice implanted with MT373 mouse sarcoma tumors upon receiving treatment with vehicle (2Q7Dx4); anti-PD-1 200 µg (Q3Dx7); Compound 2, 50 mg/kg (QDx44); Compound 2, 100 mg/kg (QDx71); Compound 2, 150 mg/kg (2Q7Dx10); Compound 2, 300 mg/kg (2Q7Dx111); Compound 2 50 mg/kg (QDx71)+anti-PD-1 200 µg (Q3Dx24); or Compound 2, 150 mg/kg (2Q7Dx11)+anti-PD-1 200 µg (Q3Dx24). TABLE 36 shows individual mouse body weights across the study from days 0-69. TABLE 37 shows individual mouse body weights across the study from days 72-182. Only mice left in the study are shown in groups 4 and 6-8. TABLE 38 shows the average percent change in body weight across the study (n=10 unless noted).

TABLE 36

| Days | Mouse | 0 | 2 | 6 | 8 | 13 | 16 | 20 | 23 | 28 | 31 | 34 |
|---|---|---|---|---|---|---|---|---|---|---|---|---|
| Group 1 | 1 | 18.70 | 19.10 | 20.40 | 19.60 | 20.80 | 21.30 | 23.10 | | | | |
| Vehicle | 2 | 18.30 | 19.20 | 19.20 | 19.80 | 19.70 | 20.30 | 21.10 | 22.40 | | | |
| Control | 3 | 18.40 | 18.60 | 1890 | 19.00 | 19.80 | 20.30 | 22.20 | | | | |
| 2Q7Dx4 | 4 | 17.60 | 18.00 | 18.10 | 18.40 | 18.90 | 16.50 | 19.50 | | | | |
| | 5 | 18.00 | 1830 | 18.70 | 18.70 | 19.30 | 20.60 | 21.30 | | | | |
| | 6 | 19.20 | 19.00 | 18.70 | 19.10 | 19.50 | 20.80 | 23.10 | | | | |
| | 7 | 19.20 | 19.70 | 20.20 | 2020 | 20.90 | 21.60 | 23.30 | | | | |
| | 8 | 17.30 | 17.70 | 17.80 | 18.10 | 19.40 | 19.80 | | | | | |
| | 9 | 17.70 | 17.60 | 18.10 | 17.80 | 19.20 | 20.10 | | | | | |
| | 10 | 19.00 | 16.70 | 17.10 | 16.90 | 18.10 | 19.40 | 21.80 | | | | |
| | Ave | 18.34 | 18.39 | 18.72 | 18.76 | 19.56 | 20.07 | 21.93 | 22.40 | | | |
| | SD | 0.68 | 0.91 | 1.03 | 1.00 | 0.83 | 1.42 | 1.29 | | | | |
| Group 2 | 1 | 17.00 | 17.50 | 17.90 | 17.60 | 17.80 | 18.20 | 18.60 | 18.50 | | | |
| Anti-PD-1 | 2 | 17.30 | 18.10 | 18.30 | 18.20 | 19.10 | 19.40 | 20.40 | 20.50 | 23.20 | | |
| 200 μg | 3 | 18.30 | 1820 | 19.20 | 18.60 | 20.00 | 20.30 | 20.40 | 21.60 | 23.50 | | |
| Q3Dx7 | 4 | 17.90 | 17.60 | 18.50 | 19.30 | 19.90 | 20.60 | 21.00 | 22.60 | | | |
| | 5 | 17.70 | 18.30 | 18.10 | 1820 | 1860 | 19.40 | 19.40 | 20.40 | | | |
| | 6 | 18.80 | 19.10 | 19.10 | 19.60 | 19.90 | 20.30 | 21.00 | 22.00 | 24.10 | | |
| | 7 | 17.70 | 17.50 | 18.20 | 18.10 | 19.40 | 19.40 | 20.20 | 20.10 | 20.40 | 21.50 | |
| | 8 | 18.70 | 18.60 | 19.00 | 19.20 | 19.40 | 19.70 | 20.10 | 20.40 | 21.60 | | |
| | 9 | 19.30 | 18.60 | 1920 | 19.30 | 20.10 | 19.30 | 20.30 | 20.50 | 20.90 | 20.50 | 20.80 |
| | 10 | 16.80 | 17.50 | 17.50 | 17.60 | 18.70 | 18.60 | 19.10 | 19.10 | 19.80 | 20.40 | 21.70 |
| | Ave | 17.95 | 18.16 | 18.53 | 18.55 | 19.19 | 19.54 | 20.05 | 20.57 | 22.07 | 20.20 | 21.25 |
| | SD | 0.82 | 0.61 | 0.64 | 0.75 | 0.80 | 0.75 | 1.25 | 1.68 | 0.61 | 0.64 | |
| Group 3 | 1 | 16.30 | 16.10 | 16.40 | 16.60 | 16.30 | 16.80 | 17.30 | 17.90 | 19.00 | 19.80 | |
| Compound 1 | 2 | 17.40 | 17.30 | 18.10 | 18.30 | 18.40 | 18.90 | 19.30 | 19.40 | 20.20 | | |
| 50 mg/kg | 3 | 16.60 | 16.90 | 17.00 | 17.10 | 17.00 | 18.00 | 17.30 | 1720 | 17.60 | 18.00 | 1820 |
| QDx44 | 4 | 15.80 | 15.80 | 16.10 | 16.20 | | | | | | | |
| | 5 | 19.00 | 19.00 | 18.90 | 19.30 | 20.30 | 20.60 | 20.60 | 22.00 | 22.70 | 23.30 | |
| | 6 | 19.60 | 19.90 | 20.40 | 20.90 | 21.90 | 22.30 | 23.60 | 24.00 | | | |
| | 7 | 15.80 | 15.60 | 16.40 | 17.10 | 1830 | 18.70 | 19.70 | 20.50 | 21.20 | 21.70 | |
| | 8 | 17.90 | 16.60 | 16.60 | 16.90 | 17.30 | 17.30 | 17.80 | 19.30 | | | |
| | 9 | 18.70 | 18.10 | 18.10 | 18.50 | 19.10 | 18.60 | 19.20 | 20.00 | 21.60 | | |
| | 10 | 16.10 | 14.00 | 14.30 | 15.40 | 16.00 | 16.80 | 17.80 | 19.00 | | | |
| | Pose | 17.32 | 16.94 | 17.23 | 17.63 | 18.31 | 18.67 | 19.18 | 19.99 | 20.38 | 20.70 | 18.80 |
| | SD | 1.41 | 1.71 | 1.70 | 1.63 | 1.92 | 1.81 | 2.02 | 1.98 | 1.86 | 2.30 | |
| Group 4 | 1 | 17.30 | 16.50 | 17.70 | 17.40 | 17.10 | 17.30 | 17.60 | 17.40 | 18.10 | 18.30 | 18.50 |
| Compound 1 | 2 | 17.50 | 17.50 | 17.00 | | | | | | | | |
| 100 mg/kg | 3 | 19.10 | 19.00 | 18.80 | 19.10 | 1920 | 19.50 | 19.70 | 19.80 | 20.80 | 2080 | 20.30 |
| QDx71 | 4 | 17.00 | 17.40 | 17.30 | 17.40 | 17.60 | 17.70 | 18.10 | 18.10 | 18.20 | 18.20 | 18.40 |
| | 5 | 18.40 | 1870 | 18.40 | 18.80 | 18.80 | 19.70 | 19.40 | 20.10 | 19.60 | 19.90 | 20.10 |
| | 6 | 17.60 | 18.30 | 18.60 | 18.30 | 18.10 | 18.50 | 18.40 | 19.00 | 18.00 | 18.20 | 17.70 |
| | 7 | 19.00 | 19.90 | 1980 | 19.80 | 20.40 | 20.80 | 20.20 | 21.00 | 20.80 | 20.20 | 20.80 |
| | 8 | 18.20 | 18.20 | 18.10 | 18.30 | 18.60 | 1900 | 19.00 | 18.90 | 19.10 | 19.10 | 19.30 |
| | 9 | 18.00 | 16.30 | | | | | | | | | |
| | 10 | 19.30 | 17.40 | | | | | | | | | |
| | Ave | 18.14 | 17.92 | 18.21 | 18.44 | 1844 | 18.93 | 18.91 | 13.19 | 19.23 | 13.13 | 19.30 |
| | SD | 0.80 | 1.12 | 030 | 0.88 | 1.09 | 1.21 | 0.93 | 1.22 | 1.22 | 0.98 | 1.15 |
| Group 5 | 1 | 18.70 | 18.90 | 18.80 | 17.70 | 18.80 | 18.90 | 19.50 | 19.90 | 21.10 | 21.60 | |
| Compound 2 | 2 | 17.40 | 17.80 | 17.90 | 16.40 | 18.30 | 16.50 | 1810 | 17.30 | 19.50 | 18.30 | 19.60 |
| 150 mg/kg | 3 | 19.60 | 19.10 | 19.50 | 18.40 | 19.90 | 18.90 | 19.20 | 19.40 | 20.70 | 20.50 | 20.40 |
| 2Q7Dx10 | 4 | 16.80 | 16.70 | 16.70 | 16.10 | 16.80 | 17.10 | 17.10 | 17.50 | 19.10 | | |
| | 5 | 18.40 | 18.30 | 18.40 | 17.80 | 19.00 | 19.20 | 19.50 | 19.80 | 20.50 | 21.30 | |
| | 6 | 18.20 | 17.90 | 18.90 | 18.70 | 19.90 | 19.70 | 19.80 | 19.90 | 21.50 | 22.20 | 23.60 |
| | 7 | 1620 | 16.70 | 16.80 | 16.70 | 16.90 | | | | | | |
| | 8 | 19.80 | 20.00 | 20.30 | 19.90 | 20.60 | 20.70 | 21.00 | 21.80 | 23.10 | | |
| | 9 | 17.20 | 17.90 | 18.40 | 17.70 | 18.50 | 17.90 | 18.30 | 19.20 | 19.40 | 19.20 | 19.70 |
| | 10 | 19.60 | 19.70 | 20.10 | 19.70 | 20.30 | 20.00 | 20.30 | 20.60 | 22.20 | 23.00 | |
| | Ave | 18.31 | 18.30 | 18.58 | 17.91 | 18.90 | 18.77 | 19.20 | 19.19 | 20.79 | 20.87 | 20.83 |
| | SD | 1.12 | 1.13 | 1.22 | 1.30 | 1.32 | 1.37 | 1.19 | 1.41 | 1.34 | 1.66 | 1.88 |
| Group 6 | 1 | 17.30 | 15.40 | 18.00 | 16.60 | 17.40 | 18.40 | 18.30 | 18.10 | 19.00 | 19.30 | 19.90 |
| Compound 2 | 2 | 17.00 | 17.70 | 17.80 | 16.80 | 18.40 | 18.40 | 19.00 | 19.60 | 20.60 | 21.20 | 22.70 |
| 300 mg/kg | 3 | 17.20 | 17.60 | 17.40 | 16.20 | 18.10 | 1150 | 19.30 | 19.20 | 20.20 | 20.90 | 20.60 |
| 2Q7Dx11 | 4 | 18.80 | 17.60 | 18.30 | 17.70 | 18.50 | 18.50 | 19.50 | 18.30 | 19.90 | 19.60 | 20.10 |
| | 5 | 16.10 | 15.80 | 16.40 | 15.90 | 17.10 | 16.30 | 17.70 | 16.60 | 18.00 | 18.00 | 18.70 |
| | 6 | 17.20 | 17.30 | 18.20 | 17.70 | 18.90 | 19.60 | 19.30 | 19.30 | 19.70 | 20.00 | 20.30 |
| | 7 | 19.10 | 18.70 | 18.90 | 18.30 | 18.70 | 19.10 | 19.50 | 19.80 | 19.70 | 20.10 | 19.90 |
| | 8 | 18.70 | 19.10 | 19.30 | 18.70 | 19.80 | 19.80 | 19.80 | 2000 | 20.30 | 20.70 | 20.90 |
| | 9 | 18.10 | 17.70 | 18.60 | 17.70 | 18.90 | 18.70 | 19.40 | 18.90 | 19.30 | 19.60 | 19.40 |
| | 10 | 17.00 | 16.30 | 17.90 | 16.60 | 17.80 | 17.50 | 17.70 | 17.70 | 18.60 | 18.90 | 19.50 |
| | Ave | 17.65 | 17.32 | 18.08 | 17.22 | 18.36 | 18.48 | 18.95 | 18.75 | 19.53 | 19.83 | 20.20 |
| | SD | 0.97 | 1.18 | 0.81 | 0.93 | 0.79 | 1.01 | 0.77 | 1.07 | 0.81 | 0.97 | 1.08 |

TABLE 36-continued

| | | | | | | | | | | | |
|---|---|---|---|---|---|---|---|---|---|---|---|
| Group 7 | 1 | 17.70 | 18.30 | 17.90 | 18.00 | 18.50 | 18.70 | 18.60 | 19.10 | 19.10 | 19.00 | 19.30 |
| Compound 2 | 2 | 17.70 | 17.90 | 18.40 | 18.60 | 18.40 | 18.70 | 19.00 | 18.90 | 19.10 | 19.40 | 19.4 |
| 50 mg/kg | 3 | 17.70 | 18.60 | 18.80 | 18.80 | 18.90 | 19.30 | 19.20 | 19.60 | 20.50 | 20.60 | 21.40 |
| QDx71 + | 4 | 18.10 | 16.70 | 18.20 | 18.50 | 19.40 | 19.20 | 19.70 | 20.10 | 20.10 | 19.30 | |
| Anti-PD-1 | 5 | 17.70 | 17.60 | 18.20 | 17.90 | 18.30 | 18.80 | 18.70 | 18.20 | 1820 | 19.10 | 19.10 |
| 200 μg | 6 | 18.40 | | | | | | | | | | |
| Q3Dx24 | 7 | 17.60 | 17.90 | 18.00 | 18.40 | 18.90 | 19.30 | 19.30 | 19.40 | 19.00 | 19.3 | 19.20 |
| | 8 | 16.60 | 17.00 | 1690 | 1660 | 17.10 | 17.40 | 17.40 | 1800 | 17.70 | 18.20 | 17.70 |
| | 9 | 17.80 | 16.80 | 14.50 | 15.30 | 16.50 | 16.80 | 17.60 | 17.90 | 18.10 | 18.50 | 18.80 |
| | 10 | 17.20 | 17.20 | 1750 | 1780 | 17.80 | 18.40 | 1780 | 1850 | 18.50 | 19.10 | 19.00 |
| | Ave | 17.65 | 17.56 | 17.60 | 17.77 | 18.11 | 18.53 | 18.53 | 18.81 | 18.99 | 19.26 | 19.24 |
| | SD | 0.48 | 0.67 | 1.28 | 1.13 | 0.83 | 0.89 | 0.74 | 0.69 | 0.89 | 0.74 | 0.96 |
| Group 8 | 1 | 15.60 | 15.40 | 15.30 | 14.80 | 15.50 | 1580 | 15.70 | 15.70 | 16.30 | 16.70 | 16.70 |
| Compound 2 | 2 | 16.10 | 16.50 | 17.20 | 17.10 | 18.00 | 17.70 | 17.70 | 17.10 | 18.00 | 18.40 | 18.60 |
| 150 mg/kg | 3 | 18.00 | 18.00 | 18.70 | 18.20 | 18.90 | 19.20 | 1880 | 18.70 | 20.10 | 20.60 | |
| 2Q7Dx11 + | 4 | 16.60 | 17.00 | 17.20 | 16.30 | 17.50 | 18.20 | 17.60 | 17.80 | 18.00 | 19.40 | 19.10 |
| Anti-PD-1 | 5 | 15.90 | 15.50 | 16.10 | 15.80 | 16.60 | | | | | | |
| 200 μg | 6 | 18.60 | 18.40 | 18.70 | 18.60 | 19.90 | 19.80 | 20.20 | 20.00 | 21.20 | 20.60 | 21.40 |
| Q3Dx24 | 7 | 16.20 | 16.70 | 17.20 | 17.00 | 17.30 | 18.30 | 17.90 | 18.00 | 18.30 | 17.80 | 18.30 |
| | 8 | 17.40 | 17.80 | 17.50 | 17.10 | 18.10 | 18.10 | 18.00 | 17.90 | 18.30 | 18.70 | 18.70 |
| | 9 | 18.20 | 18.40 | 18.40 | 17.80 | 18.60 | 18.50 | 18.00 | 18.40 | 18.20 | 18.40 | 18.80 |
| | 10 | 17.50 | 18.10 | 1820 | 17.90 | 19.30 | 19.10 | 18.08 | 18.90 | 20.10 | 20.10 | 20.20 |
| | Ave | 17.01 | 17.18 | 17.45 | 17.06 | 17.97 | 18.30 | 18.08 | 18.06 | 18.72 | 18.97 | 18.98 |
| | SD | 1.06 | 1.14 | 1.12 | 1.16 | 1.31 | 1.14 | 1.20 | 1.20 | 1.48 | 1.32 | 1.38 |

| | Days | Mouse | 37 | 41 | 44 | 47 | 51 | 55 | 62 | 65 | 69 |
|---|---|---|---|---|---|---|---|---|---|---|---|
| Group 1 | | 1 | | | | | | | | | |
| Vehicle | | 2 | | | | | | | | | |
| Control | | 3 | | | | | | | | | |
| 2Q7Dx4 | | 4 | | | | | | | | | |
| | | 5 | | | | | | | | | |
| | | 6 | | | | | | | | | |
| | | 7 | | | | | | | | | |
| | | 8 | | | | | | | | | |
| | | 9 | | | | | | | | | |
| | | 10 | | | | | | | | | |
| | | Ave | | | | | | | | | |
| | | SD | | | | | | | | | |
| Group 2 | | 1 | | | | | | | | | |
| Anti-PD-1 | | 2 | | | | | | | | | |
| 200 μg | | 3 | | | | | | | | | |
| Q3Dx7 | | 4 | | | | | | | | | |
| | | 5 | | | | | | | | | |
| | | 6 | | | | | | | | | |
| | | 7 | | | | | | | | | |
| | | 8 | | | | | | | | | |
| | | 9 | 21.30 | | | | | | | | |
| | | 10 | 23.10 | | | | | | | | |
| | | Ave | 22.20 | | | | | | | | |
| | | SD | 1.27 | | | | | | | | |
| Group 3 | | 1 | | | | | | | | | |
| Compound 1 | | 2 | | | | | | | | | |
| 50 mg/kg | | 3 | 1950 | MO) | 21.00 | | | | | | |
| QDx44 | | 4 | | | | | | | | | |
| | | 5 | | | | | | | | | |
| | | 6 | | | | | | | | | |
| | | 7 | | | | | | | | | |
| | | 8 | | | | | | | | | |
| | | 9 | | | | | | | | | |
| | | 10 | | | | | | | | | |
| | | Pose | 19.50 | 20.00 | 21.00 | | | | | | |
| | | SD | | | | | | | | | |
| Group 4 | | 1 | 18.80 | 19.00 | 19.80 | 20.00 | 20.50 | | | | |
| Compound 1 | | 2 | | | | | | | | | |
| 100 mg/kg | | 3 | 20.30 | 20.50 | 21.90 | 21.30 | 21.10 | 22.00 | 21.90 | 21.80 | 22.30 |
| QDx71 | | 4 | 18.60 | 19.10 | 19.10 | 19.10 | 19.70 | 19.60 | 19.50 | 20.10 | |
| | | 5 | 20.40 | 20.00 | 2130 | 21.40 | 21.10 | 22.00 | 21.30 | 22.00 | 22.30 |
| | | 6 | 18.00 | 18.20 | 18.10 | 18.40 | 18.20 | 18.70 | 19.30 | 19.40 | 19.80 |
| | | 7 | 21.10 | 21.00 | 21.80 | 22.40 | 22.60 | 22.60 | 22.60 | 22.50 | 23.20 |
| | | 8 | 19.70 | 19.60 | 19.60 | 20.20 | 20.00 | 20.60 | 21.30 | 21.30 | 21.60 |
| | | 9 | | | | | | | | | |
| | | 10 | | | | | | | | | |
| | | Ave | 19.56 | 19.63 | 20.26 | 20.40 | 2037 | 20.93 | 21.00 | 2108 | 21.55 |
| | | SD | 1.12 | 0.96 | 1.49 | 1.40 | 1.44 | 1.53 | 1.30 | 1.32 | 1.34 |
| Group 5 | | 1 | | | | | | | | | |
| Compound 2 | | 2 | | | | | | | | | |
| 150 mg/kg | | 3 | | | | | | | | | |
| 2Q7Dx10 | | 4 | | | | | | | | | |
| | | 5 | | | | | | | | | |

TABLE 36-continued

|  |  |  | | | | | | | | |
|---|---|---|---|---|---|---|---|---|---|---|
| | | 6 | | | | | | | | |
| | | 7 | | | | | | | | |
| | | 8 | | | | | | | | |
| | | 9 | 19.90 | 20.00 | 20.10 | 20.10 | 19.90 | 20.70 | 21.70 | 21.80 |
| | | 10 | | | | | | | | |
| | | Ave | 19.90 | 20.00 | 20.10 | 20.10 | 19.90 | 20.70 | 21.70 | 21.20 |
| | | SD | | | | | | | | |
| Group 6 | | 1 | 20.40 | 21.40 | | | | | | |
| Compound 2 | | 2 | | | | | | | | |
| 300 mg/kg | | 3 | 19.80 | 21.60 | | | | | | |
| 2Q7Dx11 | | 4 | 20.30 | 21.30 | 21.40 | 22.70 | 22.90 | | | |
| | | 5 | 18.60 | 19.30 | 18.10 | 18.80 | 18.00 | 19.10 | 20.90 | 20.80 | 23.5 |
| | | 6 | 20.00 | 20.60 | 19.80 | 21.90 | 22.20 | | | |
| | | 7 | 19.40 | 20.20 | 20.30 | 20.40 | 20.30 | 20.90 | 21.20 | 20.90 | 21.8 |
| | | 8 | 2000 | 20.60 | 19.80 | 20.70 | 20.40 | 21.90 | 22.10 | 21.90 | 22.2 |
| | | 9 | 19.00 | 19.60 | 19.50 | 21.30 | 21.90 | | | |
| | | 10 | 19.30 | 20.70 | | | | | | |
| | | Ave | 19.64 | 20.59 | 19.82 | 20.97 | 20.95 | 20.63 | 21.40 | 2120 | 22.5 |
| | | SD | 0.61 | 0.79 | 1.08 | 1.35 | 1.77 | 1.42 | 0.62 | 0.61 | 0.89 |
| Group 7 | | 1 | 19.50 | 19.80 | 20.40 | 20.50 | 19.80 | 20.60 | 20.00 | 2020 | 20.7 |
| Compound 2 | | 2 | 20.00 | 20.00 | 20.90 | 21.00 | 20.20 | 21.30 | 21.50 | 21.50 | 21.7 |
| 50 mg/kg | | 3 | | | | | | | | |
| QDx71 + | | 4 | 19.80 | 20.10 | 20.20 | 20.60 | 20.00 | 20.50 | 20.00 | 20.00 | 21.0 |
| Anti-PD-1 | | 5 | 19.60 | 20.00 | 20.20 | 20.60 | 19.60 | 20.20 | 19.00 | 19.40 | 20.0 |
| 200 μg | | 6 | | | | | | | | |
| Q3Dx24 | | 7 | 19.90 | 20.30 | 20.40 | 20.50 | 18.90 | 20.10 | 21.10 | 20.50 | 20.9 |
| | | 8 | 18.40 | 18.50 | 18.50 | 18.90 | 18.60 | 19.00 | 18.80 | 1880 | 18.8 |
| | | 9 | 19.60 | 19.30 | 19.90 | 20.00 | 19.60 | 19.90 | 20.10 | 2050 | 21.3 |
| | | 10 | 1930 | 19.40 | 19.60 | 20.10 | 18.20 | 20.40 | 20.00 | 19.70 | 20.1 |
| | | Ave | 19.51 | 19.68 | 20.01 | 20.28 | 19.36 | 2025 | 20.06 | 20.08 | 20.56 |
| | | SD | 0.50 | 0.58 | 0.72 | 0.64 | 0.71 | 0.66 | 0.92 | 0.81 | 0.91 |
| Group 8 | | 1 | 16.40 | 16.90 | 17.00 | 17.10 | 16.70 | 17.00 | 16.60 | 17.10 | 17.2 |
| Compound 2 | | 2 | 18.50 | 19.50 | 19.40 | 19.80 | 20.00 | 19.70 | 19.50 | 20.60 | 20.1 |
| 150 mg/kg | | 3 | | | | | | | | |
| 2Q7Dx11 + | | 4 | 20.00 | 20.30 | 20.00 | 18.90 | 19.50 | 19.40 | 19.60 | 20.70 | 20.4 |
| Anti-PD-1 | | 5 | | | | | | | | |
| 200 μg | | 6 | 21.40 | 23.70 | | | | | | |
| Q3Dx24 | | 7 | 18.40 | 19.20 | 20.00 | 19.70 | 19.00 | 19.40 | 19.30 | 19.20 | 18.9 |
| | | 8 | 19.60 | 19.60 | 19.10 | 19.20 | 18.00 | 19.60 | 19.40 | 19.90 | 19.6 |
| | | 9 | 19.00 | 19.20 | 20.00 | 19.30 | 19.10 | 19.60 | 19.80 | 19.70 | 20.2 |
| | | 10 | 20.50 | 20.90 | 20.40 | 20.20 | 20.20 | 20.70 | 21.20 | 21.50 | 22.1 |
| | | Ave | 19.23 | 19.91 | 19.41 | 19.17 | 18.93 | 19.34 | 19.34 | 29.81 | 19.9 |
| | | SD | 1.53 | 1.92 | 1.15 | 1.01 | 1.22 | 1.13 | 1.37 | 1.41 | 1.50 |

TABLE 37

| Days | Mouse | 72 | 76 | 84 | 93 | 100 | 107 | 115 | 121 | 129 |
|---|---|---|---|---|---|---|---|---|---|---|
| Group 4 | 3 | 22.40 | 22.50 | 24.36 | 23.60 | 23.30 | 24.80 | 24.50 | 24.90 | 24.87 |
| Compound 2 | 4 | 19.90 | 19.90 | 20.27 | 21.40 | 21.50 | 21.40 | 20.90 | 21.20 | 21.40 |
| 100 mg/kg | 5 | 21.70 | 21.90 | 22.80 | 22.20 | 22.70 | 22.90 | 22.30 | 22.70 | 23.27 |
| QDx71 | 6 | 19.10 | 19.40 | 19.41 | 19.70 | 19.90 | 19.40 | 20.40 | 20.60 | 20.35 |
| | 7 | 23.70 | 23.60 | 24.00 | 25.20 | 24.70 | 24.10 | 24.60 | 26.70 | 28.99 |
| | 8 | 21.90 | 22.10 | 23.20 | 22.60 | 2240 | 22.90 | 23.30 | 24.40 | 24.35 |
| | Ave | 21.45 | 21.57 | 22.34 | 22.45 | 22.42 | 22.58 | 22.67 | 23.42 | 23.87 |
| | SD | 1.68 | 1.60 | 2.03 | 1.88 | 1.63 | 1.95 | 1.78 | 2.34 | 3.04 |
| Group 6 | 7 | 21.20 | 22.20 | 23.15 | 22.30 | 22.50 | 23.50 | 22.70 | 23.20 | 23.55 |
| Compound2 | 8 | 21.50 | 22.90 | 23.43 | 23.80 | 23.30 | 23.50 | 2320 | 24.40 | 23.30 |
| 300 mg/kg | Ave | 21.35 | 22.55 | 23.29 | 23.05 | 22.90 | 23.50 | 22.95 | 23.80 | 2343 |
| 2Q7Dx11 | SD | 0.21 | 0.49 | 0.20 | 1.06 | 0.57 | 0.00 | 0.35 | 0.85 | 0.18 |
| Group 7 | 1 | 20.70 | 20.80 | 21.60 | 21.90 | 22.00 | 22.40 | 23.30 | 23.50 | 22.69 |
| Compound 2 | 2 | 21.60 | 21.30 | 22.27 | 22.10 | 22.20 | 21.60 | 21.90 | 22.20 | 23.08 |
| 50 mg/kg | 4 | 20.00 | 21.00 | 21.99 | 21.90 | 22.00 | 22.00 | 22.20 | 22.10 | 22.00 |
| QDx71 + | 5 | 20.10 | 20.20 | 21.51 | 21.10 | 21.40 | 21.90 | 21.60 | 21.46 |
| Anti-PD-1 | 7 | 21.00 | 22.00 | 22.66 | 22.90 | 22.80 | 24.40 | 22.00 | 23.10 | 23.23 |
| 200 μg | 8 | 19.40 | 19.60 | 19.78 | 21.30 | 19.80 | 20.30 | 20.10 | 21.10 | 21.40 |
| Q3Dx24 | 9 | 21.20 | 21.20 | 21.68 | 22.20 | 22.20 | 22.30 | 20.80 | 22.20 | 2122 |
| | 10 | 19.60 | 20.80 | 21.85 | 21.40 | 21.60 | 22.70 | 20.50 | 22.20 | 22.33 |
| | Ave | 20.45 | 20.46 | 21.67 | 21.85 | 21.63 | 22.14 | 21.59 | 22.25 | 22.30 |
| | SD | 0.79 | 0.72 | 0.85 | 0.58 | 1.01 | 1.18 | 1.05 | 0.76 | 0.68 |
| Group 8 | 1 | 17.60 | 17.60 | 18.40 | 18.70 | 18.90 | 19.00 | 18.20 | 18.80 | 18.90 |
| Compound 2 | 2 | 20.70 | 20.40 | 21.15 | 21.70 | 22.80 | 22.00 | 23.20 | 22.90 | 23.20 |
| 150 mg/kg | 4 | 20.30 | 20.60 | 20.20 | 20.90 | 20.70 | 26.90 | 20.40 | 21.60 | 21.78 |
| 2Q7Dx11 + | 7 | 19.20 | 18.60 | 19.75 | 20.20 | 20.20 | 20.70 | 21.00 | 20.90 | 20.99 |
| Anti-PD-1 | 8 | 19.20 | 19.60 | 20.42 | 21.00 | 20.60 | 20.40 | 21.20 | 21.30 | 2143 |
| 200 μg | 9 | 20.60 | 19.90 | 20.90 | 2140 | 20.60 | 20.70 | 21.20 | 21.40 | 21.56 |
| Q3Dx24 | 10 | 22.50 | 23.10 | 22.00 | 23.70 | 22.50 | 23.30 | 24.10 | 23.50 | 24.10 |

TABLE 37-continued

|  | | | | | | | | | |
|---|---|---|---|---|---|---|---|---|---|
| Ave | 20.10 | 19.97 | 20.40 | 21.09 | 20.90 | 21.00 | 21.13 | 21.49 | 21.71 |
| SD | 1.50 | 1.73 | 1.14 | 1.52 | 1.35 | 1.34 | 1.91 | 1.51 | 1.66 |

| Days | Mouse | 135 | 143 | 149 | 156 | 164 | 170 | 182 |
|---|---|---|---|---|---|---|---|---|
| Group 4 | 3 | 25.50 | 26.30 | 26.45 | 27.30 | 27.50 | 27.10 | 28.50 |
| Compound 2 | 4 | 21.50 | 21.40 | 22.50 | 22.50 | 22.80 | 22.50 | 23.30 |
| 100 mg/kg | 5 | 22.90 | 23.90 | 23.88 | 24.00 | 24.40 | 24.10 | 24.80 |
| QDx71 | 6 | 20.70 | 20.90 | 20.76 | 21.10 | 20.90 | 21.20 | 21.20 |
|  | 7 | | | | | | | |
|  | 8 | 24.00 | 25.40 | 24.99 | 25.20 | 2500 | 25.50 | 27.10 |
|  | Ave | 22.92 | 23.58 | 23.72 | 24.02 | 24.12 | 24.08 | 24.98 |
|  | SD | 1.92 | 2.38 | 2.20 | 2.40 | 2.47 | 2.34 | 2.92 |
| Group 6 | 7 | 22.40 | 24.00 | 2430 | 24.30 | 23.40 | 23.30 | 23.10 |
| Compound2 | 8 | 23.80 | 24.30 | 24.92 | 25.30 | 25.10 | 25.40 | 25.40 |
| 300 mg/kg | Ave | 23.10 | 24.15 | 24.61 | 24.80 | 24.25 | 2835 | 24.25 |
| 2Q7Dx11 | SD | 0.99 | 0.21 | 0.44 | 0.71 | 1.20 | 1.48 | 1.63 |
| Group 7 | 1 | 23.40 | 22.80 | 22.76 | 23.10 | 22.90 | 23.00 | 24.40 |
| Compound 2 | 2 | 22.40 | 22.60 | 22.65 | 23.40 | 23.20 | 23.10 | 24.60 |
| 50 mg/kg | 4 | 22.40 | 22.00 | 22.12 | 22.90 | 2350 | 22.90 | 24.20 |
| QDx71 + | 5 | 21.90 | 22.00 | 22.04 | 23.20 | 23.30 | 23.80 | 23.70 |
| Anti-PD-1 | 7 | 23.60 | 24.10 | 24.15 | 24.30 | 25.00 | 24.60 | 24.80 |
| 200 μg | 8 | 21.10 | 21.60 | 21.56 | 21.80 | 21.80 | 22.00 | 21.90 |
| Q3Dx24 | 9 | 22.10 | 22.30 | 22.70 | 23.80 | 22.30 | 23.00 | 22.30 |
|  | 10 | 23.70 | 22.10 | 22.22 | 22.80 | 23.20 | 23.10 | 24.90 |
|  | Ave | 22.58 | 22.44 | 2253 | 23.16 | 23.15 | 23.19 | 2328 |
|  | SD | 0.92 | 0.77 | 0.77 | 0.74 | 0.94 | 0.75 | 1.11 |
| Group 8 | 1 | 18.80 | 19.40 | 19.54 | 19.20 | 19.00 | 19.30 | 20.20 |
| Compound 2 | 2 | 22.50 | 23.60 | 23.43 | 23.70 | 24.50 | 23.80 | 24.70 |
| 150 mg/kg | 4 | 21.00 | 21.70 | 21.77 | 21.30 | 21.40 | 21.00 | 2190 |
| 2Q7Dx11 + | 7 | 20.90 | 21.20 | 21.22 | 20.80 | 21.70 | 21.90 | 21.70 |
| Anti-PD-1 | 8 | 21.20 | 21.30 | 21.27 | 22.20 | 21.80 | 21.90 | 23.10 |
| 200 μg | 9 | 22.00 | 22.00 | 22.15 | 22.70 | 21.70 | 21.30 | 22.90 |
| Q3Dx24 | 10 | 25.40 | 24.40 | 24.56 | 24.40 | 25.50 | 24.70 | 25.90 |
|  | Ave | 21.69 | 21.94 | 21.99 | 22.04 | 22.23 | 21.99 | 23.00 |
|  | SD | 2.01 | 1.65 | 1.63 | 1.78 | 2.15 | 1.79 | 1.78 |

TABLE 38

| Day of Study | Group 1- Vehicle Control 2Q7D44 | Group 2- Anti PD-1 200 μg Q3Dx7 | Group 3- Compound 2 50 mg/kg QDx44 | Group 4- Compound 2 100 mg/kg QDx71 | Group 5- Compound 2 150 mg/kg 2Q7Dx10 | Group 6- Compound 2 300 mg/kg 2QDx11 | Group 7- Compound 2 50 mg/kg QDx71 + Anti-PD-1 200 μg Q3Dx24 | Group 8- Compound 2 150 mg/kg 2QDx11 + Anti-PD-1 200 μg Q3Dx24 |
|---|---|---|---|---|---|---|---|---|
| 2 | 0.33 ± 4.68 | 1.25 ± 2.81 | −2.26 ± 4.41 | −1.17 ± 5.17 | −0.05 ± 1.42 | −1.85 ± 4.52 | −0.02 14.17 (N = 9) | 0.99 ± 2.08 |
| 6 | 2.12 ± 5 16 | 3.28 ± 1.69 | −0 54 ± 5 19 | 1.12 ± 2.91 (N = 8) | 1.46 ± 1 73 | 2 52 ± 2.75 | 0 22 ± 7.23 (N = 9) | 2 61 ± 2.75 |
| 8 | 2.35 ± 5.30 | 3.38 ± 2.23 | 1.80 ± 4.46 | 1.98 ± 1.69 (N = 7) | −2.20 ± 3.11 | −2.40 ± 2.71 | 1.15 ± 6.04 (N = 9) | 0.31 ± 3.44 |
| 13 | 6.74 ± 4.92 | 6.97 ± 3.18 | 4.67 ± 6.48 (N = 9) | 2.50 ± 2.66 (N = 7) | 3.20 ± 2.79 | 4.15 ± 3.99 | 3.11 ± 4.23 (N = 9) | 5.63 ± 3.63 |
| 16 | 9.43 ± 6.67 | 8.95 ± 3.88 | 6.79 ± 6.78 (N = 9) | 4.61 ± 3.10 (N = 7) | 1.54 ± 4.10 (N = 9) | 4.79 ± 4.58 | 5.51 ± 4.46 (N = 9) | 6.86 ± 3.97 (N = 9) |
| 20 | 18.13 ± 4 21 (N = 8) | 11.79 ± 4 08 | 9.72 ± 8 22 (N = 9) | 4 58 ± 1.71 (N = 7) | 3.92 ± 3 04 (N = 9) | 7.49 ± 3.79 | 5.50 ± 3.13 (N = 9) | 5.55 ± 4.04 (N = 9) |
| 23 | 22.40 ± 0.00 (N = 1) | 14.64 ± 5 82 | 14.37 ± 7.87 (N = 9) | 6.04 ± 3.52 (N = 7) | 5 45 ± 4 00 (N = 9) | 6.34 ± 5.30 | 7.10 ± 3.35 (N = 9) | 5.40 ± 3.49 (N = 9) |
| 28 | (NA) | 21.85 ± 8.92 (N = 7) | 17.97 ± 9.16 (N = 7) | 6.26 ± 2.53 (N = 7) | 12.52 ± 3.75 (N = 9) | 10.84 ± 5.53 | 8.08 ± 3.80 (N = 9) | 9.26 ± 5.07 (N = 9) |
| 31 | (NA) | 16.37 ± 8.79 (N = 3) | 22.47 ± 11.82 (N = 4) | 6.07 ±. 1.55 (N = 7) | 12.60 ± 6.72 | 12.55 ± 6.58 | 9.62 ± 3.36 (N = 9) | 10.75 ± 4.98 (N = 9) |
| 34 | (NA) | 18.47 ± 15.13 (N = 2) | 13 ± 25 ± 0.00 (N = 1) | 6.68 ± 3.02 (N = 7) | 14.27 ± 10.90 (N = 4) | 14.73 ± 8.36 | 9.54 ± 4.55 (N = 9) | 11.48 ± 4.82 (N = 8) |
| 37 | (NA) | 23.93 ± 19.19 (N = 2) | 17.47. ± 0.00 (N = 1) | 8.11 ± 3.05 (N = 7) | 11.80 ± 0.00 (N = 1) | 11.09 ± 5.81 | 11.19 ± 1.39 (N = 8) | 12.92 ± 5.57 (N = 8) |
| 41 | (NA) | (NA) | 20.48 ± 0.00 (N = 1) | 8.55 ± 2 85 (N = 7) | 12 36 ± 0 00 (N = 1) | 16 47 ± 7 22 (N = 9) | 12 11 ± 1.99 (N = 8) | 16.91 ± 7 45 (N = 8) |
| 44 | (NA) | (NA) | 26.51 ± 0.00 (N = 1) | 11.94 ± 4.94 (N = 7) | 12.92 ± 0.00 (N = 1) | 10.21 ± 4.06 (N = 6) | 14.02 ± 2.36 (N = 8) (N = 8) | 15.66 ± 6.07 (N = 7) |

TABLE 38-continued

| Day of Study | Group 1- Vehicle Control 2Q7D44 | Group 2- Anti PD-1 200 μg Q3Dx7 | Group 3- Compound 2 50 mg/kg QDx44 | Group 4- Compound 2 100 mg/kg QDx71 | Group 5- Compound 2 150 mg/kg 2Q7Dx10 | Group 6- Compound 2 300 mg/kg 2Q7Dx11 | Group 7- Compound 2 50 mg/kg QDx71 + Anti-PD-1 200 μg Q3Dx24 | Group 8- Compound 2 150 mg/kg 2QDx11 + Anti-PD-1 200 μg Q3Dx24 |
|---|---|---|---|---|---|---|---|---|
| 47 | (NA) | (NA) | (NA) | 12.74 ± 4.46 (N = 7) | 12.92 ± 0.00 (N = 1) | 16.67 ± 7.27 (N = 6) | 15.53 ± 2.03 (N = 8) | 14.27 ± 6.27 (N = 7) |
| 51 | (NA) | (NA) | (NA) | 12.61 ± 5.41 (N = 7) | 11.80 ± 0.00 (N = 1) | 16.51 ± 8.81 (N = 6) | 10.32 ± 2.65 (N = 8) | 12.84 ± 7.76 (N = 7) |
| 55 | (NA) | (NA) | (NA) | 14.84 ± 4.84 (N = 6) | 16.29 ± 0.00 (N = 1) | 15.06 ± 4.94 (N = 3) | 15.40 ± 2.86 (N = 8) | 15.23 ± 5.57 (N = 7) |
| 62 | (NA) | (NA) | (NA) | 15.23 ± 3.12 (N = 6) | 21.91 ± 0.00 (N = 1) | 19.66 ± 9.50 (N = 3) | 14.33 ± 4.69 (N = 8) | 15.17 ± 6.14 (N = 7) |
| 65 | (NA) | (NA) | (NA) | 15.68 ± 3 39 (N = 6) | 22.47 ± 0.00 (N = 1) | 18.58 ± 9.97 (N = 3) | 14.39 ± 3.67 (N = 13) | 18.04 ± 7 60 (N = 7) |
| 69 | (NA) | (NA) | (NA) | 18.25 ± 3.44 (N = 6) | (NA) | 26.27 ± 17.21 (N = 3) | 17.14 ± 3.22 (N = 8) | 17.80 ± 6.82 (N = 7) |
| 72 | (NA) | (NA) | (NA) | 17.64 ± 5.32 (N = 6) | (NA) | 12 98 ± 2 81 (N = 2) | 16.53 ± 3.72 (N = 8) | 19.68 ± 6 95 (N = 7) |
| 76 | (NA) | (NA) | (NA) | 18.29 ± 4.74 (N = 6) | (NA) | 19.35 ± 4.40 (N = 2) | 18.89 ± 3.32 (N = 8) | 18.92 ±. 8.60 (N = 7) |
| 84 | (NA) | (NA) | (NA) | 22.46 ± 6.73 (N = 6) | (NA) | 23.25 ± 2.89 (N = 2) | 23.46 ±. 3.32 (N = 8) | 21.55 ± 5.62 (N = 7) |
| 93 | (NA) | (NA) | (NA) | 23.14 ± 6.79 (N = 6) | (NA) | 22.01 ± 7.44 (N = 2) | 24.54 ± 3.53 (N = 8) | 25.56 ± 7.11 (N = 7) |
| 100 | (NA) | (NA) | (NA) | 23.00. ± 5.67 (N = 6) | (NA) | 21.20 ± 4.81 (N = 2) | 23.21 ± 4.40 (N = 8) | 24.62 ± 9.00 (N = 7) |
| 107 | (NA) | (NA) | (NA) | 23.85 ± 6.91 (N = 6) | (NA) | 24.35 ± 1.86 (N = 2) | 26.15 ± 6.26 (N = 8) | 25.18 ± 8.24 (N = 7) |
| 115 | (NA) | (NA) | (NA) | 24.30 ± 5 26 (N = 6) | (NA) | 21.46 ± 3 69 (N = 2) | 22.98 ± 4.40 (N = 8) | 27.05 ± 10.61 (N = 7) |
| 121 | (NA) | (NA) | (NA) | 28.35 ± 8.38 (N = 6) | (NA) | 25.97 ± 6.37 (N = 2) | 26.81 ± 3.99 (N = 4) | 28.02 ± 8.60 (N = 7) |
| 129 | (NA) | (NA) | (NA) | 30.76 ± 12.30 (N = 6) | (NA) | 23.95 ± 0 92 (N = 2) | 27.12 ± 409 (N = 8) | 29.34 ± 9 26 (N = 7) |
| 135 | (NA) | (NA) | (NA) | 26.78 ± 6.34 (N = 5) | (NA) | 22.28 ± 7.07 (N = 2) | 28.67 ± 5.36 (N = 8) | 29.09 ± 9.76 (N = 7) |
| 143 | (NA) | (NA) | (NA) | 30.36 ± 8.57 (N = 5) | (NA) | 27.80 ± 3.03 (N = 2) | 27.89 ± 4.60 (N = 8) | 30.75 ± 9.43 (N = 7) |
| 149 | (NA) | (NA) | (NA) | 31.18 ± 8.20 (N = 5) | (NA) | 30.24 ± 4.27 (N = 2) | 28.39 ± 4.39 (N = 8) | 31.03 ± 9.08 (N = 7) |
| 156 | (NA) | (NA) | (NA) | 32 81 ± 8 76 (N = 5) | (NA) | 31.26 ± 5.71 (N = 2) | 32.00 ± 3.24 (N = 8) | 31.25 ± 8.77 (N = 7) |
| 164 | (NA) | (NA) | (NA) | 33.36 ± 9.27 (N = 5) | (NA) | 28.37 ± 8.28 (N = 2) | 31.93 ± 4.89 (N = 8) | 32.44 ± 12.3 (N = 7) |
| 170 | (NA) | (NA) | (NA) | 33.16 ± 8.53 (N = 5) | (NA) | 28.91 ± 9.79 (N = 2) | 32.16 ± 4.07 (N = 8) | 31.04 ± 10.79 (N = 7) |
| 182 | (NA) | (NA) | (NA) | 38.08 ± 11.87 (N = 5) | (NA) | 28.39 ± 10.53 (N = 2) | 36.06 ± 5.75 (N = 8) | 37.03 ± 9.85 (N = 7) |

N/A. no mice in the group

Clinical Observations: In general, Compound 2 was well tolerated throughout the study. Some lab accidents and moribund mice were recorded in TABLE 38. These included one mouse (#4) in Group 3, mice administered Compound 2 50 mg/kg QDx44, 3 mice (#2, #9, #10) in Group 4 administered Compound 2 100 mg/kg QDx71, one mouse (#7) in group 5 administered Compound 2 150 mg/kg 2Q7Dx10, one mouse (#6) in group 7 administered Compound 2 50 mg/kg QDx71+Anti-PD-1 200 μg Q3Dx24 and one mouse (#5) in group 8 administered Compound 2 150 mg/kg 2Q7Dx11+Anti-PD-1 200 μg Q3Dx24.

This study was designed to test the dose responsive anti-tumor effect of Compound 2 alone and in combination with Anti-PD-1 in a mouse syngeneic model of sarcoma (MT373). Single agent activity was evaluated with two dosing regimens, daily and twice daily once per week. Compound 2 was dosed PO daily at 50 mg/kg or 100 mg/kg, and exhibited 74% TGI and 39.9% regression, respectively by day 20. Compound 2 was also dosed PO twice daily once a week at 150 mg/kg or 300 mg/kg and exhibited 92% and 99.2% TGI, respectively. To evaluate the combination of Anti-PD-1 and Compound 2, Anti-PD-1 as a single agent was dosed IP at 200 μg per mouse and exhibited 72.3% TGI at day 20. Mice dosed with the combination of Compound 2 and Anti-PD-1 exhibited 38.6% regression for the 50 mg/kg daily dose of Compound 2+Anti-PD-1 and 23.5% regression for the 150 mg/kg twice daily once a week dose of Compound 2+Anti-PD-1, respectively. Compound 2 alone and in combination with Anti-PD-1 was well tolerated throughout the dosing period.

The study was terminated at Day 182, median survival was calculated for all groups as a measure of time for tumors to reach 2000 mm$^3$. Mice administered vehicle control had a median survival time of 17.3 days whereas mice administered Anti-PD-1 only had a slightly improved median survival of 24 days. Compound 2 dosed PO daily at 50 mg/kg or 100 mg/kg exhibited median survival times of 28 and >182 days, respectively. Compound 2 dosed PO twice daily once a week at 150 mg/kg or 300 mg/kg exhibited median survival times of 30.8 and 47.7 days, respectively.

The combination of Compound 2+Anti-PD-1 improved median survival times versus either single agents with both dosing groups, 50 mg/kg QD+Anti-PD-1 and 150 mg/kg 2Q7D+Anti-PD-1, exhibiting a median survival of >182 days, a >164 day extension in survival compared to vehicle control.

Following cessation of dosing on day 70, mice were continuously monitored for tumor growth until day 182. Two of the single agent groups had some residual tumors or cures. The Compound 2 100 mg/kg group had 71% of mice surviving and the Compound 2 300 mg/kg group had 20% of mice surviving at the termination of the study. However, an increase in the number of tumors in stasis or cures in both combination groups as compared to single agent was observed. The Compound 2 50 mg/kg+Anti-PD-1 group had 89% of mice surviving, and the Compound 2 150 mg/kg+Anti-PD-1 group had 78% of mice surviving at termination of the study.

Overall, administration of Compound 2 either daily or twice daily once per week resulted in a dose responsive anti-tumor effect with tumor grow delay and tumor regression at higher doses. Combining sub-efficacious dose levels of Compound 2 with Anti-PD-1 significantly improved the anti-tumor effect demonstrating regression, cures, and a significant increase in median survival time.

EMBODIMENTS

The following non-limiting embodiments provide illustrative examples of the invention, but do not limit the scope of the invention.

Embodiment 1. A method of treating cancer in a subject in need thereof, the method comprising: (i) administering to the subject a therapeutically-effective amount of a compound, wherein the compound binds to a mutant p53 protein and reconforms the mutant p53 protein to a conformation of p53 that exhibits anti-cancer activity; and (ii) administering to the subject a therapeutically-effective amount of an anti-cancer agent that functions through a pathway other than p53-induced apoptosis.

Embodiment 2. The method of embodiment 1, wherein the compound increases a stability of the mutant p53 protein.

Embodiment 3. The method of embodiment 1 or 2, wherein the cancer expresses the mutant p53 protein.

Embodiment 4. The method of any one of embodiments 1-3, wherein the mutant p53 protein has a mutation at amino acid 220.

Embodiment 5. The method of any one of embodiments 1-4, wherein the mutant p53 protein is p53 Y220C.

Embodiment 6. The method of any one of embodiments 1-5, wherein the compound selectively binds the mutant p53 protein as compared to a wild type p53.

Embodiment 7. The method of any one of embodiments 1-6, wherein the cancer is ovarian cancer.

Embodiment 8. The method of any one of embodiments 1-6, wherein the cancer is breast cancer.

Embodiment 9. The method of any one of embodiments 1-6, wherein the cancer is lung cancer.

Embodiment 10. The method of any one of embodiments 1-9, wherein the administering of the compound is oral.

Embodiment 11. The method of any one of embodiments 1-9, wherein the administering of the compound is subcutaneous.

Embodiment 12. The method of any one of embodiments 1-9, wherein the administering of the compound is topical.

Embodiment 13. The method of any one of embodiments 1-12, wherein the therapeutically-effective amount of the compound is from about 500 mg to about 1200 mg.

Embodiment 14. The method of any one of embodiments 1-13, wherein the therapeutically-effective amount of the compound is about 500 mg.

Embodiment 15. The method of any one of embodiments 1-13, wherein the therapeutically-effective amount of the compound is about 1200 mg.

Embodiment 16. The method of any one of embodiments 1-13, wherein the therapeutically-effective amount of the compound is about 2000 mg/kg.

Embodiment 17. The method of any one of embodiments 1-16, wherein the subject is human.

Embodiment 18. The method of any one of embodiments 1-17, wherein the anti-cancer agent is a small molecule.

Embodiment 19. The method of any one of embodiments 1-17, wherein the anti-cancer agent is an antibody.

Embodiment 20. The method of any one of embodiments 1-17, wherein the anti-cancer agent is an immune checkpoint inhibitor.

Embodiment 21. The method of any one of embodiments 1-17 or 20, wherein the immune checkpoint inhibitor is an anti-PD-1 agent.

Embodiment 22. The method of any one of embodiments 1-17, 20, or 21, wherein the anti-PD-1 agent is nivolumab.

Embodiment 23. The method of any one of embodiments 1-17, 20, or 21, wherein the anti-PD-1 agent is pembrolizumab.

Embodiment 24. The method of any one of embodiments 1-17, 20, or 21, wherein the anti-PD-1 agent is cemiplimab.

Embodiment 25. The method of any one of embodiments 1-17 or 20, wherein the immune checkpoint inhibitor is an anti-PD-L1 agent.

Embodiment 26. The method of any one of embodiments 1-17, 20, or 25, wherein the anti-PD-L1 agent is atezolizumab.

Embodiment 27. The method of any one of embodiments 1-17, 20, or 25, wherein the anti-PD-L1 agent is avelumab.

Embodiment 28. The method of any one of embodiments 1-17, 20, or 25, wherein the anti-PD-L1 agent is durvalumab.

Embodiment 29. The method of any one of embodiments 1-28, wherein the administering of the anti-cancer agent is oral.

Embodiment 30. The method of any one of embodiments 1-28, wherein the administering of the anti-cancer agent is subcutaneous.

Embodiment 31. The method of any one of embodiments 1-28, wherein the administering of the anti-cancer agent is topical.

Embodiment 32. The method of any one of embodiments 1-31, wherein the therapeutically-effective amount of the anti-cancer agent is from about 5 mg/kg to about 500 mg/kg.

Embodiment 33. The method of any one of embodiments 1-31, wherein the therapeutically-effective amount of the anti-cancer agent is from about 10 µg to about 500 µg.

Embodiment 34. The method of any one of embodiments 1-31 or 33, wherein the therapeutically-effective amount of the anti-cancer agent is about 200 µg.

Embodiment 35. The method of any one of embodiments 1-34, wherein the compound is of the formula:

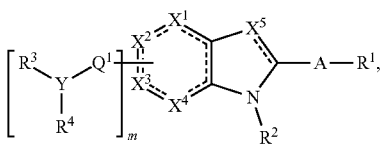

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or NR.
wherein at least one of $X^1$, $X^2$, $X^3$, and $X^4$ is a carbon atom connected to $Q^1$;
A is a linking group;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{11}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

Embodiment 36. The method of embodiment 35, wherein A is alkylene, alkenylene, or alkynylene, each of which is substituted or unsubstituted.

Embodiment 37. The method of embodiment 35, wherein A is aryl, heteroaryl, or heterocyclyl, each of which is substituted or unsubstituted.

Embodiment 38. The method of embodiment 35 or 36, wherein the compound is of the formula:

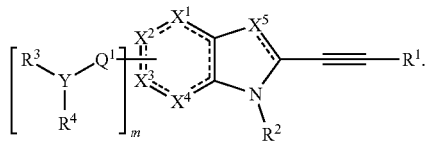

Embodiment 39. The method of any one of embodiments 35-38, wherein $Q^1$ is $C_1$-alkylene.

Embodiment 40. The method of any one of embodiments 35-38, wherein $Q^1$ is a bond.

Embodiment 41. The method of any one of embodiments 35-40, wherein m is 1.

Embodiment 42. The method of any one of embodiments 35-40, wherein m is 2.

Embodiment 43. The method of any one of embodiments 35-42, wherein Y is N.

Embodiment 44. The method of any one of embodiments 35-42, wherein Y is O.

Embodiment 45. The method of any one of embodiments 35-44, wherein each $R^3$ and $R^4$ is independently alkyl, alkylene, alkenyl, alkenylene, alkynyl, aryl, heteroaryl, or heterocyclyl, each of which is independently substituted or unsubstituted; or hydrogen.

Embodiment 46. The method of any one of embodiments 35-45, wherein $R^3$ is alkyl, alkylene, alkenyl, alkenylene, alkynyl, each of which is independently substituted or unsubstituted; and $R^4$ is aryl, heteroaryl, or heterocyclyl, each of which is independently substituted or unsubstituted.

Embodiment 47. The method of any one of embodiments 35-45, wherein $R^3$ is H; and $R^4$ is aryl, heteroaryl, or heterocyclyl, each of which is independently substituted or unsubstituted.

Embodiment 48. The method of any one of embodiments 35-47, wherein $R^{13}$ is hydrogen.

Embodiment 49. The method of any one of embodiments 35, 36, 38, 40, 41, 43, 45-48, wherein the compound is of the formula:

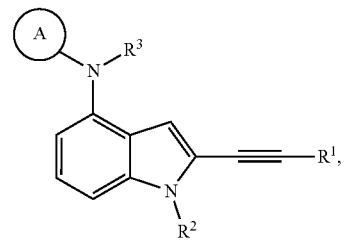

wherein ring A is a cyclic group that is substituted or unsubstituted.

Embodiment 50. The method of any one of embodiments 35-49, wherein $R^2$ is substituted or unsubstituted alkyl.

Embodiment 51. The method of any one of embodiments 35-50, wherein $R^2$ is methyl, ethyl, propyl, iso-propyl, butyl, or tert-butyl, each of which is substituted or unsubstituted.

Embodiment 52. The method of any one of embodiments 35-51, wherein $R^2$ is substituted ethyl.

Embodiment 53. The method of any one of embodiments 35-52, wherein $R^2$ is trifluoroethyl.

Embodiment 54. The method of any one of embodiments 35, 36, 38, 40, 41, 43, or 45-53, wherein the compound is of the formula:

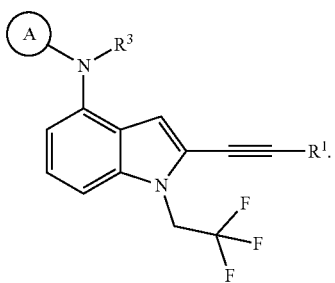

Embodiment 55. The method of any one of embodiments 35, 36, 38, 40, 41, 43, or 45-54, wherein ring A is aryl, heteroaryl, or heterocyclyl, each of which is substituted or unsubstituted.

Embodiment 56. The method of any one of embodiments 35, 36, 38, 40, 41, 43, or 45-55, wherein ring A is substituted aryl.

Embodiment 57. The method of any one of embodiments 35, 36, 38, 40, 41, 43, or 45-55, wherein ring A is substituted heteroaryl.

Embodiment 58. The method of any one of embodiments 35, 36, 38, 40, 41, 43, or 45-55, wherein ring A is substituted heterocyclyl.

Embodiment 59. The method of any one of embodiments 35-58, wherein $R^1$ is alkyl, alkenyl, —C(O)$R^{16}$, —C(O)O$R^{16}$, or —C(O)N$R^{16}R^{17}$, each of which is unsubstituted or substituted.

Embodiment 60. The method of any one of embodiments 35-59, wherein $R^1$ is substituted alkyl.

Embodiment 61. The method of any one of embodiments 35-60, wherein $R^1$ is alkyl substituted with N$R^{16}R^{17}$.

Embodiment 62. The method of any one of embodiments 35, 36, 38, 40, 41, 43, or 45-61, wherein the compound is of the formula:

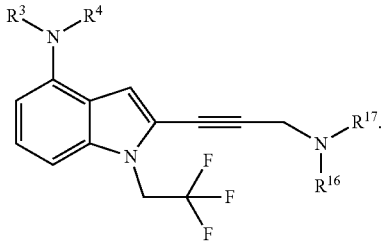

Embodiment 63. The method of any one of embodiments 35-62, wherein each $R^{16}$ and $R^{17}$ is independently alkyl, alkenyl, aryl, heteroaryl, heterocyclyl, each of which is independently substituted or unsubstituted; or hydrogen.

Embodiment 64. The method of any one of embodiments 35-63, wherein $R^{16}$ is hydrogen or alkyl.

Embodiment 65. The method of any one of embodiments 35-64, wherein $R^{17}$ is aryl, heteroaryl, or heterocyclyl, each of which is independently substituted or unsubstituted.

Embodiment 66. The method of any one of embodiments 35-65, wherein $R^{17}$ is substituted aryl.

Embodiment 67. The method of any one of embodiments 35-66, wherein $R^{17}$ is substituted phenyl.

Embodiment 68. The method of any one of embodiments 35-67, wherein $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted.

Embodiment 69. The method of any one of embodiments 35-68, wherein $R^{17}$ is phenyl substituted with methoxy.

Embodiment 70. The method of any one of embodiments 35-69, wherein $R^{17}$ is phenyl substituted with a substituted sulfoxide group.

Embodiment 71. The method of any one of embodiments 35-70, wherein $R^{17}$ is phenyl substituted with a carboxyl group.

Embodiment 72. The method of any one of embodiments 35-71, wherein $R^{17}$ is phenyl substituted with an amide group.

Embodiment 73. The method of embodiment 35, wherein the compound is 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide.

Embodiment 74. The method of any one of embodiments 35, wherein the compound is 2-(3-((2-methoxy-4-(methylsulfonyl)phenyl)amino)prop-1-yn-1-yl)-N-((1r,4r)-4-morpholinocyclohexyl)-1-(oxiran-2-ylmethyl)-1H-indol-4-amine.

Embodiment 75. The method of any one of embodiments 35, wherein the compound is 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide.

Embodiment 76. The method of any one of embodiments 35, wherein the compound is 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide.

Embodiment 77. The method of any one of embodiments 35, wherein the compound is N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide.

Embodiment 78. The method of any one of embodiments 35, wherein the compound is 3-methoxy-N-(2-methoxyethyl)-N-methyl-4-((3-(4-((tetrahydro-2H-pyran-4-yl)amino)-1-(2,2,2-trifluoroethyl)-1H-indol-2-yl)prop-2-yn-1-yl)amino)benzenesulfonamide.

Embodiment 79. The method of any one of embodiments 35, wherein the compound is N-(2,3-dihydroxypropyl)-4-((3-(4-((1,1-dioxidotetrahydro-2H-thiopyran-4-yl)amino)-1-(2,2,2-trifluoroethyl)-1H-indol-2-yl)prop-2-yn-1-yl)amino)-3-methoxybenzenesulfonamide.

Embodiment 80. The method of any one of embodiments 35, wherein the compound is 3-methoxy-4-((3-(4-(3-(1-methylpiperidin-4-yl)ureido)-1-(2,2,2-trifluoroethyl)-1H-indol-2-yl)prop-2-yn-1-yl)amino)benzamide.

Embodiment 81. The method of any one of embodiments 35, wherein the compound is N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine.

Embodiment 82. A method of treating a cancer in a subject in need thereof, the method comprising: (i) administering to the subject a therapeutically-effective amount of a compound that increases anti-cancer activity of a mutant p53 protein in the subject; and (ii) administering to the subject a therapeutically-effective amount of an anti-cancer agent that functions through a pathway other than p53-induced apoptosis.

Embodiment 83. The method of embodiment 82, wherein the compound binds to the mutant p53 protein and reconforms the mutant p53 protein to a conformation of p53 that exhibits anti-cancer activity.

Embodiment 84. The method of embodiment 82 or 83, wherein the compound increases a stability of the mutant p53 protein.

Embodiment 85. The method of any one of embodiments 82-84, wherein the cancer expresses the mutant p53 protein.

Embodiment 86. The method of any one of embodiments 82-85, wherein the mutant p53 protein has a mutation at amino acid 220.

Embodiment 87. The method of any one of embodiments 82-86, wherein the mutant p53 protein is p53 Y220C.

Embodiment 88. The method of any one of embodiments 82-87, wherein the compound selectively binds the mutant p53 protein as compared to a wild type p53.

Embodiment 89. The method of any one of embodiments 82-88, wherein the cancer is ovarian cancer.

Embodiment 90. The method of any one of embodiments 82-88, wherein the cancer is breast cancer.

Embodiment 91. The method of any one of embodiments 82-88, wherein the cancer is lung cancer.

Embodiment 92. The method of any one of embodiments 82-91, wherein the administering of the compound is oral.

Embodiment 93. The method of any one of embodiments 82-91, wherein the administering of the compound is subcutaneous.

Embodiment 94. The method of any one of embodiments 82-93, wherein the administering of the compound is topical.

Embodiment 95. The method of any one of embodiments 82-94, wherein the therapeutically-effective amount of the compound is from about 500 mg to about 2000 mg.

Embodiment 96. The method of any one of embodiments 82-95, wherein the therapeutically-effective amount of the compound is about 500 mg.

Embodiment 97. The method of any one of embodiments 82-95, wherein the therapeutically-effective amount of the compound is about 1200 mg.

Embodiment 98. The method of any one of embodiments 82-95, wherein the therapeutically-effective amount of the compound is about 2000 mg.

Embodiment 99. The method of any one of embodiments 82-98, wherein the subject is human.

Embodiment 100. The method of any one of embodiments 82-99, wherein the anti-cancer agent is a small molecule.

Embodiment 101. The method of any one of embodiments 82-99, wherein the anti-cancer agent is an antibody.

Embodiment 102. The method of any one of embodiments 82-99, wherein the anti-cancer agent is an immune checkpoint inhibitor.

Embodiment 103. The method of any one of embodiments 82-99 or 102, wherein the immune checkpoint inhibitor is an anti-PD-1 agent.

Embodiment 104. The method of any one of embodiments 82-99, 102, or 103, wherein the anti-PD-1 agent is nivolumab.

Embodiment 105. The method of any one of embodiments 82-99, 102, or 103, wherein the anti-PD-1 agent is pembrolizumab.

Embodiment 106. The method of any one of embodiments 82-99, 102, or 103, wherein the anti-PD-1 agent is cemiplimab.

Embodiment 107. The method of any one of embodiments 82-99 or 102, wherein the immune checkpoint inhibitor is an anti-PD-L1 agent.

Embodiment 108. The method of any one of embodiments 82-99, 102, or 107, wherein the anti-PD-L1 agent is atezolizumab.

Embodiment 109. The method of any one of embodiments 82-99, 102, or 107, wherein the anti-PD-L1 agent is avelumab.

Embodiment 110. The method of any one of embodiments 82-99, 102, or 107, wherein the anti-PD-L1 agent is durvalumab.

Embodiment 111. The method of any one of embodiments 82-110, wherein the administering of the anti-cancer agent is oral.

Embodiment 112. The method of any one of embodiments 82-110, wherein the administering of the anti-cancer agent is subcutaneous.

Embodiment 113. The method of any one of embodiments 82-110, wherein the administering of the anti-cancer agent is topical.

Embodiment 114. The method of any one of embodiments 82-113, wherein the therapeutically-effective amount of the anti-cancer agent is from about 5 mg/kg to about 500 mg/kg.

Embodiment 115. The method of any one of embodiments 82-114, wherein the therapeutically-effective amount of the anti-cancer agent is from about 10 μg to about 500 μg.

Embodiment 116. The method of any one of embodiments 82-115, wherein the therapeutically-effective amount of the anti-cancer agent is about 200 μg.

Embodiment 117. The method of any one of embodiments 82-116, wherein the compound is of the formula:

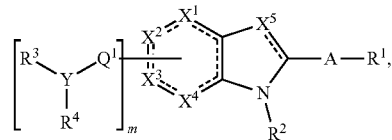

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or NR.
wherein at least one of $X^1$, $X^2$, $X^3$, and $X^4$ is a carbon atom connected to $Q^1$;
A is a linking group;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —$C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —$C(O)R^{19}$, —$C(O)OR^{11}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —C(O)$R^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

Embodiment 118. The method of embodiment 117, wherein A is alkylene, alkenylene, or alkynylene, each of which is substituted or unsubstituted.

Embodiment 119. The method of embodiment 117, wherein A is aryl, heteroaryl, or heterocyclyl, each of which is substituted or unsubstituted.

Embodiment 120. The method of embodiment 117 or 118, wherein the compound is of the formula:

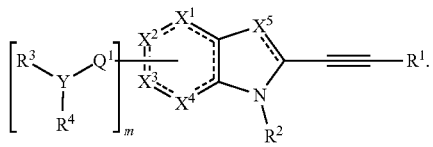

Embodiment 121. The method of any one of embodiments 117-120, wherein $Q^1$ is $C_1$-alkylene.

Embodiment 122. The method of any one of embodiments 117-120, wherein $Q^1$ is a bond.

Embodiment 123. The method of any one of embodiments 117-122, wherein m is 1.

Embodiment 124. The method of any one of embodiments 117-122, wherein m is 2.

Embodiment 125. The method of any one of embodiments 117-124, wherein Y is N.

Embodiment 126. The method of any one of embodiments 117-124, wherein Y is O.

Embodiment 127. The method of any one of embodiments 117-126, wherein each $R^3$ and $R^4$ is independently alkyl, alkylene, alkenyl, alkenylene, alkynyl, aryl, heteroaryl, or heterocyclyl, each of which is independently substituted or unsubstituted; or hydrogen.

Embodiment 128. The method of any one of embodiments 117-127, wherein $R^3$ is alkyl, alkylene, alkenyl, alkenylene, alkynyl, each of which is independently substituted or unsubstituted; and $R^4$ is aryl, heteroaryl, or heterocyclyl, each of which is independently substituted or unsubstituted.

Embodiment 129. The method of any one of embodiments 117-128, wherein $R^3$ is H; and $R^4$ is aryl, heteroaryl, or heterocyclyl, each of which is independently substituted or unsubstituted.

Embodiment 130. The method of any one of embodiments 117-129, wherein $R^{13}$ is hydrogen.

Embodiment 131. The method of any one of embodiments 117, 118, 122, 125, or 127-130, wherein the compound is of the formula:

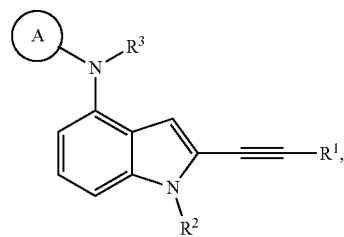

wherein ring A is a cyclic group that is substituted or unsubstituted.

Embodiment 132. The method of any one of embodiments 117-131, wherein $R^2$ is substituted or unsubstituted alkyl.

Embodiment 133. The method of any one of embodiments 117-132, wherein $R^2$ is methyl, ethyl, propyl, iso-propyl, butyl, or tert-butyl, each of which is substituted or unsubstituted.

Embodiment 134. The method of any one of embodiments 117-133, wherein $R^2$ is substituted ethyl.

Embodiment 135. The method of any one of embodiments 117-134, wherein $R^2$ is trifluoroethyl.

Embodiment 136. The method of any one of embodiments 117, 118, 122, 125, or 127-135, wherein the compound is of the formula:

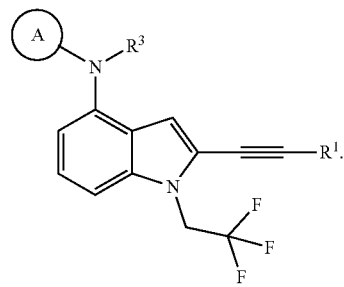

Embodiment 137. The method of any one of embodiments 117, 118, 122, 125, or 127-136, wherein ring A is aryl, heteroaryl, or heterocyclyl, each of which is substituted or unsubstituted.

Embodiment 138. The method of any one of embodiments 117, 118, 122, 125, or 127-137, wherein ring A is substituted aryl.

Embodiment 139. The method of any one of embodiments 117, 118, 122, 125, or 127-137, wherein ring A is substituted heteroaryl.

Embodiment 140. The method of any one of embodiments 117, 118, 122, 125, or 127-137, wherein ring A is substituted heterocyclyl.

Embodiment 141. The method of any one of embodiments 117-140, wherein $R^1$ is alkyl, alkenyl, —C(O)$R^{16}$, —C(O)OR$^{16}$, or —C(O)NR$^{16}$R$^{17}$, each of which is unsubstituted or substituted.

Embodiment 142. The method of any one of embodiments 117-141, wherein R¹ is substituted alkyl.

Embodiment 143. The method of any one of embodiments 117-142, wherein R¹ is alkyl substituted with NR¹⁶R¹⁷.

Embodiment 144. The method of any one of embodiments 117, 118, 122, 125, or 127-143, wherein the compound is of the formula:

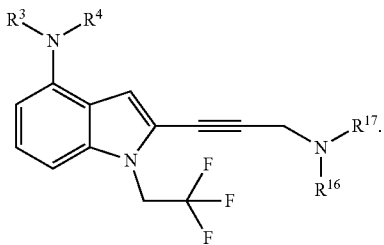

Embodiment 145. The method of any one of embodiments 117, 118, 122, 125, or 127-144, wherein each R¹⁶ and R¹⁷ is independently alkyl, alkenyl, aryl, heteroaryl, heterocyclyl, each of which is independently substituted or unsubstituted; or hydrogen.

Embodiment 146. The method of any one of embodiments 117, 118, 122, 125, or 127-145, wherein R¹⁶ is hydrogen or alkyl.

Embodiment 147. The method of any one of embodiments 117, 118, 122, 125, or 127-146, wherein R¹⁷ is aryl, heteroaryl, or heterocyclyl, each of which is independently substituted or unsubstituted.

Embodiment 148. The method of any one of embodiments 117, 118, 122, 125, or 127-147, wherein R¹⁷ is substituted aryl.

Embodiment 149. The method of any one of embodiments 117, 118, 122, 125, or 127-148, wherein R¹⁷ is substituted phenyl.

Embodiment 150. The method of any one of embodiments 117, 118, 122, 125, or 127-149, wherein R¹⁷ is phenyl substituted with a sulfoxide group, carboxyl group, amide group, amino group, alkyl, alkoxy, hydroxy, halo, cyano, or heterocyclyl, each of which is independently substituted or unsubstituted.

Embodiment 151. The method of any one of embodiments 117, 118, 122, 125, or 127-150, wherein R¹⁷ is phenyl substituted with methoxy.

Embodiment 152. The method of any one of embodiments 117, 118, 122, 125, or 127-151, wherein R¹⁷ is phenyl substituted with a substituted sulfoxide group.

Embodiment 153. The method of any one of embodiments 117, 118, 122, 125, or 127-152, wherein R¹⁷ is phenyl substituted with a carboxyl group.

Embodiment 154. The method of any one of embodiments 117, 118, 122, 125, or 127-153, wherein R¹⁷ is phenyl substituted with an amide group.

Embodiment 155. The method of any one of embodiments 117, wherein the compound is 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide.

Embodiment 156. The method of any one of embodiments 117, wherein the compound is 2-(3-((2-methoxy-4-(methylsulfonyl)phenyl)amino)prop-1-yn-1-yl)-N-((1r,4r)-4-morpholinocyclohexyl)-1-(oxiran-2-ylmethyl)-1H-indol-4-amine.

Embodiment 157. The method of any one of embodiments 117, wherein the compound is 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide.

Embodiment 158. The method of any one of embodiments 117, wherein the compound is 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide.

Embodiment 159. The method of any one of embodiments 117, wherein the compound is N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide.

Embodiment 160. The method of any one of embodiments 117, wherein the compound is 3-methoxy-N-(2-methoxyethyl)-N-methyl-4-((3-(4-((tetrahydro-2H-pyran-4-yl)amino)-1-(2,2,2-trifluoroethyl)-1H-indol-2-yl)prop-2-yn-1-yl)amino)benzenesulfonamide.

Embodiment 161. The method of any one of embodiments 117, wherein the compound is N-(2,3-dihydroxypropyl)-4-((3-(4-((1,1-dioxidotetrahydro-2H-thiopyran-4-yl)amino)-1-(2,2,2-trifluoroethyl)-1H-indol-2-yl)prop-2-yn-1-yl)amino)-3-methoxybenzenesulfonamide.

Embodiment 162. The method of any one of embodiments 117, wherein the compound is 3-methoxy-4-((3-(4-(3-(1-methylpiperidin-4-yl)ureido)-1-(2,2,2-trifluoroethyl)-1H-indol-2-yl)prop-2-yn-1-yl)amino)benzamide.

Embodiment 163. The method of any one of embodiments 117, wherein the compound is N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine.

Embodiment 164. A method of treating cancer, the method comprising: (i) administering to a subject in need thereof a therapeutically-effective amount of a compound that binds to a mutant p53 protein and reconforms the mutant p53 protein to a conformation of p53 that exhibits anti-cancer activity; and (ii) administering to the subject a therapeutically-effective amount of an additional anti-cancer agent that functions through a pathway other than p53-induced apoptosis, wherein if in a controlled study of treatment of the cancer in a first patient population and a second patient population: (a) a first median survival time of the first patient population is determined, wherein the first patient population is treated with the therapeutically-effective amount of the compound that binds to a mutant p53 protein and reconforms the mutant p53 protein to a conformation of p53 that exhibits anti-cancer activity; and (b) a second median survival time of the second patient population is determined, wherein the second patient population is treated with the therapeutically-effective amount of the compound that binds to a mutant p53 protein and reconforms the mutant p53 protein to a conformation of p53 that exhibits anti-cancer activity and the therapeutically-effective amount of the additional therapeutic agent; then the second median survival time is at least about 50% greater than is the first median survival time.

Embodiment 165. The method of embodiment 164, wherein the second median survival time is at least about 100% greater than the first median survival time.

Embodiment 166. The method of embodiment 164 or 165, wherein the second median survival time is at least about 200% greater than the first median survival time.

Embodiment 167. The method of any one of embodiments 164-166, wherein the compound increases a stability of the mutant p53 protein.

Embodiment 168. The method of any one of embodiments 164-167, wherein the cancer expresses the mutant p53 protein.

Embodiment 169. The method of any one of embodiments 164-168, wherein the mutant p53 protein has a mutation at amino acid 220.

Embodiment 170. The method of any one of embodiments 164-169, wherein the mutant p53 protein is p53 Y220C.

Embodiment 171. The method of e any one of embodiments 164-170, wherein the compound selectively binds the mutant p53 protein as compared to a wild type p53.

Embodiment 172. The method of any one of embodiments 164-171, wherein the cancer is ovarian cancer.

Embodiment 173. The method of any one of embodiments 164-171, wherein the cancer is breast cancer.

Embodiment 174. The method of any one of embodiments 164-171, wherein the cancer is lung cancer.

Embodiment 175. The method of any one of embodiments 164-174, wherein the administering of the compound is oral.

Embodiment 176. The method of any one of embodiments 164-174, wherein the administering of the compound is subcutaneous.

Embodiment 177. The method of any one of embodiments 164-174, wherein the administering of the compound is topical.

Embodiment 178. The method of any one of embodiments 164-177, wherein the therapeutically-effective amount of the compound is from about 500 mg to about 2000 mg.

Embodiment 179. The method of any one of embodiments 164-178, wherein the therapeutically-effective amount of the compound is about 500 mg.

Embodiment 180. The method of any one of embodiments 164-178, wherein the therapeutically-effective amount of the compound is about 1200 mg.

Embodiment 181. The method of any one of embodiments 164-178, wherein the therapeutically-effective amount of the compound is about 2000 mg.

Embodiment 182. The method of any one of embodiments 164-181, wherein the subject is human.

Embodiment 183. The method of any one of embodiments 164-182, wherein the anti-cancer agent is a small molecule.

Embodiment 184. The method of any one of embodiments 164-182, wherein the anti-cancer agent is an antibody.

Embodiment 185. The method of any one of embodiments 164-182, wherein the anti-cancer agent is an immune checkpoint inhibitor.

Embodiment 186. The method of any one of embodiments 164-182 or 185, wherein the immune checkpoint inhibitor is an anti-PD-1 agent.

Embodiment 187. The method of any one of embodiments 164-182, 185, or 186, wherein the anti-PD-1 agent is nivolumab.

Embodiment 188. The method of any one of embodiments 164-182, 185, or 186, wherein the anti-PD-1 agent is pembrolizumab.

Embodiment 189. The method of any one of embodiments 164-182, 185, or 186, wherein the anti-PD-1 agent is cemiplimab.

Embodiment 190. The method of any one of embodiments 164-182, or 185, wherein the immune checkpoint inhibitor is an anti-PD-L1 agent.

Embodiment 191. The method of any one of embodiments 164-182, 185, or 190, wherein the anti-PD-L1 agent is atezolizumab.

Embodiment 192. The method of any one of embodiments 164-182, 185, or 190, wherein the anti-PD-L1 agent is avelumab.

Embodiment 193. The method of any one of embodiments 164-182, 185, or 190, wherein the anti-PD-L1 agent is durvalumab.

Embodiment 194. The method of any one of embodiments 164-193, wherein the administering of the anti-cancer agent is oral.

Embodiment 195. The method of any one of embodiments 164-193, wherein the administering of the anti-cancer agent is subcutaneous.

Embodiment 196. The method of any one of embodiments 164-193, wherein the administering of the anti-cancer agent is topical.

Embodiment 197. The method of any one of embodiments 164-196, wherein the therapeutically-effective amount of the anti-cancer agent is from about 5 mg/kg to about 500 mg/kg.

Embodiment 198. The method of any one of embodiments 164-197, wherein the therapeutically-effective amount of the anti-cancer agent is from about 10 μg to about 500 μg.

Embodiment 199. The method of any one of embodiments 164-198, wherein the therapeutically-effective amount of the anti-cancer agent is about 200 μg.

Embodiment 200. The method of any one of embodiments 164-199, wherein the compound is of the formula:

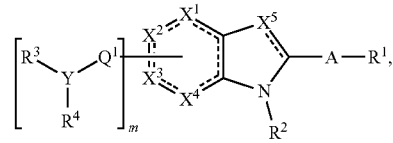

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$.
wherein at least one of $X^1$, $X^2$, $X^3$, and $X^4$ is a carbon atom connected to $Q^1$;
A is a linking group;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

Embodiment 201. The method of embodiment 200, wherein A is alkylene, alkenylene, or alkynylene, each of which is substituted or unsubstituted.

Embodiment 202. The method of embodiment 200, wherein A is aryl, heteroaryl, or heterocyclyl, each of which is substituted or unsubstituted.

Embodiment 203. The method of embodiment 200 or 201, wherein the compound is of the formula:

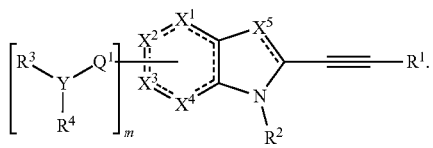

Embodiment 204. The method of any one of embodiments 200-203, wherein $Q^1$ is $C_1$-alkylene.

Embodiment 205. The method of any one of embodiments 200-203, wherein $Q^1$ is a bond.

Embodiment 206. The method of any one of embodiments 200-205, wherein m is 1.

Embodiment 207. The method of any one of embodiments 200-205, wherein m is 2.

Embodiment 208. The method of any one of embodiments 200-207, wherein Y is N.

Embodiment 209. The method of any one of embodiments 200-207, wherein Y is O.

Embodiment 210. The method of any one of embodiments 200-209, wherein each $R^3$ and $R^4$ is independently alkyl, alkylene, alkenyl, alkenylene, alkynyl, aryl, heteroaryl, or heterocyclyl, each of which is independently substituted or unsubstituted; or hydrogen.

Embodiment 211. The method of any one of embodiments 200-210, wherein $R^3$ is alkyl, alkylene, alkenyl, alkenylene, alkynyl, each of which is independently substituted or unsubstituted; and $R^4$ is aryl, heteroaryl, or heterocyclyl, each of which is independently substituted or unsubstituted.

Embodiment 212. The method of any one of embodiments 200-211, wherein $R^3$ is H; and $R^4$ is aryl, heteroaryl, or heterocyclyl, each of which is independently substituted or unsubstituted.

Embodiment 213. The method of any one of embodiments 200-212, wherein $R^{13}$ is hydrogen.

Embodiment 214. The method of any one of embodiments 200, 201, 203, 205, 206, 208, or 210-213, wherein the compound is of the formula:

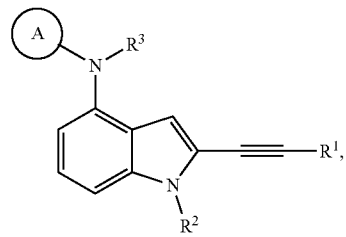

wherein ring A is a cyclic group that is substituted or unsubstituted.

Embodiment 215. The method of any one of embodiments 200, 201, 203, 205, 206, 208, or 210-214, wherein $R^2$ is substituted or unsubstituted alkyl.

Embodiment 216. The method of any one of embodiments 200, 201, 203, 205, 206, 208, or 210-215, wherein $R^2$ is methyl, ethyl, propyl, iso-propyl, butyl, or tert-butyl, each of which is substituted or unsubstituted.

Embodiment 217. The method of any one of embodiments 200, 201, 203, 205, 206, 208, or 210-216, wherein $R^2$ is substituted ethyl.

Embodiment 218. The method of any one of embodiments 200, 201, 203, 205, 206, 208, or 210-217, wherein $R^2$ is trifluoroethyl.

Embodiment 219. The method of any one of embodiments 200, 201, 203, 205, 206, 208, or 210-218, wherein the compound is of the formula:

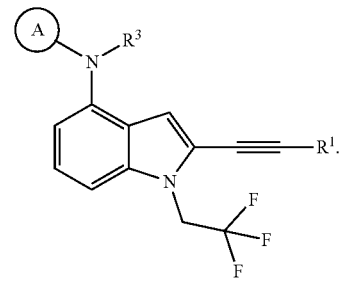

Embodiment 220. The method of any one of embodiments 200, 201, 203, 205, 206, 208, or 210-219, wherein ring A is aryl, heteroaryl, or heterocyclyl, each of which is substituted or unsubstituted.

Embodiment 221. The method of any one of embodiments 200, 201, 203, 205, 206, 208, or 210-220, wherein ring A is substituted aryl.

Embodiment 222. The method of any one of embodiments 200, 201, 203, 205, 206, 208, or 210-220, wherein ring A is substituted heteroaryl.

Embodiment 223. The method of any one of embodiments 200, 201, 203, 205, 206, 208, or 210-220, wherein ring A is substituted heterocyclyl.

Embodiment 224. The method of any one of embodiments 200-223, wherein $R^1$ is alkyl, alkenyl, —C(O)$R^{16}$, —C(O)O$R^{16}$, or —C(O)N$R^{16}R^{17}$, each of which is unsubstituted or substituted.

Embodiment 225. The method of any one of embodiments 200-224, wherein $R^1$ is substituted alkyl.

Embodiment 226. The method of any one of embodiments 200-225, wherein $R^1$ is alkyl substituted with $NR^{16}R^{17}$.

Embodiment 227. The method of any one of embodiments 200, 201, 203, 205, 206, 208, or 210-226, wherein the compound is of the formula:

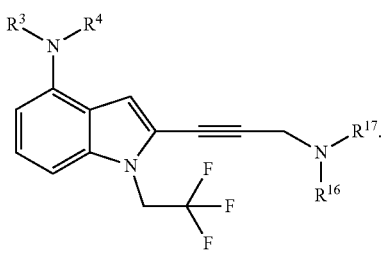

Embodiment 228. The method of any one of embodiments 200, 201, 203, 205, 206, 208, or 210-227, wherein each $R^{16}$ and $R^{17}$ is independently alkyl, alkenyl, aryl, heteroaryl, heterocyclyl, each of which is independently substituted or unsubstituted; or hydrogen.

Embodiment 229. The method of any one of embodiments 200, 201, 203, 205, 206, 208, or 210-228, wherein $R^{16}$ is hydrogen or alkyl.

Embodiment 230. The method of any one of embodiments 200, 201, 203, 205, 206, 208, or 210-229, wherein $R^{17}$ is aryl, heteroaryl, or heterocyclyl, each of which is independently substituted or unsubstituted.

Embodiment 231. The method of any one of embodiments 200, 201, 203, 205, 206, 208, or 210-230, wherein $R^{17}$ is substituted aryl.

Embodiment 232. The method of any one of embodiments 200, 201, 203, 205, 206, 208, or 210-231, wherein $R^{17}$ is substituted phenyl.

Embodiment 233. The method of any one of embodiments 200, 201, 203, 205, 206, 208, or 210-232, wherein $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted.

Embodiment 234. The method of any one of embodiments 200, 201, 203, 205, 206, 208, or 210-233, wherein $R^{17}$ is phenyl substituted with methoxy.

Embodiment 235. The method of any one of embodiments 200, 201, 203, 205, 206, 208, or 210-234, wherein $R^{17}$ is phenyl substituted with a substituted sulfoxide group.

Embodiment 236. The method of any one of embodiments 200, 201, 203, 205, 206, 208, or 210-235, wherein $R^{17}$ is phenyl substituted with a carboxyl group.

Embodiment 237. The method of any one of embodiments 200, 201, 203, 205, 206, 208, or 210-236, wherein $R^{17}$ is phenyl substituted with an amide group.

Embodiment 238. The method of embodiment 200, wherein the compound is 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide.

Embodiment 239. The method of any one of embodiments 200, wherein the compound is 2-(3-((2-methoxy-4-(methylsulfonyl)phenyl)amino)prop-1-yn-1-yl)-N-((1r,4r)-4-morpholinocyclohexyl)-1-(oxiran-2-ylmethyl)-1H-indol-4-amine.

Embodiment 240. The method of any one of embodiments 200, wherein the compound is 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide.

Embodiment 241. The method of any one of embodiments 200, wherein the compound is 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide.

Embodiment 242. The method of any one of embodiments 200, wherein the compound is N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide.

Embodiment 243. The method of any one of embodiments 200, wherein the compound is 3-methoxy-N-(2-methoxyethyl)-N-methyl-4-((3-(4-((tetrahydro-2H-pyran-4-yl)amino)-1-(2,2,2-trifluoroethyl)-1H-indol-2-yl)prop-2-yn-1-yl)amino)benzenesulfonamide.

Embodiment 244. The method of any one of embodiments 200, wherein the compound is N-(2,3-dihydroxypropyl)-4-((3-(4-((1,1-dioxidotetrahydro-2H-thiopyran-4-yl)amino)-1-(2,2,2-trifluoroethyl)-1H-indol-2-yl)prop-2-yn-1-yl)amino)-3-methoxybenzenesulfonamide.

Embodiment 245. The method of any one of embodiments 200, wherein the compound is 3-methoxy-4-((3-(4-(3-(1-methylpiperidin-4-yl)ureido)-1-(2,2,2-trifluoroethyl)-1H-indol-2-yl)prop-2-yn-1-yl)amino)benzamide.

Embodiment 246. The method of any one of embodiments 200, wherein the compound is N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine.

What is claimed is:

1. A method of treating a cancer in a subject in need thereof, the method comprising:
   (i) administering to the subject a therapeutically-effective amount of a compound of the formula:

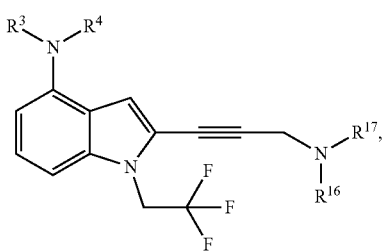

wherein:
   $R^3$ is H;
   $R^4$ is $C_4$-$C_6$-heterocyclyl substituted with at least halo-;
   $R^{16}$ is hydrogen; and
   $R^{17}$ is aryl that is substituted or unsubstituted,
   or a pharmaceutically-acceptable salt thereof; and
   (ii) administering to the subject a therapeutically-effective amount of an immune checkpoint inhibitor.

2. The method of claim 1, wherein the cancer expresses a mutant p53 protein.

3. The method of claim 2, wherein the mutant p53 protein has a mutation at amino acid 220.

4. The method of claim 2, wherein the mutant p53 protein is p53 Y220C.

5. The method of claim 1, wherein the cancer is lung cancer.

6. The method of claim 1, wherein the administering of the compound is oral.

7. The method of claim 1, wherein the therapeutically-effective amount of the compound is from about 500 mg to about 5000 mg.

8. The method of claim 1, wherein the subject is human.

9. The method of claim 1, wherein the immune checkpoint inhibitor is an anti-PD-1 agent.

10. The method of claim 1, wherein the immune checkpoint inhibitor is an anti-PD-L1 agent.

11. The method of claim 1, wherein $R^{17}$ is phenyl substituted with a sulfoxide group, carboxyl group, amide group, amino group, alkyl, alkoxy, hydroxy, or heterocyclyl, each of which is independently substituted or unsubstituted, or halo or cyano.

12. The method of claim 1, wherein $R^{17}$ is phenyl substituted with at least methoxy.

13. The method of claim 1, wherein $R^{17}$ is methylpiperidinyl substituted with halo-.

14. The method of claim 9, wherein the anti-PD-1 agent is nivolumab.

15. The method of claim 9, wherein the anti-PD-1 agent is pembrolizumab.

16. The method of claim 9, wherein the anti-PD-1 agent is cemiplimab.

17. The method of claim 10, wherein the anti-PD-L1 agent is atezolizumab.

18. The method of claim 10, wherein the anti-PD-L1 agent is avelumab.

19. The method of claim 10, wherein the anti-PD-L1 agent is durvalumab.

20. The method of claim 1, wherein the compound is:
    4-((3-(4-(((3S,4R)-3-fluoro-1-methylpiperidin-4-yl)amino)-1-(2,2,2-trifluoroethyl)-1H-indol-2-yl)prop-2- yn-1-yl)amino)-3-methoxy-N-methylbenzamide, or a pharmaceutically-acceptable salt thereof.

21. The method of claim 1, wherein the compound is: N-(2,3-dihydroxypropyl)-4-{[3-(4-{[(3 S,4R)-3-fluoro-1-methylpiperidin-4-yl]amino}-1-(2,2,2-trifluoroethyl)-1H-indol-2-yl)prop-2-yn-1-yl]amino}-3-methoxybenzamide, or a pharmaceutically-acceptable salt thereof.

22. The method of claim 1, wherein the compound is: N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine, or a pharmaceutically-acceptable salt thereof.

23. The method of claim 1, wherein the compound is:

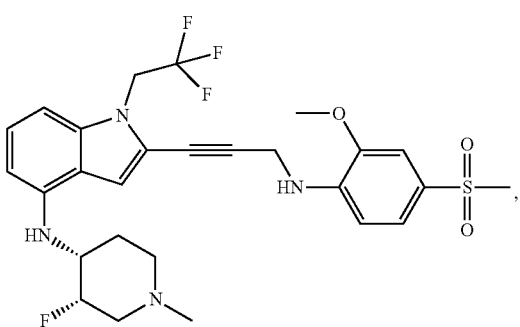 [SMILES: COc1cc(S(C)(=O)=O)ccc1NCC#Cc1cc2c(N[C@@H]3CCN(C)C[C@@H]3F)cccc2n1CC(F)(F)F]

or a pharmaceutically-acceptable salt thereof.

24. The method of claim 1, wherein the compound is:

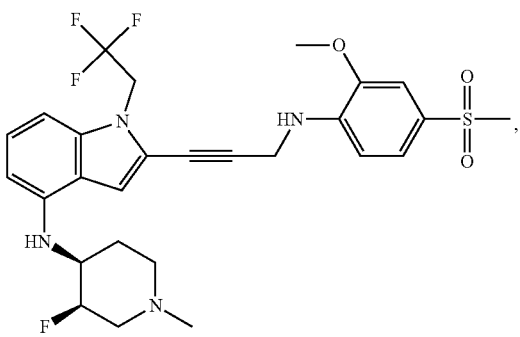 [SMILES: COc1cc(S(C)(=O)=O)ccc1NCC#Cc1cc2c(N[C@H]3CCN(C)C[C@H]3F)cccc2n1CC(F)(F)F]

or a pharmaceutically-acceptable salt thereof.

25. The method of claim 1, wherein the compound is:

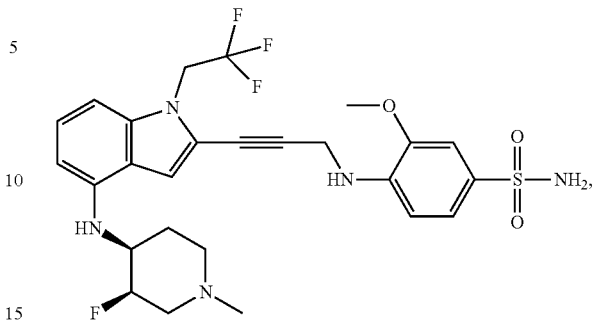

or a pharmaceutically-acceptable salt thereof.

26. The method of claim 1, wherein the compound is:

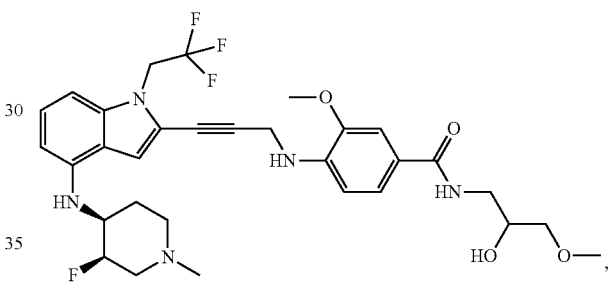

or a pharmaceutically-acceptable salt thereof.

27. The method of claim 1, wherein the cancer is ovarian cancer.

28. The method of claim 1, wherein the cancer is breast cancer.

* * * * *

UNITED STATES PATENT AND TRADEMARK OFFICE
CERTIFICATE OF CORRECTION

| | |
|---|---|
| PATENT NO. | : 11,938,124 B2 |
| APPLICATION NO. | : 17/348490 |
| DATED | : March 26, 2024 |
| INVENTOR(S) | : Levine et al. |

It is certified that error appears in the above-identified patent and that said Letters Patent is hereby corrected as shown below:

In the Claims

Claim 13; Column 484; Line 51:
Delete: "$R^{17}$"
And replace with: --$R^4$--

Claim 21; Column 485; Line 4:
Delete: "(3 S,4R)"
And replace with: --(3S,4R)--

Signed and Sealed this
Eighteenth Day of June, 2024

*Katherine Kelly Vidal*

Katherine Kelly Vidal
*Director of the United States Patent and Trademark Office*